United States Patent
Allen et al.

(10) Patent No.: US 8,637,500 B2
(45) Date of Patent: Jan. 28, 2014

(54) AMINOPYRIDINE AND CARBOXYPYRIDINE COMPOUNDS AS PHOSPHODIESTERASE 10 INHIBITORS

(75) Inventors: Jennifer R. Allen, Newbury Park, CA (US); Ning Chen, Thousand Oaks, CA (US); James R. Falsey, Moorpark, CA (US); Michael J. Frohn, Thousand Oaks, CA (US); Paul E. Harrington, Camarillo, CA (US); Essa Hu Harrington, Camarillo, CA (US); Matthew R. Kaller, Ventura, CA (US); Roxanne K. Kunz, Santa Monica, CA (US); Thomas T. Nguyen, Newbury Park, CA (US); Alexander J. Pickrell, Westlake Village, CA (US); Andreas Reichelt, Moorpark, CA (US); Shannon Rumfelt, Camarillo, CA (US); Robert M. Rzasa, Ventura, CA (US); Kelvin Sham, Thousand Oaks, CA (US); Aaron C. Siegmund, Ventura, CA (US); Guomin Yao, Mililani, HI (US)

(73) Assignee: Amgen Inc., Thousand Oaks, CA (US)

(*) Notice: Subject to any disclaimer, the term of this patent is extended or adjusted under 35 U.S.C. 154(b) by 711 days.

(21) Appl. No.: 12/639,931

(22) Filed: Dec. 16, 2009

(65) Prior Publication Data

US 2010/0160280 A1  Jun. 24, 2010

Related U.S. Application Data

(60) Provisional application No. 61/138,443, filed on Dec. 17, 2008, provisional application No. 61/138,434, filed on Dec. 17, 2008.

(51) Int. Cl.
| | |
|---|---|
| A61K 31/551 | (2006.01) |
| A61K 31/553 | (2006.01) |
| A61K 31/5377 | (2006.01) |
| A61K 31/497 | (2006.01) |
| C07D 243/08 | (2006.01) |
| C07D 267/10 | (2006.01) |
| C07D 401/12 | (2006.01) |
| C07D 401/14 | (2006.01) |
| C07D 413/14 | (2006.01) |

(52) U.S. Cl.
USPC ............... 514/211.15; 514/218; 514/235.8; 514/252.11; 514/255.05; 540/544; 540/575; 544/120; 544/357; 544/405

(58) Field of Classification Search
None
See application file for complete search history.

(56) References Cited

U.S. PATENT DOCUMENTS

| 4,198,417 | A | 4/1980 | Ong et al. |
|---|---|---|---|
| 6,800,651 | B2 | 10/2004 | Coleman |

(Continued)

FOREIGN PATENT DOCUMENTS

| WO | WO 01/56990 A2 | 8/2001 |
|---|---|---|
| WO | WO 2004/087155 A1 | 10/2004 |

(Continued)

OTHER PUBLICATIONS

Akagi, Toshio et al, "Quantitative Structure-Activity Relationships of Fluazinam and Related Fungicidal N-Phenylpyridinamines: Preventive Activity against *Botrytis cinerea*," J. Pesticide Sci., 20, 279-290 (1995).

(Continued)

*Primary Examiner* — Alicia L Otton
(74) *Attorney, Agent, or Firm* — Elsa D. Lemoine

(57) ABSTRACT

Pyridine and pyrimidine compounds:

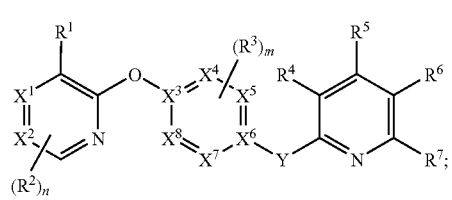

(I)

or a pharmaceutically acceptable salt thereof, wherein m, n, $R^1$, $R^2$, $R^3$, $R^4$, $R^5$, $R^6$, $R^7$, $X^1$, $X^2$, $X^3$, $X^4$, $X^5$, $X^6$, $X^7$, $X^8$, and Y are as defined in the specification;

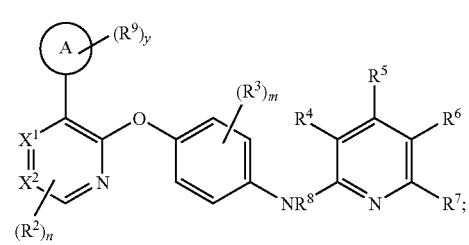

(II)

or a pharmaceutically acceptable salt thereof, wherein ring A, m, n, y, $R^2$, $R^3$, $R^4$, $R^5$, $R^6$, $R^7$, $R^8$, $R^9$, $X^1$, $X^2$, and ring A are as defined in the specification; and

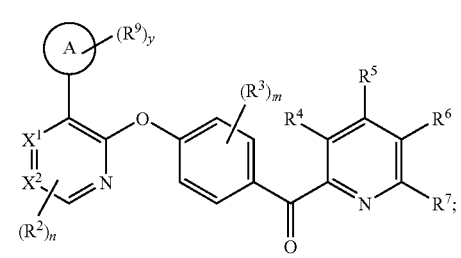

(III)

or a pharmaceutically acceptable salt thereof, wherein m, n, y, $R^2$, $R^3$, $R^4$, $R^5$, $R^6$, $R^7$, $R^9$, $X^1$, $X^2$, and ring A are as defined in the specification; compositions containing them, and processes for preparing such compounds. Provided herein also are methods of treating disorders or diseases treatable by inhibition of PDE10, such as obesity, non-insulin dependent diabetes, schizophrenia, bipolar disorder, obsessive-compulsive disorder, and the like.

18 Claims, No Drawings

(56) References Cited

U.S. PATENT DOCUMENTS

| | | | |
|---|---|---|---|
| 2007/0185111 A1 | 8/2007 | Cee | |
| 2010/0137278 A1* | 6/2010 | Allen et al. | 514/210.18 |
| 2011/0160182 A1* | 6/2011 | Allen et al. | 514/210.18 |
| 2011/0160202 A1* | 6/2011 | Allen et al. | 514/232.8 |

FOREIGN PATENT DOCUMENTS

| | | |
|---|---|---|
| WO | WO 2005/021529 A1 | 3/2005 |
| WO | WO 2005/086904 A2 | 9/2005 |
| WO | WO 2007/077490 A2 | 7/2007 |
| WO | WO 2007/087276 A1 | 8/2007 |
| WO | WO 2007/129183 A2 | 11/2007 |
| WO | WO 2008/004117 A1 | 1/2008 |
| WO | WO 2008/057280 A1 | 5/2008 |
| WO | WO 2008/079294 A1 | 7/2008 |
| WO | WO 2009/081259 A1 | 7/2009 |
| WO | WO 2010/008739 A2 | 1/2010 |
| WO | WO 2010/057121 * | 5/2010 ........... C07D 403/12 |

OTHER PUBLICATIONS

Dounay et al., "Design, synthesis, and pharmacological evaluation of phenoxy pyridyl derivatives as dual norepinephrine reuptake inhibitors and 5-HT1A partial agonists," Bioorganic & Medicinal Chemistry Letters, 2010, 20(3):1114-1117.

Villani et al., "Benzopyranopyridine Derivatives. 1. Aminoalkyl Derivatives of the Azaxanthenes as Bronchodilating Agents," Journal of Medicinal Chemistry, 1975, 18(1):1-8.

* cited by examiner

AMINOPYRIDINE AND CARBOXYPYRIDINE COMPOUNDS AS PHOSPHODIESTERASE 10 INHIBITORS

CROSS-REFERENCE TO RELATED APPLICATIONS

This application claims the benefit of U.S. Provisional Application No. 61/138,443, filed 17 Dec. 2008, and U.S. Provisional Application No. 61/138,434, filed 17 Dec. 2008, which are hereby incorporated by reference.

FIELD OF THE INVENTION

Provided herein are certain aminopyridine and carboxypyridine compounds that are PDE10 inhibitors, pharmaceutical compositions containing such compounds, and processes for preparing such compounds. Provided herein also are methods of treating disorders or diseases treatable by inhibition of PDE10, such as obesity, non-insulin dependent diabetes, schizophrenia, bipolar disorder, obsessive-compulsive disorder, and the like.

BACKGROUND

Neurotransmitters and hormones, as well as other types of extracellular signals such as light and odors, create intracellular signals by altering the amounts of cyclic nucleotide monophosphates (cAMP and cGMP) within cells. These intracellular messengers alter the functions of many intracellular proteins. Cyclic AMP regulates the activity of cAMP-dependent protein kinase (PKA). PKA phosphorylates and regulates the function of many types of proteins, including ion channels, enzymes, and transcription factors. Downstream mediators of cGMP signaling also include kinases and ion channels. In addition to actions mediated by kinases, cAMP and cGMP bind directly to some cell proteins and directly regulate their activities.

Cyclic nucleotides are produced from the actions of adenylyl cyclase and guanylyl cyclase, which convert ATP to cAMP and GTP to cGMP. Extracellular signals, often through the actions of G protein-coupled receptors, regulate the activities of the cyclases. Alternatively, the amount of cAMP and cGMP may be altered by regulating the activities of the enzymes that degrade cyclic nucleotides. Cell homeostasis is maintained by the rapid degradation of cyclic nucleotides after stimulus-induced increases. The enzymes that degrade cyclic nucleotides are called 3',5'-cyclic nucleotide-specific phosphodiesterases (PDEs).

Eleven PDE gene families (PDE1-PDE11) have been identified based on their distinct amino acid sequences, catalytic and regulatory characteristics, and sensitivity to small molecule inhibitors. These families are coded for by 21 genes; and further multiple splice variants are transcribed from many of these genes. Expression patterns of each of the gene families are distinct. PDEs differ with respect to their affinity for cAMP and cGMP. Activities of different PDEs are regulated by different signals. For example, PDE1 is stimulated by $Ca^{2+}$/calmodulin. PDE2 activity is stimulated by cGMP. PDE3 is inhibited by cGMP. PDE4 is cAMP specific and is specifically inhibited by rolipram. PDE5 is cGMP-specific. PDE6 is expressed in retina.

PDE10 sequences were identified by using bioinformatics and sequence information from other PDE gene families (Fujishige et al., *J. Biol. Chem.* 274:18438-18445, 1999; Loughney et al., *Gene* 234:109-117, 1999; Soderling et al., *Proc. Natl. Acad. Sci. USA* 96:7071-7076, 1999). The PDE10 gene family is distinguished based on its amino acid sequence, functional properties and tissue distribution. The human PDE10 gene is large, over 200 kb, with up to 24 exons coding for each of the splice variants. The amino acid sequence is characterized by two GAF domains (which bind cGMP), a catalytic region, and alternatively spliced N and C termini. Numerous splice variants are possible because at least three alternative exons encode N termini and two exons encode C-termini. PDE10A1 is a 779 amino acid protein that hydrolyzes both cAMP and cGMP. The $K_m$ values for cAMP and cGMP are 0.05 and 3.0 micromolar, respectively. In addition to human variants, several variants with high homology have been isolated from both rat and mouse tissues and sequence banks.

PDE10 RNA transcripts were initially detected in human testis and brain. Subsequent immunohistochemical analysis revealed that the highest levels of PDE10 are expressed in the basal ganglia. Specifically, striatal neurons in the olfactory tubercle, caudate nucleus and nucleus accumbens are enriched in PDE10. Western blots did not reveal the expression of PDE10 in other brain tissues, although immunoprecipitation of the PDE10 complex was possible in hippocampal and cortical tissues. This suggests that the expression level of PDE10 in these other tissues is 100-fold less than in striatal neurons. Expression in hippocampus is limited to the cell bodies, whereas PDE10 is expressed in terminals, dendrites and axons of striatal neurons.

The tissue distribution of PDE10 indicates that PDE10 inhibitors can be used to raise levels of cAMP and/or cGMP within cells that express the PDE10 enzyme, for example, in neurons that comprise the basal ganglia and therefore would be useful in treating a variety of neuropsychiatric conditions involving the basal ganglia such as obesity, non-insulin dependent diabetes, schizophrenia, bipolar disorder, obsessive compulsive disorder, and the like.

SUMMARY OF THE INVENTION

The present invention comprises a new class of aminopyridine and carboxypyridine compounds useful in the treatment of diseases, such as PDE10-mediated diseases and other maladies, such as schizophrenia, bipolar disorder, or obsessive-compulsive disorder. Accordingly, the invention also comprises pharmaceutical compositions comprising the compounds, methods for the treatment of PDE10-mediated diseases and other maladies, such as schizophrenia, bipolar disorder, or obsessive-compulsive disorder, using the compounds and compositions of the invention, and intermediates and processes useful for the preparation of the compounds of the invention.

The compounds of the invention are represented by the following general structure:

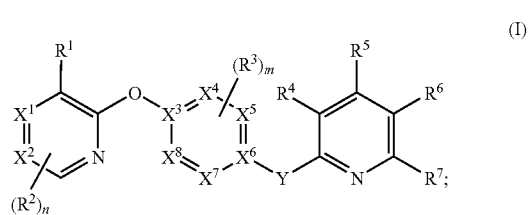

(I)

or a pharmaceutically acceptable salt thereof, wherein m, n, $R^1, R^2, R^3, R^4, R^5, R^6, R^7, X^1, X^2, X^3, X^4, X^5, X^6, X^7, X^8$, and Y are defined below.

Other compounds of the invention are represented by the following general structure:

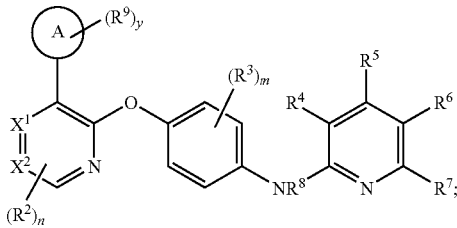
(II)

or a pharmaceutically acceptable salt thereof, wherein ring A, m, n, y, $R^2$, $R^3$, $R^4$, $R^5$, $R^6$, $R^7$, $R^8$, $R^9$, $X^1$, $X^2$, and ring A are defined below.

Other compounds of the invention are represented by the following general structure:

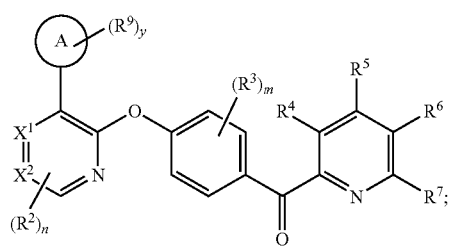
(III)

or a pharmaceutically acceptable salt thereof, wherein m, n, y, $R^2$, $R^3$, $R^4$, $R^5$, $R^6$, $R^7$, $R^9$, $X^1$, $X^2$, and ring A are defined below.

The foregoing merely summarizes certain aspects of the invention and is not intended, nor should it be construed, as limiting the invention in any way. All patents, patent applications and other publications recited herein are hereby incorporated by reference in their entirety.

DETAILED DESCRIPTION OF THE INVENTION

One aspect of the current invention relates to compounds having the general structure of formula (I):

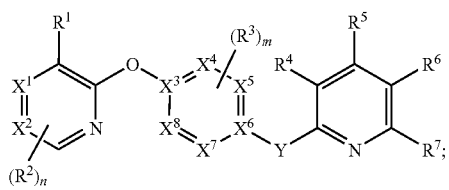
(I)

or any pharmaceutically-acceptable salt thereof, wherein:
$X^1$ is N or C;
$X^2$ is N or C; wherein 1 or 2 of $X^1$ and $X^2$ is C;
Each of $X^4$, $X^5$, $X^7$, and $X^8$ is independently N or C; each of $X^3$ and $X^6$ is C; wherein no more than three of $X^4$, $X^5$, $X^7$, and $X^8$ are N;
m is independently in each instance 0, 1, 2, 3 or 4;
n is independently in each instance 0, 1, 2 or 3;
Y is $NR^8$ or C(=O); or alternatively when Y is $NR^8$, Y and $R^3$ may form a 5- to 6-membered ring fused to the ring containing both said Y and $R^3$;
$R^1$ is selected from:
H, F, Cl, Br, I, $C_{1-8}$alk, $C_{1-4}$haloalk, —$OR^a$, —$NR^aR^a$, —$NR^aR^c$, —$N(R^a)C(=O)R^b$, —$C(=O)NR^aR^a$, —$C(=O)NR^aR^c$, —$C(=O)NR^an^d$, —$C(=O)R^a$, —$C(=O)R^c$, —$C(=O)R^d$, —$C(=O)$—O—$R^a$, —$C(=O)$—O—$R^c$, —$C(=O)$—O—$R^d$, —OR', —$NR^aR^e$, —$SR^c$, —$S(=O)R^c$, —$S(=O)_2R^c$, —$N(R^c)S(=O)_2R^b$, —$S(=O)_2NR^aR^c$, —$N(R^c)C(=O)R^b$, —$N(R^a)C(=O)R^c$, or —$C(=O)NR^aR^c$; or
Ring A, wherein said ring A is selected from the group consisting of $R^b$, $R^c$, and $R^d$; with the proviso that when Ring A is $R^c$, said $R^c$ is not cyclopentadienyl; or
$C_{0-4}$alk-linked unsaturated 5- or 6-membered monocyclic; or 9- or 10-membered bicyclic ring containing 0, 1, 2 or 3 N atoms and 0, 1, or 2 atoms selected from O and S;
And when Y is —$NR^8$, Ring A is not

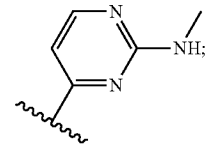 [SMILES: *c1ccnc(NC)n1]

$R^2$ is, independently in each instance, F, Cl, Br, CN, OH, $OC_{1-4}$alk, $C_{1-4}$alk or $C_{1-4}$haloalk;
$R^3$ is, independently in each instance, F, Br, CN, OH, $OC_{1-4}$alk, $C_{1-4}$alk or $C_{1-4}$haloalk;
$R^4$ is selected from H, F, Br, CN, —O—$C_{1-4}$alk, $C_{1-2}$alk, and $C_{1-2}$haloalk;
$R^5$ is selected from H, F, Cl, Br, CN, —O—$C_{1-4}$alk, $C_{1-2}$alk, and $C_{1-2}$haloalk;
$R^6$ is selected from H, F, Cl, Br, CN, —O—$C_{1-4}$alk, $C_{1-2}$alk, and $C_{1-2}$haloalk;
$R^7$ is selected from H, F, Cl, Br, CN, —O—$C_{1-4}$alk, $C_{1-2}$alk, and $C_{1-2}$haloalk;
$R^8$ is selected from H, $C_{1-8}$alk, and $C_{1-4}$haloalk;
$R^a$ is independently, at each instance, H or $R^b$;
$R^b$ is independently, at each instance, phenyl, benzyl, or $C_{1-6}$alk, wherein said phenyl, benzyl, and $C_{1-6}$alk is independently substituted by 0, 1, 2 or 3 substituents selected from halo, OH, $C_{1-4}$alk, $C_{1-3}$haloalk, —$OC_{1-4}$alk, —$NH_2$, —$NHC_{1-4}$alk, —$N(C_{1-4}alk)C_{1-4}$alk, $C_{1-4}$alk-$NH_2$, COOH, CN, —C(=O)—O—$C_{1-6}$alk, —C(=O)—$N(C_{1-4}$alk)$C_{1-4}$alk, and —S—$C_{1-4}$alk;
$R^c$ is a $C_{0-4}$alk-linked saturated, partially-saturated or unsaturated 3-, 4-, 5-, 6-, or 7-membered monocyclic or 8-, 9-, 10-, 11-, or 12-membered bicyclic ring containing 0, 1, 2 or 3 N atoms and 0, 1, or 2 atoms selected from O and S, which is substituted by 0, 1 or 2 groups selected from F, Cl, Br, $R^e$, $C_{1-6}$alk, $C_{1-4}$haloalk, —$OR^a$, —$OC_{1-4}$haloalk, CN, —$C(=O)R^b$, —$C(=O)R^e$, —$C(=O)OR^a$, —$C(=O)NR^aR^a$, —$C(=NR^a)NR^aR^a$, —$OC(=O)R^b$, —$OC(=O)NR^aR^a$, —$OC_{2-6}$alkNR^aR^a$, —$OC_{2-6}$alk(OR^a)_{1-3}$, —$SR^a$, —$S(=O)R^b$, —$S(=O)_2R^b$, —$S(=O)(OH)R^b$, —$S(=O)_2NR^aR^a$, —$NR^aR^a$, —$NR^aR^e$, —$NR^an^d$, —$N(R^a)C(=O)R^b$, —$N(R^a)C(=O)OR^b$, —$N(R^a)C(=O)NR^aR^a$, —$N(R^a)C(=NR^a)NR^aR^a$, —$N(R^a)S(=O)_2R^b$, —$N(R^a)S(=O)_2NR^aR^a$, —$NR^aC_{2-6}$alkNR^aR^a$, —$NR^aC_{2-6}$alkOR^a$, —$C_{1-6}$alkNR^aR^a$, —$C_{1-6}$alk(OR^a)_{1-3}$, —$C_{1-6}$alkN(R^a)C(=O)R^b$, —$C_{1-6}$alkOC(=O)R^b$, —$C_{1-6}$alkC(=O)NR^aR^a$, —$C_{1-6}$alkC(=O)OR^a$ and oxo;

R$^d$ is a nitrogen-linked saturated, partially-saturated or unsaturated 4-, 5-, 6- or 7-membered ring heterocycle containing the linking nitrogen and 0, 1 or 2 additional nitrogen atoms and containing 0 or 1 sulfur or oxygen atoms, the heterocycle being substituted by 0, 1, 2 or 3 substituents selected from oxo, halo, OH, CN, C$_{1-4}$alk, C$_{1-3}$haloalk, —OC$_{1-4}$alk, R$^e$, —OR$^e$, —NH$_2$, —NHC$_{1-4}$alk, —N(C$_{1-4}$alk)C$_{1-4}$alk, C(=O)OR$^a$, —C$_{1-6}$alk(OR$^a$)$_{1-3}$, —NH—C(=O)OC$_{1-4}$alk, C(=O)R$^a$, C(=O)R$^e$, C(=O)NR$^a$R$^a$, and C(=O)NR$^a$R$^a$; and R$^e$ is:

(a) C$_{0-4}$alk-linked saturated, partially-saturated or unsaturated 3-, 4-, 5-, 6-, or 7-membered monocyclic containing 0, 1, 2 or 3 N atoms and 0, 1, or 2 atoms selected from O and S; which is substituted by 0, 1, 2 or 3 groups selected from oxo, halo, OH, C$_{1-4}$alk, C$_{1-3}$haloalk, —OC$_{1-4}$alk, —NH$_2$, —NHC$_{1-4}$alk, —N(C$_{1-4}$alk)C$_{1-4}$alk, C$_{1-4}$alk-NH$_2$, COOH, CN, —C(=O)—O—C$_{1-6}$alk, —C(=O)—N(C$_{1-4}$alk)C$_{1-4}$alk, and —S—C$_{1-4}$alk; or (b) nitrogen-linked saturated, partially-saturated or unsaturated 4-, 5-, 6- or 7-membered ring heterocycle containing the linking nitrogen and 0, 1 or 2 additional nitrogen atoms and containing 0 or 1 sulfur or oxygen atoms; which is substituted by 0, 1, 2 or 3 groups selected from oxo, halo, OH, C$_{1-4}$alk, C$_{1-3}$haloalk, —OC$_{1-4}$alk, —NH$_2$, —NHC$_{1-4}$alk, —N(C$_{1-4}$alk)C$_{1-4}$alk, C$_{1-4}$alk-NH$_2$, COOH, CN, —C(=O)—O—C$_{1-6}$alk, —C(=O)—N(C$_{1-4}$alk)C$_{1-4}$alk, and —S—C$_{1-4}$alk.

In another embodiment, Y is NR$^8$.

In another embodiment, Y is NH.

In another embodiment, Y is —C(=O).

In another embodiment, the group:

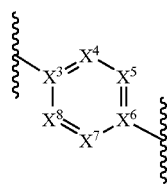

is selected from the group consisting of;

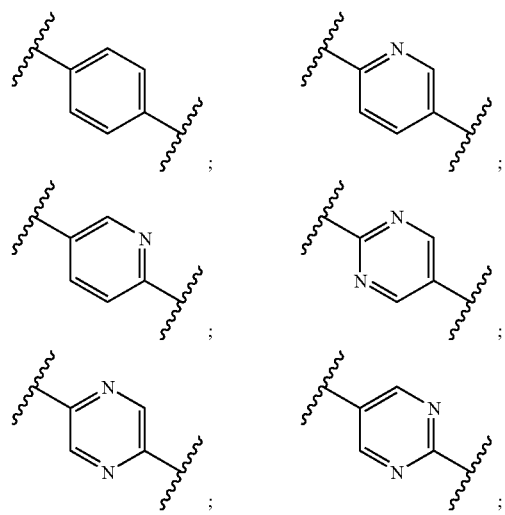

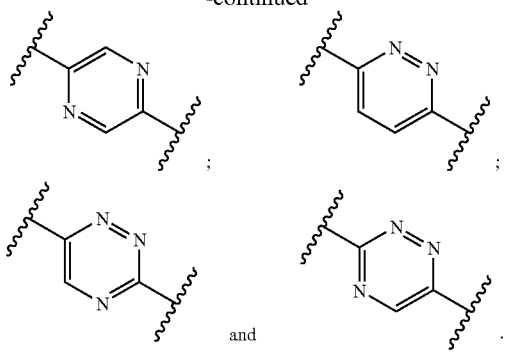

and

In another embodiment, the group

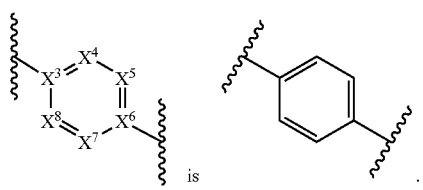

is

In another embodiment, the group

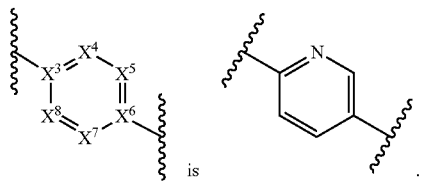

is

In another embodiment, the group is

In another embodiment, the group

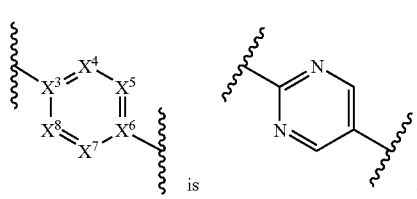

is

In another embodiment, the group

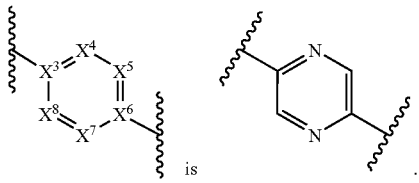 is .

In another embodiment, the group

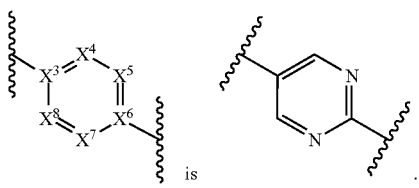 is .

In another embodiment, the group

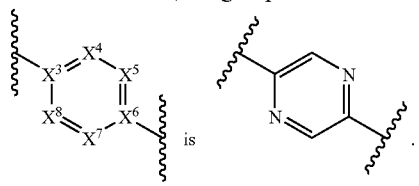 is .

In another embodiment, the group

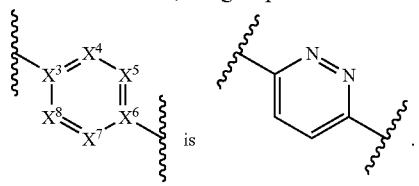 is .

In another embodiment, the group

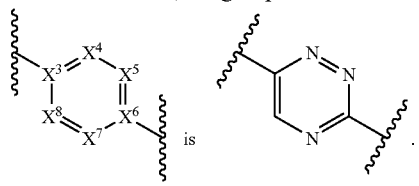 is .

In another embodiment, the group

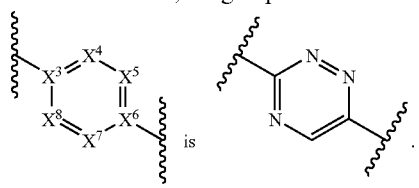 is .

In another embodiment, the group

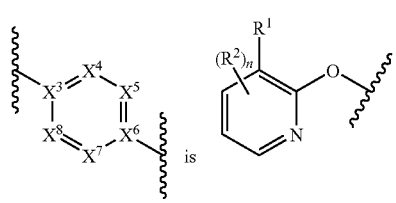 is .

In another embodiment, the group

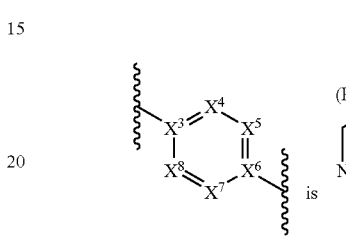 is .

Another aspect of the current invention relates to compounds having the general structure of formula (Ia):

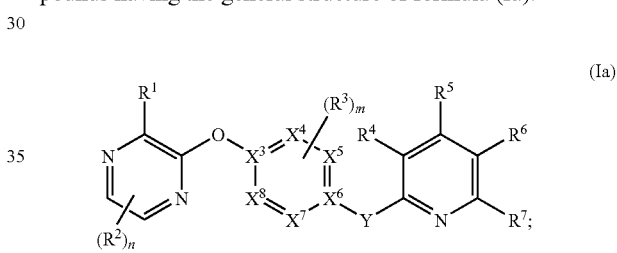

(Ia)

or a pharmaceutically acceptable salt thereof, wherein m, n, $R^1, R^2, R^3, R^4, R^5, R^6, R^7, X^3, X^4, X^5, X^6, X^7, X^8$, and Y are as defined in compounds of formula (I), and any other embodiments below.

Another aspect of the current invention relates to compounds having the general structure of formula (Ib):

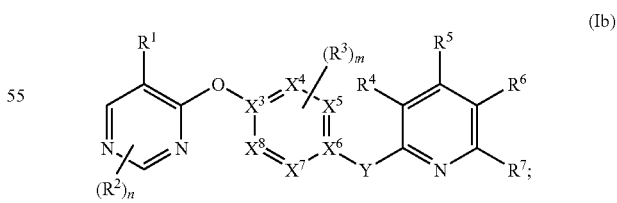

(Ib)

or a pharmaceutically acceptable salt thereof, wherein m, n, $R^1, R^2, R^3, R^4, R^5, R^6, R^7, X^3, X^4, X^5, X^6, X^7, X^8$, and Y are as defined in compounds of formula (I), and any other embodiments below.

Another aspect of the current invention relates to compounds having the general structure of formula (Ic):

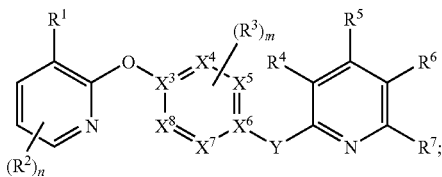
(Ic)

or a pharmaceutically acceptable salt thereof, wherein m, n, $R^1$, $R^2$, $R^3$, $R^4$, $R^5$, $R^6$, $R^7$, $X^3$, $X^4$, $X^5$, $X^6$, $X^7$, $X^8$, and Y are as defined in compounds of formula (I), and any other embodiments below.

Another aspect of the current invention relates to compounds having the general structure of formula (Id):

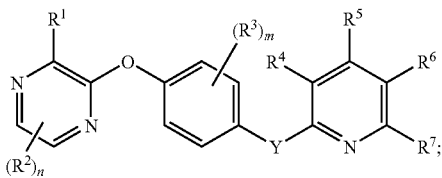
(Id)

or a pharmaceutically acceptable salt thereof, wherein m, n, $R^1$, $R^2$, $R^3$, $R^4$, $R^5$, $R^6$, $R^7$, and Y are as defined in compounds of formula (I), and any other embodiments below.

Another aspect of the current invention relates to compounds having the general structure of formula (Ie):

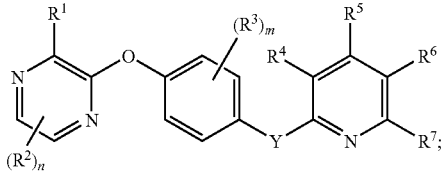
(Ie)

or a pharmaceutically acceptable salt thereof, wherein m, n, $R^1$, $R^2$, $R^3$, $R^4$, $R^5$, $R^6$, $R^7$, and Y are as defined in compounds of formula (I), and any other embodiments below.

Another aspect of the current invention relates to compounds having the general structure of formula (If):

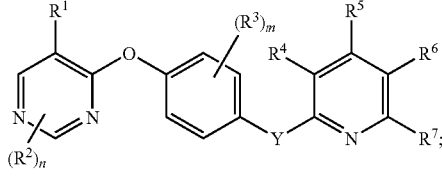
(If)

or a pharmaceutically acceptable salt thereof, wherein m, n, $R^1$, $R^2$, $R^3$, $R^4$, $R^5$, $R^6$, $R^7$, and Y are as defined in compounds of formula (I), and any other embodiments below.

Another aspect of the current invention relates to compounds having the general structure of formula (Ig):

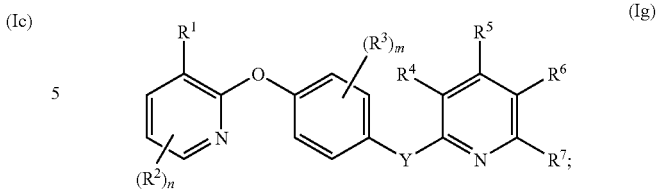
(Ig)

or a pharmaceutically acceptable salt thereof, wherein m, n, $R^1$, $R^2$, $R^3$, $R^4$, $R^5$, $R^6$, $R^7$, and Y are as defined in compounds of formula (I), and any other embodiments below.

In another embodiment, Y is NH; and said Y and $R^3$ form a 5- to 6-membered ring fused to the ring containing both said Y and $R^3$.

In another embodiment, each of $X^1$ and $X^2$ is CH, and each of $X^4$, $X^5$, $X^7$, and $X^8$ is CH.

In another embodiment, $X^1$ is CH and $X^2$ is N, and each of $X^4$, $X^5$, $X^7$, and $X^8$ is CH.

In another embodiment, $X^1$ is N and $X^2$ is CH, and each of $X^4$, $X^5$, $X^7$, and $X^8$ is CH.

In another embodiment, $R^1$ is selected from H, F, Cl, Br, I, $C_{1-8}$alk, $C_{1-4}$haloalk, —$OR^a$, —$NR^aR^a$, —$NR^aR^c$, —$N(R^a)$ $C(=O)R^b$, —$C(=O)NR^aR^a$, —$C(=O)NR^aR^c$, —$C(=O)$ $NR^aR^d$, —$C(=O)R^a$, —$C(=O)R^c$, —$C(=O)R^d$, —$C(=O)$—$O$—$R^a$, —$C(=O)$—$O$—$R^c$, —$C(=O)$—$O$— $R^d$, —$OR^c$, —$NR^aR^c$, —$SR^c$, —$S(=O)R^c$, —$S(=O)_2R^c$, —$N(R^c)S(=O)_2R^b$, —$S(=O)_2NR^aR^c$, —$N(R^c)C(=O)R^b$, —$N(R^a)C(=O)R^c$, and —$C(=O)NR^aR^c$.

In another embodiment, $R^1$ is selected from —$C(=O)$ $NR^aR^a$, —$C(=O)NR^aR^c$, —$C(=O)NR^aR^d$, —$C(=O)R^c$, —$C(=O)R^d$, —$NR^aR^a$, and —$NR^aR^c$.

In another embodiment, $R^1$ is Ring A, wherein said ring A is $R^b$ selected from the group consisting of phenyl, benzyl and $C_{1-6}$alk, wherein said phenyl, benzyl, or $C_{1-6}$alk is independently substituted by 0, 1, 2 or 3 substituents selected from halo, OH, $C_{1-4}$alk, $C_{1-3}$haloalk, —$OC_{1-4}$alk, —$NH_2$, —$NHC_{1-4}$alk, —$N(C_{1-4}$alk$)C_{1-4}$alk, $C_{1-4}$alk-$NH_2$, COOH, CN, —$C(=O)$—$O$—$C_{1-6}$alk, —$C(=O)$—$N(C_{1-4}$alk$)C_{1-4}$ alk, and —$S$—$C_{1-4}$alk.

In another embodiment, $R^1$ is Ring A, wherein said ring A is $R^c$, which is $C_{0-4}$alk-linked saturated 3-, 4-, 5-, 6-, or 7-membered monocyclic or 8-, 9-, 10-, 11-, or 12-membered bicyclic ring containing 0, 1, 2 or 3 N atoms and 0, 1, or 2 atoms selected from O and S, which is substituted by 0, 1, 2 or 3 groups selected from F, Cl, Br, $R^e$, $C_{1-6}$alk, $C_{1-4}$haloalk, —$OR^a$, —$OC_{1-4}$haloalk, CN, —$C(=O)R^b$, —$C(=O)R^c$, —$C(=O)OR^a$, —$C(=O)NR^aR^a$, —$C(=NR^a)NR^aR^a$, —$OC(=O)R^b$, —$OC(=O)NR^aR^a$, —$OC_{2-6}$alkNR$^aR^a$, —$OC_{2-6}$alk$(OR^a)_{1-3}$, such as —$OC_{1-4}$alk$(OH)_{1-3}$, —$SR^a$, —$S(=O)R^b$, —$S(=O)_2R^b$, —$S(=O)(OH)R^b$, —$S(=O)_2$ $NR^aR^a$, —$NR^aR^a$, —$NR^aR^e$, —$NR^aR^d$, —$N(R^a)C(=O)R^b$, —$N(R^a)C(=O)OR^b$, —$N(R^a)C(=O)NR^aR^a$, —$N(R^a)C$ $(=NR^a)NR^aR^a$, —$N(R^a)S(=O)_2R^b$, —$N(R^a)S(=O)_2$ $NR^aR^a$, —$NR^aC_{2-6}$alkNR$^aR^a$, —$NR^aC_{2-6}$alkOR$^a$, —$C_{1-6}$ alkNR$^aR^a$, —$C_{1-6}$alk$(OR^a)_{1-3}$, such as —$C_{1-4}$alk$(OH)_{1-3}$, —$C_{1-6}$alkN$(R^a)C(=O)R^b$, —$C_{1-6}$alkOC$(=O)R^b$, —$C_{1-6}$ alkC$(=O)NR^aR^a$, —$C_{1-6}$alkC$(=O)OR^a$ and oxo.

In another embodiment, $R^1$ is Ring A, wherein said ring A is $R^c$, which is $C_{0-4}$alk-linked partially-saturated 4-, 5-, 6-, or 7-membered monocyclic or 8-, 9-, 10-membered bicyclic ring containing 0, 1, 2 or 3 N atoms and 0, 1, or 2 atoms selected from O and S, which is substituted by 0, 1, or 2 groups selected from F, Cl, Br, $R^e$, $C_{1-6}$alk, $C_{1-4}$haloalk, —$OR^a$, —$OC_{1-4}$haloalk, CN, —$C(=O)R^b$, —$C(=O)R^e$, —$C(=O)OR^a$, —$C(=O)NR^aR^a$, —$C(=NRa)NR^aR^a$, —OC(=O)R$^b$, —OC(=O)NR$^a$R$^a$, —OC$_{2-6}$alkNR$^a$R$^a$, —OC$_{2-6}$alk(OR$^a$)$_{1-3}$, such as —OC$_{1-4}$alk(OH)$_{1-3}$, —SR$^a$, —S(=O)R$^b$, —S(=O)$_2$R$^b$, —S(=O)(OH)R$^b$, —S(=O)$_2$NR$^a$R$^a$, —NR$^a$R$^a$, —NR$^a$R$^e$, —NR$^a$R$^d$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkNR$^a$R$^a$, —NR$^a$C$_{2-6}$alkOR$^a$, —C$_{1-6}$alkNR$^a$R$^a$, —C$_{1-6}$alk(OR$^a$)$_{1-3}$, such as —C$_{1-4}$alk(OH)$_{1-3}$, —C$_{1-6}$alkN(R$^a$)C(=O)R$^b$, —C$_{1-6}$alkOC(=O)R$^b$, —C$_{1-6}$alkC(=O)NR$^a$R$^a$, —C$_{1-6}$alkC(=O)OR$^a$ and oxo; with the proviso that when Y is —NR$^8$, R$^1$ is not

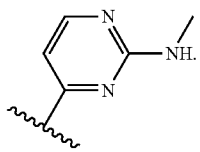 [SMILES: *c1ccnc(NC)n1]

In another embodiment, R$^1$ is Ring A, wherein said ring A is R$^c$ which is C$_{0-4}$alk-linked unsaturated 4-, 5-, or 6-membered monocyclic or 8-, 9-, 10-membered bicyclic ring containing 0, 1, 2 or 3 N atoms and 0, 1, or 2 atoms selected from O and S, which is substituted by 0, 1, 2 or 3 groups selected from F, Cl, Br, R$^e$, C$_{1-6}$alk, C$_{1-4}$haloalk, —OR$^a$, —OC$_{1-4}$haloalk, CN, —C(=O)R$^b$, —C(=O)R$^e$, —C(=O)OR$^a$, —C(=O)NR$^a$R$^a$, —C(=NR$^a$)NR$^a$R$^a$, —OC(=O)R$^b$, —OC(=O)NR$^a$R$^a$, —OC$_{2-6}$alkNR$^a$R$^a$, —OC$_{2-6}$alk(OR$^a$)$_{1-3}$, such as —OC$_{1-4}$alk(OH)$_{1-3}$, —SR$^a$, —S(=O)R$^b$, —S(=O)$_2$R$^b$, —S(=O)(OH)R$^b$, —S(=O)$_2$NR$^a$R$^a$, —NR$^a$R$^a$, —NR$^a$R$^e$, —NR$^a$R$^d$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkNR$^a$R$^a$, —NR$^a$C$_{2-6}$alkOR$^a$, —C$_{1-6}$alkNR$^a$R$^a$, —C$_{1-6}$alk(OR$^a$)$_{1-3}$, such as —C$_{1-4}$alk(OH)$_{1-3}$, —C$_{1-6}$alkN(R$^a$)C(=O)R$^b$, —C$_{1-6}$alkOC(=O)R$^b$, —C$_{1-6}$alkC(=O)NR$^a$R$^a$, —C$_{1-6}$alkC(=O)OR$^a$ and oxo.

In another embodiment, R$^1$ is Ring A, wherein said ring A is R$^d$ selected from the group consisting of nitrogen-linked saturated, partially-saturated, or unsaturated 4-, 5-, 6- or 7-membered ring heterocycle containing the linking nitrogen and 0, 1 or 2 additional nitrogen atoms and containing 0 or 1 sulfur or oxygen atoms, the heterocycle being substituted by 0, 1, 2 or 3 substituents selected from oxo, halo, OH, CN, C$_{1-4}$alk, C$_{1-3}$haloalk, —OC$_{1-4}$alk, R$^e$, —OR$^e$, —NH$_2$, —NHC$_{1-4}$alk, —N(C$_{1-4}$alk)C$_{1-4}$alk, C(=O)OR$^a$, —C$_{1-6}$alk(OR$^a$)$_{1-3}$, such as —C$_{1-4}$alk(OH)$_{1-3}$, —NH—C(=O)OC$_{1-4}$alk, C(=O)R$^a$, C(=O)R$^e$, C(=O)NR$^a$R$^a$, and C(=O)NR$^a$R$^a$.

In another embodiment, R$^1$ is selected from the group consisting of: Cl, Br, I, COOH,

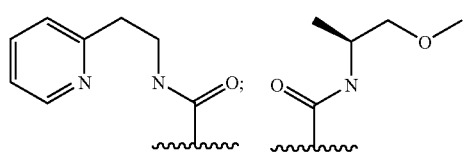

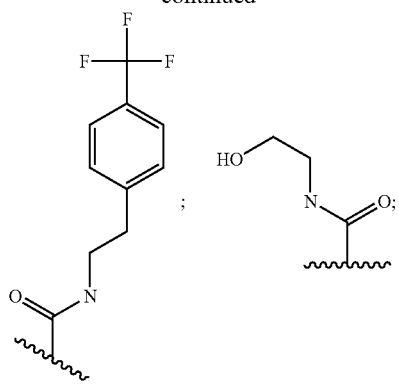

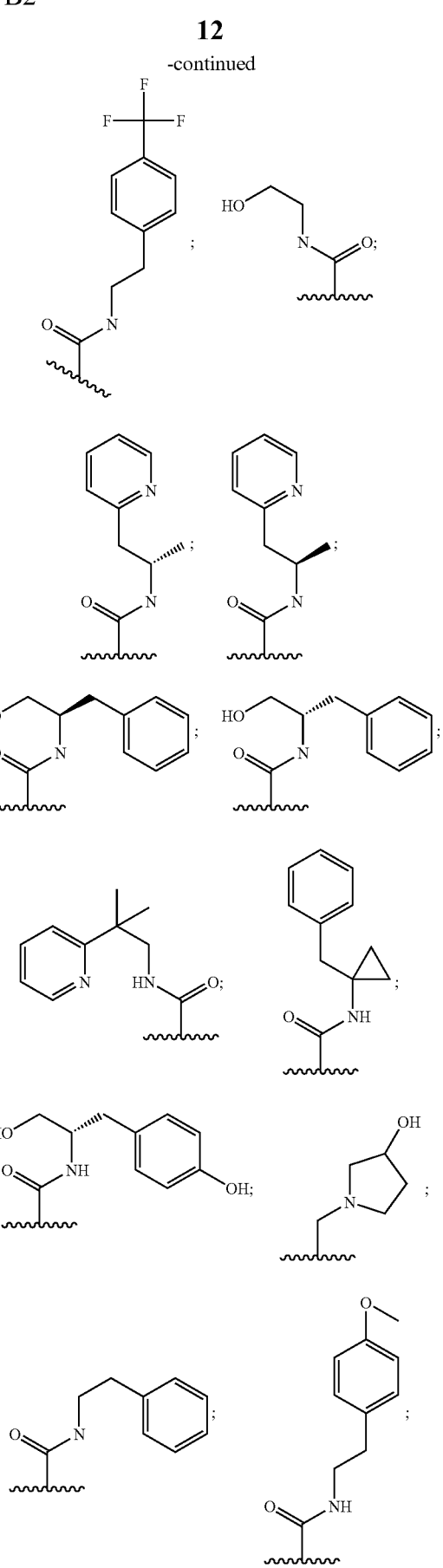

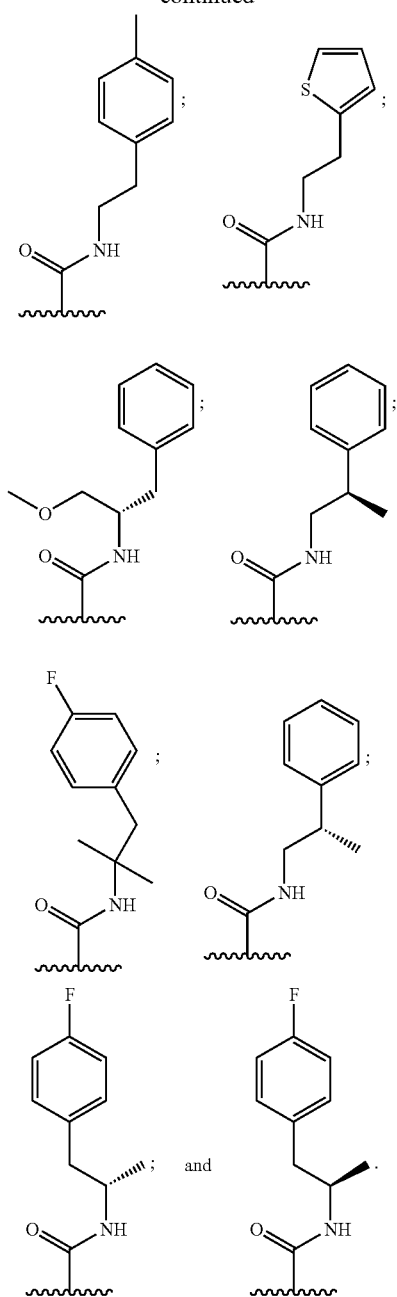
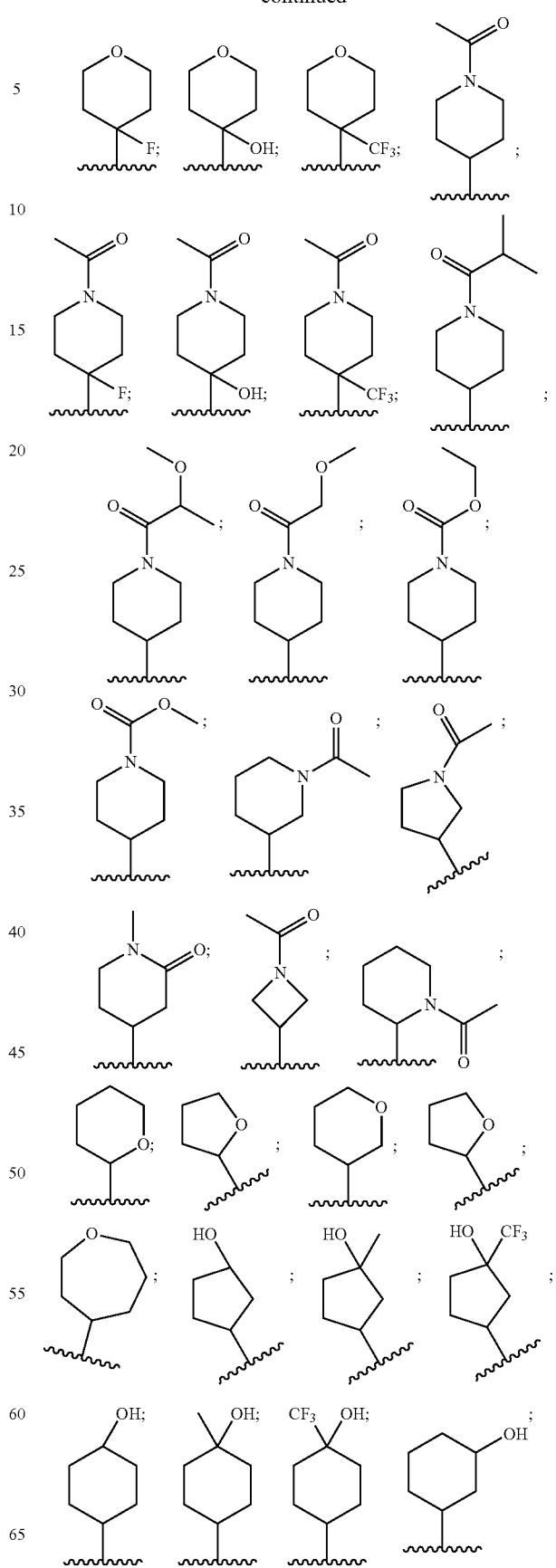
In another embodiment, $R^1$ is Ring A, wherein said ring A is selected from the group consisting of:

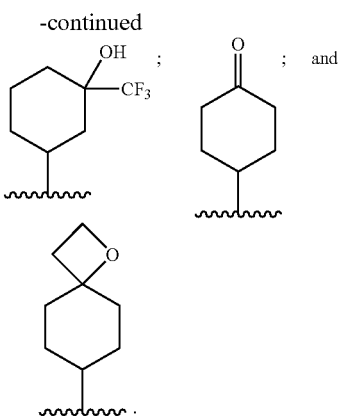

In another embodiment, $R^1$ is Ring A, wherein said ring A is unsubstituted pyrimidyl, methoxy pyrimidinyl, or aminopyrimidyl.

In another embodiment, $R^1$ is Ring A, wherein said ring A is $R^c$ selected from the group consisting of cyclopropyl, cyclopentyl, cyclopentenyl, cyclohexyl, cyclohexenyl, cycloheptyl, dihydropyranyl, pyridyl, morpholinyl, piperidinyl, tetrahydropyranyl, tetrahydrofuranyl, phenyl, benzyl, quinolinyl, isoquinolinyl, dihydrofuranyl, tetrahydropyridinyl, pyrazolyl, pyrolidinyl, imidazolyl, benzamidazolyl, benzo[d][1,3]dioxolyl, azetidinyl, oxepanyl, oxazepanyl, naphthyl, benzothiophenyl, thiophenyl, piperazinyl, tetrahydrothiopyranyl, and oxaspiro[3.5]nonyl, azepanyl, all of which are substituted by 0, 1, 2 or 3 groups selected from F, Cl, Br, $R^e$, —$CH_3$, $C_{1-4}$haloalk, —OH, —$OCH_3$, —$OCH_2CH_3$, CN, —C(=O)—$CH_3$, —C(=O)$OR^a$, —$SR^a$, —$NR^aR^a$, —$NR^aR^e$, —$NR^aR^d$, —$C_{1-6}$alk$(OR^a)_{1-3}$, such as —$C_{1-4}$alk$(OH)_{1-3}$, and oxo.

In another embodiment, $R^1$ is Ring A, wherein said ring A is $R^c$ selected from the group consisting of cyclopropyl, cyclopentyl, cyclopentenyl, cyclohexyl, cyclohexenyl, cycloheptyl, dihydropyranyl, 3-pyridyl, 2-pyridyl, morpholinyl, piperidinyl, tetrahydropyranyl, tetrahydrofuranyl, phenyl, benzyl, 5-quinolinyl, isoquinolinyl, dihydrofuranyl, tetrahydropyridinyl, pyrrolidinyl, benzo[d][1,3]dioxolyl, azetidinyl, oxepanyl, oxazepanyl, naphthyl, benzothiophenyl, piperazinyl, tetrahydrothiopyranyl, oxaspiro[3.5]nonyl, and azepanyl, all of which are substituted by 0, 1, 2 or 3 groups selected from F, Cl, Br, $R^e$, —$CH_3$, $C_{1-4}$haloalk, —OH, —$OCH_3$, —$OCH_2CH_3$, CN, —C(=O)—$CH_3$, —C(=O)$OR^a$, —$SR^a$, —$NR^aR^a$, —$NR^aR^e$, —$NR^aR^d$, —$C_{1-6}$alk$(OR^a)_{1-3}$, such as —$C_{1-4}$alk$(OH)_{1-3}$, and oxo.

In another embodiment, $R^1$ is Ring A, wherein said ring A is $R^d$ selected from the group consisting of nitrogen-linked piperidinyl, morpholinyl, pyrrolidinyl, piperazinyl, and diazepanyl, all of which are substituted by 0, 1, 2 or 3 groups selected from F, Cl, Br, $R^e$, —$CH_3$, $C_{1-4}$haloalk, —OH, —$OCH_3$, —$OCH_2CH_3$, CN, —C(=O)—$CH_3$, —C(=O)$OR^a$, —$SR^a$, —$NR^aR^a$, —$NR^aR^e$, —$NR^aR^d$, —$C_{1-6}$alk$(OR^a)_{1-3}$, such as —$C_{1-4}$alk$(OH)_{1-3}$, and oxo.

In another embodiment, $R^4$ is H, F, Br, methyl, or ethyl.

In another embodiment, $R^5$ is H.

In another embodiment, $R^6$ is H, F, Cl, Br, methyl, ethyl, $C_{1-2}$haloalk, CN, or —O—$C_{1-4}$haloalk.

In another embodiment, $R^7$ is H or —O—$C_{1-4}$haloalk.

In another embodiment, $R^8$ is H.

In another embodiment, $R^a$ is independently, at each instance, H, phenyl, benzyl or $C_{1-6}$alk, wherein said phenyl, benzyl and $C_{1-6}$alk is independently substituted by 0, 1, 2 or 3 substituents selected from halo, OH, $C_{1-4}$alk, $C_{1-3}$haloalk, —$OC_{1-4}$alk, —$NH_2$, —$NHC_{1-4}$alk, —N($C_{1-4}$alk)$C_{1-4}$alk, $C_{1-4}$alk-$NH_2$, COOH, CN, —C(=O)—O—$C_{1-6}$alk, —C(=O)—N($C_{1-4}$alk)$C_{1-4}$alk, and —S—$C_{1-4}$alk.

In another embodiment, $R^c$ is a $C_{0-4}$alk-linked saturated, partially-saturated or unsaturated 3-, 4-, 5-, 6-, or 7-membered monocyclic or 8-, 9-, 10-membered bicyclic ring containing 0, 1, 2 or 3 N atoms and 0, 1, or 2 atoms selected from O and S, which is substituted by 0, 1 or 2 groups selected from F, Cl, Br, $R^e$, $C_{1-6}$alk, $C_{1-4}$haloalk, —$OR^a$, CN, —C(=O)$R^b$, —C(=O)$R^e$, —C(=O)$OR^a$, —S(=O)$_2R^b$, —S(=O)(OH)$R^b$, —$NR^aR^a$, —$NR^aR^e$, —$NR^aR^d$, —$C_{1-6}$alk$(OR^a)_{1-3}$, such as —$C_{1-4}$alk$(OH)_{1-3}$, and oxo.

In another embodiment, $R^d$ is a nitrogen-linked saturated or partially-saturated 4-, 5-, 6- or 7-membered ring heterocycle containing the linking nitrogen and 0 additional nitrogen atoms and containing 0 or 1 sulfur or oxygen atoms, the heterocycle being substituted by 0, 1 or 2 substituents selected from oxo, halo, OH, CN, $C_{1-4}$alk, $C_{1-3}$haloalk, —$OC_{1-4}$alk, $R^e$, —$OR^e$, C(=O)$OR^a$, —$C_{1-6}$alk$(OR^a)_{1-3}$, such as —$C_{1-4}$alk$(OH)_{1-3}$, —NH—C(=O)$OC_{1-4}$alk, C(=O)$R^a$, C(=O)$R^e$, C(=O)$NR^aR^a$, and C(=O)$NR^aR^a$.

In another embodiment, $R^e$ is selected from the group consisting of $C_{0-4}$alk-linked oxadiazolyl, $C_{0-4}$alk-linked pyridyl, $C_{0-4}$alk-linked phenyl, and $C_{0-4}$alk-linked piperidinyl, which is substituted by 0, 1 or 2 groups selected from oxo, halo, OH, $C_{1-4}$alk, $C_{1-3}$haloalk, —$OC_{1-4}$alk, —$NH_2$, —$NHC_{1-4}$alk, —N($C_{1-4}$alk)$C_{1-4}$alk, $C_{1-4}$alk-$NH_2$, COOH, CN, —C(=O)—O—$C_{1-6}$alk, —C(=O)—N($C_{1-4}$alk)$C_{1-4}$alk, and —S—$C_{1-4}$alk.

In another embodiment, m is 0 and n is 0.

In another embodiment, m is 0 and n is 1.

In another embodiment, $R^2$ is $OC_{1-4}$alk.

In another embodiment, $R^4$ is selected from H, F, Br, —O—$C_{1-4}$alk, methyl, ethyl, and $CF_3$.

In another embodiment, $R^5$ is selected from H, F, Cl, Br, CN, methyl, ethyl, and $CF_3$.

In another embodiment, $R^6$ is selected from H, F, Cl, Br, methyl, ethyl, and $CF_3$.

In another embodiment, $R^7$ is selected from H, F, methyl, ethyl, and $CF_3$.

Another aspect of the invention relates to a method of treating conditions that may be treated with PDE10 inhibitors comprising the step of administering a compound of formula (I).

Another aspect of the invention relates to a method wherein said condition that may be treated with PDE10 inhibitors is selected from the group consisting of psychoses, Parkinson's disease, dementias, obsessive compulsive disorder, tardive dyskinesia, choreas, depression, mood disorders, impulsivity, drug addiction, attention deficit/hyperactivity disorder (ADHD), depression with parkinsonian states, personality changes with caudate or putamen disease, dementia and mania with caudate and pallidal diseases, and compulsions with pallidal disease.

Another aspect of the invention relates to a method wherein said condition that may be treated with PDE10 inhibitors is selected from the group consisting of schizophrenia, bipolar disorder, and obsessive-compulsive disorder.

Another aspect of the invention relates to a pharmaceutical composition comprising a compound of formula (I) and a pharmaceutically-acceptable diluent or carrier.

Another aspect of the current invention relates to compounds having the general structure of formula (II):

(II)

or any pharmaceutically-acceptable salt thereof, wherein:
$X^1$ is N or CH;
$X^2$ is N or CH; wherein 1 or 2 of $X^1$ and $X^2$ is CH;
m is independently in each instance 0, 1, 2, 3 or 4;
n is independently in each instance 0, 1, 2 or 3;
y is 0, 1, 2, 3 or 4;
Ring A is a carbon-linked-saturated or carbon-linked-partially-unsaturated 4-, 5-, 6-, 7-, 8-, 9-, 10-, 11-, or 12-membered carbocyclic ring containing 0, 1 or 2 N atoms and containing 0 or 1 S or O atom; or a nitrogen-linked-saturated, nitrogen-linked-partially-saturated, or nitrogen-linked-unsaturated 4-, 5-, 6-, 7-, 8-, 9-, 10-, 11-, or 12-membered ring heterocycle containing the linking nitrogen and 0, 1 or 2 additional N atoms and containing 0 or 1 S or O atom;
$R^2$ is, independently in each instance, F, Cl, Br, CN, OH, $OC_{1-4}$alk, $C_{1-4}$alk or $C_{1-4}$haloalk;
$R^3$ is, independently in each instance, F, Br, CN, OH, $OC_{1-4}$alk, $C_{1-4}$alk or $C_{1-4}$haloalk;
$R^4$ is selected from H, F, Br, CN, —O—$C_{1-4}$alk, $C_{1-2}$alk, and $C_{1-2}$haloalk;
$R^5$ is selected from H, F, Cl, Br, CN, —O—$C_{1-4}$alk, $C_{1-2}$alk, and $C_{1-2}$haloalk;
$R^6$ is selected from H, F, Cl, Br, CN, —O—$C_{1-4}$alk, $C_{1-2}$alk, and $C_{1-2}$haloalk;
$R^7$ is selected from H, F, Cl, Br, CN, —O—$C_{1-4}$alk, $C_{1-2}$alk, and $C_{1-2}$haloalk;
$R^8$ is selected from H, $C_{1-8}$alk, and $C_{1-4}$haloalk;
$R^9$ is independently selected from the group consisting of H, F, Cl, Br, $C_{1-6}$alk, $C_{1-4}$haloalk, —$OR^a$, —$OC_{1-4}$haloalk, CN, —$C(=O)R^b$, —$C(=O)OR^a$, —$C(=O)NR^aR^a$, —$C(=NR^a)NR^aR^a$, —$OC(=O)R^b$, —$OC(=O)NR^aR^a$, —$OC_{2-6}$alkNR^aR^a$, —$OC_{2-6}$alkOR^a$, —$SR^a$, —$S(=O)R^b$, —$S(=O)_2R^b$, —$S(=O)_2NR^aR^a$, —$NR^aR^a$, —$NR^aR^e$, —$N(R^a)C(=O)R^b$, —$N(R^a)C(=O)OR^b$, —$N(R^a)C(=O)NR^aR^a$, —$N(R^a)C(=NR^a)NR^aR^a$, —$N(R^a)S(=O)_2R^b$, —$N(R^a)S(=O)_2NR^aR^a$, —$NR^aC_{2-6}$alkNR^aR^a$, —$NR^aC_{2-6}$alkOR^a$, —$C_{1-6}$alkNR^aR^a$, —$C_{1-6}$alkOR^a$, —$C_{1-6}$alkN(R^a)C(=O)R^b$, —$C_{1-6}$alkOC(=O)R^b$, —$C_{1-6}$alkC(=O)NR^aR^a$, —$C_{1-6}$alkC(=O)OR^a$, $R^e$ and oxo;
$R^a$ is independently, at each instance, H or $R^b$;
$R^b$ is independently, at each instance, phenyl, benzyl, or $C_{1-6}$alk, wherein said phenyl, benzyl, and $C_{1-6}$alk is independently substituted by 0, 1, 2 or 3 substituents selected from halo, OH, $C_{1-4}$alk, $C_{1-3}$haloalk, —$OC_{1-4}$alk, —$NH_2$, —$NHC_{1-4}$alk, —$N(C_{1-4}$alk$)C_{1-4}$alk, $C_{1-4}$alk-$NH_2$, COOH, CN, —$C(=O)$—O—$C_{1-6}$alk, —$C(=O)$—$N(C_{1-4}$alk$)C_{1-4}$alk, and —S—$C_{1-4}$alk;
$R^c$ is a $C_{0-4}$-alk-linked saturated, partially-saturated or unsaturated 3-, 4-, 5-, 6-, or 7-membered monocyclic or 8-, 9-, 10-, 11-, or 12-membered bicyclic ring containing 0, 1, 2 or 3 N atoms and 0, 1, or 2 atoms selected from O and S, which is substituted by 0, 1, 2 or 3 groups selected from F, Cl, Br, $R^e$, $C_{1-6}$alk, $C_{1-4}$haloalk, —$OR^a$, —$OC_{1-4}$haloalk, CN, —$C(=O)R^b$, —$C(=O)R^e$, —$C(=O)OR^a$, —$C(=O)NR^aR^a$, —$C(=NR^a)NR^aR^a$, —$OC(=O)R^b$, —$OC(=O)$ $NR^aR^a$, —$OC_{2-6}$alkNR^aR^a$, —$OC_{2-6}$alk(OR^a)_{1-3}$, such as —$OC_{1-4}$alk(OH)_{1-3}$, —$SR^a$, —$S(=O)R^b$, —$S(=O)_2R^b$, —$S(=O)(OH)R^b$, —$S(=O)_2NR^aR^a$, —$NR^aR^a$, —$NR^aR^e$, —$NR^an^d$, —$N(R^a)C(=O)R^b$, —$N(R^a)C(=O)OR^b$, —$N(R^a)C(=O)NR^aR^a$, —$N(R^a)C(=NR^a)NR^aR^a$, —$N(R^a)S(=O)_2R^b$, —$N(R^a)S(=O)_2NR^aR^a$, —$NR^aC_{2-6}$alkNR^aR^a$, —$NR^aC_{2-6}$alkOR^a$, —$C_{1-6}$alkNR^aR^a$, —$C_{1-6}$alk(OR^a)_{1-3}$, such as —$C_{1-4}$alk(OH)_{1-3}$, —$C_{1-6}$alkN(R^a)C(=O)R^b$, —$C_{1-6}$alkOC(=O)R^b$, —$C_{1-6}$alkC(=O)NR^aR^a$, —$C_{1-6}$alkC(=O)OR^a$ and oxo;

$R^d$ is a nitrogen-linked saturated, partially-saturated or unsaturated 4-, 5-, 6- or 7-membered ring heterocycle containing the linking nitrogen and 0, 1 or 2 additional nitrogen atoms and containing 0 or 1 sulfur or oxygen atoms, the heterocycle being substituted by 0, 1, 2 or 3 substituents selected from oxo, halo, OH, CN, $C_{1-4}$alk, $C_{1-3}$haloalk, —$OC_{1-4}$alk, $R^e$, —$ORe$, —$NH_2$, —$NHC_{1-4}$alk, —$N(C_{1-4}$alk$)C_{1-4}$alk, $C(=O)OR^a$, —$C_{1-6}$alk(OR^a)_{1-3}$, such as —$C_{1-4}$alk(OH)_{1-3}$, —$NH$—$C(=O)OC_{1-4}$alk, $C(=O)R^a$, $C(=O)R^e$, $C(=O)NR^aR^a$, and $C(=O)NR^aR^a$; and $R^e$ is:
(a) $C_{0-4}$-alk-linked saturated, partially-saturated or unsaturated 3-, 4-, 5-, 6-, or 7-membered monocyclic containing 0, 1, 2 or 3 N atoms and 0, 1, or 2 atoms selected from 0 and S; which is substituted by 0, 1, 2 or 3 groups selected from oxo, halo, OH, $C_{1-4}$alk, $C_{1-3}$haloalk, —$OC_{1-4}$alk, —$NH_2$, —$NHC_{1-4}$alk, —$N(C_{1-4}$alk$)C_{1-4}$alk, $C_{1-4}$alk-$NH_2$, COOH, CN, —$C(=O)$—O—$C_{1-6}$alk, —$C(=O)$—$N(C_{1-4}$alk$)C_{1-4}$alk, and —S—$C_{1-4}$alk; or (b) nitrogen-linked saturated, partially-saturated or unsaturated 4-, 5-, 6- or 7-membered ring heterocycle containing the linking nitrogen and 0, 1 or 2 additional nitrogen atoms and containing 0 or 1 sulfur or oxygen atoms; which is substituted by 0, 1, 2 or 3 groups selected from oxo, halo, OH, $C_{1-4}$alk, $C_{1-3}$haloalk, —$OC_{1-4}$alk, —$NH_2$, —$NHC_{1-4}$alk, —$N(C_{1-4}$alk$)C_{1-4}$alk, $C_{1-4}$alk-$NH_2$, COOH, CN, —$C(=O)$—O—$C_{1-6}$alk, —$C(=O)$—$N(C_{1-4}$alk$)C_{1-4}$alk, and —S—$C_{1-4}$alk.

Another aspect of the current invention relates to compounds having the general structure of formula (II) selected from the group consisting of (IIa), (IIb), and (IIc):

(IIa)

(IIb)

-continued

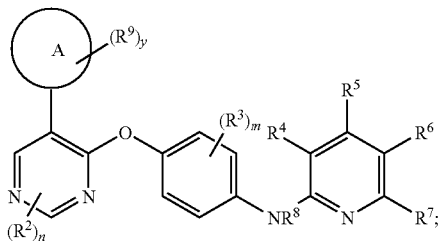

(IIc)

or a pharmaceutically acceptable salt thereof, wherein m, n, y, $R^2$, $R^3$, $R^4$, $R^5$, $R^6$, $R^7$, $R^8$, and $R^9$ are as defined in compounds of formula (II), and any other embodiments below.

In one embodiment of compounds of formula (IIa), (IIb), or (IIc), ring A is bonded to the 3-pyridinyl ring via a carbon atom having an sp3 hybridization.

In one embodiment of compounds of formula (IIa), (IIb), or (IIc), ring A is bonded to the 3-pyridinyl ring via a carbon atom having an sp2 hybridization.

In one embodiment of compounds of formula (IIb), ring A is bonded to the 3-pyridinyl ring via a carbon atom having an sp hybridization.

In one embodiment of compounds of formula (IIa), (IIb), or (IIc), ring A is bonded to the 3-pyridinyl ring via a nitrogen atom having an sp3 hybridization.

In one embodiment of compounds of formula (IIa), (IIb), or (IIc), ring A is bonded to the 3-pyridinyl ring via a nitrogen atom having an sp2 hybridization.

In another embodiment of compounds of formula (IIa), (IIb), or (IIc), ring A is a 5-membered ring saturated heterocycle, which is optionally substituted with —C(=O)$R^b$, —C(=O)O$R^a$, —C(=O)NR$^a$R$^a$, —C(=NR$^a$)NR$^a$R$^a$, —OC(=O)$R^b$, —OC(=O)NR$^a$R$^a$, —N(R$^a$)C(=O)$R^b$, —N(R$^a$)C(=O)O$R^b$, —N(R$^a$)C(=O)NR$^a$R$^a$, —C$_{1-6}$alkN(R$^a$)C(=O)$R^b$, —C$_{1-6}$alkOC(=O)$R^b$, —C$_{1-6}$alkC(=O)NR$^a$R$^a$, —C$_{1-6}$alkC(=O)O$R^a$, or oxo.

In another embodiment of compounds of formula (IIa), (IIb), or (IIc), ring A is a 6-membered ring saturated heterocycle, which is optionally substituted with —C(=O)$R^b$, —C(=O)O$R^a$, —C(=O)NR$^a$R$^a$, —C(=NR$^a$)NR$^a$R$^a$, —OC(=O)$R^b$, —OC(=O)NR$^a$R$^a$, —N(R$^a$)C(=O)$R^b$, —N(R$^a$)C(=O)O$R^b$, —N(R$^a$)C(=O)NR$^a$R$^a$, —C$_{1-6}$alkN(R$^a$)C(=O)$R^b$, —C$_{1-6}$alkOC(=O)$R^b$, —C$_{1-6}$alkC(=O)NR$^a$R$^a$, —C$_{1-6}$alkC(=O)O$R^a$, or oxo.

In another embodiment of compounds of formula (IIa), (IIb), or (IIc), ring A is a 4-membered ring unsaturated carbocycle, which is optionally substituted with —C(=O)$R^b$, —C(=O)O$R^a$, —C(=O)NR$^a$R$^a$, —C(=NR$^a$)NR$^a$R$^a$, —OC(=O)$R^b$, —OC(=O)NR$^a$R$^a$, —N(R$^a$)C(=O)$R^b$, —N(R$^a$)C(=O)O$R^b$, —N(R$^a$)C(=O)NR$^a$R$^a$, —C$_{1-6}$alkN(R$^a$)C(=O)$R^b$, —C$_{1-6}$alkOC(=O)$R^b$, —C$_{1-6}$alkC(=O)NR$^a$R$^a$, —C$_{1-6}$alkC(=O)O$R^a$, or oxo.

In another embodiment of compounds of formula (IIa), (IIb), or (IIc), ring A is a 5-membered ring saturated carbocycle, which is optionally substituted with —C(=O)$R^b$, —C(=O)O$R^a$, —C(=O)NR$^a$R$^a$, —C(=NR$^a$)NR$^a$R$^a$, —OC(=O)$R^b$, —OC(=O)NR$^a$R$^a$, —N(R$^a$)C(=O)$R^b$, —N(R$^a$)C(=O)O$R^b$, —N(R$^a$)C(=O)NR$^a$R$^a$, —C$_{1-6}$alkN(R$^a$)C(=O)$R^b$, —C$_{1-6}$alkOC(=O)$R^b$, —C$_{1-6}$alkC(=O)NR$^a$R$^a$, —C$_{1-6}$alkC(=O)O$R^a$, or oxo.

In another embodiment of compounds of formula (IIa), (IIb), or (IIc), ring A is a 6-membered ring saturated carbocycle, which is optionally substituted with —C(=O)$R^b$, —C(=O)O$R^a$, —C(=O)NR$^a$R$^a$, —C(=NR$^a$)NR$^a$R$^a$, —OC(=O)$R^b$, —OC(=O)NR$^a$R$^a$, —N(R$^a$)C(=O)$R^b$, —N(R$^a$)C(=O)O$R^b$, —N(R$^a$)C(=O)NR$^a$R$^a$, —C$_{1-6}$alkN(R$^a$)C(=O)$R^b$, —C$_{1-6}$alkOC(=O)$R^b$, —C$_{1-6}$alkC(=O)NR$^a$R$^a$, —C$_{1-6}$alkC(=O)O$R^a$, or oxo.

In another embodiment of compounds of formula (IIa), (IIb), or (IIc), ring A is a 7-membered ring saturated carbocycle, which is optionally substituted with —C(=O)$R^b$, —C(=O)O$R^a$, —C(=O)NR$^a$R$^a$, —C(=NR$^a$)NR$^a$R$^a$, —OC(=O)$R^b$, —OC(=O)NR$^a$R$^a$, —N(R$^a$)C(=O)$R^b$, —N(R$^a$)C(=O)O$R^b$, —N(R$^a$)C(=O)NR$^a$R$^a$, —C$_{1-6}$alkN(R$^a$)C(=O)$R^b$, —C$_{1-6}$alkOC(=O)$R^b$, —C$_{1-6}$alkC(=O)NR$^a$R$^a$, —C$_{1-6}$alkC(=O)O$R^a$, or oxo.

Another aspect of the invention relates to a method of treating conditions that may be treated with PDE10 inhibitors comprising the step of administering a compound of formula (II).

Another aspect of the invention relates to a method of treating conditions that may be treated with PDE10 inhibitors comprising the step of administering a compound of formula (II); wherein said condition is selected from the group consisting of psychoses, Parkinson's disease, dementias, obsessive compulsive disorder, tardive dyskinesia, choreas, depression, mood disorders, impulsivity, drug addiction, attention deficit/hyperactivity disorder (ADHD), depression with parkinsonian states, personality changes with caudate or putamen disease, dementia and mania with caudate and pallidal diseases, and compulsions with pallidal disease.

Another aspect of the invention relates to a method of treating conditions that may be treated with PDE10 inhibitors comprising the step of administering a compound of formula (II); wherein said condition is selected from the group consisting of schizophrenia, bipolar disorder, and obsessive-compulsive disorder.

Another aspect of the invention relates to a pharmaceutical composition comprising a compound of formula (II) and a pharmaceutically-acceptable diluent or carrier.

Another aspect of the current invention relates to compounds having the general structure of formula (III):

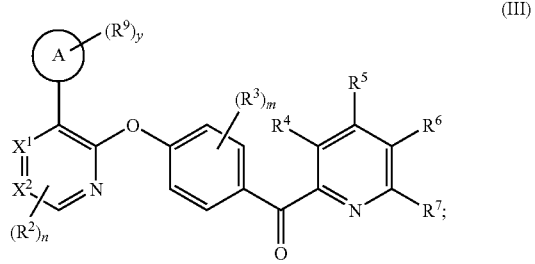

(III)

or any pharmaceutically-acceptable salt thereof, wherein:
$X^1$ is N or CH;
$X^2$ is N or CH; wherein 1 or 2 of $X^1$ and $X^2$ is CH;
m is independently in each instance 0, 1, 2, 3 or 4;
n is independently in each instance 0, 1, 2 or 3;
y is 0, 1, 2, 3 or 4;
Ring A is a carbon-linked-saturated or carbon-linked-partially-unsaturated 4-, 5-, 6-, 7-, 8-, 9-, 10-, 11-, or 12-membered carbocyclic ring containing 0, 1 or 2 N atoms and containing 0 or 1 S or O atom; or a nitrogen-linked-saturated, nitrogen-linked-partially-saturated, or nitrogen-linked-unsaturated 4-, 5-, 6-, 7-, 8-, 9-, 10-, 11-, or 12-membered ring heterocycle containing the linking nitrogen and 0, 1 or 2 additional N atoms and containing 0 or 1 S or O atom;

$R^2$ is, independently in each instance, F, Cl, Br, CN, OH, $OC_{1-4}$alk, $C_{1-4}$alk or $C_{1-4}$haloalk;

$R^3$ is, independently in each instance, F, Br, CN, OH, $OC_{1-4}$alk, $C_{1-4}$alk or $C_{1-4}$haloalk;

$R^4$ is selected from H, F, Br, CN, —O—$C_{1-4}$alk, $C_{1-2}$alk, and $C_{1-2}$haloalk;

$R^5$ is selected from H, F, Cl, Br, CN, —O—$C_{1-4}$alk, $C_{1-2}$alk, and $C_{1-2}$haloalk;

$R^6$ is selected from H, F, Cl, Br, CN, —O—$C_{1-4}$alk, $C_{1-2}$alk, and $C_{1-2}$haloalk;

$R^7$ is selected from H, F, Cl, Br, CN, —O—$C_{1-4}$alk, $C_{1-2}$alk, and $C_{1-2}$haloalk;

$R^9$ is independently selected from the group consisting of H, F, Cl, Br, $C_{1-6}$alk, $C_{1-4}$haloalk, —$OR^a$, —$OC_{1-4}$haloalk, CN, —C(=O)$R^b$, —C(=O)$OR^a$, —C(=O)$NR^aR^a$, —C(=$NR^a$)$NR^aR^a$, —OC(=O)$R^b$, —OC(=O)$NR^aR^a$, —$OC_{2-6}$alk($NR^a$Ra, —$OC_{2-6}$alk$OR^a$, —$SR^a$, —S(=O)$R^b$, —S(=O)$_2R^b$, —S(=O)$_2NR^aR^a$, —$NR^aR^a$, —$NR^aR^e$, —N($R^a$)C(=O)$R^b$, —N($R^a$)C(=O)$OR^b$, —N($R^a$)C(=O)$NR^aR^a$, —N($R^a$)C(=$NR^a$)$NR^aR^a$, —N($R^a$)S(=O)$_2R^b$, —N(Ra)S(=O)$_2NR^aR^a$, —$NR^aC_{2-6}$alk$NR^aR^a$, —$NR^aC_{2-6}$alk$OR^a$, —$C_{1-6}$alk$NR^aR^a$, —$C_{1-6}$alk$OR^a$, —$C_{1-6}$alkN($R^a$)C(=O)$R^b$, —$C_{1-6}$alkOC(=O)$R^b$, —$C_{1-6}$alkC(=O)$NR^aR^a$, —$C_{1-6}$alkC(=O)$OR^a$, $R^e$ and oxo;

$R^a$ is independently, at each instance, H or $R^b$;

$R^b$ is independently, at each instance, phenyl, benzyl, or $C_{1-6}$alk, wherein said phenyl, benzyl, and $C_{1-6}$alk is independently substituted by 0, 1, 2 or 3 substituents selected from halo, OH, $C_{1-4}$alk, $C_{1-3}$haloalk, —$OC_{1-4}$alk, —$NH_2$, —$NHC_{1-4}$alk, —N($C_{1-4}$alk)$C_{1-4}$alk, $C_{1-4}$alk-$NH_2$, COOH, CN, —C(=O)—O—$C_{1-6}$alk, —C(=O)—N($C_{1-4}$alk)$C_{1-4}$alk, and —S—$C_{1-4}$alk;

$R^c$ is a $C_{0-4}$-alk-linked saturated, partially-saturated or unsaturated 3-, 4-, 5-, 6-, or 7-membered monocyclic or 8-, 9-, 10-, 11-, or 12-membered bicyclic ring containing 0, 1, 2 or 3 N atoms and 0, 1, or 2 atoms selected from O and S, which is substituted by 0, 1, 2 or 3 groups selected from F, Cl, Br, $R^e$, $C_{1-6}$alk, $C_{1-4}$haloalk, —$OR^a$, —$OC_{1-4}$haloalk, CN, —C(=O)$R^b$, —C(=O)$R^e$, —C(=O)$OR^a$, —C(=O)$NR^aR^a$, —C(=$NR^a$)$NR^aR^a$, —OC(=O)$R^b$, —OC(=O)$NR^aR^a$, —$OC_{2-6}$alk$NR^aR^a$, —$OC_{2-6}$alk($OR^a$)$_{1-3}$, such as —$OC_{1-4}$alk(OH)$_{1-3}$, —$SR^a$, —S(=O)$R^b$, —S(=O)$_2R^b$, —S(=O)(OH)$R^b$, —S(=O)$_2NR^aR^a$, —$NR^aR^a$, —$NR^aR^e$, —$NR^an^d$, —N($R^a$)C(=O)$R^b$, —N($R^a$)C(=O)$OR^b$, —N($R^a$)C(=O)$NR^aR^a$, —N($R^a$)C(=$NR^a$)$NR^aR^a$, —N($R^a$)S(=O)$_2R^b$, —N($R^a$)S(=O)$_2NR^aR^a$, —$NR^aC_{2-6}$alk$NR^aR^a$, —$NR^aC_{2-6}$alk$OR^a$, —$C_{1-6}$alk$NR^aR^a$, —$C_{1-6}$alk($OR^a$)$_{1-3}$ (such as —$C_{1-4}$alk(OH)$_{1-3}$), —$C_{1-6}$alkN($R^a$)C(=O)$R^b$, —$C_{1-6}$alkOC(=O)$R^b$, —$C_{1-6}$alkC(=O)$NR^aR^a$, —$C_{1-6}$alkC(=O)$OR^a$ and oxo;

$R^d$ is a nitrogen-linked saturated, partially-saturated or unsaturated 4-, 5-, 6- or 7-membered ring heterocycle containing the linking nitrogen and 0, 1 or 2 additional nitrogen atoms and containing 0 or 1 sulfur or oxygen atoms, the heterocycle being substituted by 0, 1, 2 or 3 substituents selected from oxo, halo, OH, CN, $C_{1-4}$alk, $C_{1-3}$haloalk, —$OC_{1-4}$alk, $R^e$, —$OR^e$, —$NH_2$, —$NHC_{1-4}$alk, —N($C_{1-4}$alk)$C_{1-4}$alk, C(=O)$OR^a$, —$C_{1-6}$alk($OR^a$)$_{1-3}$ (such as —$C_{1-4}$alk(OH)$_{1-3}$), —NH—C(=O)O$C_{1-4}$alk, C(=O)$R^a$, C(=O)$R^e$, C(=O)$NR^aR^a$, and C(=O)$NR^aR^a$; and $R^e$ is:
(a) $C_{0-4}$alk-linked saturated, partially-saturated or unsaturated 3-, 4-, 5-, 6-, or 7-membered monocyclic containing 0, 1, 2 or 3 N atoms and 0, 1, or 2 atoms selected from O and S; which is substituted by 0, 1, 2 or 3 groups selected from oxo, halo, OH, $C_{1-4}$alk, $C_{1-3}$haloalk, —$OC_{1-4}$alk, —$NH_2$, —$NHC_{1-4}$alk, —N($C_{1-4}$alk)$C_{1-4}$alk, $C_{1-4}$alk-$NH_2$, COOH, CN, —C(=O)—O—$C_{1-6}$alk, —C(=O)—N($C_{1-4}$alk)$C_{1-4}$alk, and —S—$C_{1-4}$alk; or (b) nitrogen-linked saturated, partially-saturated or unsaturated 4-, 5-, 6- or 7-membered ring heterocycle containing the linking nitrogen and 0, 1 or 2 additional nitrogen atoms and containing 0 or 1 sulfur or oxygen atoms; which is substituted by 0, 1, 2 or 3 groups selected from oxo, halo, OH, $C_{1-4}$alk, $C_{1-3}$haloalk, —$OC_{1-4}$alk, —$NH_2$, —$NHC_{1-4}$alk, —N($C_{1-4}$alk)$C_{1-4}$alk, $C_{1-4}$alk-$NH_2$, COOH, CN, —C(=O)—O—$C_{1-6}$alk, —C(=O)—N($C_{1-4}$alk)$C_{1-4}$alk, and —S—$C_{1-4}$alk.

Another aspect of the current invention relates to compounds having the general structure of formula (III) selected from the group consisting of (IIIa), (IIIb), and (IIIc):

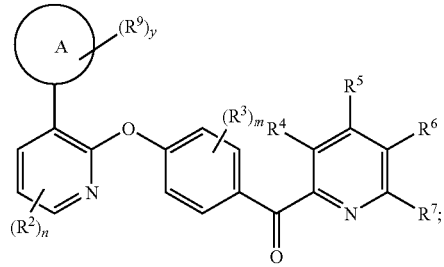

(IIIa)

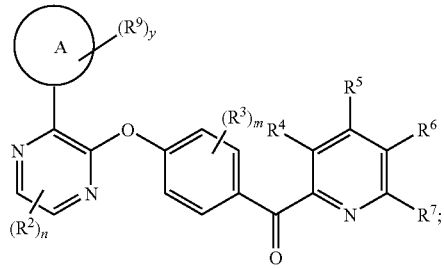

(IIIb)

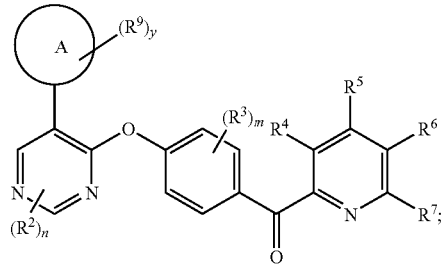

(IIIc)

or a pharmaceutically acceptable salt thereof, wherein m, n, y, $R^2$, $R^3$, $R^4$, $R^5$, $R^6$, $R^7$ and $R^9$ are as defined in compounds of formula (III), and any other embodiments below.

In one embodiment of compounds of formula (IIIa), (IIIb), or (IIIc), ring A is bonded to the 3-pyridinyl ring via a carbon atom having an sp3 hybridization.

In one embodiment of compounds of formula (IIIa), (IIIb), or (IIIc), ring A is bonded to the 3-pyridinyl ring via a carbon atom having an sp2 hybridization.

In one embodiment of compounds of formula (IIIb), ring A is bonded to the 3-pyridinyl ring via a carbon atom having an sp hybridization.

In one embodiment of compounds of formula (IIIa), (IIIb), or (IIIc), ring A is bonded to the 3-pyridinyl ring via a nitrogen atom having an sp3 hybridization.

In one embodiment of compounds of formula (IIIa), (IIIb), or (IIIc), ring A is bonded to the 3-pyridinyl ring via a nitrogen atom having an sp2 hybridization.

In another embodiment of compounds of formula (IIIa), (IIIb), or (IIIc), ring A is a 5-membered ring saturated heterocycle, which is optionally substituted with —C(=O)$R^b$, —C(=O)O$R^a$, —C(=O)N$R^a R^a$, —C(=N$R^a$)N$R^a R^a$, —OC(=O)$R^b$, —OC(=O)N$R^a R^a$, —N($R^a$)C(=O)$R^b$, —N($R^a$)C(=O)O$R^b$, —N($R^a$)C(=O)N$R^a R^a$, —$C_{1-6}$alkN($R^a$)C(=O)$R^b$, —$C_{1-6}$alkOC(=O)$R^b$, —$C_{1-6}$alkC(=O)N$R^a R^a$, —$C_{1-6}$alkC(=O)O$R^a$, or oxo.

In another embodiment of compounds of formula (IIIa), (IIIb), or (IIIc), ring A is a 6-membered ring saturated heterocycle, which is optionally substituted with —C(=O)$R^b$, —C(=O)O$R^a$, —C(=O)N$R^a R^a$, —C(=N$R^a$)N$R^a R^a$, —OC(=O)$R^b$, —OC(=O)N$R^a R^a$, —N($R^a$)C(=O)$R^b$, —N($R^a$)C(=O)O$R^b$, —N($R^a$)C(=O)N$R^a R^a$, —$C_{1-6}$alkN($R^a$)C(=O)$R^b$, —$C_{1-6}$alkOC(=O)$R^b$, —$C_{1-6}$alkC(=O)N$R^a R^a$, —$C_{1-6}$alkC(=O)O$R^a$, or oxo.

In another embodiment of compounds of formula (IIIa), (IIIb), or (IIIc), ring A is a 4-membered ring unsaturated carbocycle, which is optionally substituted with —C(=O)$R^b$, —C(=O)O$R^a$, —C(=O)N$R^a R^a$, —C(=N$R^a$)N$R^a R^a$, —OC(=O)$R^b$, —OC(=O)N$R^a R^a$, —N($R^a$)C(=O)$R^b$, —N($R^a$)C(=O)O$R^b$, —N($R^a$)C(=O)N$R^a R^a$, —$C_{1-6}$alkN($R^a$)C(=O)$R^b$, —$C_{1-6}$alkOC(=O)$R^b$, —$C_{1-6}$alkC(=O)N$R^a R^a$, —$C_{1-6}$alkC(=O)O$R^a$, or oxo.

In another embodiment of compounds of formula (IIIa), (IIIb), or (IIIc), ring A is a 5-membered ring saturated carbocycle, which is optionally substituted with —C(=O)$R^b$, —C(=O)O$R^a$, —C(=O)N$R^a R^a$, —C(=N$R^a$)N$R^a R^a$, —OC(=O)$R^b$, —OC(=O)N$R^a R^a$, —N($R^a$)C(=O)$R^b$, —N($R^a$)C(=O)O$R^b$, —N($R^a$)C(=O)N$R^a R^a$, —$C_{1-6}$alkN($R^a$)C(=O)$R^b$, —$C_{1-6}$alkOC(=O)$R^b$, —$C_{1-6}$alkC(=O)N$R^a R^a$, —$C_{1-6}$alkC(=O)O$R^a$, or oxo.

In another embodiment of compounds of formula (IIIa), (IIIb), or (IIIc), ring A is a 6-membered ring saturated carbocycle, which is optionally substituted with —C(=O)$R^b$, —C(=O)O$R^a$, —C(=O)N$R^a R^a$, —C(=N$R^a$)N$R^a R^a$, —OC(=O)$R^b$, —OC(=O)N$R^a R^a$, —N($R^a$)C(=O)$R^b$, —N($R^a$)C(=O)O$R^b$, —N($R^a$)C(=O)N$R^a R^a$, —$C_{1-6}$alkN($R^a$)C(=O)$R^b$, —$C_{1-6}$alkOC(=O)$R^b$, —$C_{1-6}$alkC(=O)N$R^a R^a$, —$C_{1-6}$alkC(=O)O$R^a$, or oxo.

In another embodiment of compounds of formula (IIIa), (IIIb), or (IIIc), ring A is a 7-membered ring saturated carbocycle, which is optionally substituted with —C(=O)$R^b$, —C(=O)O$R^a$, —C(=O)N$R^a R^a$, —C(=N$R^a$)N$R^a R^a$, —OC(=O)$R^b$, —OC(=O)N$R^a R^a$, —N($R^a$)C(=O)$R^b$, —N($R^a$)C(=O)O$R^b$, —N($R^a$)C(=O)N$R^a R^a$, —$C_{1-6}$alkN($R^a$)C(=O)$R^b$, —$C_{1-6}$alkOC(=O)$R^b$, —$C_{1-6}$alkC(=O)N$R^a R^a$, —$C_{1-6}$alkC(=O)O$R^a$, or oxo.

Another aspect of the invention relates to a method of treating conditions that may be treated with PDE10 inhibitors comprising the step of administering a compound of formula (III).

Another aspect of the invention relates to a method of treating conditions that may be treated with PDE10 inhibitors comprising the step of administering a compound of formula (III); wherein said condition is selected from the group consisting of psychoses, Parkinson's disease, dementias, obsessive compulsive disorder, tardive dyskinesia, choreas, depression, mood disorders, impulsivity, drug addiction, attention deficit/hyperactivity disorder (ADHD), depression with parkinsonian states, personality changes with caudate or putamen disease, dementia and mania with caudate and pallidal diseases, and compulsions with pallidal disease.

Another aspect of the invention relates to a method of treating conditions that may be treated with PDE10 inhibitors comprising the step of administering a compound of formula (III); wherein said condition is selected from the group consisting of schizophrenia, bipolar disorder, and obsessive-compulsive disorder.

Another aspect of the invention relates to a pharmaceutical composition comprising a compound of formula (III) and a pharmaceutically-acceptable diluent or carrier.

Another aspect of the current invention relates to compounds having the general structure of formula (IV):

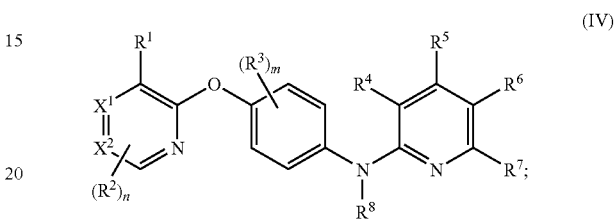

(IV)

or any pharmaceutically-acceptable salt thereof, wherein:

$X^1$ is N or CH;

$X^2$ is N or CH; wherein 1 or 2 of $X^1$ and $X^2$ is CH;

m is independently in each instance 0, 1, 2, 3 or 4;

n is independently in each instance 0, 1, 2 or 3;

$R^1$ is selected from H, F, Cl, Br, $C_{1-8}$alk, $C_{1-4}$haloalk, —O$R^a$, —N$R^a R^a$, —N($R^a$)C(=O)$R^b$ and —C(=O)N$R^a R^a$, —C(=O)$R^d$, $R^c$, —O$R^c$, —N$R^a R^c$, —S$R^c$, —S(=O)$R^c$, —S(=O)$_2 R^c$, —N($R^c$)S(=O)$_2 R^b$, —S(=O)$_2$N$R^a R^c$, —N($R^c$)C(=O)$R^b$, —N($R^a$)C(=O)$R^c$ and —C(=O)N$R^a R^c$; with the proviso that $R^1$ is not 2-methylaminopyrimidin-4-yl;

$R^2$ is, independently in each instance, F, Cl, Br, CN, OH, O$C_{1-4}$alk, $C_{1-4}$alk or $C_{1-4}$haloalk;

$R^3$ is, independently in each instance, F, Cl, Br, CN, OH, O$C_{1-4}$alk, $C_{1-4}$alk or $C_{1-4}$haloalk;

$R^4$ is selected from H, F, Cl, Br, $C_{1-2}$alk and $C_{1-2}$haloalk;

$R^5$ is selected from H, F, Cl, Br, $C_{1-2}$alk and $C_{1-2}$haloalk;

$R^6$ is selected from H, F, Cl, Br, $C_{1-2}$alk and $C_{1-2}$haloalk;

$R^7$ is selected from H, F, Cl, Br, $C_{1-2}$alk and $C_{1-2}$haloalk;

$R^8$ is H, $C_{1-8}$alk, $C_{1-4}$haloalk or —C(=O)$R^b$;

$R^a$ is independently, at each instance, H or $R^b$;

$R^b$ is independently, at each instance, phenyl, benzyl or $C_{1-6}$alk, the phenyl, benzyl and $C_{1-6}$alk being substituted by 0, 1, 2 or 3 substituents selected from halo, $C_{1-4}$alk, $C_{1-3}$haloalk, —O$C_{1-4}$alk, —NH$_2$, —NH$C_{1-4}$alk, and —N($C_{1-4}$alk)$C_{1-4}$alk;

$R^c$ is a $C_{0-3}$alk-linked saturated, partially-saturated or unsaturated 3-, 4-, 5-, 6-, or 7-membered monocyclic or 8-, 9-, 10-, 11-, or 12-membered bicyclic ring containing 0, 1, 2 or 3 N atoms and 0 or 1 atoms selected from O and S, which is substituted by 0, 1, 2 or 3 groups selected from F, Cl, Br, $C_{1-6}$alk, $C_{1-4}$haloalk, —O$R^a$, —O$C_{1-4}$haloalk, CN, —C(=O)$R^b$, —C(=O)O$R^a$, —C(=O)N$R^a R^a$, —C(=N$R^a$)N$R^a R^a$, —OC(=O)$R^b$, —OC(=O)N$R^a R^a$, —O$C_{2-6}$alkN$R^a R^a$, —O$C_{2-6}$alkO$R^a$, —S$R^a$, —S(=O)$R^b$, —S(=O)$_2 R^b$, —S(=O)$_2$N$R^a R^a$, —N$R^a R^a$, —N($R^a$)C(=O)$R^b$, —N($R^a$)C(=O)O$R^b$, —N($R^a$)C(=O)N$R^a R^a$, —N(Ra)C(=NRa)N$R^a R^a$, —N(Ra)S(=O)$_2 R^b$, —N($R^a$)S(=O)$_2$N$R^a R^a$, —N$R^a C_{2-6}$alkN$R^a R^a$, —N$R^a C_{2-6}$alkO$R^a$, —$C_{1-6}$alkN$R^a R^a$, —$C_{1-6}$alkO$R^a$, —$C_{1-6}$alkN($R^a$)C(=O)$R^b$, —$C_{1-6}$alkOC(=O)$R^b$, —$C_{1-6}$alkC(=O)N$R^a R^a$, —$C_{1-6}$alkC(=O)O$R^a$ and oxo; and $R^d$ is a nitrogen-linked saturated, partially-saturated or unsaturated 5-, 6- or 7-membered ring heterocycle containing the linking nitrogen and 0, 1 or 2 additional nitrogen atoms and containing 0 or 1 sulfur or oxygen atoms, the heterocycle being substituted by 0, 1, 2 or 3 substituents selected from oxo, halo, $C_{1-4}$alk, $C_{1-3}$haloalk, —$OC_{1-4}$alk, —$NH_2$, —$NHC_{1-4}$alk, and —$N(C_{1-4}alk)C_{1-4}$alk.

In another embodiment, in conjunction with any above or below embodiment, $R^1$ is $C_{3-4}$alk substituted by 0, 1, 2 or 3 groups selected from F, Cl, Br, $C_{1-6}$alk, $C_{1-4}$haloalk, —$OR^a$, —$OC_{1-4}$haloalk, CN, —$C(=O)R^b$, —$C(=O)OR^b$, —$C(=O)NR^aR^a$, —$C(=NR^a)NR^aR^a$, —$OC(=O)R^b$, —$OC(=O)NR^aR^a$, —$OC_{2-6}$alkNR$^a$R$^a$, —$OC_{2-6}$alkOR$^a$, —$SR^a$, —$S(=O)R^b$, —$S(=O)_2R^b$, —$S(=O)_2NR^aR^a$, —$NR^aR^a$, —$N(R^a)C(=O)R^b$, —$N(R^a)C(=O)OR^b$, —$N(R^a)C(=O)NR^aR^a$, —$N(R^a)C(=NR^a)NR^aR^a$, —$N(R^a)S(=O)_2R^b$, —$N(R^a)S(=O)_2NR^aR^a$, —$NR^aC_{2-6}$alkNR$^a$R$^a$, —$NR^aC_{2-6}$alkOR$^a$, —$C_{1-6}$alkNR$^a$R$^a$, —$C_{1-6}$alkOR$^a$ and oxo.

In another embodiment, in conjunction with any above or below embodiment, $R^1$ is selected from piperidine, piperazine, pyrrolidine, morpholine, and pyridine, all of which are substituted by 0, 1, 2 or 3 groups selected from F, Cl, Br, $C_{1-6}$alk, $C_{1-4}$haloalk, —$OR^a$, —$OC_{1-4}$haloalk, CN, —$C(=O)R^b$, —$C(=O)OR^b$, —$C(=O)NR^aR^a$, —$C(=NR^a)NR^aR^a$, —$OC(=O)R^b$, —$OC(=O)NR^aR^a$, —$OC_{2-6}$alkNR$^a$R$^a$, —$OC_{2-6}$alkOR$^a$, —$SR^a$, —$S(=O)R^b$, —$S(=O)_2R^b$, —$S(=O)_2NR^aR^a$, —$NR^aR^a$, —$N(R^a)C(=O)R^b$, —$N(R^a)C(=O)OR^b$, —$N(R^a)C(=O)NR^aR^a$, —$N(R^a)C(=NR^a)NR^aR^a$, —$N(R^a)S(=O)_2R^b$, —$N(R^a)S(=O)_2NR^aR^a$, —$NR^aC_{2-6}$alkNR$^a$R$^a$, —$NR^aC_{2-6}$alkOR$^a$, —$C_{1-6}$alkNR$^a$R$^a$, —$C_{1-6}$alkOR$^a$ and oxo.

In another embodiment, in conjunction with any above or below embodiment, $R^1$ is pyrimidine substituted by 0, 1, 2 or 3 groups selected from F, Cl, Br, $C_{1-6}$alk, $C_{1-4}$haloalk, —$OR^a$, —$OC_{1-4}$haloalk, CN, —$C(=O)R^b$, —$C(=O)OR^b$, —$C(=O)NR^aR^a$, —$C(=NR^a)NR^aR^a$, —$OC(=O)R^b$, —$OC(=O)NR^aR^a$, —$OC_{2-6}$alkNR$^a$R$^a$, —$OC_{2-6}$alkOR$^a$, —$SR^a$, —$S(=O)R^b$, —$S(=O)_2R^b$, —$S(=O)_2NR^aR^a$, —$N(R^a)C(=O)R^b$, —$N(R^a)C(=O)OR^b$, —$N(R^a)C(=O)NR^aR^a$, —$N(R^a)C(=NR^a)NR^aR^a$, —$N(R^a)S(=O)_2R^b$, —$N(R^a)S(=O)_2NR^aR^a$, —$NR^aC_{2-6}$alkNR$^a$R$^a$, —$NR^aC_{2-6}$alkOR$^a$, —$C_{1-6}$alkNR$^a$R$^a$, —$C_{1-6}$alkOR$^a$ and oxo.

In another embodiment, in conjunction with any above or below embodiment, $R^1$ is phenyl, all of which are substituted by 0, 1, 2 or 3 groups selected from F, Cl, Br, $C_{1-6}$alk, $C_{1-4}$haloalk, —$OR^a$, —$OC_{1-4}$haloalk, CN, —$C(=O)R^b$, —$C(=O)OR^b$, —$C(=O)NR^aR^a$, —$C(=NR^a)NR^aR^a$, —$OC(=O)R^b$, —$OC(=O)NR^aR^a$, —$OC_{2-6}$alkNR$^a$R$^a$, —$OC_{2-6}$alkOR$^a$, —$SR^a$, —$S(=O)R^b$, —$S(=O)_2R^b$, —$S(=O)_2NR^aR^a$, —$NR^aR^a$, —$N(R^a)C(=O)R^b$, —$N(R^a)C(=O)OR^b$, —$N(R^a)C(=O)NR^aR^a$, —$N(R^a)C(=NR^a)NR^aR^a$, —$N(R^a)S(=O)_2R^b$, —$N(R^a)S(=O)_2NR^aR^a$, —$NR^aC_{2-6}$alkNR$^a$R$^a$, —$NR^aC_{2-6}$alkOR$^a$, —$C_{1-6}$alkNR$^a$R$^a$, —$C_{1-6}$alkOR$^a$ and oxo.

In another embodiment, in conjunction with any above or below embodiment, $R^1$ is selected from piperidine, piperazine, pyrrolidine and morpholine, all of which are substituted by 0, 1, 2 or 3 groups selected from F, Cl, Br, $C_{1-6}$alk, $C_{1-4}$haloalk, —$OR^a$, —$OC_{1-4}$haloalk, CN, —$C(=O)R^b$, —$C(=O)OR^b$, —$C(=O)NR^aR^a$, —$C(=NR^a)NR^aR^a$, —$OC(=O)R^b$, —$OC(=O)NR^aR^a$, —$OC_{2-6}$alkNR$^a$R$^a$, —$OC_{2-6}$alkOR$^a$, —$SR^a$, —$S(=O)R^b$, —$S(=O)_2R^b$, —$S(=O)_2NR^aR^a$, —$NR^aR^a$, —$N(R^a)C(=O)R^b$, —$N(R^a)C(=O)OR^b$, —$N(R^a)C(=O)NR^aR^a$, —$N(R^a)C(=NR^a)NR^aR^a$, —$N(R^a)S(=O)_2R^b$, —$N(R^a)S(=O)_2NR^aR^a$, —$NR^aC_{2-6}$alkNR$^a$R$^a$, —$NR^aC_{2-6}$alkOR$^a$, —$C_{1-6}$alkNR$^a$R$^a$, —$C_{1-6}$alkOR$^a$ and oxo.

In another embodiment, in conjunction with any above or below embodiment, $R^1$ is selected from pyridine and pyrimidine, each of which are substituted by 0, 1, 2 or 3 groups selected from F, Cl, Br, $C_{1-6}$alk, $C_{1-4}$haloalk, —$OR^a$, —$OC_{1-4}$haloalk, CN, —$C(=O)R^b$, —$C(=O)OR^b$, —$C(=O)NR^aR^a$, —$C(=NR^a)NR^aR^a$, —$OC(=O)R^b$, —$OC(=O)NR^aR^a$, —$OC_{2-6}$alkNR$^a$R$^a$, —$OC_{2-6}$alkOR$^a$, —$SR^a$, —$S(=O)R^b$, —$S(=O)_2R^b$, —$S(=O)_2NR^aR^a$, —$NR^aR^a$, —$N(R^a)C(=O)R^b$, —$N(R^a)C(=O)OR^b$, —$N(R^a)C(=O)NR^aR^a$, —$N(R^a)C(=NR^a)NR^aR^a$, —$N(R^a)S(=O)_2R^b$, —$N(R^a)S(=O)_2NR^aR^a$, —$NR^aC_{2-6}$alkNR$^a$R$^a$, —$NR^aC_{2-6}$alkOR$^a$, —$C_{1-6}$alkNR$^a$R$^a$, —$C_{1-6}$alkOR$^a$ and oxo.

In another embodiment, in conjunction with any above or below embodiment, $R^1$ is a saturated 5- or 6-membered carbocyclic ring substituted by 0, 1, 2 or 3 groups selected from F, Cl, Br, $C_{1-6}$alk, $C_{1-4}$haloalk, —$OR^a$, —$OC_{1-4}$haloalk, CN, —$C(=O)R^b$, —$C(=O)OR^b$, —$C(=O)NR^aR^a$, —$C(=NR^a)NR^aR^a$, —$OC(=O)R^b$, —$OC(=O)NR^aR^a$, —$OC_{2-6}$alkNR$^a$R$^a$, —$OC_{2-6}$alkOR$^a$, —$SR^a$, —$S(=O)R^b$, —$S(=O)_2R^b$, —$S(=O)_2NR^aR^a$, —$NR^aR^a$, —$N(R^a)C(=O)R^b$, —$N(R^a)C(=O)OR^b$, —$N(R^a)C(=O)NR^aR^a$, —$N(R^a)C(=NR^a)NR^aR^a$, —$N(R^a)S(=O)_2R^b$, —$N(R^a)S(=O)_2NR^aR^a$, —$NR^aC_{2-6}$alkNR$^a$R$^a$, —$NR^aC_{2-6}$alkOR$^a$, —$C_{1-6}$alkNR$^a$R$^a$, —$C_{1-6}$alkOR$^a$ and oxo.

In another embodiment, in conjunction with any above or below embodiment, $R^1$ is selected from

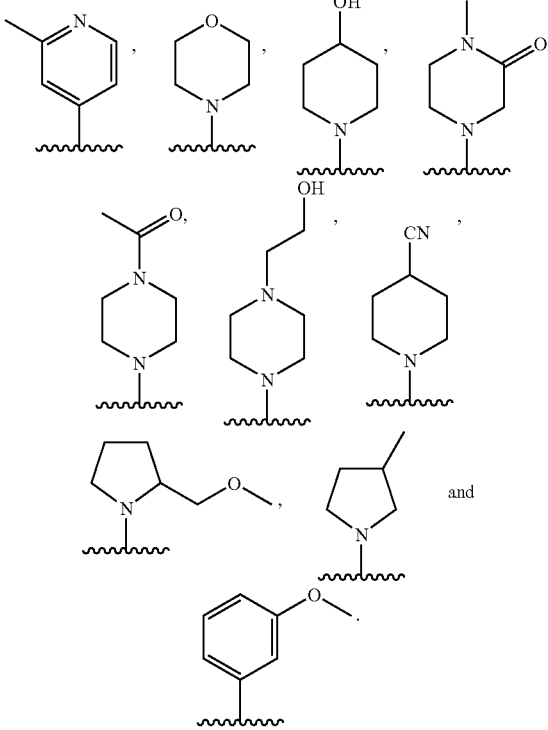

In another embodiment, in conjunction with any above or below embodiment, $R^4$ is selected from F, Cl, Br, $C_{1-2}$alk and $C_{1-2}$haloalk.

In another embodiment, in conjunction with any above or below embodiment, $R^4$ is H.

In another embodiment, in conjunction with any above or below embodiment, $R^5$ is selected from F, Cl, Br, $C_{1-2}$alk and $C_{1-2}$haloalk.

In another embodiment, in conjunction with any above or below embodiment, $R^5$ is H.

In another embodiment, in conjunction with any above or below embodiment, $R^6$ is selected from F, Cl, Br, $C_{1-2}$alk and $C_{1-2}$haloalk.

In another embodiment, in conjunction with any above or below embodiment, $R^6$ is H.

In another embodiment, in conjunction with any above or below embodiment, $R^7$ is selected from F, Cl, Br, $C_{1-2}$alk and $C_{1-2}$haloalk.

In another embodiment, in conjunction with any above or below embodiment, $R^7$ is H.

In another embodiment, in conjunction with any above or below embodiment, $R^8$ is $C_{1-8}$alk, $C_{1-4}$haloalk, or —C(═O)$R^b$.

In another embodiment, in conjunction with any above or below embodiment, $R^8$ is H.

In another embodiment, in conjunction with any above or below embodiment, $R^c$ is a saturated, partially-saturated or unsaturated 3-, 4-, 5-, 6-, or 7-membered monocyclic or 8-, 9-, 10-, 11-, or 12-membered bicyclic ring containing 0, 1, 2 or 3 N atoms and 0 or 1 atoms selected from O and S, which is substituted by 0, 1, 2 or 3 groups selected from F, Cl, Br, $C_{1-6}$alk, $C_{1-4}$haloalk, —OR$^a$, —OC$_{1-4}$haloalk, —C(═O)R$^b$, —C(═O)OR$^a$, —C(═O)NR$^a$R$^a$, —C(═NR$^a$)NR$^a$R$^a$, —OC(═O)R$^b$, —OC(═O)NR$^a$R$^a$, —OC$_{2-6}$alkNR$^a$R$^a$, —OC$_{2-6}$alkOR$^a$, —SR$^a$, —S(═O)R$^b$, —S(═O)$_2$R$^b$, —S(═O)$_2$NR$^a$R$^a$, —NR$^a$R$^a$, —N(R$^a$)C(═O)R$^b$, —N(R$^a$)C(═O)OR$^b$, —N(R$^a$)C(═O)NR$^a$R$^a$, —N(R$^a$)C(═NR$^a$)NR$^a$R$^a$, —N(R$^a$)S(═O)$_2$R$^b$, —N(R$^a$)S(═O)$_2$NR$^a$R$^a$, —NR$^a$C$_{2-6}$alkNR$^a$R$^a$, —NR$^a$C$_{2-6}$alkOR$^a$, —C$_{1-6}$alkNR$^a$R$^a$, —C$_{1-6}$alkOR$^a$, —C$_{1-6}$alkN(R$^a$)C(═O)R$^b$, —C$_{1-6}$alkOC(═O)R$^b$, —C$_{1-6}$alkC(═O)NR$^a$R$^a$, —C$_{1-6}$alkC(═O)OR$^a$ and oxo.

In another embodiment, in conjunction with any above or below embodiment, $R^c$ is a $C_1$alk-linked saturated, partially-saturated or unsaturated 3-, 4-, 5-, 6-, or 7-membered monocyclic or 8-, 9-, 10-, 11-, or 12-membered bicyclic ring containing 0, 1, 2 or 3 N atoms and 0 or 1 atoms selected from O and S, which is substituted by 0, 1, 2 or 3 groups selected from F, Cl, Br, $C_{1-6}$alk, $C_{1-4}$haloalk, —OR$^a$, —OC$_{1-4}$haloalk, CN, —C(═O)R$^b$, —C(═O)OR$^a$, —C(═O)NR$^a$R$^a$, —C(═NR$^a$)NR$^a$R$^a$, —OC(═O)R$^b$, —OC(═O)NR$^a$R$^a$, —OC$_{2-6}$alkNR$^a$R$^a$, —OC$_{2-6}$alkOR$^a$, —SR$^a$, —S(═O)R$^b$, —S(═O)$_2$R$^b$, —S(═O)$_2$NR$^a$R$^a$, —NR$^a$R$^a$, —N(R$^a$)C(═O)R$^b$, —N(R$^a$)C(═O)OR$^b$, —N(R$^a$)C(═O)NR$^a$R$^a$, —N(R$^a$)C(═NR$^a$)NR$^a$R$^a$, —N(R$^a$)S(═O)$_2$R$^b$, —N(R$^a$)S(═O)$_2$NR$^a$R$^a$, —NR$^a$C$_{2-6}$alkNR$^a$R$^a$, —NR$^a$C$_{2-6}$alkOR$^a$, —C$_{1-6}$alkNR$^a$R$^a$, —C$_{1-6}$alkOR$^a$, —C$_{1-6}$alkN(R$^a$)C(═O)R$^b$, —C$_{1-6}$alkOC(═O)R$^b$, —C$_{1-6}$alkC(═O)NR$^a$R$^a$, —C$_{1-6}$alkC(═O)OR$^a$ and oxo.

In another embodiment, in conjunction with any above or below embodiment, $R^c$ is a saturated, partially-saturated or unsaturated 3-, 4-, 5-, 6-, or 7-membered monocyclic ring containing 0, 1, 2 or 3 N atoms and 0 or 1 atoms selected from O and S, which is substituted by 0, 1, 2 or 3 groups selected from F, Cl, Br, $C_{1-6}$alk, $C_{1-4}$haloalk, —OR$^a$, —OC$_{1-4}$haloalk, CN, —C(═O)R$^b$, —C(═O)OR$^a$, —C(═O)NR$^a$R$^a$, —C(═NR$^a$)NR$^a$R$^a$, —OC(═O)R$^b$, —OC(═O)NR$^a$R$^a$, —OC$_{2-6}$alkNR$^a$R$^a$, —OC$_{2-6}$alkOR$^a$, —SR$^a$, —S(═O)R$^b$, —S(═O)$_2$R$^b$, —S(═O)$_2$NR$^a$R$^a$, —NR$^a$R$^a$, —N(R$^a$)C(═O)R$^b$, —N(R$^a$)C(═O)OR$^b$, —N(R$^a$)C(═O)NR$^a$R$^a$, —N(R$^a$)C(═NR$^a$)NR$^a$R$^a$, —N(R$^a$)S(═O)$_2$R$^b$, —N(R$^a$)S(═O)$_2$NR$^a$R$^a$, —NR$^a$C$_{2-6}$alkNR$^a$R$^a$, —NR$^a$C$_{2-6}$alkOR$^a$, —C$_{1-6}$alkNR$^a$R$^a$, —C$_{1-6}$alkOR$^a$, —C$_{1-6}$alkN(R$^a$)C(═O)R$^b$, —C$_{1-6}$alkOC(═O)R$^b$, —C$_{1-6}$alkC(═O)NR$^a$R$^a$, —C$_{1-6}$alkC(═O)OR$^a$ and oxo.

In another embodiment, in conjunction with any above or below embodiment, $R^c$ is a $C_1$alk-linked saturated, partially-saturated or unsaturated 3-, 4-, 5-, 6-, or 7-membered monocyclic ring containing 0, 1, 2 or 3 N atoms and 0 or 1 atoms selected from O and S, which is substituted by 0, 1, 2 or 3 groups selected from F, Cl, Br, $C_{1-6}$alk, $C_{1-4}$haloalk, —OR$^a$, —OC$_{1-4}$haloalk, CN, —C(═O)R$^b$, —C(═O)OR$^a$, —C(═O)NR$^a$R$^a$, —C(═NR$^a$)NR$^a$R$^a$, —OC(═O)R$^b$, —OC(═O)NR$^a$R$^a$, —OC$_{2-6}$alkNR$^a$R$^a$, —OC$_{2-6}$alkOR$^a$, —SR$^a$, —S(═O)R$^b$, —S(═O)$_2$R$^b$, —S(═O)$_2$NR$^a$R$^a$, —NR$^a$R$^a$, —N(R$^a$)C(═O)R$^b$, —N(R$^a$)C(═O)OR$^b$, —N(R$^a$)C(═O)NR$^a$R$^a$, —N(R$^a$)C(═NR$^a$)NR$^a$R$^a$, —N(R$^a$)S(═O)$_2$R$^b$, —N(R$^a$)S(═O)$_2$NR$^a$R$^a$, —NR$^a$C$_{2-6}$alkNR$^a$R$^a$, —NR$^a$C$_{2-6}$alkOR$^a$, —C$_{1-6}$alkNR$^a$R$^a$, —C$_{1-6}$alkOR$^a$, —C$_{1-6}$alkN(R$^a$)C(═O)R$^b$, —C$_{1-6}$alkOC(═O)R$^b$, —C$_{1-6}$alkC(═O)NR$^a$R$^a$, —C$_{1-6}$alkC(═O)OR$^a$ and oxo.

In another embodiment, in conjunction with any above or below embodiment, $X^1$ is N and $X^2$ is CH.

In another embodiment, in conjunction with any above or below embodiment, $X^2$ is N and $X^1$ is CH.

In another embodiment, in conjunction with any above or below embodiment, $X^1$ is CH and $X^2$ is CH.

Another aspect of the invention relates to a method of treating schizophrenia, bipolar disorder, or obsessive-compulsive disorder using an effective amount of any of the above embodiments.

Another aspect of the invention relates to a method of treating a disorder treatable by inhibition of PDE10 in a patient which method comprises administering to the patient a pharmaceutical composition comprising an effective amount of a compound according to any of the above embodiments.

Another aspect of the invention relates to a pharmaceutical composition comprising a compound of formula (IV) and a pharmaceutically-acceptable diluent or carrier.

Another aspect of the invention relates to the use of a compound according to any of the above embodiments as a medicament.

Another aspect of the invention relates to the use of a compound according to any of the above embodiments in the manufacture of a medicament for the treatment of schizophrenia, bipolar disorder, or obsessive-compulsive disorder.

Another aspect of the current invention relates to compounds having the general structure (V):

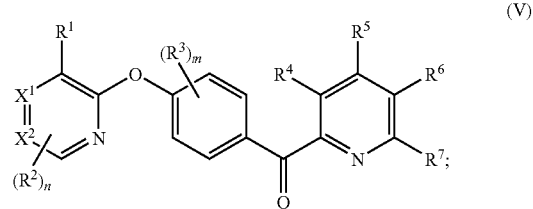

or any pharmaceutically-acceptable salt thereof, wherein:
$X^1$ is N or CH;
$X^2$ is N or CH; wherein 1 or 2 of $X^1$ and $X^2$ is CH;
m is independently in each instance 0, 1, 2, 3 or 4;
n is independently in each instance 0, 1, 2 or 3;
$R^1$ is selected from H, F, Cl, Br, $C_{1-8}$alk, $C_{1-4}$haloalk, —OR$^a$, —NR$^a$R$^a$, —N(R$^a$)C(═O)R$^b$ and —C(═O)NR$^a$R$^a$, —C(═O)R$^d$, R$^c$, —OR$^c$, —NR$^a$R$^c$, —SR$^c$, —S(═O)R$^c$, —S(═O)$_2$R$^c$, —N(R$^c$)S(═O)$_2$R$^b$, —S(═O)$_2$NR$^a$R$^c$, —N(R$^c$)C(═O)R$^b$, —N(R$^a$)C(═O)R$^c$ and —C(═O)NR$^a$R$^c$;

R² is, independently in each instance, F, Cl, Br, CN, OH, $OC_{1-4}alk$, $C_{1-4}alk$ or $C_{1-4}haloalk$;

R³ is, independently in each instance, F, Cl, Br, CN, OH, $OC_{1-4}alk$, $C_{1-4}alk$ or $C_{1-4}haloalk$;

R⁴ is selected from H, F, Cl, Br, $C_{1-2}alk$ and $C_{1-2}haloalk$;

R⁵ is selected from H, F, Cl, Br, $C_{1-2}alk$ and $C_{1-2}haloalk$;

R⁶ is selected from H, F, Cl, Br, $C_{1-2}alk$ and $C_{1-2}haloalk$;

R⁷ is selected from H, F, Cl, Br, $C_{1-2}alk$ and $C_{1-2}haloalk$;

$R^a$ is independently, at each instance, H or $R^b$;

$R^b$ is independently, at each instance, phenyl, benzyl or $C_{1-6}alk$, the phenyl, benzyl and $C_{1-6}alk$ being substituted by 0, 1, 2 or 3 substituents selected from halo, $C_{1-4}alk$, $C_{1-3}haloalk$, —$OC_{1-4}alk$, —$NH_2$, —$NHC_{1-4}alk$, and —$N(C_{1-4}alk)C_{1-4}alk$;

$R^c$ is a $C_{0-3}alk$-linked saturated, partially-saturated or unsaturated 3-, 4-, 5-, 6-, or 7-membered monocyclic or 8-, 9-, 10-, 11-, or 12-membered bicyclic ring containing 0, 1, 2 or 3 N atoms and 0 or 1 atoms selected from O and S, which is substituted by 0, 1, 2 or 3 groups selected from F, Cl, Br, $C_{1-6}alk$, $C_{1-4}haloalk$, —$OR^a$, —$OC_{1-4}haloalk$, CN, —C(=O)$R^b$, —C(=O)$OR^a$, —C(=O)$NR^aR^a$, —C(=$NR^a$)$NR^aR^a$, —OC(=O)$R^b$, —OC(=O)$NR^aR^a$, —$OC_{2-6}alkNR^aR^a$, —$OC_{2-6}alkOR^a$, —$SR^a$, —S(=O)$R^b$, —S(=O)$_2R^b$, —S(=O)$_2NR^aR^a$, —$NR^aR^a$, —N(Ra)C(=O)$R^b$, —N($R^a$)C(=O)$OR^b$, —N($R^a$)C(=O)$NR^aR^a$, —N($R^a$)C(=NRa)$NR^aR^a$, —N($R^a$)S(=O)$_2R^b$, —N($R^a$)S(=O)$_2NR^aR^a$, —$NR^aC_{2-6}alkNR^aR^a$, —$NR^aC_{2-6}alkOR^a$, —$C_{1-6}alkNR^aR^a$, —$C_{1-6}alkOR^a$, —$C_{1-6}alkN(R^a$)C(=O)$R^b$, —$C_{1-6}alkOC(=O)R^b$, —$C_{1-6}alkC(=O)NR^aR^a$, —$C_{1-6}alkC(=O)OR^a$ and oxo; and $R^d$ is a nitrogen-linked saturated, partially-saturated or unsaturated 5-, 6- or 7-membered ring heterocycle containing the linking nitrogen and 0, 1 or 2 additional nitrogen atoms and containing 0 or 1 sulfur or oxygen atoms, the heterocycle being substituted by 0, 1, 2 or 3 substituents selected from oxo, halo, $C_{1-4}alk$, $C_{1-3}haloalk$, —$OC_{1-4}alk$, —$NH_2$, —$NHC_{1-4}alk$, and —$N(C_{1-4}alk)C_{1-4}alk$.

In another embodiment, in conjunction with any above or below embodiment, R¹ is $C_{3-4}alk$ substituted by 0, 1, 2 or 3 groups selected from F, Cl, Br, $C_{1-6}alk$, $C_{1-4}haloalk$, —$OR^a$, —$OC_{1-4}haloalk$, CN, —C(=O)$R^b$, —C(=O)$OR^b$, —C(=O)$NR^aR^a$, —C(=$NR^a$)$NR^aR^a$, —OC(=O)$R^b$, —OC(=O)$NR^aR^a$, —$OC_{2-6}alkNR^aR^a$, —$OC_{2-6}alkOR^a$, —$SR^a$, —S(=O)$R^b$, —S(=O)$_2R^b$, —S(=O)$_2NR^aR^a$, —$NR^aR^a$, —N($R^a$)C(=O)$R^b$, —N($R^a$)C(=O)$OR^b$, —N($R^a$)C(=O)$NR^aR^a$, —N($R^a$)C(=$NR^a$)$NR^aR^a$, —N($R^a$)S(=O)$_2R^b$, —N($R^a$)S(=O)$_2NR^aR^a$, —$NR^aC_{2-6}alkNR^aR^a$, —$NR^aC_{2-6}alkOR^a$, —$C_{1-6}alkNR^aR^a$, —$C_{1-6}alkOR^a$ and oxo.

In another embodiment, in conjunction with any above or below embodiment, R¹ is selected from piperidine, piperazine, pyrrolidine, morpholine, pyridine and pyrimidine, all of which are substituted by 0, 1, 2 or 3 groups selected from F, Cl, Br, $C_{1-6}alk$, $C_{1-4}haloalk$, —$OR^a$, —$OC_{1-4}haloalk$, CN, —C(=O)$R^b$, —C(=O)$OR^b$, —C(=O)$NR^aR^a$, —C(=$NR^a$)$NR^aR^a$, —OC(=O)$R^b$, —OC(=O)$NR^aR^a$, —$OC_{2-6}alkNR^aR^a$, —$OC_{2-6}alkOR^a$, —$SR^a$, —S(=O)$R^b$, —S(=O)$_2R^b$, —S(=O)$_2NR^aR^a$, —$NR^aR^a$, —N($R^a$)C(=O)$R^b$, —N($R^a$)C(=O)$OR^b$, —N($R^a$)C(=O)$NR^aR^a$, —N($R^a$)C(=$NR^a$)$NR^aR^a$, —N($R^a$)S(=O)$_2R^b$, —N($R^a$)S(=O)$_2NR^aR^a$, —$NR^aC_{2-6}alkNR^aR^a$, —$NR^aC_{2-6}alkOR^a$, —$C_{1-6}alkNR^aR^a$, —$C_{1-6}alkOR^a$ and oxo.

In another embodiment, in conjunction with any above or below embodiment, R¹ is phenyl, all of which are substituted by 0, 1, 2 or 3 groups selected from F, Cl, Br, $C_{1-6}alk$, $C_{1-4}haloalk$, —$OR^a$, —$OC_{1-4}haloalk$, CN, —C(=O)$R^b$, —C(=O)$OR^b$, —C(=O)$NR^aR^a$, —C(=$NR^a$)$NR^aR^a$, —OC(=O)$R^b$, —OC(=O)$NR^aR^a$, —$OC_{2-6}alkNR^aR^a$, —$OC_{2-6}alkOR^a$, —$SR^a$, —S(=O)$R^b$, —S(=O)$_2R^b$, —S(=O)$_2NR^aR^a$, —$NR^aR^a$, —N($R^a$)C(=O)$R^b$, —N($R^a$)C(=O)$OR^b$, —N($R^a$)C(=O)$NR^aR^a$, —N($R^a$)C(=$NR^a$)$NR^aR^a$, —N($R^a$)S(=O)$_2R^b$, —N($R^a$)S(=O)$_2NR^aR^a$, —$NR^aC_{2-6}alkNR^aR^a$, —$NR^aC_{2-6}alkOR^a$, —$C_{1-6}alkNR^aR^a$, —$C_{1-6}alkOR^a$ and oxo.

In another embodiment, in conjunction with any above or below embodiment, R¹ is selected from piperidine, piperazine, pyrrolidine and morpholine, all of which are substituted by 0, 1, 2 or 3 groups selected from F, Cl, Br, $C_{1-6}alk$, $C_{1-4}haloalk$, —$OR^a$, —$OC_{1-4}haloalk$, CN, —C(=O)$R^b$, —C(=O)$OR^b$, —C(=O)$NR^aR^a$, —C(=$NR^a$)$NR^aR^a$, —OC(=O)$R^b$, —OC(=O)$NR^aR^a$, —$OC_{2-6}alkNR^aR^a$, —$OC_{2-6}alkOR^a$, —$SR^a$, —S(=O)$R^b$, —S(=O)$_2R^b$, —S(=O)$_2NR^aR^a$, —$NR^aR^a$, —N($R^a$)C(=O)$R^b$, —N($R^a$)C(=O)$OR^b$, —N($R^a$)C(=O)$NR^aR^a$, —N($R^a$)C(=$NR^a$)$NR^aR^a$, —N($R^a$)S(=O)$_2R^b$, —N($R^a$)S(=O)$_2NR^aR^a$, —$NR^aC_{2-6}alkNR^aR^a$, —$NR^aC_{2-6}alkOR^a$, —$C_{1-6}alkNR^aR^a$, —$C_{1-6}alkOR^a$ and oxo.

In another embodiment, in conjunction with any above or below embodiment, R¹ is selected from pyridine and pyrimidine, each of which are substituted by 0, 1, 2 or 3 groups selected from F, Cl, Br, $C_{1-6}alk$, $C_{1-4}haloalk$, —$OR^a$, —$OC_{1-4}haloalk$, CN, —C(=O)$R^b$, —C(=O)$OR^b$, —C(=O)$NR^aR^a$, —C(=$NR^a$)$NR^aR^a$, —OC(=O)$R^b$, —OC(=O)$NR^aR^a$, —$OC_{2-6}alkNR^aR^a$, —$OC_{2-6}alkOR^a$, —$SR^a$, —S(=O)$R^b$, —S(=O)$_2R^b$, —S(=O)$_2NR^aR^a$, —$NR^aR^a$, —N($R^a$)C(=O)$R^b$, —N($R^a$)C(=O)$OR^b$, —N($R^a$)C(=O)$NR^aR^a$, —N($R^a$)C(=$NR^a$)$NR^aR^a$, —N($R^a$)S(=O)$_2R^b$, —N($R^a$)S(=O)$_2NR^aR^a$, —$NR^aC_{2-6}alkNR^aR^a$, —$NR^aC_{2-6}alkOR^a$, —$C_{1-6}alkNR^aR^a$, —$C_{1-6}alkOR^a$ and oxo.

In another embodiment, in conjunction with any above or below embodiment, R¹ is a saturated 5- or 6-membered carbocyclic ring substituted by 0, 1, 2 or 3 groups selected from F, Cl, Br, $C_{1-6}alk$, $C_{1-4}haloalk$, —$OR^a$, —$OC_{1-4}haloalk$, CN, —C(=O)$R^b$, —C(=O)$OR^b$, —C(=O)$NR^aR^a$, —C(=$NR^a$)$NR^aR^a$, —OC(=O)$R^b$, —OC(=O)$NR^aR^a$, —$OC_{2-6}alkNR^aR^a$, —$OC_{2-6}alkOR^a$, —$SR^a$, —S(=O)$R^b$, —S(=O)$_2R^b$, —S(=O)$_2NR^aR^a$, —$NR^aR^a$, —N($R^a$)C(=O)$R^b$, —N($R^a$)C(=O)$OR^b$, —N($R^a$)C(=O)$NR^aR^a$, —N($R^a$)C(=$NR^a$)$NR^aR^a$, —N($R^a$)S(=O)$_2R^b$, —N($R^a$)S(=O)$_2NR^aR^a$, —$NR^aC_{2-6}alkNR^aR^a$, —$NR^aC_{2-6}alkOR^a$, —$C_{1-6}alkNR^aR^a$, —$C_{1-6}alkOR^a$ and oxo.

In another embodiment, in conjunction with any above or below embodiment, R¹ is selected from

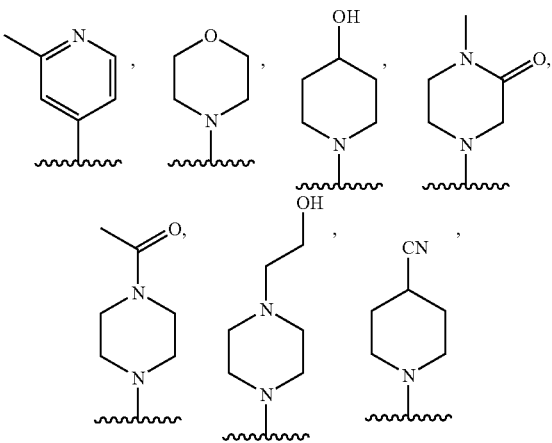

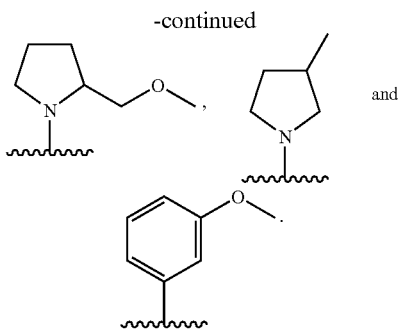

In another embodiment, in conjunction with any above or below embodiment, $R^4$ is selected from F, Cl, Br, $C_{1-2}$alk and $C_{1-2}$haloalk.

In another embodiment, in conjunction with any above or below embodiment, $R^4$ is H.

In another embodiment, in conjunction with any above or below embodiment, $R^5$ is selected from F, Cl, Br, $C_{1-2}$alk and $C_{1-2}$haloalk.

In another embodiment, in conjunction with any above or below embodiment, $R^5$ is H.

In another embodiment, in conjunction with any above or below embodiment, $R^6$ is selected from F, Cl, Br, $C_{1-2}$alk and $C_{1-2}$haloalk.

In another embodiment, in conjunction with any above or below embodiment, $R^6$ is H.

In another embodiment, in conjunction with any above or below embodiment, $R^7$ is selected from F, Cl, Br, $C_{1-2}$alk and $C_{1-2}$haloalk.

In another embodiment, in conjunction with any above or below embodiment, $R^7$ is H.

In another embodiment, in conjunction with any above or below embodiment, $R^c$ is a saturated, partially-saturated or unsaturated 3-, 4-, 5-, 6-, or 7-membered monocyclic or 8-, 9-, 10-, 11-, or 12-membered bicyclic ring containing 0, 1, 2 or 3 N atoms and 0 or 1 atoms selected from O and S, which is substituted by 0, 1, 2 or 3 groups selected from F, Cl, Br, $C_{1-6}$alk, $C_{1-4}$haloalk, —$OR^a$, —$OC_{1-4}$haloalk, CN, —$C(=O)R^b$, —$C(=O)OR^a$, —$C(=O)NR^aR^a$, —$C(=NR^a)NR^aR^a$, —$OC(=O)R^b$, —$OC(=O)NR^aR^a$, —$OC_{2-6}$alkNR$^a$R$^a$, —$OC_{2-6}$alkOR$^a$, —$SR^a$, —$S(=O)R^b$, —$S(=O)_2R^b$, —$S(=O)_2NR^aR^a$, —$NR^aR^a$, —$N(R^a)C(=O)R^b$, —$N(R^a)C(=O)OR^b$, —$N(R^a)C(=O)NR^aR^a$, —$N(R^a)C(=NR^a)NR^aR^a$, —$N(R^a)S(=O)_2R^b$, —$N(R^a)S(=O)_2NR^aR^a$, —$NR^aC_{2-6}$alkNR$^a$R$^a$, —$NR^aC_{2-6}$alkOR$^a$, —$C_{1-6}$alkNR$^a$R$^a$, —$C_{1-6}$alkOR$^a$, —$C_{1-6}$alkN(R$^a$)C(=O)R$^b$, —$C_{1-6}$alkOC(=O)R$^b$, —$C_{1-6}$alkC(=O)NR$^a$R$^a$, —$C_{1-6}$alkC(=O)OR$^a$ and oxo.

In another embodiment, in conjunction with any above or below embodiment, $R^c$ is a $C_1$alk-linked saturated, partially-saturated or unsaturated 3-, 4-, 5-, 6-, or 7-membered monocyclic or 8-, 9-, 10-, 11-, or 12-membered bicyclic ring containing 0, 1, 2 or 3 N atoms and 0 or 1 atoms selected from O and S, which is substituted by 0, 1, 2 or 3 groups selected from F, Cl, Br, $C_{1-6}$alk, $C_{1-4}$haloalk, —$OR^a$, —$OC_{1-4}$haloalk, CN, —$C(=O)R^b$, —$C(=O)OR^a$, —$C(=O)NR^aR^a$, —$C(=NR^a)NR^aR^a$, —$OC(=O)R^b$, —$OC(=O)NR^aR^a$, —$OC_{2-6}$alkNR$^a$R$^a$, —$OC_{2-6}$alkOR$^a$, —$SR^a$, —$S(=O)R^b$, —$S(=O)_2R^b$, —$S(=O)_2NR^aR^a$, —$NR^aR^a$, —$N(R^a)C(=O)R^b$, —$N(R^a)C(=O)OR^b$, —$N(R^a)C(=O)NR^aR^a$, —$N(R^a)C(=NR^a)NR^aR^a$, —$N(R^a)S(=O)_2R^b$, —$N(R^a)S(=O)_2NR^aR^a$, —$NR^aC_{2-6}$alkNR$^a$R$^a$, —$NR^aC_{2-6}$alkOR$^a$, —$C_{1-6}$alkNR$^a$R$^a$, —$C_{1-6}$alkOR$^a$, —$C_{1-6}$alkN(R$^a$)C(=O)R$^b$, —$C_{1-6}$alkOC(=O)R$^b$, —$C_{1-6}$alkC(=O)NR$^a$R$^a$, —$C_{1-6}$alkC(=O)OR$^a$ and oxo.

In another embodiment, in conjunction with any above or below embodiment, $R^c$ is a saturated, partially-saturated or unsaturated 3-, 4-, 5-, 6-, or 7-membered monocyclic ring containing 0, 1, 2 or 3 N atoms and 0 or 1 atoms selected from O and S, which is substituted by 0, 1, 2 or 3 groups selected from F, Cl, Br, $C_{1-6}$alk, $C_{1-4}$haloalk, —$OR^a$, —$OC_{1-4}$haloalk, CN, —$C(=O)R^b$, —$C(=O)OR^a$, —$C(=O)NR^aR^a$, —$C(=NR^a)NR^aR^a$, —$OC(=O)R^b$, —$OC(=O)NR^aR^a$, —$OC_{2-6}$alkNR$^a$R$^a$, —$OC_{2-6}$alkOR$^a$, —$SR^a$, —$S(=O)R^b$, —$S(=O)_2R^b$, —$S(=O)_2NR^aR^a$, —$NR^aR^a$, —$N(R^a)C(=O)R^b$, —$N(R^a)C(=O)OR^b$, —$N(R^a)C(=O)NR^aR^a$, —$N(R^a)C(=NR^a)NR^aR^a$, —$N(R^a)S(=O)_2R^b$, —$N(R^a)S(=O)_2NR^aR^a$, —$NR^aC_{2-6}$alkNR$^a$R$^a$, —$NR^aC_{2-6}$alkOR$^a$, —$C_{1-6}$alkNR$^a$R$^a$, —$C_{1-6}$alkOR$^a$, —$C_{1-6}$alkN(R$^a$)C(=O)R$^b$, —$C_{1-6}$alkOC(=O)R$^b$, —$C_{1-6}$alkC(=O)NR$^a$R$^a$, —$C_{1-6}$alkC(=O)OR$^a$ and oxo.

$R^c$ is a $C_1$alk-linked saturated, partially-saturated or unsaturated 3-, 4-, 5-, 6-, or 7-membered monocyclic ring containing 0, 1, 2 or 3 N atoms and 0 or 1 atoms selected from O and S, which is substituted by 0, 1, 2 or 3 groups selected from F, Cl, Br, $C_{1-6}$alk, $C_{1-4}$haloalk, —$OR^a$, —$OC_{1-4}$haloalk, CN, —$C(=O)R^b$, —$C(=O)OR^a$, —$C(=O)NR^aR^a$, —$C(=NR^a)NR^aR^a$, —$OC(=O)R^b$, —$OC(=O)NR^aR^a$, —$OC_{2-6}$alkNR$^a$R$^a$, —$OC_{2-6}$alkOR$^a$, —$SR^a$, —$S(=O)R^b$, —$S(=O)_2R^b$, —$S(=O)_2NR^aR^a$, —$NR^aR^a$, —$N(R^a)C(=O)R^b$, —$N(R^a)C(=O)OR^b$, —$N(R^a)C(=O)NR^aR^a$, —$N(R^a)C(=NR^a)NR^aR^a$, —$N(R^a)S(=O)_2R^b$, —$N(R^a)S(=O)_2NR^aR^a$, —$NR^aC_{2-6}$alkNR$^a$R$^a$, —$NR^aC_{2-6}$alkOR$^a$, —$C_{1-6}$alkNR$^a$R$^a$, —$C_{1-6}$alkOR$^a$, —$C_{1-6}$alkN(R$^a$)C(=O)R$^b$, —$C_{1-6}$alkOC(=O)R$^b$, —$C_{1-6}$alkC(=O)NR$^a$R$^a$, —$C_{1-6}$alkC(=O)OR$^a$ and oxo.

In another embodiment, in conjunction with any above or below embodiment, $X^1$ is N and $X^2$ is CH.

In another embodiment, in conjunction with any above or below embodiment, $X^2$ is N and $X^1$ is CH.

In another embodiment, in conjunction with any above or below embodiment, $X^1$ is CH and $X^2$ is CH.

Another aspect of the invention relates to a method of treating schizophrenia, bipolar disorder, or obsessive-compulsive disorder using an effective amount of a compound of formula (V).

Another aspect of the invention relates to a method of treating a disorder treatable by inhibition of PDE10 in a patient which method comprises administering to the patient a pharmaceutical composition comprising an effective amount of a compound of formula (V).

Another aspect of the invention relates to a pharmaceutical composition comprising a compound of formula (V) and a pharmaceutically-acceptable diluent or carrier.

Another aspect of the invention relates to the use of a compound according to any of the above embodiments as a medicament.

Another aspect of the invention relates to the use of a compound according to any of the above embodiments in the manufacture of a medicament for the treatment of schizophrenia, bipolar disorder, or obsessive-compulsive disorder.

Another aspect of the invention relates to a compound, or a pharmaceutically acceptable salt thereof, selected from the group consisting of:

N-(4-(3-(trifluoromethyl)pyridin-2-yloxy)phenyl)pyridin-2-amine;

4-Methyl-N-(4-(3-(trifluoromethyl)pyridin-2-yloxy)phenyl)pyridin-2-amine;

5-chloro-N-(4-(3-(trifluoromethyl)pyridin-2-yloxy)phenyl)pyridin-2-amine;
5-fluoro-3-methyl-N-(4-(3-(trifluoromethyl)pyridin-2-yloxy)phenyl)pyridin-2-amine;
3-(trifluoromethyl)-N-(4-(3-(trifluoromethyl)pyridin-2-yloxy)phenyl)pyridin-2-amine;
6-tert-butoxy-N-(4-(3-(trifluoromethyl)pyridin-2-yloxy)phenyl)pyridin-2-amine;
6-methoxy-N-(4-(3-(trifluoromethyl)pyridin-2-yloxy)phenyl)pyridin-2-amine;
6-(trifluoromethyl)-N-(4-(3-(trifluoromethyl)pyridin-2-yloxy)phenyl)pyridin-2-amine;
4-chloro-N-(4-(3-(trifluoromethyl)pyridin-2-yloxy)phenyl)pyridin-2-amine;
6-methyl-N-(4-(3-(trifluoromethyl)pyridin-2-yloxy)phenyl)pyridin-2-amine;
5-(morpholinomethyl)-N-(4-(3-(trifluoromethyl)pyridin-2-yloxy)phenyl)pyridin-2-amine;
6-methyl-N-(4-(3-(trifluoromethyl)pyridin-2-yloxy)phenyl)pyridin-2-amine;
N-(4-(3-(trifluoromethyl)pyridin-2-yloxy)phenyl)pyrimidin-2-amine;
N-(4-(3-cyclopropylpyridin-2-yloxy)phenyl)-3-fluoro-5-methylpyridin-2-amine;
N-(4-(3,4'-bipyridin-2-yloxy)phenyl)-4-chloropyridin-2-amine;
2-(4-(3,4'-bipyridin-2-yloxy)phenylamino)isonicotinonitrile;
2-(4-(3-phenylpyridin-2-yloxy)phenylamino)isonicotinonitrile;
3-fluoro-N-(4-(3-phenylpyridin-2-yloxy)phenyl)pyridin-2-amine;
N-(4-(3-phenylpyridin-2-yloxy)phenyl)-4-(trifluoromethyl)pyridin-2-amine;
4-methyl-N-(4-(3-phenylpyridin-2-yloxy)phenyl)pyridin-2-amine;
N-(4-(3-(pyrimidin-4-yl)pyridin-2-yloxy)phenyl)pyridin-2-amine;
N-(4-(3-(pyrimidin-4-yl)pyridin-2-yloxy)phenyl)-5-(trifluoromethyl)pyridin-2-amine;
4-fluoro-N-(4-(3-(pyrimidin-4-yl)pyridin-2-yloxy)phenyl)pyridin-2-amine;
N-(4-(3-(pyrimidin-4-yl)pyridin-2-yloxy)phenyl)-6-(trifluoromethyl)pyridin-2-amine;
N-(4-(3-(pyrimidin-4-yl)pyridin-2-yloxy)phenyl)-4-(trifluoromethyl)pyridin-2-amine;
2-(4-(3-(pyrimidin-4-yl)pyridin-2-yloxy)phenylamino)isonicotinonitrile;
N-(4-(3-phenylpyridin-2-yloxy)phenyl)pyridin-2-amine;
N-(4-(2'-(methylamino)-3,4'-bipyridin-2-yloxy)phenyl)quinolin-2-amine;
N-(4-(3,4'-bipyridin-2-yloxy)phenyl)quinolin-2-amine;
N-(4-(3-(2-Methylpyridin-4-yl)pyridin-2-yloxy)phenyl)pyridin-2-amine;
N-(4-(3-(2-Methylpyridin-4-yl)pyridin-2-yloxy)phenyl)pyridin-2-amine;
N-(4-(3-(pyrrolidin-1-yl)pyridin-2-yloxy)phenyl)pyridin-2-amine;
(S)—N-(4-(3-(2-(methoxymethyl)pyrrolidin-1-yl)pyridin-2-yloxy)phenyl)pyridin-2-amine;
N-(4-(3-(3-(methoxymethyl)pyrrolidin-1-yl)pyridin-2-yloxy)phenyl)pyridin-2-amine;
(R)-1-(2-(4-(pyridin-2-ylamino)phenoxy)pyridin-3-yl)pyrrolidin-3-ol;
(S)-1-(2-(4-(pyridin-2-ylamino)phenoxy)pyridin-3-yl)pyrrolidin-3-ol;
1-(2-(4-(pyridin-2-ylamino)phenoxy)pyridin-3-yl)piperidine-4-carbonitrile;
1-(2-(4-(pyridin-2-ylamino)phenoxy)pyridin-3-yl)piperidine-3-carbonitrile;
(R)-(1-(2-(4-(pyridin-2-ylamino)phenoxy)pyridin-3-yl)pyrrolidin-3-yl)methanol;
(S)-(1-(2-(4-(pyridin-2-ylamino)phenoxy)pyridin-3-yl)pyrrolidin-3-yl)methanol;
(S)-(1-(2-(4-(pyridin-2-ylamino)phenoxy)pyridin-3-yl)pyrrolidin-2-yl)methanol;
(R)-(1-(2-(4-(pyridin-2-ylamino)phenoxy)pyridin-3-yl)pyrrolidin-2-yl)methanol;
1-(2-(4-(pyridin-2-ylamino)phenoxy)pyridin-3-yl)pyrrolidine-3-carbonitrile;
N-(4-(3-(3-methoxypyrrolidin-1-yl)pyridin-2-yloxy)phenyl)pyridin-2-amine;
N-(4-(3-(3-(3-methyl-1,2,4-oxadiazol-5-yl)pyrrolidin-1-yl)pyridin-2-yloxy)phenyl)pyridin-2-amine;
N-(4-(3-(piperidin-1-yl)pyridin-2-yloxy)phenyl)pyridin-2-amine;
1-(2-(4-(pyridin-2-ylamino)phenoxy)pyridin-3-yl)piperidin-4-ol;
1-(2-(4-(pyridin-2-ylamino)phenoxy)pyridin-3-yl)piperidin-3-ol;
N-(4-(3-(4-methoxypiperidin-1-yl)pyridin-2-yloxy)phenyl)pyridin-2-amine;
methyl 1-(2-(4-(pyridin-2-ylamino)phenoxy)pyridin-3-yl)piperidine-4-carboxylate;
2-(1-(2-(4-(pyridin-2-ylamino)phenoxy)pyridin-3-yl)piperidin-4-yl)propan-2-ol;
N-(4-(3-(4-(methoxymethyl)piperidin-1-yl)pyridin-2-yloxy)phenyl)pyridin-2-amine;
1-(2-(4-(pyridin-2-ylamino)phenoxy)pyridin-3-yl)piperidin-4-one;
methyl 1-(2-(4-(pyridin-2-ylamino)phenoxy)pyridin-3-yl)pyrrolidine-3-carboxylate;
N-(4-(3-(4-methylpiperazin-1-yl)pyridin-2-yloxy)phenyl)pyridin-2-amine;
2-(4-(2-(4-(pyridin-2-ylamino)phenoxy)pyridin-3-yl)piperazin-1-yl)ethanol;
(R)-tert-butyl 1-(2-(4-(pyridin-2-ylamino)phenoxy)pyridin-3-yl)pyrrolidin-3-ylcarbamate;
(S)-tert-butyl 1-(2-(4-(pyridin-2-ylamino)phenoxy)pyridin-3-yl)pyrrolidin-3-ylcarbamate;
(1-(2-(4-(pyridin-2-ylamino)phenoxy)pyridin-3-yl)piperidin-3-yl)methanol;
ethyl 1-(2-(4-(pyridin-2-ylamino)phenoxy)pyridin-3-yl)piperidine-3-carboxylate;
N-methyl-1-(2-(4-(pyridin-2-ylamino)phenoxy)pyridin-3-yl)piperidine-4-carboxamide;
N-(4-(3-(pyridin-4-ylamino)pyridin-2-yloxy)phenyl)pyridin-2-amine;
methyl 4-(2-(4-(pyridin-2-ylamino)phenoxy)pyridin-3-ylamino)benzoate;
(1-(2-(4-(pyridin-2-ylamino)phenoxy)pyridin-3-yl)piperidin-4-yl)methanol;
1-(3-(4-(Pyridin-2-ylamino)phenoxy)pyrazin-2-yl)piperidine-4-carbonitrile;
2-(1-(3-(4-(pyridin-2-ylamino)phenoxy)pyrazin-2-yl)pyrrolidin-3-yl)propan-2-ol;
2-(1-(3-(4-(pyridin-2-ylamino)phenoxy)pyrazin-2-yl)piperidin-4-yl)propan-2-ol;
1-(3-(4-(pyridin-2-ylamino)phenoxy)pyrazin-2-yl)piperidin-4-ol;
1-(3-(4-(pyridin-2-ylamino)phenoxy)pyrazin-2-yl)piperidin-3-ol;

N-(4-(3-(pyrrolidin-1-yl)pyrazin-2-yloxy)phenyl)pyridin-2-amine;
N-(4-(3-(2,6-dimethylmorpholino)pyrazin-2-yloxy)phenyl)pyridin-2-amine;
(S)—N-(4-(3-(2-(methoxymethyl)pyrrolidin-1-yl)pyrazin-2-yloxy)phenyl)pyridin-2-amine;
(S)-(1-(3-(4-(pyridin-2-ylamino)phenoxy)pyrazin-2-yl)pyrrolidin-2-yl)methanol;
1-(3-(4-(pyridin-2-ylamino)phenoxy)pyrazin-2-yl)azetidine-3-carboxylic acid;
(R)—N-(4-(3-(2-(4-methoxyphenyl)morpholino)pyrazin-2-yloxy)phenyl)pyridin-2-amine;
(S)—N-(4-(3-(2-(4-methoxyphenyl)morpholino)pyrazin-2-yloxy)phenyl)pyridin-2-amine;
(R)—N-(4-(3-(2-(methoxymethyl)pyrrolidin-1-yl)pyrazin-2-yloxy)phenyl)pyridin-2-amine;
(R)-(1-(3-(4-(pyridin-2-ylamino)phenoxy)pyrazin-2-yl)pyrrolidin-2-yl)methanol;
(1-(3-(4-(pyridin-2-ylamino)phenoxy)pyrazin-2-yl)piperidin-3-yl)methanol;
N-(4-(3-(3-(methoxymethyl)piperidin-1-yl)pyrazin-2-yloxy)phenyl)pyridin-2-amine;
(1-(3-(4-(pyridin-2-ylamino)phenoxy)pyrazin-2-yl)piperidin-2-yl)methanol;
methyl 1-(3-(4-(pyridin-2-ylamino)phenoxy)pyrazin-2-yl)pyrrolidine-3-carboxylate;
N-cyclopropyl-3-(4-(pyridin-2-ylamino)phenoxy)pyrazin-2-amine;
N-(cyclopropylmethyl)-3-(4-(pyridin-2-ylamino)phenoxy)pyrazin-2-amine;
N-ethyl-3-(4-(pyridin-2-ylamino)phenoxy)pyrazin-2-amine;
N-isopropyl-3-(4-(pyridin-2-ylamino)phenoxy)pyrazin-2-amine;
N-benzyl-3-(4-(pyridin-2-ylamino)phenoxy)pyrazin-2-amine;
3-(4-(pyridin-2-ylamino)phenoxy)-N-(pyridin-2-ylmethyl)pyrazin-2-amine;
3-(4-(pyridin-2-ylamino)phenoxy)-N-(pyridin-3-ylmethyl)pyrazin-2-amine;
3-(4-(pyridin-2-ylamino)phenoxy)-N-(pyridin-4-ylmethyl)pyrazin-2-amine;
N-phenethyl-3-(4-(pyridin-2-ylamino)phenoxy)pyrazin-2-amine;
N-(2-(pyridin-2-yl)ethyl)-3-(4-(pyridin-2-ylamino)phenoxy)pyrazin-2-amine;
3-(4-(pyridin-2-ylamino)phenoxy)-N-(2-(pyridin-3-yl)ethyl)pyrazin-2-amine;
3-(4-(pyridin-2-ylamino)phenoxy)-N-(2-(pyridin-4-yl)ethyl)pyrazin-2-amine;
3-(4-(pyridin-2-ylamino)phenoxy)-N-(tetrahydro-2H-pyran-4-yl)pyrazin-2-amine;
N-isobutyl-3-(4-(pyridin-2-ylamino)phenoxy)pyrazin-2-amine;
3-(4-(pyridin-2-ylamino)phenoxy)-N-(tetrahydrofuran-3-yl)pyrazin-2-amine;
N-(2-(piperidin-1-yl)ethyl)-3-(4-(pyridin-2-ylamino)phenoxy)pyrazin-2-amine;
tert-butyl 4-((3-(4-(pyridin-2-ylamino)phenoxy)pyrazin-2-ylamino)methyl)piperidine-1-carboxylate;
N-(2-methoxyethyl)-3-(4-(pyridin-2-ylamino)phenoxy)pyrazin-2-amine;
N-(piperidin-4-ylmethyl)-3-(4-(pyridin-2-ylamino)phenoxy)pyrazin-2-amine;
N-(4-(3-morpholinopyrazin-2-yloxy)phenyl)pyridin-2-amine;
2-(3-(4-(pyridin-2-ylamino)phenoxy)pyrazin-2-ylamino)ethanol;
N-(4-(3-(piperidin-1-yl)pyrazin-2-yloxy)phenyl)pyridin-2-amine;
(R)-1-(3-(4-(pyridin-2-ylamino)phenoxy)pyrazin-2-yl)pyrrolidin-3-ol;
N-(4-(3-(4-methylpiperazin-1-yl)pyrazin-2-yloxy)phenyl)pyridin-2-amine;
N-(4-(3-(piperazin-1-yl)pyrazin-2-yloxy)phenyl)pyridin-2-amine;
N-(4-(3-(4-methoxypiperidin-1-yl)pyrazin-2-yloxy)phenyl)pyridin-2-amine;
(S)-1-(3-(4-(pyridin-2-ylamino)phenoxy)pyrazin-2-yl)pyrrolidin-3-ol;
(R)-(1-(3-(4-(pyridin-2-ylamino)phenoxy)pyrazin-2-yl)pyrrolidin-3-yl)methanol;
(S)-(1-(3-(4-(pyridin-2-ylamino)phenoxy)pyrazin-2-yl)pyrrolidin-3-yl)methanol;
N-(4-(3-(1,4-oxazepan-4-yl)pyrazin-2-yloxy)phenyl)pyridin-2-amine;
1-(4-(3-(4-(pyridin-2-ylamino)phenoxy)pyrazin-2-yl)-1,4-diazepan-1-yl)ethanone;
(rac)-N-(4-(3-(3-benzylpiperidin-1-yl)pyrazin-2-yloxy)phenyl)pyridin-2-amine;
(4-(3-chloropyrazin-2-yloxy)phenyl)(pyridin-2-yl)methanone;
1-(4-(3-(4-Picolinoylphenoxy)pyrazin-2-yl)piperazin-1-yl)ethanone;
(S)-(4-(3-(2-(methoxymethyl)pyrrolidin-1-yl)pyrazin-2-yloxy)phenyl)(pyridin-2-yl)methanone;
(4-(3-morpholinopyrazin-2-yloxy)phenyl)(pyridin-2-yl)methanone;
1-(3-(4-picolinoylphenoxy)pyrazin-2-yl)piperidine-4-carbonitrile;
(4-(3-(4-(2-hydroxyethyl)piperazin-1-yl)pyrazin-2-yloxy)phenyl)(pyridin-2-yl)methanone;
N-(4-(3,3'-Bipyridin-2-yloxy)phenyl)pyridin-2-amine;
N-(4-(2'-methoxy-3,3'-bipyridin-2-yloxy)phenyl)pyridin-2-amine;
3-(2-(4-(pyridin-2-ylamino)phenoxy)pyridin-3-yl)benzonitrile;
N-(4-(3-(4-methoxyphenyl)pyridin-2-yloxy)phenyl)pyridin-2-amine;
4-(2-(4-(pyridin-2-ylamino)phenoxy)pyridin-3-yl)phenol;
3-(2-(4-(pyridin-2-ylamino)phenoxy)pyridin-3-yl)phenol;
(3-(2-(4-(pyridin-2-ylamino)phenoxy)pyridin-3-yl)phenyl)methanol;
4-(2-(4-(pyridin-2-ylamino)phenoxy)pyridin-3-yl)benzoic acid;
N-(4-(3-(3-(aminomethyl)phenyl)pyridin-2-yloxy)phenyl)pyridin-2-amine;
4-(2-(4-(pyridin-2-ylamino)phenoxy)pyridin-3-yl)benzonitrile;
tert-butyl 4-(2-(4-(pyridin-2-ylamino)phenoxy)pyridin-3-yl)-5,6-dihydropyridine-1(2H)-carboxylate;
N-(4-(6'-methoxy-3,3'-bipyridin-2-yloxy)phenyl)pyridin-2-amine;
N-(4-(3-(pyrimidin-5-yl)pyridin-2-yloxy)phenyl)pyridin-2-amine;
N-(4-(5'-methoxy-3,3'-bipyridin-2-yloxy)phenyl)pyridin-2-amine;
N-(4-(3-(3-methoxyphenyl)pyridin-2-yloxy)phenyl)pyridin-2-amine;
2'-(4-(pyridin-2-ylamino)phenoxy)-3,3'-bipyridine-5-carbonitrile;
N-(4-(5'-fluoro-3,3'-bipyridin-2-yloxy)phenyl)pyridin-2-amine;

N-(4-(3-(3-(methylthio)phenyl)pyridin-2-yloxy)phenyl)pyridin-2-amine;
N-(4-(3-(4-(methylthio)phenyl)pyridin-2-yloxy)phenyl)pyridin-2-amine;
N-(4-(3-m-tolylpyridin-2-yloxy)phenyl)pyridin-2-amine;
N-(4-(3-(3-fluorophenyl)pyridin-2-yloxy)phenyl)pyridin-2-amine;
N-(4-(3-(3,5-difluorophenyl)pyridin-2-yloxy)phenyl)pyridin-2-amine;
N-(4-(3-(3,4-difluorophenyl)pyridin-2-yloxy)phenyl)pyridin-2-amine;
N-(4-(3-(3-fluoro-4-methoxyphenyl)pyridin-2-yloxy)phenyl)pyridin-2-amine;
N-(4-(3-cyclohexenylpyridin-2-yloxy)phenyl)pyridin-2-amine;
N-(4-(3-cyclohexylpyridin-2-yloxy)phenyl)pyridin-2-amine;
N-(4-(3-cyclopentenylpyridin-2-yloxy)phenyl)pyridin-2-amine;
N-(4-(3-cyclopentylpyridin-2-yloxy)phenyl)pyridin-2-amine;
3-fluoro-N-(4-(2'-methoxy-3,3'-bipyridin-2-yloxy)phenyl)pyridin-2-amine;
N-(4-(3-(isoquinolin-5-yl)pyridin-2-yloxy)phenyl)pyridin-2-amine;
5-(2-(4-(pyridin-2-ylamino)phenoxy)pyridin-3-yl)pyrimidin-2-amine;
N-(4-(3-(quinolin-5-yl)pyridin-2-yloxy)phenyl)pyridin-2-amine;
N-(4-(3-(1-methyl-1H-benzo[d]imidazol-6-yl)pyridin-2-yloxy)phenyl)pyridin-2-amine;
N-(4-(3-(2-methoxypyrimidin-5-yl)pyridin-2-yloxy)phenyl)pyridin-2-amine;
5-chloro-3-fluoro-N-(4-(2'-methoxy-3,3'-bipyridin-2-yloxy)phenyl)pyridin-2-amine;
3-(2-(4-(Pyridin-2-ylamino)phenoxy)pyridin-3-yl)prop-2-yn-1-ol;
N-(4-(3-(3-methoxyprop-1-ynyl)pyridin-2-yloxy)phenyl)pyridin-2-amine;
N-(4-(3-(3-methylbut-1-ynyl)pyridin-2-yloxy)phenyl)pyridin-2-amine;
2-methyl-4-(2-(4-(pyridin-2-ylamino)phenoxy)pyridin-3-yl)but-3-yn-2-ol;
(S)-4-(2-(4-(pyridin-2-ylamino)phenoxy)pyridin-3-yl)but-3-yn-2-ol;
N-(2-fluoro-4-(3-(2-methoxypyridin-3-yl)pyrazin-2-yloxy)phenyl)pyridin-2-amine;
N-(4-(3-(3-aminophenyl)pyrazin-2-yloxy)phenyl)pyridin-2-amine;
4-(3-(4-(pyridin-2-ylamino)phenoxy)pyrazin-2-yl)benzonitrile;
3-(3-(4-(pyridin-2-ylamino)phenoxy)pyrazin-2-yl)benzonitrile;
N-(4-(3-(4-aminophenyl)pyrazin-2-yloxy)phenyl)pyridin-2-amine;
N-(4-(3-phenylpyrazin-2-yloxy)phenyl)pyridin-2-amine;
N-(4-(3-(pyridin-3-yl)pyrazin-2-yloxy)phenyl)pyridin-2-amine;
(3-(3-(4-(pyridin-2-ylamino)phenoxy)pyrazin-2-yl)phenyl)methanol;
N-(4-(3-(isoquinolin-5-yl)pyrazin-2-yloxy)phenyl)pyridin-2-amine;
N-(4-(3-(3-chlorophenyl)pyrazin-2-yloxy)phenyl)pyridin-2-amine;
N-(4-(3-(3-(aminomethyl)phenyl)pyrazin-2-yloxy)phenyl)pyridin-2-amine;
N-(4-(3-(4-methoxyphenyl)pyrazin-2-yloxy)phenyl)pyridin-2-amine;
N-(4-(3-(2-methoxyphenyl)pyrazin-2-yloxy)phenyl)pyridin-2-amine;
N-(4-(3-(benzo[d][1,3]dioxol-5-yl)pyrazin-2-yloxy)phenyl)pyridin-2-amine;
N-(4-(3-(3-methoxyphenyl)pyrazin-2-yloxy)phenyl)pyridin-2-amine;
2-fluoro-3-(3-(4-(pyridin-2-ylamino)phenoxy)pyrazin-2-yl)benzonitrile;
N-(4-(3-(quinolin-5-yl)pyrazin-2-yloxy)phenyl)pyridin-2-amine;
4-fluoro-3-(3-(4-(pyridin-2-ylamino)phenoxy)pyrazin-2-yl)benzonitrile;
N-(4-(3-(pyrimidin-5-yl)pyrazin-2-yloxy)phenyl)pyridin-2-amine;
3-(3-(4-(pyridin-2-ylamino)phenoxy)pyrazin-2-yl)phenol;
N-(4-(3-(quinolin-4-yl)pyrazin-2-yloxy)phenyl)pyridin-2-amine;
N-(4-(3-(1-methyl-1H-benzo[d]imidazol-6-yl)pyrazin-2-yloxy)phenyl)pyridin-2-amine;
N-(4-(3-(naphthalen-1-yl)pyrazin-2-yloxy)phenyl)pyridin-2-amine;
5-(3-(4-(pyridin-2-ylamino)phenoxy)pyrazin-2-yl)pyrimidin-2-amine;
N-(4-(3-(2-methoxypyrimidin-5-yl)pyrazin-2-yloxy)phenyl)pyridin-2-amine;
N-(4-(3-(1-(piperidin-4-yl)-1H-pyrazol-4-yl)pyrazin-2-yloxy)phenyl)pyridin-2-amine;
N-(4-(3-(benzo[b]thiophen-7-yl)pyrazin-2-yloxy)phenyl)pyridin-2-amine;
N-(4-(3-(pyridin-3-yl)pyrazin-2-yloxy)phenyl)pyridin-2-amine;
N-(4-(3-cyclohexenylpyrazin-2-yloxy)phenyl)pyridin-2-amine;
N-(4-(3-cyclopentenylpyrazin-2-yloxy)phenyl)pyridin-2-amine;
N-(4-(3-(2-Methoxypyridin-3-yl)pyrazin-2-yloxy)phenyl)pyridin-2-amine;
N-(4-(3-benzylpyrazin-2-yloxy)phenyl)pyridin-2-amine;
tert-butyl 2-(3-(4-(pyridin-2-ylamino)phenoxy)pyrazin-2-yl)acetate;
pyridin-2-yl(4-(3-(pyridin-4-yl)pyrazin-2-yloxy)phenyl)methanone;
pyridin-2-yl(4-(3-(pyrimidin-5-yl)pyrazin-2-yloxy)phenyl)methanone;
N-(4-(3-(Tetrahydro-2H-pyran-4-yl)pyridin-2-yloxy)phenyl)quinolin-2-amine;
3,5-difluoro-N-(4-(3-(tetrahydro-2H-pyran-4-yl)pyridin-2-yloxy)phenyl)pyridin-2-amine;
5-methyl-N-(4-(3-(tetrahydro-2H-pyran-4-yl)pyridin-2-yloxy)phenyl)pyridin-2-amine;
5-chloro-N-(4-(3-(tetrahydro-2H-pyran-4-yl)pyridin-2-yloxy)phenyl)pyridin-2-amine;
6-(4-(3-(tetrahydro-2H-pyran-4-yl)pyridin-2-yloxy)phenylamino)nicotinonitrile;
3-Methyl-N-(4-(3-(tetrahydro-2H-pyran-4-yl)pyridin-2-yloxy)phenyl)pyridin-2-amine;
N-(4-(3-(3,6-dihydro-2H-pyran-4-yl)pyridin-2-yloxy)phenyl)pyridin-2-amine;
N-(4-(3-(tetrahydro-2H-pyran-4-yl)pyridin-2-yloxy)phenyl)pyridin-2-amine;
4-(2-(4-(pyridin-2-ylamino)phenoxy)pyridin-3-yl)tetrahydro-2H-pyran-4-ol;
(1S,4R)-4-(2-(4-(pyridin-2-ylamino)phenoxy)pyridin-3-yl)cyclohexanol;

(1S,4S)-4-(2-(4-(pyridin-2-ylamino)phenoxy)pyridin-3-yl)cyclohexanol;
(1S,4S)-1-methyl-4-(2-(4-(pyridin-2-ylamino)phenoxy)pyridin-3-yl)cyclohexanol;
(1R,4R)-1-methyl-4-(2-(4-(pyridin-2-ylamino)phenoxy)pyridin-3-yl)cyclohexanol;
4-(2-(4-(pyridin-2-ylamino)phenoxy)pyridin-3-yl)cyclohexanone;
N-(4-(3-(tetrahydro-2H-pyran-3-yl)pyridin-2-yloxy)phenyl)pyridin-2-amine;
(rac)-cis-3-(2-(4-(Pyridin-2-ylamino)phenoxy)pyridin-3-yl)cyclohexanol;
(rac)-E-1-Methyl-3-(2-(4-(pyridin-2-ylamino)phenoxy)pyridin-3-yl)cyclohexanol;
(rac)-Z-1-Methyl-3-(2-(4-(pyridin-2-ylamino)phenoxy)pyridin-3-yl)cyclohexanol;
(±)-N-(4-(3-(tetrahydro-2H-pyran-2-yl)pyridin-2-yloxy)phenyl)pyridin-2-amine;
N-(4-(3-(tetrahydrofuran-2-yl)pyridin-2-yloxy)phenyl)pyridin-2-amine;
N-(4-(3-(tetrahydrofuran-3-yl)pyridin-2-yloxy)phenyl)pyridin-2-amine;
3-(2-(4-(pyridin-2-ylamino)phenoxy)pyridin-3-yl)cyclopent-2-enone;
3-(2-(4-(pyridin-2-ylamino)phenoxy)pyridin-3-yl)cyclopentanol;
1-methyl-3-(2-(4-(pyridin-2-ylamino)phenoxy)pyridin-3-yl)cyclopentanol;
N-(4-(3-(oxepan-4-yl)pyridin-2-yloxy)phenyl)pyridin-2-amine;
3-fluoro-N-(4-(3-(tetrahydro-2H-pyran-4-yl)pyrazin-2-yloxy)phenyl)pyridin-2-amine;
3,5-difluoro-N-(4-(3-(tetrahydro-2H-pyran-4-yl)pyridin-2-yloxy)phenyl)pyridin-2-amine;
N-(2-Fluoro-4-(3-(tetrahydro-2H-pyran-4-yl)pyrazin-2-yloxy)phenyl)pyridin-2-amine;
5-Methyl-N-(4-(3-(tetrahydro-2H-pyran-4-yl)pyrazin-2-yloxy)phenyl)pyridin-2-amine;
N-(4-(3-(Tetrahydro-2H-pyran-4-yl)pyrazin-2-yloxy)phenyl)-5-(trifluoromethyl)pyridin-2-amine;
5-Ethyl-N-(4-(3-(tetrahydro-2H-pyran-4-yl)pyrazin-2-yloxy)phenyl)pyridin-2-amine;
5-Methoxy-N-(4-(3-(tetrahydro-2H-pyran-4-yl)pyrazin-2-yloxy)phenyl)pyridin-2-amine;
N-(4-(3-(tetrahydro-2H-pyran-3-yl)pyrazin-2-yloxy)phenyl)pyridin-2-amine;
(rac)-cis-3-(3-(4-(Pyridin-2-ylamino)phenoxy)pyrazin-2-yl)cyclohexanol;
(rac)-trans-3-(3-(4-(Pyridin-2-ylamino)phenoxy)pyrazin-2-yl)cyclohexanol;
N-(4-(3-(Tetrahydrofuran-3-yl)pyridin-2-yloxy)phenyl)pyridin-2-amine;
N-(4-(3-(2,3-dihydrofuran-3-yl)pyridin-2-yloxy)phenyl)pyridin-2-amine;
N-(4-(3-(tetrahydrofuran-3-yl)pyrazin-2-yloxy)phenyl)pyridin-2-amine;
N-(4-(pyrazin-2-yloxy)phenyl)pyridin-2-amine;
((1R,3R)-3-(2-(4-(pyridin-2-ylamino)phenoxy)pyridin-3-yl)cyclopentyl)methanol;
((1S,3R)-3-(2-(4-(pyridin-2-ylamino)phenoxy)pyridin-3-yl)cyclopentyl)methanol;
((1R,3S)-3-(2-(4-(pyridin-2-ylamino)phenoxy)pyridin-3-yl)cyclopentyl)methanol;
((1S,3S)-3-(2-(4-(pyridin-2-ylamino)phenoxy)pyridin-3-yl)cyclopentyl)methanol;
Pyridin-2-yl(4-(3-(tetrahydro-2H-pyran-4-yl)pyridin-2-yloxy)phenyl)methanone;
1-(4-(2-(4-(pyridin-2-ylamino)phenoxy)pyridin-3-yl)-5,6-dihydropyridin-1(2H)-yl)ethanone;
1-(4-(2-(4-(pyridin-2-ylamino)phenoxy)pyridin-3-yl)piperidin-1-yl)ethanone;
1-(4-(2-(4-(5-Methylpyridin-2-ylamino)phenoxy)pyridin-3-yl)piperidin-1-yl)ethanone;
1-(4-(2-(4-(3-Fluoropyridin-2-ylamino)phenoxy)pyridin-3-yl)piperidin-1-yl)ethanone;
1-(4-(2-(4-(4-Fluoropyridin-2-ylamino)phenoxy)pyridin-3-yl)piperidin-1-yl)ethanone;
1-(4-(2-(4-(6-Methylpyridin-2-ylamino)phenoxy)pyridin-3-yl)piperidin-1-yl)ethanone;
1-(4-(2-(4-(5-Chloropyridin-2-ylamino)phenoxy)pyridin-3-yl)piperidin-1-yl)ethanone;
1-(4-(2-(4-(5-Fluoropyridin-2-ylamino)phenoxy)pyridin-3-yl)piperidin-1-yl)ethanone;
1-(4-(2-(4-(5-Methoxypyridin-2-ylamino)phenoxy)pyridin-3-yl)piperidin-1-yl)ethanone;
1-(4-(3-(4-(pyridin-2-ylamino)phenoxy)pyrazin-2-yl)piperidin-1-yl)ethanone;
1-(4-(3-(2-fluoro-4-(pyridin-2-ylamino)phenoxy)pyrazin-2-yl)piperidin-1-yl)ethanone;
1-(4-(3-(4-(5-Methylpyridin-2-ylamino)phenoxy)pyrazin-2-yl)piperidin-1-yl)ethanone;
1-(4-(3-(4-(5-Chloropyridin-2-ylamino)phenoxy)pyrazin-2-yl)piperidin-1-yl)ethanone;
tert-butyl 4-(3-(4-(pyridin-2-ylamino)phenoxy)pyrazin-2-yl)-5,6-dihydropyridine-1(2H)-carboxylate;
N-(4-(3-(piperidin-4-yl)pyrazin-2-yloxy)phenyl)pyridin-2-amine;
2,2,2-trifluoro-1-(4-(3-(4-(pyridin-2-ylamino)phenoxy)pyrazin-2-yl)piperidin-1-yl)ethanone;
1-(4-(3-(4-(pyridin-2-ylamino)phenoxy)pyrazin-2-yl)-5,6-dihydropyridin-1(2H)-yl)ethanone;
2-methoxy-1-(4-(3-(4-(5-methylpyridin-2-ylamino)phenoxy)pyrazin-2-yl)piperidin-1-yl)ethanone;
methyl 4-(3-(4-(5-methylpyridin-2-ylamino)phenoxy)pyrazin-2-yl)piperidine-1-carboxylate;
(R)-2-methoxy-1-(4-(3-(4-(5-methylpyridin-2-ylamino)phenoxy)pyrazin-2-yl)piperidin-1-yl)propan-1-one;
(S)-2-methoxy-1-(4-(3-(4-(5-methylpyridin-2-ylamino)phenoxy)pyrazin-2-yl)piperidin-1-yl)propan-1-one;
2-methyl-1-(4-(3-(4-(pyridin-2-ylamino)phenoxy)pyrazin-2-yl)piperidin-1-yl)propan-1-one;
N-(4-(3-(1-(methylsulfonyl)piperidin-4-yl)pyrazin-2-yloxy)phenyl)pyridin-2-amine;
methyl 4-(3-(4-(pyridin-2-ylamino)phenoxy)pyrazin-2-yl)piperidine-1-carboxylate;
tert-butyl 4-(2-(4-(5-methylpyridin-2-ylamino)phenoxy)pyridin-3-yl)-5,6-dihydropyridine-1(2H)-carboxylate;
tert-butyl 4-(2-(4-(5-methylpyridin-2-ylamino)phenoxy)pyridin-3-yl)piperidine-1-carboxylate;
5-methyl-N-(4-(3-(1-(methylsulfonyl)piperidin-4-yl)pyridin-2-yloxy)phenyl)pyridin-2-amine;
methyl 4-(2-(4-(5-methylpyridin-2-ylamino)phenoxy)pyridin-3-yl)piperidine-1-carboxylate;
2-methyl-1-(4-(2-(4-(5-methylpyridin-2-ylamino)phenoxy)pyridin-3-yl)piperidin-1-yl)propan-1-one;
2-methoxy-1-(4-(2-(4-(5-methylpyridin-2-ylamino)phenoxy)pyridin-3-yl)piperidin-1-yl)ethanone;
5-methyl-N-(4-(3-(1-(methylsulfonyl)piperidin-4-yl)pyrazin-2-yloxo)phenyl)pyridine-2-amine;
2-methyl-1-(4-(3-(4-(5-methylpyridin-2-ylamino)phenoxy)pyrazin-2-yl)piperidin-1-yl)propan-1-one;
ethyl 4-(3-(4-(5-methylpyridin-2-ylamino)phenoxy)pyrazin-2-yl)piperidine-1-carboxylate;

cyclopropyl(4-(3-(4-(5-methylpyridin-2-ylamino)phenoxy)pyrazin-2-yl)piperidin-1-yl)methanone;
N,N-dimethyl-4-(3-(4-(5-methylpyridin-2-ylamino)phenoxy)pyrazin-2-yl)piperidine-1-carboxamide;
(rac) N-(4-((3-((3)-1-acetyl-3-piperidinyl)-2-pyridinyl)oxy)phenyl)-2-pyridinamine;
1-(3-(2-(4-(5-methylpyridin-2-ylamino)phenoxy)pyridin-3-yl)piperidin-1-yl)ethanone;
1-Methyl-4-(2-(4-(pyridin-2-ylamino)phenoxy)pyridin-3-yl)piperidin-2-one;
1-(3-(3-(4-(pyridin-2-ylamino)phenoxy)pyrazin-2-yl)pyrrolidin-1-yl)ethanone;
1-methyl-4-(2-(4-(pyridin-2-ylamino)phenoxy)pyridin-3-yl)pyrrolidin-2-one;
N-(4-(3-cyclopentylpyrazin-2-yloxy)phenyl)pyridin-2-amine;
2-(4-(pyridin-2-ylamino)phenoxy)nicotinic acid;
3-(4-(pyridin-2-ylamino)phenoxy)pyrazine-2-carboxylic acid;
2-(4-(Pyridin-2-ylamino)phenoxy)nicotinamide;
Methyl 2-(4-(pyridin-2-ylamino)phenoxy)nicotinate;
N-Isobutyl-2-(4-(pyridin-2-ylamino)phenoxy)nicotinamide;
N-(Cyclopropylmethyl)-2-(4-(pyridin-2-ylamino)phenoxy)nicotinamide;
N-methyl-2-(4-(pyridin-2-ylamino)phenoxy)nicotinamide;
N-allyl-2-(4-(pyridin-2-ylamino)phenoxy)nicotinamide;
N-(prop-2-ynyl)-2-(4-(pyridin-2-ylamino)phenoxy)nicotinamide;
N-(cyclohexylmethyl)-2-(4-(pyridin-2-ylamino)phenoxy)nicotinamide;
N,N-dimethyl-2-(4-(pyridin-2-ylamino)phenoxy)nicotinamide;
(rac)-N-(1-methoxypropan-2-yl)-2-(4-(pyridin-2-ylamino)phenoxy)nicotinamide;
(S)—N-(1-methoxypropan-2-yl)-2-(4-(pyridin-2-ylamino)phenoxy)nicotinamide;
N-phenethyl-2-(4-(pyridin-2-ylamino)phenoxy)nicotinamide;
N-(4-methylphenethyl)-2-(4-(pyridin-2-ylamino)phenoxy)nicotinamide;
2-(4-(pyridin-2-ylamino)phenoxy)-N-(4-(trifluoromethyl)phenethyl)nicotinamide;
(S)—N-(1-hydroxy-3-phenylpropan-2-yl)-2-(4-(pyridin-2-ylamino)phenoxy)nicotinamide;
(R)—N-(1-hydroxy-3-phenylpropan-2-yl)-2-(4-(pyridin-2-ylamino)phenoxy)nicotinamide;
(S)—N-(1-methoxy-3-phenylpropan-2-yl)-2-(4-(pyridin-2-ylamino)phenoxy)nicotinamide;
(S)—N-(2-phenylpropyl)-2-(4-(pyridin-2-ylamino)phenoxy)nicotinamide;
(S)—N-(1-methoxypropan-2-yl)-3-(4-(pyridin-2-ylamino)phenoxy)pyrazine-2-carboxamide;
N-phenethyl-3-(4-(pyridin-2-ylamino)phenoxy)pyrazine-2-carboxamide;
3-(4-(pyridin-2-ylamino)phenoxy)-N-(4-(trifluoromethyl)phenethyl)pyrazine-2-carboxamide;
(rac)-N-(3-methyl-2-(pyridin-2-yl)butyl)-2-(4-(pyridin-2-ylamino)phenoxy)nicotinamide;
(rac)-N-(3-methyl-2-(pyridin-2-yl)butyl)-3-(4-(pyridin-2-ylamino)phenoxy)pyrazine-2-carboxamide;
N-(2-(pyridin-2-yl)ethyl)-3-(4-(pyridin-2-ylamino)phenoxy)pyrazine-2-carboxamide;
N-(2-methyl-2-(pyridin-2-yl)propyl)-2-(4-(pyridin-2-ylamino)phenoxy)nicotinamide;
N-(2-methyl-2-(pyridin-2-yl)propyl)-3-(4-(pyridin-2-ylamino)phenoxy)pyrazine-2-carboxamide;
N-(2-hydroxyethyl)-2-(4-(pyridin-2-ylamino)phenoxy)nicotinamide;
N-(2-hydroxyethyl)-3-(4-(pyridin-2-ylamino)phenoxy)pyrazine-2-carboxamide;
(rac)-N-(1-(pyridin-2-yl)propan-2-yl)-2-(4-(pyridin-2-ylamino)phenoxy)nicotinamide;
(rac)-N-methyl-2-(4-(pyridin-2-ylamino)phenoxy)nicotinamide;
N-(1-benzylcyclopropyl)-2-(4-(pyridin-2-ylamino)phenoxy)nicotinamide;
N-(1-benzylcyclopropyl)-3-(4-(pyridin-2-ylamino)phenoxy)pyrazine-2-carboxamide;
(S)—N-(1-hydroxy-3-(4-methoxyphenyl)propan-2-yl)-2-(4-(pyridin-2-ylamino)phenoxy)nicotinamide;
(S)—N-(1-hydroxy-3-(4-hydroxyphenyl)propan-2-yl)-2-(4-(pyridin-2-ylamino)phenoxy)nicotinamide;
(R)—N-(2-phenylpropyl)-2-(4-(pyridin-2-ylamino)phenoxy)nicotinamide;
N-(2,3-dihydro-1H-inden-2-yl)-2-(4-(pyridin-2-ylamino)phenoxy)nicotinamide;
N-(1-(4-fluorophenyl)-2-methylpropan-2-yl)-2-(4-(pyridin-2-ylamino)phenoxy)nicotinamide;
(rac)-N-(1-(4-fluorophenyl)propan-2-yl)-2-(4-(pyridin-2-ylamino)phenoxy)nicotinamide;
(S)—N-(1-(4-fluorophenyl)propan-2-yl)-2-(4-(pyridin-2-ylamino)phenoxy)nicotinamide;
(R)—N-(1-(4-fluorophenyl)propan-2-yl)-2-(4-(pyridin-2-ylamino)phenoxy)nicotinamide;
N-(cyclopropylmethyl)-2-(4-(pyridin-2-ylamino)phenoxy)nicotinamide;
N-(furan-2-ylmethyl)-2-(4-(pyridin-2-ylamino)phenoxy)nicotinamide;
N-(but-3-enyl)-2-(4-(pyridin-2-ylamino)phenoxy)nicotinamide;
N-(2-methoxyethyl)-2-(4-(pyridin-2-ylamino)phenoxy)nicotinamide;
(rac)-(3-methoxypiperidin-1-yl)(2-(4-(pyridin-2-ylamino)phenoxy)pyridin-3-yl)methanone;
2-(4-(pyridin-2-ylamino)phenoxy)-N-(2-(pyridin-4-yl)ethyl)nicotinamide;
N-(2-(methylthio)ethyl)-2-(4-(pyridin-2-ylamino)phenoxy)nicotinamide;
azetidin-1-yl(2-(4-(pyridin-2-ylamino)phenoxy)pyridin-3-yl)methanone;
(rac)-N-(1-methoxybutan-2-yl)-2-(4-(pyridin-2-ylamino)phenoxy)nicotinamide;
(2-(4-(pyridin-2-ylamino)phenoxy)pyridin-3-yl)(2H-pyrrol-1(5H)-yl)methanone;
(4-methoxypiperidin-1-yl)(2-(4-(pyridin-2-ylamino)phenoxy)pyridin-3-yl)methanone;
(rac)-2-(4-(pyridin-2-ylamino)phenoxy)-N-((tetrahydrofuran-2-yl)methyl)nicotinamide;
2-(4-(pyridin-2-ylamino)phenoxy)-N-((tetrahydro-2H-pyran-4-yl)methyl)nicotinamide;
N,N-diethyl-2-(4-(pyridin-2-ylamino)phenoxy)nicotinamide;
N-(3-(methylthio)propyl)-2-(4-(pyridin-2-ylamino)phenoxy)nicotinamide;
(2-(4-(pyridin-2-ylamino)phenoxy)pyridin-3-yl)(thiazolidin-3-yl)methanone;
N-(3-chloropropyl)-2-(4-(pyridin-2-ylamino)phenoxy)nicotinamide;
N-(2-(pyridin-2-yl)ethyl)-2-(4-(pyridin-2-ylamino)phenoxy)nicotinamide;
N-(3-methoxypropyl)-2-(4-(pyridin-2-ylamino)phenoxy)nicotinamide;

(1,4-oxazepan-4-yl)(2-(4-(pyridin-2-ylamino)phenoxy)pyridin-3-yl)methanone;
N-methyl-N-(prop-2-ynyl)-2-(4-(pyridin-2-ylamino)phenoxy)nicotinamide;
(R)—N-sec-butyl-2-(4-(pyridin-2-ylamino)phenoxy)nicotinamide;
N-(3-ethoxypropyl)-2-(4-(pyridin-2-ylamino)phenoxy)nicotinamide;
((2S,6R)-2,6-dimethylmorpholino)(2-(4-(pyridin-2-ylamino)phenoxy)pyridin-3-yl)methanone;
N-(2-isopropoxyethyl)-2-(4-(pyridin-2-ylamino)phenoxy)nicotinamide;
N-allyl-N-methyl-2-(4-(pyridin-2-ylamino)phenoxy)nicotinamide;
N-isobutyl-N-methyl-2-(4-(pyridin-2-ylamino)phenoxy)nicotinamide;
N-(2-methylallyl)-2-(4-(pyridin-2-ylamino)phenoxy)nicotinamide;
(2-methylthiazolidin-3-yl)(2-(4-(pyridin-2-ylamino)phenoxy)pyridin-3-yl)methanone;
N-ethyl-N-propyl-2-(4-(pyridin-2-ylamino)phenoxy)nicotinamide;
N-propyl-2-(4-(pyridin-2-ylamino)phenoxy)nicotinamide;
N-(2-methoxyethyl)-N-methyl-2-(4-(pyridin-2-ylamino)phenoxy)nicotinamide;
N-methyl-N-propyl-2-(4-(pyridin-2-ylamino)phenoxy)nicotinamide;
(rac)-N-(2-phenylpropyl)-2-(4-(pyridin-2-ylamino)phenoxy)nicotinamide;
N-(4-methoxyphenethyl)-2-(4-(pyridin-2-ylamino)phenoxy)nicotinamide;
2-(4-(pyridin-2-ylamino)phenoxy)-N-(pyridin-3-ylmethyl)nicotinamide;
N-(4-fluorophenethyl)-2-(4-(pyridin-2-ylamino)phenoxy)nicotinamide;
N-(2-methoxyphenethyl)-2-(4-(pyridin-2-ylamino)phenoxy)nicotinamide;
N-(4-chlorophenethyl)-2-(4-(pyridin-2-ylamino)phenoxy)nicotinamide;
2-(4-(pyridin-2-ylamino)phenoxy)-N-(2-(pyridin-3-yl)ethyl)nicotinamide;
N-(2-(piperidin-1-yl)ethyl)-2-(4-(pyridin-2-ylamino)phenoxy)nicotinamide;
N-(3-fluorophenethyl)-2-(4-(pyridin-2-ylamino)phenoxy)nicotinamide;
N-(4-(dimethylamino)butyl)-2-(4-(pyridin-2-ylamino)phenoxy)nicotinamide;
N-(2-fluorophenethyl)-2-(4-(pyridin-2-ylamino)phenoxy)nicotinamide;
2-(4-(pyridin-2-ylamino)phenoxy)-N-((6-(trifluoromethyl)pyridin-3-yl)methyl)nicotinamide;
N-cyclopentyl-2-(4-(pyridin-2-ylamino)phenoxy)nicotinamide;
2-(4-(pyridin-2-ylamino)phenoxy)-N-(2-(pyrrolidin-1-yl)ethyl)nicotinamide;
N-ethyl-2-(4-(pyridin-2-ylamino)phenoxy)nicotinamide;
N-(2-chlorophenethyl)-2-(4-(pyridin-2-ylamino)phenoxy)nicotinamide;
2-(4-(pyridin-2-ylamino)phenoxy)-N-(2-(thiophen-2-yl)ethyl)nicotinamide;
N-(3-methoxyphenethyl)-2-(4-(pyridin-2-ylamino)phenoxy)nicotinamide;
N-benzyl-2-(4-(pyridin-2-ylamino)phenoxy)nicotinamide;
(2-(4-(pyridin-2-ylamino)phenoxy)pyridin-3-yl)(pyrrolidin-1-yl)methanone;
(S)—N-(1-(4-fluorophenyl)ethyl)-2-(4-(pyridin-2-ylamino)phenoxy)nicotinamide;
N-(1-hydroxy-2-methylpropan-2-yl)-2-(4-(pyridin-2-ylamino)phenoxy)nicotinamide;
N-neopentyl-2-(4-(pyridin-2-ylamino)phenoxy)nicotinamide;
N-tert-butyl-2-(4-(pyridin-2-ylamino)phenoxy)nicotinamide;
N-((1S,2R)-2-phenylcyclopropyl)-2-(4-(pyridin-2-ylamino)phenoxy)nicotinamide hydrochloride;
N-(1-(pyridin-2-yl)cyclopropyl)-2-(4-(pyridin-2-ylamino)phenoxy)nicotinamide;
N-methyl-N-(2-(pyridin-2-yl)ethyl)-2-(4-(pyridin-2-ylamino)phenoxy)nicotinamide;
N-(2-morpholinoethyl)-2-(4-(pyridin-2-ylamino)phenoxy)nicotinamide;
N-(piperidin-1-yl)-2-(4-(pyridin-2-ylamino)phenoxy)nicotinamide;
(3-(4-chlorophenoxy)azetidin-1-yl)(2-(4-(pyridin-2-ylamino)phenoxy)pyridin-3-yl)methanone;
(R)—N-(2-(methoxymethyl)pyrrolidin-1-yl)-2-(4-(pyridin-2-ylamino)phenoxy)nicotinamide;
N',N'-dimethyl-2-(4-(pyridin-2-ylamino)phenoxy)nicotinohydrazide;
N-phenyl-2-(4-(pyridin-2-ylamino)phenoxy)nicotinamide;
N-(1-ethynylcyclohexyl)-2-(4-(pyridin-2-ylamino)phenoxy)nicotinamide;
N-(2,6-dimethylpiperidin-1-yl)-2-(4-(pyridin-2-ylamino)phenoxy)nicotinamide;
(rac)-N-(2-phenylpropyl)-2-(4-(pyridin-2-ylamino)phenoxy)nicotinamide;
2-(4-(pyridin-2-ylamino)phenoxy)-N-(pyrimidin-2-yl)nicotinamide;
(rac)-N-sec-butyl-2-(4-(pyridin-2-ylamino)phenoxy)nicotinamide;
(rac)-N-(2-(1-methylpyrrolidin-2-yl)ethyl)-2-(4-(pyridin-2-ylamino)phenoxy)nicotinamide;
N-(2-cyclohexenylethyl)-2-(4-(pyridin-2-ylamino)phenoxy)nicotinamide;
N-(2-(1,3-dioxolan-2-yl)ethyl)-2-(4-(pyridin-2-ylamino)phenoxy)nicotinamide;
N-(2-(5-methyl-1H-indol-3-yl)ethyl)-2-(4-(pyridin-2-ylamino)phenoxy)nicotinamide;
N-(2-(1H-imidazol-4-yl)ethyl)-2-(4-(pyridin-2-ylamino)phenoxy)nicotinamide;
N-(2-(6-methylpyridin-2-yl)ethyl)-2-(4-(pyridin-2-ylamino)phenoxy)nicotinamide;
N-(2-cyclohexylethyl)-2-(4-(pyridin-2-ylamino)phenoxy)nicotinamide;
(rac)-N-(cyano(phenyl)methyl)-2-(4-(pyridin-2-ylamino)phenoxy)nicotinamide;
(rac)-N-(1-cyano-2-(methylamino)-2-oxoethyl)-2-(4-(pyridin-2-ylamino)phenoxy)nicotinamide;
N-(1-(hydroxymethyl)cyclopentyl)-2-(4-(pyridin-2-ylamino)phenoxy)nicotinamide;
(rac)-N-((1S,2S)-2-(benzyloxy)cyclopentyl)-2-(4-(pyridin-2-ylamino)phenoxy)nicotinamide;
(2-(4-(pyridin-2-ylamino)phenoxy)pyridin-3-yl)(3-(3-(trifluoromethyl)phenoxy)azetidin-1-yl)methanone;
2-(4-(pyridin-2-ylamino)phenoxy)-N-(2-(3-(pyridin-4-yl)-1H-1,2,4-triazol-5-yl)ethyl)nicotinamide;
N-(2-(4-methylthiazol-5-yl)ethyl)-2-(4-(pyridin-2-ylamino)phenoxy)nicotinamide;
N-(2-(3,5-dimethyl-1H-pyrazol-4-yl)ethyl)-2-(4-(pyridin-2-ylamino)phenoxy)nicotinamide;
N-cyclohexyl-2-(4-(pyridin-2-ylamino)phenoxy)nicotinamide;
(rac)-N-(3-methylcyclohexyl)-2-(4-(pyridin-2-ylamino)phenoxy)nicotinamide;

N-(4-methylcyclohexyl)-2-(4-(pyridin-2-ylamino)phenoxy)nicotinamide;
N-((1R,2R,4S)-bicyclo[2.2.1]heptan-2-yl)-2-(4-(pyridin-2-ylamino)phenoxy)nicotinamide;
N-(2-(1H-imidazol-4-yl)ethyl)-2-(4-(pyridin-2-ylamino)phenoxy)nicotinamide;
(1R,3S)-3-(2-(4-(pyridin-2-ylamino)phenoxy)pyridin-3-yl)cyclohexanol;
(1S,3R)-3-(2-(4-(pyridin-2-ylamino)phenoxy)pyridin-3-yl)cyclohexanol;
(1S,3S)-1-methyl-3-(2-(4-(pyridin-2-ylamino)phenoxy)pyridin-3-yl)cyclohexanol;
(1R,3R)-1-methyl-3-(2-(4-(pyridin-2-ylamino)phenoxy)pyridin-3-yl)cyclohexanol;
(1R,3R)-3-(2-(4-(pyridin-2-ylamino)phenoxy)pyridin-3-yl)cyclopentanol;
(1R,3S)-3-(2-(4-(pyridin-2-ylamino)phenoxy)pyridin-3-yl)cyclopentanol;
(1S,3R)-3-(2-(4-(pyridin-2-ylamino)phenoxy)pyridin-3-yl)cyclopentanol;
(1S,3S)-3-(2-(4-(pyridin-2-ylamino)phenoxy)pyridin-3-yl)cyclopentanol;
(1R,3S)-3-(3-(4-(pyridin-2-ylamino)phenoxy)pyrazin-2-yl)cyclohexanol;
(1S,3R)-3-(3-(4-(pyridin-2-ylamino)phenoxy)pyrazin-2-yl)cyclohexanol;
(1R,3R)-3-(3-(4-(pyridin-2-ylamino)phenoxy)pyrazin-2-yl)cyclohexanol;
(1S,3S)-3-(3-(4-(pyridin-2-ylamino)phenoxy)pyrazin-2-yl)cyclohexanol;
(S)-1-(3-(2-(4-(5-methylpyridin-2-ylamino)phenoxy)pyridin-3-yl)piperidin-1-yl)ethanone; and
(R)-1-(3-(2-(4-(5-methylpyridin-2-ylamino)phenoxy)pyridin-3-yl)piperidin-1-yl)ethanone.

Another aspect of the invention relates to a compound, or a pharmaceutically acceptable salt thereof, selected from the group consisting of:
N-(4-(3-(pyridin-4-yl)pyridin-2-yloxy)phenyl)pyridin-2-amine;
N-Methyl-4-(2-(4-(pyridin-2-ylamino)phenoxy)pyridin-3-yl)pyridin-2-amine;
N-(4-(3,4'-bipyridin-2-yloxy)phenyl)-5-fluoropyridin-2-amine;
N-(4-(3,4'-bipyridin-2-yloxy)phenyl)-4-(trifluoromethyl)pyridine-2-amine;
N-(4-(3,4'-bipyridin-2-yloxy)phenyl)-3-fluoro-5-methylpyridin-2-amine;
N-(4-(3-phenylpyridin-2-yloxy)phenyl)-5-(trifluoromethyl)pyridin-2-amine;
5-fluoro-N-(4-(2'-methyl-3,4'-bipyridin-2-yloxy)phenyl)pyridine-2-amine;
N-(4-(2'-(trifluoromethyl)-3,4'-bipyridin-2-yloxy)phenyl)pyridin-2-amine;
N-(4-(2'-Methoxy-3,4'-bipyridin-2-yloxy)phenyl)-5-methylpyridin-2-amine;
N-(4-(2'-methoxy-3,4'-bipyridin-2-yloxy)phenyl)pyridin-2-amine;
N-(4-(2'-fluoro-3,4'-bipyridin-2-yloxy)phenyl)pyridin-2-amine;
N-(4-(3-(1H-pyrazol-4-yl)pyridin-2-yloxy)phenyl)pyridin-2-amine;
N-(4-(3-(thiophen-3-yl)pyridin-2-yloxy)phenyl)pyridin-2-amine;
3-fluoro-N-(4-(2'-fluoro-3,4'-bipyridin-2-yloxy)phenyl)pyridin-2-amine;
N-(4-(3-(quinolin-4-yl)pyridin-2-yloxy)phenyl)pyridin-2-amine;
4-(2-(4-(pyridin-2-ylamino)phenoxy)pyridin-3-yl)quinoline-7-carbonitrile;
N-(4-(2'-fluoro-3,4'-bipyridin-2-yloxy)phenyl)-5-methylpyridin-2-amine;
N-(4-(3-(2-Methylpyridin-4-yl)pyrazin-2-yloxy)phenyl)pyridin-2-amine;
N-(4-(3-(1-methyl-1H-pyrazol-4-yl)pyrazin-2-yloxy)phenyl)pyridin-2-amine;
N-(2-fluoro-4-(3-(2-fluoropyridin-4-yl)pyrazin-2-yloxy)phenyl)pyridin-2-amine;
N-(4-(3-(2-chloropyridin-4-yl)pyrazin-2-yloxy)phenyl)pyridin-2-amine;
4-(3-(4-(pyridin-2-ylamino)phenoxy)pyrazin-2-yl)picolinonitrile;
N-(4-(3-(2-fluoropyridin-4-yl)pyrazin-2-yloxy)phenyl)pyridin-2-amine;
N-(4-(3-(pyridin-4-yl)pyrazin-2-yloxy)phenyl)pyridin-2-amine;
N-(4-(3-(2-methoxypyridin-4-yl)pyrazin-2-yloxy)phenyl)pyridin-2-amine;
N-(4-(3-(7-chloroquinolin-4-yl)pyrazin-2-yloxy)phenyl)pyridin-2-amine;
N-(4-(3-(1-methyl-1H-imidazol-5-yl)pyrazin-2-yloxy)phenyl)pyridin-2-amine;
(4-(3-(2-Methylpyridin-4-yl)pyrazin-2-yloxy)phenyl)(pyridin-2-yl)methanone;
N-(4-(2'-fluoro-6-methoxy-3,4'-bipyridin-2-yloxy)phenyl)-5-methylpyridin-2-amine;
N-(4-(5-(2-fluoropyridin-4-yl)-2-methoxypyrimidin-4-yloxy)phenyl)-5-methylpyridin-2-amine; and
N-(4-(2'-fluoro-5-methoxy-3,4'-bipyridin-2-yloxy)phenyl)-5-methylpyridin-2-amine.

The compounds of this invention may have in general several asymmetric centers and are typically depicted in the form of racemic mixtures. This invention is intended to encompass racemic mixtures, partially racemic mixtures and separate enantiomers and diastereomers.

The present invention includes all pharmaceutically acceptable isotopically-labelled compounds of the present invention wherein one or more atoms are replaced by atoms having the same atomic number, but an atomic mass or mass number different from the atomic mass or mass number which predominates in nature.

Examples of isotopes suitable for inclusion in the compounds of the invention include, but are not limited to, isotopes of hydrogen, such as $^2H$ and $^3H$, carbon, such as $^{11}C$, $^{13}C$ and $^{14}C$, chlorine, such as $^{38}Cl$, fluorine, such as $^{18}F$, iodine, such as $^{123}I$ and $^{125}I$, nitrogen, such as $^{13}N$ and $^{15}N$, oxygen, such as $^{15}O$, $^{17}O$ and $^{18}O$, phosphorus, such as $^{32}P$, and sulphur, such as $^{35}S$.

Certain isotopically-labelled compounds of the present invention, for example, those incorporating a radioactive isotope, are useful in drug and/or substrate tissue distribution studies. The radioactive isotopes tritium, i.e. $^3H$, and carbon-14, i.e. $^{14}C$, are particularly useful for this purpose in view of their ease of incorporation and ready means of detection.

Substitution with heavier isotopes such as deuterium, i.e. $^2H$, may afford certain therapeutic advantages resulting from greater metabolic stability, for example, increased in vivo half-life or reduced dosage requirements, and hence may be preferred in some circumstances.

Substitution with positron emitting isotopes, such as $^{11}C$, $^{18}F$, $^{15}O$ and $^{13}N$, can be useful in Positron Emission Topography (PET) studies for examining substrate receptor occupancy.

Isotopically-labeled compounds of the present invention can generally be prepared by conventional techniques known to those skilled in the art or by processes analogous to those described in the accompanying Examples and Preparations using an appropriate isotopically-labeled reagent in place of the non-labeled reagent previously employed.

Pharmaceutically acceptable solvates in accordance with the invention include those wherein the solvent of crystallization may be isotopically substituted, e.g. $D_2O$, $d_6$-acetone, $d_6$-DMSO.

Specific embodiments of the present invention include the compounds exemplified in the Examples below and their pharmaceutically acceptable salts, complexes, solvates, polymorphs, stereoisomers, metabolites, prodrugs, and other derivatives thereof, Unless otherwise specified, the following definitions apply to terms found in the specification and claims:

"$C\alpha$-$\beta$alk" means an alkyl group comprising a minimum of $\alpha$ and a maximum of $\beta$ carbon atoms in a branched, cyclical or linear relationship or any combination of the three, wherein $\alpha$ and $\beta$ represent integers. The alkyl groups described in this section may also contain one or two double or triple bonds. A designation of $C_0$alk indicates a direct bond. Examples of $C_{1-6}$alkyl include, but are not limited to the following:

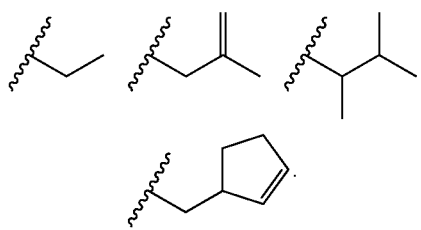

"$C\alpha$-$\beta$alk-linked" means an alkyl group comprising a minimum of $\alpha$ and a maximum of $\beta$ carbon atoms in a branched, cyclical or linear relationship or any combination of the three, wherein $\alpha$ and $\beta$ represent integers, said alkyl group is linked through one of its carbon atom to a specified ring system. The alkyl groups described in this section may also contain one or two double or triple bonds. A designation of $C_0$alk indicates a direct bond. For example, the term "$C_{0-4}$alk-linked saturated, partially-saturated or unsaturated 3-, 4-, 5-, 6-, or 7-membered monocyclic containing 0, 1, 2 or 3 N atoms and 0, 1, or 2 atoms selected from O and S, which is substituted by 0, 1, 2 or 3 groups selected from F, Cl, Br, $R^e$, $C_{1-6}$alk, and oxo" include, but are not limited to the following:

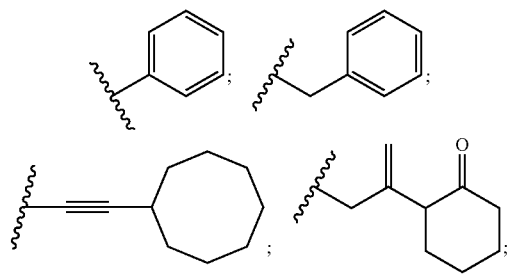

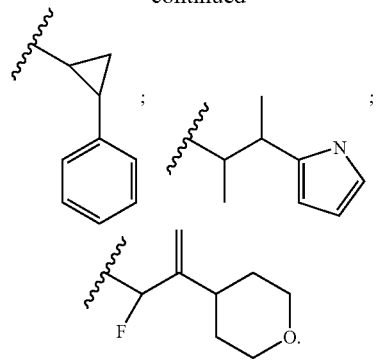

"Benzo group", alone or in combination, means the divalent radical $C_4H_4$=, one representation of which is —CH=CH—CH=CH—, that when vicinally attached to another ring forms a benzene-like ring—for example tetrahydronaphthylene, indole and the like.

The terms "oxo" and "thioxo" represent the groups =O (as in carbonyl) and =S (as in thiocarbonyl), respectively.

"Halo" or "halogen" means a halogen atoms selected from F, Cl, Br and I.

"$C_{V\text{-}W}$haloalk" means an alk group, as described above, wherein any number—at least one—of the hydrogen atoms attached to the alk chain are replaced by F, Cl, Br or I.

The group $N(R^a)R^a$ and the like include substituents where the two $R^a$ groups together form a ring, optionally including a N, O or S atom, and include groups such as:

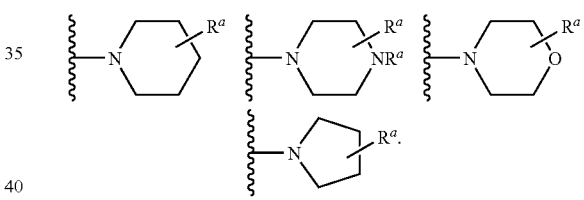

The group $N(C\alpha$-$\beta$alk)$C\alpha$-$\beta$alk, wherein $\alpha$ and $\beta$ are as defined above, include substituents where the two $C\alpha$-$\beta$alk groups together form a ring, optionally including a N, O or S atom, and include groups such as:

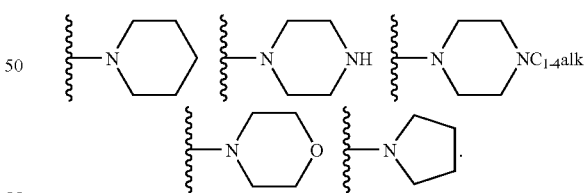

"Carbocycle" means a ring comprising by itself or in combination with other terms, represents, unless otherwise stated, cyclic version of "$C\alpha$-$\beta$alk". Thus, the term "carbocycle" is meant to be included in the terms "$C\alpha$-$\beta$alk". Examples of carbocycle include cyclopentyl, cyclohexyl, 1-cyclohexenyl, 3-cyclohexenyl, cycloheptyl, cyclobutylene, cyclohexylene and the like.

"Heterocycle" means a ring comprising at least one carbon atom and at least one other atom selected from N, O and S. Examples of heterocycles that may be found in the claims include, but are not limited to, the following:

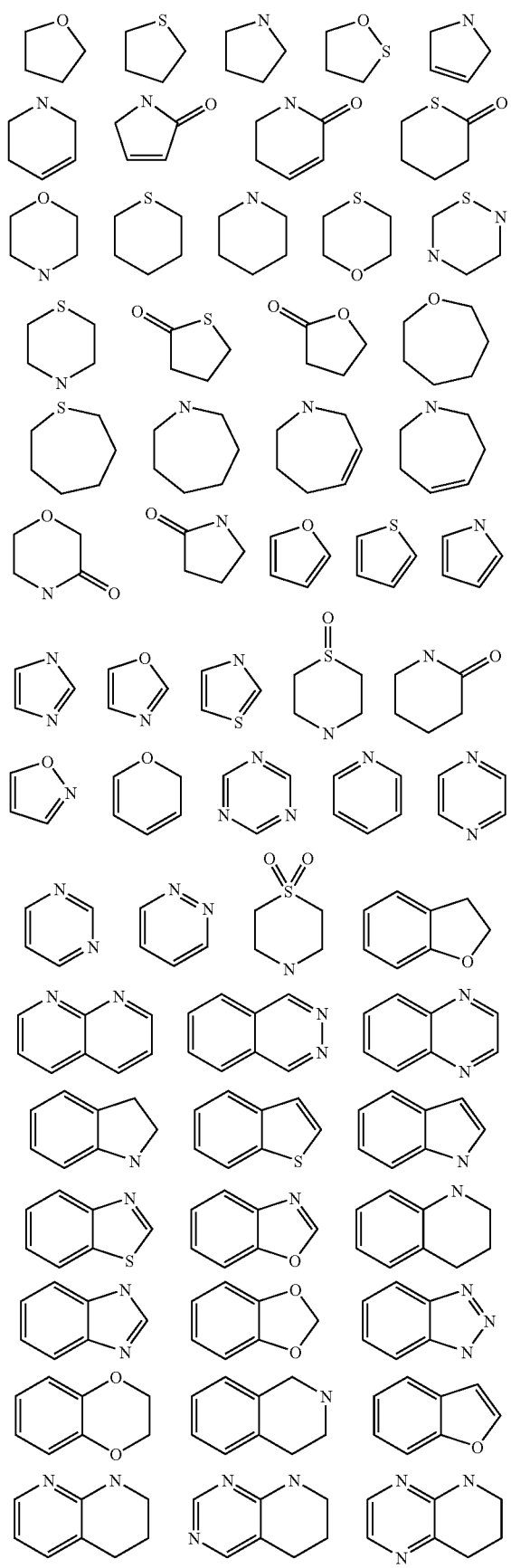

"Nitrogen-linked" heterocycles means any of the heterocycles as defined above wherein said heterocycles are linked to another moiety via one of its ring nitrogen atoms. Examples include but are not limited to the following, which may be carbon-linked or nitrogen-linked:

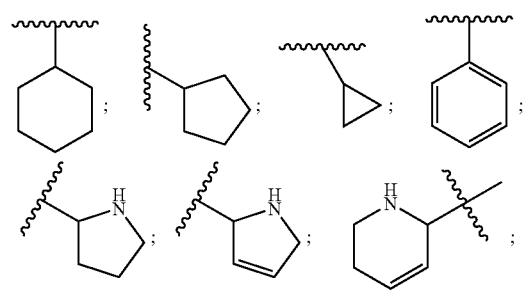

"Carbon-linked" system means any of the carbocycles or heterocycles as defined above wherein said carbocycles or heterocycles are linked to another moiety via one of its ring carbon atoms. Examples include but are not limited to the following:

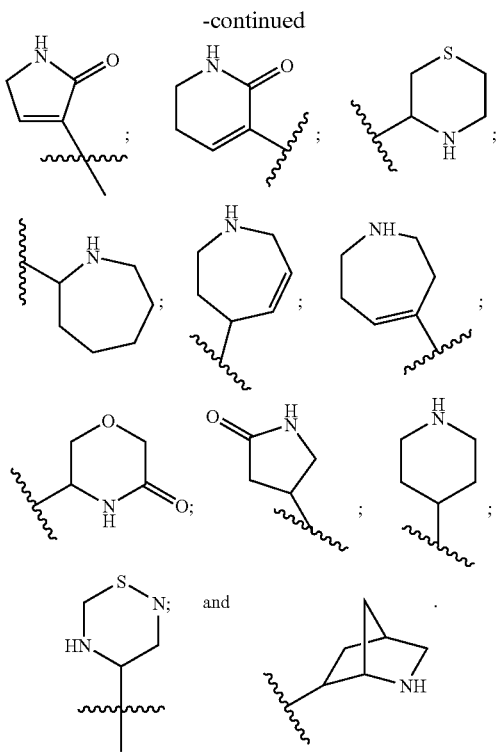

"Pharmaceutically-acceptable salt" means a salt prepared by conventional means, and are well known by those skilled in the art. The "pharmacologically acceptable salts" include basic salts of inorganic and organic acids, including but not limited to hydrochloric acid, hydrobromic acid, sulfuric acid, phosphoric acid, methanesulfonic acid, ethanesulfonic acid, malic acid, acetic acid, oxalic acid, tartaric acid, citric acid, lactic acid, fumaric acid, succinic acid, maleic acid, salicylic acid, benzoic acid, phenylacetic acid, mandelic acid and the like. When compounds of the invention include an acidic function such as a carboxy group, then suitable pharmaceutically acceptable cation pairs for the carboxy group are well known to those skilled in the art and include alkaline, alkaline earth, ammonium, quaternary ammonium cations and the like. For additional examples of "pharmacologically acceptable salts," see infra and Berge et al., J. Pharm. Sci. 66:1 (1977).

"Saturated, partially-saturated or unsaturated" includes substituents saturated with hydrogens, substituents completely unsaturated with hydrogens and substituents partially saturated with hydrogens.

"Leaving group" generally refers to groups readily displaceable by a nucleophile, such as an amine, a thiol or an alcohol nucleophile. Such leaving groups are well known in the art. Examples of such leaving groups include, but are not limited to, N-hydroxysuccinimide, N-hydroxybenzotriazole, halides, triflates, tosylates and the like. Preferred leaving groups are indicated herein where appropriate.

"Protecting group" generally refers to groups well known in the art which are used to prevent selected reactive groups, such as carboxy, amino, hydroxy, mercapto and the like, from undergoing undesired reactions, such as nucleophilic, electrophilic, oxidation, reduction and the like. Preferred protecting groups are indicated herein where appropriate. Examples of amino protecting groups include, but are not limited to, aralkyl, substituted aralkyl, cycloalkenylalkyl and substituted cycloalkenyl alkyl, allyl, substituted allyl, acyl, alkoxycarbonyl, aralkoxycarbonyl, silyl and the like. Examples of aralkyl include, but are not limited to, benzyl, ortho-methylbenzyl, trityl and benzhydryl, which can be optionally substituted with halogen, alkyl, alkoxy, hydroxy, nitro, acylamino, acyl and the like, and salts, such as phosphonium and ammonium salts. Examples of aryl groups include phenyl, naphthyl, indanyl, anthracenyl, 9-(9-phenylfluorenyl), phenanthrenyl, durenyl and the like. Examples of cycloalkenylalkyl or substituted cycloalkylenylalkyl radicals, preferably have 6-10 carbon atoms, include, but are not limited to, cyclohexenyl methyl and the like. Suitable acyl, alkoxycarbonyl and aralkoxycarbonyl groups include benzyloxycarbonyl, t-butoxycarbonyl, iso-butoxycarbonyl, benzoyl, substituted benzoyl, butyryl, acetyl, trifluoroacetyl, trichloro acetyl, phthaloyl and the like. A mixture of protecting groups can be used to protect the same amino group, such as a primary amino group can be protected by both an aralkyl group and an aralkoxycarbonyl group. Amino protecting groups can also form a heterocyclic ring with the nitrogen to which they are attached, for example, 1,2-bis(methylene)benzene, phthalimidyl, succinimidyl, maleimidyl and the like and where these heterocyclic groups can further include adjoining aryl and cycloalkyl rings. In addition, the heterocyclic groups can be mono-, di- or tri-substituted, such as nitrophthalimidyl. Amino groups may also be protected against undesired reactions, such as oxidation, through the formation of an addition salt, such as hydrochloride, toluenesulfonic acid, trifluoroacetic acid and the like. Many of the amino protecting groups are also suitable for protecting carboxy, hydroxy and mercapto groups. For example, aralkyl groups. Alkyl groups are also suitable groups for protecting hydroxy and mercapto groups, such as tert-butyl.

Silyl protecting groups are silicon atoms optionally substituted by one or more alkyl, aryl and aralkyl groups. Suitable silyl protecting groups include, but are not limited to, trimethylsilyl, triethylsilyl, triisopropylsilyl, tert-butyldimethylsilyl, dimethylphenylsilyl, 1,2-bis(dimethylsilyl)benzene, 1,2-bis(dimethylsilyl)ethane and diphenylmethylsilyl. Silylation of an amino groups provide mono- or di-silylamino groups. Silylation of aminoalcohol compounds can lead to a N,N,O-trisilyl derivative. Removal of the silyl function from a silyl ether function is readily accomplished by treatment with, for example, a metal hydroxide or ammonium fluoride reagent, either as a discrete reaction step or in situ during a reaction with the alcohol group. Suitable silylating agents are, for example, trimethylsilyl chloride, tert-butyl-dimethylsilyl chloride, phenyldimethylsilyl chloride, diphenylmethyl silyl chloride or their combination products with imidazole or DMF. Methods for silylation of amines and removal of silyl protecting groups are well known to those skilled in the art. Methods of preparation of these amine derivatives from corresponding amino acids, amino acid amides or amino acid esters are also well known to those skilled in the art of organic chemistry including amino acid/amino acid ester or aminoalcohol chemistry.

Protecting groups are removed under conditions which will not affect the remaining portion of the molecule. These methods are well known in the art and include acid hydrolysis, hydrogenolysis and the like. A preferred method involves removal of a protecting group, such as removal of a benzyloxycarbonyl group by hydrogenolysis utilizing palladium on carbon in a suitable solvent system such as an alcohol, acetic acid, and the like or mixtures thereof. A t-butoxycarbonyl protecting group can be removed utilizing an inorganic or organic acid, such as HCl or trifluoroacetic acid, in a suitable solvent system, such as dioxane or methylene chloride. The resulting amino salt can readily be neutralized to yield the free amine. Carboxy protecting group, such as methyl, ethyl, benzyl, tert-butyl, 4-methoxyphenylmethyl and the like, can be removed under hydrolysis and hydrogenolysis conditions well known to those skilled in the art.

It should be noted that compounds of the invention may contain groups that may exist in tautomeric forms, such as cyclic and acyclic amidine and guanidine groups, heteroatom substituted heteroaryl groups (Y'=O, S, NR), and the like, which are illustrated in the following examples:

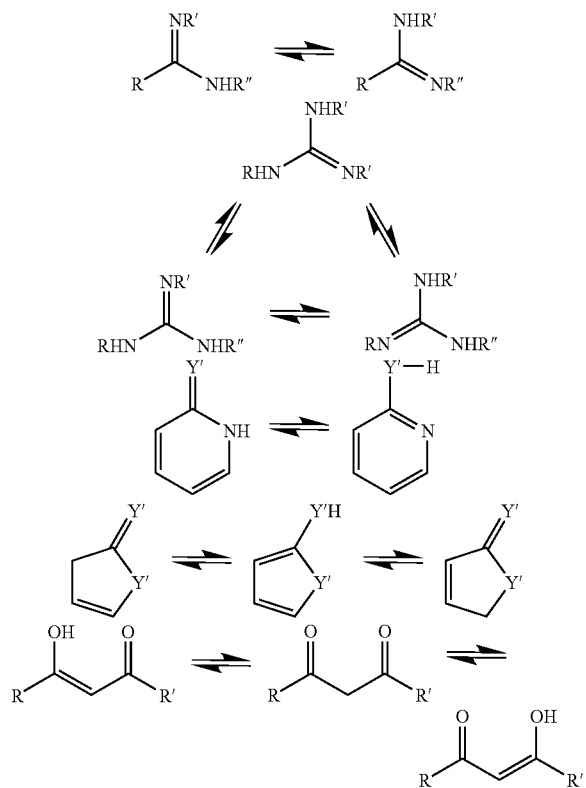

and though one form is named, described, displayed and/or claimed herein, all the tautomeric forms are intended to be inherently included in such name, description, display and/or claim.

Prodrugs of the compounds of this invention are also contemplated by this invention. A prodrug is an active or inactive compound that is modified chemically through in vivo physiological action, such as hydrolysis, metabolism and the like, into a compound of this invention following administration of the prodrug to a patient. The suitability and techniques involved in making and using prodrugs are well known by those skilled in the art. For a general discussion of prodrugs involving esters see Svensson and Tunek Drug Metabolism Reviews 165 (1988) and Bundgaard Design of Prodrugs, Elsevier (1985). Examples of a masked carboxylate anion include a variety of esters, such as alkyl (for example, methyl, ethyl), cycloalkyl (for example, cyclohexyl), aralkyl (for example, benzyl, p-methoxybenzyl), and alkylcarbonyloxyalkyl (for example, pivaloyloxymethyl). Amines have been masked as arylcarbonyloxymethyl substituted derivatives which are cleaved by esterases in vivo releasing the free drug and formaldehyde (Bungaard J. Med. Chem. 2503 (1989)). Also, drugs containing an acidic NH group, such as imidazole, imide, indole and the like, have been masked with N-acyloxymethyl groups (Bundgaard Design of Prodrugs, Elsevier (1985)). Hydroxy groups have been masked as esters and ethers. EP 039,051 (Sloan and Little, Apr. 11, 1981) discloses Mannich-base hydroxamic acid prodrugs, their preparation and use.

The specification and claims contain listing of species using the language "selected from . . . and . . . " and "is . . . or . . . " (sometimes referred to as Markush groups). When this language is used in this application, unless otherwise stated it is meant to include the group as a whole, or any single members thereof, or any subgroups thereof. The use of this language is merely for shorthand purposes and is not meant in any way to limit the removal of individual elements or subgroups as needed.

Utility and Methods of Use

Provided herein are methods for treating a disorder or disease by inhibiting PDE10 enzyme. The methods, in general, comprises the step of administering a therapeutically effective amount of any compounds of the invention or an individual stereoisomer, a mixture of stereoisomers, or a pharmaceutically acceptable salt or solvate thereof, to a patient in need thereof to treat the disorder or disease.

In certain embodiments, this invention provides a use of a compound as described herein in the manufacture of a medicament for treating a disorder or disease treatable by inhibition of PDE10.

The compounds of the present invention inhibit PDE10 enzyme activity, and hence raise the levels of cAMP or cGMP within cells that express PDE10. Accordingly, inhibition of PDE10 enzyme activity would be useful in the treatment of diseases caused by deficient amounts of cAMP or cGMP in cells. PDE10 inhibitors would also be of benefit in cases wherein raising the amount of cAMP or cGMP above normal levels results in a therapeutic effect. Inhibitors of PDE10 may be used to treat disorders of the peripheral and central nervous system, cardiovascular diseases, cancer, gastro-enterological diseases, endocrinological diseases and urological diseases.

Indications that may be treated with PDE10 inhibitors, either alone or in combination with other drugs, include, but are not limited to, those diseases thought to be mediated in part by the basal ganglia, prefrontal cortex, and hippocampus. These indications include psychoses, Parkinson's disease, dementias, obsessive compulsive disorder, tardive dyskinesia, choreas, depression, mood disorders, impulsivity, drug addiction, attention deficit/hyperactivity disorder (ADHD), depression with parkinsonian states, personality changes with caudate or putamen disease, dementia and mania with caudate and pallidal diseases, and compulsions with pallidal disease.

Psychoses are disorders that affect an individual's perception of reality. Psychoses are characterized by delusions and hallucinations. The compounds of the present invention are suitable for use in treating patients suffering from all forms of psychoses, including, but not limited to, schizophrenia, late-onset schizophrenia, schizoaffective disorders, prodromal schizophrenia, and bipolar disorders. Treatment can be for the positive symptoms of schizophrenia as well as for the cognitive deficits and negative symptoms. Other indications for PDE10 inhibitors include psychoses resulting from drug abuse (including amphetamines and PCP), encephalitis, alcoholism, epilepsy, Lupus, sarcoidosis, brain tumors, multiple sclerosis, dementia with Lewy bodies, or hypoglycemia. Other psychiatric disorders, like posttraumatic stress disorder (PTSD), and schizoid personality can also be treated with PDE10 inhibitors.

Obsessive-compulsive disorder (OCD) has been linked to deficits in the frontal-striatal neuronal pathways (Saxena et al., *Br. J. Psychiatry Suppl*, 35:26-37, 1998). Neurons in these pathways project to striatal neurons that express PDE10. PDE10 inhibitors cause cAMP to be elevated in these neurons; elevations in cAMP result in an increase in CREB phosphorylation and thereby improve the functional state of these neurons. The compounds of the present invention are therefore suitable for use in the indication of OCD. OCD may result, in some cases, from streptococcal infections that cause autoimmune reactions in the basal ganglia (Giedd et al., *Am J Psychiatry.* 157:281-283, 2000). Because PDE10 inhibitors may serve a neuroprotective role, administration of PDE10 inhibitors may prevent the damage to the basal ganglia after repeated streptococcal infections and thereby prevent the development of OCD.

In the brain, the level of cAMP or cGMP within neurons is believed to be related to the quality of memory, especially long term memory. Without wishing to be bound to any particular mechanism, it is proposed that, since PDE10 degrades cAMP or cGMP, the level of this enzyme affects memory in animals, for example, in humans. A compound that inhibits cAMP phosphodiesterase (PDE) can thereby increase intracellular levels of cAMP, which in turn activate a protein kinase that phosphorylates a transcription factor (cAMP response binding protein). The phosphorylated transcription factor then binds to a DNA promoter sequence to activate genes that are important in long term memory. The more active such genes are, the better is long-term memory. Thus, by inhibiting a phosphodiesterase, long term memory can be enhanced.

Dementias are diseases that include memory loss and additional intellectual impairment separate from memory. The compounds of the present invention are suitable for use in treating patients suffering from memory impairment in all forms of dementia. Dementias are classified according to their cause and include: neurodegenerative dementias (e.g., Alzheimer's, Parkinson's disease, Huntington's disease, Pick's disease), vascular (e.g., infarcts, hemorrhage, cardiac disorders), mixed vascular and Alzheimer's, bacterial meningitis, Creutzfeld-Jacob Disease, multiple sclerosis, traumatic (e.g., subdural hematoma or traumatic brain injury), infectious (e.g., HIV), genetic (down syndrome), toxic (e.g., heavy metals, alcohol, some medications), metabolic (e.g., vitamin B12 or folate deficiency), CNS hypoxia, Cushing's disease, psychiatric (e.g., depression and schizophrenia), and hydrocephalus.

The condition of memory impairment is manifested by impairment of the ability to learn new information and/or the inability to recall previously learned information. The present invention includes methods for dealing with memory loss separate from dementia, including mild cognitive impairment (MCI) and age-related cognitive decline. The present invention includes methods of treatment for memory impairment as a result of disease. Memory impairment is a primary symptom of dementia and can also be a symptom associated with such diseases as Alzheimer's disease, schizophrenia, Parkinson's disease, Huntington's disease, Pick's disease, Creutzfeld-Jakob disease, HIV, cardiovascular disease, and head trauma as well as age-related cognitive decline. The compounds of the present invention are suitable for use in the treatment of memory impairment due to, for example, Alzheimer's disease, multiple sclerosis, amyolaterosclerosis (ALS), multiple systems atrophy (MSA), schizophrenia, Parkinson's disease, Huntington's disease, Pick's disease, Creutzfeld-Jakob disease, depression, aging, head trauma, stroke, spinal cord injury, CNS hypoxia, cerebral senility, diabetes associated cognitive impairment, memory deficits from early exposure of anesthetic agents, multiinfarct dementia and other neurological conditions including acute neuronal diseases, as well as HIV and cardiovascular diseases.

The compounds of the present invention are also suitable for use in the treatment of a class of disorders known as polyglutamine-repeat diseases. These diseases share a common pathogenic mutation. The expansion of a CAG repeat, which encodes the amino acid glutamine, within the genome leads to production of a mutant protein having an expanded polyglutamine region. For example, Huntington's disease has been linked to a mutation of the protein huntingtin. In individuals who do not have Huntington's disease, huntingtin has a polyglutamine region containing about 8 to 31 glutamine residues. For individuals who have Huntington's disease, huntingtin has a polyglutamine region with over 37 glutamine residues. Aside from Huntington's disease (HD), other known polyglutamine-repeat diseases and the associated proteins include dentatorubral-pallidoluysian atrophy, DRPLA (atrophin-1); spinocerebellar ataxia type-1 (ataxin-1); spinocerebellar ataxia type-2 (ataxin-2); spinocerebellar ataxia type-3 (also called Machado-Joseph disease or MJD) (ataxin-3); spinocerebellar ataxia type-6 (alpha 1a-voltage dependent calcium channel); spinocerebellar ataxia type-7 (ataxin-7); and spinal and bulbar muscular atrophy (SBMA, also know as Kennedy disease).

The basal ganglia are important for regulating the function of motor neurons; disorders of the basal ganglia result in movement disorders. Most prominent among the movement disorders related to basal ganglia function is Parkinson's disease (Obeso et al., *Neurology.* 62(1 Suppl 1):S17-30, 2004). Other movement disorders related to dysfunction of the basal ganglia include tardive dyskinesia, progressive supranuclear palsy and cerebral palsy, corticobasal degeneration, multiple system atrophy, Wilson disease, dystonia, tics, and chorea. The compounds of the invention are also suitable for use to treat movement disorders related to dysfunction of basal ganglia neurons.

PDE10 inhibitors are useful in raising cAMP or cGMP levels and prevent neurons from undergoing apoptosis. PDE10 inhibitors may be anti-inflammatory by raising cAMP in glial cells. The combination of anti-apoptotic and anti-inflammatory properties, as well as positive effects on synaptic plasticity and neurogenesis, make these compounds useful to treat neurodegeneration resulting from any disease or injury, including stroke, spinal cord injury, Alzheimer's disease, multiple sclerosis, amylolaterosclerosis (ALS), and multiple systems atrophy (MSA).

Autoimmune diseases or infectious diseases that affect the basal ganglia may result in disorders of the basal ganglia including ADHD, OCD, tics, Tourette's disease, Sydenham chorea. In addition, any insult to the brain can potentially damage the basal ganglia including strokes, metabolic abnormalities, liver disease, multiple sclerosis, infections, tumors, drug overdoses or side effects, and head trauma. Accordingly, the compounds of the invention can be used to stop disease progression or restore damaged circuits in the brain by a combination of effects including increased synaptic plasticity, neurogenesis, anti-inflammatory, nerve cell regeneration and decreased apoptosis.

The growth of some cancer cells is inhibited by cAMP and cGMP. Upon transformation, cells may become cancerous by expressing PDE10 and reducing the amount of cAMP or cGMP within cells. In these types of cancer cells, inhibition of PDE10 activity inhibits cell growth by raising cAMP. In some cases, PDE10 may be expressed in the transformed, cancerous cell but not in the parent cell line. In transformed renal carcinoma cells, PDE10 is expressed and PDE10 inhibitors reduce the growth rate of the cells in culture. Similarly, breast cancer cells are inhibited by administration of PDE10 inhibitors. Many other types of cancer cells may also be sensitive to growth arrest by inhibition of PDE10. Therefore, compounds disclosed in this invention can be used to stop the growth of cancer cells that express PDE10.

The compounds of the invention are also suitable for use in the treatment of diabetes and related disorders such as obesity, by focusing on regulation of the cAMP signaling system. By inhibiting PDE-10, especially PDE-10A, intracellular levels of cAMP are increased, thereby increasing the release of insulin-containing secretory granules and, therefore, increasing insulin secretion. See, for example, WO 2005/012485, which is hereby incorporated by reference in its entirety. The compounds of the present invention can also be used to treat diseases disclosed in US Patent application publication No. 2006/019975, the disclosure of which is incorporated herein by reference in its entirety.

Administration and Pharmaceutical Compositions

In general, the compounds of this invention can be administered in a therapeutically effective amount by any of the accepted modes of administration for agents that serve similar utilities. The actual amount of a compound of this invention, i.e., the active ingredient, depends upon numerous factors, such as the severity of the disease to be treated, the age and relative health of the subject, the potency of the compound used, the route and form of administration, and other factors.

Therapeutically effective amounts of compounds of formula (I) may range from approximately 0.1-1000 mg per day; preferably 0.5 to 250 mg/day, more preferably 3.5 mg to 70 mg per day.

In general, compounds of this invention can be administered as pharmaceutical compositions by any one of the following routes: oral, systemic (e.g., transdermal, intranasal or by suppository), or parenteral (e.g., intramuscular, intravenous or subcutaneous) administration. The preferred manner of administration is oral using a convenient daily dosage regimen, which can be adjusted according to the degree of affliction. Compositions can take the form of tablets, pills, capsules, semisolids, powders, sustained release formulations, solutions, suspensions, elixirs, aerosols, or any other appropriate compositions.

The choice of formulation depends on various factors, such as the mode of drug administration (e.g., for oral administration, formulations in the form of tablets, pills or capsules are preferred) and the bioavailability of the drug substance. Recently, pharmaceutical formulations have been developed especially for drugs that show poor bioavailability based upon the principle that bioavailability can be increased by increasing the surface area, i.e., decreasing particle size. For example, U.S. Pat. No. 4,107,288 describes a pharmaceutical formulation having particles in the size range from 10 to 1,000 nm in which the active material is supported on a crosslinked matrix of macromolecules. U.S. Pat. No. 5,145,684 describes the production of a pharmaceutical formulation in which the drug substance is pulverized to nanoparticles (average particle size of 400 nm) in the presence of a surface modifier and then dispersed in a liquid medium to give a pharmaceutical formulation that exhibits remarkably high bioavailability.

The compositions are comprised of, in general, the compound of the invention in combination with at least one pharmaceutically acceptable excipient. Acceptable excipients are non-toxic, aid administration, and do not adversely affect the therapeutic benefit of the compound of the invention. Such excipient may be any solid, liquid, semi-solid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Preferred liquid carriers, particularly for injectable solutions, include water, saline, aqueous dextrose, and glycols.

Compressed gases may be used to disperse a compound of this invention in aerosol form. Inert gases suitable for this purpose are nitrogen, carbon dioxide, etc.

Other suitable pharmaceutical excipients and their formulations are described in *Remington's Pharmaceutical Sciences*, Gennaro, A. R. (Mack Publishing Company, 18th ed., 1995).

The level of the compound in a formulation can vary within the full range employed by those skilled in the art. Typically, the formulation contains, on a weight percent (wt %) basis, from about 0.01-99.99 wt % of a compound of the invention based on the total formulation, with the balance being one or more suitable pharmaceutical excipients. Preferably, the compound is present at a level of about 1-80 wt %.

The compounds can be administered as the sole active agent or in combination with other pharmaceutical agents such as other agents used in the treatment of psychoses, especially schizophrenia and bipolar disorder, obsessive-compulsive disorder, Parkinson's disease, Alzheimer's disease, cognitive impairment and/or memory loss, e.g., nicotinic α-7 agonists, PDE4 inhibitors, other PDE10 inhibitors, calcium channel blockers, muscarinic m1 and m2 modulators, adenosine receptor modulators, ampakines, NMDA-R modulators, mGluR modulators, dopamine modulators, serotonin modulators, canabinoid modulators, and cholinesterase inhibitors (e.g., donepezil, rivastigimine, and galanthanamine). In such combinations, each active ingredient can be administered either in accordance with their usual dosage range or a dose below their usual dosage range, and can be administered either simultaneously or sequentially.

Drugs suitable in combination with the compounds of the present invention include, but are not limited to, other suitable schizophrenia drugs such as Clozaril, Zyprexa, Risperidone, and Seroquel; bipolar disorder drugs, including, but not limited to, Lithium, Zyprexa, and Depakote; Parkinson's disease drugs, including, but not limited to, Levodopa, Parlodel, Permax, Mirapex, Tasmar, Contan, Kemadin, Artane, and Cogentin; agents used in the treatment of Alzheimer's disease, including, but not limited to, Reminyl, Cognex, Aricept, Exelon, Akatinol, Neotropin, Eldepryl, Estrogen and Cliquinol; agents used in the treatment of dementia, including, but not limited to, Thioridazine, Haloperidol, Risperidone, Cognex, Aricept, and Exelon; agents used in the treatment of epilepsy, including, but not limited to, Dilantin, Luminol, Tegretol, Depakote, Depakene, Zarontin, Neurontin, Barbita, Solfeton, and Felbatol; agents used in the treatment of multiple sclerosis, including, but not limited to, Detrol, Ditropan XL, OxyContin, Betaseron, Avonex, Azothioprine, Methotrexate, and Copaxone; agents used in the treatment of Huntington's disease, including, but not limited to, Amitriptyline, Imipramine, Despiramine, Nortriptyline, Paroxetine, Fluoxetine, Setraline, Terabenazine, Haloperidol, Chloropromazine, Thioridazine, Sulpride, Quetiapine, Clozapine, and Risperidone; agents useful in the treatment of diabetes, including, but not limited to, PPAR ligands (e.g. agonists, antagonists, such as Rosiglitazone, Troglitazone and Pioglitazone), insulin secretagogues (e.g., sulfonylurea drugs, such as Glyburide, Glimepiride, Chlorpropamide, Tolbutamide, and Glipizide, and non-sulfonyl secretagogues), α-glucosidase inhibitors (such as Acarbose, Miglitol, and Voglibose), insulin sensitizers (such as the PPAR-γ agonists, e.g., the glitazones; biguanides, PTP-1B inhibitors, DPP-IV inhibitors, and 11beta-HSD inhibitors), hepatic glucose output lowering compounds (such as glucagon antagonists and metaformin, e.g., Glucophage and Glucophage XR), insulin and insulin derivatives (both long and short acting forms and formulations of insulin); and anti-obesity drugs, including, but not limited to, β-3 agonists, CB-1 agonists, neuropeptide Y5 inhibitors, Ciliary Neurotrophic Factor and derivatives (e.g., Axokine), appetite suppressants (e.g., Sibutramine), and lipase inhibitors (e.g., Orlistat).

EXPERIMENTAL

Unless otherwise noted, all materials were obtained from commercial suppliers and used without further purification. All parts are by weight and temperatures are in degrees centigrade unless otherwise indicated. All microwave assisted reactions were conducted with a Smith Synthesizer™ from Biotage™. All compounds showed NMR spectra consistent with their assigned structures. Melting points were determined on a Buchi apparatus and are uncorrected. Mass spectral data was determined by electrospray ionization technique. All examples were purified to >90% purity as determined by high-performance liquid chromatography. Unless otherwise stated, reactions were run at RT.

The following abbreviations are used:
DCM—DCM
DMSO—dimethyl sulfoxide
DMF—N,N-dimethylformamide
THF—tetrahydrofuran
$Et_2O$—diethyl ether
EtOAc—ethyl acetate
MeOH—methyl alcohol
EtOH—ethyl alcohol
IPA—isopropyl alcohol
MeCN—acetonitrile
MeI—iodomethane
NMP—1-methyl-2-pyrrolidinone
DCM—DCM
TFA—trifluoroacetic acid
MTBE—methyl tert-butyl ether
DIPEA—diisopropylethyl amine
HBTU—2-(1H-Benzotriazole-1-yl)-1,1,3,3-tetramethylaminium hexafluorophosphate
HATU—O-(7-Azobenzotriazol-1-yl)-1,1,3,3-tetramethyluronium hexafluorophosphate
Sat.—saturated
h—hour
min—min
mL—milliliters
g—grams
mg—milligrams
RT—room temperature
mw—microwave
rac—racemic In in the event that a salt, such as a TFA or HCl salt form of a compound of the invention has been prepared, the free base form is also compounds of the present invention. Such free bases can be obtained by known methods, for example: the TFA or HCl salts were dissolved in DCM, and washed with saturated $NaHCO_3$ solution. The aqueous layer was back extracted with DCM (2×) and the combined organic layers were dried ($Na_2CO_3$) and concentrated to give the free bases of the corresponding compound.

In the following schemes, the compounds of the invention, along with their definitions, such as m, n, $R^1$, $R^2$, $R^3$, $R^4$, $R^5$, $R^6$, $R^7$, $R^8$, $R^9$, $X^1$, $X^2$, $X^3$, $X^4$, $X^5$, $X^6$, $X^7$, $X^8$, and Y are as described above. Exemplary compounds of the invention have useful PDE10 activity as measured by mPDE10A7 Enzyme Activity and Inhibition Assay of Biological Example 1 below. The IC50 data represent an average IC50 data for each compound.

SCHEME 1

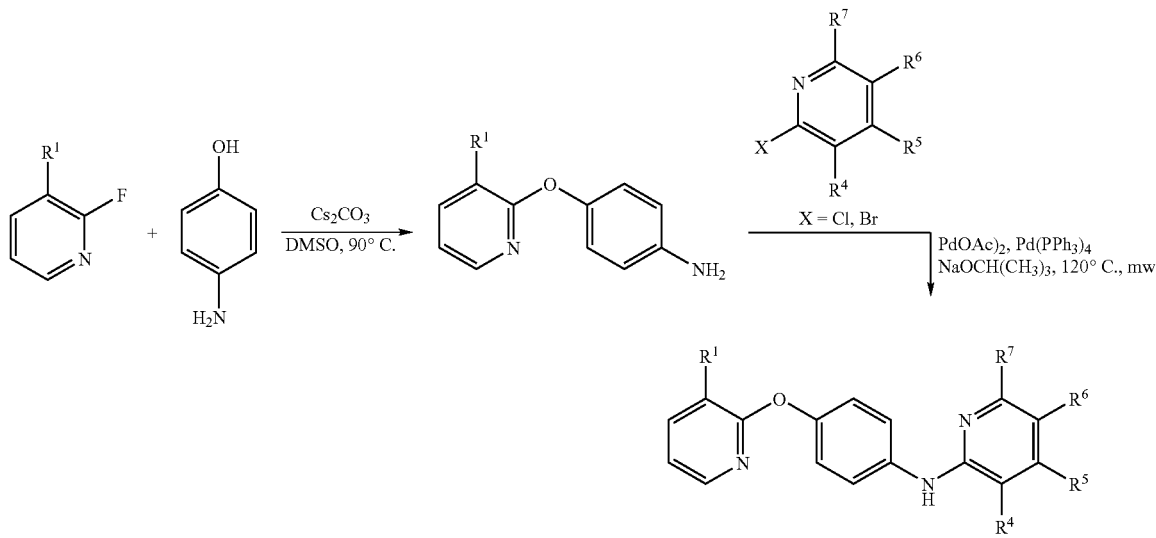

Example 1

N-(4-(3-(PYRIDIN-4-YL)PYRIDIN-2-YLOXY)PHENYL)PYRIDIN-2-AMINE

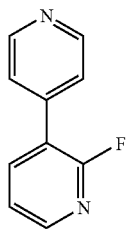

STEP 1. 2-FLUORO-3-(PYRIDIN-4-YL)PYRIDINE

To a 50 mL round-bottomed flask was added 3-bromo-2-fluoropyridine (1.0135 g, 5.759 mmol), 4-(4,4,5,5-tetramethyl-1,3,2-dioxaborolan-2-yl)pyridine (1.4577 g, 7.141 mmol), and trans-dichlorobis(triphenylphosphine)palladium (ii) (0.2138 g, 0.2879 mmol) in 1,2-dimethoxyethane. An aqueous solution of cesium carbonate (1.567 mL, 15.55 mmol) was added and the temperature was brought to 80° C. The reaction was monitored by LCMS to completion. The reaction mixture was diluted with water (10 mL) and extracted with DCM (3×10 mL). The organic extract was washed with water (1×10 mL), satd sodium chloride solution (1×10 mL), dried with magnesium sulfate, filtered, and concentrated. The solid was washed with ether and filtered to give 2-fluoro-3-(pyridin-4-yl)pyridine.

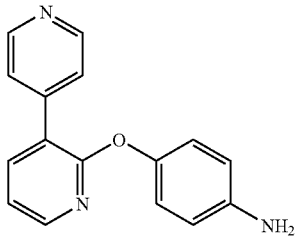 [SMILES: Nc1ccc(Oc2ncccc2-c2ccncc2)cc1]

STEP 2. 4-(3-(PYRIDIN-4-YL)PYRIDIN-2-YLOXY)BENZENAMINE

To a 50 mL round-bottomed flask was added 2-fluoro-3-(pyridin-4-yl)pyridine (1.0080 g, 5.787 mmol), 4-aminophenol (0.7102 g, 5.793 mmol), and cesium carbonate (2.387 g, 6.945 mmol) in dimethyl sulfoxide at 90° C. The reaction was monitored by LCMS to completion. The reaction mixture was diluted with water (10 mL) and extracted with DCM (3×10 mL). The organic extract was washed with water (3×10 mL), satd sodium chloride solution (3×10 mL), dried with magnesium sulfate, filtered, and concentrated. The crude product was adsorbed onto a plug of silica gel and chromatographed through a Biotage™ pre-packed silica gel column (40M), eluting with a gradient of 1% to 5% methanol in DCM, to provide 4-(3-(pyridin-4-yl)pyridin-2-yloxy)benzenamine.

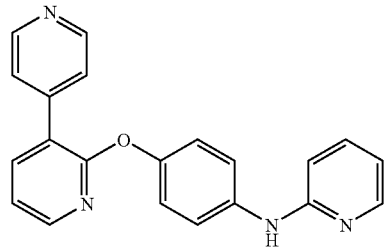 [SMILES: c1ccc(Nc2ccc(Oc3ncccc3-c3ccncc3)cc2)nc1]

STEP 3. N-(4-(3-(PYRIDIN-4-YL)PYRIDIN-2-YLOXY)PHENYL)PYRIDIN-2-AMINE

A glass microwave reaction vessel was charged with 4-(3-(pyridin-4-yl)pyridin-2-yloxy)benzenamine (0.0965 g, 0.37 mmol), 2-chloropyridine (0.034 mL, 0.36 mmol), palladium (II) acetate (0.0098 g, 0.018 mmol), BINAP (0.0213 g, 0.037 mmol), and sodium tert-butoxide (0.0503 g, 0.55 mmol). The reaction mixture was stirred and heated in a Smith Synthesizer® microwave reactor (Personal Chemistry, Inc., Upssala, Sweden) at 120° C. for 45 min. Reaction was concentrated. The crude product was adsorbed onto a plug of silica gel and chromatographed through a Biotage™ pre-packed silica gel column (25M), eluting with a gradient of 1% to 5% methanol in DCM, to provide N-(4-(3-(pyridin-4-yl)pyridin-2-yloxy)phenyl)pyridin-2-amine. MS (ESI, pos. ion) m/z: 341.1 (M+1). IC50 (uM) 0.000659.

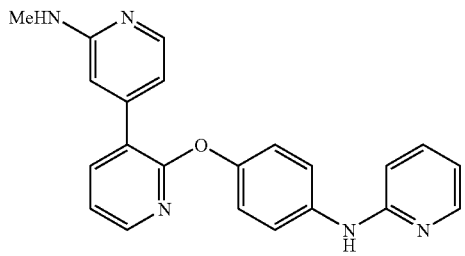 [SMILES: CNc1cc(-c2cccnc2Oc2ccc(Nc3ccccn3)cc2)ccn1]

Example 2

N-METHYL-4-(2-(4-(PYRIDIN-2-YLAMINO)PHENOXY)PYRIDIN-3-YL)PYRIDIN-2-AMINE

To a solution of 4-(2-(4-aminophenoxy)pyridin-3-yl)-N-methylpyridin-2-amine (1.0 g, 3.42 mmol) in THF (25 mL) was added Boc$_2$O (3.7 g, 17.10 mmol) and DMAP (42.0 mg, 0.342 mmol). The reaction mixture was stirred at RT. Additional amounts of Boc$_2$O and DMAP were added until complete conversion. The reaction mixture was diluted with CH$_2$Cl$_2$ and washed with saturated NaHCO$_3$ solution. The organic layer was dried over Na$_2$SO$_4$, filtered and concentrated in vacuum. The residue was purified by silica gel chromatography (EtOAc/Hexane) to afford the bis-Boc protected product. Under an atmosphere of nitrogen, the bis-Boc protected compound (50 mg, 0.10 mmol) was combined with Pd$_2$(dba)$_3$ (0.006 mmol), BINAP (0.03 mmol), NaOtBu (0.33 mmol) and chloropyridine (0.019 mL, 0.20 mmol) in toluene (1.0 mL). The resulting mixture was heated at 150° C. for 10 min in the microwave oven. The resulting solution was diluted with EtOAc and washed with saturated NaHCO$_3$ solution. The organic layer was dried over Na$_2$SO$_4$, filtered, and concentrated. Purification by silica gel chromatography (EtOAc/hexane) afforded the product N-methyl-4-(2-(4-(pyridin-2-ylamino)phenoxy)pyridin-3-yl)pyridin-2-amine. MS (ESI, pos. ion) m/z: 370.0 (M+1). IC50 (uM) 0.01401.

TABLE IA

EXAMPLES 3 TO 33 ARE TABULATED BELOW:

| Ex. No. | Compound Structure | Compound Name | MS | PDE10 IC50 (uM) |
|---|---|---|---|---|
| 3 | 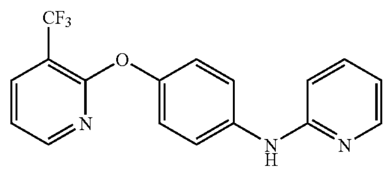 [SMILES: FC(F)(F)c1cccnc1Oc1ccc(Nc2ccccn2)cc1] | N-(4-(3-(trifluoromethyl)pyridin-2-yloxy)phenyl)pyridin-2-amine | 332.1 | 0.70295 |
| 4 | 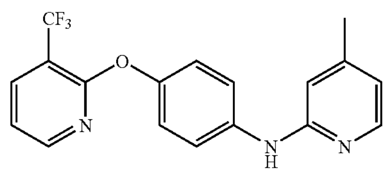 [SMILES: Cc1ccnc(Nc2ccc(Oc3ncccc3C(F)(F)F)cc2)c1] | 4-Methyl-N-(4-(3-(trifluoromethyl)pyridin-2-yloxy)phenyl)pyridin-2-amine | 346 | 1.69615 |
| 5 | 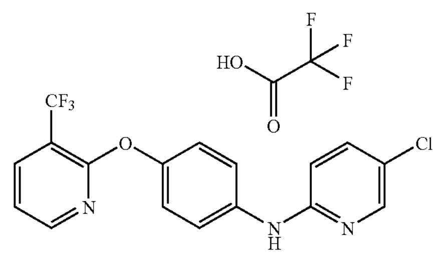 | 5-chloro-N-(4-(3-(trifluoromethyl)pyridin-2-yloxy)phenyl)pyridin-2-amine | 366 | 0.9195 |
| 6 | 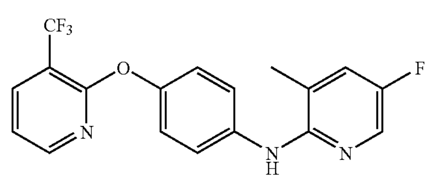 [SMILES: Cc1cc(F)cnc1Nc1ccc(Oc2ncccc2C(F)(F)F)cc1] | 5-fluoro-3-methyl-N-(4-(3-(trifluoromethyl)pyridin-2-yloxy)phenyl)pyridin-2-amine | 364 | 1.765 |
| 7 | 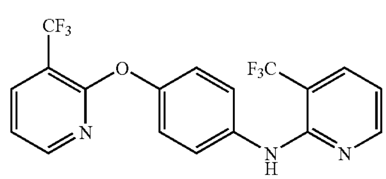 [SMILES: FC(F)(F)c1cccnc1Nc1ccc(Oc2ncccc2C(F)(F)F)cc1] | 3-(trifluoromethyl)-N-(4-(3-(trifluoromethyl)pyridin-2-yloxy)phenyl)pyridin-2-amine | 400 | 10 |
| 8 | 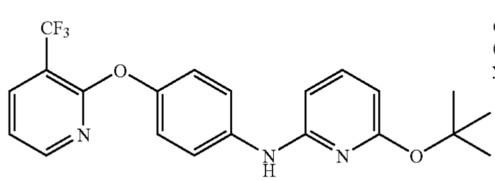 | 6-tert-butoxy-N-(4-(3-(trifluoromethyl)pyridin-2-yloxy)phenyl)pyridin-2-amine | 404 | 10 |
| 9 | 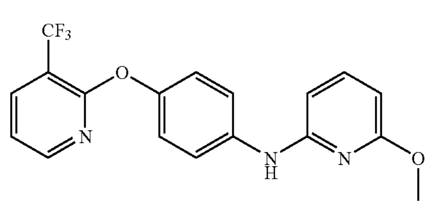 [SMILES: COc1cccc(Nc2ccc(Oc3ncccc3C(F)(F)F)cc2)n1] | 6-methoxy-N-(4-(3-(trifluoromethyl)pyridin-2-yloxy)phenyl)pyridin-2-amine | 362 | 2.658 |

TABLE IA-continued

EXAMPLES 3 TO 33 ARE TABULATED BELOW:

| Ex. No. | Compound Structure | Compound Name | MS | PDE10 IC50 (uM) |
|---|---|---|---|---|
| 10 | 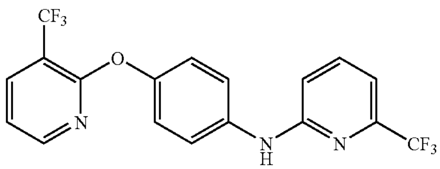 [SMILES: FC(F)(F)c1cccc(Nc2ccc(Oc3ncccc3C(F)(F)F)cc2)n1] | 6-(trifluoromethyl)-N-(4-(3-(trifluoromethyl)pyridin-2-yloxy)phenyl)pyridin-2-amine | 400 | 10 |
| 11 | 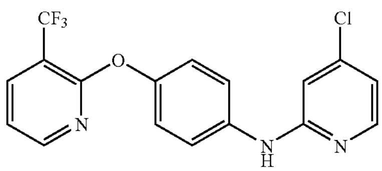 | 4-chloro-N-(4-(3-(trifluoromethyl)pyridin-2-yloxy)phenyl)pyridin-2-amine | 366 | 6.303 |
| 12 | 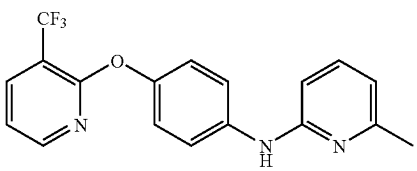 [SMILES: Cc1cccc(Nc2ccc(Oc3ncccc3C(F)(F)F)cc2)n1] | 6-methyl-N-(4-(3-(trifluoromethyl)pyridin-2-yloxy)phenyl)pyridin-2-amine | 346 | 10 |
| 13 | 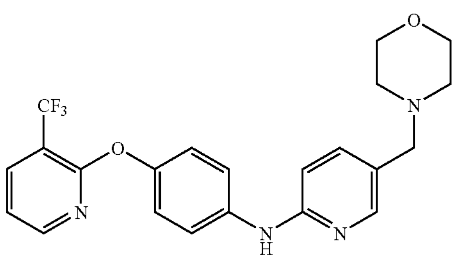 [SMILES: FC(F)(F)c1cccnc1Oc1ccc(Nc2ccc(CN3CCOCC3)cn2)cc1] | 5-(morpholinomethyl)-N-(4-(3-(trifluoromethyl)pyridin-2-yloxy)phenyl)pyridin-2-amine | 431.2 | 10 |
| 14 | 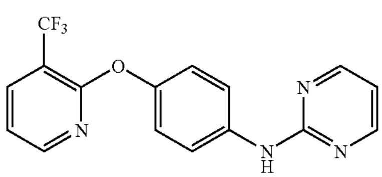 [SMILES: FC(F)(F)c1cccnc1Oc1ccc(Nc2ncccn2)cc1] | N-(4-(3-(trifluoromethyl)pyridin-2-yloxy)phenyl)pyrimidin-2-amine | 333.1 | 1.425 |
| 15 | 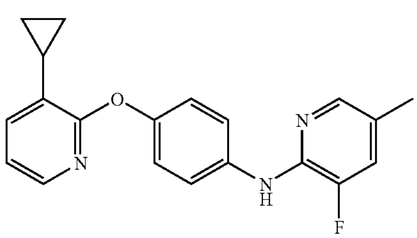 [SMILES: Cc1cnc(Nc2ccc(Oc3ncccc3C3CC3)cc2)c(F)c1] | N-(4-(3-cyclopropylpyridin-2-yloxy)phenyl)-3-fluoro-5-methylpyridin-2-amine | 336.1 | 0.18434 |
| 16 | 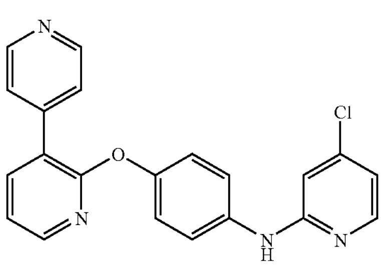 [SMILES: Clc1ccnc(Nc2ccc(Oc3ncccc3-c3ccncc3)cc2)c1] | N-(4-(3,4'-bipyridin-2-yloxy)phenyl)-4-chloropyridin-2-amine | 375 | 0.013455 |

TABLE IA-continued

EXAMPLES 3 TO 33 ARE TABULATED BELOW:

| Ex. No. | Compound Structure | Compound Name | MS | PDE10 IC50 (uM) |
|---|---|---|---|---|
| 17 | 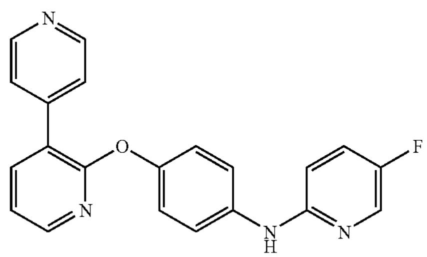 [SMILES: Fc1ccc(Nc2ccc(Oc3ncccc3-c3ccncc3)cc2)nc1] | N-(4-(3,4'-bipyridin-2-yloxy)phenyl)-5-fluoropyridin-2-amine | 359 | 0.02433 |
| 18 | 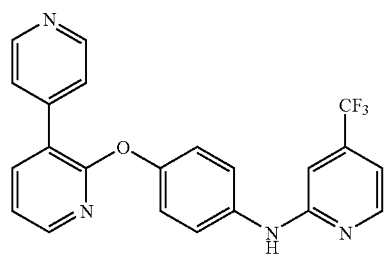 | N-(4-(3,4'-bipyridin-2-yloxy)phenyl)-4-(trifluoromethyl)pyridin-2-amine | 409 | 0.07236 |
| 19 | 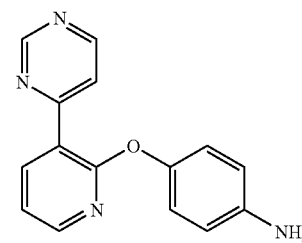 | N-(4-(3,4'-bipyridin-2-yloxy)phenyl)-3-fluoro-5-methylpyridin-2-amine | 373.1 | 0.00097 |
| 20 | 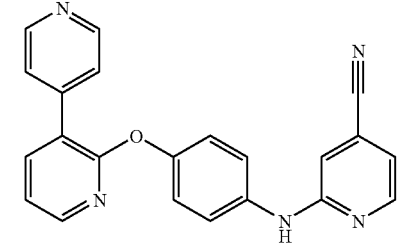 [SMILES: N#Cc1ccnc(Nc2ccc(Oc3ncccc3-c3ccncc3)cc2)c1] | 2-(4-(3,4'-bipyridin-2-yloxy)phenylamino)isonicotinonitrile | 366 | 0.037737 |
| 21 | 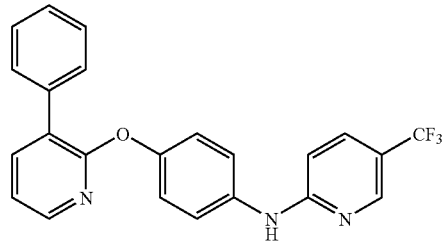 [SMILES: FC(F)(F)c1ccc(Nc2ccc(Oc3ncccc3-c3ccccc3)cc2)nc1] | N-(4-(3-phenylpyridin-2-yloxy)phenyl)-5-(trifluoromethyl)pyridin-2-amine | 408 | 0.91245 |

TABLE IA-continued

EXAMPLES 3 TO 33 ARE TABULATED BELOW:

| Ex. No. | Compound Structure | Compound Name | MS | PDE10 IC50 (uM) |
|---|---|---|---|---|
| 22 | 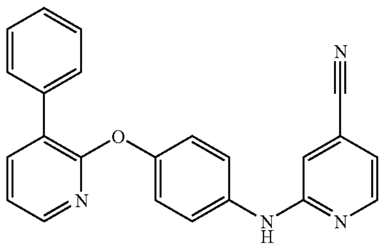 [SMILES: N#Cc1ccnc(Nc2ccc(Oc3ncccc3-c3ccccc3)cc2)c1] | 2-(4-(3-phenylpyridin-2-yloxy)phenylamino)isonicotinonitrile | 365 | 0.932925 |
| 23 | 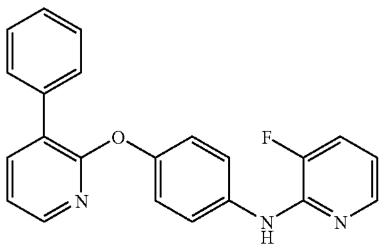 [SMILES: Fc1cccnc1Nc1ccc(Oc2ncccc2-c2ccccc2)cc1] | 3-fluoro-N-(4-(3-phenylpyridin-2-yloxy)phenyl)pyridin-2-amine | 358.1 | 0.16367 |
| 24 | 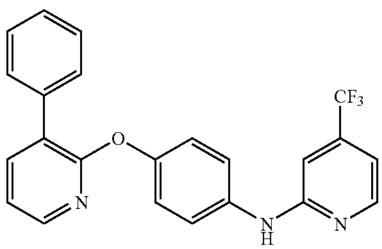 [SMILES: FC(F)(F)c1ccnc(Nc2ccc(Oc3ncccc3-c3ccccc3)cc2)c1] | N-(4-(3-phenylpyridin-2-yloxy)phenyl)-4-(trifluoromethyl)pyridin-2-amine | 408.1 | 1.472 |
| 25 | 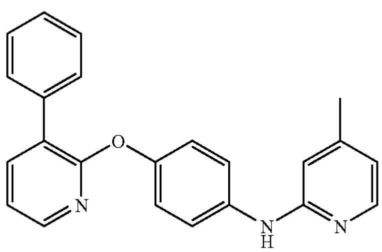 [SMILES: Cc1ccnc(Nc2ccc(Oc3ncccc3-c3ccccc3)cc2)c1] | 4-methyl-N-(4-(3-phenylpyridin-2-yloxy)phenyl)pyridin-2-amine | 354.1 | 0.230793 |
| 26 | 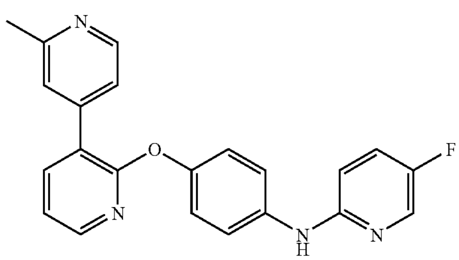 [SMILES: Cc1cc(-c2cccnc2Oc2ccc(Nc3ccc(F)cn3)cc2)ccn1] | 5-fluoro-N-(4-(2'-methyl-3,4'-bipyridin-2-yloxy)phenyl)pyridin-2-amine | 373.1 | 0.03234 |
| 27 | 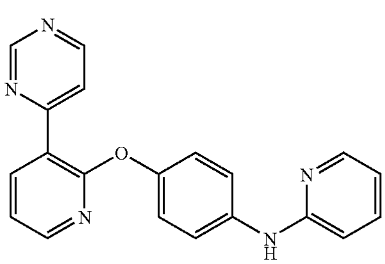 [SMILES: c1ccc(Nc2ccc(Oc3ncccc3-c3ccncn3)cc2)nc1] | N-(4-(3-(pyrimidin-4-yl)pyridin-2-yloxy)phenyl)pyridin-2-amine | 342.1 | 0.067 |

TABLE IA-continued

EXAMPLES 3 TO 33 ARE TABULATED BELOW:

| Ex. No. | Compound Structure | Compound Name | MS | PDE10 IC50 (uM) |
|---|---|---|---|---|
| 28 | 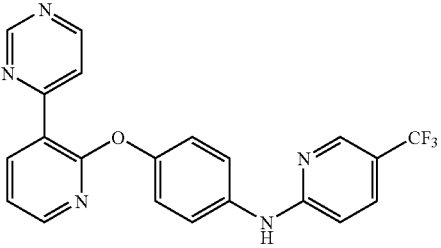 [SMILES: FC(F)(F)c1ccc(Nc2ccc(Oc3ncccc3-c3ccncn3)cc2)nc1] | N-(4-(3-(pyrimidin-4-yl)pyridin-2-yloxy)phenyl)-5-(trifluoromethyl)pyridin-2-amine | 410.0 | 0.548 |
| 29 | 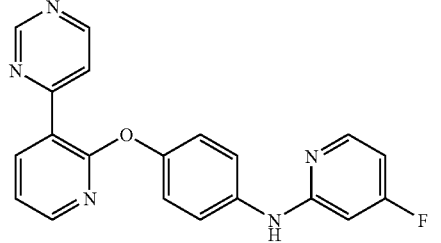 [SMILES: Fc1ccnc(Nc2ccc(Oc3ncccc3-c3ccncn3)cc2)c1] | 4-fluoro-N-(4-(3-(pyrimidin-4-yl)pyridin-2-yloxy)phenyl)pyridin-2-amine | 360.0 | 0.189 |
| 30 | 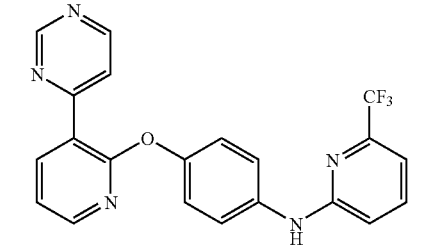 [SMILES: FC(F)(F)c1cccc(Nc2ccc(Oc3ncccc3-c3ccncn3)cc2)n1] | N-(4-(3-(pyrimidin-4-yl)pyridin-2-yloxy)phenyl)-6-(trifluoromethyl)pyridin-2-amine | 410.0 | 7.28 |
| 31 | 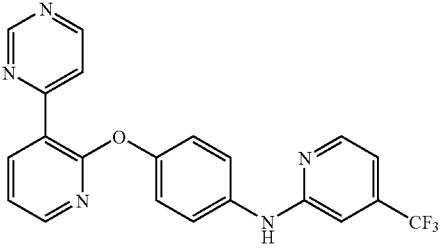 [SMILES: FC(F)(F)c1ccnc(Nc2ccc(Oc3ncccc3-c3ccncn3)cc2)c1] | N-(4-(3-(pyrimidin-4-yl)pyridin-2-yloxy)phenyl)-4-(trifluoromethyl)pyridin-2-amine | 410.0 | 1.88 |
| 32 | 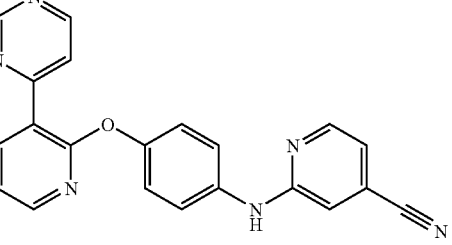 | 2-(4-(3-(pyrimidin-4-yl)pyridin-2-yloxy)phenylamino)isonicotinonitrile | 367.0 | 0.704 |

TABLE IA-continued

EXAMPLES 3 TO 33 ARE TABULATED BELOW:

| Ex. No. | Compound Structure | Compound Name | MS | PDE10 IC50 (uM) |
|---|---|---|---|---|
| 33 | 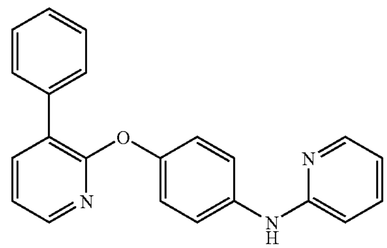 [SMILES: c1ccc(-c2cccnc2Oc2ccc(Nc3ccccn3)cc2)cc1] | N-(4-(3-phenylpyridin-2-yloxy)phenyl)pyridin-2-amine | 340.1 | 0.145 |

TABLE IB

PREPARATION OF EXAMPLES 3 TO 33 ARE TABULATED BELOW:

| Ex. No. | Scheme | Starting material 1 | Starting material 2 | Conditions or reagents that differ from scheme |
|---|---|---|---|---|
| 3 | 1 | | | |
| 4 | 1 | | | |
| 5 | 1 | | | |
| 6 | 1 | | | |
| 7 | 1 | | | |
| 8 | 1 | | | |

TABLE IB-continued

PREPARATION OF EXAMPLES 3 TO 33 ARE TABULATED BELOW:

| Ex. No. | Scheme | Starting material 1 | Starting material 2 | Conditions or reagents that differ from scheme |
|---|---|---|---|---|
| 9 | 1 | 3-(trifluoromethyl)-2-(4-aminophenoxy)pyridine | 2-chloro-6-methoxypyridine | |
| 10 | 1 | 3-(trifluoromethyl)-2-(4-aminophenoxy)pyridine | 2-chloro-6-(trifluoromethyl)pyridine | |
| 11 | 1 | 3-(trifluoromethyl)-2-(4-aminophenoxy)pyridine | 2,4-dichloropyridine | |
| 12 | 1 | 3-(trifluoromethyl)-2-(4-aminophenoxy)pyridine | 2-chloro-6-methylpyridine | |
| 13 | 1 | 3-(trifluoromethyl)-2-(4-aminophenoxy)pyridine | 2-chloro-5-(morpholinomethyl)pyridine | |
| 14 | 1 | 3-(trifluoromethyl)-2-(4-aminophenoxy)pyridine | 2-bromopyrimidine | |
| 15 | 1 | 3-cyclopropyl-2-(4-aminophenoxy)pyridine | 2-chloro-3-fluoro-5-methylpyridine | |
| 16 | 1 | 3-(pyridin-4-yl)-2-(4-aminophenoxy)pyridine | 2,4-dichloropyridine | |

TABLE IB-continued
PREPARATION OF EXAMPLES 3 TO 33 ARE TABULATED BELOW:
| Ex. No. | Scheme | Starting material 1 | Starting material 2 | Conditions or reagents that differ from scheme |
|---|---|---|---|---|
| 17 | 1 | 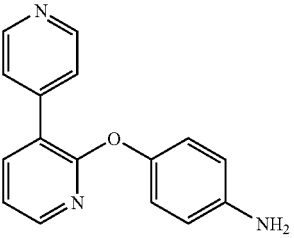 [SMILES: Nc1ccc(Oc2ncccc2-c2ccncc2)cc1] | 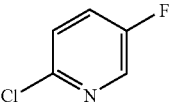 | 120° C. |
| 18 | 1 | 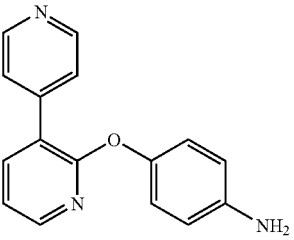 | 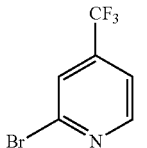 | 120° C. |
| 19 | 1 | 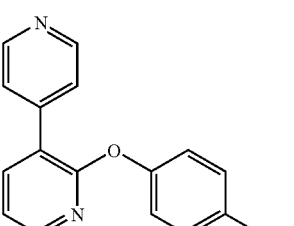 | 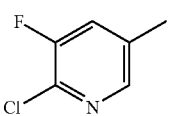 | 120° C. |
| 20 | 1 | 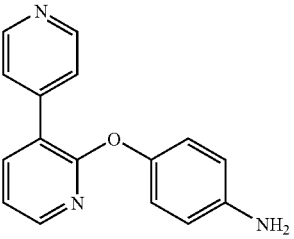 [SMILES: Nc1ccc(Oc2ncccc2-c2ccncc2)cc1] | 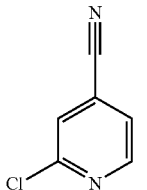 | 120° C. |
| 21 | 1 | 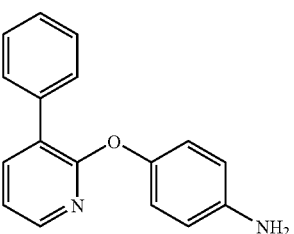 | 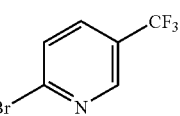 | |
| 22 | 1 | 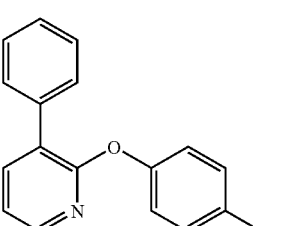 | 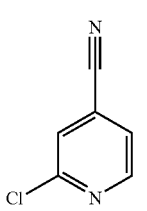 | |

TABLE IB-continued

PREPARATION OF EXAMPLES 3 TO 33 ARE TABULATED BELOW:

| Ex. No. | Scheme | Starting material 1 | Starting material 2 | Conditions or reagents that differ from scheme |
|---|---|---|---|---|
| 23 | 1 | 3-phenyl-2-(4-aminophenoxy)pyridine | 2-chloro-3-fluoropyridine | |
| 24 | 1 | 3-phenyl-2-(4-aminophenoxy)pyridine | 2-chloro-4-(trifluoromethyl)pyridine | |
| 25 | 1 | 3-phenyl-2-(4-aminophenoxy)pyridine | 2-chloro-4-methylpyridine | |
| 26 | 1 | 3-(2-methylpyridin-4-yl)-2-(4-aminophenoxy)pyridine | 2-chloro-5-fluoropyridine | |
| 27 | 1 | 3-(pyrimidin-4-yl)-2-(4-aminophenoxy)pyridine | 2-chloropyridine | |
| 28 | 1 | 3-(pyrimidin-4-yl)-2-(4-aminophenoxy)pyridine | 2-bromo-5-(trifluoromethyl)pyridine | |

TABLE IB-continued

PREPARATION OF EXAMPLES 3 TO 33 ARE TABULATED BELOW:

| Ex. No. | Scheme | Starting material 1 | Starting material 2 | Conditions or reagents that differ from scheme |
|---|---|---|---|---|
| 29 | 1 | 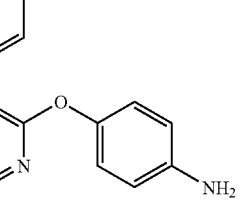 | 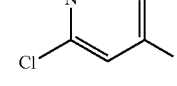 | |
| 30 | 1 | 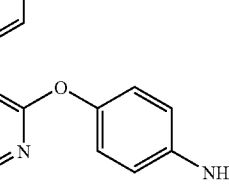 | 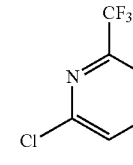 | 2-(dicyclohexylphosphino)-2'-methylbiphenyl was used in place of BINAP |
| 31 | 1 | 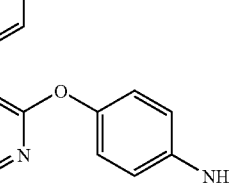 | 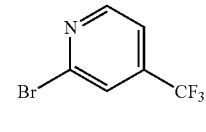 | 2-(dicyclohexylphosphino)-2'-methylbiphenyl was used in place of BINAP |
| 32 | 1 | 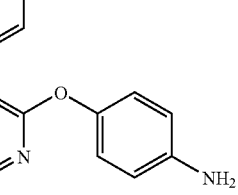 | 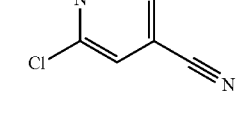 | 2-(dicyclohexylphosphino)-2'-methylbiphenyl was used in place of BINAP |
| 33 | 1 | 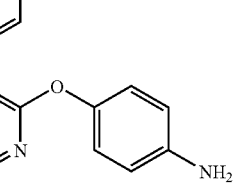 | 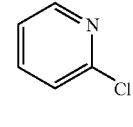 | |

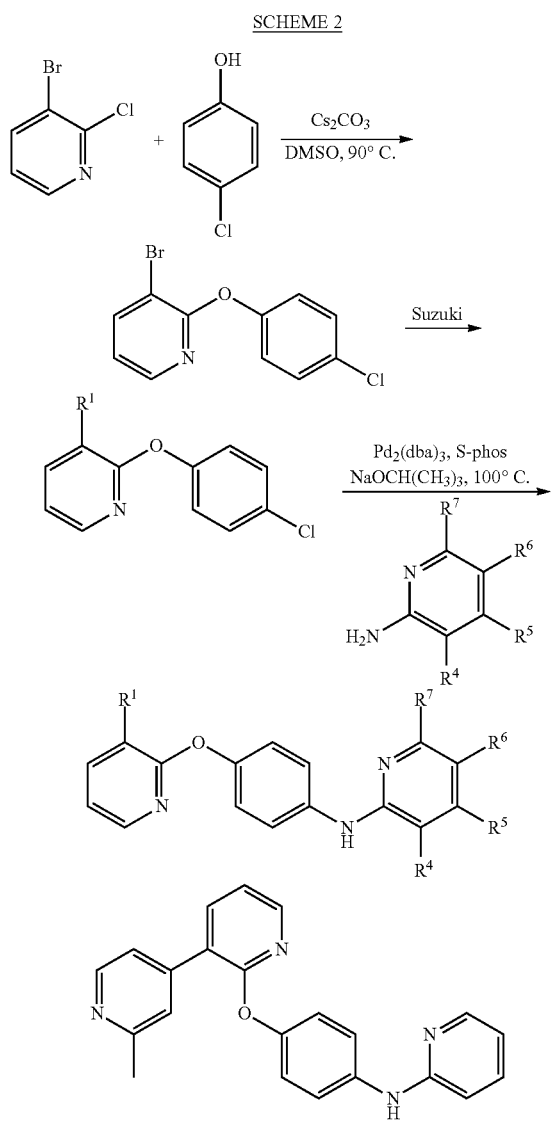

Example 34

N-(4-(3-(2-METHYLPYRIDIN-4-YL)PYRIDIN-2-YLOXY)PHENYL)-PYRIDIN-2-AMINE

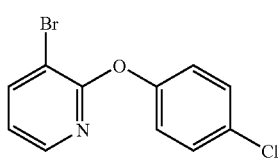 [SMILES: Clc1ccc(Oc2ncccc2Br)cc1]

STEP 1.
3-BROMO-2-(4-CHLOROPHENOXY)PYRIDINE

A mixture of 3-bromo-2-chloropyridine (10 g, 52 mmol), 4-chlorophenol (6.7 g, 52 mmol), cesium carbonate (34 g, 104 mmol) in 100 mL DMSO was heated to 90° C. with stirring overnight. The reaction mixture was dilution with DCM and washed with water and brine. The organic layer was dried over Na$_2$SO$_4$ and concentrated. The residue was purified by silica gel chromatography (0-30% EtOAc/hexane) to provide the title compound.

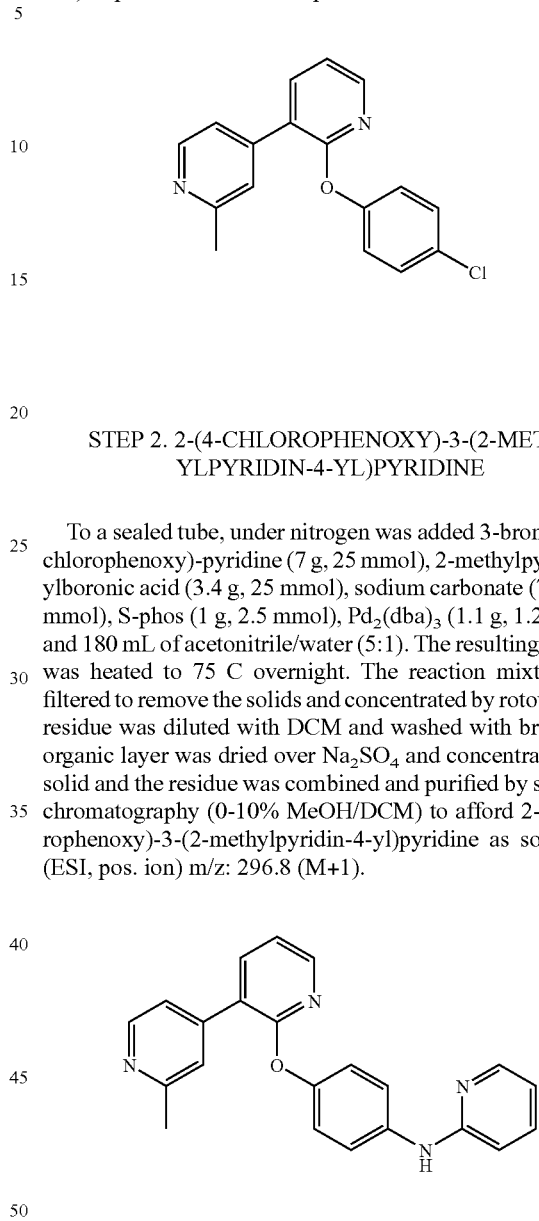

STEP 2. 2-(4-CHLOROPHENOXY)-3-(2-METHYLPYRIDIN-4-YL)PYRIDINE

To a sealed tube, under nitrogen was added 3-bromo-2-(4-chlorophenoxy)-pyridine (7 g, 25 mmol), 2-methylpyridin-4-ylboronic acid (3.4 g, 25 mmol), sodium carbonate (7.8 g, 74 mmol), S-phos (1 g, 2.5 mmol), Pd$_2$(dba)$_3$ (1.1 g, 1.2 mmol), and 180 mL of acetonitrile/water (5:1). The resulting mixture was heated to 75 C overnight. The reaction mixture was filtered to remove the solids and concentrated by rotovap. The residue was diluted with DCM and washed with brine. The organic layer was dried over Na$_2$SO$_4$ and concentrated. The solid and the residue was combined and purified by silica gel chromatography (0-10% MeOH/DCM) to afford 2-(4-chlorophenoxy)-3-(2-methylpyridin-4-yl)pyridine as solid. MS (ESI, pos. ion) m/z: 296.8 (M+1).

STEP 3. N-(4-(3-(2-METHYLPYRIDIN-4-YL)PYRIDIN-2-YLOXY)PHENYL)PYRIDIN-2-AMINE

To a sealed tube, under nitrogen, was added Pd$_2$(dba)$_3$ (0.19 g, 0.21 mmol), S-phos (0.36 g, 0.84 mmol), sodium 2-methylpropan-2-olate (2.0 g, 21 mmol), pyridin-2-amine (0.95 g, 10 mmol), 2-(4-chlorophenoxy)-3-(2-methylpyridin-4-yl)pyridine (2.5 g, 8.4 mmol), and toluene (18 mL). Reaction mixture was heated to 100° C. overnight. The reaction mixture was directly purified by silica gel chromatography (0-100% EtOAc/hexane). Solid precipitate formed upon rotovap of rich cut. The solid was collected and rinsed with EtOAc to afford N-(4-(3-(2-methylpyridin-4-yl)pyridin-2-yloxy)phenyl)pyridin-2-amine. MS (ESI, pos. ion) m/z: 355.1 (M+1). IC50 (uM) 0.003343.

SCHEME 3

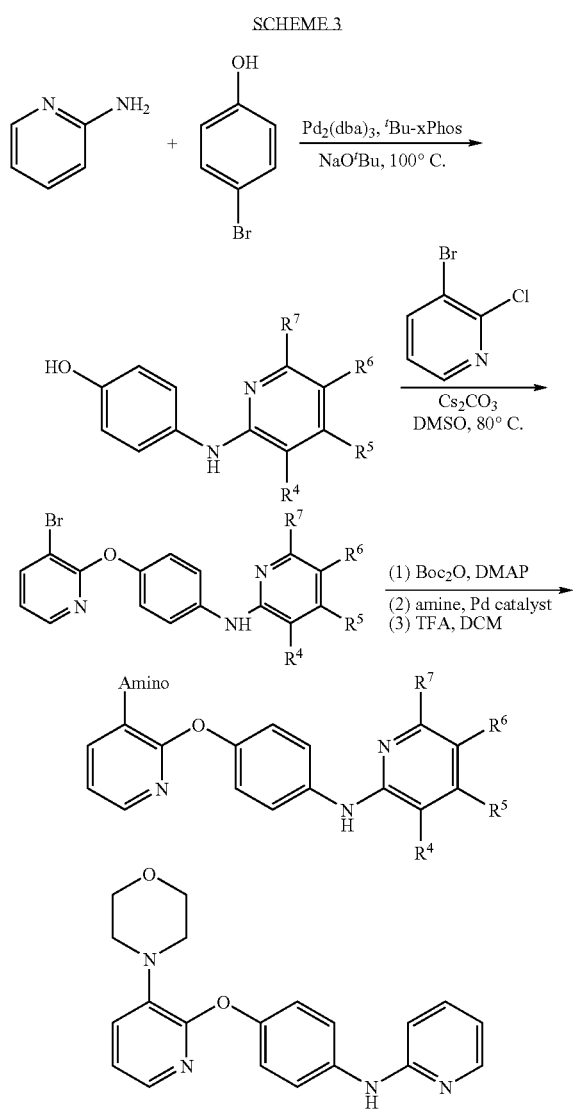

Example 35

N-(4-(3-(2-METHYLPYRIDIN-4-YL)PYRIDIN-2-YLOXY)PHENYL)-PYRIDIN-2-AMINE

STEP 1. 4-(PYRIDIN-2-YLAMINO)PHENOL

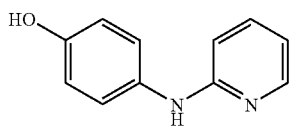 [SMILES: Oc1ccc(Nc2ccccn2)cc1]

To a microwave reaction vessel was added 4-bromophenol (5.5773 mL, 59.317 mmol), 2-aminopyridine (5.5942 g, 59.317 mmol), Pd₂(dba)₃ (1.3658 g, 1.4829 mmol), 2-di-t-butylphosphino-2',4',6'-tri-isopropyl-1,1'-biphenyl (2.5346 g, 5.9317 mmol), and sodium tert-butoxide (10.0798 g, 118.63 mmol). The vessel was capped and flushed with argon. Toluene was added and the vessel was flushed with argon. The temperature was brought to 100° C. to stir overnight. The reaction was monitored by LCMS to completion. The solvent was evaporated. The crude product was adsorbed onto a plug of silica gel and chromatographed through a Biotage™ SNAP cartridge (KP-Sil 340 g), eluting with a gradient of 1.5% to 6% methanol in DCM, to provide 4-(pyridin-2-ylamino)phenol. MS (ESI, pos. ion) m/z: 187.0 (M+1).

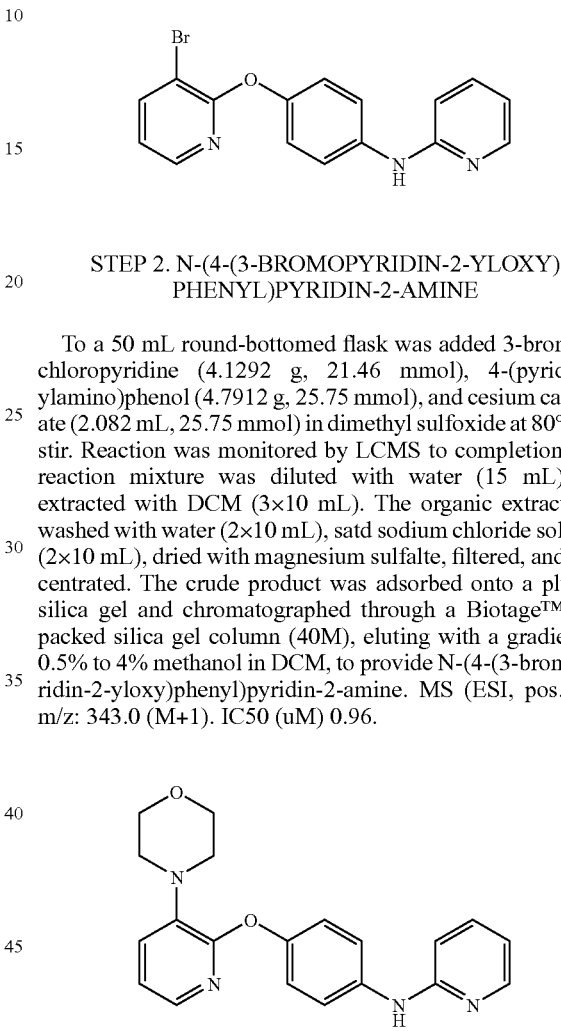

STEP 2. N-(4-(3-BROMOPYRIDIN-2-YLOXY)PHENYL)PYRIDIN-2-AMINE

To a 50 mL round-bottomed flask was added 3-bromo-2-chloropyridine (4.1292 g, 21.46 mmol), 4-(pyridin-2-ylamino)phenol (4.7912 g, 25.75 mmol), and cesium carbonate (2.082 mL, 25.75 mmol) in dimethyl sulfoxide at 80° C. to stir. Reaction was monitored by LCMS to completion. The reaction mixture was diluted with water (15 mL) and extracted with DCM (3×10 mL). The organic extract was washed with water (2×10 mL), satd sodium chloride solution (2×10 mL), dried with magnesium sulfalte, filtered, and concentrated. The crude product was adsorbed onto a plug of silica gel and chromatographed through a Biotage™ pre-packed silica gel column (40M), eluting with a gradient of 0.5% to 4% methanol in DCM, to provide N-(4-(3-bromopyridin-2-yloxy)phenyl)pyridin-2-amine. MS (ESI, pos. ion) m/z: 343.0 (M+1). IC50 (uM) 0.96.

STEP 3. N-(4-(3-MORPHOLINOPYRIDIN-2-YLOXY)PHENYL)PYRIDIN-2-AMINE

To a 50 mL round-bottomed flask was added N-(4-(3-bromopyridin-2-yloxy)-phenyl)pyridin-2-amine (1.0330 g, 3.019 mmol), Di-tent-butyl dicarbonate (0.8353 mL, 3.636 mmol), and 4-dimethylaminopyridine (0.3688 g, 3.019 mmol) in THF (10 mL) to stir at 50° C. overnight. The solvent was evaporated. The crude product was adsorbed onto a plug of silica gel and chromatographed through a Biotage™ pre-packed silica gel column (25M), eluting with a gradient of 10% to 100% EtOAc in hexane, to provide tent-butyl 4-(3-bromopyridin-2-yloxy)-phenyl(pyridin-2-yl)carbamate.

A microwave reaction vessel was charged with tert-butyl 4-(3-bromopyridin-2-yloxy)phenyl(pyridin-2-yl)carbamate (0.6142 g, 1.39 mmol), palladium (II) acetate (0.0306 g, 0.0833 mmol), 2-dicyclohexylphosphino-2',6'-dimethoxy-1, 1'-biphenyl (0.0932 g, 0.167 mmol), and sodium tert-butoxide (0.5219 g, 4.17 mmol). The vessel was put under vacuum for 5 min. A solution of morpholine (0.316 mL, 2.78 mmol) in toluene was added to the vessel. The reaction was allowed to heat at 90° C. for 10 min. The crude product was adsorbed onto a plug of silica gel and chromatographed through a Biotage™ pre-packed silica gel column (40M), eluting with a gradient of 10% to 50% acetone in hexane. Product was taken up in DCM and TFA was added to stir overnight. The solvent was removed and the residue was filtered through a carbonate filter to provide N-(4-(3-morpholinopyridin-2-yloxy)phenyl)pyridin-2-amine. MS (ESI, pos. ion) m/z: 349.1 (M+1). IC50 (uM) 0.030207.

SCHEME 4

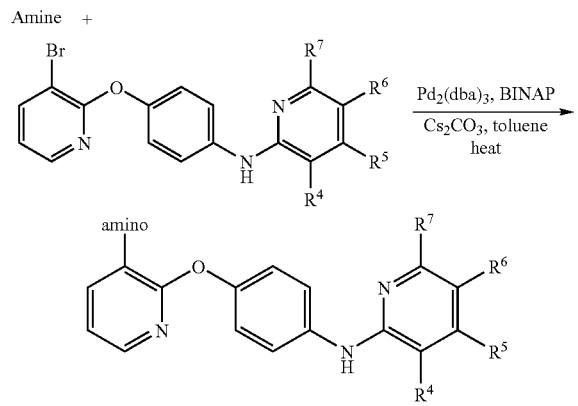

-continued

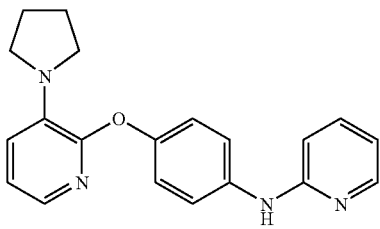

Example 36

N-(4-(3-(PYRROLIDIN-1-YL)PYRIDIN-2-YLOXY)PHENYL)PYRIDIN-2-AMINE

A mixture of N-(4-(3-bromopyridin-2-yloxy)phenyl)pyridin-2-amine (300 mg, 0.88 mmol), rac-BINAP (109 mg, 0.17 mmol), $Pd_2(dba)_3$ (80 mg, 0.088 mmol), $Cs_2CO_3$ (857 mg, 2.6 mmol) and pyrrolidine (1.31 mmol) in toluene (3.5 mL) was heated to 95° C. for 18 h. The mixture was cooled to room temperature, diluted with MeOH and filtered through Celite. The filtrate was concentrated, dissolved in MeOH and purified with reverse-phase HPLC (Phenomenex Gemini 80 A column, 100×50 mm, 80 ml/min, 10-95% $CH_3CN/H_2O$, 0.1% TFA, 15 min gradient). The residue was re-purified by column chromatography (EtOAc/Hexanes=0-40%, followed by recrystallization from MeOH to give the title compound. MS (ESI, pos. ion) m/z: 333 (M+1). IC50 (uM) 0.063.

TABLE IIA

EXAMPLES 37 TO 68 ARE TABULATED BELOW:

| Ex. No. | Compound Structure | Compound Name | MS | PDE10 IC50 (μM) |
|---|---|---|---|---|
| 37 | 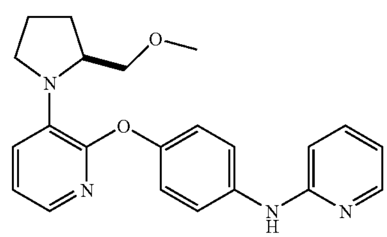 [SMILES: COC[C@@H]1CCCN1c1cccnc1Oc1ccc(Nc2ccccn2)cc1] | (S)-N-(4-(3-(2-(methoxymethyl)pyrrolidin-1-yl)pyridin-2-yloxy)phenyl)pyridin-2-amine | 377 | 0.009241 |
| 38 | 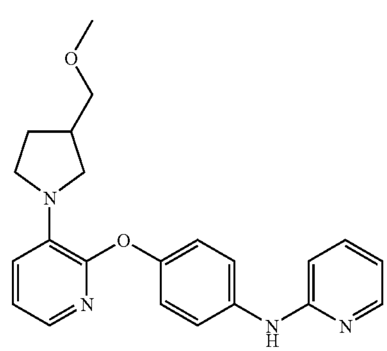 [SMILES: COCC1CCN(c2cccnc2Oc2ccc(Nc3ccccn3)cc2)C1] | N-(4-(3-(3-(methoxymethyl)pyrrolidin-1-yl)pyridin-2-yloxy)phenyl)pyridin-2-amine | 377 | 0.0875 |

TABLE IIA-continued

EXAMPLES 37 TO 68 ARE TABULATED BELOW:

| Ex. No. | Compound Structure | Compound Name | MS | PDE10 IC50 (μM) |
|---|---|---|---|---|
| 39 | 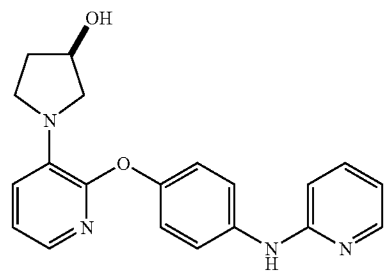 [SMILES: O[C@@H]1CCN(c2cccnc2Oc2ccc(Nc3ccccn3)cc2)C1] | (R)-1-(2-(4-(pyridin-2-ylamino)phenoxy)pyridin-3-yl)pyrrolidin-3-ol | 349 | 0.1034 |
| 40 | 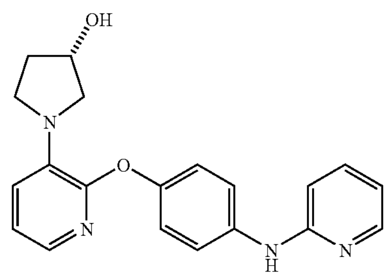 [SMILES: O[C@H]1CCN(c2cccnc2Oc2ccc(Nc3ccccn3)cc2)C1] | (S)-1-(2-(4-(pyridin-2-ylamino)phenoxy)pyridin-3-yl)pyrrolidin-3-ol | 349 | 0.1597 |
| 41 | 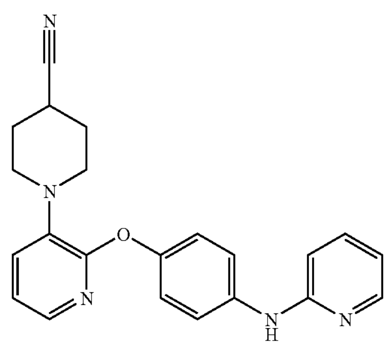 [SMILES: N#CC1CCN(c2cccnc2Oc2ccc(Nc3ccccn3)cc2)CC1] | 1-(2-(4-(pyridin-2-ylamino)phenoxy)pyridin-3-yl)piperidine-4-carbonitrile | 372 | 0.0464 |
| 42 | 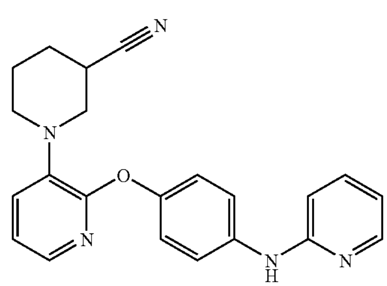 [SMILES: N#CC1CCCN(c2cccnc2Oc2ccc(Nc3ccccn3)cc2)C1] | 1-(2-(4-(pyridin-2-ylamino)phenoxy)pyridin-3-yl)piperidine-3-carbonitrile | 372 | 0.0743 |
| 43 | 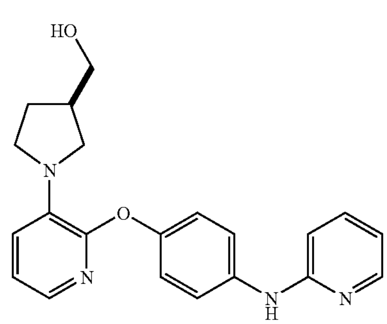 | (R)-(1-(2-(4-(pyridine-2-ylamino)phenoxy)pyridin-3-yl)pyrrolidin-3-yl)methanol | 363 | 0.08608 |

TABLE IIA-continued

EXAMPLES 37 TO 68 ARE TABULATED BELOW:

| Ex. No. | Compound Structure | Compound Name | MS | PDE10 IC50 (μM) |
|---|---|---|---|---|
| 44 | 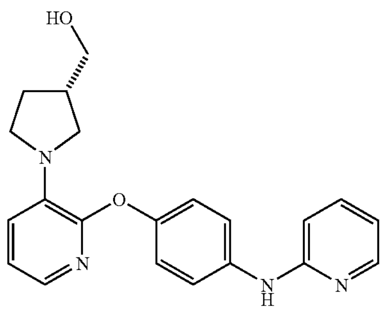 | (S)-(1-(2-(4-(pyridine-2-ylamino)phenoxy)pyridin-3-yl)pyrrolidin-3-yl)methanol | 363 | 0.08707 |
| 45 | 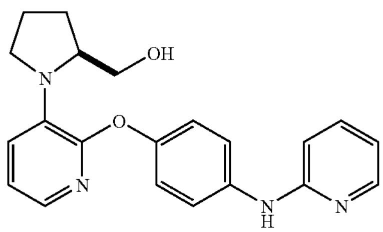 | (S)-(1-(2-(4-(pyridine-2-ylamino)phenoxy)pyridin-3-yl)pyrrolidin-2-yl)methanol | 363 | 0.07339 |
| 46 | 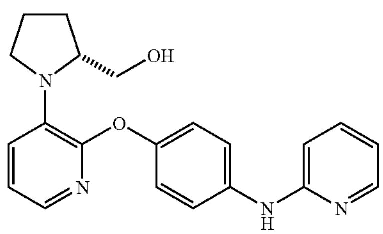 | (R)-(1-(2-(4-(pyridine-2-ylamino)phenoxy)pyridin-3-yl)pyrrolidin-2-yl)methanol | 363 | 0.2106 |
| 47 | 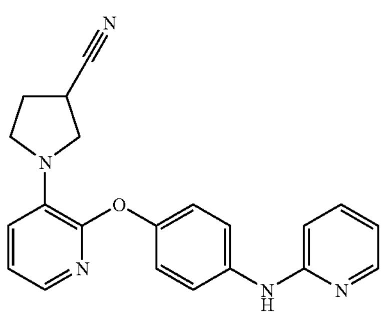 [SMILES: N#CC1CCN(c2cccnc2Oc2ccc(Nc3ccccn3)cc2)C1] | 1-(2-(4-(pyridin-2-ylamino)phenoxy)pyridin-3-yl)pyrrolidine-3-carbonitrile | 358 | 0.022355 |
| 48 | 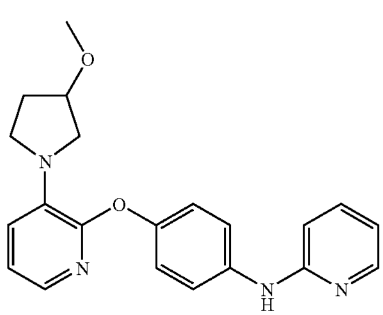 [SMILES: COC1CCN(c2cccnc2Oc2ccc(Nc3ccccn3)cc2)C1] | N-(4-(3-(3-methoxypyrrolidin-1-yl)pyridin-2-yloxy)phenyl)pyridin-2-amine | 363 | 0.1551 |

TABLE IIA-continued

EXAMPLES 37 TO 68 ARE TABULATED BELOW:

| Ex. No. | Compound Structure | Compound Name | MS | PDE10 IC50 (μM) |
|---|---|---|---|---|
| 49 | 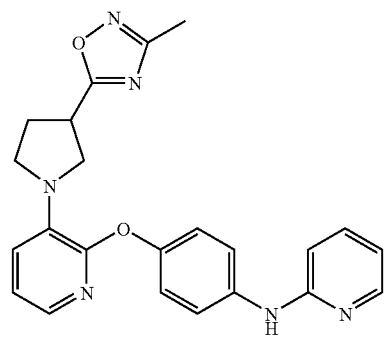 [SMILES: Cc1noc(C2CCN(c3cccnc3Oc3ccc(Nc4ccccn4)cc3)C2)n1] | N-(4-(3-(3-methyl-1,2,4-oxadiazol-5-yl)pyrrolidin-1-yl)pyridin-2-yloxy)phenyl)pyridin-2-amine | 415 | 0.06047 |
| 50 | 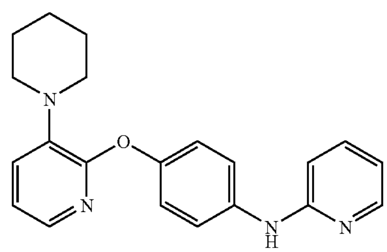 [SMILES: c1ccc(Nc2ccc(Oc3ncccc3N3CCCCC3)cc2)nc1] | N-(4-(3-(piperidin-1-yl)pyridin-2-yloxy)phenyl)pyridin-2-amine | 347 | 0.07817 |
| 51 | 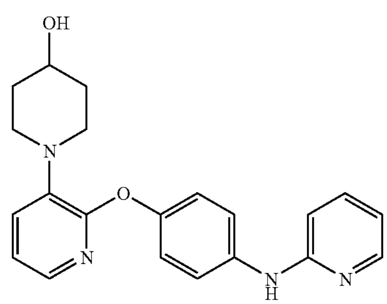 [SMILES: OC1CCN(c2cccnc2Oc2ccc(Nc3ccccn3)cc2)CC1] | 1-(2-(4-(pyridin-2-ylamino)phenoxy)pyridin-3-yl)piperidin-4-ol | 363 | 0.09483 |
| 52 | 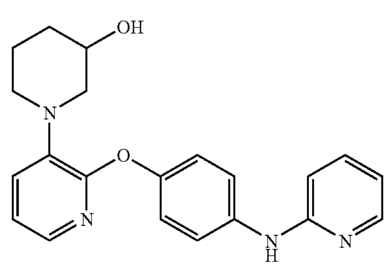 [SMILES: OC1CCCN(c2cccnc2Oc2ccc(Nc3ccccn3)cc2)C1] | 1-(2-(4-(pyridin-2-ylamino)phenoxy)pyridin-3-yl)piperidin-3-ol | 363 | 0.01763 |
| 53 | 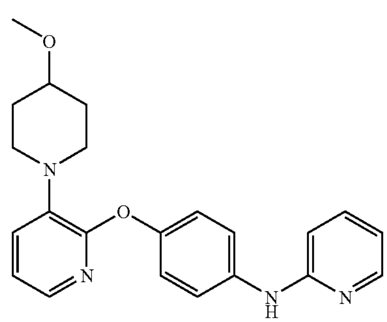 [SMILES: COC1CCN(c2cccnc2Oc2ccc(Nc3ccccn3)cc2)CC1] | N-(4-(3-(4-methoxypiperidin-1-yl)pyridin-2-yloxy)phenyl)pyridin-2-amine | 377 | 0.02748 |

TABLE IIA-continued

EXAMPLES 37 TO 68 ARE TABULATED BELOW:

| Ex. No. | Compound Structure | Compound Name | MS | PDE10 IC50 (μM) |
|---|---|---|---|---|
| 54 | 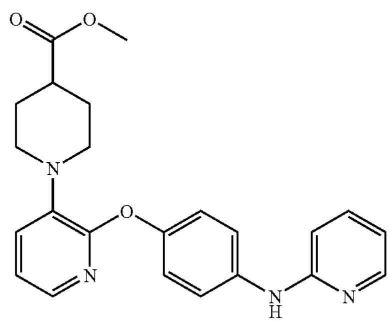 [SMILES: COC(=O)C1CCN(c2cccnc2Oc2ccc(Nc3ccccn3)cc2)CC1] | methyl 1-(2-(4-(pyridin-2-ylamino)phenoxy)pyridin-3-yl)piperidine-4-carboxylate | 405 | 0.04989 |
| 55 | 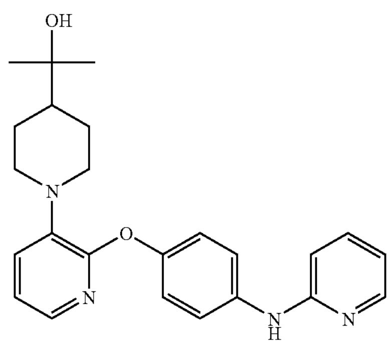 [SMILES: CC(C)(O)C1CCN(c2cccnc2Oc2ccc(Nc3ccccn3)cc2)CC1] | 2-(1-(2-(4-(pyridin-2-ylamino)phenoxy)pyridin-3-yl)piperidin-4-yl)propan-2-ol | 405 | 0.1938 |
| 56 | 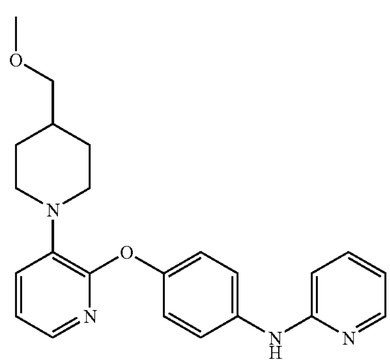 [SMILES: COCC1CCN(c2cccnc2Oc2ccc(Nc3ccccn3)cc2)CC1] | N-(4-(3-(4-(methoxymethyl)piperidin-1-yl)pyridin-2-yloxy)phenyl)pyridin-2-amine | 391 | 0.3066 |
| 57 | 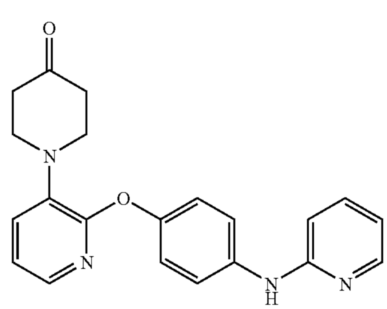 [SMILES: O=C1CCN(c2cccnc2Oc2ccc(Nc3ccccn3)cc2)CC1] | 1-(2-(4-(pyridin-2-ylamino)phenoxy)pyridin-3-yl)piperidin-4-one | 361 | 0.03082 |

TABLE IIA-continued

EXAMPLES 37 TO 68 ARE TABULATED BELOW:

| Ex. No. | Compound Structure | Compound Name | MS | PDE10 IC50 (μM) |
|---|---|---|---|---|
| 58 | 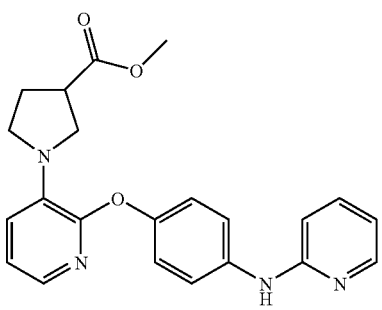 [SMILES: COC(=O)C1CCN(c2cccnc2Oc2ccc(Nc3ccccn3)cc2)C1] | methyl 1-(2-(4-(pyridin-2-ylamino)phenoxy)pyridin-3-yl)pyrrolidine-3-carboxylate | 391 | 0.1164 |
| 59 | 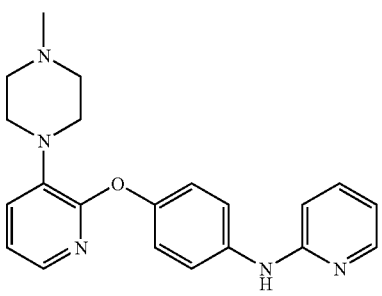 [SMILES: CN1CCN(c2cccnc2Oc2ccc(Nc3ccccn3)cc2)CC1] | N-(4-(3-(4-methylpiperazin-1-yl)pyridin-2-yloxy)phenyl)pyridin-2-amine | 362 | 1.019 |
| 60 | 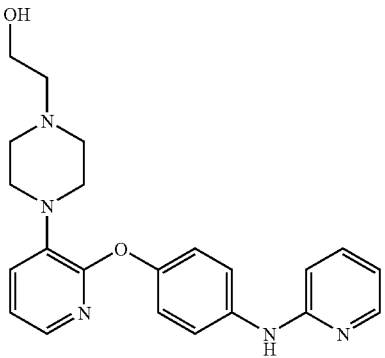 [SMILES: OCCN1CCN(c2cccnc2Oc2ccc(Nc3ccccn3)cc2)CC1] | 2-(4-(2-(4-(pyridin-2-ylamino)phenoxy)pyridin-3-yl)piperazin-1-yl)ethanol | 392 | 0.7732 |
| 61 | 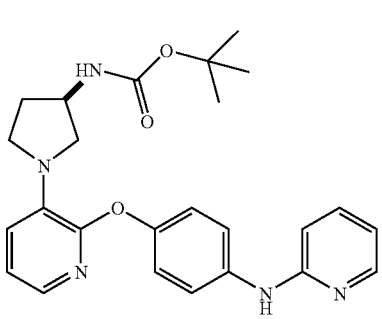 | (R)-tert-butyl 1-(2-(4-(pyridin-2-ylamino)phenoxy)pyridin-3-yl)pyrrolidin-3-ylcarbamate | 448 | 0.122 |

TABLE IIA-continued

EXAMPLES 37 TO 68 ARE TABULATED BELOW:

| Ex. No. | Compound Structure | Compound Name | MS | PDE10 IC50 (μM) |
|---|---|---|---|---|
| 62 | 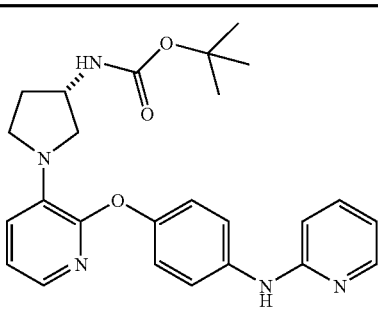 | (S)-tert-butyl 1-(2-(4-(pyridin-2-ylamino)phenoxy)pyridin-3-yl)pyrrolidin-3-ylcarbamate | 448 | 0.03359 |
| 63 | 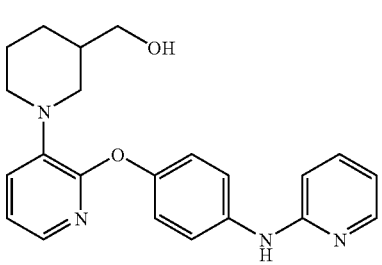 [SMILES: OCC1CCCN(c2cccnc2Oc2ccc(Nc3ccccn3)cc2)C1] | (1-(2-(4-(pyridin-2-ylamino)phenoxy)pyridin-3-yl)piperidin-3-yl)methanol | 377 | 0.2162 |
| 64 | 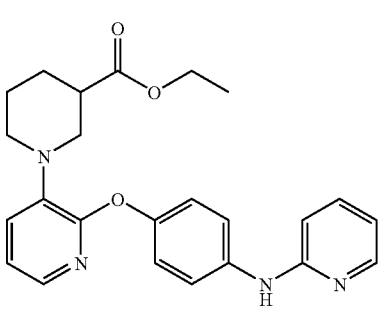 [SMILES: CCOC(=O)C1CCCN(c2cccnc2Oc2ccc(Nc3ccccn3)cc2)C1] | ethyl 1-(2-(4-(pyridine-2-ylamino)phenoxy)pyridin-3-yl)piperidine-3-carboxylate | 419 | 0.01884 |
| 65 | 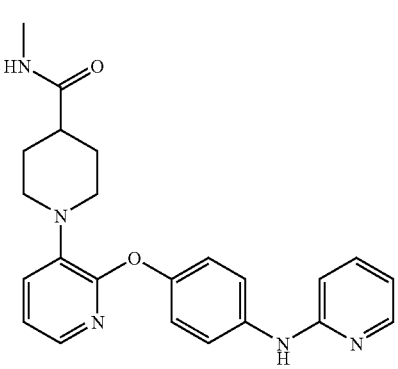 [SMILES: CNC(=O)C1CCN(c2cccnc2Oc2ccc(Nc3ccccn3)cc2)CC1] | N-methyl-1-(2-(4-(pyridin-2-ylamino)phenoxy)pyridin-3-yl)piperidine-4-carboxamide | 404 | 0.2295 |
| 66 | 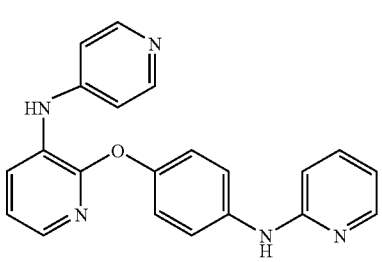 [SMILES: c1ccc(Nc2ccc(Oc3ncccc3Nc3ccncc3)cc2)nc1] | N-(4-(3-(pyridin-4-ylamino)pyridin-2-yloxy)phenyl)pyridin-2-amine | 356 | 0.6201 |

TABLE IIA-continued

EXAMPLES 37 TO 68 ARE TABULATED BELOW:

| Ex. No. | Compound Structure | Compound Name | MS | PDE10 IC50 (μM) |
|---|---|---|---|---|
| 67 | 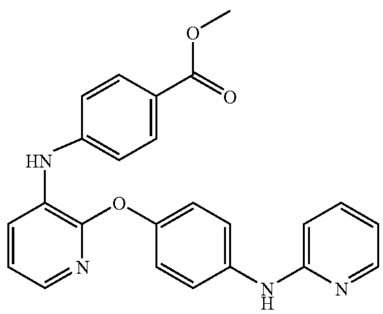 [SMILES: COC(=O)c1ccc(Nc2cccnc2Oc2ccc(Nc3ccccn3)cc2)cc1] | methyl 4-(2-(4-(pyridin-2-ylamino)phenoxy)pyridin-3-ylamino)benzoate | 412 | 0.0878 |
| 68 | 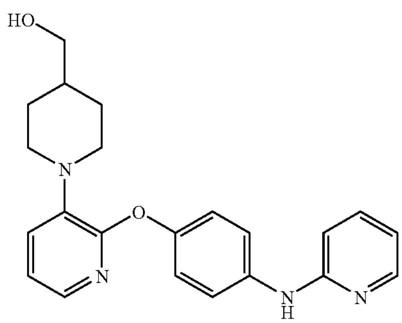 [SMILES: OCC1CCN(c2cccnc2Oc2ccc(Nc3ccccn3)cc2)CC1] | (1-(2-(4-(pyridin-2-ylamino)phenoxy)pyridin-3-yl)piperidin-4-yl)methanol | 377 | 0.001661 |

TABLE IIB

PREPARATION OF EXAMPLES 37 TO 68 ARE TABULATED BELOW:

| Ex. No. | Scheme | Starting material 1 | Starting Material 2 | Conditions or reagents that differ from scheme |
|---|---|---|---|---|
| 37 | 4 | | | |
| 38 | 4 | | | |
| 39 | 4 | | | |

TABLE IIB-continued

PREPARATION OF EXAMPLES 37 TO 68 ARE TABULATED BELOW:

| Ex. No. | Scheme | Starting material 1 | Starting Material 2 | Conditions or reagents that differ from scheme |
|---|---|---|---|---|
| 40 | 4 | (S)-3-hydroxypyrrolidine | 3-bromo-2-(4-(pyridin-2-ylamino)phenoxy)pyridine | |
| 41 | 4 | piperidine-4-carbonitrile | 3-bromo-2-(4-(pyridin-2-ylamino)phenoxy)pyridine | |
| 42 | 4 | piperidine-3-carbonitrile | 3-bromo-2-(4-(pyridin-2-ylamino)phenoxy)pyridine | |
| 43 | 4 | (S)-pyrrolidin-3-ylmethanol | 3-bromo-2-(4-(pyridin-2-ylamino)phenoxy)pyridine | |
| 44 | 4 | (R)-pyrrolidin-3-ylmethanol | 3-bromo-2-(4-(pyridin-2-ylamino)phenoxy)pyridine | |
| 45 | 4 | (S)-pyrrolidin-2-ylmethanol | 3-bromo-2-(4-(pyridin-2-ylamino)phenoxy)pyridine | |
| 46 | 4 | (R)-pyrrolidin-2-ylmethanol | 3-bromo-2-(4-(pyridin-2-ylamino)phenoxy)pyridine | |

TABLE IIB-continued

PREPARATION OF EXAMPLES 37 TO 68 ARE TABULATED BELOW:

| Ex. No. | Scheme | Starting material 1 | Starting Material 2 | Conditions or reagents that differ from scheme |
|---|---|---|---|---|
| 47 | 4 | pyrrolidine-3-carbonitrile | 3-bromo-2-(4-(pyridin-2-ylamino)phenoxy)pyridine | |
| 48 | 4 | 3-methoxypyrrolidine | 3-bromo-2-(4-(pyridin-2-ylamino)phenoxy)pyridine | |
| 49 | 4 | 3-methyl-5-(pyrrolidin-3-yl)-1,2,4-oxadiazole | 3-bromo-2-(4-(pyridin-2-ylamino)phenoxy)pyridine | |
| 50 | 4 | piperidine | 3-bromo-2-(4-(pyridin-2-ylamino)phenoxy)pyridine | |
| 51 | 4 | piperidin-4-ol | 3-bromo-2-(4-(pyridin-2-ylamino)phenoxy)pyridine | |
| 52 | 4 | piperidin-3-ol | 3-bromo-2-(4-(pyridin-2-ylamino)phenoxy)pyridine | |
| 53 | 4 | 4-methoxypiperidine | 3-bromo-2-(4-(pyridin-2-ylamino)phenoxy)pyridine | |

TABLE IIB-continued

PREPARATION OF EXAMPLES 37 TO 68 ARE TABULATED BELOW:

| Ex. No. | Scheme | Starting material 1 | Starting Material 2 | Conditions or reagents that differ from scheme |
|---|---|---|---|---|
| 54 | 4 | methyl piperidine-4-carboxylate | 3-bromo-2-(4-(pyridin-2-ylamino)phenoxy)pyridine | |
| 55 | 4 | 2-(piperidin-4-yl)propan-2-ol | 3-bromo-2-(4-(pyridin-2-ylamino)phenoxy)pyridine | |
| 56 | 4 | 4-(methoxymethyl)piperidine | 3-bromo-2-(4-(pyridin-2-ylamino)phenoxy)pyridine | |
| 57 | 4 | piperidin-4-one | 3-bromo-2-(4-(pyridin-2-ylamino)phenoxy)pyridine | |
| 58 | 4 | methyl pyrrolidine-3-carboxylate | 3-bromo-2-(4-(pyridin-2-ylamino)phenoxy)pyridine | |
| 59 | 4 | 1-methylpiperazine | 3-bromo-2-(4-(pyridin-2-ylamino)phenoxy)pyridine | |
| 60 | 4 | 2-(piperazin-1-yl)ethanol | 3-bromo-2-(4-(pyridin-2-ylamino)phenoxy)pyridine | |

TABLE IIB-continued

PREPARATION OF EXAMPLES 37 TO 68 ARE TABULATED BELOW:

| Ex. No. | Scheme | Starting material 1 | Starting Material 2 | Conditions or reagents that differ from scheme |
|---|---|---|---|---|
| 61 | 4 | | | |
| 62 | 4 | | | |
| 63 | 4 | | | |
| 64 | 4 | | | |
| 65 | 4 | | | |
| 66 | 4 | | | |
| 67 | 4 | | | |

TABLE IIB-continued

PREPARATION OF EXAMPLES 37 TO 68 ARE TABULATED BELOW:

| Ex. No. | Scheme | Starting material 1 | Starting Material 2 | Conditions or reagents that differ from scheme |
|---|---|---|---|---|
| 68 | 4 | 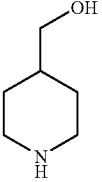 | 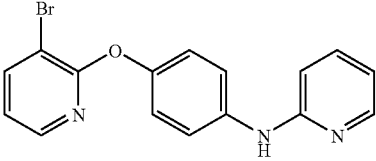 [SMILES: Brc1cccnc1Oc1ccc(Nc2ccccn2)cc1] | |

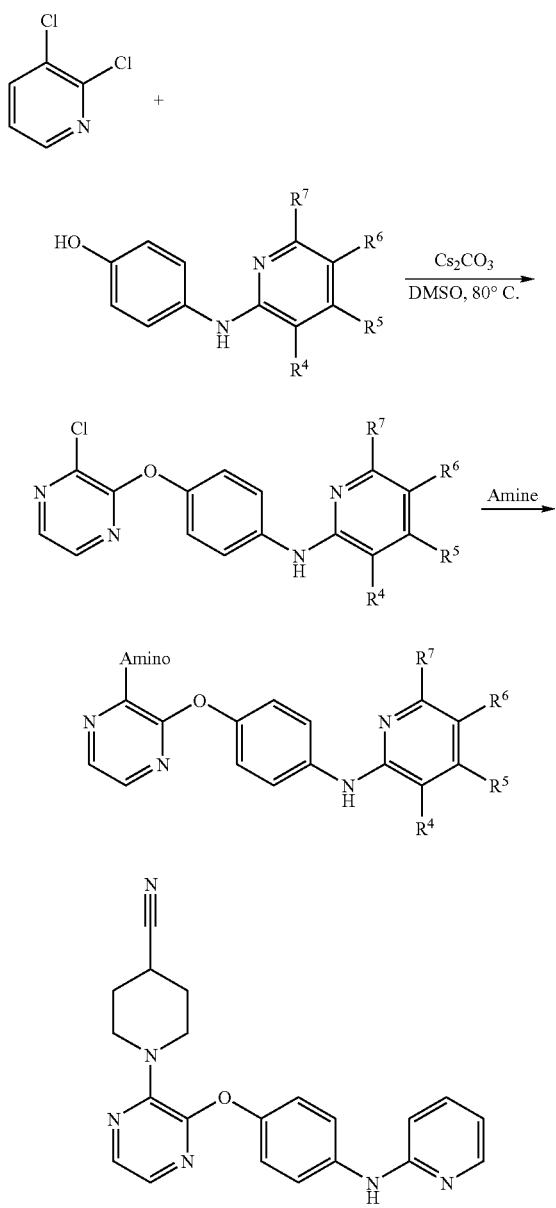

SCHEME 5

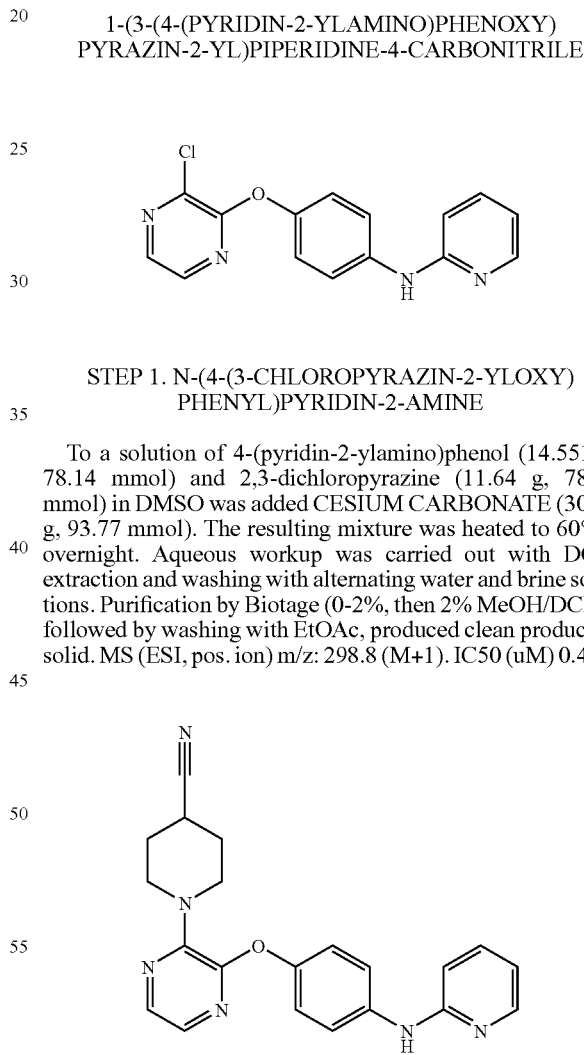

Example 69

1-(3-(4-(PYRIDIN-2-YLAMINO)PHENOXY) PYRAZIN-2-YL)PIPERIDINE-4-CARBONITRILE

STEP 1. N-(4-(3-CHLOROPYRAZIN-2-YLOXY) PHENYL)PYRIDIN-2-AMINE

To a solution of 4-(pyridin-2-ylamino)phenol (14.551 g, 78.14 mmol) and 2,3-dichloropyrazine (11.64 g, 78.14 mmol) in DMSO was added CESIUM CARBONATE (30.55 g, 93.77 mmol). The resulting mixture was heated to 60° C. overnight. Aqueous workup was carried out with DCM extraction and washing with alternating water and brine solutions. Purification by Biotage (0-2%, then 2% MeOH/DCM), followed by washing with EtOAc, produced clean product as solid. MS (ESI, pos. ion) m/z: 298.8 (M+1). IC50 (uM) 0.475.

STEP 2. 1-(3-(4-(PYRIDIN-2-YLAMINO)PHENOXY)PYRAZIN-2-YL)PIPERIDINE-4-CARBONITRILE

In a 50 mL round-bottomed flask was placed N-(4-(3-chloropyrazin-2-yloxy)-phenyl)pyridin-2-amine (0.2376 g, 0.7954 mmol) in DMSO. Piperidine-4-carbonitrile (0.4363 g, 3.977 mmol) was added and the temperature was brought to 80° C. to stir overnight. The reaction mixture was diluted with water (10 mL) and extracted with DCM (3×10 mL). The organic extract was washed with water (3×10 mL), satd sodium chloride solution (3×10 mL), dried with magnesium sulfate, filtered, and concentrated. The crude product was adsorbed onto a plug of silica gel and chromatographed through a Biotage™ pre-packed silica gel column (25M), eluting with a gradient of 1% to 5% methanol in DCM, to provide 1-(3-(4-(pyridin-2-ylamino)-phenoxy)pyrazin-2-yl) piperidine-4-carbonitrile. MS (ESI, pos. ion) m/z: 373.1 (M+1). IC50 (uM) 0.006048.

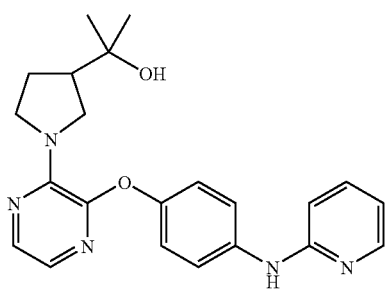 [SMILES: CC(C)(O)C1CCN(c2nccnc2Oc2ccc(Nc3ccccn3)cc2)C1]

Example 70

2-(1-(3-(4-(PYRIDIN-2-YLAMINO)PHENOXY) PYRAZIN-2-YL)PYRROLIDIN-3-YL)PROPAN-2-OL

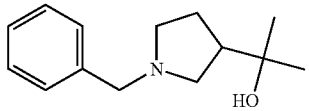 [SMILES: CC(C)(O)C1CCN(Cc2ccccc2)C1]

STEP 1.
2-(1-BENZYLPYRROLIDIN-3-YL)PROPAN-2-OL

To a cooled (0° C.) solution of methyl N-benzyl-3-pyrrolidinecarboxylate (1.013 g, 4.62 mmol, Tyger) in THF (50 mL) was added methylmagnesium bromide (3.0M solution in diethyl ether, 7.5 mL, 22.50 mmol) dropwise. After 30 min the mixture was warmed to rt for 2 h. The reaction was cooled (0° C.) and carefully quenched with saturated NH$_4$Cl (50 mL) and then diluted with water (25 mL). The mixture was extracted with EtOAc (3×50 mL) and the combined organic layers were washed with brine and dried over Na$_2$SO$_4$. Concentration in vacuo gave a light-yellow oil. m/z: 220.0 [M+1].

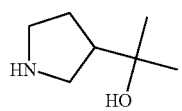

STEP 2. 2-(PYRROLIDIN-3-YL)PROPAN-2-OL

A pressure vessel was charged with 2-(1-benzylpyrrolidin-3-yl)propan-2-ol (1.013 g, 4.62 mmol), palladium, 10 wt. % (dry basis) on activated carbon (wet) (0.904 g, 0.425 mmol) and EtOH (20 mL). The reaction vessel was pressurized (50 psi) with hydrogen and purged 3 times. The vessel was pressurized at 50 psi and allowed to stir overnight at rt. The reaction was filtered and the filtrate was concentrated to dryness.

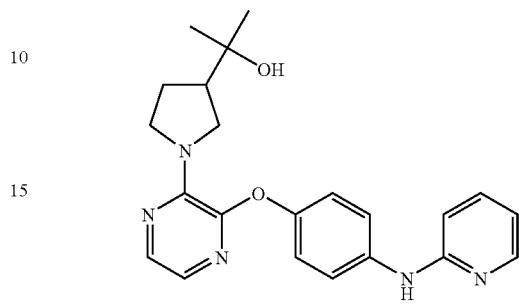

STEP 3. 2-(1-(3-(4-(PYRIDIN-2-YLAMINO)PHE-NOXY)PYRAZIN-2-YL)PYRROLIDIN-3-YL) PROPAN-2-OL

A mixture of N-(4-(3-chloropyrazin-2-yloxy)phenyl)pyridin-2-amine (0.150 g, 0.502 mmol) and 2-(pyrrolidin-3-yl) propan-2-ol (0.187 g, 1.447 mmol) in 3 mL of DMSO was sealed in a microwave tube and heated at 80° C. overnight. The reaction was cooled to RT, filtered and purified by purified by reverse-phase HPLC (Gilson; Gemini-NX 10m C18 110A AXIA, 100×50 mm column) eluting with 0.1% TFA-H$_2$O:0.1% TFA CH$_3$CN (9:1→1:9). The fractions containing the desired product were combined and basified with satd NaHCO$_3$ and extracted with DCM (3×). The combined organic layers were dried over Na$_2$SO$_4$ filtered and concentrated to dryness to give the title compound as a light-yellow crystalline solid. MS (ESI, pos. ion) m/z: 392 (M+1). IC50 (uM) 0.02882.

SCHEME 6

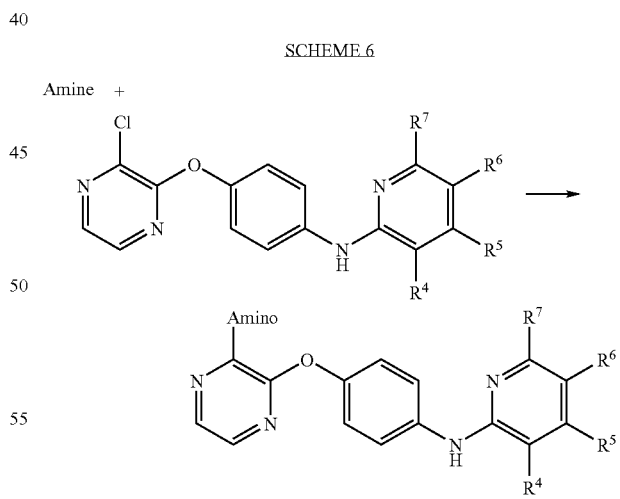

Representative Experimental for Amine Compounds

A solution of amine (280 mg, 937 µmol), cesium carbonate (1.5 equiv) and amine (4687 µmol) in DMSO (2 mL) was heated to 70° C. for 72 hours. Reaction was then partitioned between 9:1 CHCl$_3$/IPA (30 mL) and 1 M NaOH (30 mL). The organic layer was dried over MgSO$_4$, concentrated under reduced pressure, then purified on silica gel eluting with 0-5% of MeOH/DCM to produce product.

TABLE IIIA

EXAMPLES 71 TO 118 ARE TABULATED BELOW:

| Ex. No. | Compound Structure | Compound Name | MS | PDE10 IC50 (uM) |
|---|---|---|---|---|
| 71 | 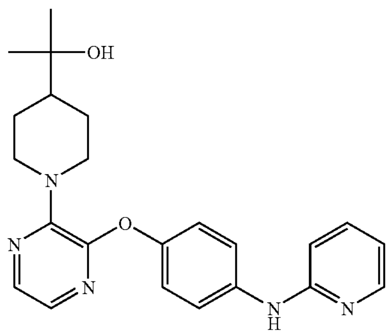 [SMILES: CC(C)(O)C1CCN(c2nccnc2Oc2ccc(Nc3ccccn3)cc2)CC1] | 2-(1-(3-(4-(pyridin-2-ylamino)phenoxy)pyrazin-2-yl)piperidin-4-yl)propan-2-ol | 406.1 | 0.1745 |
| 72 | | 1-(3-(4-(pyridin-2-ylamino)phenoxy)pyrazin-2-yl)piperidin-4-ol | 364.1 | 0.0985 |
| 73 | | 1-(3-(4-(pyridin-2-ylamino)phenoxy)pyrazin-2-yl)piperidin-3-ol | 364.1 | 0.293 |
| 74 | 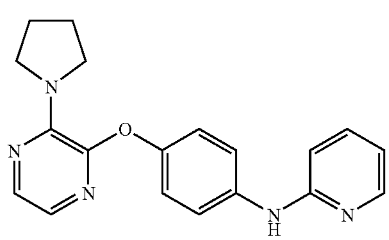 [SMILES: c1ccc(Nc2ccc(Oc3nccnc3N3CCCC3)cc2)nc1] | N-(4-(3-(pyrrolidin-1-yl)pyrazin-2-yloxy)phenyl)pyridin-2-amine | 334.1 | 0.0305 |
| 75 | 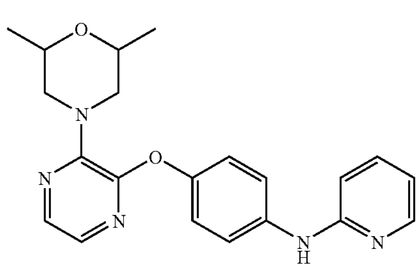 [SMILES: CC1CN(c2nccnc2Oc2ccc(Nc3ccccn3)cc2)CC(C)O1] | N-(4-(3-(2,6-dimethylmorpholino)pyrazin-2-yloxy)phenyl)pyridin-2-amine | 378.1 | 0.114 |

TABLE IIIA-continued

EXAMPLES 71 TO 118 ARE TABULATED BELOW:

| Ex. No. | Compound Structure | Compound Name | MS | PDE10 IC50 (uM) |
|---|---|---|---|---|
| 76 | 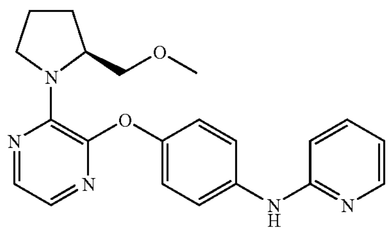 | (S)-N-(4-(3-(2-(methoxymethyl)pyrrolidin-1-yl)pyrazin-2-yloxy)phenyl)pyridin-2-amine | 378.7 | 0.00525 |
| 77 | 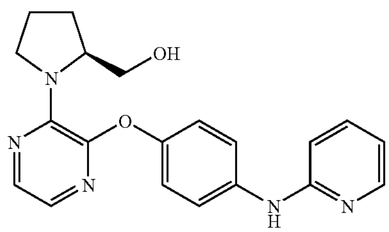 [SMILES: OC[C@@H]1CCCN1c1nccnc1Oc1ccc(Nc2ccccn2)cc1] | (S)-(1-(3-(4-(pyridin-2-ylamino)phenoxy)pyrazin-2-yl)pyrrolidin-2-yl)methanol | 364.1 | 0.013667 |
| 78 | 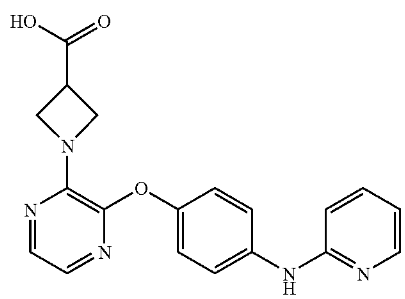 [SMILES: O=C(O)C1CN(c2nccnc2Oc2ccc(Nc3ccccn3)cc2)C1] | 1-(3-(4-(pyridin-2-ylamino)phenoxy)pyrazin-2-yl)azetidine-3-carboxylic acid | 364 | 0.150333 |
| 79 | 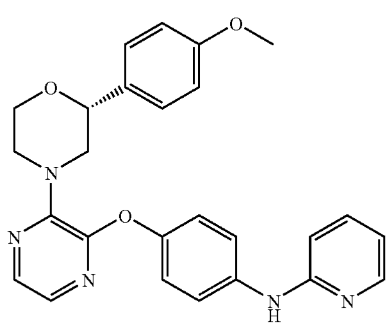 [SMILES: COc1ccc([C@@H]2CN(c3nccnc3Oc3ccc(Nc4ccccn4)cc3)CCO2)cc1] | (R)-N-(4-(3-(2-(4-methoxyphenyl)morpholino)pyrazin-2-yloxy)phenyl)pyridin-2-amine | 456.1 | 0.046333 |
| 80 | 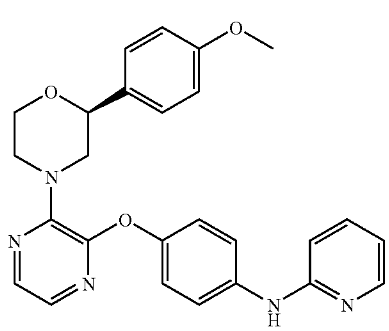 [SMILES: COc1ccc([C@H]2CN(c3nccnc3Oc3ccc(Nc4ccccn4)cc3)CCO2)cc1] | (S)-N-(4-(3-(2-(4-methoxyphenyl)morpholino)pyrazin-2-yloxy)phenyl)pyridin-2-amine | 456.1 | 0.547 |

TABLE IIIA-continued

EXAMPLES 71 TO 118 ARE TABULATED BELOW:

| Ex. No. | Compound Structure | Compound Name | MS | PDE10 IC50 (uM) |
|---|---|---|---|---|
| 81 | 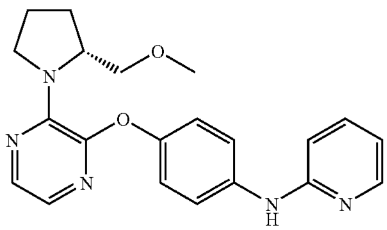 [SMILES: COC[C@H]1CCCN1c1nccnc1Oc1ccc(Nc2ccccn2)cc1] | (R)-N-(4-(3-(2-(methoxymethyl)pyrrolidin-1-yl)pyrazin-2-yloxy)phenyl)pyridin-2-amine | 378.1 | 0.099 |
| 82 | 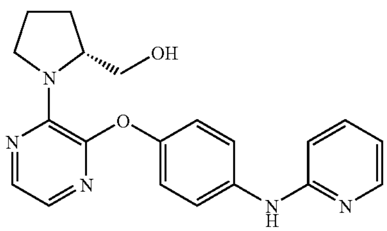 [SMILES: OC[C@H]1CCCN1c1nccnc1Oc1ccc(Nc2ccccn2)cc1] | (R)-(1-(3-(4-(pyridin-2-ylamino)phenoxy)pyrazin-2-yl)pyrrolidin-2-yl)methanol | 364.1 | 0.177 |
| 83 | 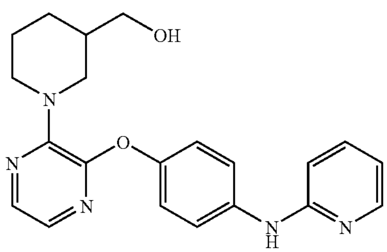 [SMILES: OCC1CCCN(c2nccnc2Oc2ccc(Nc3ccccn3)cc2)C1] | (1-(3-(4-(pyridin-2-ylamino)phenoxy)pyrazin-2-yl)piperidin-3-yl)methanol | 378.1 | 0.043 |
| 84 | 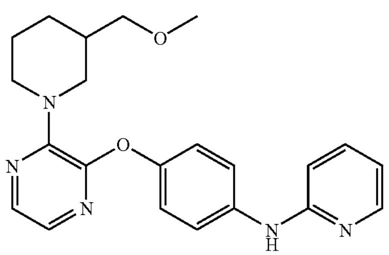 [SMILES: COCC1CCCN(c2nccnc2Oc2ccc(Nc3ccccn3)cc2)C1] | N-(4-(3-(3-(methoxymethyl)piperidin-1-yl)pyrazin-2-yloxy)phenyl)pyridin-2-amine | 392.1 | 0.01483 |
| 85 | 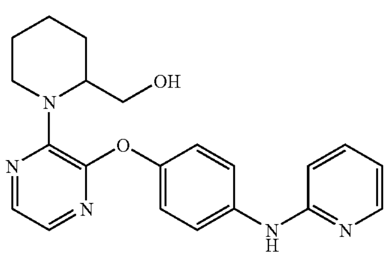 [SMILES: OCC1CCCCN1c1nccnc1Oc1ccc(Nc2ccccn2)cc1] | (1-(3-(4-(pyridin-2-ylamino)phenoxy)pyrazin-2-yl)piperidin-2-yl)methanol | 378.1 | 0.1537 |
| 86 | 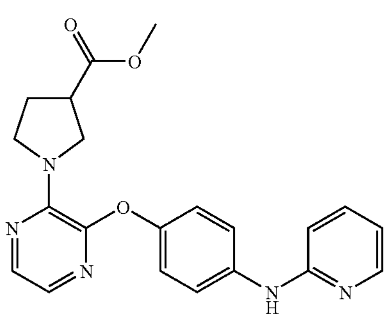 [SMILES: COC(=O)C1CCN(c2nccnc2Oc2ccc(Nc3ccccn3)cc2)C1] | methyl 1-(3-(4-(pyridin-2-ylamino)phenoxy)pyrazin-2-yl)pyrrolidine-3-carboxylate | 392.1 | 0.015 |

TABLE IIIA-continued

EXAMPLES 71 TO 118 ARE TABULATED BELOW:

| Ex. No. | Compound Structure | Compound Name | MS | PDE10 IC50 (uM) |
|---|---|---|---|---|
| 87 | 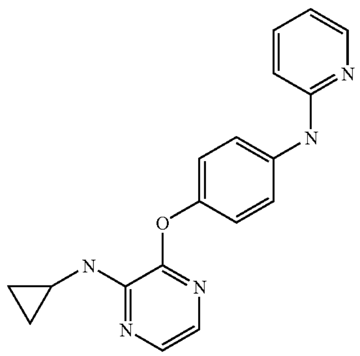 [SMILES: c1ccc(Nc2ccc(Oc3nccnc3NC3CC3)cc2)nc1] | N-cyclopropyl-3-(4-(pyridin-2-ylamino)phenoxy)pyrazin-2-amine | 320.0 | 1.699 |
| 88 | 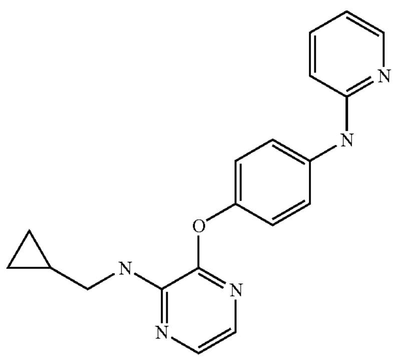 [SMILES: c1ccc(Nc2ccc(Oc3nccnc3NCC3CC3)cc2)nc1] | N-(cyclopropylmethyl)-3-(4-(pyridin-2-ylamino)phenoxy)pyrazin-2-amine | 334.0 | 0.8299 |
| 89 | 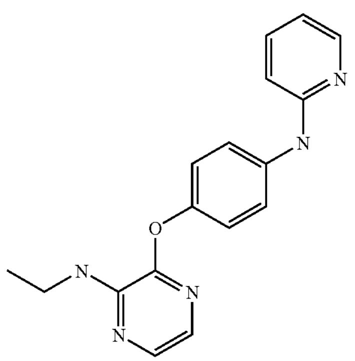 [SMILES: CCNc1nccnc1Oc1ccc(Nc2ccccn2)cc1] | N-ethyl-3-(4-(pyridin-2-ylamino)phenoxy)pyrazin-2-amine | 308.0 | 0.7997 |
| 90 | 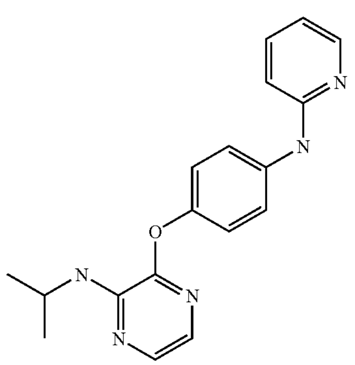 [SMILES: CC(C)Nc1nccnc1Oc1ccc(Nc2ccccn2)cc1] | N-isopropyl-3-(4-(pyridin-2-ylamino)phenoxy)pyrazin-2-amine | 322.0 | 0.2469 |

TABLE IIIA-continued

EXAMPLES 71 TO 118 ARE TABULATED BELOW:

| Ex. No. | Compound Structure | Compound Name | MS | PDE10 IC50 (uM) |
|---|---|---|---|---|
| 91 | 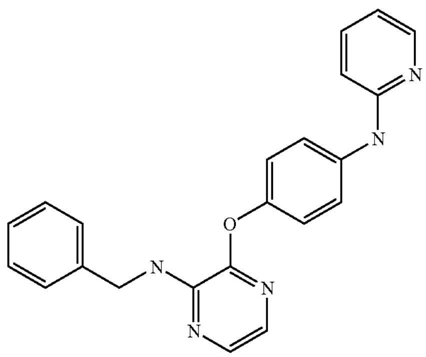 [SMILES: c1ccc(CNc2nccnc2Oc2ccc(Nc3ccccn3)cc2)cc1] | N-benzyl-3-(4-(pyridin-2-ylamino)phenoxy)pyrazin-2-amine | 370.0 | 0.4889 |
| 92 | 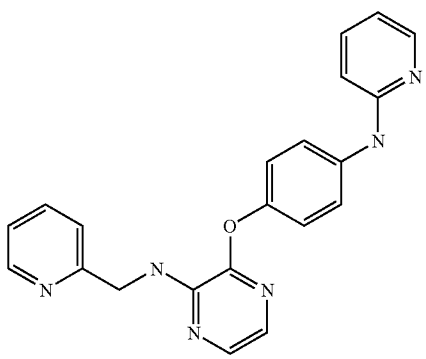 [SMILES: c1ccc(CNc2nccnc2Oc2ccc(Nc3ccccn3)cc2)nc1] | 3-(4-(pyridin-2-ylamino)phenoxy)-N-(pyridin-2-ylmethyl)pyrazin-2-amine | 371.0 | 1.1114 |
| 93 | 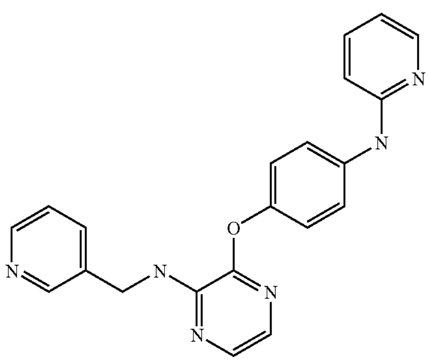 [SMILES: c1ccc(Nc2ccc(Oc3nccnc3NCc3cccnc3)cc2)nc1] | 3-(4-(pyridin-2-ylamino)phenoxy)-N-(pyridin-3-ylmethyl)pyrazin-2-amine | 371.0 | 0.3083 |
| 94 | 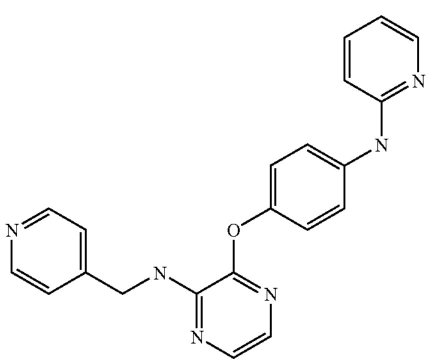 [SMILES: c1ccc(Nc2ccc(Oc3nccnc3NCc3ccncc3)cc2)nc1] | 3-(4-(pyridin-2-ylamino)phenoxy)-N-(pyridin-4-ylmethyl)pyrazin-2-amine | 371.0 | 0.27315 |

TABLE IIIA-continued
EXAMPLES 71 TO 118 ARE TABULATED BELOW:
| Ex. No. | Compound Structure | Compound Name | MS | PDE10 IC50 (uM) |
|---|---|---|---|---|
| 95 | 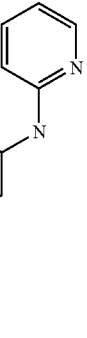 | N-phenethyl-3-(4-(pyridin-2-ylamino)phenoxy)pyrazin-2-amine | 384.0 | 0.1803 |
| 96 | 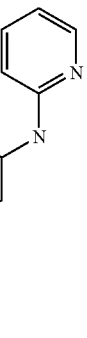 | N-(2-(pyridin-2-yl)ethyl)-3-(4-(pyridin-2-ylamino)phenoxy)pyrazin-2-amine | 385.0 | 0.09766 |
| 97 | 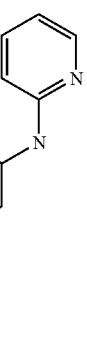 | 3-(4-(pyridin-2-ylamino)phenoxy)-N-(2-(pyridin-3-yl)ethyl)pyrazin-2-amine | 385.0 | 0.04618 |
| 98 | 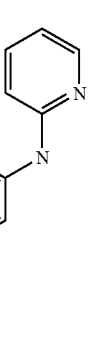 | 3-(4-(pyridin-2-ylamino)phenoxy)-N-(2-(pyridin-4-yl)ethyl)pyrazin-2-amine | 385.0 | 0.04712 |

TABLE IIIA-continued

EXAMPLES 71 TO 118 ARE TABULATED BELOW:

| Ex. No. | Compound Structure | Compound Name | MS | PDE10 IC50 (uM) |
|---|---|---|---|---|
| 99 | 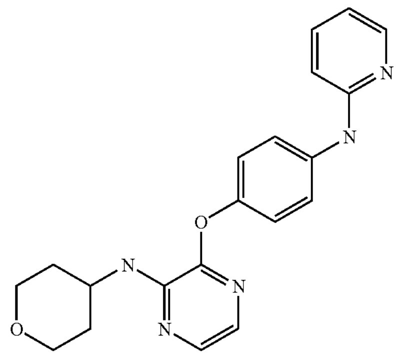 [SMILES: c1ccc(Nc2ccc(Oc3nccnc3NC3CCOCC3)cc2)nc1] | 3-(4-(pyridin-2-ylamino)phenoxy)-N-(tetrahydro-2H-pyran-4-yl)pyrazin-2-amine | 364.0 | 0.791 |
| 100 | 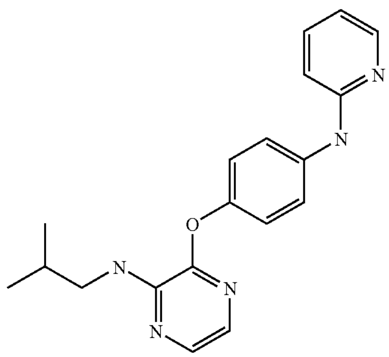 [SMILES: CC(C)CNc1nccnc1Oc1ccc(Nc2ccccn2)cc1] | N-isobutyl-3-(4-(pyridin-2-ylamino)phenoxy)pyrazin-2-amine | 336.0 | 0.6033 |
| 101 | 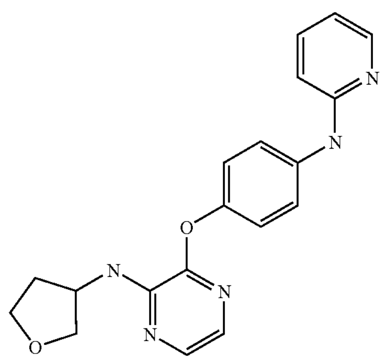 [SMILES: c1ccc(Nc2ccc(Oc3nccnc3NC3CCOC3)cc2)nc1] | 3-(4-(pyridin-2-ylamino)phenoxy)-N-(tetrahydrofuran-3-yl)pyrazin-2-amine | 350.0 | 0.2257 |
| 102 | 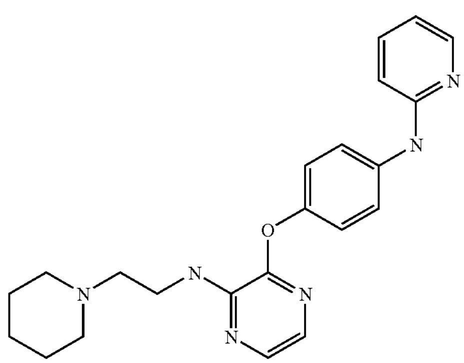 [SMILES: c1ccc(Nc2ccc(Oc3nccnc3NCCN3CCCCC3)cc2)nc1] | N-(2-(piperidin-1-yl)ethyl)-3-(4-(pyridin-2-ylamino)phenoxy)pyrazin-2-amine | 391.1 | 5.323 |

TABLE IIIA-continued

EXAMPLES 71 TO 118 ARE TABULATED BELOW:

| Ex. No. | Compound Structure | Compound Name | MS | PDE10 IC50 (uM) |
|---|---|---|---|---|
| 103 | 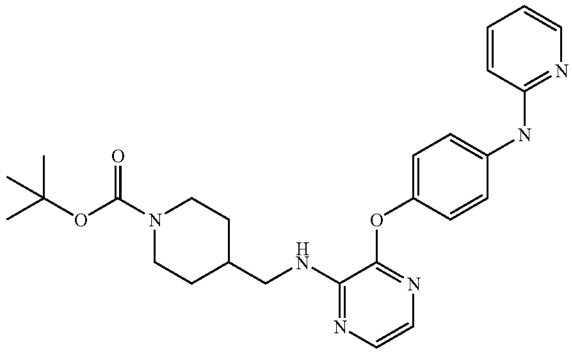 [SMILES: CC(C)(C)OC(=O)N1CCC(CNc2nccnc2Oc2ccc(Nc3ccccn3)cc2)CC1] | tert-butyl 4-((3-(4-(pyridin-2-ylamino)phenoxy)pyrazin-2-ylamino)methyl)piperidine-1-carboxylate | 477.1 | 0.2288 |
| 104 | 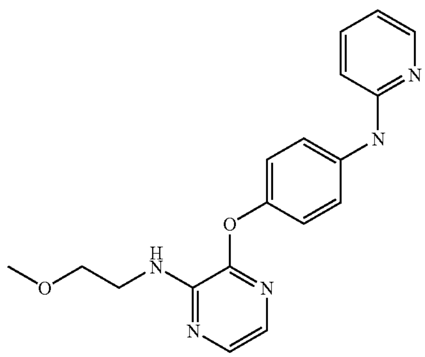 [SMILES: COCCNc1nccnc1Oc1ccc(Nc2ccccn2)cc1] | N-(2-methoxyethyl)-3-(4-(pyridin-2-ylamino)phenoxy)pyrazin-2-amine | 338.2 | 0.1631 |
| 105 | 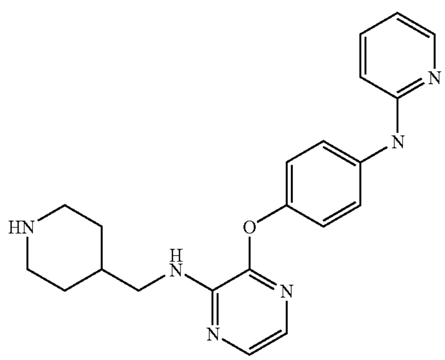 [SMILES: c1ccc(Nc2ccc(Oc3nccnc3NCC3CCNCC3)cc2)nc1] | N-(piperidin-4-ylmethyl)-3-(4-(pyridin-2-ylamino)phenoxy)pyrazin-2-amine | 377.3 | 0.8144 |
| 106 | 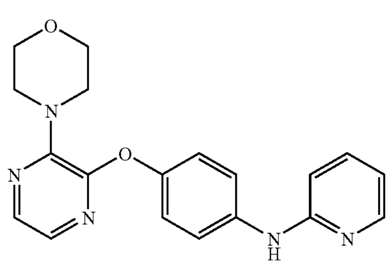 | N-(4-(3-morpholinopyrazin-2-yloxy)phenyl)pyridin-2-amine | 350 | 0.038 |

TABLE IIIA-continued

EXAMPLES 71 TO 118 ARE TABULATED BELOW:

| Ex. No. | Compound Structure | Compound Name | MS | PDE10 IC50 (uM) |
|---|---|---|---|---|
| 107 | 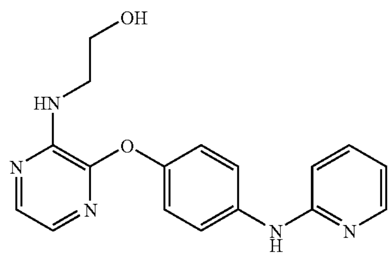 [SMILES: OCCNc1nccnc1Oc1ccc(Nc2ccccn2)cc1] | 2-(3-(4-(pyridin-2-ylamino)phenoxy)pyrazin-2-ylamino)ethanol | 324 | 0.299 |
| 108 | 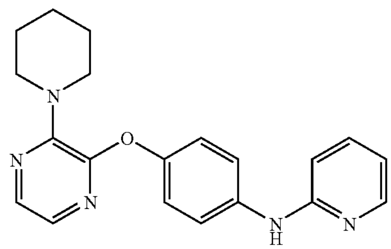 [SMILES: c1ccc(Nc2ccc(Oc3nccnc3N3CCCCC3)cc2)nc1] | N-(4-(3-(piperidin-1-yl)pyrazin-2-yloxy)phenyl)pyridin-2-amine | 348 | 0.072 |
| 109 | 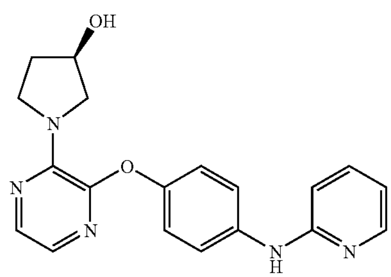 [SMILES: O[C@@H]1CCN(c2nccnc2Oc2ccc(Nc3ccccn3)cc2)C1] | (R)-1-(3-(4-(pyridin-2-ylamino)phenoxy)pyrazin-2-yl)pyrrolidin-3-ol | 350 | 0.032 |
| 110 | 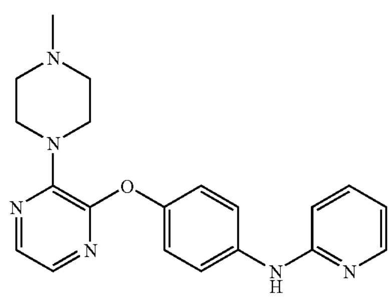 [SMILES: CN1CCN(c2nccnc2Oc2ccc(Nc3ccccn3)cc2)CC1] | N-(4-(3-(4-methylpiperazin-1-yl)pyrazin-2-yloxy)phenyl)pyridin-2-amine | 363 | 0.666 |
| 111 | 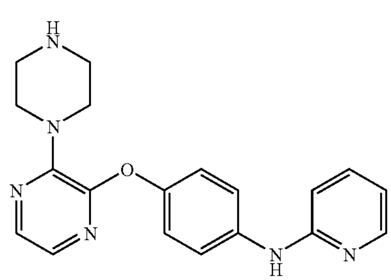 [SMILES: c1ccc(Nc2ccc(Oc3nccnc3N3CCNCC3)cc2)nc1] | N-(4-(3-(piperazin-1-yl)pyrazin-2-yloxy)phenyl)pyridin-2-amine | 349 | 0.007 |

TABLE IIIA-continued

EXAMPLES 71 TO 118 ARE TABULATED BELOW:

| Ex. No. | Compound Structure | Compound Name | MS | PDE10 IC50 (uM) |
|---|---|---|---|---|
| 112 | 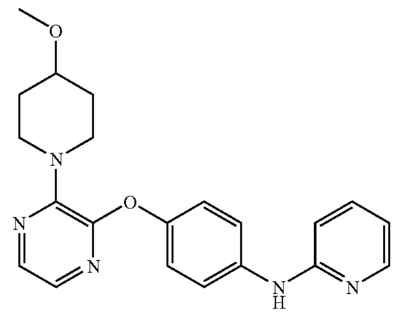 [SMILES: COC1CCN(c2nccnc2Oc2ccc(Nc3ccccn3)cc2)CC1] | N-(4-(3-(4-methoxypiperidin-1-yl)pyrazin-2-yloxy)phenyl)pyridin-2-amine | 378 | 0.075 |
| 113 | 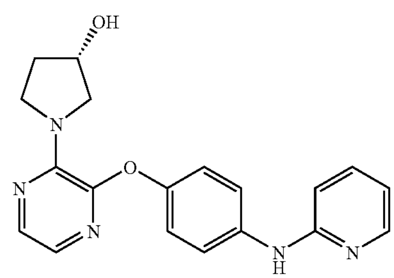 [SMILES: O[C@H]1CCN(c2nccnc2Oc2ccc(Nc3ccccn3)cc2)C1] | (S)-1-(3-(4-(pyridin-2-ylamino)phenoxy)pyrazin-2-yl)pyrrolidin-3-ol | 350 | 0.056 |
| 114 | 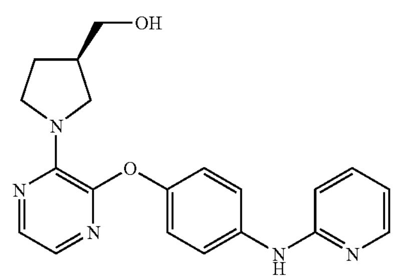 [SMILES: OC[C@@H]1CCN(c2nccnc2Oc2ccc(Nc3ccccn3)cc2)C1] | (R)-(1-(3-(4-(pyridin-2-ylamino)phenoxy)pyrazin-2-yl)pyrrolidin-3-yl)methanol | 364 | 0.022 |
| 115 | 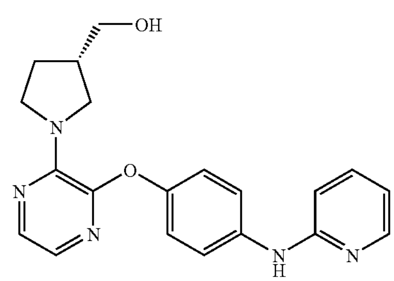 [SMILES: OC[C@H]1CCN(c2nccnc2Oc2ccc(Nc3ccccn3)cc2)C1] | (S)-(1-(3-(4-(pyridin-2-ylamino)phenoxy)pyrazin-2-yl)pyrrolidin-3-yl)methanol | 364 | 0.014 |
| 116 | 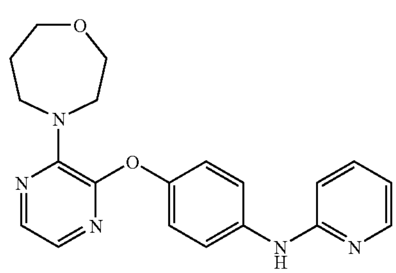 [SMILES: c1ccc(Nc2ccc(Oc3nccnc3N3CCCOCC3)cc2)nc1] | N-(4-(3-(1,4-oxazepan-4-yl)pyrazin-2-yloxy)phenyl)pyridin-2-amine | 364 | 0.02069 |

TABLE IIIA-continued

EXAMPLES 71 TO 118 ARE TABULATED BELOW:

| Ex. No. | Compound Structure | Compound Name | MS | PDE10 IC50 (uM) |
|---|---|---|---|---|
| 117 | 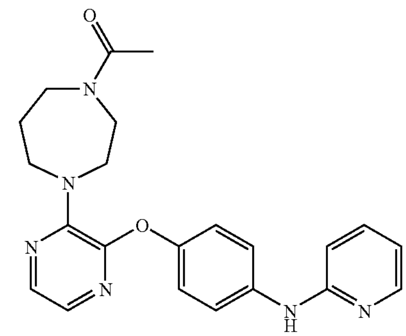 [SMILES: CC(=O)N1CCCN(c2nccnc2Oc2ccc(Nc3ccccn3)cc2)CC1] | 1-(4-(3-(4-(pyridin-2-ylamino)phenoxy)pyrazin-2-yl)-1,4-diazepan-1-yl)ethanone | 405 | 0.02106 |
| 118 | 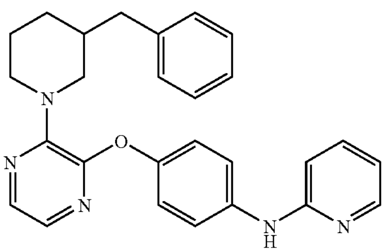 [SMILES: c1ccc(CC2CCCN(c3nccnc3Oc3ccc(Nc4ccccn4)cc3)C2)cc1] | (rac)-N-(4-(3-(3-benzylpiperidin-1-yl)pyrazin-2-yloxy)phenyl)pyridin-2-amine | 438.0 | 0.07499 |

TABLE IIIB

PREPARATION OF EXAMPLES 71 TO 118 ARE TABULATED BELOW:

| Ex. No. | Scheme | Starting material 1 | Starting material 2 | Conditions or reagents that differ from scheme |
|---|---|---|---|---|
| 71 | 5 | | | |
| 72 | 5 | | | |
| 73 | 5 | | | |

TABLE IIIB-continued
PREPARATION OF EXAMPLES 71 TO 118 ARE TABULATED BELOW:
| Ex. No. | Scheme | Starting material 1 | Starting material 2 | Conditions or reagents that differ from scheme |
|---|---|---|---|---|
| 74 | 5 | 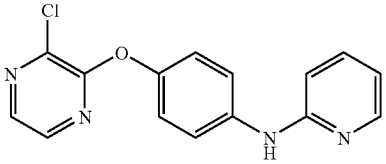 [SMILES: Clc1nccnc1Oc1ccc(Nc2ccccn2)cc1] |  | |
| 75 | 5 | 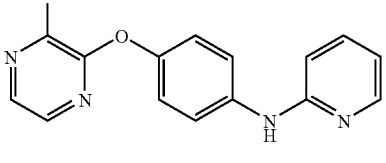 | 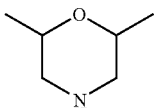 | |
| 76 | 5 | 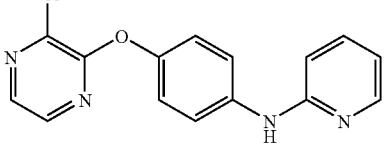 | 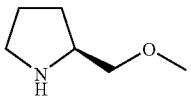 | |
| 77 | 5 | 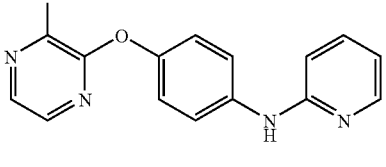 | 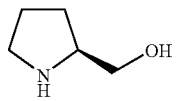 | |
| 78 | 5 | 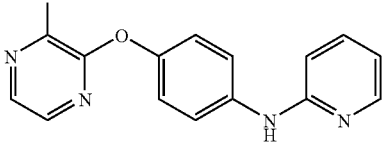 | 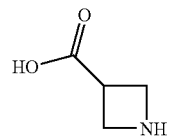 | |
| 79 | 5 | 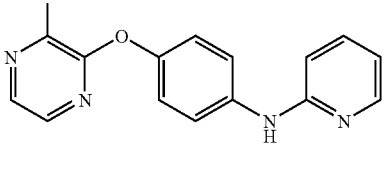 | 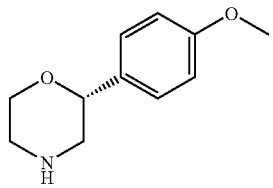 | |
| 80 | 5 | 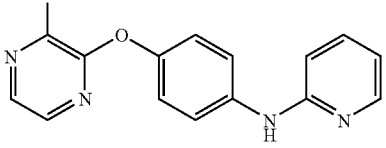 | 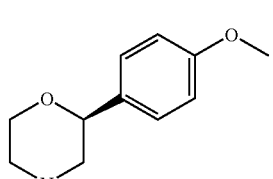 | |
| 81 | 5 | 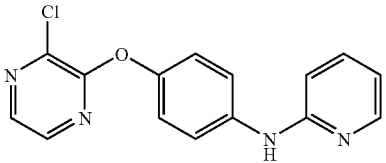 [SMILES: Clc1nccnc1Oc1ccc(Nc2ccccn2)cc1] | 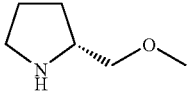 | |

TABLE IIIB-continued

PREPARATION OF EXAMPLES 71 TO 118 ARE TABULATED BELOW:

| Ex. No. | Scheme | Starting material 1 | Starting material 2 | Conditions or reagents that differ from scheme |
|---|---|---|---|---|
| 82 | 5 | | | |
| 83 | 5 | | | |
| 84 | 5 | | | |
| 85 | 5 | | | |
| 86 | 5 | | | |
| 87 | 6 | | | |
| 88 | 6 | | | |
| 89 | 6 | | | |

TABLE IIIB-continued

PREPARATION OF EXAMPLES 71 TO 118 ARE TABULATED BELOW:

| Ex. No. | Scheme | Starting material 1 | Starting material 2 | Conditions or reagents that differ from scheme |
|---|---|---|---|---|
| 90 | 6 | isopropylamine | 3-chloro-2-(4-(pyridin-2-ylamino)phenoxy)pyrazine | |
| 91 | 6 | benzylamine | 3-chloro-2-(4-(pyridin-2-ylamino)phenoxy)pyrazine | |
| 92 | 6 | (pyridin-2-yl)methanamine | 3-chloro-2-(4-(pyridin-2-ylamino)phenoxy)pyrazine | |
| 93 | 6 | (pyridin-3-yl)methanamine | 3-chloro-2-(4-(pyridin-2-ylamino)phenoxy)pyrazine | |
| 94 | 6 | (pyridin-4-yl)methanamine | 3-chloro-2-(4-(pyridin-2-ylamino)phenoxy)pyrazine | |
| 95 | 6 | 2-phenylethanamine | 3-chloro-2-(4-(pyridin-2-ylamino)phenoxy)pyrazine | |
| 96 | 6 | 2-(pyridin-2-yl)ethanamine | 3-chloro-2-(4-(pyridin-2-ylamino)phenoxy)pyrazine | |
| 97 | 6 | 2-(pyridin-3-yl)ethanamine | 3-chloro-2-(4-(pyridin-2-ylamino)phenoxy)pyrazine | |
| 98 | 6 | 2-(pyridin-4-yl)ethanamine | 3-chloro-2-(4-(pyridin-2-ylamino)phenoxy)pyrazine | |

TABLE IIIB-continued
PREPARATION OF EXAMPLES 71 TO 118 ARE TABULATED BELOW:
| Ex. No. | Scheme | Starting material 1 | Starting material 2 | Conditions or reagents that differ from scheme |
|---|---|---|---|---|
| 99 | 6 | 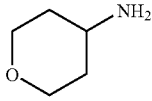 | 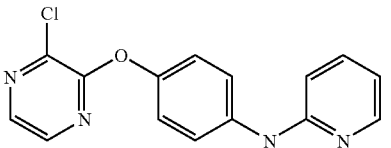 [SMILES: Clc1nccnc1Oc1ccc(Nc2ccccn2)cc1] | |
| 100 | 6 | 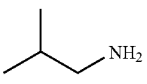 | 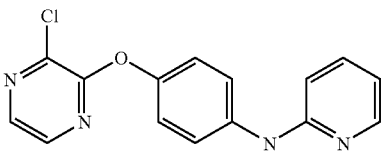 [SMILES: Clc1nccnc1Oc1ccc(Nc2ccccn2)cc1] | |
| 101 | 6 | 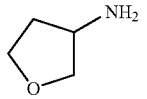 | 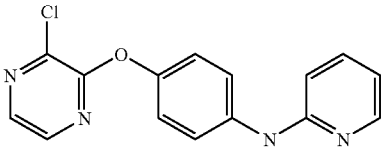 [SMILES: Clc1nccnc1Oc1ccc(Nc2ccccn2)cc1] | |
| 102 | 6 | 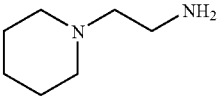 | 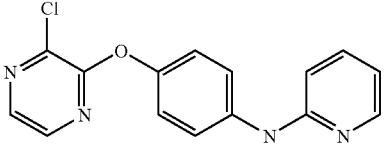 [SMILES: Clc1nccnc1Oc1ccc(Nc2ccccn2)cc1] | |
| 103 | 6 | 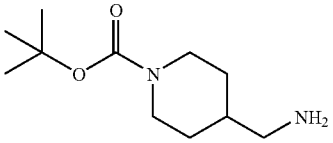 | 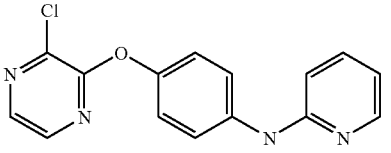 [SMILES: Clc1nccnc1Oc1ccc(Nc2ccccn2)cc1] | |
| 104 | 6 | 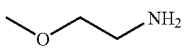 | 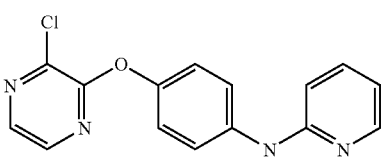 [SMILES: Clc1nccnc1Oc1ccc(Nc2ccccn2)cc1] | |
| 105 | 6 | 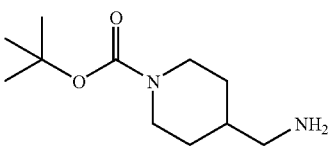 | 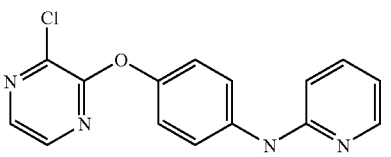 [SMILES: Clc1nccnc1Oc1ccc(Nc2ccccn2)cc1] | After 1$^{st}$ coupling step, reaction mixture was subjected to TFA to remove Boc protecting group |
| 106 | 5 | 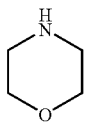 | 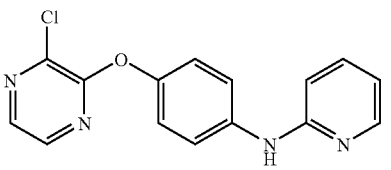 [SMILES: Clc1nccnc1Oc1ccc(Nc2ccccn2)cc1] | Commercial amine |
| 107 | 5 | 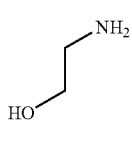 | 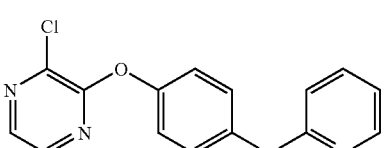 | Commercial amine |

TABLE IIIB-continued
PREPARATION OF EXAMPLES 71 TO 118 ARE TABULATED BELOW:
| Ex. No. | Scheme | Starting material 1 | Starting material 2 | Conditions or reagents that differ from scheme |
|---|---|---|---|---|
| 108 | 5 |  | 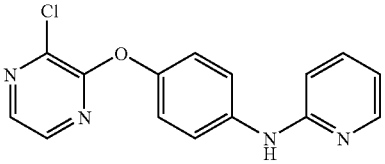 [SMILES: Clc1nccnc1Oc1ccc(Nc2ccccn2)cc1] | Commercial amine |
| 109 | 5 | 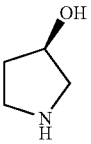 | 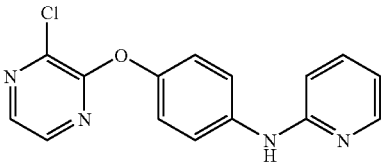 [SMILES: Clc1nccnc1Oc1ccc(Nc2ccccn2)cc1] | Commercial amine |
| 110 | 5 | 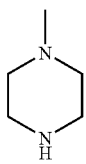 | 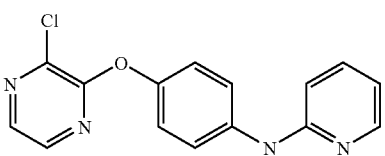 | Commercial amine |
| 111 | 5 | 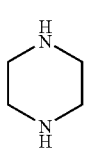 | 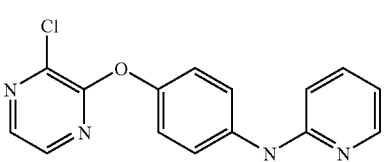 | Commercial amine |
| 112 | 5 | 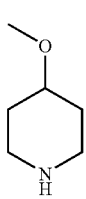 | 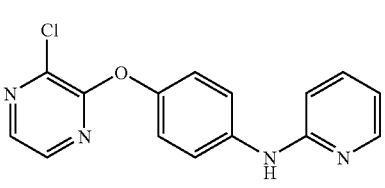 | Commercial amine |
| 113 | 5 | 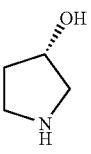 | 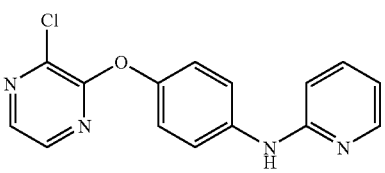 | Commercial amine |
| 114 | 5 | 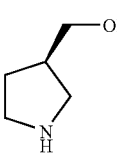 | 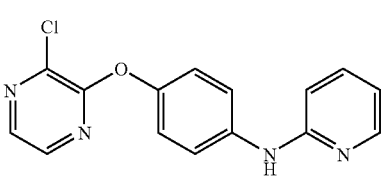 [SMILES: Clc1nccnc1Oc1ccc(Nc2ccccn2)cc1] | Commercial amine |
| 115 | 5 |  | 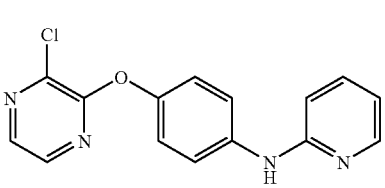 [SMILES: Clc1nccnc1Oc1ccc(Nc2ccccn2)cc1] | Commercial amine |

TABLE IIIB-continued
PREPARATION OF EXAMPLES 71 TO 118 ARE TABULATED BELOW:
| Ex. No. | Scheme | Starting material 1 | Starting material 2 | Conditions or reagents that differ from scheme |
|---|---|---|---|---|
| 116 | 5 | | | |
| 117 | 5 | | | Purified by rev phase HPLC; free-based |
| 118 | 5 | | | $^i$Pr$_2$NEt was used as base |
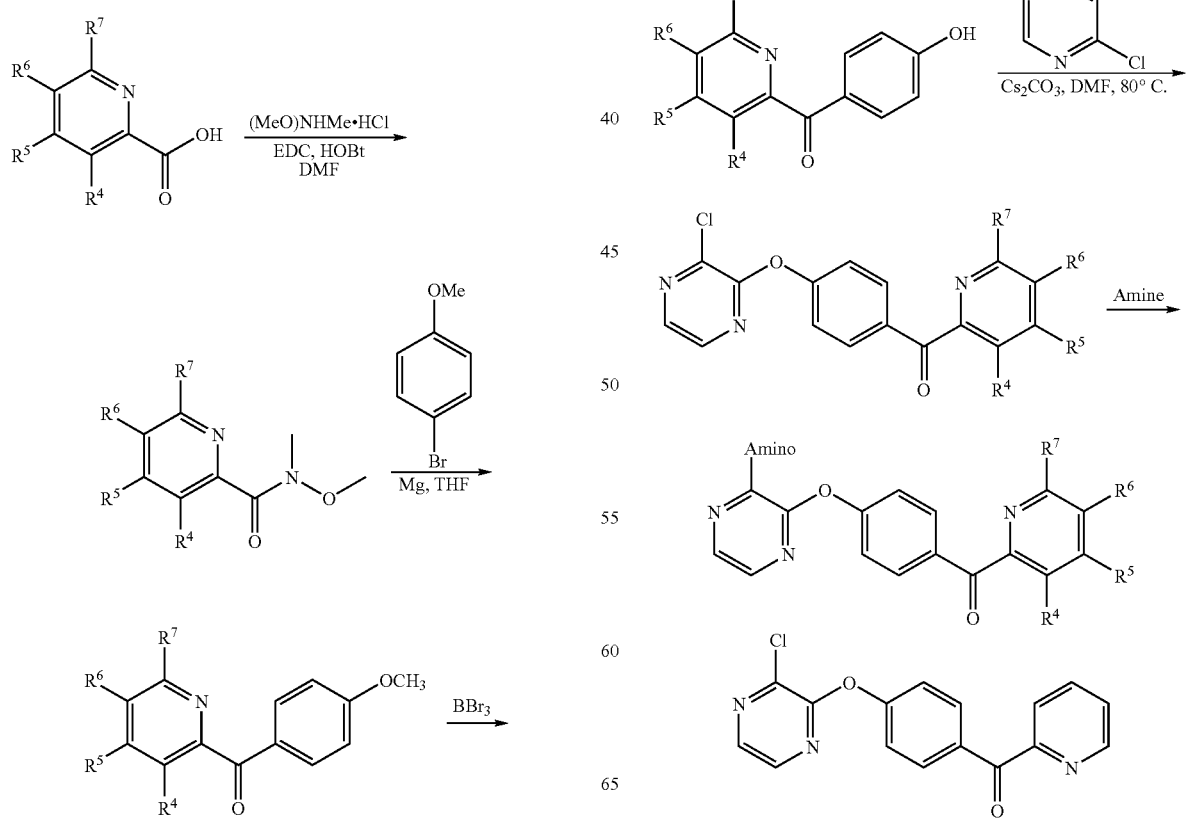

Example 119

(4-(3-CHLOROPYRAZIN-2-YLOXY)PHENYL)(PYRIDIN-2-YL)METHANONE

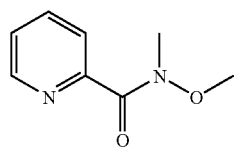

STEP 1.
N-METHOXY-N-METHYLPICOLINAMIDE

EDCI (2.30 g, 0.012 mol) and 1-hydroxy benztriazole (1.36 g, 0.009 mol) were added o a stirred solution of pyridine-2-carboxylic acid (1.0 g, 0.008 mol) in N,N-dimethyl formamide (16 mL) at 0° C. The reaction mixture was allowed to stir for 15 min then triethyl amine was added followed by addition of N,O-dimethyl hydroxyl amine hydrochloride at 0° C. The resulting mixture was stirred at RT overnight. The reaction mixture was partitioned between water (30 mL) and ethyl acetate (2×30 mL). The organic layer was dried over sodium sulphate and concentrated. The crude product was purified by column chromatography using 100-200 mesh silica gel and 0-20% EtOAc: Hexane as eluant to obtain product.

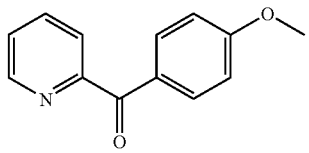 [SMILES: COc1ccc(C(=O)c2ccccn2)cc1]

STEP 2.
(4-METHOXYPHENYL)(PYRIDIN-2-YL)METHANONE

To a stirred solution of pyridine-2-carboxylic acid methoxy-methyl-amide (10.0 g, 0.060 mol) in anhydrous THF (150 mL) at −78° C. was added freshly prepared Grignard reagent of 4-bromo anisole (20.0 g, 0.106 mol). The reaction mixture was allowed to warm to room temperature. Reaction mixture was quenched with saturated ammonium chloride (100 mL) and extracted with ethyl acetate (2×200 mL). Organic layer was dried over sodium sulphate and concentrated. Purification by 100-200-mesh sized silica gel column with 0-20% EtoAc:Hexane as eluent provided the product.

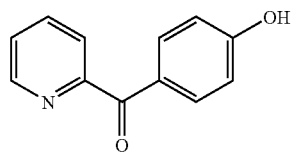 [SMILES: O=C(c1ccc(O)cc1)c1ccccn1]

STEP 3.
(4-HYDROXYPHENYL)(PYRIDIN-2-YL)METHANONE

To a stirred solution of (4-Methoxy-phenyl)-pyridin-2-yl-methanone (10.0 g, 0.046 mol) in DCM(140 mL) was added boron tribromide (17.8 mL, 0.187 mol) at −78° C. slowly. The reaction mixture was allowed to warm to room temperature and stirred for 24 h. Reaction mixture was quenched with saturated Sodium bicarbonate solution (250 mL) and extracted with ethyl acetate (2×250 mL). The organic layer was dried over sodium sulphate and concentrated. Purification by 100-200-mesh sized silica gel column with 0-40% EtOAc:Hexane as eluent provided the product.

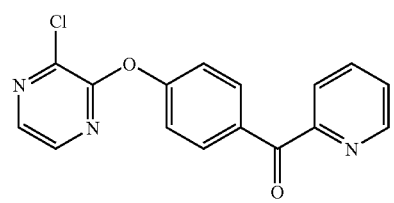 [SMILES: O=C(c1ccc(Oc2nccnc2Cl)cc1)c1ccccn1]

STEP 4. (4-(3-CHLOROPYRAZIN-2-YLOXY)PHENYL)(PYRIDIN-2-YL)METHANONE

To a stirred solution of (4-hydroxy-phenyl)-pyridin-2-yl-methanone (2.5 g, 0.0125 mol) in DMF (35 mL) was added cesium carbonate (6.14 g, 0.0188 mol). The resulting mixture was stirred for 15 minutes before addition of 2,3-dichloro pyrazine(1.87 g, 0.0125 mol) at 0° C. The reaction mixture was heated to 80° C. for 16 h. The reaction mixture was partitioned between water (100 mL) and ethyl acetate (2×100 mL). The organic layer was dried over sodium sulphate and concentrated to afford the product. MS (ESI, pos. ion) m/z: 312 (M+1). IC50 (uM) 30.

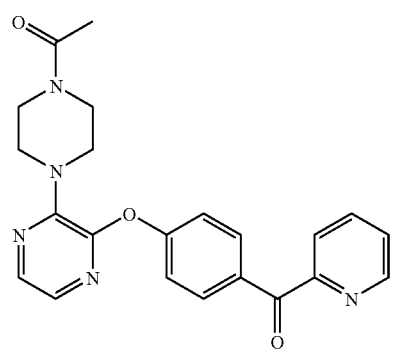 [SMILES: CC(=O)N1CCN(c2nccnc2Oc2ccc(C(=O)c3ccccn3)cc2)CC1]

Example 120

1-(4-(3-(4-PICOLINOYLPHENOXY)PYRAZIN-2-YL)PIPERAZIN-1-YL)ETHANONE

To a glass microwave rxn vessel was added (4-(3-chloropyrazin-2-yloxy)phenyl)(pyridin-2-yl)methanone (0.2505 g, 0.804 mmol) and 1-acetylpiperazine (0.412 g, 3.21 mmol) in DMSO (2.68 mL) at 80° C. to stir. Upon completion, the reaction mixture was diluted with water and brine and extracted with dichloromethane. The organic extract was washed with water, sat NaCl, dried with magnesium sulfate, filtered, and concentrated. The crude product was adsorbed onto a plug of silica gel and chromatographed to provide 1-(4-(3-(4-picolinoylphenoxy)pyrazin-2-yl)piperazin-1-yl)ethanone. MS (ESI, pos. ion) m/z: 404.1 (M+1). IC50 (uM) 3.498.

TABLE IVA

EXAMPLES 121 TO 124 ARE TABULATED BELOW:

| Ex. No. | Compound Structure | Compound Name | MS | PDE10 IC50 (uM) |
|---|---|---|---|---|
| 121 | 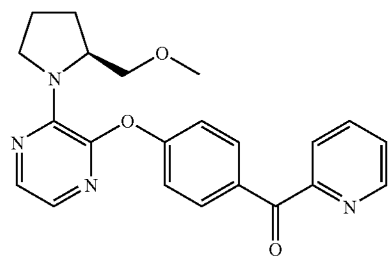 [SMILES: COC[C@@H]1CCCN1c1nccnc1Oc1ccc(C(=O)c2ccccn2)cc1] | (S)-(4-(3-(2-(methoxymethyl)pyrrolidin-1-yl)pyrazin-2-yloxy)phenyl)(pyridin-2-yl)methanone | 391.1 | 0.1161 |
| 122 | 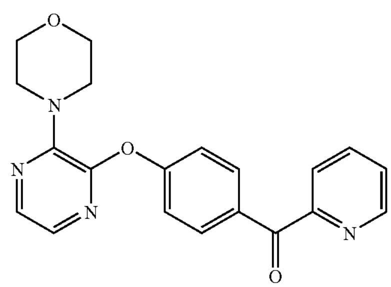 [SMILES: O=C(c1ccc(Oc2nccnc2N2CCOCC2)cc1)c1ccccn1] | (4-(3-morpholinopyrazin-2-yloxy)phenyl)(pyridin-2-yl)methanone | 363 | 2.5 |
| 123 | 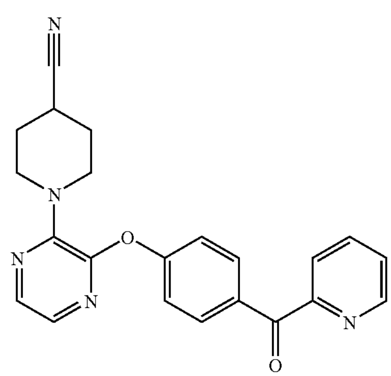 [SMILES: N#CC1CCN(c2nccnc2Oc2ccc(C(=O)c3ccccn3)cc2)CC1] | 1-(3-(4-picolinoylphenoxy)pyrazin-2-yl)piperidine-4-carbonitrile | 386.1 | 0.2239 |
| 124 | 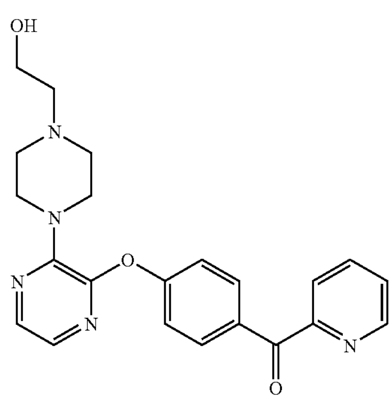 [SMILES: O=C(c1ccc(Oc2nccnc2N2CCN(CCO)CC2)cc1)c1ccccn1] | (4-(3-(4-(2-hydroxyethyl)piperazin-1-yl)pyrazin-2-yloxy)phenyl)(pyridin-2-yl)methanone | 406.1 | 3.009 |

TABLE IVB
PREPARATION OF EXAMPLES 121 TO 124 ARE TABULATED BELOW:
| Ex. No. | Scheme | Starting material 1 | Starting material 2 | Conditions or reagents that differ from scheme |
|---|---|---|---|---|
| 121 | 7 | 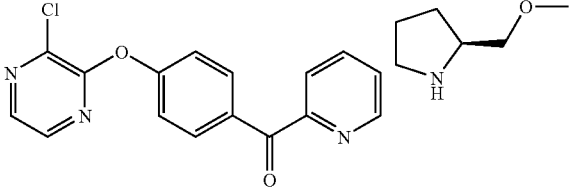 | 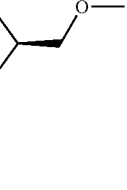 | |
| 122 | 7 | 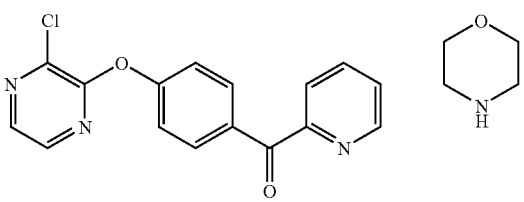 | 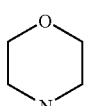 | |
| 123 | 7 | 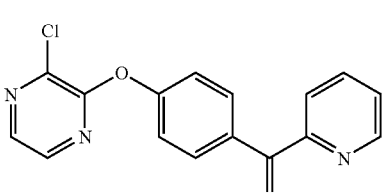 | 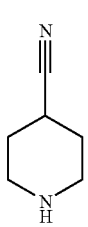 | |
| 124 | 7 | 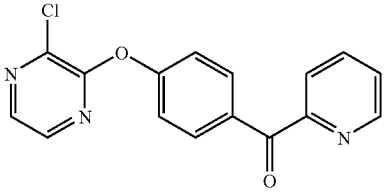 [SMILES: O=C(c1ccc(Oc2nccnc2Cl)cc1)c1ccccn1] | 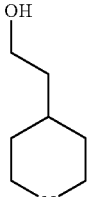 | |
SCHEME 8
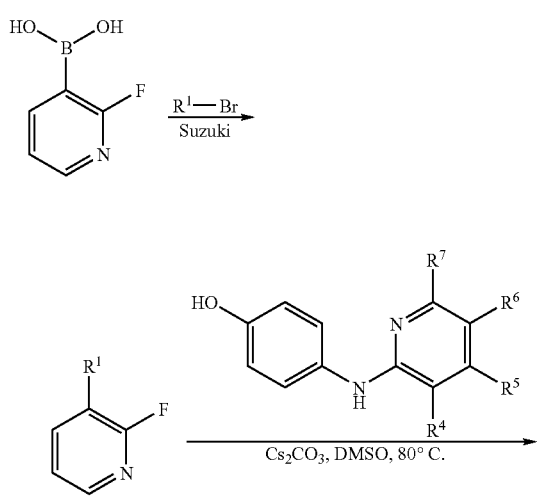
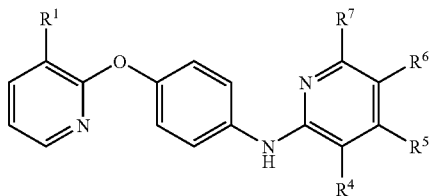
-continued
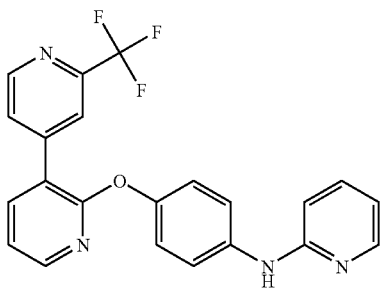

Example 125

N-(4-(2'-(TRIFLUOROMETHYL)-3,4'-BIPYRIDIN-2-YLOXY)PHENYL)PYRIDIN-2-AMINE

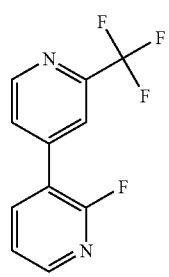 [SMILES: Fc1ncccc1-c1ccnc(C(F)(F)F)c1]

STEP 1. 2-FLUORO-2'-(TRIFLUOROMETHYL)-3,4'-BIPYRIDINE

A mixture of 2-fluoropyridin-3-ylboronic acid (0.748 g, 5.3 mmol), 4-bromo-2-(trifluoromethyl)pyridine (1.00 g, 4.4 mmol), Pd(PPh$_3$)$_2$Cl$_2$ (0.155 g, 0.22 mmol) and sodium carbonate (0.797 g, 13.3 mmol) in DME (6.5 mL), ethanol (1.9 mL) and water (0.47 mL) was heated to 95° C. for 2 h. After cooling to room temperature, the mixture was diluted with H$_2$O and extracted with CH$_2$Cl$_2$ (3×). The combined organics were dried over Na$_2$SO$_4$, filtered and concentrated. The residue was purified using column chromatography (EtOAc/Hexanes=0→20%) to give the title compound. MS (ESI, pos. ion) m/z: 243 (M+1).

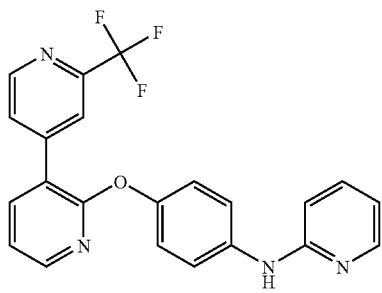 [SMILES: FC(F)(F)c1cc(-c2cccnc2Oc2ccc(Nc3ccccn3)cc2)ccn1]

STEP 2. N-(4-(2'-(TRIFLUOROMETHYL)-3,4'-BIPYRIDIN-2-YLOXY)PHENYL)PYRIDIN-2-AMINE

A mixture of 2-fluoro-2'-(trifluoromethyl)-3,4'-bipyridine (200 mg, 0.83 mmol), 4-(pyridin-2-ylamino)phenol (185 mg, 0.99 mmol) and cesium carbonate (323 mg, 0.99 mmol) in DMSO (3.3 mL) was heated to 80° C. for 4 h. The mixture was cooled to room temperature, diluted with H$_2$O and filtered. The solids were washed with H$_2$O and air-dried. The solids were suspended in sat aq. NaHCO$_3$ and extracted with CH$_2$Cl$_2$ (3×). The combined organics were dried over Na$_2$SO$_4$, filtered and concentrated. The residue was purified using column chromatography (EtOAc/Hexanes=0→40%) to give the title compound. MS (ESI, pos. ion) m/z: 409 (M+1). IC50 (uM) 0.022.

SCHEME 9

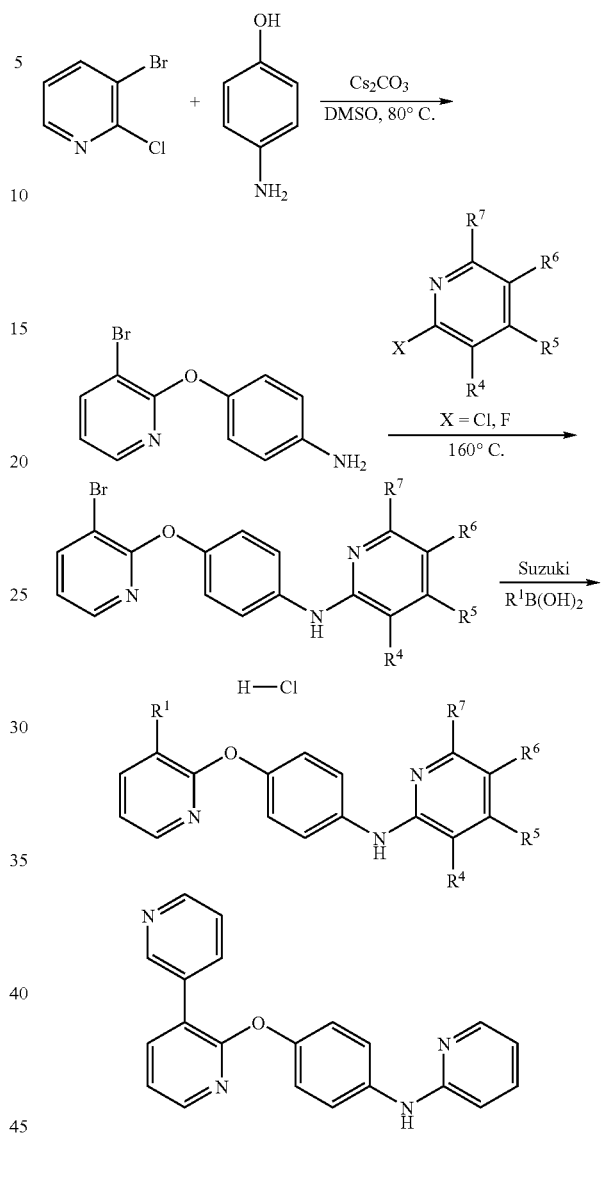

Example 126

N-(4-(3,3'-BIPYRIDIN-2-YLOXY)PHENYL)PYRIDIN-2-AMINE

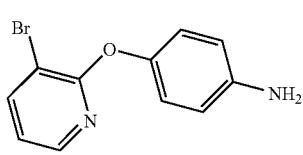 [SMILES: Nc1ccc(Oc2ncccc2Br)cc1]

STEP 1. 4-(3-BROMOPYRIDIN-2-YLOXY)ANILINE

A mixture of 3-bromo-2-chloropyridine (75.50 g, 392.3 mmol), 4-aminophenol (51.46 g, 471.6 mmol) and cesium carbonate (256.80 g, 788.2 mmol) in DMSO (400 mL) was heated at 80° C. overnight. The reaction was cooled (0° C.) and diluted with water. After stirring for 30 min the mixture was filtered and the solid was partitioned between 50% EtOAc/hexane (1 L) and water (300 mL). The organic layer was washed with water (3×300 mL) and with brine (1×200 mL) then dried over Na₂SO₄. Filtration and concentration in vacuo gave a brown amorphous solid. MS (ESI, pos. ion) m/z: 264.9, 266.9 [M+1].

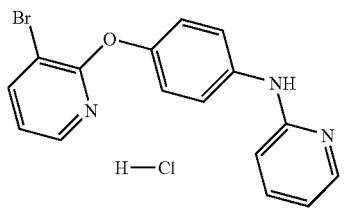 [SMILES: Brc1cccnc1Oc1ccc(Nc2ccccn2)cc1 ; Cl]

STEP 2. N-(4-(3-BROMOPYRIDIN-2-YLOXY)PHENYL)PYRIDIN-2-AMINE HYDROCHLORIDE

A mixture of 4-(3-bromopyridin-2-yloxy)aniline (50.01 g, 188.6 mmol) and 2-chloropyridine (22.50 ml, 238.8 mmol, Aldrich) was sealed neat in a 350 mL screw-cap flask and heated at 160° C. for 3.5 h. The reaction was cooled to room temperature and stirred over Et₂O overnight. The solid was filtered, washed with Et₂O and dried in vacuo to give a gray amorphous solid. MS (ESI, pos. ion) m/z: 341.9, 343.9 [M+1]. PDE10 IC50 (uM) 0.96.

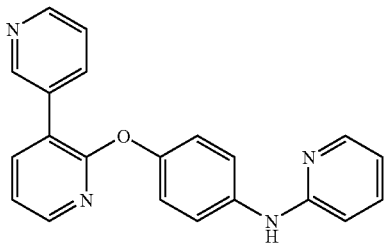

STEP 3. N-(4-(3,3'-BIPYRIDIN-2-YLOXY)PHENYL)PYRIDIN-2-AMINE

A mixture of N-(4-(3-Bromopyridin-2-yloxy)phenyl)pyridin-2-amine hydrochloride (0.257 g, 0.68 mmol), 3-pyridineboronic acid (0.115 g, 0.94 mmol), sodium carbonate anhydrous (0.358 g, 3.4 mmol) and trans-dichlorobis(triphenylphosphine)palladium (II) (0.045 g, 0.064 mmol) in 6:3:2 DME:H₂O:EtOH was sealed under argon in a microwave tube and heated at 145° C. for 15 min in the microwave (Emrys by Personal Chemistry). The reaction was filtered and the filtrate was partitioned between EtOAc/brine. The aqueous layer was extracted with EtOAc (3×) and the combined organic layers were evaporated onto silica gel and purified by flash chromatography [Isco, (40 gram)] eluting with 2M NH₃ in MeOH:CH₂Cl₂ (0:1→3:97) to give a white amorphous solid. MS (ESI, pos. ion) m/z: 341.1 [M+1]. IC50 (uM) 0.002612.

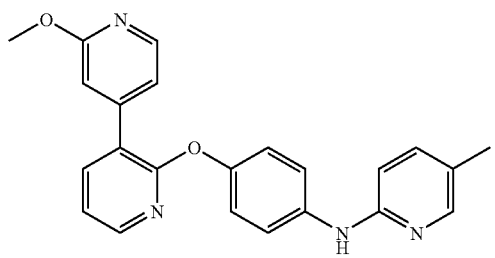

Example 127

N-(4-(2'-METHOXY-3,4'-BIPYRIDIN-2-YLOXY)PHENYL)-5-METHYLPYRIDIN-2-AMINE

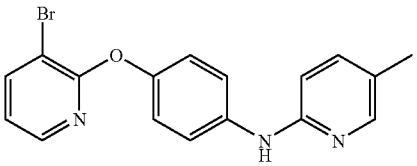 [SMILES: Cc1ccc(Nc2ccc(Oc3ncccc3Br)cc2)nc1]

STEP 1. N-(4-(3-BROMOPYRIDIN-2-YLOXY)PHENYL)-5-METHYLPYRIDIN-2-AMINE

To a pressure vessel was added 4-(3-bromopyridin-2-yloxy)aniline (7.23 g, 27.3 mmol) and 2-fluoro-5-methylpyridine (3.03 mL, 27.2 mmol) in NMP (13.61 mL) to stir at 170° C. Upon completion, the reaction mixture was diluted with water and extracted with EtOAc. The organic extract was washed with water, sat NaCl, dried with magnesium sulfate, filtered, and concentrated. The crude product was adsorbed onto a plug of silica gel and chromatographed to provide N-(4-(3-bromopyridin-2-yloxy)phenyl)-5-methylpyridin-2-amine.

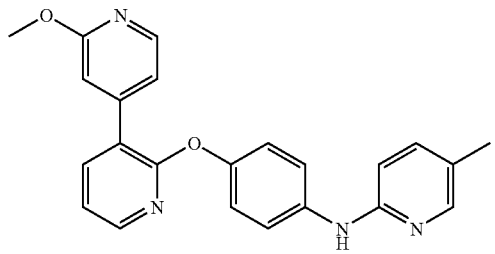

STEP 2: N-(4-(2'-METHOXY-3,4'-BIPYRIDIN-2-YLOXY)PHENYL)-5-METHYLPYRIDIN-2-AMINE

To a glass microwave vial was added N-(4-(3-bromopyridin-2-yloxy)phenyl)-5-methylpyridin-2-amine (0.2017 g, 0.566 mmol), 2-methoxypyridin-4-ylboronic acid, trans-dichlorobis(triphenylphosphine) palladium (II) (0.032 g, 0.045 mmol), and sodium carbonate (0.300 g, 2.83 mmol) in DME (0.906 mL) and water (0.226 mL). The reaction mixture was stirred and heated in a Biotage Initiator microwave reactor at 100° C. for 30 min. The crude product was purified by chromatography to give the title compound. MS (ESI, pos. ion) m/z: 356 (M+1). IC50 (uM) 0.003548.

TABLE VA

EXAMPLES 128 TO 169 ARE TABULATED BELOW:

| Ex. No. | Compound Structure | Compound Name | MS | PDE 10 IC50 (uM) |
|---|---|---|---|---|
| 128 | 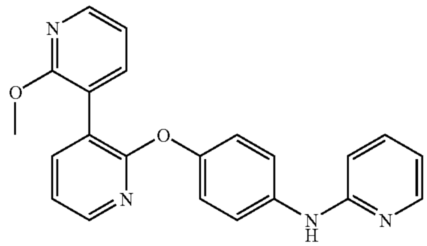 [SMILES: COc1ncccc1-c1cccnc1Oc1ccc(Nc2ccccn2)cc1] | N-(4-(2'-methoxy-3,3'-bipyridin-2-yloxy)phenyl)pyridin-2-amine | 371.1 | 0.00539 |
| 129 | 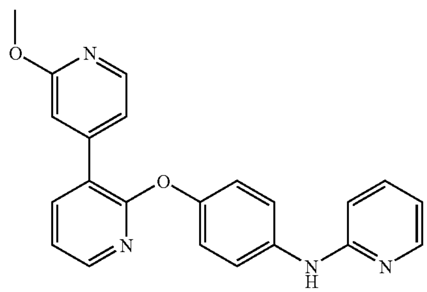 [SMILES: COc1cc(-c2cccnc2Oc2ccc(Nc3ccccn3)cc2)ccn1] | N-(4-(2'-methoxy-3,4'-bipyridin-2-yloxy)phenyl)pyridin-2-amine | 371.1 | 0.007393 |
| 130 | 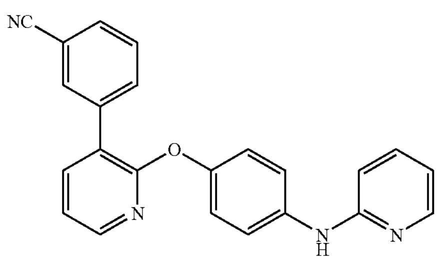 | 3-(2-(4-(pyridin-2-ylamino)phenoxy)pyridin-3-yl)benzonitrile | 365 | 0.012859 |
| 131 | 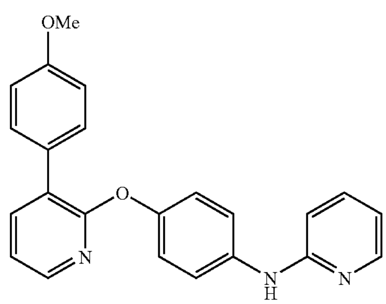 [SMILES: COc1ccc(-c2cccnc2Oc2ccc(Nc3ccccn3)cc2)cc1] | N-(4-(3-(4-methoxyphenyl)pyridin-2-yloxy)phenyl)pyridin-2-amine | 370 | 0.02651 |
| 132 | 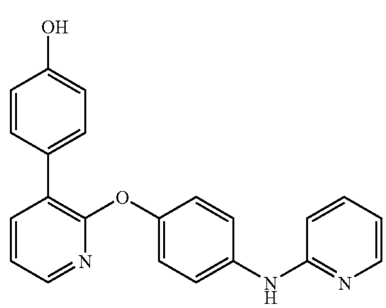 | 4-(2-(4-(pyridin-2-ylamino)phenoxy)pyridin-3-yl)phenol | 356 | 0.012095 |

161 162

TABLE VA-continued

EXAMPLES 128 TO 169 ARE TABULATED BELOW:

| Ex. No. | Compound Structure | Compound Name | MS | PDE 10 IC50 (uM) |
|---|---|---|---|---|
| 133 | 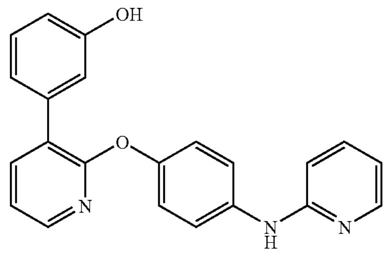 [SMILES: Oc1cccc(-c2cccnc2Oc2ccc(Nc3ccccn3)cc2)c1] | 3-(2-(4-(pyridin-2-ylamino)phenoxy)pyridin-3-yl)phenol | 356 | 0.007529 |
| 134 | 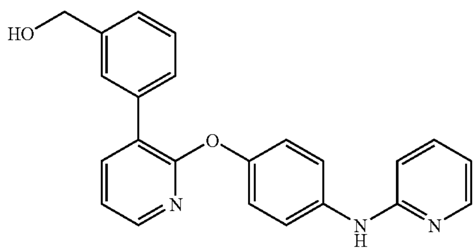 [SMILES: OCc1cccc(-c2cccnc2Oc2ccc(Nc3ccccn3)cc2)c1] | (3-(2-(4-(pyridin-2-ylamino)phenoxy)pyridin-3-yl)phenyl)methanol | 370 | 0.02389 |
| 135 | 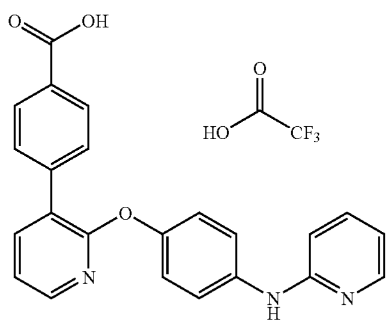 [SMILES: O=C(O)c1ccc(-c2cccnc2Oc2ccc(Nc3ccccn3)cc2)cc1 ; O=C(O)C(F)(F)F] | 4-(2-(4-(pyridin-2-ylamino)phenoxy)pyridin-3-yl)benzoic acid 2,2,2-trifluoroacetate | 384 | 0.004944 |
| 136 | 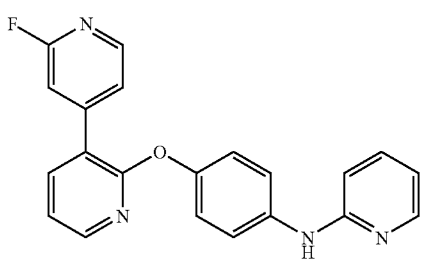 [SMILES: Fc1cc(-c2cccnc2Oc2ccc(Nc3ccccn3)cc2)ccn1] | N-(4-(2'-fluoro-3,4'-bipyridin-2-yloxy)phenyl)pyridin-2-amine | 359 | 0.008696 |
| 137 | 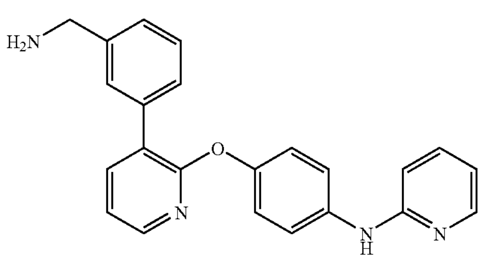 [SMILES: NCc1cccc(-c2cccnc2Oc2ccc(Nc3ccccn3)cc2)c1] | N-(4-(3-(3-(aminomethyl)phenyl)pyridin-2-yloxy)phenyl)pyridin-2-amine | 369 | 0.04 |

TABLE VA-continued

EXAMPLES 128 TO 169 ARE TABULATED BELOW:

| Ex. No. | Compound Structure | Compound Name | MS | PDE 10 IC50 (uM) |
|---|---|---|---|---|
| 138 | 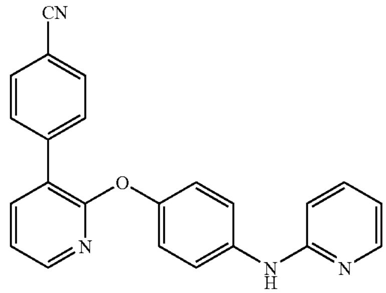 [SMILES: N#Cc1ccc(-c2cccnc2Oc2ccc(Nc3ccccn3)cc2)cc1] | 4-(2-(4-(pyridin-2-ylamino)phenoxy)pyridin-3-yl)benzonitrile | 365 | 0.01472 |
| 139 | 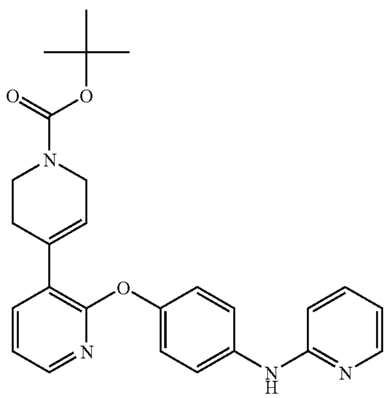 [SMILES: CC(C)(C)OC(=O)N1CC=C(c2cccnc2Oc2ccc(Nc3ccccn3)cc2)CC1] | tert-butyl 4-(2-(4-(pyridin-2-ylamino)phenoxy)pyridin-3-yl)-5,6-dihydropyridine-1(2H)-carboxylate | 445 | 0.028 |
| 140 | 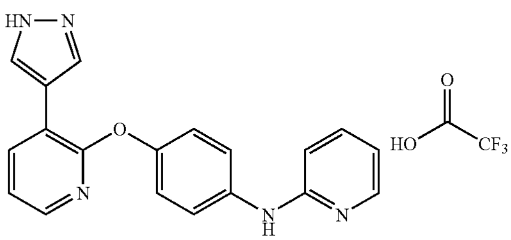 | N-(4-(3-(1H-pyrazol-4-yl)pyridin-2-yloxy)phenyl)pyridin-2-amine 2,2,2-trifluoroacetate | 330 | 0.04093 |
| 141 | 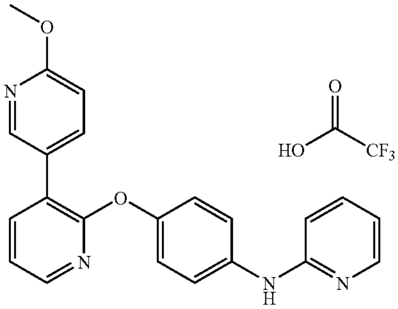 | N-(4-(6'-methoxy-3,3'-bipyridin-2-yloxy)phenyl)pyridin-2-amine 2,2,2-trifluoroacetate | 371 | 0.02194 |
| 142 | 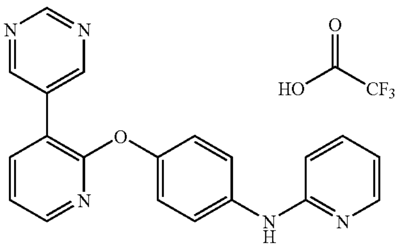 | N-(4-(3-(pyrimidin-5-yl)pyridin-2-yloxy)phenyl)pyridin-2-amine 2,2,2-trifluoroacetate | 342 | 0.005914 |

TABLE VA-continued

EXAMPLES 128 TO 169 ARE TABULATED BELOW:

| Ex. No. | Compound Structure | Compound Name | MS | PDE 10 IC50 (uM) |
|---|---|---|---|---|
| 143 | 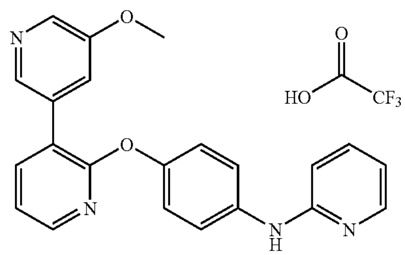 | N-(4-(5'-methoxy-3,3'-bipyridin-2-yloxy)phenyl)pyridin-2-amine 2,2,2-trifluoroacetate | 371 | 0.01312 |
| 144 | 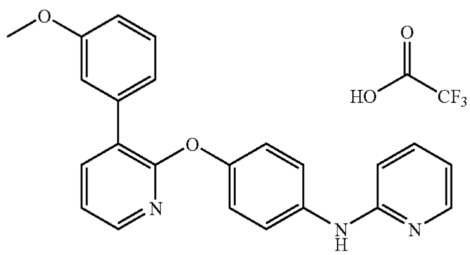 | N-(4-(3-(3-methoxyphenyl)pyridin-2-yloxy)phenyl)pyridin-2-amine 2,2,2-trifluoroacetate | 370 | 0.06401 |
| 145 | 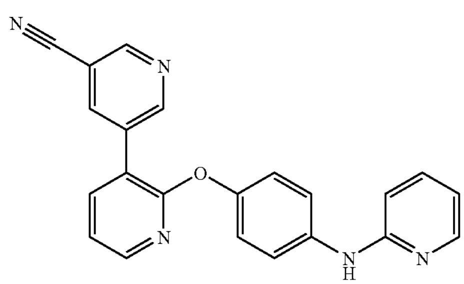 [SMILES: N#Cc1cncc(-c2cccnc2Oc2ccc(Nc3ccccn3)cc2)c1] | 2'-(4-(pyridin-2-ylamino)phenoxy)-3,3'-bipyridine-5-carbonitrile | 366 | 0.014215 |
| 146 | 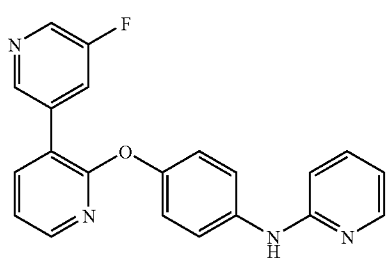 [SMILES: Fc1cncc(-c2cccnc2Oc2ccc(Nc3ccccn3)cc2)c1] | N-(4-(5'-fluoro-3,3'-bipyridin-2-yloxy)phenyl)pyridin-2-amine | 359 | 0.005012 |
| 147 | 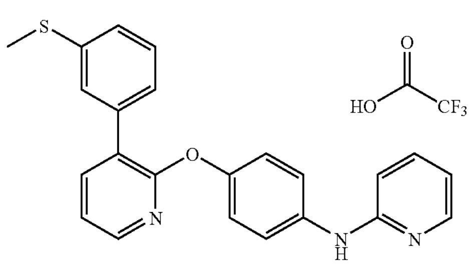 | N-(4-(3-(3-(methylthio)phenyl)pyridin-2-yloxy)phenyl)pyridin-2-amine 2,2,2-trifluoroacetate | 386 | 0.05641 |

TABLE VA-continued

EXAMPLES 128 TO 169 ARE TABULATED BELOW:

| Ex. No. | Compound Structure | Compound Name | MS | PDE 10 IC50 (uM) |
|---|---|---|---|---|
| 148 | 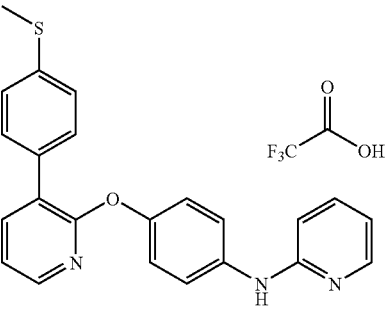 | N-(4-(3-(4-(methylthio)phenyl)pyridin-2-yloxy)phenyl)pyridin-2-amine 2,2,2-trifluoroacetate | 386 | 0.2216 |
| 149 | 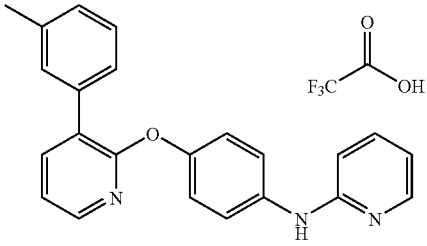 | N-(4-(3-m-tolylpyridin-2-yloxy)phenyl)pyridin-2-amine 2,2,2-trifluoroacetate | 354 | 0.1057 |
| 150 | 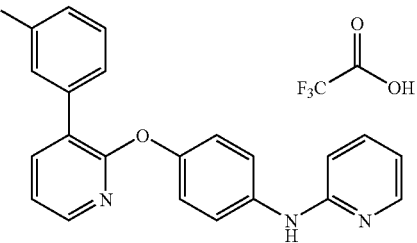 | N-(4-(3-(3-fluorophenyl)pyridin-2-yloxy)phenyl)pyridin-2-amine 2,2,2-trifluoroacetate | 358 | 0.06648 |
| 151 | 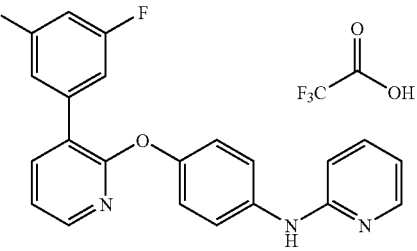 | N-(4-(3-(3,5-difluorophenyl)pyridin-2-yloxy)phenyl)pyridin-2-amine 2,2,2-trifluoroacetate | 376 | 0.1219 |
| 152 | 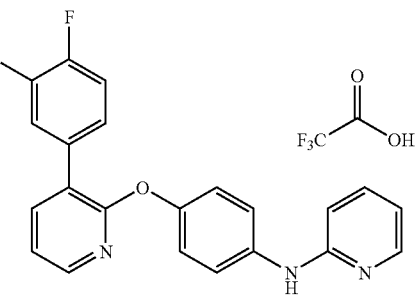 | N-(4-(3-(3,4-difluorophenyl)pyridin-2-yloxy)phenyl)pyridin-2-amine 2,2,2-trifluoroacetate | 376 | 0.1034 |

TABLE VA-continued

EXAMPLES 128 TO 169 ARE TABULATED BELOW:

| Ex. No. | Compound Structure | Compound Name | MS | PDE 10 IC50 (uM) |
|---|---|---|---|---|
| 153 | 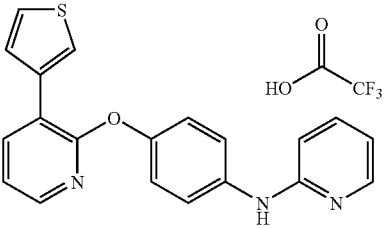 | N-(4-(3-(thiophen-3-yl)pyridin-2-yloxy)phenyl)pyridin-2-amine 2,2,2-trifluoroacetate | 346 | 0.1103 |
| 154 | 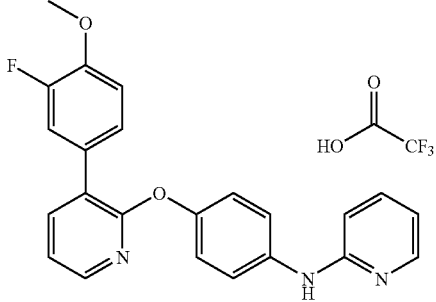 | N-(4-(3-(3-fluoro-4-methoxyphenyl)pyridin-2-yloxy)phenyl)pyridin-2-amine 2,2,2-trifluoroacetate | 388 | 0.04711 |
| 155 | 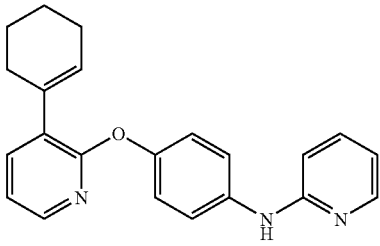 | N-(4-(3-cyclohexenylpyridin-2-yloxy)phenyl)pyridin-2-amine | 344 | 0.05578 |
| 156 | 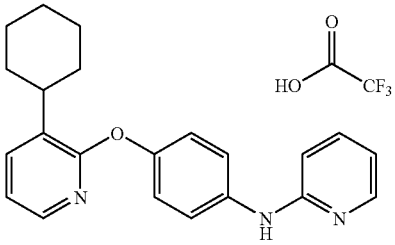 | N-(4-(3-cyclohexylpyridin-2-yloxy)phenyl)pyridin-2-amine 2,2,2-trifluoroacetate | 346 | 0.03646 |
| 157 | 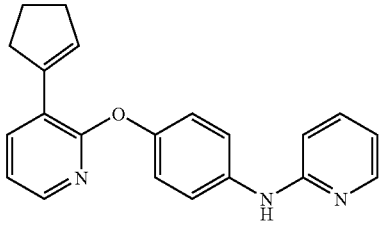 [SMILES: C1=C(c2cccnc2Oc2ccc(Nc3ccccn3)cc2)CCC1] | N-(4-(3-cyclopentenylpyridin-2-yloxy)phenyl)pyridin-2-amine | 330 | 0.3047 |
| 158 | 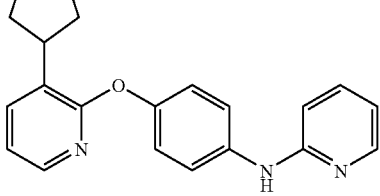 | N-(4-(3-cyclopentylpyridin-2-yloxy)phenyl)pyridin-2-amine | 332.0 | 0.05528 |

TABLE VA-continued

EXAMPLES 128 TO 169 ARE TABULATED BELOW:

| Ex. No. | Compound Structure | Compound Name | MS | PDE 10 IC50 (uM) |
|---|---|---|---|---|
| 159 | 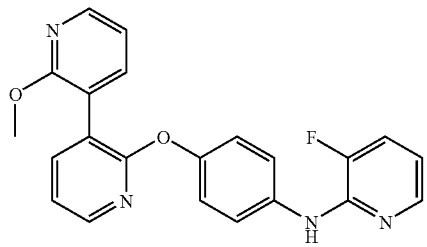 [SMILES: COc1ncccc1-c1cccnc1Oc1ccc(Nc2ncccc2F)cc1] | 3-fluoro-N-(4-(2'-methoxy-3,3'-bipyridin-2-yloxy)phenyl)pyridin-2-amine | 389.1 | 0.01072 |
| 160 | 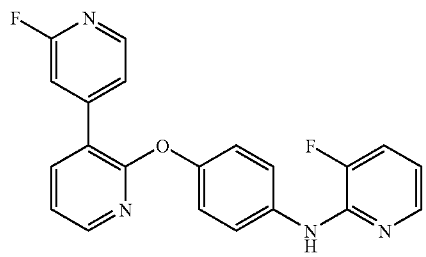 [SMILES: Fc1cc(-c2cccnc2Oc2ccc(Nc3ncccc3F)cc2)ccn1] | 3-fluoro-N-(4-(2'-fluoro-3,4'-bipyridin-2-yloxy)phenyl)pyridin-2-amine | 377 | 0.0139 |
| 161 | 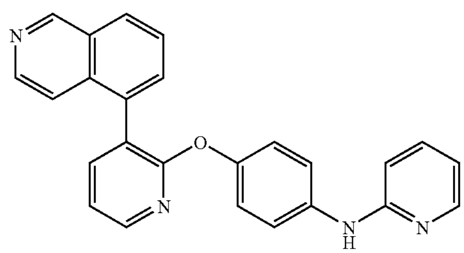 [SMILES: c1ccc(Nc2ccc(Oc3ncccc3-c3cccc4cnccc34)cc2)nc1] | N-(4-(3-(isoquinolin-5-yl)pyridin-2-yloxy)phenyl)pyridin-2-amine | 390 | 0.001 |
| 162 | 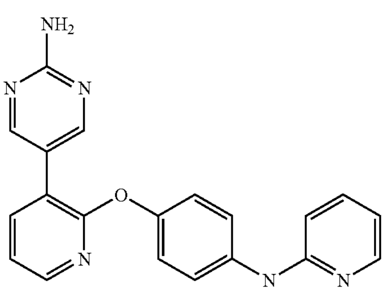 [SMILES: Nc1ncc(-c2cccnc2Oc2ccc(Nc3ccccn3)cc2)cn1] | 5-(2-(4-(pyridin-2-ylamino)phenoxy)pyridin-3-yl)pyrimidin-2-amine | 356 | 0.008 |
| 163 | 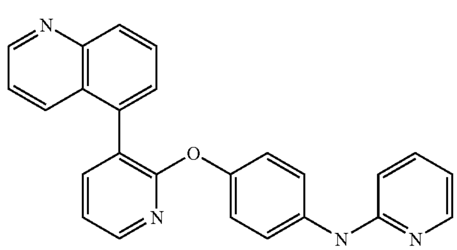 [SMILES: c1ccc(Nc2ccc(Oc3ncccc3-c3cccc4ncccc34)cc2)nc1] | N-(4-(3-(quinolin-5-yl)pyridin-2-yloxy)phenyl)pyridin-2-amine | 390 | 0.003 |

TABLE VA-continued

EXAMPLES 128 TO 169 ARE TABULATED BELOW:

| Ex. No. | Compound Structure | Compound Name | MS | PDE 10 IC50 (uM) |
|---|---|---|---|---|
| 164 | 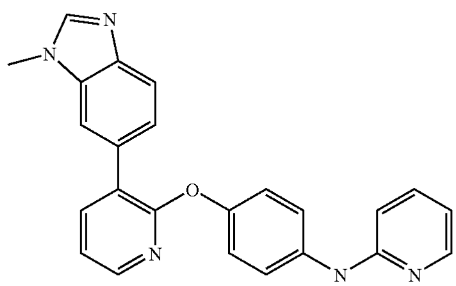 [SMILES: Cn1cnc2ccc(-c3cccnc3Oc3ccc(Nc4ccccn4)cc3)cc21] | N-(4-(3-(1-methyl-1H-benzo[d]imidazol-6-yl)pyridin-2-yloxy)phenyl)pyridin-2-amine | 393 | 0.009 |
| 165 | 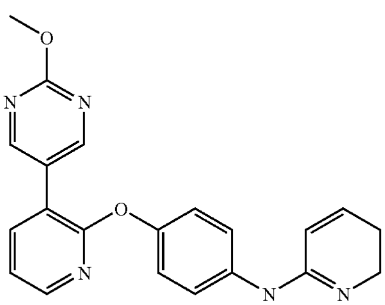 [SMILES: COc1ncc(-c2cccnc2Oc2ccc(NC3=NCCC=C3)cc2)cn1] | N-(4-(3-(2-methoxypyrimidin-5-yl)pyridin-2-yloxy)phenyl)pyridin-2-amine | 371 | 0.005 |
| 166 | 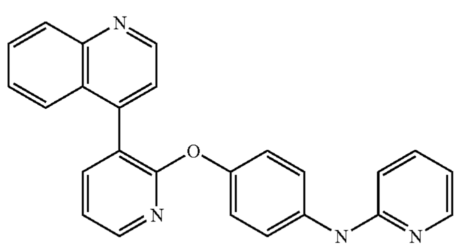 [SMILES: c1ccc(Nc2ccc(Oc3ncccc3-c3ccnc4ccccc34)cc2)nc1] | N-(4-(3-(quinolin-4-yl)pyridin-2-yloxy)phenyl)pyridin-2-amine | 390 | 0.003 |
| 167 | 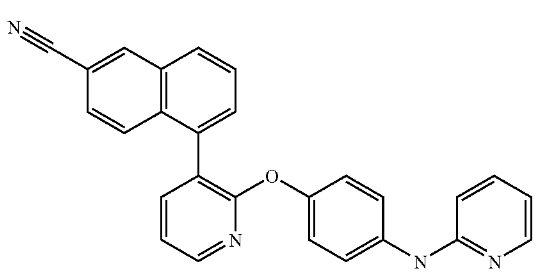 [SMILES: N#Cc1ccc2c(-c3cccnc3Oc3ccc(Nc4ccccn4)cc3)cccc2c1] | 4-(2-(4-(pyridin-2-ylamino)phenoxy)pyridin-3-yl)quinoline-7-carbonitrile | 415 | 0.002 |
| 168 | 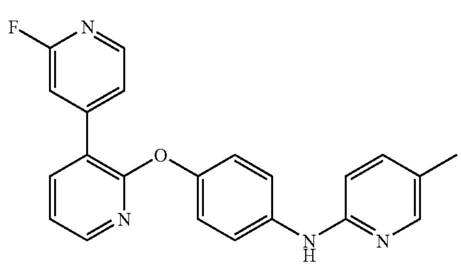 [SMILES: Cc1ccc(Nc2ccc(Oc3ncccc3-c3ccnc(F)c3)cc2)nc1] | N-(4-(2'-fluoro-3,4'-bipyridin-2-yloxy)phenyl)-5-methylpyridin-2-amine | 373.1 | 0.001422 |

TABLE VA-continued

EXAMPLES 128 TO 169 ARE TABULATED BELOW:

| Ex. No. | Compound Structure | Compound Name | MS | PDE 10 IC50 (uM) |
|---|---|---|---|---|
| 169 | 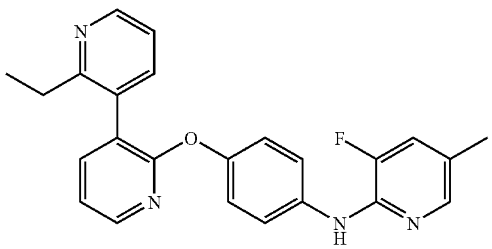 [SMILES: CCc1ncccc1-c1cccnc1Oc1ccc(Nc2ncc(C)cc2F)cc1] | 5-chloro-3-fluoro-N-(4-(2'-methoxy-3,3'-bipyridin-2-yloxy)phenyl)pyridin-2-amine | 395 | 0.01578 |

TABLE VB

PREPARATION OF EXAMPLES 128 TO 169 ARE TABULATED BELOW:

| Ex. No. | Scheme | Starting material 1 | Starting material 2 | Conditions or reagents that differ from scheme |
|---|---|---|---|---|
| 128 | 9 | | | |
| 129 | 9 | | | |
| 130 | 9 | | | |
| 131 | 9 | | | |

TABLE VB-continued

PREPARATION OF EXAMPLES 128 TO 169 ARE TABULATED BELOW:

| Ex. No. | Scheme | Starting material 1 | Starting material 2 | Conditions or reagents that differ from scheme |
|---|---|---|---|---|
| 132 | 9 | 3-bromo-2-(4-(pyridin-2-ylamino)phenoxy)pyridine HCl | 4-hydroxyphenylboronic acid | |
| 133 | 9 | 3-bromo-2-(4-(pyridin-2-ylamino)phenoxy)pyridine HCl | 3-hydroxyphenylboronic acid | |
| 134 | 9 | 3-bromo-2-(4-(pyridin-2-ylamino)phenoxy)pyridine HCl | 3-(hydroxymethyl)phenylboronic acid | |
| 135 | 9 | 3-bromo-2-(4-(pyridin-2-ylamino)phenoxy)pyridine HCl | 4-carboxyphenylboronic acid | Purified by rev phase HPLC |
| 136 | 9 | 3-bromo-2-(4-(pyridin-2-ylamino)phenoxy)pyridine HCl | 2-fluoropyridin-4-ylboronic acid | |
| 137 | 9 | 3-bromo-2-(4-(pyridin-2-ylamino)phenoxy)pyridine HCl | 3-(aminomethyl)phenylboronic acid HCl | |

TABLE VB-continued

PREPARATION OF EXAMPLES 128 TO 169 ARE TABULATED BELOW:

| Ex. No. | Scheme | Starting material 1 | Starting material 2 | Conditions or reagents that differ from scheme |
|---|---|---|---|---|
| 138 | 9 | | | |
| 139 | 9 | | | |
| 140 | 9 | | | Purified by rev phase HPLC |
| 141 | 9 | | | Purified by rev phase HPLC |
| 142 | 9 | | | Purified by rev phase HPLC |
| 143 | 9 | | | Purified by rev phase HPLC |

TABLE VB-continued

PREPARATION OF EXAMPLES 128 TO 169 ARE TABULATED BELOW:

| Ex. No. | Scheme | Starting material 1 | Starting material 2 | Conditions or reagents that differ from scheme |
|---|---|---|---|---|
| 144 | 9 | | | Purified by rev phase HPLC |
| 145 | 9 | | | |
| 146 | 9 | | | |
| 147 | 9 | | | Purified by rev phase HPLC |
| 148 | 9 | | | Purified by rev phase HPLC |
| 149 | 9 | | | Purified by rev phase HPLC |

TABLE VB-continued
PREPARATION OF EXAMPLES 128 TO 169 ARE TABULATED BELOW:
| Ex. No. | Scheme | Starting material 1 | Starting material 2 | Conditions or reagents that differ from scheme |
|---|---|---|---|---|
| 150 | 9 | 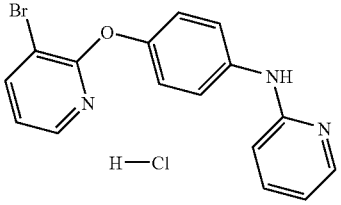 [SMILES: Brc1cccnc1Oc1ccc(Nc2ccccn2)cc1 ; Cl] | 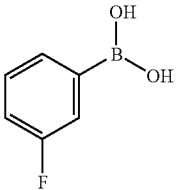 | Purified by rev phase HPLC |
| 151 | 9 | 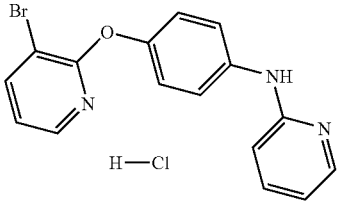 [SMILES: Brc1cccnc1Oc1ccc(Nc2ccccn2)cc1 ; Cl] | 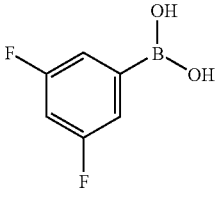 [SMILES: OB(O)c1cc(F)cc(F)c1] | Purified by rev phase HPLC |
| 152 | 9 | 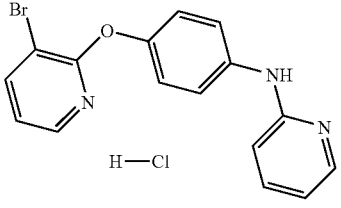 [SMILES: Brc1cccnc1Oc1ccc(Nc2ccccn2)cc1 ; Cl] | 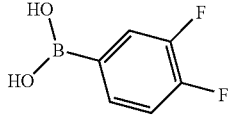 [SMILES: OB(O)c1ccc(F)c(F)c1] | Purified by rev phase HPLC |
| 153 | 9 | 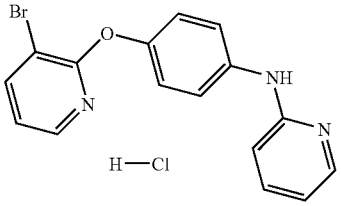 [SMILES: Brc1cccnc1Oc1ccc(Nc2ccccn2)cc1 ; Cl] | 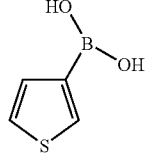 | Purified by rev phase HPLC |
| 154 | 9 | 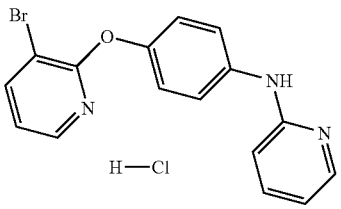 [SMILES: Brc1cccnc1Oc1ccc(Nc2ccccn2)cc1 ; Cl] | 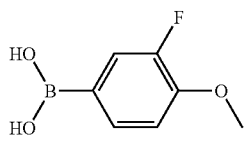 | Purified by rev phase HPLC |
| 155 | 9 | 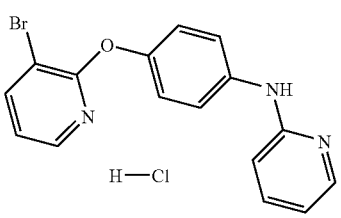 [SMILES: Brc1cccnc1Oc1ccc(Nc2ccccn2)cc1 ; Cl] | 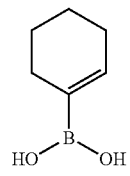 | |

TABLE VB-continued

PREPARATION OF EXAMPLES 128 TO 169 ARE TABULATED BELOW:

| Ex. No. | Scheme | Starting material 1 | Starting material 2 | Conditions or reagents that differ from scheme |
|---|---|---|---|---|
| 156 | | (3-cyclohexenyl-pyridin-2-yl) oxy-phenyl-N-phenylamine | H₂ | Heated @ 40 C. for 8 h then rt overnight; rev phase HPLC purification |
| 157 | 9 | 3-bromo-pyridin-2-yloxy-phenyl-NH-pyridin-2-yl, H—Cl | cyclopentenyl boronic acid (HO-B-OH) | |
| 158 | | 3-cyclopentenyl-pyridin-2-yloxy-phenyl-NH-pyridin-2-yl | H₂ | |
| 159 | 9 | 3-bromo-pyridin-2-yloxy-phenyl-NH-(3-fluoropyridin-2-yl) | 2-methoxy-3-pyridinyl pinacol boronate | |
| 160 | 9 | 3-bromo-pyridin-2-yloxy-phenyl-NH-(3-fluoropyridin-2-yl) | 2-fluoro-4-pyridinyl pinacol boronate | |
| 161 | 9 | isoquinoline-5-B(OH)₂ | 3-bromo-pyridin-2-yloxy-phenyl-N-pyridin-2-yl | None |

TABLE VB-continued

PREPARATION OF EXAMPLES 128 TO 169 ARE TABULATED BELOW:

| Ex. No. | Scheme | Starting material 1 | Starting material 2 | Conditions or reagents that differ from scheme |
|---|---|---|---|---|
| 162 | 9 | 2-amino-pyrimidine-5-boronic acid pinacol ester | 3-bromo-2-(4-(pyridin-2-ylamino)phenoxy)pyridine | None |
| 163 | 9 | quinoline-5-boronic acid | 3-bromo-2-(4-(pyridin-2-ylamino)phenoxy)pyridine | None |
| 164 | 9 | 1-methyl-1H-benzimidazole-6-boronic acid | 3-bromo-2-(4-(pyridin-2-ylamino)phenoxy)pyridine | None |
| 165 | 9 | 2-methoxy-pyrimidine-5-boronic acid | 3-bromo-2-(4-(pyridin-2-ylamino)phenoxy)pyridine | None |
| 166 | 9 | quinoline-4-boronic acid | 3-bromo-2-(4-(pyridin-2-ylamino)phenoxy)pyridine | None |
| 167 | 9 | 7-cyano-quinoline-4-boronic acid pinacol ester | 3-bromo-2-(4-(pyridin-2-ylamino)phenoxy)pyridine | None |

TABLE VB-continued

PREPARATION OF EXAMPLES 128 TO 169 ARE TABULATED BELOW:

| Ex. No. | Scheme | Starting material 1 | Starting material 2 | Conditions or reagents that differ from scheme |
|---|---|---|---|---|
| 168 | 9 | 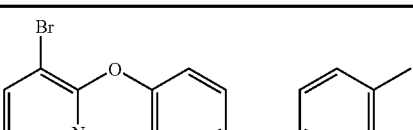 | 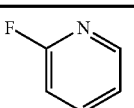 | |
| 169 | 9 | 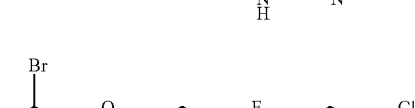 | 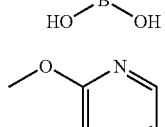 | |

SCHEME 10

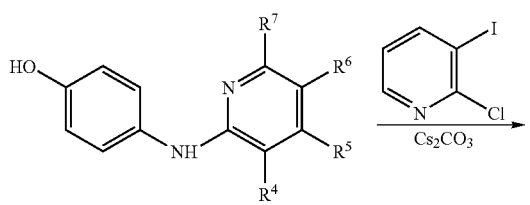

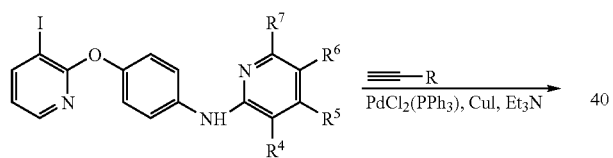

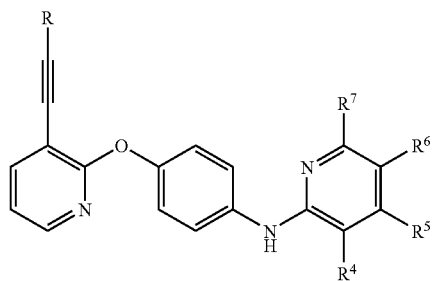

Example 170

3-(2-(4-(PYRIDIN-2-YLAMINO)PHENOXY)PYRIDIN-3-YL)PROP-2-YN-1-OL

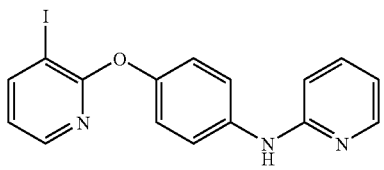

STEP 1. N-(4-(3-IODOPYRIDIN-2-YLOXY)PHENYL)PYRIDIN-2-AMINE

To a 250-mL round-bottomed flask was added 2-chloro-3-iodopyridine (5.32 g, 22.22 mmol), 4-(pyridin-2-ylamino)phenol (4.96 g, 26.6 mmol) and cesium carbonate (11.27 g, 34.6 mmol) in DMSO (100 mL) and the reaction was heated at 80° C. overnight. The reaction was cooled to rt and poured into water (400 mL). The solution was extracted with EtOAc (4×100 mL) and the combined organic layers were washed with brine and dried over $Na_2SO_4$. The solution was filtered, evaporated onto silica gel and purified by flash chromatography (Isco, (330 gram)) eluting with 2M $NH_3$ in MeOH: $CH_2Cl_2$ (0:1→1:19). The material was dissolved in MeOH, evaporated onto silica gel and further purified by flash chromatography (Isco (330 gram)) eluting with EtOAc:hexanes (0:1→3:1) to give a white amorphous solid. MS (ESI, pos. ion) m/z: 389.9. IC$_{50}$ (uM)=0.2284.

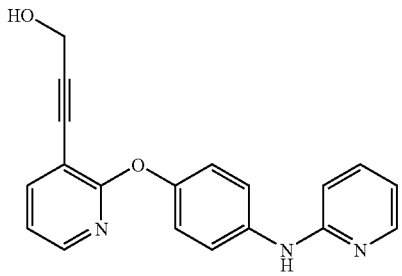 [SMILES: OCC#Cc1cccnc1Oc1ccc(Nc2ccccn2)cc1]

STEP 2. 3-(2-(4-(PYRIDIN-2-YLAMINO)PHE-NOXY)PYRIDIN-3-YL)PROP-2-YN-1-OL

A mixture of N-(4-(3-iodopyridin-2-yloxy)phenyl)pyridin-2-amine (0.300 g, 0.771 mmol), copper(I) iodide (3.91 µL, 0.116 mmol), trans-dichlorobis(triphenyl-phosphine) palladium (II) (0.034 g, 0.048 mmol), triethylamine (0.800 mL, 5.74 mmol) and propargyl alcohol (0.150 mL, 2.54 mmol) in THF (5 mL) was stirred at rt under an atmosphere of argon for 3.5 h. The reaction was evaporated onto silica gel and purified by flash chromatography (Isco, (60 gram)) eluting with 2M NH$_3$ in MeOH:CH$_2$Cl$_2$ (0:1→3:97). The material was stirred over MeOH, filtered and dried in vacuo to give a white crystalline solid. MS (ESI, pos. ion) m/z: 318.0. IC$_{50}$ (uM)=0.2612.

TABLE VIA

EXAMPLES 171 TO 174 ARE TABULATED BELOW:

| Ex. No. | Compound Structure | Compound Name | MS | PDE10 IC50 (uM) |
|---|---|---|---|---|
| 171 | 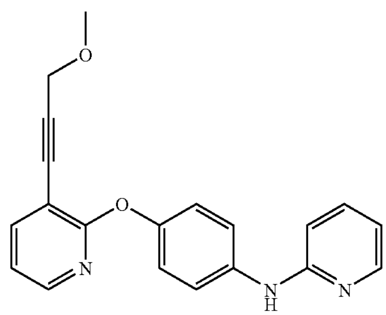 [SMILES: COCC#Cc1cccnc1Oc1ccc(Nc2ccccn2)cc1] | N-(4-(3-(3-methoxyprop-1-ynyl)pyridin-2-yloxy)phenyl)pyridin-2-amine | 332 | 0.1653 |
| 172 | 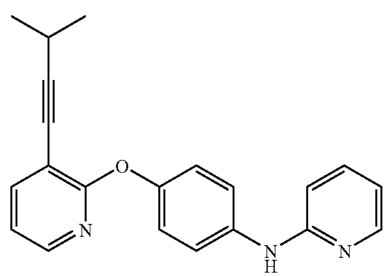 [SMILES: CC(C)C#Cc1cccnc1Oc1ccc(Nc2ccccn2)cc1] | N-(4-(3-(3-methylbut-1-ynyl)pyridin-2-yloxy)phenyl)pyridin-2-amine | 330 | 1.454 |
| 173 | 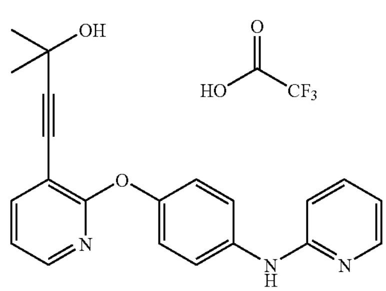 [SMILES: CC(C)(O)C#Cc1cccnc1Oc1ccc(Nc2ccccn2)cc1 ; O=C(O)C(F)(F)F] | 2-methyl-4-(2-(4-(pyridin-2-ylamino)phenoxy)pyridin-3-yl)but-3-yn-2-ol 2,2,2-trifluoroacetate | 346 | 1.244 |

TABLE VIA-continued

EXAMPLES 171 TO 174 ARE TABULATED BELOW:

| Ex. No. | Compound Structure | Compound Name | MS | PDE10 IC50 (uM) |
|---|---|---|---|---|
| 174 | 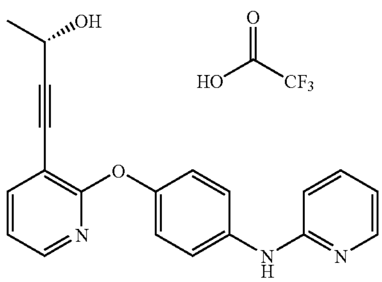 [SMILES: C[C@H](O)C#Cc1cccnc1Oc1ccc(Nc2ccccn2)cc1 ; O=C(O)C(F)(F)F] | (S)-4-(2-(4-(pyridin-2-ylamino)phenoxy)pyridin-3-yl)but-3-yn-2-ol 2,2,2-trifluoroacetate | 332 | 0.6077 |

TABLE VIB

PREPARATION OF EXAMPLES 171 TO 174 ARE TABULATED BELOW:

| Ex. No. | Scheme | Starting material 1 | Starting material 2 | Conditions or reagents that differ from scheme |
|---|---|---|---|---|
| 171 | 10 | | | Purified by rev phase HPLC; free-based |
| 172 | 10 | | | Purified by rev phase HPLC; free-based |
| 173 | 10 | | | Purified by rev phase HPLC |
| 174 | 10 | | | Purified by rev phase HPLC |

195

SCHEME 11

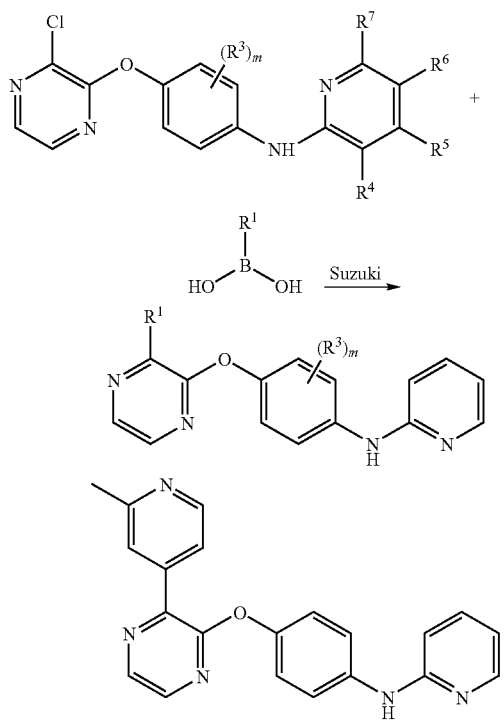

Example 175

N-(4-(3-(2-METHYLPYRIDIN-4-YL)PYRAZIN-2-YLOXY)PHENYL)PYRIDIN-2-AMINE

To a 50 mL round-bottomed flask was added N-(4-(3-chloropyrazin-2-yloxy)phenyl)pyridin-2-amine (0.2890 g, 0.967 mmol), 2-methylpyridin-4-ylboronic acid (0.1684 g, 1.20 mmol), and trans-dichlorobis(triphenylphosphine)palladium (II) (0.0355 g, 0.0484 mmol) in DME. An aqueous solution of cesium carbonate (0.213 ml, 2.61 mmol) was added and the temperature was brought to 80° C. to stir overnight. The crude product was adsorbed onto a plug of silica gel and chromatographed to provide N-(4-(3-(2-methylpyridin-4-yl)pyrazin-2-yloxy)phenyl)pyridin-2-amine. MS (ESI, pos. ion) m/z: 356.1. $IC_{50}$ (uM)=0.033.

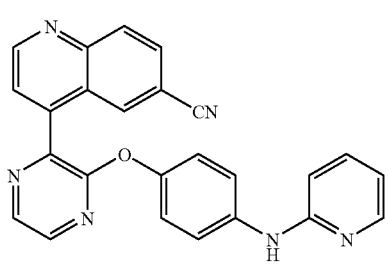

196

Example 176

N-(4-(3-(1-METHYL-1H-PYRAZOL-4-YL)PYRAZIN-2-YLOXY)PHENYL)PYRIDIN-2-AMINE

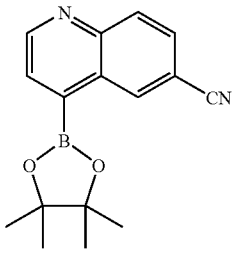 [SMILES: CC1(C)OB(c2ccnc3ccc(C#N)cc23)OC1(C)C]

STEP 1. 4-(4,4,5,5-TETRAMETHYL-1,3,2-DIOXABOROLAN-2-YL)QUINOLINE-6-CARBONITRILE

A suspension of 4-chloroquinoline-7-carbonitrile (725 mg, 3.84 mmol), bis(pinacolato)diboron (1074 mg, 4.23 mmol), $PdCl_2(dppf)_2$-$CH_2Cl_2$ (157 mg, 0.192 mmol), and potassium acetate (943 mg, 9.61 mmol) in 1,4-dioxane (10 mL) was sparged with argon for 5 minutes then heated to 125° C. in an appropriately sealed vial for 40 minutes. The reaction was then partitioned between EtOAc (30 mL) and 5% $NaHCO_3$ (15 mL). The separated organic was then dried over $MgSO_4$, concentrated under reduced pressure, then purified on silica (40 g) eluting products with 20>60% of EtOAc/Hex to afford title compound as a white solid. MS (ESI positive ion) m/z: 199.1 (M+1) for boronic acid.

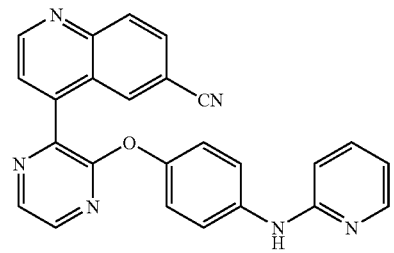 [SMILES: N#Cc1ccc2nccc(-c3nccnc3Oc3ccc(Nc4ccccn4)cc3)c2c1]

STEP 2. N-(4-(3-(1-METHYL-1H-PYRAZOL-4-YL)PYRAZIN-2-YLOXY)PHENYL)PYRIDIN-2-AMINE

A suspension of N-(4-(3-chloropyrazin-2-yloxy)phenyl)pyridin-2-amine (300 mg, 1.004 mmol), 4-(4,4,5,5-tetramethyl-1,3,2-dioxaborolan-2-yl)quinoline-6-carbonitrile (563 mg, 2.009 mmol), $PdCl_2(dppf)_2$-$CH_2Cl_2$ (82 mg, 0.100 mmol), sodium carbonate (532 mg, 5.02 mmol) in 1,4-dioxane (3 mL) and water (3 mL) was sparged with argon for 5 min then heated to 95° C. for 30 minutes. The reaction was then partitioned between EtOAc (30 mL) and 5% $NaHCO_3$ (30 mL). The separated organic was then dried over $MgSO_4$, concentrated onto dry silica (10 g) under reduced pressure, then purified on silica (40 g) eluting with 2.0-3.5% of MeOH/DCM to afford title compound as a white solid. MS (ESI positive ion) m/z: 417.1 (M+1). IC50 (uM) 0.0038.

TABLE VIIA

EXAMPLES 177 TO 214 ARE TABULATED BELOW:

| Ex. No. | Compound Name | MS | PDE10 IC50 (uM) |
|---|---|---|---|
| 177 | N-(2-fluoro-4-(3-(2-fluoropyridin-4-yl)pyrazin-2-yloxy)phenyl)pyridin-2-amine | 378 | 0.1424 |
| 178 | N-(2-fluoro-4-(3-(2-methoxypyridin-3-yl)pyrazin-2-yloxy)phenyl)pyridin-2-amine | 390 | 0.003418 |
| 179 | N-(4-(3-(1-methyl-1H-pyrazol-4-yl)pyrazin-2-yloxy)phenyl)pyridin-2-amine | 345 | 0.019 |
| 180 | N-(4-(3-(3-aminophenyloxy)phenyl)pyridin | 356 | 0.066 |
| 181 | N-(4-(3-(2-chloropyridin-4-yl)pyrazin-2-yloxy)phenyl)pyridin-2-amine | 376 | 0.016 |

TABLE VIIA-continued

EXAMPLES 177 TO 214 ARE TABULATED BELOW:

| Ex. No. | Compound Structure | Compound Name | MS | PDE10 IC50 (uM) |
|---|---|---|---|---|
| 182 | 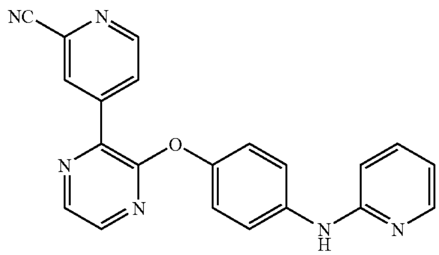 | 4-(3-(4-(pyridin-2-ylamino)phenoxy)pyrazin-2-yl)picolinonitrile | 367 | 0.016 |
| 183 | 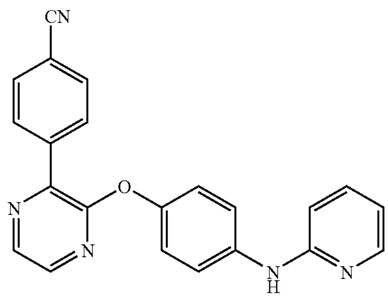 [SMILES: N#Cc1ccc(-c2nccnc2Oc2ccc(Nc3ccccn3)cc2)cc1] | 4-(3-(4-(pyridin-2-ylamino)phenoxy)pyrazin-2-yl)benzonitrile | 366 | 0.022 |
| 184 | 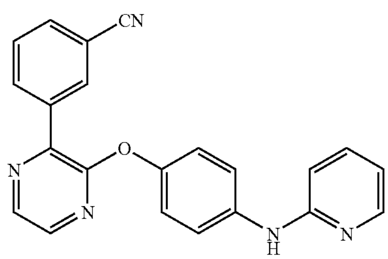 [SMILES: N#Cc1cccc(-c2nccnc2Oc2ccc(Nc3ccccn3)cc2)c1] | 3-(3-(4-(pyridin-2-ylamino)phenoxy)pyrazin-2-yl)benzonitrile | 366 | 0.008 |
| 185 | 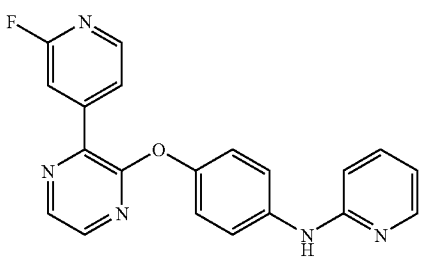 | N-(4-(3-(2-fluoropyridin-4-yl)pyrazin-2-yloxy)phenyl)pyridin-2-amine | 360 | 0.027 |
| 186 | 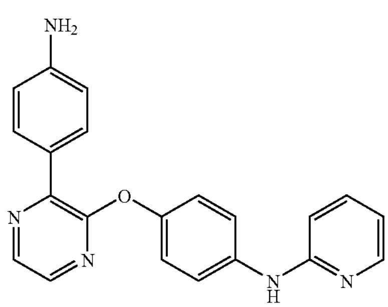 | N-(4-(3-(4-aminophenyl)pyrazin-2-yloxy)phenyl)pyridin-2-amine | 356 | 0.015 |

TABLE VIIA-continued

EXAMPLES 177 TO 214 ARE TABULATED BELOW:

| Ex. No. | Compound Structure | Compound Name | MS | PDE10 IC50 (uM) |
|---|---|---|---|---|
| 187 | 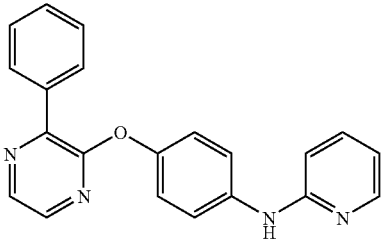 | N-(4-(3-phenylpyrazin-2-yloxy)phenyl)pyridin-2-amine | 341 | 0.032 |
| 188 | 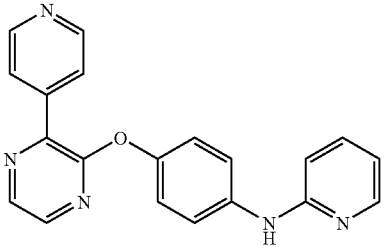 [SMILES: c1ccc(Nc2ccc(Oc3nccnc3-c3ccncc3)cc2)nc1] | N-(4-(3-(pyridin-4-yl)pyrazin-2-yloxy)phenyl)pyridin-2-amine | 342 | 0.005 |
| 189 | 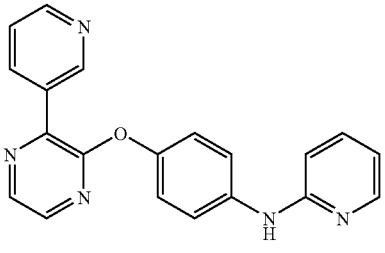 [SMILES: c1ccc(Nc2ccc(Oc3nccnc3-c3cccnc3)cc2)nc1] | N-(4-(3-(pyridin-3-yl)pyrazin-2-yloxy)phenyl)pyridin-2-amine | 342 | 0.007 |
| 190 | 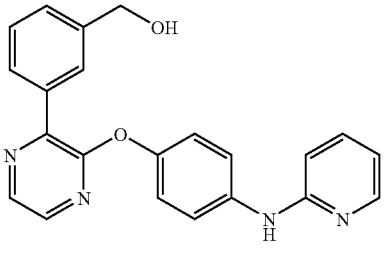 [SMILES: OCc1cccc(-c2nccnc2Oc2ccc(Nc3ccccn3)cc2)c1] | (3-(3-(4-(pyridin-2-ylamino)phenoxy)pyrazin-2-yl)phenyl)methanol | 371 | 0.018 |
| 191 | 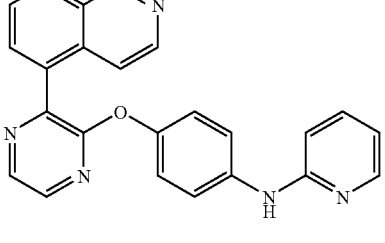 | N-(4-(3-(isoquinolin-5-yl)pyrazin-2-yloxy)phenyl)pyridin-2-amine | 392 | 0.002 |
| 192 | 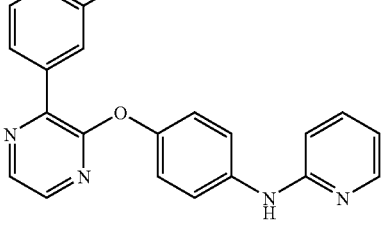 | N-(4-(3-(3-chlorophenyl)pyrazin-2-yloxy)phenyl)pyridin-2-amine | 375 | 0.13 |

TABLE VIIA-continued

EXAMPLES 177 TO 214 ARE TABULATED BELOW:

| Ex. No. | Compound Structure | Compound Name | MS | PDE10 IC50 (uM) |
|---|---|---|---|---|
| 193 | 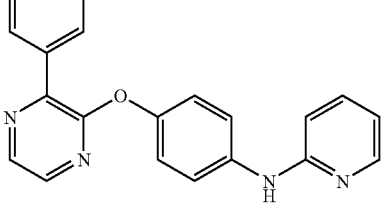 | N-(4-(3-(3-(aminomethyl)phenyl)pyrazin-2-yloxy)phenyl)pyridin-2-amine | 370 | |
| 194 | 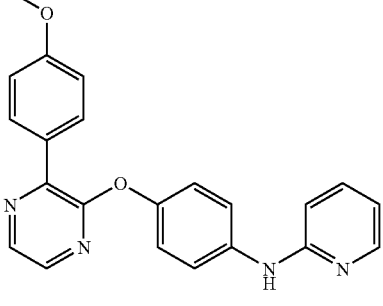 | N-(4-(3-(4-methoxyphenyl)pyrazin-2-yloxy)phenyl)pyridin-2-amine | 371 | |
| 195 | 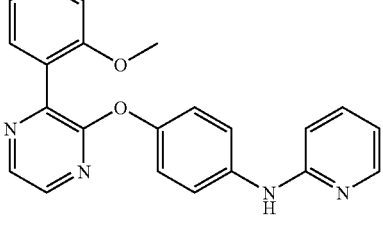 | N-(4-(3-(2-methoxyphenyl)pyrazin-2-yloxy)phenyl)pyridin-2-amine | 371 | |
| 196 | 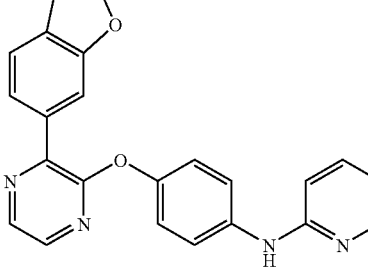 | N-(4-(3-(benzo[d][1,3]dioxol-5-yl)pyrazin-2-yloxy)phenyl)pyridin-2-amine | 385 | |
| 197 | 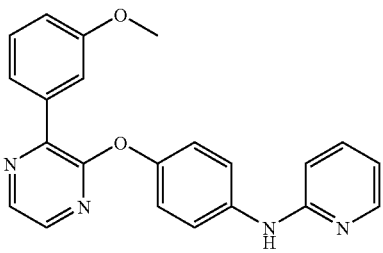 [SMILES: COc1cccc(-c2nccnc2Oc2ccc(Nc3ccccn3)cc2)c1] | N-(4-(3-(3-methoxyphenyl)pyrazin-2-yloxy)phenyl)pyridin-2-amine | 371 | |

TABLE VIIA-continued

EXAMPLES 177 TO 214 ARE TABULATED BELOW:

| Ex. No. | Compound Structure | Compound Name | MS | PDE10 IC50 (uM) |
|---|---|---|---|---|
| 198 | 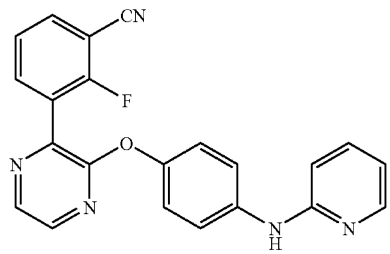 [SMILES: N#Cc1cccc(-c2nccnc2Oc2ccc(Nc3ccccn3)cc2)c1F] | 2-fluoro-2-(3-(4-(pyridin-2-ylamino)phenoxy)pyrazin-2-yl)benzonitrile | 384 | |
| 199 | 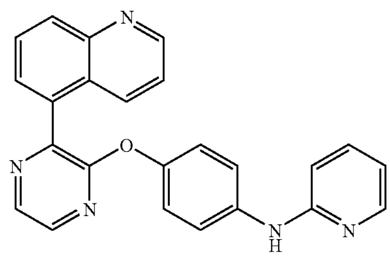 [SMILES: c1ccc(Nc2ccc(Oc3nccnc3-c3cccc4ncccc34)cc2)nc1] | N-(4-(3-(quinolin-5-yl)pyrazin-2-yloxy)phenyl)pyridin-2-amine | 392 | |
| 200 | 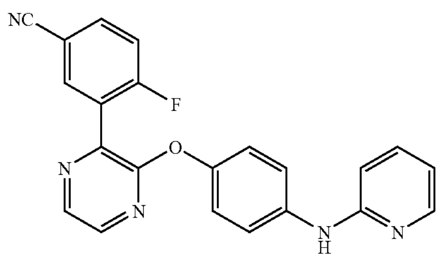 | 4-fluoro-3-(3-(4-(pyridin-2-ylamino)phenoxy)pyrazin-2-yl)benzonitrile | 384 | |
| 201 | 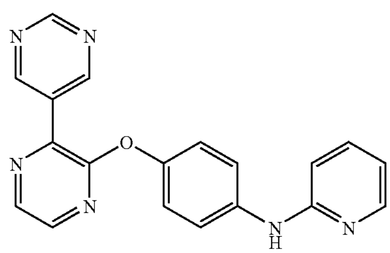 | N-(4-(3-(pyrimidin-5-yl)pyrazin-2-yloxy)phenyl)pyridin-2-amine | 343 | |
| 202 | 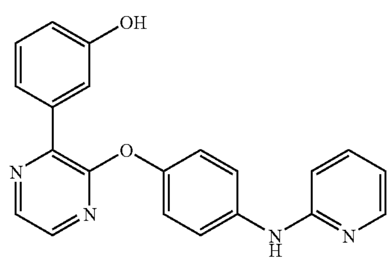 | 3-(3-(4-(pyridin-2-ylamino)phenoxy)pyrazin-2-yl)phenol | 357 | |
| 203 | 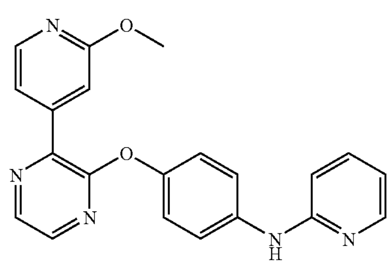 [SMILES: COc1cc(-c2nccnc2Oc2ccc(Nc3ccccn3)cc2)ccn1] | N-(4-(3-(2-methoxypyridin-4-yl)pyrazin-2-yloxy)phenyl)pyridin-2-amine | 372 | |

TABLE VIIA-continued

EXAMPLES 177 TO 214 ARE TABULATED BELOW:

| Ex. No. | Compound Structure | Compound Name | MS | PDE10 IC50 (uM) |
|---|---|---|---|---|
| 204 | 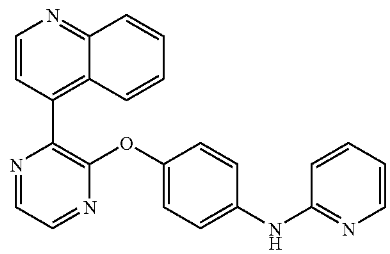 [SMILES: c1ccc(Nc2ccc(Oc3nccnc3-c3ccnc4ccccc34)cc2)nc1] | N-(4-(3-(quinolin-4-yl)pyrazin-2-yloxy)phenyl)pyridin-2-amine | 392 | |
| 205 | 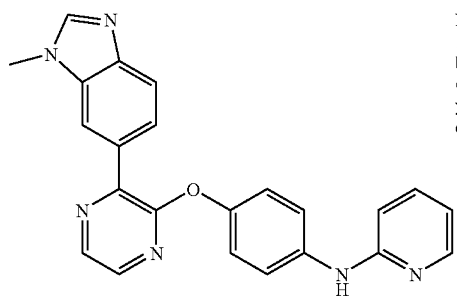 [SMILES: Cn1cnc2ccc(-c3nccnc3Oc3ccc(Nc4ccccn4)cc3)cc21] | N-(4-(3-(1-methyl-1H-benzo[d]imidazol-6-yl)pyrazin-2-yloxy)phenyl)pyridin-2-amine | 395 | 0.0039 |
| 206 | 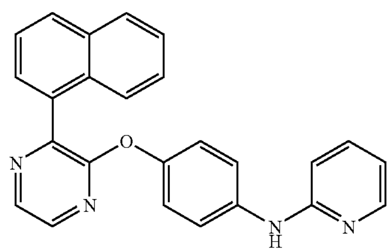 [SMILES: c1ccc(Nc2ccc(Oc3nccnc3-c3cccc4ccccc34)cc2)nc1] | N-(4-(3-(naphthalen-1-yl)pyrazin-2-yloxy)phenyl)pyridin-2-amine | 391 | 0.096 |
| 207 | 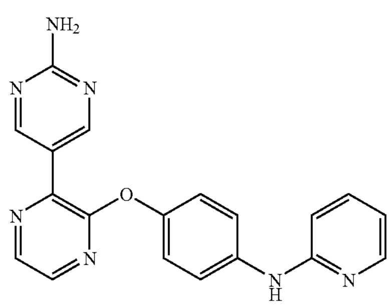 [SMILES: Nc1ncc(-c2nccnc2Oc2ccc(Nc3ccccn3)cc2)cn1] | 5-(3-(4-(pyridin-2-ylamino)phenoxy)pyrazin-2-yl)pyrimidin-2-amine | 358 | 0.007 |
| 208 | 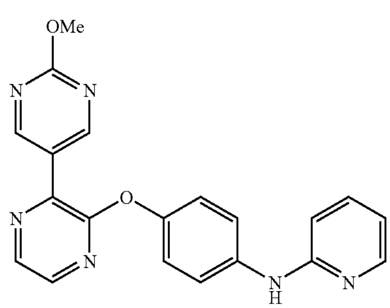 | N-(4-(3-(2-methoxypyrimidin-5-yl)pyrazin-2-yloxy)phenyl)pyridin-2-amine | 373 | 0.020 |

TABLE VIIA-continued

EXAMPLES 177 TO 214 ARE TABULATED BELOW:

| Ex. No. | Compound Structure | Compound Name | MS | PDE10 IC50 (uM) |
|---|---|---|---|---|
| 209 | 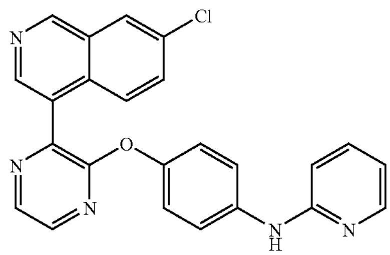 [SMILES: Clc1ccc2c(-c3nccnc3Oc3ccc(Nc4ccccn4)cc3)cncc2c1] | N-(4-(3-(7-chloroquinolin-4-yl)pyrazin-2-yloxy)phenyl)pyridin-2-amine | 426 | 0.012 |
| 210 | 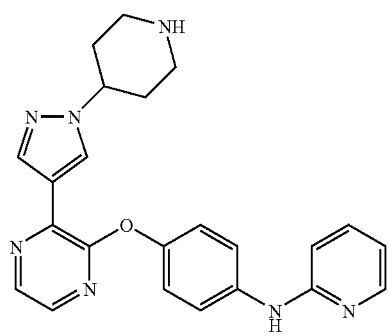 [SMILES: c1ccc(Nc2ccc(Oc3nccnc3-c3cnn(C4CCNCC4)c3)cc2)nc1] | N-(4-(3-(1-(piperidin-4-yl)-1H-pyrazol-4-yl)pyraizn-2-yloxy)phenyl)pyridin-2-amine | 414 | 0.023 |
| 211 | 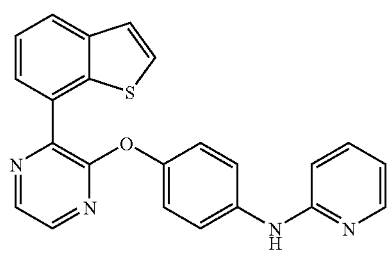 [SMILES: c1ccc(Nc2ccc(Oc3nccnc3-c3cccc4ccsc34)cc2)nc1] | N-(4-(3-(benzo[b]thiophen-7-yl)pyrazin-2-yloxy)phenyl)pyridin-2-amine | 397 | 0.520 |
| 212 | 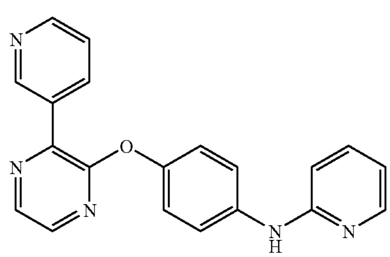 [SMILES: c1ccc(Nc2ccc(Oc3nccnc3-c3cccnc3)cc2)nc1] | N-(4-(3-(pyridin-3-yl)pyrazin-2-yloxy)phenyl)pyridin-2-amine | 342 | 0.008 |
| 213 | 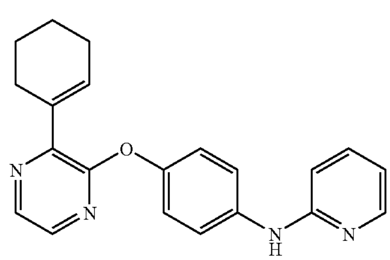 [SMILES: C1=C(c2nccnc2Oc2ccc(Nc3ccccn3)cc2)CCCC1] | N-(4-(3-cyclohexenylpyrazin-2-yloxy)phenyl)pyridin-2-amine | 345 | 0.076855 |

TABLE VIIA-continued

EXAMPLES 177 TO 214 ARE TABULATED BELOW:

| Ex. No. | Compound Structure | Compound Name | MS | PDE10 IC50 (uM) |
|---|---|---|---|---|
| 214 | 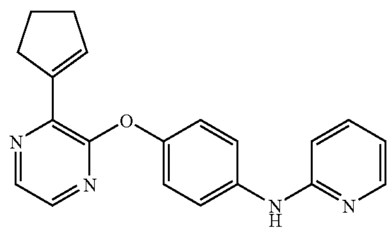 [SMILES: C1=C(c2nccnc2Oc2ccc(Nc3ccccn3)cc2)CCC1] | N-(4-(3-cyclopentenylpyrazin-2-yloxy)phenyl)pyridin-2-amine | 331 | 0.1282 |

TABLE VIIB

PREPARATION OF EXAMPLES 177 TO 214 ARE TABULATED BELOW:

| Ex. No. | Scheme | Starting material 1 | Starting material 2 | Conditions or reagents that differ from scheme |
|---|---|---|---|---|
| 177 | 11 | | | |
| 178 | 11 | | | |
| 179 | 11 | | | Commercial Boronic ester |
| 180 | 11 | | | Commercial boronic acid |

TABLE VIIB-continued

PREPARATION OF EXAMPLES 177 TO 214 ARE TABULATED BELOW:

| Ex. No. | Scheme | Starting material 1 | Starting material 2 | Conditions or reagents that differ from scheme |
|---|---|---|---|---|
| 181 | 11 | 2-chloropyridine-4-boronic acid | 3-chloro-2-(4-(pyridin-2-ylamino)phenoxy)pyrazine | Commercial boronic acid |
| 182 | 11 | 2-cyanopyridine-4-boronic acid pinacol ester | 3-chloro-2-(4-(pyridin-2-ylamino)phenoxy)pyrazine | Commercial Boronic ester |
| 183 | 11 | 4-cyanophenylboronic acid | 3-chloro-2-(4-(pyridin-2-ylamino)phenoxy)pyrazine | Commercial boronic acid |
| 184 | 11 | 3-cyanophenylboronic acid | 3-chloro-2-(4-(pyridin-2-ylamino)phenoxy)pyrazine | Commercial boronic acid |
| 185 | 11 | 2-fluoropyridine-4-boronic acid | 3-chloro-2-(4-(pyridin-2-ylamino)phenoxy)pyrazine | Commercial boronic acid |
| 186 | 11 | 4-aminophenylboronic acid pinacol ester | 3-chloro-2-(4-(pyridin-2-ylamino)phenoxy)pyrazine | Commercial Boronic ester |
| 187 | 11 | phenylboronic acid | 3-chloro-2-(4-(pyridin-2-ylamino)phenoxy)pyrazine | Commercial boronic acid |

TABLE VIIB-continued

PREPARATION OF EXAMPLES 177 TO 214 ARE TABULATED BELOW:

| Ex. No. | Scheme | Starting material 1 | Starting material 2 | Conditions or reagents that differ from scheme |
|---|---|---|---|---|
| 188 | 11 | 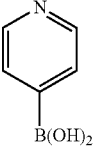 | 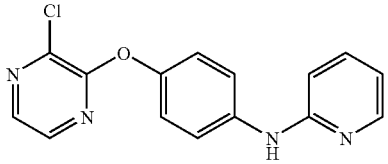 [SMILES: Clc1nccnc1Oc1ccc(Nc2ccccn2)cc1] | Commercial boronic acid |
| 189 | 11 |  | 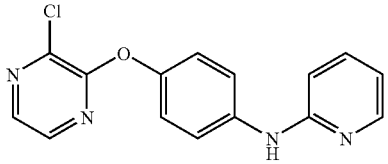 [SMILES: Clc1nccnc1Oc1ccc(Nc2ccccn2)cc1] | Commercial boronic acid |
| 190 | 11 | 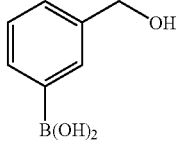 [SMILES: OCc1cccc(B(O)O)c1] | 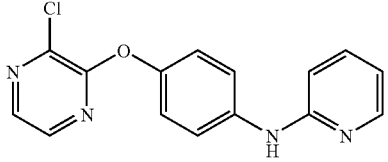 [SMILES: Clc1nccnc1Oc1ccc(Nc2ccccn2)cc1] | Commercial boronic acid |
| 191 | 11 | 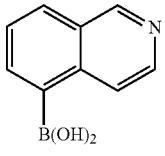 | 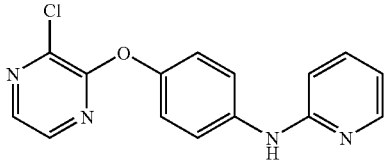 [SMILES: Clc1nccnc1Oc1ccc(Nc2ccccn2)cc1] | Commercial boronic acid |
| 192 | 11 | 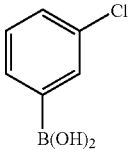 | 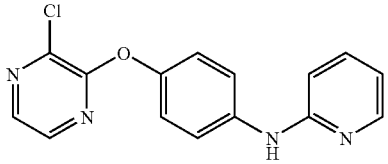 [SMILES: Clc1nccnc1Oc1ccc(Nc2ccccn2)cc1] | Commercial boronic acid |
| 193 | 11 | 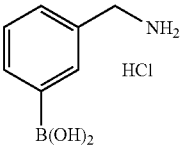 [SMILES: NCc1cccc(B(O)O)c1 ; Cl] | 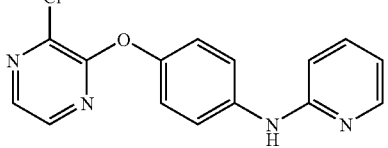 | Commercial boronic acid |
| 194 | 11 | 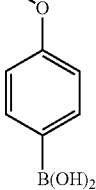 | 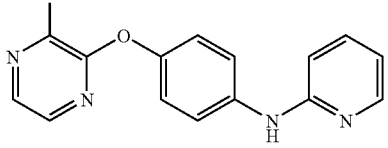 | Commercial boronic acid |
| 195 | 11 | 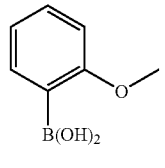 | 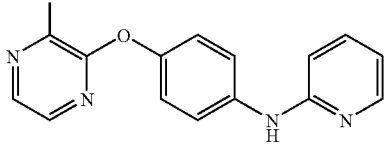 | Commercial boronic acid |

TABLE VIIB-continued

PREPARATION OF EXAMPLES 177 TO 214 ARE TABULATED BELOW:

| Ex. No. | Scheme | Starting material 1 | Starting material 2 | Conditions or reagents that differ from scheme |
|---|---|---|---|---|
| 196 | 11 | benzo[1,3]dioxol-5-yl-B(OH)₂ | 3-chloro-2-(4-(pyridin-2-ylamino)phenoxy)pyrazine | Commercial boronic acid |
| 197 | 11 | 3-methoxyphenyl pinacol boronate | 3-chloro-2-(4-(pyridin-2-ylamino)phenoxy)pyrazine | Commercial Boronic ester |
| 198 | 11 | 3-cyano-2-fluorophenylboronic acid | 3-chloro-2-(4-(pyridin-2-ylamino)phenoxy)pyrazine | Commercial boronic acid |
| 199 | 11 | quinolin-5-ylboronic acid | 3-chloro-2-(4-(pyridin-2-ylamino)phenoxy)pyrazine | Commercial boronic acid |
| 200 | 11 | 5-cyano-2-fluorophenylboronic acid | 3-chloro-2-(4-(pyridin-2-ylamino)phenoxy)pyrazine | Commercial boronic acid |
| 201 | 11 | pyrimidin-5-ylboronic acid | 3-chloro-2-(4-(pyridin-2-ylamino)phenoxy)pyrazine | Commercial boronic acid |
| 202 | 11 | 3-hydroxyphenylboronic acid | 3-chloro-2-(4-(pyridin-2-ylamino)phenoxy)pyrazine | Commercial boronic acid |

TABLE VIIB-continued
PREPARATION OF EXAMPLES 177 TO 214 ARE TABULATED BELOW:
| Ex. No. | Scheme | Starting material 1 | Starting material 2 | Conditions or reagents that differ from scheme |
|---|---|---|---|---|
| 203 | 11 | 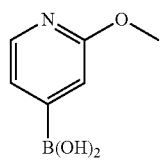 | 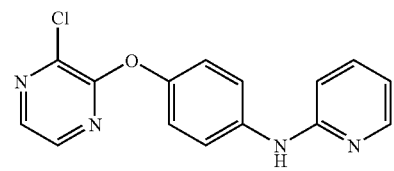 [SMILES: Clc1nccnc1Oc1ccc(Nc2ccccn2)cc1] | Commercial boronic acid |
| 204 | 11 | 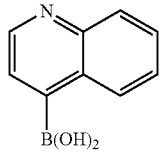 | 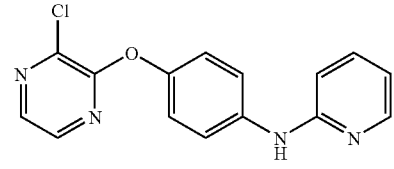 [SMILES: Clc1nccnc1Oc1ccc(Nc2ccccn2)cc1] | Commercial boronic acid |
| 205 | 11 | 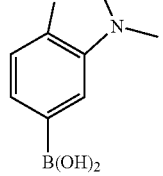 | 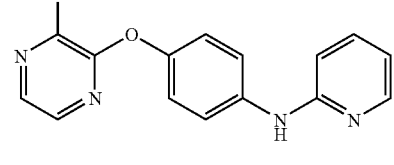 | Commercial boronic acid |
| 206 | 11 | 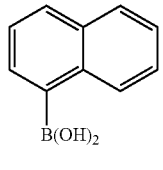 | 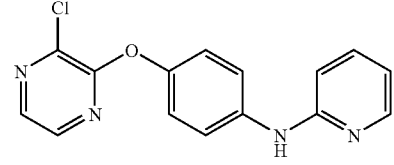 [SMILES: Clc1nccnc1Oc1ccc(Nc2ccccn2)cc1] | Commercial boronic acid |
| 207 | 11 | 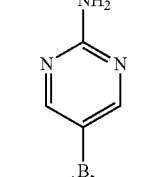 | 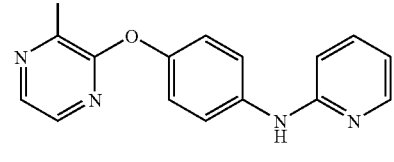 | Commercial Boronic ester |
| 208 | 11 | 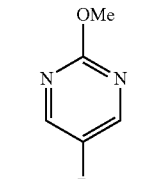 | 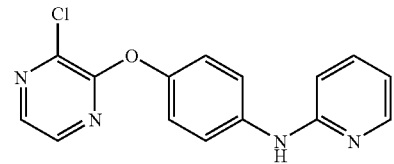 [SMILES: Clc1nccnc1Oc1ccc(Nc2ccccn2)cc1] | Commercial Boronic ester |

TABLE VIIB-continued

PREPARATION OF EXAMPLES 177 TO 214 ARE TABULATED BELOW:

| Ex. No. | Scheme | Starting material 1 | Starting material 2 | Conditions or reagents that differ from scheme |
|---|---|---|---|---|
| 209 | 11 | 7-chloroquinolin-4-yl pinacol boronate | 3-chloro-2-(4-(pyridin-2-ylamino)phenoxy)pyrazine | |
| 210 | 11 | 1-Boc-4-(4-(pinacolboronate)-1H-pyrazol-1-yl)piperidine | 3-chloro-2-(4-(pyridin-2-ylamino)phenoxy)pyrazine | Boc deprotection with TFA after coupling boronate ester |
| 211 | 11 | benzo[b]thiophen-7-ylboronic acid | 3-chloro-2-(4-(pyridin-2-ylamino)phenoxy)pyrazine | Commercial boronic acid |
| 212 | 11 | pyridin-3-ylboronic acid | 3-chloro-2-(4-(pyridin-2-ylamino)phenoxy)pyrazine | Commercial boronic acid |
| 213 | 11 | cyclohex-1-en-1-ylboronic acid | 3-chloro-2-(4-(pyridin-2-ylamino)phenoxy)pyrazine | |
| 214 | 11 | cyclopent-1-en-1-ylboronic acid | 3-chloro-2-(4-(pyridin-2-ylamino)phenoxy)pyrazine | |

SCHEME 12

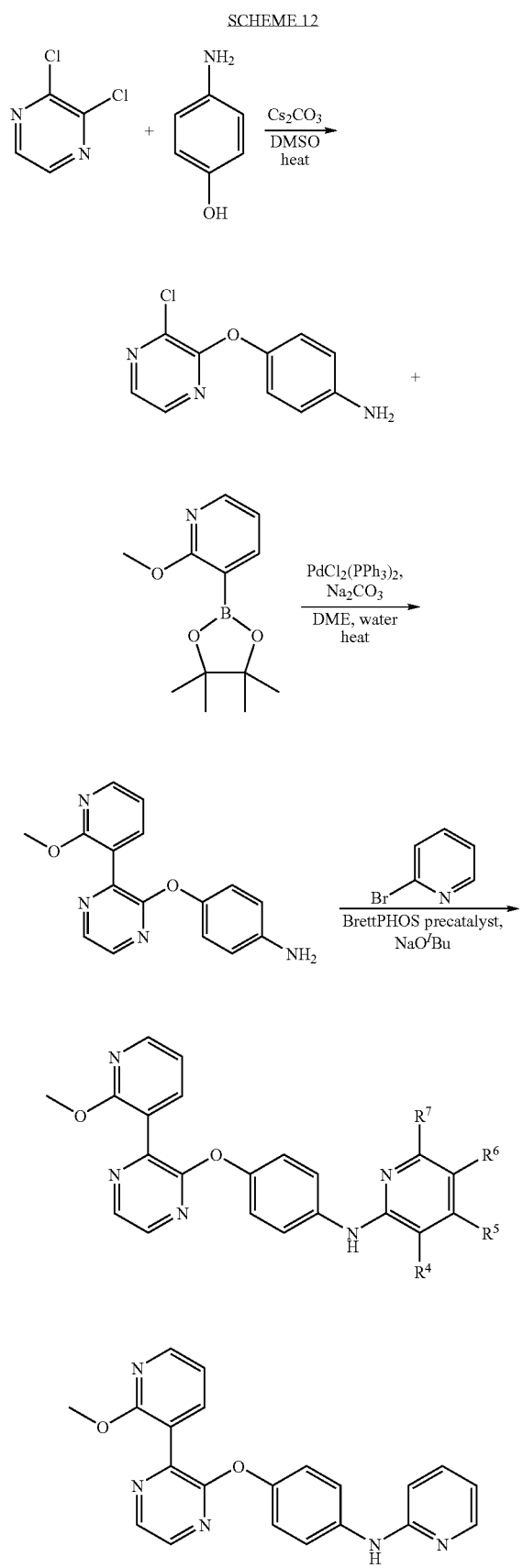

Example 215

N-(4-(3-(2-METHOXYPYRIDIN-3-YL)PYRAZIN-2-YLOXY)PHENYL)PYRIDIN-2-AMINE

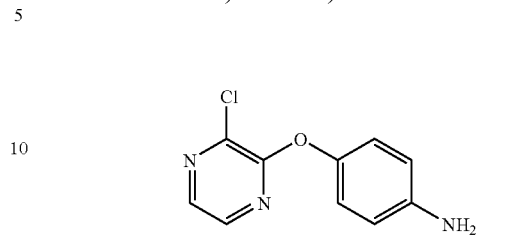

STEP 1.
4-(3-CHLOROPYRAZIN-2-YLOXY)ANILINE

To a round-bottomed flask was added 2,3-dichloropyrazine (7.3582 g, 49.4 mmol), 4-aminophenol (5.39 g, 49.4 mmol), and cesium carbonate (48.3 g, 148 mmol) in DMSO (165 mL) at 110° C. to stir overnight. The reaction mixture was diluted with water and extracted with EtOAc. The organic extract was washed with water, sat NaCl, sat sodium bicarbonate, dried with magnesium sulfate, filtered, and concentrated to give the title compound. MS (ESI, pos. ion) m/z: 222.1.

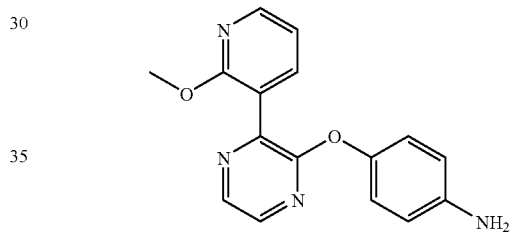

STEP 2. 4-(3-(2-METHOXYPYRIDIN-3-YL)PYRAZIN-2-YLOXY)ANILINE

To a glass microwave vial was added 4-(3-chloropyrazin-2-yloxy)aniline (1.0591 g, 4.78 mmol), 2-methoxy-3-(4,4,5,5-tetramethyl-1,3,2-dioxaborolan-2-yl)pyridine hydrate, trans-dichlorobis(triphenylphosphine) palladium (II) (0.268 g, 0.382 mmol), and sodium carbonate (2.53 g, 23.89 mmol) in DME (7.65 mL) and water (1.911 mL). The reaction mixture was stirred and heated in a Biotage Initiator microwave reactor at 100° C. for 15 min. The crude product was adsorbed onto a plug of silica gel and chromatographed to provide 4(3-(2-methoxypyridin-3-yl)pyrazin-2-yloxy)aniline. MS (ESI, pos. ion) m/z:295.2.

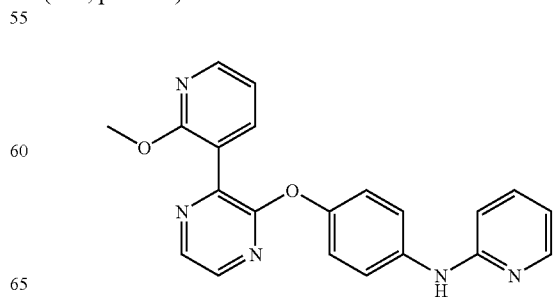

STEP 3. N-(4-(3-(2-METHOXYPYRIDIN-3-YL)PYRAZIN-2-YLOXY)PHENYL)PYRIDIN-2-AMINE

A glass microwave reaction vessel was charged with 4-(3-(2-methoxypyridin-3-yl)pyrazin-2-yloxy)aniline (0.1874 g, 0.637 mmol), 2-bromopyridine (0.075 mL, 0.764 mmol), BrettPHOS precatalyst (10.19 mg, 0.013 mmol), and sodium tert-butoxide (0.153 g, 1.592 mmol). The flask was placed under vacuum then flushed with argon. Dioxane (2.122 mL) was added and the reaction was heated to 90° C. to stir overnight. The crude product was adsorbed onto a plug of silica gel and chromatographed to give the title compound. MS (ESI, pos. ion) m/z: 372.0, $IC_{50}$ (uM)=0.002903.

white solid. MS (ESI pos. ion) m/z: 345.1 (M+1). IC50 (uM) 0.034.

SCHEME 14

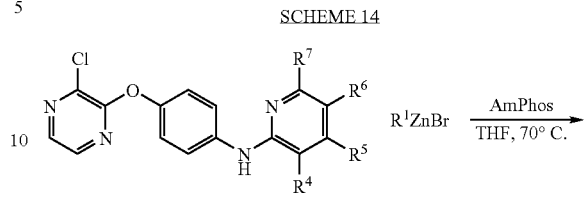

SCHEME 13

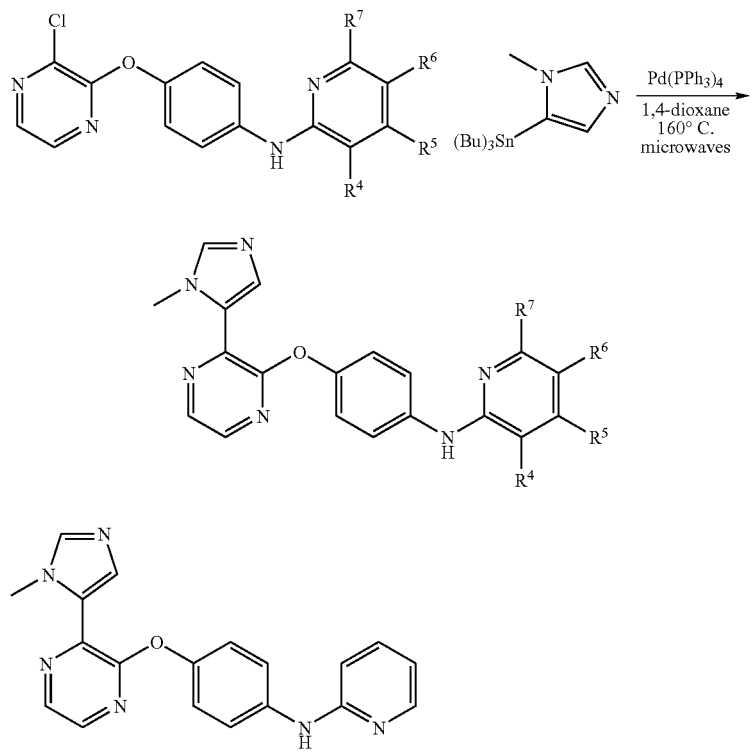

Example 216

N-(4-(3-(1-METHYL-1H-IMIDAZOL-5-YL)PYRAZIN-2-YLOXY)PHENYL)PYRIDIN-2-AMINE

A suspension of N-(4-(3-chloropyrazin-2-yloxy)phenyl)pyridin-2-amine (350 mg, 1172 μmol), 1-methyl-5-(tributylstannyl)-1H-imidazole (870 mg, 2343 μmol), and tetrakis(triphenylphosphine)palladium (0) (271 mg, 234 μmol) in 1,4-dioxane (4 mL) was sparged with argon for 3 minutes then the vessel was appropriately sealed. The vessel was then heated to 160° C. with microwaves (3 bar; 130 watts) for 20 minutes. The solvents were removed under reduced pressure and the residue was purified on silica (40 g) eluting products with 2-4% of MeOH/DCM to afford the title compound as a -continued

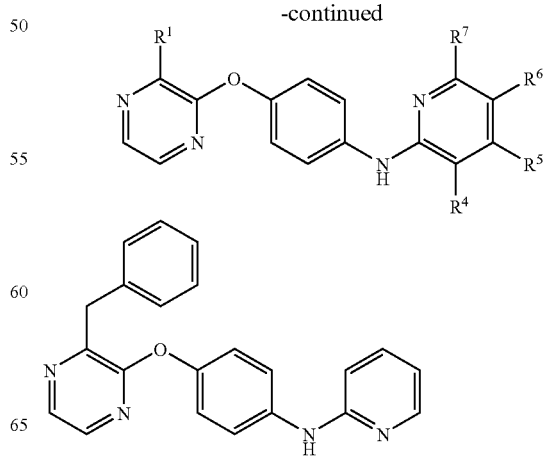

Example 217

N-(4-(3-BENZYLPYRAZIN-2-YLOXY)PHENYL)PYRIDIN-2-AMINE

A suspension of N-(4-(3-chloropyrazin-2-yloxy)phenyl)pyridin-2-amine (200 mg, 0.670 mmol), benzylzinc bromide, 0.5M in THF (6.7 mL, 3.35 mmol), and bis(di-t-butyl(4-dimethylaminophenyl)phosphine)dichloropalladium(II) (80 mg, 0.11 mmol) was sparged with argon for 5 minutes then heated to 70° C. for 2 h. The reaction was then partitioned between EtOAc (30 mL) and sat NH$_4$Cl (10 mL). The separated organic layer was dried over MgSO$_4$, concentrated under reduced pressure, then purified on silica (40 g) eluting with 1.5-2.0% MeOH/DCM. The resulting residue was then dissolved in MeOH (5 mL) and 0.105 mL of HCl (5 M; 0.105 mL, 0.525 mmol) added. The resulting solid was isolated by filtration to give the title compound. MS (ESI positive ion) m/z: 355.1 (M+1). IC50 (uM) 0.250.

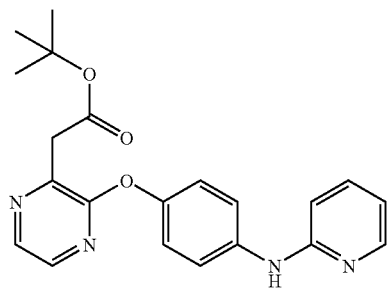 [SMILES: CC(C)(C)OC(=O)Cc1nccnc1Oc1ccc(Nc2ccccn2)cc1]

Example 218

TERT-BUTYL 2-(3-(4-(PYRIDIN-2-YLAMINO)PHENOXY)PYRAZIN-2-YL)ACETATE

To a N$_2$ purged solution of N-(4-(3-chloropyrazin-2-yloxy)phenyl)pyridin-2-amine (100 mg, 0.335 mmol), (2-tert-butoxy-2-oxoethyl)zinc(II) chloride, 0.5M in ether (2.2 mL, 1.100 mmol), and dioxane (3 mL) was added catalyst (34.2 mg, 0.067 mmol) and A-Phos (23.70 mg, 0.033 mmol). The solution was heated to 60° C. After stirring for 1 hours, LC-MS shows a developing peak with m/z=379 (MH+). After a further 16 hours, LC-MS shows no further progress than the initial LC-MS. Further ZnCl solution (4 mL) was added and heating continued. After 16 hours, the reaction was quenched with sat'd rochelle's salt and stirred for several days. The solution was then extracted with EtOAc (3×10 mL). The combined organic layers were washed with water (10 mL), brine (10 mL), and concentrated in vacuo to give a golden oil. The crude oil was purified by reverse-phase preparative HPLC (Shimadzu) on a Phenomenex Gemini column (5 micron, C18, 110 Å, Axia, 100×50 mm) eluting at 90 mL/min with an linear gradient of 10% to 100% MeCN (0.1% TFA) in water (0.1% TFA) over 20 minutes to give tert-butyl 2-(3-(4-(pyridin-2-ylamino)phenoxy)pyrazin-2-yl)acetate tris(2,2,2-trifluoroacetate) as a TFA salt. MS (ESI positive ion) m/z: 379.1 (M+1). IC50 (uM) 0.3341.

SCHEME 15

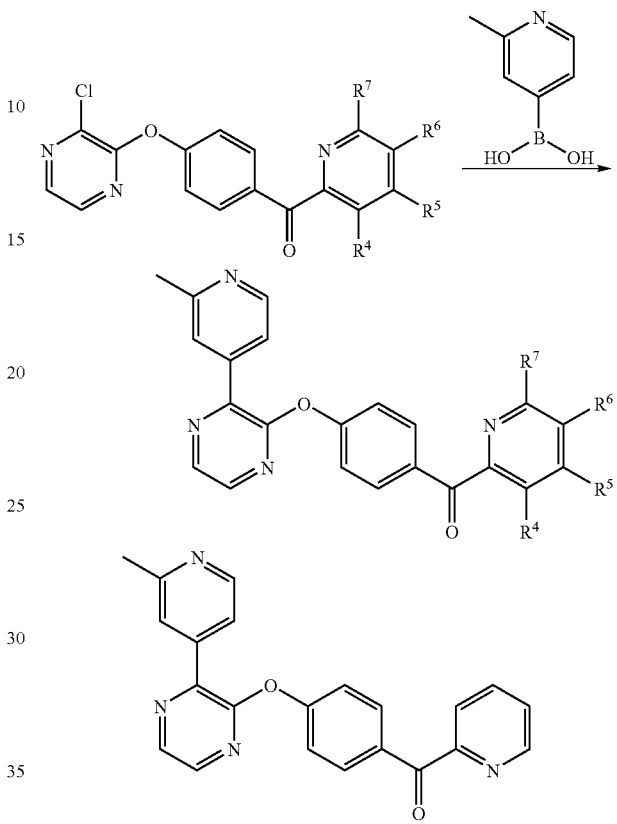

Example 219

(4-(3-(2-METHYLPYRIDIN-4-YL)PYRAZIN-2-YLOXY)PHENYL)(PYRIDIN-2-YL)METHANONE

To a round-bottomed flask was added (4-(3-(2-methylpyridin-4-yl)pyrazin-2-yloxy)phenyl)(pyridin-2-yl)methanone (0.0617 g, 0.167 mmol, 18.99% yield), 2-methylpyridin-4-ylboronic acid (0.362 g, 2.65 mmol), trans-dichlorobis(triphenylphosphine)palladium (II) (0.050 g, 0.071 mmol), and sodium carbonate (0.547 g, 4.41 mmol) in DME and water at 80° C. Upon completion, the reaction mixture was diluted with water and brine and extracted with dichloromethane. The organic extract was washed with water, sat NaCl, dried with magnesium sulfate, filtered, and concentrated. The crude product was adsorbed onto a plug of silica gel and chromatographed to provide (4-(3-(2-methylpyridin-4-yl)pyrazin-2-yloxy)phenyl)(pyridin-2-yl)methanone (0.0617 g, 0.167 mmol, 18.99% yield). MS (ESI, pos. ion) m/z: 369 (M+1). IC50 (uM) 0.4939.

TABLE VIIIA

EXAMPLES 220 TO 221 ARE TABULATED BELOW:

| Ex. No. | Compound Structure | Compound Name | MS | PDE10 IC50 (uM) |
|---|---|---|---|---|
| 220 | 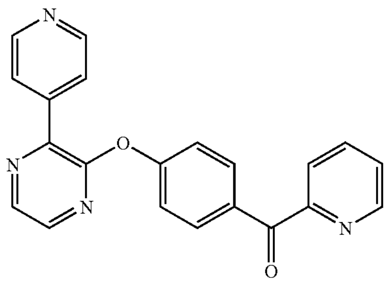 [SMILES: O=C(c1ccc(Oc2nccnc2-c2ccncc2)cc1)c1ccccn1] | pyridin-2-yl(4-(3-(pyridin-4-yl)pyrazin-2-yloxy)phenyl)methanone | 355 | 0.8984 |
| 221 | 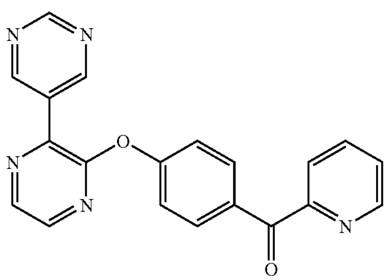 [SMILES: O=C(c1ccc(Oc2nccnc2-c2cncnc2)cc1)c1ccccn1] | pyridin-2-yl(4-(3-(pyrimidin-5-yl)pyrazin-2-yloxy)phenyl)methanone | 356 | 6.247 |

TABLE VIIIB

PREPARATION OF EXAMPLES 220 TO 221 ARE TABULATED BELOW:

| Ex. No. | Scheme | Starting material 1 | Starting material 2 | Conditions or reagents that differ from scheme |
|---|---|---|---|---|
| 220 | 15 | | | |
| 221 | 15 | | | |

SCHEME 16

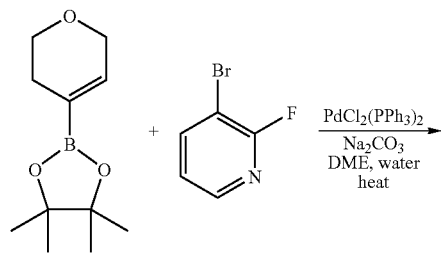

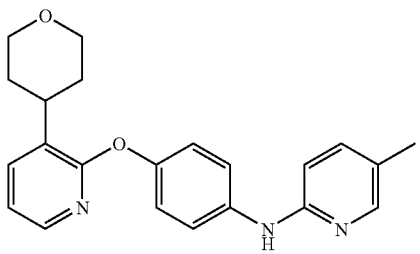

Example 222

5-METHYL-N-(4-(3-(TETRAHYDRO-2H-PY-RAN-4-YL)PYRIDIN-2-YLOXY)PHENYL)PYRI-DIN-2-AMINE

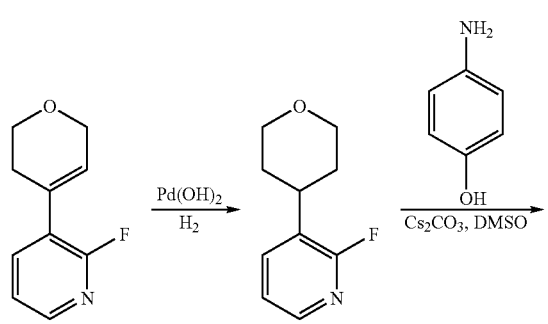

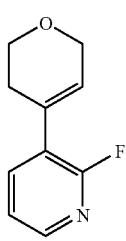 [SMILES: Fc1ncccc1C1=CCOCC1]

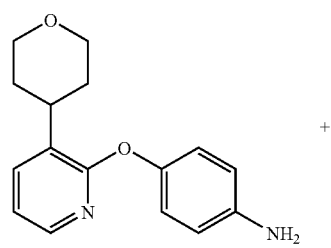

STEP 1. 3-(3,6-DIHYDRO-2H-PYRAN-4-YL)-2-FLUOROPYRIDINE

To a glass microwave vial was added 3-bromo-2-fluoropyridine (4.6132 g, 26.2 mmol), 2-(3,6-dihydro-2H-pyran-4-yl)-4,4,5,5-tetramethyl-1,3,2-dioxaborolane (6.88 g, 32.8 mmol), trans-dichlorobis(triphenylphosphine) palladium (II) (1.472 g, 2.097 mmol), and sodium carbonate (13.89 g, 131 mmol) in DME (41.9 mL) and water (10.49 mL) to stir at 80° C. overnight. Upon completion, the reaction mixture was diluted with water and extracted with dichloromethane. The organic extract was washed with water, sat NaCl, dried with magnesium sulfate, filtered, and concentrated. The crude product was adsorbed onto a plug of silica gel and chromatographed to provide 3-(3,6-dihydro-2H-pyran-4-yl)-2-fluoropyridine. MS (ESI, pos. ion) m/z: 180.1.

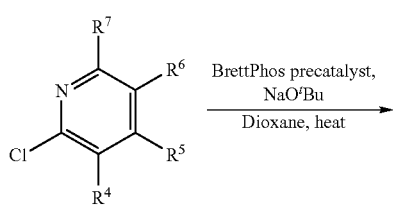

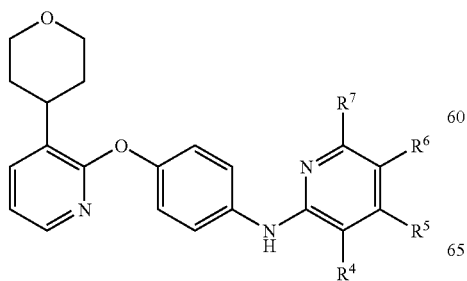

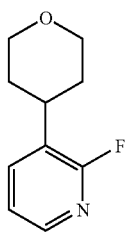

STEP 2. 2-FLUORO-3-(TETRAHYDRO-2H-PYRAN-4-YL)PYRIDINE

To a rbf was added 3-(3,6-dihydro-2H-pyran-4-yl)-2-fluoropyridine (2.1320 g, 11.90 mmol) and palladium hydroxide (0.835 g, 1.190 mmol) in EtOAc (39.7 mL). The rbf was flushed with argon and then placed under vacuum three times. A hydrogen balloon was then attached to the reaction. Upon completion, the reaction was filtered through celite and concentrated. MS (ESI, pos. ion) m/z: 182.1.

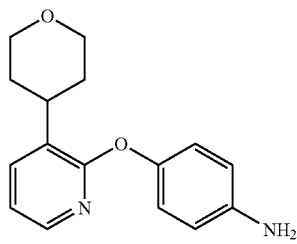 [SMILES: Nc1ccc(Oc2ncccc2C2CCOCC2)cc1]

STEP 3. 4-(3-(TETRAHYDRO-2H-PYRAN-4-YL)PYRIDIN-2-YLOXY)ANILINE

To a rbf was added 2-fluoro-3-(tetrahydro-2H-pyran-4-yl)pyridine (2.156 g, 11.90 mmol), 4-aminophenol (1.948 g, 17.85 mmol), and cesium carbonate (11.63 g, 35.7 mmol) in DMSO (39.7 mL) at 110° C. to stir overnight. Upon completion, the reaction mixture was diluted with water and sat sodium chloride solution and extracted with dichloromethane. The organic extract was washed with water and sat sodium chloride solution, dried with magnesium sulfate, filtered, and concentrated. MS (ESI, pos. ion) m/z: 271.1.

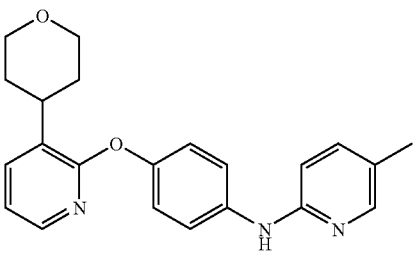 [SMILES: Cc1ccc(Nc2ccc(Oc3ncccc3C3CCOCC3)cc2)nc1]

STEP 4. 5-METHYL-N-(4-(3-(TETRAHYDRO-2H-PYRAN-4-YL)PYRIDIN-2-YLOXY)PHENYL)PYRIDIN-2-AMINE

A glass microwave reaction vessel was charged with 4-(3-(tetrahydro-2H-pyran-4-yl)pyridin-2-yloxy)aniline (0.167 g, 0.619 mmol), 2-bromo-5-methylpyridine (0.0888 g, 0.516 mmol), BrettPHOS precatalyst (8.26 mg, 10.32 μmol), and sodium tert-butoxide (0.124 g, 1.291 mmol). The flask was placed under vacuum then flushed with argon. Dioxane (1.7 mL) was added and the reaction was heated to 90° C. to stir overnight. After cooling to room temperature, the reaction mixture was concentrated and the crude product was adsorbed onto a plug of silica gel and chromatographed through a Biotage pre-packed silica gel column (40S), eluting with a gradient of 10% to 100% EtOAc in hexane, to provide 5-methyl-N-(4-(3-(tetrahydro-2H-pyran-4-yl)pyridin-2-yloxy)phenyl)pyridin-2-amine. MS (ESI, pos. ion) m/z: 362.1 (M+1). IC50 (uM) 0.002387.

TABLE IXA

EXAMPLES 223 TO 225 ARE TABULATED BELOW:

| Ex. | Compound Structure | Compound Name | MS | PDE10 IC50 (uM) |
|-----|-------------------|---------------|-----|------|
| 223 | 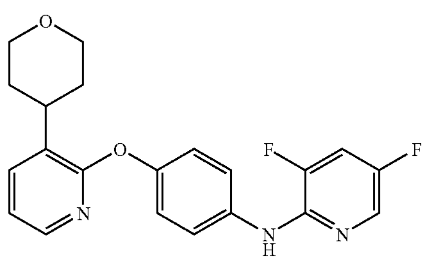 [SMILES: Fc1cnc(Nc2ccc(Oc3ncccc3C3CCOCC3)cc2)c(F)c1] | 3,5-difluoro-N-(4-(3-(tetrahydro-2H-pyran-4-yl)pyridin-2-yloxy)phenyl)pyridine-2-amine | 384.1 | 0.06907 |
| 224 | 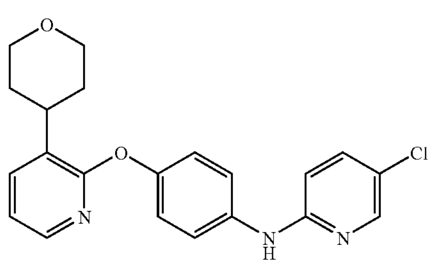 [SMILES: Clc1ccc(Nc2ccc(Oc3ncccc3C3CCOCC3)cc2)nc1] | 5-chloro-N-(4-(3-(tetrahydro-2H-pyran-4-yl)pyridin-2-yloxy)phenyl)pyridin-2-amine | 382.1 | 0.02819 |

TABLE IXA-continued

EXAMPLES 223 TO 225 ARE TABULATED BELOW:

| Ex. | Compound Structure | Compound Name | MS | PDE10 IC50 (uM) |
|---|---|---|---|---|
| 225 | 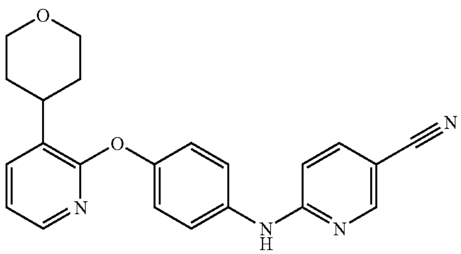 [SMILES: N#Cc1ccc(Nc2ccc(Oc3ncccc3C3CCOCC3)cc2)nc1] | 6-(4-(3-(tetrahydro-2H-pyran-4-yl)pyridin-2-yloxy)phenylamino)nicotinonitrile | 373.1 | 0.3739 |

TABLE IXB

PREPARATION OF EXAMPLES 223 TO 225 ARE TABULATED BELOW:

| Ex. No. | Scheme | Starting material 1 | Starting material 2 | Conditions or reagents that differ from scheme |
|---|---|---|---|---|
| 223 | 16 | | | |
| 224 | 16 | | | |
| 225 | 16 | | | |

SCHEME 17

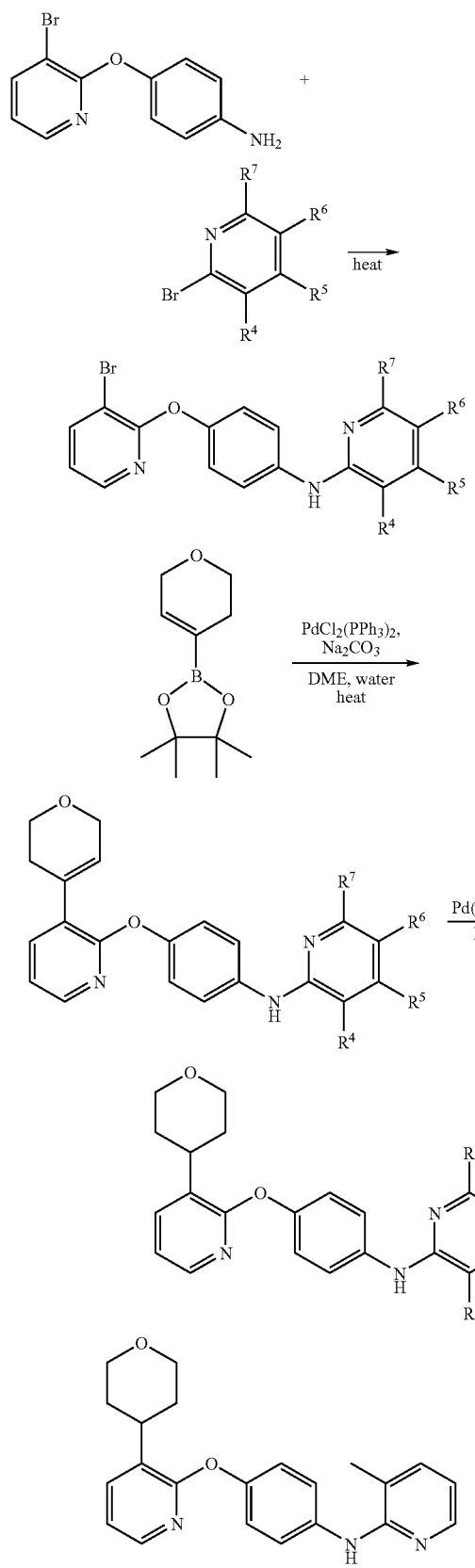

Example 226

3-METHYL-N-(4-(3-(TETRAHYDRO-2H-PYRAN-4-YL)PYRIDIN-2-YLOXY)PHENYL)PYRIDIN-2-AMINE

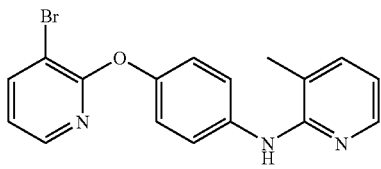

STEP 1. N-(4-(3-BROMOPYRIDIN-2-YLOXY)PHENYL)-3-METHYLPYRIDIN-2-AMINE

To a 35 ml pressure vessel was added 4-(3-bromopyridin-2-yloxy)aniline (0.7095 g, 2.68 mmol) and 2-bromo-3-methylpyridine (0.575 mL, 3.35 mmol) to stir at 160° C. for 3 hours. Upon completion, the crude product was adsorbed onto a plug of silica gel and chromatographed to provide N-(4-(3-bromopyridin-2-yloxy)phenyl)-3-methylpyridin-2-amine. MS (ESI, pos. ion) m/z: 356.0.

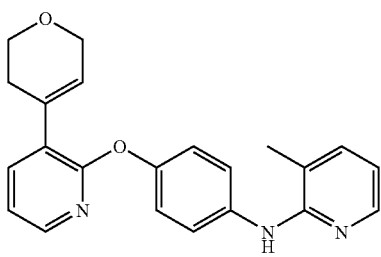 [SMILES: Cc1cccnc1Nc1ccc(Oc2ncccc2C2=CCOCC2)cc1]

STEP 2. N-(4-(3-(3,6-DIHYDRO-2H-PYRAN-4-YL)PYRIDIN-2-YLOXY)PHENYL)-3-METHYLPYRIDIN-2-AMINE

To a round-bottomed flask was added N-(4-(3-bromopyridin-2-yloxy)phenyl)-3-methylpyridin-2-amine (0.2898 g, 0.814 mmol), 2-(3,6-dihydro-2H-pyran-4-yl)-4,4,5,5-tetramethyl-1,3,2-dioxaborolane (0.214 g, 1.017 mmol), trans-dichlorobis(triphenylphosphine) palladium (II) (0.046 g, 0.065 mmol), and sodium carbonate (0.431 g, 4.07 mmol) in DME (1.302 mL) and water (0.325 mL) to stir at 80° C. overnight. The crude product was adsorbed onto a plug of silica gel and chromatographed to provide N-(4-(3-(3,6-dihydro-2H-pyran-4-yl)pyridin-2-yloxy)phenyl)-3-methylpyridin-2-amine. MS (ESI, pos. ion) m/z: 360.0. IC$_{50}$ (uM) 0.00701.

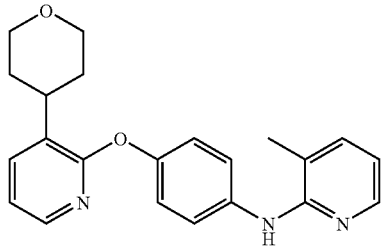 [SMILES: Cc1cccnc1Nc1ccc(Oc2ncccc2C2CCOCC2)cc1]

STEP 3. 3-METHYL-N-(4-(3-(TETRAHYDRO-2H-PYRAN-4-YL)PYRIDIN-2-YLOXY)PHENYL)PYRIDIN-2-AMINE

To a pressure vessel was added N-(4-(3-(3,6-dihydro-2H-pyran-4-yl)pyridin-2-yloxy)phenyl)-3-methylpyridin-2-amine (0.2400 g, 0.668 mmol) and palladium hydroxide on carbon (0.047 g, 0.067 mmol) in EtOAc (2.226 mL). The rbf was flushed with nitrogen and then placed under vacuum three times. Reaction was placed under 40 psi. Reaction mixture was filtered through celite. The crude product was adsorbed onto a plug of silica gel and chromatographed to provide 3-methyl-N-(4-(3-(tetrahydro-2H-pyran-4-yl)pyridin-2-yloxy)phenyl)pyridin-2-amine. MS (ESI, pos. ion) m/z: 362.1. IC$_{50}$ (uM) 0.006873.

TABLE XA

EXAMPLES 227 TO 228 ARE TABULATED BELOW:

| Ex. No. | Compound Structure | Compound Name | MS | PDE10 IC50 (uM) |
|---|---|---|---|---|
| 227 | 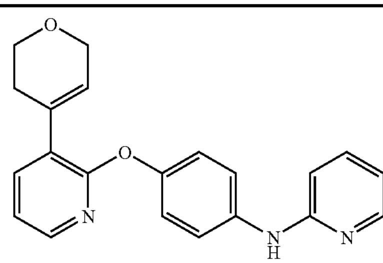 | N-(4-(3-(3,6-dihydro-2H-pyran-4-yl)pyridin-2-yloxy)phenyl)pyridin-2-amine | 346 | 0.018 |
| 228 | 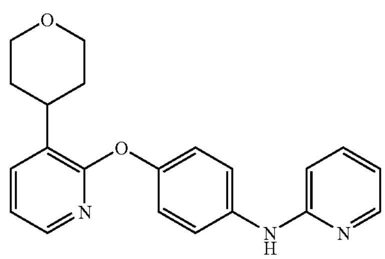 [SMILES: c1ccc(Nc2ccc(Oc3ncccc3C3CCOCC3)cc2)nc1] | N-(4-(3-(tetrahydro-2H-pyran-4-yl)pyridin-2-yloxy)phenyl)pyridin-2-amine | 348 | 0.013 |

TABLE XB

PREPARATION OF EXAMPLES 227 TO 228 ARE TABULATED BELOW:

| Ex. No. | Scheme | Starting material 1 | Starting Material 2 | Conditions or reagents that differ from scheme |
|---|---|---|---|---|
| 227 | 17 | | | |

TABLE XB-continued

PREPARATION OF EXAMPLES 227 TO 228 ARE TABULATED BELOW:

| Ex. No. | Scheme | Starting material 1 | Starting Material 2 | Conditions or reagents that differ from scheme |
|---|---|---|---|---|
| 228 | 17 | H₂ |  | |

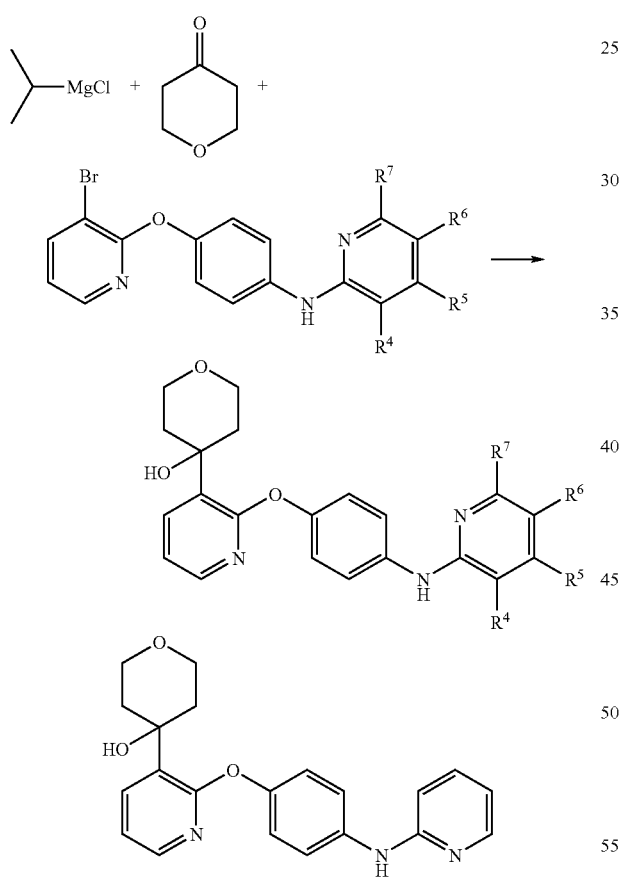

Example 229

4-(2-(4-(PYRIDIN-2-YLAMINO)PHENOXY)PYRIDIN-3-YL)TETRAHYDRO-2H-PYRAN-4-OL

To a suspension of N-(4-(3-bromopyridin-2-yloxy)phenyl)pyridin-2-amine (1 g, 2.92 mmol) in THF (10 mL) at room temperature was added isopropylmagnesium chloride (5.11 mL, 10.23 mmol). After 1 h stirring at room temperature, another equal amount of isopropylmagnesium chloride was added and the resulting mixture was stirred at room temperature overnight. To the solution was added dropwise dihydro-2H-pyran-4(3H)-one (0.540 mL, 5.84 mmol) and stirring was continued for 1 h. Reaction was quenched with saturated NH₄Cl and extracted with DCM. Purification by Biotage produced the product. MS (ESI, pos. ion) m/z: 364.0. IC$_{50}$ (uM) 0.04172.

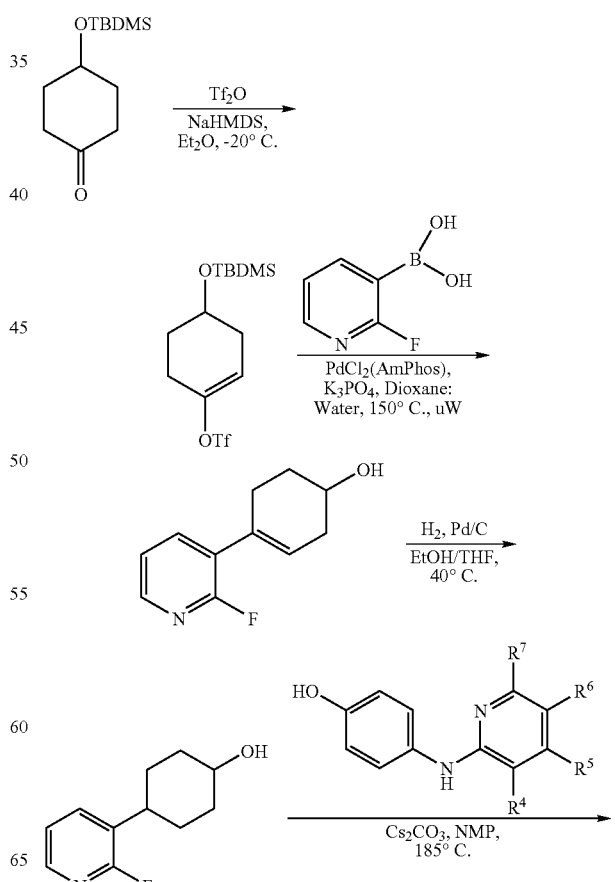

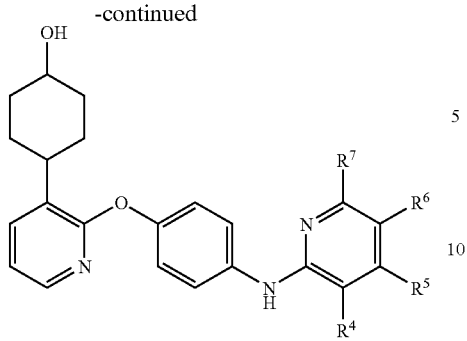

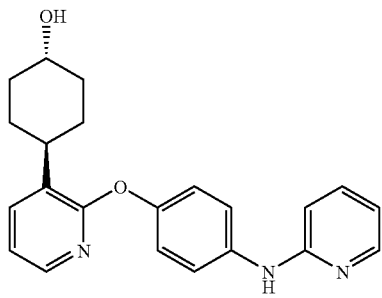

Example 230

(1S,4R)-4-(2-(4-(PYRIDIN-2-YLAMINO)PHENOXY)PYRIDIN-3-YL)CYCLOHEXANOL

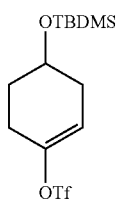

STEP 1: 4-(TERT-BUTYLDIMETHYLSILYLOXY) CYCLOHEX-1-ENYL TRIFLUOROMETHANESULFONATE

To a 500 mL round bottom was added 4-(tert-butyldimethylsilyloxy)cyclohexanone (7.71 g, 33.8 mmol). A 1M solution of NaHMDS (35.4 mL, 35.4 mmol) in THF was added dropwise after cooling the reaction to −20° C. The resulting orange solution was stirred for 1 h before adding trifluoromethanesulfonic anhydride (10.00 mL, 35.4 mmol) dropwise over 10 minutes. The yellow suspension was allowed to warm to room temperature with stirring over 12 h. It was diluted with 60 mL saturated aqueous NaHCO$_3$ before extracted with diethyl ether (2×75 mL), drying over sodium sulfate, filtering, and drying under reduced pressure to an orange oil that was used crude.

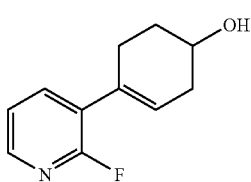 [SMILES: OC1CC=C(c2cccnc2F)CC1]

STEP 2: 4-(2-FLUOROPYRIDIN-3-YL)CYCLOHEX-3-ENOL

To a 25 mL microwave vial was added potassium phosphate tribasic (0.354 mL, 4.27 mmol), PdCl$_2$(AmPhos) (0.121 g, 0.171 mmol), 4-(tert-butyldimethylsilyloxy)cyclohex-1-enyl trifluoromethanesulfonate (0.616 g, 1.710 mmol), and 2-fluoropyridin-3-ylboronic acid (0.265 g, 1.881 mmol) before evacuating and backfilling with nitrogen (3×). A mixed solvent of Dioxane (7.12 mL):water (1.425 mL) was added, and the contents were irradiated at 150° C. for 30 minutes in an Initiator microwave reactor (Personal Chemistry, Biotage AB, Inc., Upssala, Sweden). The biphasic solution was diluted with water and extracted with DCM (3×25 mL) before drying over sodium sulfate, filtering, and concentrating under reduced pressure to a dark brown residue. The residue was taken up in 5 mL DCM and applied directly to silica (0 to 70% ethyl acetate/hexanes for followed by 5 to 10% MeOH/DCM). The resulting yellow oil was taken forward without further manipulation.

STEP 3: 4-(2-FLUOROPYRIDIN-3-YL)CYCLOHEXANOL

To a 150 mL round bottom flask was added 4-(2-fluoropyridin-3-yl)cyclohex-3-enol (324 mg, 1.677 mmol) followed by Ethanol (14.000 ml):Tetrahydrofuran (2.80 ml) and Palladium on carbon, 10% wt. (32.4 mg, 0.304 mmol). The system was evacuated and backfilled with nitrogen and hydrogen before leaving the reaction suspension exposed to the latter. It was stirred for 16 h at 1 atm. An additional 20% by weight of Pd/C was added before placing the vessel's interior under a hydrogen atmosphere using the same procedure used originally. The reaction was also heated to 40° C. After an additional 2 h, the reaction was complete. The black suspension was cooled to room temperature and filtered over Celite with two ethyl acetate rinses (2×30 mL). The clear filtrate was concentrated under reduced pressure and used without purification.

STEP 4: (1S,4R)-4-(2-(4-(PYRIDIN-2-YLAMINO) PHENOXY)PYRIDIN-3-YL)CYCLOHEXANOL

To a 5 mL microwave vial was added 4-(pyridin-2-ylamino)phenol (143 mg, 0.768 mmol), cesium carbonate (0.102 ml, 1.281 mmol), and a solution of 4-(2-fluoropyridin-3-yl)cyclohexanol (100 mg, 0.512 mmol) in NMP (1.024 ml). The reaction mixture was filtered through a 0.45 um syringe filter with methanol and purified in four aliquots with a Shimadzu HPLC (5% 0.1% TFA in water to 50% 0.1% TFA in acetonitrile). All fractions were reduced under vacuum and at low temperature over 10 h with the first set of fractions affording the trans isomer as an off-white solid. MS (ESI, pos. ion) m/z: 476 (M+1). $IC_{50}$ (uM) 0.012.

Example 231

(1S,4S)-4-(2-(4-(PYRIDIN-2-YLAMINO)PHENOXY)PYRIDIN-3-YL)CYCLOHEXANOL

Following the same steps as with Example 12, to a 5 mL microwave vial was added 4-(pyridin-2-ylamino)phenol (143 mg, 0.768 mmol), cesium carbonate (0.102 ml, 1.281 mmol), and a solution of 4-(2-fluoropyridin-3-yl)cyclohexanol (100 mg, 0.512 mmol) in NMP (1.024 ml). The reaction mixture was filtered through a 0.45 um syringe filter with methanol and purified in four aliquots with a Shimadzu HPLC (5% 0.1% TFA in water to 50% 0.1% TFA in acetonitrile). All fractions were reduced under vacuum and at low temperature over 10 h with the first set of fractions affording the cis isomer as an off-white solid. MS (ESI, pos. ion) m/z: 476 (M+1). $IC_{50}$ (uM) 0.015.

SCHEME 20

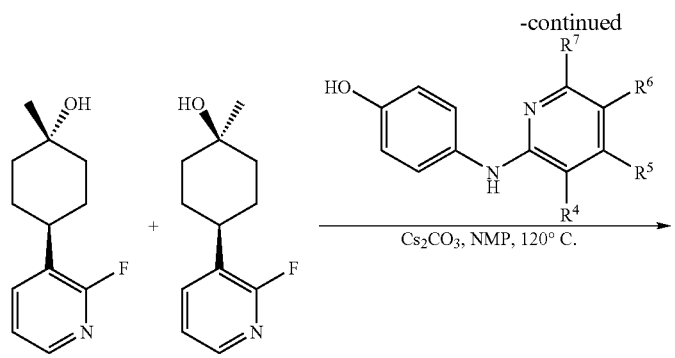

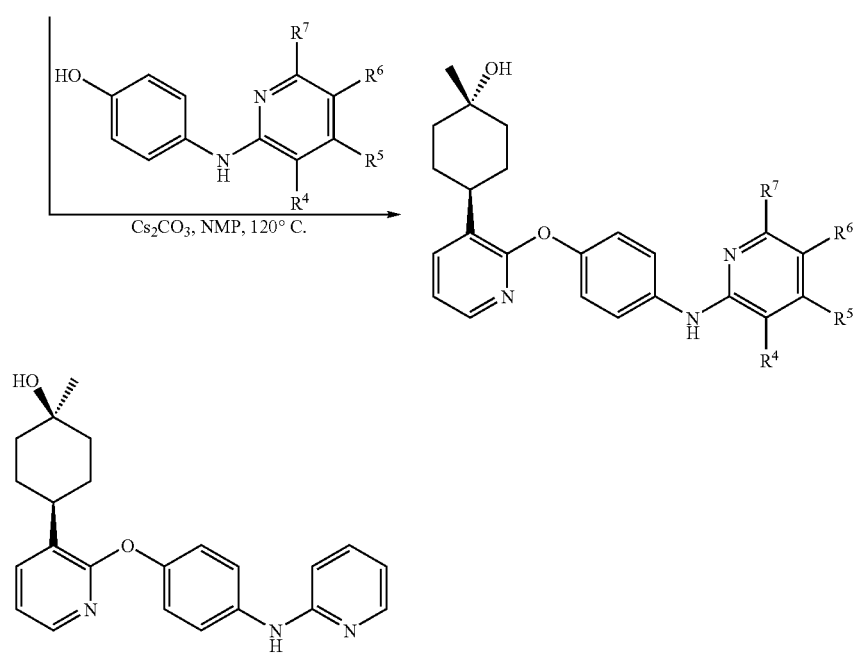

Example 232

(1S,4S)-1-METHYL-4-(2-(4-(PYRIDIN-2-YLAMINO)PHENOXY)PYRIDIN-3-YL)CYCLOHEXANOL

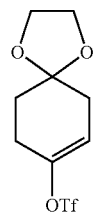

STEP 1. 1,4-DIOXASPIRO[4.5]DEC-7-EN-8-YL TRIFLUOROMETHANESULFONATE

To a solution of diisopropylamine, (6.24 mL, 44.2 mmol) in THF (60 mL) at −78° C. under argon was slowly added n-butyllithium (17.7 mL, 44.2 mmol, 2.5 M in hexanes). The mixture was stirred for 30 min at that temperature before 1,4-cyclohexanedione mono-ethylene ketal (6.00 g, 38.4 mmol) was added slowly as a solution in THF (20 mL). The mixture was stirred for an additional 30 min at −78° C. and then n-phenyltriflimide (13.7 g, 38.4 mmol) was slowly added as a suspension in THF (50 mL). This mixture was stirred overnight with gradual warming to room temperature. The solvent was removed in vacuo and the remaining oil was partitioned between 3:1 ethyl acetate/hexane and water. The layers were separated and the organic layer was washed with water (3×), dried over anhydrous magnesium sulfate, filtered, and concentrated in vacuo to give 1,4-dioxaspiro[4.5]dec-7-en-8-yltrifluoromethanesulfonate.

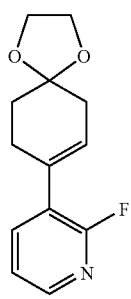 [SMILES: Fc1ncccc1C1=CCC2(CC1)OCCO2]

STEP 2. 2-FLUORO-3-(1,4-DIOXASPIRO[4.5]DEC-7-EN-8-YL)PYRIDINE

To a mixture of 1,4-dioxaspiro[4.5]dec-7-en-8-yltrifluoromethanesulfonate (10.2 g, 35.4 mmol) and 2-fluoropyridin-3-ylboronic acid (5.00 g, 35.5 mmol) in 1,2-dimethoxyethane (200 mL) and aqueous sodium carbonate (53.2 mL, 106 mmol, 2N) under argon atmosphere was added palladium tetrakis(triphenylphosphine) (1.23 g, 1.06 mmol). The mixture was heated and stirred at 85° C. for 1 h., then cooled to room temperature. Ethyl acetate was added and the mixture was washed with water (2×), saturated sodium chloride (1×), dried over anhydrous magnesium sulfate, filtered, and concentrated in vacuo. The resulting oil was purified by silica gel chromatography to give 2-fluoro-3-(1,4-dioxaspiro[4.5]dec-7-en-8-yl)pyridine. MS (ESI, pos. ion) m/z: 236.1.

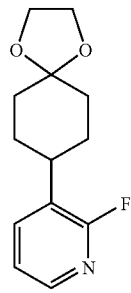 [SMILES: Fc1ncccc1C1CCC2(CC1)OCCO2]

STEP 3. 2-FLUORO-3-(1,4-DIOXASPIRO[4.5]DECAN-8-YL)PYRIDINE

To a solution of 2-fluoro-3-(1,4-dioxaspiro[4.5]dec-7-en-8-yl)pyridine (7.99 g, 34.0 mmol) in THF (40 mL) under argon atmosphere was added palladium on carbon (10% activated, 0.80 g). The mixture was placed under 1 atmosphere of hydrogen and stirred for 5 h at 40° C. After placing the mixture back under argon atmosphere, the mixture was filtered through celite and the filtrate was concentrated in vacuo to give 2-fluoro-3-(1,4-dioxaspiro[4.5]decan-8-yl)pyridine MS (ESI, pos. ion) m/z: 238.1.

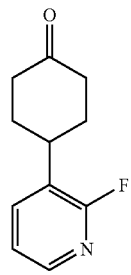

STEP 4. 4-(2-FLUOROPYRIDIN-3-YL)CYCLOHEXANONE

To a solution of 2-fluoro-3-(1,4-dioxaspiro[4.5]decan-8-yl)pyridine (7.88 g, 33.2 mmol) in acetone (350 mL) was added aqueous hydrochloric acid (39.9 mL, 39.9 mmol, 1N). The mixture was heated to 45° C. for 5 h, then cooled to room temperature. Most of the organic solvent was removed in vacuo and ethyl acetate (200 mL) was added. The resulting solution was washed with saturated aqueous sodium bicarbonate (2×), water (1×), saturated aqueous sodium chloride (1×), dried over anhydrous magnesium sulfate, filtered, and concentrated in vacuo to give 4-(2-fluoropyridin-3-yl)cyclohexanone. MS (ESI, pos. ion) m/z: 194.1.

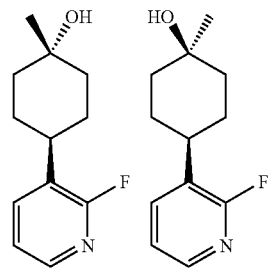

STEP 5. (1R,4R)-4-(2-FLUOROPYRIDIN-3-YL)-1-METHYLCYCLOHEXANOL AND (1S,4S)-4-(2-FLUOROPYRIDIN-3-YL)-1-METHYLCYCLOHEXANOL

A suspension of dry cerium(III) chloride (1.61 g, 6.52 mmol) in THF (15 mL) under argon was stirred at 40° C. for 2 h, then cooled to −78° C. Methylmagnesium bromide (2.17 mL, 6.52 mmol, 3M in diethyl ether) was added dropwise over 3 minutes and the mixture was stirred an additional 30 minutes at −78° C. A solution of 4-(2-fluoropyridin-3-yl)cyclohexanone (1.05 g, 5.43 mmol) in THF (3 mL) was added dropwise and the mixture was stirred at −78° C. for 1 h. The reaction was then quenched with saturated aqueous ammonium chloride, warmed to room temperature, and extracted with ethyl acetate several times. The combined organic extracts were dried over anhydrous magnesium sulfate, filtered, and concentrated in vacuo. The resulting oil was purified by silica gel chromatography to give (1r,4r)-4-(2-Fluoropyridin-3-yl)-1-methylcyclohexanol and (1s,4s)-4-(2-fluoropyridin-3-yl)-1-methylcyclohexanol as pure stereoisomeric compounds. MS (ESI, pos. ion) m/z: 210.1 for each compound. Stereochemistry was determined by 2D NMR.

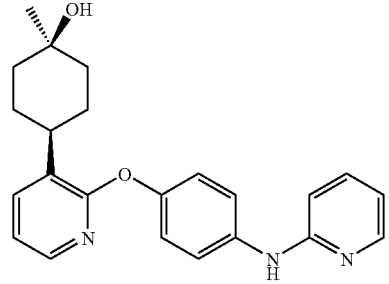 [SMILES: C[C@]1(O)CC[C@@H](c2cccnc2Oc2ccc(Nc3ccccn3)cc2)CC1]

STEP 6. (1S,4S)-1-METHYL-4-(2-(4-(PYRIDIN-2-YLAMINO)PHENOXY)PYRIDIN-3-YL)CYCLOHEXANOL

A mixture of cesium carbonate (0.47 g, 1.43 mmol), 4-(pyridin-2-ylamino)phenol (0.27 g, 1.43 mmol), and (1s,4s)-4-(2-fluoropyridin-3-yl)-1-methylcyclohexanol (0.10 g, 0.48 mmol) in NMP (2 mL) was placed under an atmosphere of argon by evacuating and backfilling with argon twice. The mixture was then heated to 120° C. for 36 h, cooled to RT and partitioned between ethyl acetate and water. The layers were separated and the organic layer was washed with aqueous 1 N sodium hydroxide (2×), water (1×), saturated aqueous sodium chloride (1×), dried over anhydrous magnesium sulfate, filtered, and concentrated in vacuo. The resulting oil was purified by silica gel chromatography to give (1s,4s)-1-methyl-4-(2-(4-(pyridin-2-ylamino)phenoxy)pyridin-3-yl)cyclohexanol. MS (ESI, pos. ion) m/z: 376.1. IC$_{50}$ (uM) 0.023.

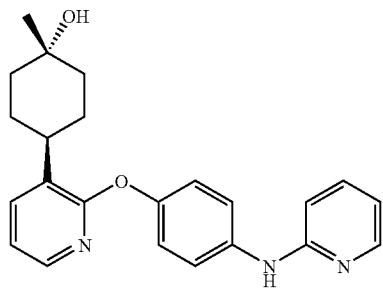 [SMILES: C[C@]1(O)CC[C@H](c2cccnc2Oc2ccc(Nc3ccccn3)cc2)CC1]

Example 233

(1R,4R)-1-METHYL-4-(2-(4-(PYRIDIN-2-YLAMINO)PHENOXY)PYRIDIN-3-YL)CYCLOHEXANOL

A mixture of cesium carbonate (0.46 g, 1.41 mmol), 4-(pyridin-2-ylamino)phenol (0.26 g, 1.41 mmol), and (1r,4r)-4-(2-fluoropyridin-3-yl)-1-methylcyclohexanol (0.098 g, 0.47 mmol) in NMP (1 mL) was placed under an atmosphere of argon by evacuating and backfilling with argon twice. The mixture was then heated to 120° C. for 24 h, cooled to RT and partitioned between ethyl acetate and water. The layers were separated and the organic layer was washed with aqueous 1 N sodium hydroxide (2×), water (1×), saturated aqueous sodium chloride (1×), dried over anhydrous magnesium sulfate, filtered, and concentrated in vacuo. The resulting oil was purified by silica gel chromatography to give (1r,4r)-1-methyl-4-(2-(4-(pyridin-2-ylamino)phenoxy)pyridin-3-yl)cyclohexanol. MS (ESI, pos. ion) m/z: 376.2. IC$_{50}$ (uM) 0.062.

SCHEME 21

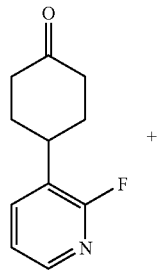

+

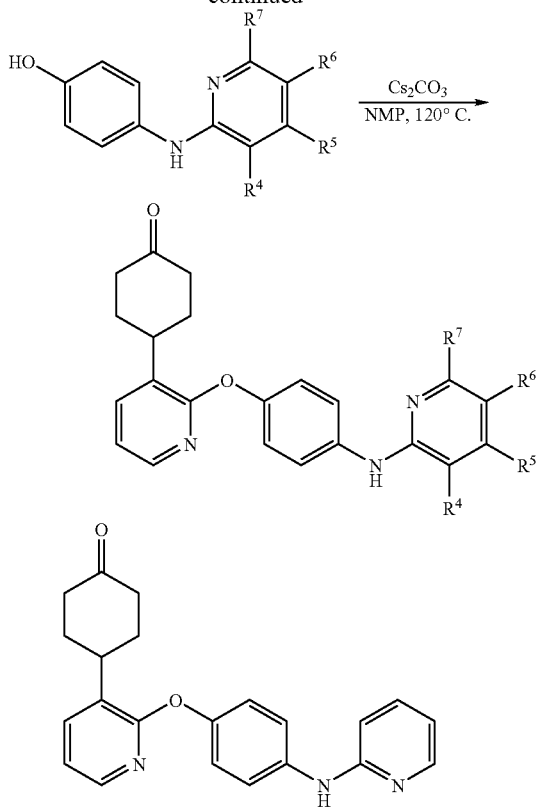

Example 234

4-(2-(4-(PYRIDIN-2-YLAMINO)PHENOXY)PYRIDIN-3-YL)CYCLOHEXANONE 4-(2-Fluoropyridin-3-yl)cyclohexanone (0.10 g, 0.52 mmol), 4-(pyridin-2-ylamino)phenol (0.29 g, 1.55 mmol), and cesium carbonate (0.51 g, 1.55 mmol) were mixed in NMP (1.5 mL). The reaction mixture was placed under a nitrogen atmosphere and stirred at 120° C. for 16 h. The reaction mixture was cooled to room temperature, diluted with water, and extracted with EtOAc (3×). The combined organic layers were washed with 1 M aqueous sodium hydroxide (1×), sat. sodium chloride (1×), dried over magnesium sulfate, filtered, and concentrated in vacuo. The resulting crude product was purified by silica gel chromatography to give 4-(2-(4-(pyridin-2-ylamino)phenoxy)pyridin-3-yl)cyclohexanone. MS (ESI, pos. ion) m/z: 360.1 (M+1). IC$_{50}$ (uM) 0.002.

SCHEME 22

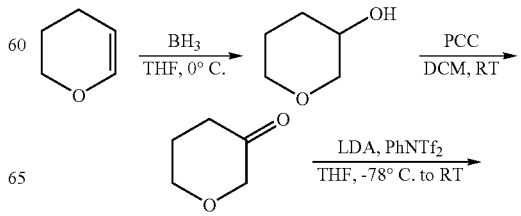

-continued

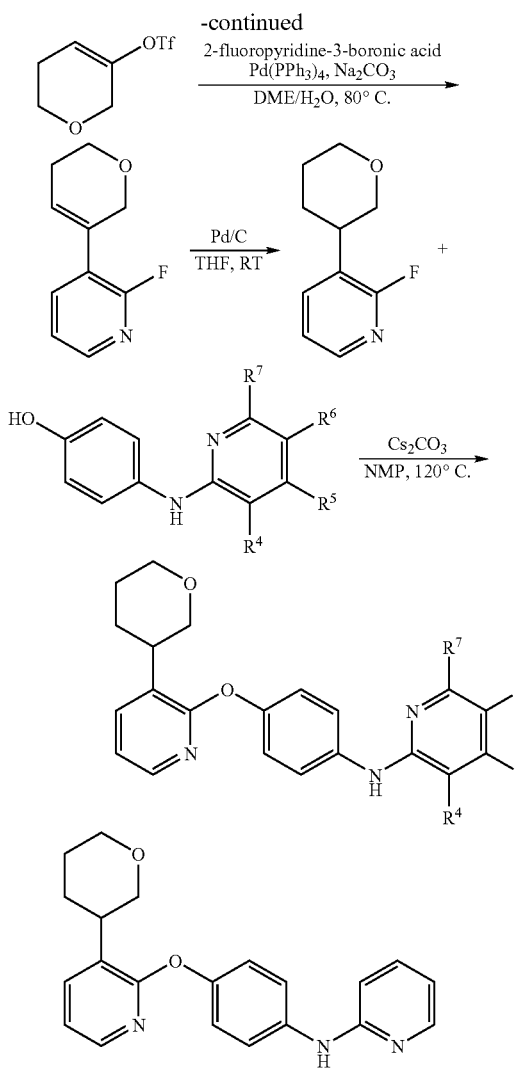

Example 235

N-(4-(3-(TETRAHYDRO-2H-PYRAN-3-YL)PYRIDIN-2-YLOXY)PHENYL)PYRIDIN-2-AMINE

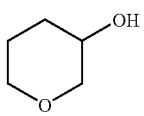

STEP 1. TETRAHYDRO-2H-PYRAN-3-OL

To a stirred solution of 3,4-dihydro-2H-pyran (5.42 mL, 59.4 mmol) in THF (100 mL) at 0° C. under a nitrogen atmosphere was added borane tetrahydrofuran complex, (29.7 mL, 29.7 mmol, 1.0 M in THF) via syringe. The reaction mixture was stirred at 0° C. for 3 h before a mixture of 5 M aqueous sodium hydroxide (40 mL) and 30% aqueous hydrogen peroxide (20 mL) was added. The reaction mixture was warmed to room temperature and stirred for 3 h. Sat. aqueous sodium bicarbonate was added, and the mixture was extracted with EtOAc (2×). The combined organic layers were washed with sat. aqueous sodium chloride, dried over magnesium sulfate, filtered, and concentrated in vacuo to give tetrahydro-2H-pyran-3-ol.

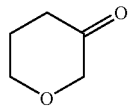

STEP 2. DIHYDRO-2H-PYRAN-3(4H)-ONE

To a stirred mixture of pyridinium chlorochromate (11.02 g, 51.1 mmol) and 3 Å molecular sieves (10.0 g) in DCM (100 mL) was added a solution of tetrahydro-2H-pyran-3-ol (3.48 g, 34.1 mmol) in DCM (100 mL). The reaction mixture was refluxed for 3 h before being cooled to room temperature and partially concentrated in vacuo. The mixture was then diluted with EtOAc and filtered through Celite. The filtrate was concentrated in vacuo and purified by silica gel chromatography to give dihydro-2H-pyran-3(4H)-one.

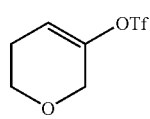 [SMILES: O=S(=O)(OC1=CCCOC1)C(F)(F)F]

STEP 3. 5,6-DIHYDRO-2H-PYRAN-3-YL TRIFLUOROMETHANESULFONATE

To a stirred solution of diisopropylamine (3.06 mL, 21.8 mmol) in THF (50 mL) at −78° C. under an argon atmosphere was added butyllithium (8.73 mL, 21.8 mmol, 2.5 M in hexanes). The mixture was stirred for 5 min before dihydro-2H-pyran-3(4H)-one (1.82 g, 18.2 mmol) in THF (15 mL) was added slowly via syringe. The mixture was stirred for an additional 15 min before n-phenyltrifluoromethanesulfonimide (7.14 g, 20.0 mmol) in THF (15 mL) was added slowly via syringe. The reaction mixture was then stirred at −78° C. for an additional 15 min before being allowed to warm to room temperature and stirred for 1 h. Sat. aqueous sodium bicarbonate was added, and the mixture was extracted with EtOAc (2×). The combined organic layers were washed with sat. sodium chloride, dried over magnesium sulfate, filtered, and concentrated in vacuo. The resulting crude oil was purified by silica gel chromatography to give 5,6-dihydro-2H-pyran-3-yltrifluoromethanesulfonate.

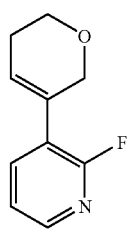 [SMILES: Fc1ncccc1C1=CCCOC1]

STEP 4. 3-(5,6-DIHYDRO-2H-PYRAN-3-YL)-2-FLUOROPYRIDINE

Sodium carbonate (29.0 mL, 58.0 mmol, 2.0 M in water) was added via syringe to a stirred mixture of 5,6-dihydro-2H-pyran-3-yl trifluoromethanesulfonate (4.49 g, 19.3 mmol), 2-fluoropyridine-3-boronic acid (2.72 g, 19.3 mmol), and tetrakis(triphenylphosphine)palladium (1.12 g, 0.97 mmol) in DME (82 mL) under an argon atmosphere. The reaction mixture was stirred at 80° C. for 17 h. The reaction mixture was then cooled to room temperature before being diluted with EtOAc and water. The organic layer was separated, washed with sat. aqueous sodium chloride, dried over magnesium sulfate, filtered, and concentrated in vacuo. The resulting crude product was purified by silica gel chromatography to give 3-(5,6-dihydro-2H-pyran-3-yl)-2-fluoropyridine. MS (ESI, pos. ion) m/z: 180.1 (M+1).

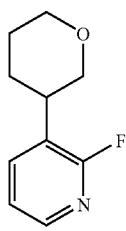

STEP 5. 2-FLUORO-3-(TETRAHYDRO-2H-PYRAN-3-YL)PYRIDINE

Palladium (0.005 g, 0.005 mmol, 10% wt. on activated carbon) was added to a stirred solution of 3-(5,6-dihydro-2H-pyran-3-yl)-2-fluoropyridine (0.10 g, 0.558 mmol) in THF (2 mL). The reaction mixture was placed under a hydrogen atmosphere (balloon) and stirred at room temperature for 4 h. The reaction mixture was filtered through Celite, and the filtrate was concentrated in vacuo to give 2-fluoro-3-(tetrahydro-2H-pyran-3-yl)pyridine. MS (ESI, pos. ion) m/z: 182.1 (M+1).

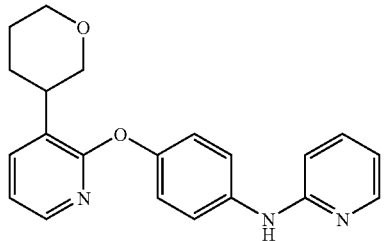 [SMILES: c1ccc(Nc2ccc(Oc3ncccc3C3CCCOC3)cc2)nc1]

STEP 6. N-(4-(3-(TETRAHYDRO-2H-PYRAN-3-YL)PYRIDIN-2-YLOXY)PHENYL)PYRIDIN-2-AMINE

2-Fluoro-3-(tetrahydro-2H-pyran-3-yl)pyridine (0.10 g, 0.55 mmol), 4-(pyridin-2-ylamino)phenol (0.26 g, 1.38 mmol), and cesium carbonate (0.54 g, 1.66 mmol) were mixed in NMP (2 mL). The reaction mixture was placed under a nitrogen atmosphere and stirred at 120° C. for 16 h. The reaction mixture was cooled to room temperature, diluted with water, and extracted with EtOAc (2×). The combined organic layers were washed with 1 M aqueous sodium hydroxide (1×), sat. sodium chloride (1×), dried over magnesium sulfate, filtered, and concentrated in vacuo. The resulting crude product was purified by silica gel chromatography to give N-(4-(3-(tetrahydro-2H-pyran-3-yl)pyridin-2-yloxy)phenyl)pyridin-2-amine. MS (ESI, pos. ion) m/z: 348.1 (M+1). $IC_{50}$ (uM) 0.012.

SCHEME 23

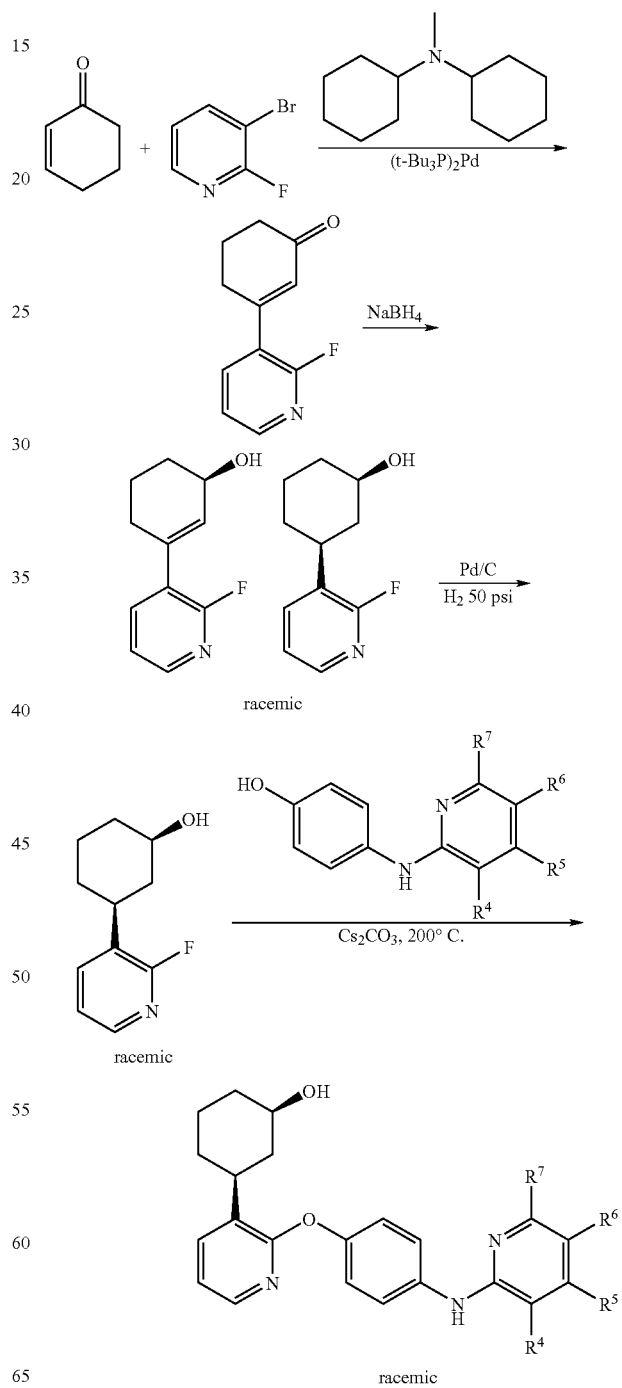

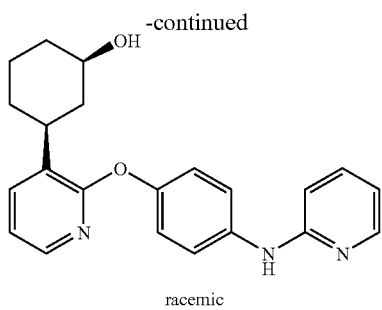

racemic

Example 236

(RAC)-CIS-3-(2-(4-(PYRIDIN-2-YLAMINO)PHENOXY)PYRIDIN-3-YL)CYCLOHEXANOL

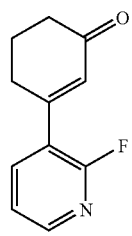

STEP 1. 3-(2-FLUOROPYRIDIN-3-YL)CYCLOHEX-2-ENONE

A solution of 3-bromo-2-fluoropyridine (11 g, 62.5 mmol), 2-cyclohexen-1-one (24.03 g, 250 mmol), N,N-dicyclohexylmethylamine (30.5 g, 156 mmol) and bis(tri-t-butylphosphine)palladium (0) (0.958 g, 1.875 mmol) in dioxane (80 mL) was heated to 105° C. for 6 h. The mixture was cooled to RT and the dioxane was evaporated under reduced pressure. Water (200 ml) was added and the mixture layer was extracted with EtOAc (2×200 ml). The combined organic layers were washed with brine and dried over sodium sulfate. Filtration and concentration under reduced pressure, followed by flash chromatography on silica gel (20% to 50% EtOAc in hexanes) afforded 3-(2-fluoropyridin-3-yl)cyclohex-2-enone as colorless crystals. MS (ESI, pos. ion) m/z: 191.9 (M+1).

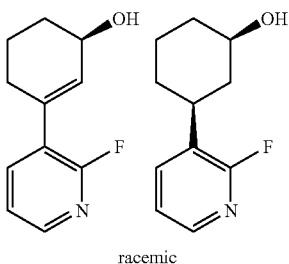

racemic

STEP 2. (RAC)-3-(2-FLUOROPYRIDIN-3-YL)CYCLOHEX-2-ENOL AND (RAC)-CIS-3-(2-FLUOROPYRIDIN-3-YL)CYCLOHEXANOL

Sodium borohydrate (1.055 g, 27.9 mmol) was added to a solution of 3-(2-fluoropyridin-3-yl)cyclohex-2-enone (4 g, 20.9 mmol) in MeOH (20 ml). The mixture was stirred for 10 min, cooled in ice-water bath, and saturated aqueous ammonium chloride (5 ml) was added. The mixture was diluted with water (100 ml) and extracted with EtOAc (2×100 ml). The organic layer was washed with brine, dried over sodium sulfate, filtered and concentrated. The mixture of products was directly used in the next step.

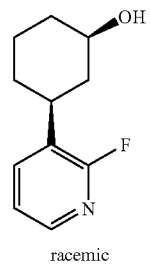 [SMILES: O[C@@H]1CCC[C@H](c2cccnc2F)C1]

racemic

STEP 3. (RAC)-CIS-3-(2-FLUOROPYRIDIN-3-YL)CYCLOHEXANOL

A mixture of the mixture of products from the previous step (1.8 g) and 10 wt. % palladium on carbon (0.20 g, 0.19 mmol) in THF (20 ml) was stirred at RT under 50 psi of hydrogen gas for 1 h. The mixture was filtered through a Celite pad that was washed with THF. The combined filtrates and washings were concentrated under reduced pressure to deliver (rac)-cis-3-(2-fluoropyridin-3-yl)cyclohexanol as an off-white solid. MS (ESI, pos. ion) m/z: 196.1 (M+1).

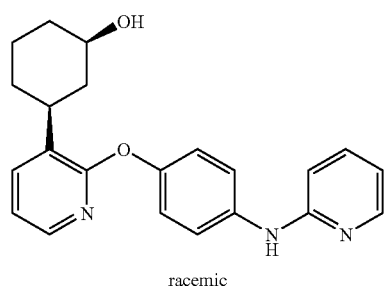 [SMILES: O[C@@H]1CCC[C@H](c2cccnc2Oc2ccc(Nc3ccccn3)cc2)C1]

racemic

STEP 4. (RAC)-CIS-3-(2-(4-(PYRIDIN-2-YLAMINO)PHENOXY)PYRIDIN-3-YL)CYCLOHEXANOL

A mixture of (rac)-cis-3-(2-fluoropyridin-3-yl)cyclohexanol (250 mg, 1.281 mmol), 4-(pyridin-2-ylamino)phenol (477 mg, 2.56 mmol), and cesium carbonate (834 mg, 2.56 mmol) in NMP (4 ml) was heated in a Biotage™ microwave reactor at 180° C. for 1.5 h. The mixture was partitioned between H₂O (15 ml) and CH₂Cl₂ (30 ml), the layers were separated, and the aqueous layer was extracted with CH₂Cl₂ (3×30 ml). The combined organic layers were dried (MgSO₄), concentrated under reduced pressure, and the resulting brown oil was purified by reversed phase HPLC (Gilson Gemini-NX 10u C18 110A, 100×50.0 mm, 10% to 95% H₂O/MeCN, 0.1% TFA). The product containing fractions were combined, neutralized by the addition of solid Na₂CO₃, and extracted with CH₂Cl₂ (3×20 mL). The combined organic layers were dried (MgSO₄) and concentrated under reduced pressure to deliver (rac)-cis-3-(2-(4-(pyridin-2-ylamino)phenoxy)pyridin-3-yl)cyclohexanol as a tan solid. MS (ESI, pos. ion) m/z: 362.0 (M+1). IC50 (uM) 0.011024.

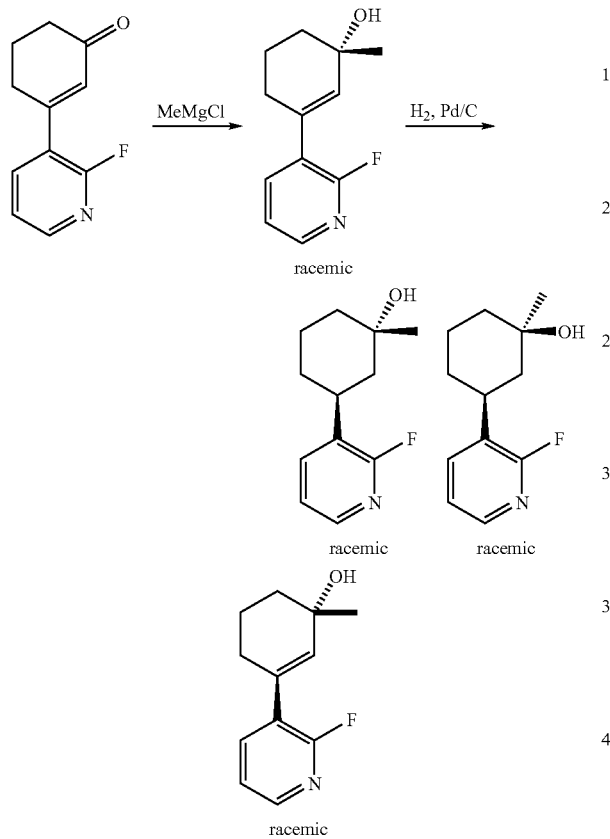

STEP 1. (RAC)-3-(2-FLUOROPYRIDIN-3-YL)-1-METHYLCYCLOHEX-2-ENOL

A 3.0 M solution of methylmagnesium chloride in tetrahydrofuran (4.88 mL, 14.64 mmol) was added slowly to a solution of 3-(2-fluoropyridin-3-yl)cyclohex-2-enone (2.00 g, 10.46 mmol) in THF (20 ml) at −78° C. After completion of the addition the reaction mixture was stirred overnight while it gradually warmed up to RT. It was cooled in an ice water bath and distilled water (5 ml) was added slowly. The mixture was concentrated under reduced pressure, saturated aqueous sodium bicarbonate (200 ml) was added, and it was extracted EtOAc (3×100 ml). The combined organic layers were washed by brine and dried over sodium sulfate. Filtration and concentration under reduced pressure gave (rac)-3-(2-fluoropyridin-3-yl)-1-methylcyclohex-2-enol as a light yellow liquid. MS (ESI, pos. ion) m/z: 208.0 (M+1).

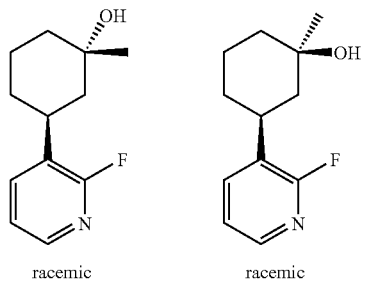

STEP 2: (RAC)-E-3-(2-FLUOROPYRIDIN-3-YL)-1-METHYLCYCLOHEXANOL

A suspension of (rac)-3-(2-fluoropyridin-3-yl)-1-methylcyclohex-2-enol (1.8 g, 8.7 mmol) and 10 wt. % palladium on carbon (0.277 g, 2.61 mmol) in THF (20 ml) was stirred in a pressure reactor under 50 psi of hydrogen gas for 7 h. The mixture was filtered through a pad of Celite that was washed with THF. Concentration of the combined filtrates and washings under reduced pressure, followed by flash chromatography on silica gel (20% to 50% EtOAc in hexanes) afforded (rac)-E-3-(2-fluoropyridin-3-yl)-1-methylcyclohexanol and (rac)-Z-3-(2-fluoropyridin-3-yl)-1-methylcyclohexanol as a white solids. MS (ESI, pos. ion) m/z: 210.0 (M+1) and 210.0 (M+1), respectively.

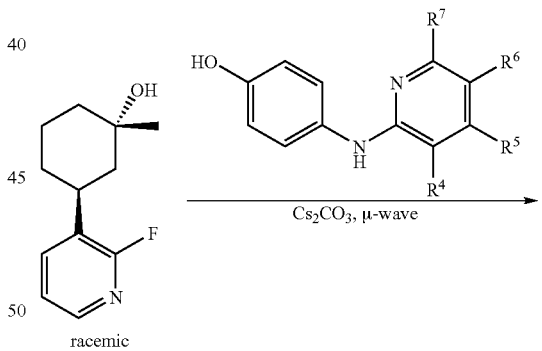

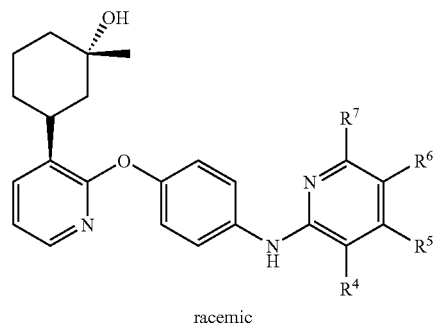

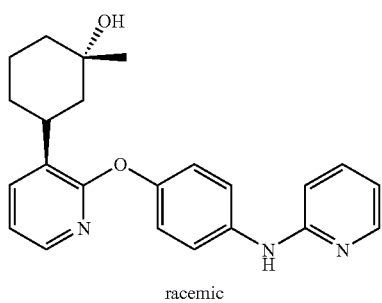

racemic

Example 237

(RAC)-E-1-METHYL-3-(2-(4-(PYRIDIN-2-YLAMINO)PHENOXY)PYRIDIN-3-YL)CYCLOHEXANOL

A mixture of (rac)-E-3-(2-fluoropyridin-3-yl)-1-methyl-cyclohexanol, as prepared according to Scheme 24a above, (197 mg, 0.941 mmol), 4-(pyridin-2-ylamino)phenol (351 mg, 1.883 mmol), and cesium carbonate (613 mg, 1.883 mmol) in NMP (4 ml) was heated in a Biotage™ microwave reactor at 180° C. two times for 1.5 h. The mixture was partitioned between H$_2$O (15 ml) and CH$_2$Cl$_2$ (30 ml), the layers were separated, and the aqueous layer was extracted with CH$_2$Cl$_2$ (3×30 ml). The combined organic layers were dried (MgSO$_4$), concentrated under reduced pressure, and the resulting brown oil was purified by reversed phase HPLC (Gilson Gemini-NX 10u C18 110A, 100×50.0 mm, 10% to 95% H$_2$O/MeCN, 0.1% TFA). The product containing fractions were combined, neutralized by the addition of solid Na$_2$CO$_3$, and extracted with CH$_2$Cl$_2$ (3×20 mL). The combined organic layers were dried (MgSO$_4$) and concentrated under reduced pressure to deliver (rac)-E-1-methyl-3-(2-(4-(pyridin-2-ylamino)phenoxy)pyridin-3-yl)cyclohexanol as a tan solid. MS (ESI, pos. ion) m/z: 376.1 (M+1). IC50 (uM) 0.02645.

SCHEME 25

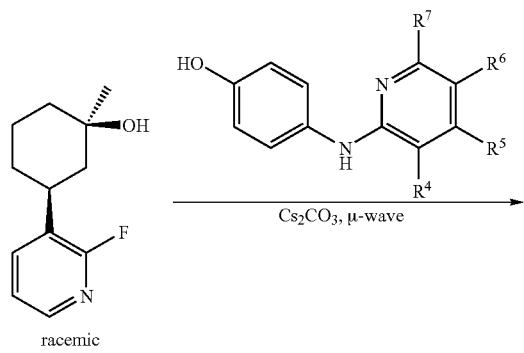

racemic

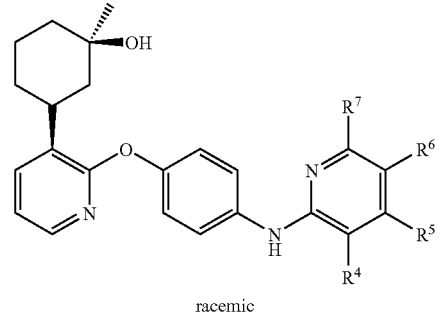

racemic

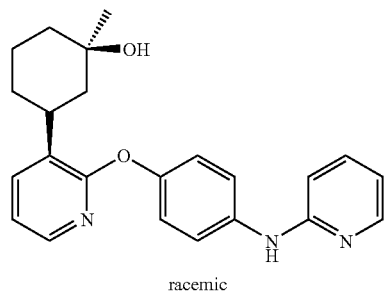

racemic

Example 238

(RAC)-Z-1-METHYL-3-(2-(4-(PYRIDIN-2-YLAMINO)PHENOXY)PYRIDIN-3-YL)CYCLOHEXANOL

A mixture of (rac)-Z-3-(2-fluoropyridin-3-yl)-1-methyl-cyclohexanol, as prepared according to Scheme 24a above, (82 mg, 0.392 mmol), 4-(pyridin-2-ylamino)phenol (146 mg, 0.784 mmol), and cesium carbonate (255 mg, 0.784 mmol) in NMP (2 ml) was heated in a Biotage™ microwave reactor at 180° C. for 1 h. The mixture was partitioned between H$_2$O (10 ml) and CH$_2$Cl$_2$ (20 ml), the layers were separated, and the aqueous layer was extracted with CH$_2$Cl$_2$ (3×20 ml). The combined organic layers were dried (MgSO$_4$), concentrated under reduced pressure, and the resulting brown oil was purified by reversed phase HPLC (Gilson Gemini-NX 10u C18 110A, 100×50.0 mm, 10% to 95% H$_2$O/MeCN, 0.1% TFA). The product containing fractions were combined, neutralized by the addition of solid Na$_2$CO$_3$, and extracted with CH$_2$Cl$_2$ (3×20 mL). The combined organic layers were dried (MgSO$_4$) and concentrated under reduced to deliver (rac)-Z-1-methyl-3-(2-(4-(pyridin-2-ylamino)phenoxy)pyridin-3-yl)cyclohexanol as an off-white solid. MS (ESI, pos. ion) m/z: 376.1 (M+1). IC50 (uM) 0.08946.

SCHEME 26

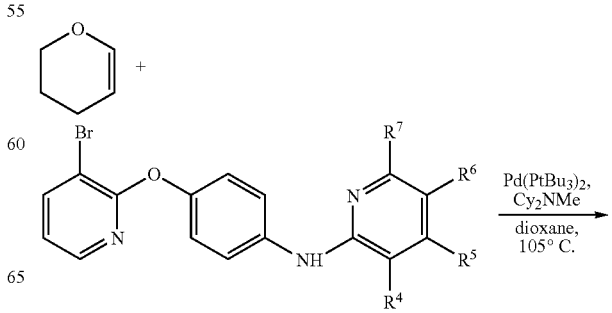

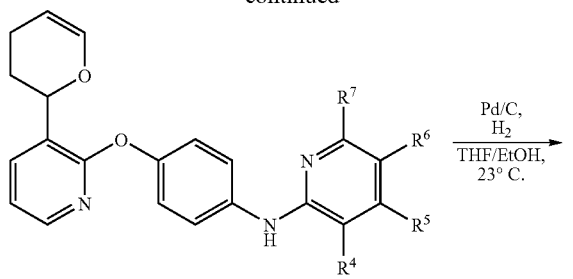

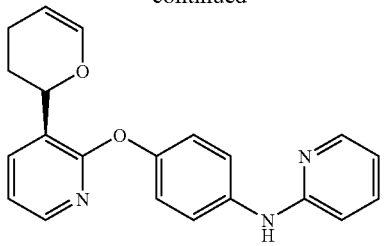

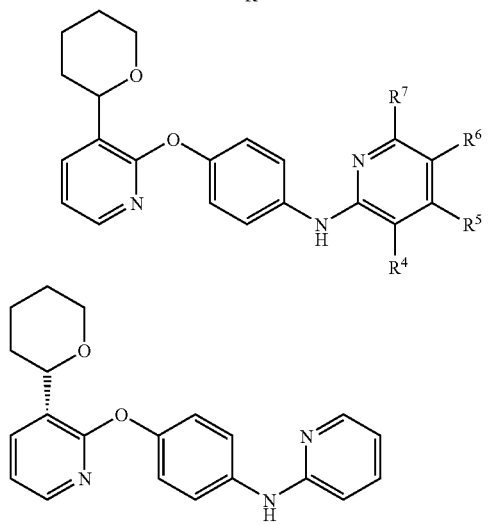

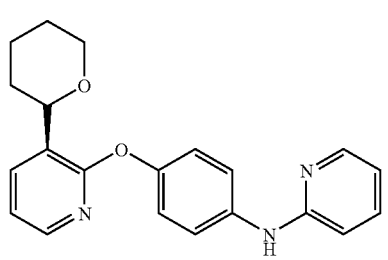

Example 239

(±)-N-(4-(3-(TETRAHYDRO-2H-PYRAN-2-YL)PYRIDIN-2-YLOXY)PHENYL)PYRIDIN-2-AMINE

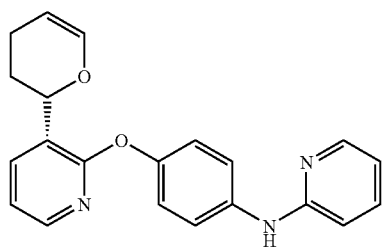

STEP 1. (±)-N-(4-(3-(3,4-DIHYDRO-2H-PYRAN-2-YL)PYRIDIN-2-YLOXY)PHENYL)PYRIDIN-2-AMINE

To a 25 mL microwave vial was added Bis(tri-tert-butylphosphine) palladium (0) (101 mg, 0.198 mmol) and N-(4-(3-bromopyridin-2-yloxy)phenyl)pyridin-2-amine hydrochloride (750 mg, 1.981 mmol) before evacuating and backfilling with nitrogen (2×). After addition of Dioxane (5.659 ml), N-cyclohexyl-N-methylcyclohexanamine (0.840 ml, 3.96 mmol), and 3,4-dihydro-2H-pyran (666 mg, 7.92 mmol) was added and the mixture was heated to 105° C. Following complete consumption of the starting material, the reaction mixture was cooled to room temperature and the volatiles were removed under reduced pressure. Following silica gel chromatography, the title compound was obtained as a racemic mixture. MS (ESI, pos. ion) m/z: 346.0. $IC_{50}$ (uM) 0.064.

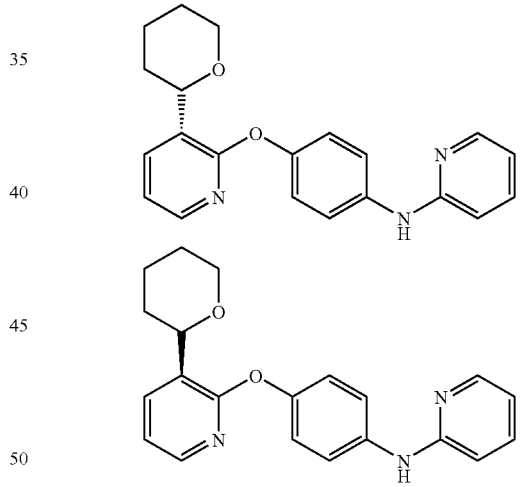

STEP 2. (±)-N-(4-(3-(TETRAHYDRO-2H-PYRAN-2-YL)PYRIDIN-2-YLOXY)PHENYL)PYRIDIN-2-AMINE

A mixture of (±)-N-(4-(3-(3,4-dihydro-2H-pyran-2-yl)pyridin-2-yloxy)phenyl)pyridin-2-amine (233 mg, 0.675 mmol) and palladium on carbon (wet) (71.8 mg, 0.067 mmol) in EtOH/dioxane was placed under an atmosphere of hydrogen gas and stirred for 24 hours. The mixture was then filtered through a cake of celite, washing with MeOH. The filtrate was concentrated and purified by silica gel chromatography, 10-100% acetone/hexanes, to give the title compound as a racemic mixture. MS (ESI, pos. ion) m/z: 348.0 (M+1). $IC_{50}$ (uM) 0.149.

SCHEME 27

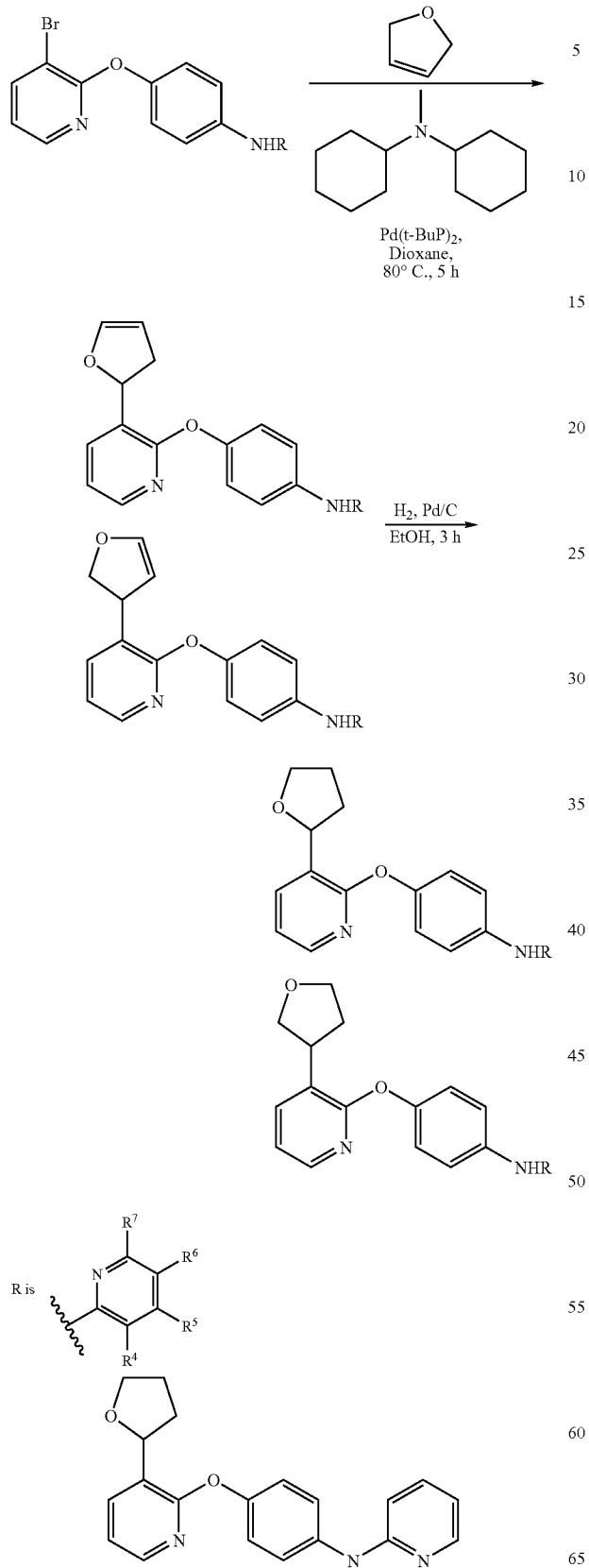

Example 240

N-(4-(3-(TETRAHYDROFURAN-2-YL)PYRIDIN-2-YLOXY)PHENYL)PYRIDIN-2-AMINE

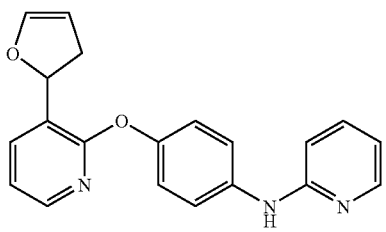 [SMILES: C1=COC(c2cccnc2Oc2ccc(Nc3ccccn3)cc2)C1]

STEP 1: N-(4-(3-(2,3-DIHYDROFURAN-2-YL)PYRIDIN-2-YLOXY)PHENYL)PYRIDIN-2-AMINE

To a 25 mL microwave vial was added Bis(tri-tert-butylphosphine) palladium (0) (121 mg, 0.238 mmol) and N-(4-(3-bromopyridin-2-yloxy)phenyl)pyridin-2-amine hydrochloride (900 mg, 2.377 mmol) before sealing and evacuating and backfilling with nitrogen (2×). After addition of dioxane (11.900 ml), N-cyclohexyl-N-methylcyclohexanamine (1.008 ml, 4.75 mmol), and 2,5-dihydrofuran (0.701 ml, 9.51 mmol), the black suspension was heated to 80° C. for 5 h. The reaction mixture was cooled to room temperature, transferred to a 100 mL round bottom flask, and concentrated under reduced pressure. The material was taken up in DCM and adsorbed onto silica before purifying by flash chromatography (0 to 75% ethyl acetate/hexanes), affording a mixture of 2- and 3-dihydrofuranyl products that was used in subsequent reactions.

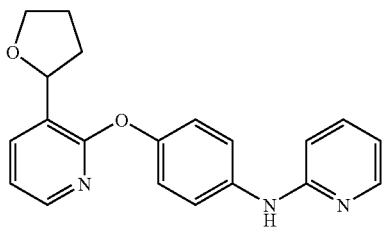 [SMILES: c1ccc(Nc2ccc(Oc3ncccc3C3CCCO3)cc2)nc1]

STEP 2: N-(4-(3-(TETRAHYDROFURAN-2-YL)PYRIDIN-2-YLOXY)PHENYL)PYRIDIN-2-AMINE

To a 150 mL round bottom flask was added N-(4-(3-(2,3-dihydrofuran-2-yl)pyridin-2-yloxy)phenyl)pyridin-2-amine (660 mg, 1.992 mmol) and ethanol (7967 µL) before adding palladium, 10% wt. on activated carbon (70 mg, 0.658 mmol) portionwise. The flask was evacuated and backfilled with hydrogen under atmospheric pressure before allowing to stir at room temperature under hydrogen. The reaction was complete after 3 h. After dilution with ethyl acetate, the black suspension was filtered through a pad of Celite while rinsing with ethyl acetate (3×25 mL) before concentrating to a pale yellow residue. The residue was taken up in 5 mL DCM and applied directly to silica for purification (0 to 50% ethyl acetate/hexanes over 35 minutes). The target compound was isolated as a white solid. MS (ESI, pos. ion) m/z: 334.2 (M+1). $IC_{50}$ (uM) 0.225.

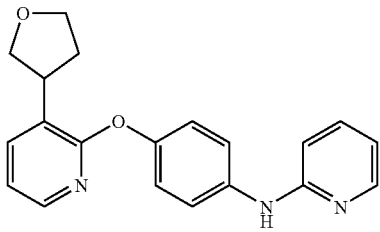 [SMILES: c1ccc(Nc2ccc(Oc3ncccc3C3CCOC3)cc2)nc1]

Example 241

N-(4-(3-(TETRAHYDROFURAN-3-YL)PYRIDIN-2-YLOXY)PHENYL)PYRIDIN-2-AMINE

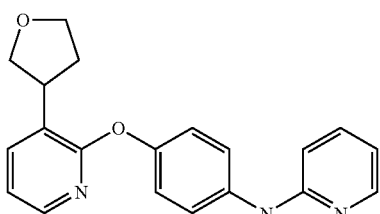

STEP 1: N-(4-(3-(2,3-DIHYDROFURAN-3-YL)PYRIDIN-2-YLOXY)PHENYL)PYRIDIN-2-AMINE

To a 25 mL microwave vial was added Bis(tri-tert-butylphosphine) palladium (0) (121 mg, 0.238 mmol) and N-(4-(3-bromopyridin-2-yloxy)phenyl)pyridin-2-amine hydrochloride (900 mg, 2.377 mmol) before sealing and evacuating and backfilling with nitrogen. After addition of dioxane (11.900 ml), N-cyclohexyl-N-methylcyclohexanamine (1.008 ml, 4.75 mmol), and 2,5-dihydrofuran (0.701 ml, 9.51 mmol), the black suspension was heated to 80° C. for 5 h. The reaction mixture was cooled to room temperature, transferred to a 100 mL round bottom flask, and concentrated under reduced pressure. The material was taken up in DCM and adsorbed onto silica before purifying by flash chromatography (0 to 75% ethyl acetate/hexanes), affording a mixture of 2- and 3-dihydrofuranyl products that was used without separation.

STEP 2: N-(4-(3-(TETRAHYDROFURAN-3-YL)PYRIDIN-2-YLOXY)PHENYL)PYRIDIN-2-AMINE

To a 150 mL round bottom flask was added N-(4-(3-(2,3-dihydrofuran-2-yl)pyridin-2-yloxy)phenyl)pyridin-2-amine (660 mg, 1.992 mmol) and ethanol (7967 μL) before adding palladium, 10% wt. on activated carbon (70 mg, 0.658 mmol) portionwise. The flask was evacuated and backfilled with hydrogen under atmospheric pressure before allowing to stir at room temperature under hydrogen. The reaction was complete after 3 h. After dilution with ethyl acetate, the black suspension was filtered through a pad of Celite while rinsing with ethyl acetate (3×25 mL) before concentrating to a pale yellow residue. The residue was taken up in 5 mL DCM and applied directly to silica for purification (0 to 50% ethyl acetate/hexanes over 35 minutes). The target compound was isolated as a white solid. MS (ESI, pos. ion) m/z: 334.2 (M+1). $IC_{50}$ (uM) 0.019.

SCHEME 28

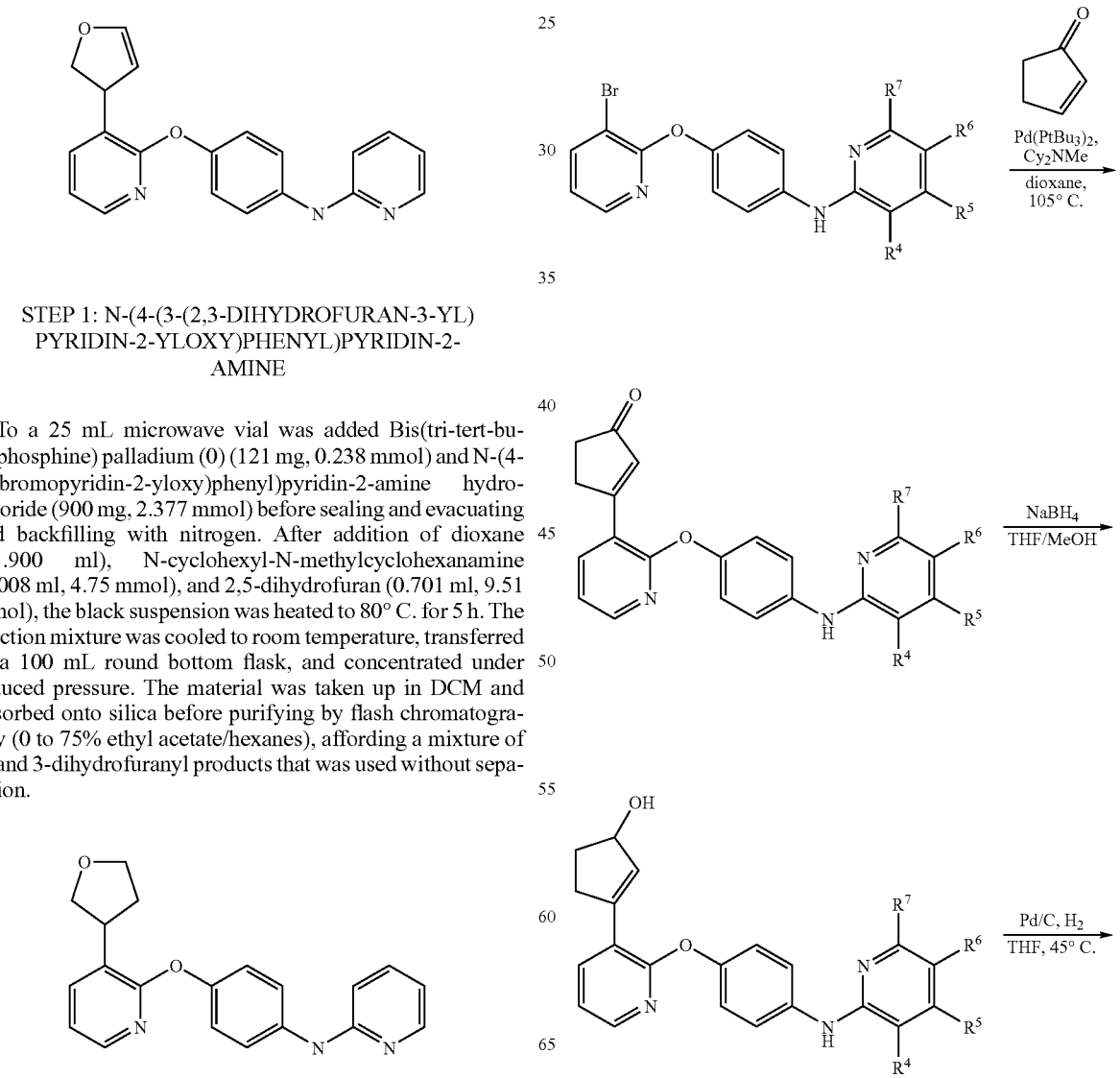

-continued

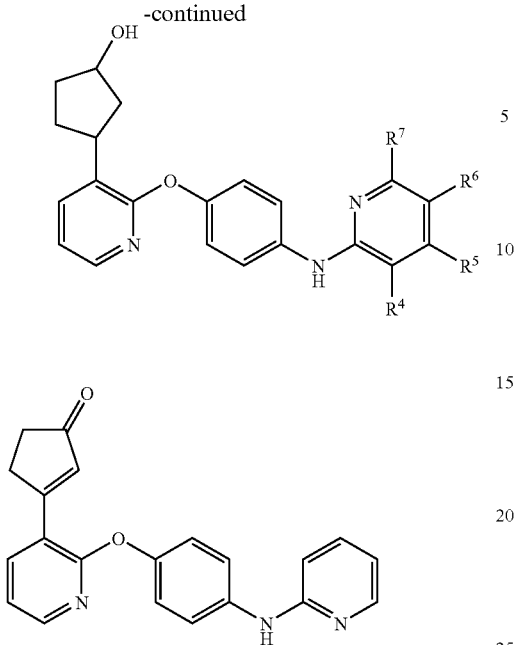

Example 242

3-(2-(4-(PYRIDIN-2-YLAMINO)PHENOXY)PYRIDIN-3-YL)CYCLOPENT-2-ENONE

A suspension of N-(4-(3-bromopyridin-2-yloxy)phenyl)pyridin-2-amine hydrochloride (600 mg, 1.585 mmol) in Dioxane (4 mL) was treated with n-methyldicyclohexylamine (1.008 mL, 4.75 mmol, 3.0 equiv). The reaction was stirred at 23° C. for 15 min, followed by the addition of 2-cyclopenten-1-one (0.641 mL, 7.92 mmol, 5.0 equiv) and bis(tri-tert-butylphosphine)palladium (0) (81 mg, 0.158 mmol, 0.1 equiv). The reaction vessel was capped, degassed and backfilled with argon, and heated at 105° C. After 6 h, the reaction was cooled to 23° C., diluted with EtOAc (100 mL) and washed with water (75 mL) and brine (75 mL), dried over MgSO$_4$, concentrated in vacuo and purified by silica gel chromatography (eluant: 0.5-3% methanol/dichloromethane), affording 3-(2-(4-(pyridin-2-ylamino)phenoxy)pyridin-3-yl)cyclopent-2-enone. MS (ESI, pos. ion) m/z: 344.1 (M+1). IC50 (uM) 0.015.

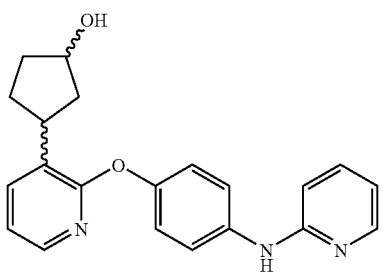 [SMILES: OC1CCC(c2cccnc2Oc2ccc(Nc3ccccn3)cc2)C1]

Example 243

3-(2-(4-(PYRIDIN-2-YLAMINO)PHENOXY)PYRIDIN-3-YL)CYCLOPENTANOL

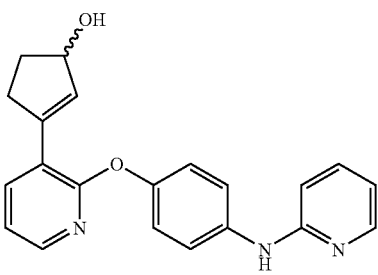 [SMILES: OC1C=C(c2cccnc2Oc2ccc(Nc3ccccn3)cc2)CC1]

STEP 1. 3-(2-(4-(PYRIDIN-2-YLAMINO)PHENOXY)PYRIDIN-3-YL)CYCLOPENT-2-ENOL

A suspension of 3-(2-(4-(pyridin-2-ylamino)phenoxy)pyridin-3-yl)cyclopent-2-enone (791 mg, 2.304 mmol, Example 1) in Tetrahydrofuran (150 mL) and Methanol (15.00 mL) was cooled to 0° C. under nitrogen, and was treated with sodium borohydride (349 mg, 9.21 mmol, 4.0 equiv) in 4 lots over 15 min. The reaction was warmed to 23° C. and was stirred under nitrogen. After 24 h, the reaction was quenched with saturated ammonium chloride solution (15 mL). The suspension was diluted with EtOAc (250 mL) and washed with saturated ammonium chloride solution (100 mL) and brine (100 mL), dried over MgSO$_4$, concentrated in vacuo and purified by silica gel chromatography (eluant: 1-4% methanol/dichloromethane), affording 3-(2-(4-(pyridin-2-ylamino)phenoxy)pyridin-3-yl)cyclopent-2-enol.

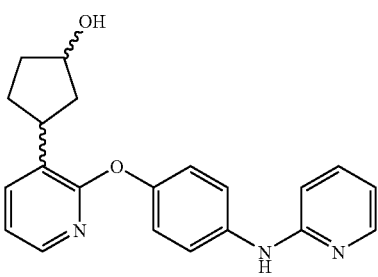 [SMILES: OC1CCC(c2cccnc2Oc2ccc(Nc3ccccn3)cc2)C1]

STEP 2. 3-(2-(4-(PYRIDIN-2-YLAMINO)PHENOXY)PYRIDIN-3-YL)CYCLOPENTANOL

A solution of 3-(2-(4-(pyridin-2-ylamino)phenoxy)pyridin-3-yl)cyclopent-2-enol (190 mg, 0.550 mmol) in Tetrahydrofuran (10 mL) was treated with palladium, 10% wt. on activated carbon (58.5 mg, 0.055 mmol, 0.1 equiv). The reaction mixture was purged with vacuum-hydrogen cycles (3×), and stirred at 23° C. under hydrogen. After 5 h, the reaction was heated to 45° C. After 24 h, the reaction was cooled to 23° C., and filtered through celite. The filter cake was washed with tetrahydrofuran (100 mL), the filtrates combined, concentrated in vacuo, and purified by silica gel chromatography (eluant: 0.5-4% methanol/dichloromethane), affording 3-(2-(4-(pyridin-2-ylamino)phenoxy)pyridin-3-yl)cyclopentanol (94 mg, 49% yield). MS (ESI, pos. ion) m/z: 348.1 (M+1). IC50 (uM) 0.010.

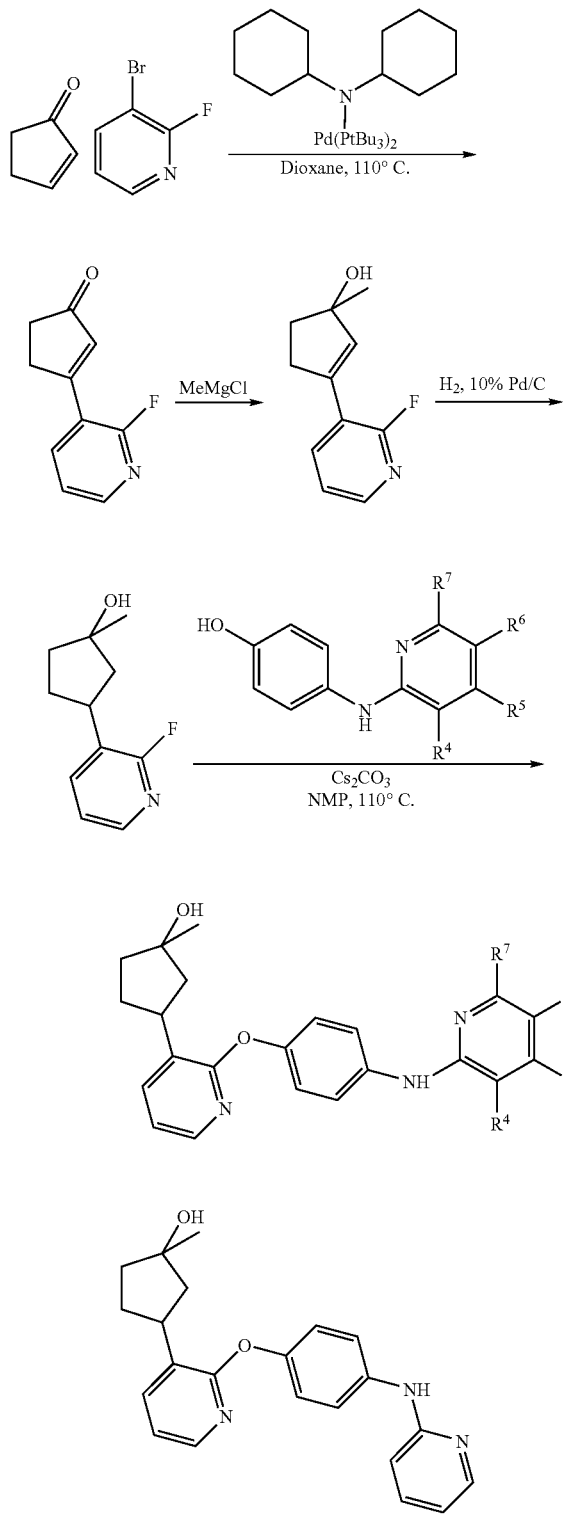

Example 244

1-METHYL-3-(2-(4-(PYRIDIN-2-YLAMINO)PHE-NOXY)PYRIDIN-3-YL)CYCLOPENTANOL

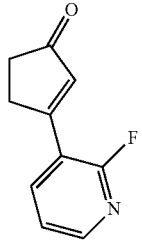 [SMILES: O=C1C=C(c2cccnc2F)CC1]

STEP 1: 3-(2-FLUOROPYRIDIN-3-YL)CYCLOPENT-2-ENONE

To a round bottom flask was added bis(tri-t-butyl)phosphine palladium (0.591 g, 1.156 mmol) before sealing and evacuating and backfilling with nitrogen. Subsequently, cyclopent-2-enone (7.48 mL, 93 mmol), N-cyclohexyl-N-methylcyclohexanamine (14.73 mL, 69.4 mmol), and 3-bromo-2-fluoropyridine (4.07 g, 23.13 mmol) were added before adding dioxane (25 mL). The reaction mixture was stirred under nitrogen at 110° C. for 16 h. The reaction mixture was cooled to room temperature and diluted with water and extracted with ethyl acetate before drying over magnesium sulfate, filtering, and concentrating under reduced pressure. The crude compound was purified by column chromatography (ethyl acetate/dichloromethane) to give 3-(2-fluoropyridin-3-yl)cyclopent-2-enone was afforded as an orange solid. MS (ESI, pos. ion) m/z: 178.0 (M+1).

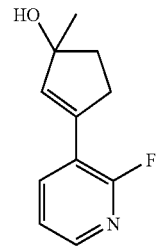

STEP 2: 3-(2-FLUOROPYRIDIN-3-YL)-1-METHYLCYCLOPENT-2-ENOL

To a solution of 3-(2-fluoropyridin-3-yl)cyclopent-2-enone (1 g, 5.64 mmol) in THF (28.2 mL) was added methylmagnesium bromide (4.70 mL, 14.11 mmol) dropwise over 5 minutes. The dark brown solution was stirred for 3 h at room temperature before. slowly quenching with aqueous ammonium chloride. The crude reaction was diluted with water and extracted with ethyl acetate, drying over magnesium sulfate, filtering, and concentrating to a dark brown oil under reduced pressure. The crude compound was purified by column chromatography (ethyl acetate/dichloromethane) to afford 3-(2-fluoropyridin-3-yl)-1-methylcyclopent-2-enol as a clear oil. MS (ESI, pos. ion) m/z: 194.1 (M+1).

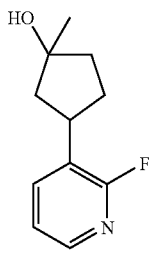

STEP 3: 3-(2-FLUOROPYRIDIN-3-YL)-1-METHYLCYCLOPENTANOL

To a 150 mL round bottom flask was added 3-(2-fluoropyridin-3-yl)-1-methylcyclopent-2-enol (282.8 mg, 1.449 mmol, 78% yield) and ethanol (14.900 ml) before adding palladium on carbon, 10% by weight (150 mg, 1.410 mmol) followed by a tetrahydrofuran (3.73 ml) rinse. The reaction vessel was purged of air and backfilled with hydrogen before stirring at room temperature for 2 h. The reaction mixture was filtered through a pad of Celite with ethyl acetate and concentrated under reduced pressure to a pale yellow oil. MS (ESI, pos. ion) m/z: 196.2 (M+1).

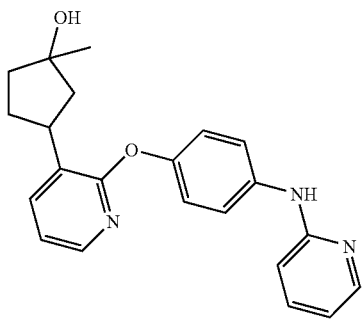 [SMILES: CC1(O)CCC(c2cccnc2Oc2ccc(Nc3ccccn3)cc2)C1]

STEP 4: 1-METHYL-3-(2-(4-(PYRIDIN-2-YLAMINO)PHENOXY)PYRIDIN-3-YL)CYCLOPENTANOL

To a 20 mL microwave vial was added cesium carbonate (834 mg, 2.56 mmol), 4-(pyridin-2-ylamino)phenol (191 mg, 1.024 mmol), and 3-(2-fluoropyridin-3-yl)-1-methylcyclopentanol (200 mg, 1.024 mmol) followed by NMP (2049 µL). The slurry was heated to 200° C. for 3 h in an Initiator microwave reactor (Personal Chemistry, Biotage AB, Inc., Upssala, Sweden). The reaction mixture was diluted with ethyl acetate (35 mL) and washed with 5N NaOH (5×30 mL) before drying over magnesium sulfate, filtering, and concentrating to a dark orange oil under reduced pressure. The oil was dissolved in 2 mL DMSO and transferred to a preparative HPLC vial through a 0.45 µm syringe filter. The crude compound was purified in three aliquots over 25 minutes per sample (5% 0.1% TFA in ACN:0.1% TFA in water to 80% over 15 minutes with a ten minute hold at 80%) on a Shimadzu Prominence Prep HPLC. The major peaks were collected and diluted with DCM (40 mL) before washed with saturated aqueous sodium bicarbonate (3×40 mL), drying over magnesium sulfate, filtering, and concentrating under reduced pressure, yielding the product as a yellow oil. MS (ESI, pos. ion) m/z: 362.3 (M+1). IC50 (uM) 0.035.

SCHEME 30

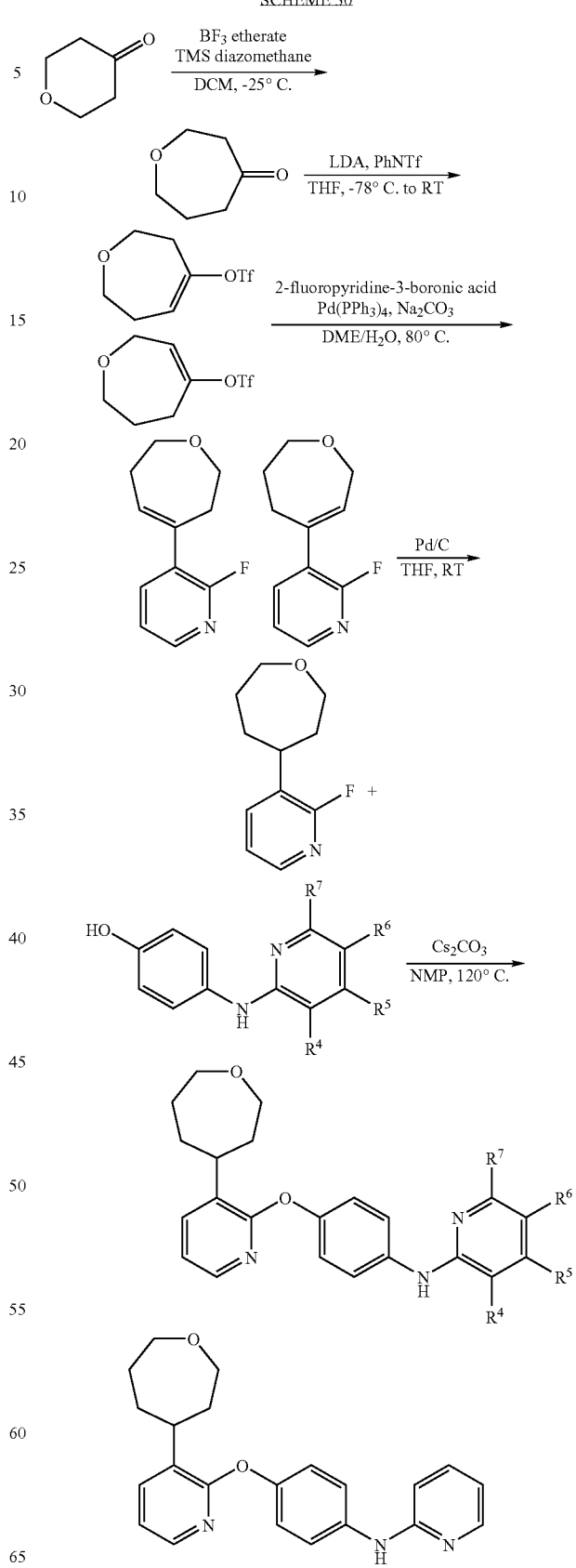

Example 245

N-(4-(3-(OXEPAN-4-YL)PYRIDIN-2-YLOXY)PHENYL)PYRIDIN-2-AMINE

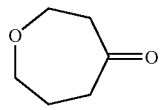

STEP 1. OXEPAN-4-ONE

To a stirred solution of dihydro-2H-pyran-4(3H)-one (9.23 mL, 100 mmol) and boron trifluoride diethyl etherate (13.80 mL, 110 mmol) in DCM (400 mL) at −25° C. was added (trimethylsilyl)diazomethane (54.90 mL, 110 mmol, 2.0 M in hexanes) slowly via syringe. The reaction mixture was stirred at −25° C. for 2.5 h. The reaction mixture was diluted with water and extracted with DCM. The organic layer was separated, washed with 10:1 sat. ammonium chloride:ammonium hydroxide, washed with sat. sodium chloride, dried over magnesium sulfate, filtered, and concentrated in vacuo. The resulting crude product was purified by silica gel chromatography to give oxepan-4-one.

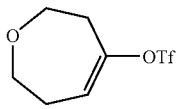 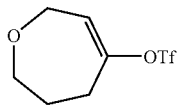

STEP 2. (E)-2,3,6,7-TETRAHYDROOXEPIN-4-YL TRIFLUOROMETHANESULFONATE AND (E)-2,5,6,7-TETRAHYDROOXEPIN-4-YL TRIFLUOROMETHANESULFONATE

To a stirred solution of diisopropylamine (1.97 mL, 14.1 mmol) in THF (20 mL) at −78° C. under an argon atmosphere was added n-butyllithium (5.40 mL, 13.50 mmol, 2.5 M in hexanes). The mixture was stirred for approximately 35 min before oxepan-4-one (1.34 g, 11.74 mmol) in THF (7 mL) was added slowly via syringe. The mixture was stirred for an additional 30 min at −78° C. before n-phenyltrifluoromethanesulfonimide (4.19 g, 11.74 mmol) in THF (10 mL) was added slowly via syringe. The reaction mixture was then stirred overnight with gradual warming to room temperature. The mixture was partially concentrated in vacuo and then partitioned between 3:1 EtOAc:hexanes and water. The organic layer was separated, washed with water (2×), washed once with sat. sodium chloride, dried over magnesium sulfate, and concentrated in vacuo to yield approximately a 7:3 mixture of (E)-2,3,6,7-tetrahydrooxepin-4-yl trifluoromethanesulfonate:(E)-2,5,6,7-tetrahydrooxepin-4-yltrifluoromethanesulfonate. The crude material was taken on to the next step without further purification.

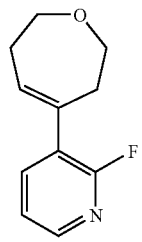 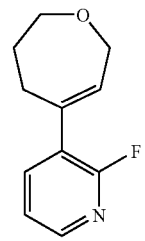

STEP 3. (E)-2-FLUORO-3-(2,3,6,7-TETRAHYDROOXEPIN-4-YL)PYRIDINE AND (E)-2-FLUORO-3-(2,5,6,7-TETRAHYDROOXEPIN-4-YL)PYRIDINE

Sodium carbonate (15.2 mL, 30.3 mmol. 2.0 M in water) was added via syringe to a stirred mixture of an approximately 7:3 mixture of (E)-2,3,6,7-tetrahydrooxepin-4-yl trifluoromethanesulfonate:(E)-2,5,6,7-tetrahydrooxepin-4-yl-trifluoromethanesulfonate (2.49 g, 10.11 mmol), 2-fluoro-3-pyridineboronic acid (1.43 g, 10.11 mmol), and tetrakis(triphenylphosphine)palladium (0.58 g, 0.51 mmol) in 1,2-dimethoxyethane (40 mL) under an argon atmosphere. The reaction mixture was stirred at 80° C. for 3 h. The reaction mixture was cooled to room temperature, diluted with water, and extracted with EtOAc. The organic layer was separated, washed with sat. sodium chloride, dried over magnesium sulfate, filtered, and concentrated in vacuo. The resulting crude product was purified by silica gel chromatography to give approximately a 7:3 mixture of (E)-2-fluoro-3-(2,3,6,7-tetrahydrooxepin-4-yl)pyridine and (E)-2-fluoro-3-(2,5,6,7-tetrahydrooxepin-4-yl)pyridine. MS (ESI, pos. ion) m/z: 194.1 (M+1).

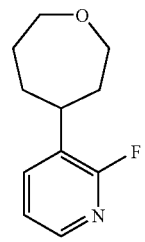 [SMILES: Fc1ncccc1C1CCCOCC1]

STEP 4. 2-FLUORO-3-(OXEPAN-4-YL)PYRIDINE

Palladium (0.20 g, 0.0188 mmol, 10% wt. on activated carbon) was added to a stirred solution of an approximately 7:3 mixture of (E)-2-fluoro-3-(2,3,6,7-tetrahydrooxepin-4-yl)pyridine:(E)-2-fluoro-3-(2,5,6,7-tetrahydrooxepin-4-yl)pyridine (0.75 g, 3.88 mmol) in THF (15 mL). The reaction mixture was placed under a hydrogen atmosphere (balloon) and stirred at room temperature for 4.5 h. The reaction mixture was filtered through Celite, and the filtrate was concentrated in vacuo to give 2-fluoro-3-(oxepan-4-yl)pyridine. MS (ESI, pos. ion) m/z: 196.1 (M+1).

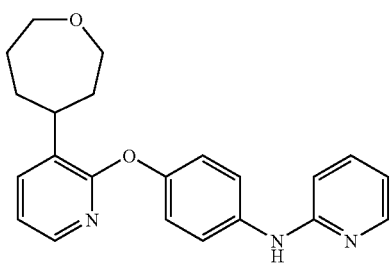

STEP 5. N-(4-(3-(OXEPAN-4-YL)PYRIDIN-2-YLOXY)PHENYL)PYRIDIN-2-AMINE

2-Fluoro-3-(oxepan-4-yl)pyridine (0.061 g, 0.31 mmol), 4-(pyridin-2-ylamino)phenol (0.18 g, 0.94 mmol), and cesium carbonate (0.31 g, 0.94 mmol) were mixed in NMP (0.75 mL). The reaction mixture was placed under a nitrogen atmosphere and stirred at 120° C. for 17 h. The reaction mixture was cooled to room temperature, diluted with water, and extracted with EtOAc (2×). The combined organic layers were washed with 1 M aqueous sodium hydroxide, washed with sat. sodium chloride, dried over magnesium sulfate, and concentrated in vacuo. The resulting crude product was purified by silica gel chromatography to give N-(4-(3-(oxepan-4-yl)pyridin-2-yloxy)phenyl)pyridin-2-amine MS (ESI, pos. ion) m/z: 362.2 (M+1). IC50 (uM) 0.026.

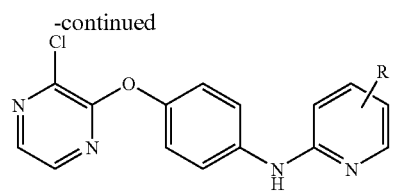

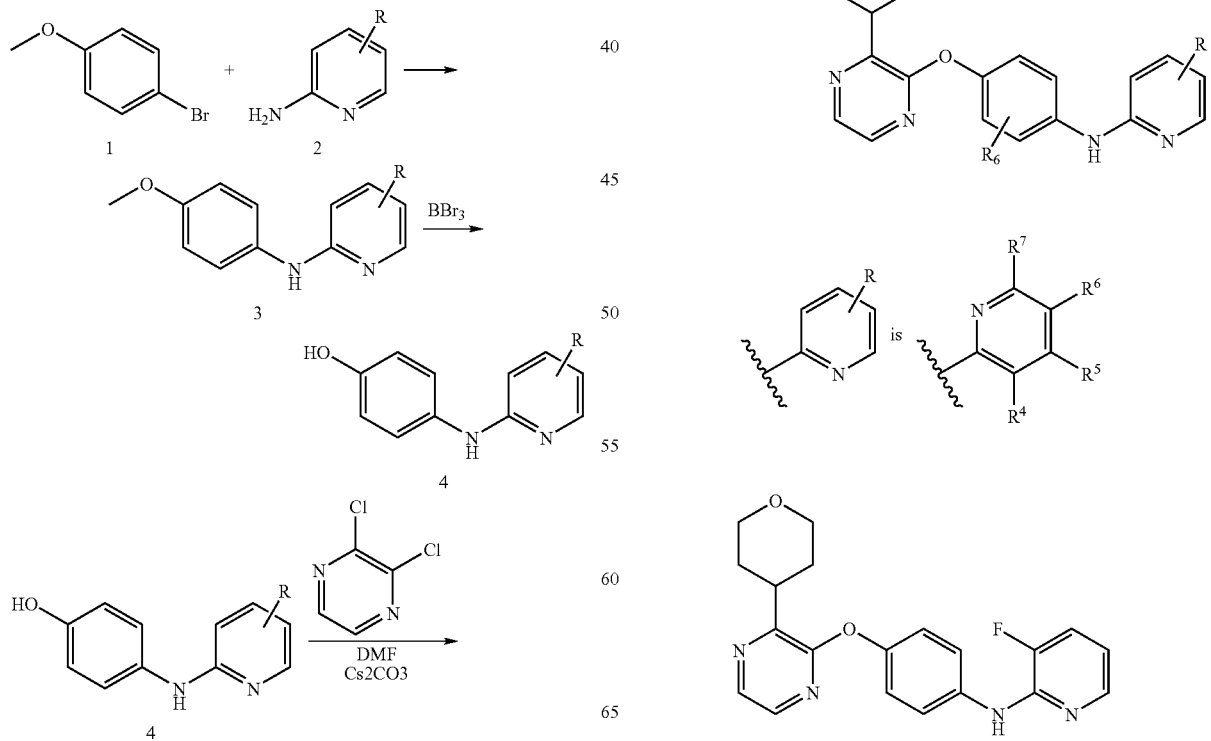

Example 246

3-FLUORO-N-(4-(3-(TETRAHYDRO-2H-PYRAN-4-YL)PYRAZIN-2-YLOXY)PHENYL)PYRIDIN-2-AMINE

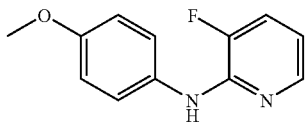 [SMILES: COc1ccc(Nc2ncccc2F)cc1]

STEP 1. 3-FLUORO-N-(4-METHOXY-PHENYL)PYRIDIN-2-AMINE

A solution of the 4-bromo aninsole (1.0 g, 0.0053 mol), 2-amino-3-fluoropyridine(0.9 g, 0.0080 mol.) and sodiuma tert-butoxide(1.017 g, 0.01 mol.) in 20 mL of toluene was purged by nitrogen for 15 mins. Then $Pd_2(dba)_3$ (75 mg, 0.10 mmol) and di-tert-butyl(2',4',6'-triisopropylbiphenyl-2-yl)phosphine) (0.112 g, 0.260 mmol) were added and the mixture was further degassed for 15 min. The reaction mixture was heated to 100° C. for 3.0 h. After cooling to RT, the reaction mixture was diluted with water and extracted by ethyl acetate(20×3 ml). Combined ethylacetate layers were filtered through celite and washed with ethyl acetate. The filtrate was dried over sodium sulfate and concentrated. The crude product was purified by column chromatography (Silica: 100-200 mess, Solvent: 15% Ethyl acetate:Hexane) to give the desired product. MS (ESI, pos. ion) m/z: 219.19 (M+1).

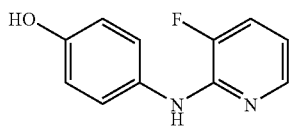 [SMILES: Oc1ccc(Nc2ncccc2F)cc1]

STEP 2. 4-(3-FLUOROPYRIDIN-2-YLAMINO)PHENOL

The solution of 3-fluoro-N-(4-methoxyphenyl)pyridin-2-amine (0.50 g, 0.002 mol) in DCM (20 mL) was cooled to −40° C. and to it was added boron tribromide (1.14 g, 0.0045 mol) dropwise under nitrogen over 30 mins. The reaction mixture was stirred at −40° C. for 1 h then at RT for another 2 h. The reaction mixture was cooled at 0° C. and saturated sodium bicarbonate was added. After stirring for 30 mins, the reaction was extracted with ethyl acetate (20×3 mL). Combined organic extracts were dried over sodium sulfate and concentrated to give the desired product which was used directly in the next step. MS (ESI, pos. ion) m/z: 205.19 (M+1).

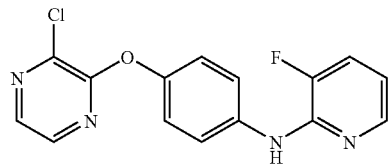 [SMILES: Fc1cccnc1Nc1ccc(Oc2nccnc2Cl)cc1]

STEP 3. N-(4-(3-CHLOROPYRAZIN-2-YLOXY)PHENYL)-3-FLUOROPYRIDIN-2-AMINE

To a solution of 4-(3-fluoropyridin-2-ylamino)phenol (1.0 g, 0.048 mol) and 2,3-dichloropyrazine (1.01 g, 0.006 mol) in DMF (10 mL) was added potassium carbonate (1.32 g, 0.0096 mol). The reaction mixture was heated to 100° C. for overnight. After cooling to RT, the reaction mixture was concentrated under high vacuum and diluted with water to get precipitate. After stirring for 1 h, the solid was collected by filtration, washed with water and ether, dried to give desired product as tan solid. MS (ESI, pos. ion) m/z: 317.05 (M+1).

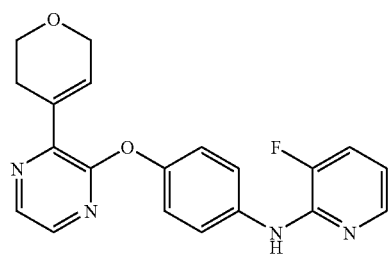 [SMILES: Fc1cccnc1Nc1ccc(Oc2nccnc2C2=CCOCC2)cc1]

STEP 4. N-(4-(3-(3,6-DIHYDRO-2H-PYRAN-4-YL)PYRAZIN-2-YLOXY)PHENYL)-3-FLUORO-PYRIDIN-2-AMINE

To a glass microwave vial was added N-(4-(3-chloropyrazin-2-yloxy)phenyl)-3-fluoropyridin-2-amine (0.2824 g, 0.892 mmol), 2-(3,6-dihydro-2H-pyran-4-yl)-4,4,5,5-tetramethyl-1,3,2-dioxaborolane (0.281 g, 1.337 mmol), trans-dichlorobis(triphenylphosphine) palladium (II) (0.050 g, 0.071 mmol), and sodium carbonate (0.473 g, 4.46 mmol) in DME (2.378 mL) and Water (0.594 mL). The reaction mixture was stirred and heated in a Discover® model microwave reactor (CEM, Matthews, N.C.) at 100° C. for 20 min (60 watts, Powermax feature on, ramp time 5 min). The crude product was adsorbed onto a plug of silica gel and chromatographed to provide N-(4-(3-(3,6-dihydro-2H-pyran-4-yl)pyrazin-2-yloxy)phenyl)-3-fluoropyridin-2-amine. MS (ESI, pos. ion) m/z: 365.0 (M+1). IC50 (uM) 0.0.0217.

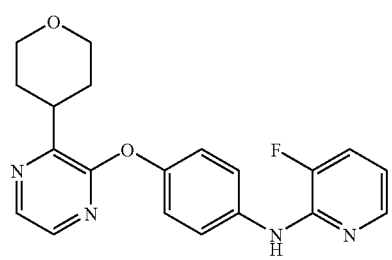 [SMILES: Fc1cccnc1Nc1ccc(Oc2nccnc2C2CCOCC2)cc1]

STEP 5. 3-FLUORO-N-(4-(3-(TETRAHYDRO-2H-PYRAN-4-YL)PYRAZIN-2-YLOXY)PHENYL)PYRIDIN-2-AMINE

To a round-bottomed flask was added N-(4-(3-(3,6-dihydro-2H-pyran-4-yl)pyrazin-2-yloxy)phenyl)-3-fluoropyridin-2-amine (0.1433 g, 0.393 mmol) in ethyl acetate. Palladium hydroxide (0.028 g, 0.039 mmol) was added. The rxn was placed under 40 psi pressure. The reaction mixture was filtered through celite. The crude product was adsorbed onto a plug of silica gel and chromatographed to provide 3-fluoro-N-(4-(3-(tetrahydro-2H-pyran-4-yl)pyrazin-2-yloxy)phenyl)pyridin-2-amine. MS (ESI, pos. ion) m/z: 367.1 (M+1). IC50 (uM) 0.01772.

TABLE XIA

EXAMPLES 247 TO 248 ARE TABULATED BELOW:

| Ex. No. | Compound Structure | Compound Name | MS | PDE10 IC50 (uM) |
|---|---|---|---|---|
| 247 | 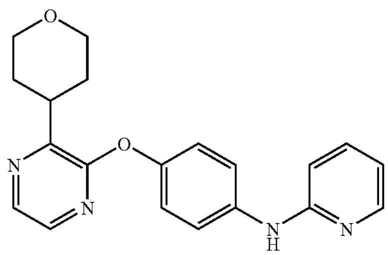 [SMILES: c1ccc(Nc2ccc(Oc3nccnc3C3CCOCC3)cc2)nc1] | 3,5-difluoro-N-(4-(3-(tetrahydro-2H-pyran-4-yl)pyridin-2-yloxy)phenyl)pyridin-2-amine | 349.1 | 0.006435 |
| 248 | 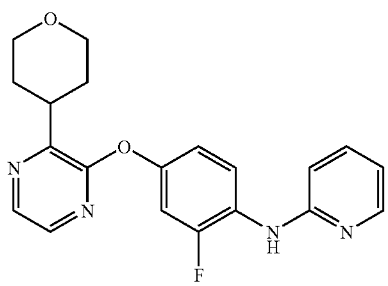 [SMILES: Fc1cc(Oc2nccnc2C2CCOCC2)ccc1Nc1ccccn1] | N-(2-Fluoro-4-(3-(tetrahydro-2H-pyran-4-yl)pyrazin-2-yloxy)phenyl)pyridin-2-amine | 367.1 | 0.02963 |

TABLE XIB

PREPARATION OF EXAMPLES 247 TO 248 ARE TABULATED BELOW:

| Ex. No. | Scheme | Starting material 1 | Starting material 2 | Conditions or reagents that differ from scheme |
|---|---|---|---|---|
| 247 | 31 | | | |
| 248 | 31 | | | |

SCHEME 32

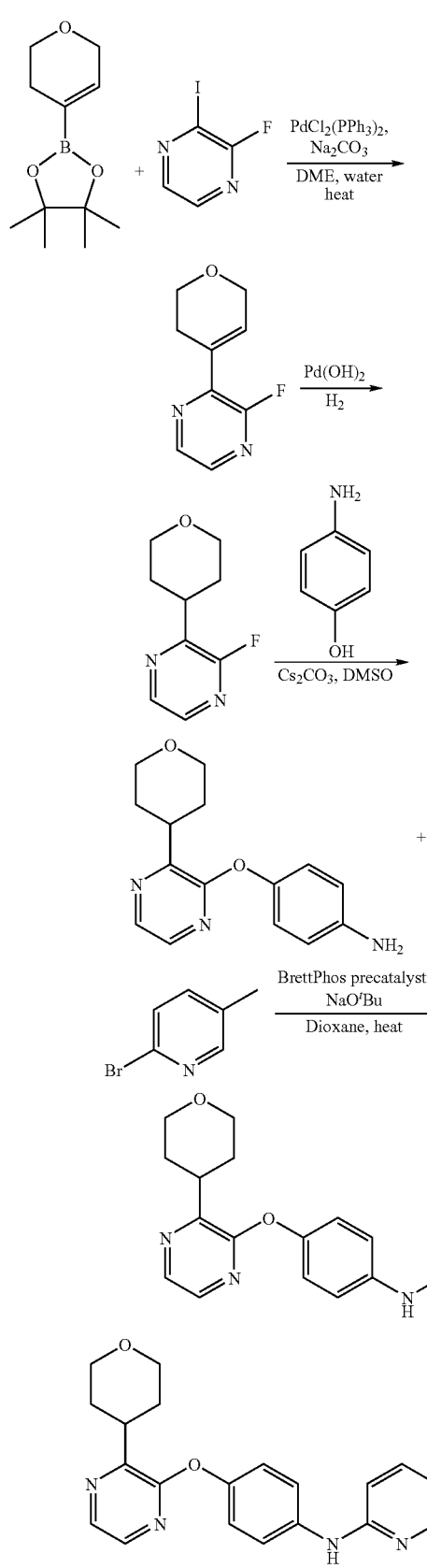

Example 249

5-METHYL-N-(4-(3-(TETRAHYDRO-2H-PYRAN-4-YL)PYRAZIN-2-YLOXY)PHENYL)PYRIDIN-2-AMINE

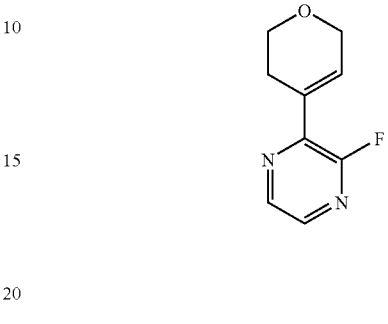

STEP 1. 2-(3,6-DIHYDRO-2H-PYRAN-4-YL)-3-FLUOROPYRAZINE

To a glass microwave vial was added 2-fluoro-3-iodopyrazine (1.6485 g, 7.36 mmol), 2-(3,6-dihydro-2H-pyran-4-yl)-4,4,5,5-tetramethyl-1,3,2-dioxaborolane (2.319 g, 11.04 mmol), trans-dichlorobis(triphenylphosphine) palladium (II) (0.413 g, 0.589 mmol), and sodium carbonate (3.90 g, 36.8 mmol) in DME (19.63 mL) and water (4.91 mL) to stir at 80° C. overnight. The reaction mixture was diluted with water and extracted with dichloromethane. The organic extract was washed with water, sat NaCl, dried with magnesium sulfate, filtered, and concentrated. The crude product was adsorbed onto a plug of silica gel and chromatographed to provide 2-(3,6-dihydro-2H-pyran-4-yl)-3-fluoropyrazine. MS (ESI, pos. ion) m/z: 181.1.

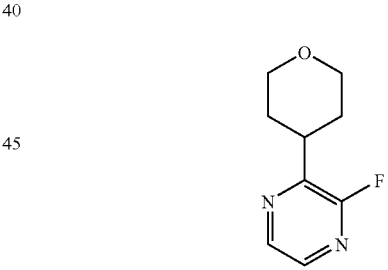

STEP 2. 2-FLUORO-3-(TETRAHYDRO-2H-PYRAN-4-YL)PYRAZINE

To a round-bottomed flask was added 2-(3,6-dihydro-2H-pyran-4-yl)-3-fluoropyrazine (1.1754 g, 6.52 mmol) and palladium hydroxide on carbon (0.458 g, 0.652 mmol) in EtOAc (21.75 mL). The reaction mixture was flushed with argon and then placed under vacuum three times. A hydrogen balloon was then attached to the reaction. After stirring overnight, the reaction mixture was filtered through celite and concentrated in vacuo to give the title compound. MS (ESI, pos. ion) m/z: 183.1.

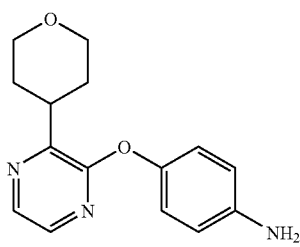 [SMILES: Nc1ccc(Oc2nccnc2C2CCOCC2)cc1]

STEP 3. 4-(3-(TETRAHYDRO-2H-PYRAN-4-YL) PYRAZIN-2-YLOXY)ANILINE

To a round-bottomed flask was added 2-fluoro-3-(tetrahydro-2H-pyran-4-yl)pyrazine (1.1147 g, 6.12 mmol), 4-aminophenol (0.801 g, 7.34 mmol), and cesium carbonate (5.98 g, 18.35 mmol) in DMSO (20.39 mL) at 110° C. to stir. The reaction mixture was diluted with water and extracted with dichloromethane. The organic extract was washed with water, brine, dried with magnesium sulfate, filtered, and concentrated. The crude product was adsorbed onto a plug of silica gel and chromatographed to provide 4-(3-(tetrahydro-2H-pyran-4-yl)pyrazin-2-yloxy)aniline. MS (ESI, pos. ion) m/z: 272.1.

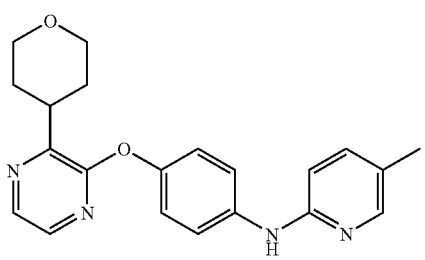 [SMILES: Cc1ccc(Nc2ccc(Oc3nccnc3C3CCOCC3)cc2)nc1]

STEP 4. 5-METHYL-N-(4-(3-(TETRAHYDRO-2H-PYRAN-4-YL)PYRAZIN-2-YLOXY)PHENYL) PYRIDIN-2-AMINE

A glass microwave reaction vessel was charged with 4-(3-(tetrahydro-2H-pyran-4-yl)pyrazin-2-yloxy)aniline (0.251 g, 0.925 mmol), 2-bromo-5-methylpyridine (0.133 g, 0.7708 mmol), BrettPHOS precatalyst (0.012 g, 0.015 mmol), and sodium tert-butoxide (0.185 g, 1.927 mmol). The flask was placed under vacuum then flushed with argon. Dioxane (2.57 mL) was added and the reaction was heated to 90° C. to stir overnight. The crude product was adsorbed onto a plug of silica gel and chromatographed to provide 5-methyl-N-(4-(3-(tetrahydro-2H-pyran-4-yl)pyrazin-2-yloxy)phenyl)pyridin-2-amine. MS (ESI, pos. ion) m/z: 363.1. IC50 (uM) 0.000178.

SCHEME 33

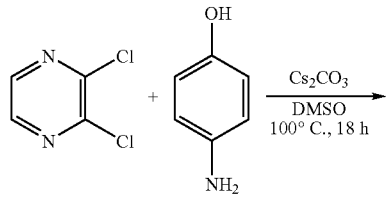

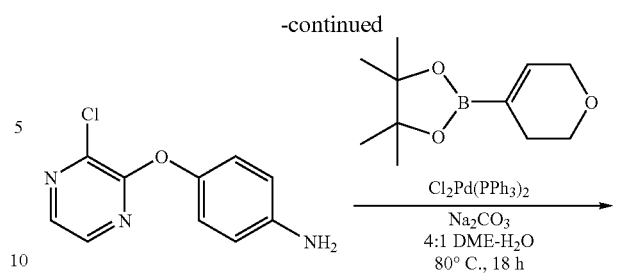

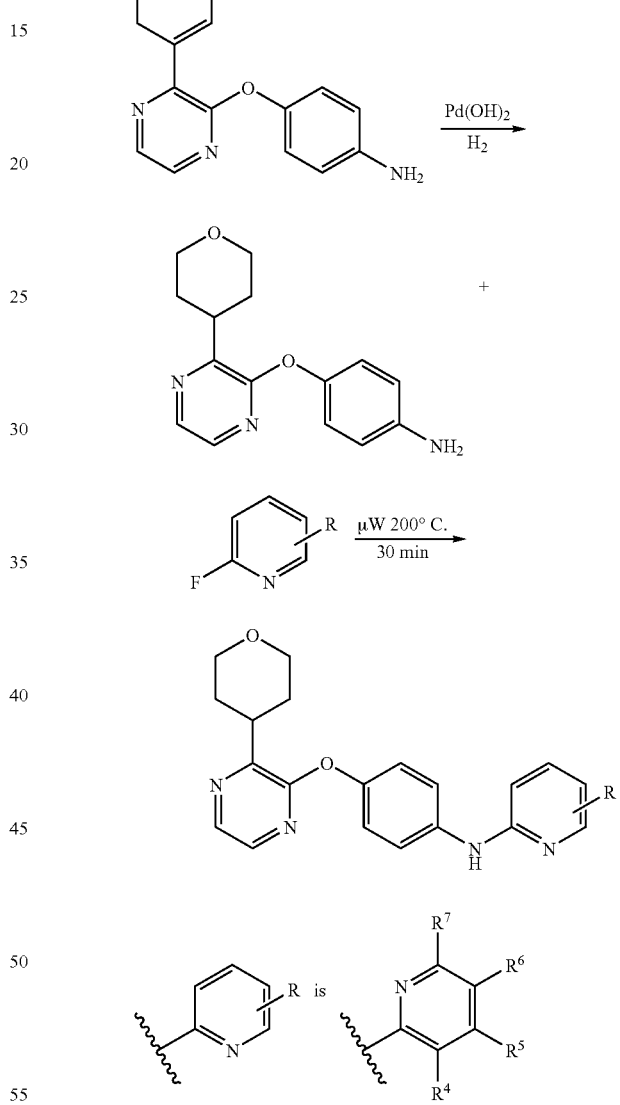

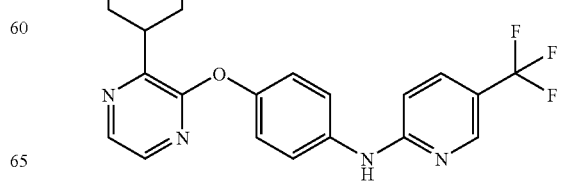

Example 250

N-(4-(3-(TETRAHYDRO-2H-PYRAN-4-YL)PYRAZIN-2-YLOXY)PHENYL)-5-(TRIFLUOROMETHYL)PYRIDIN-2-AMINE

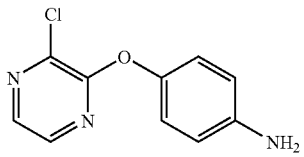 [SMILES: Nc1ccc(Oc2nccnc2Cl)cc1]

STEP 1. 4-(3-CHLOROPYRAZIN-2-YLOXY)ANILINE 2,3-Dichloropyrazine (2.67 mL, 25.6 mmol), 4-aminophenol (2.29 g, 21 mmol), and cesium carbonate (8.21 g, 25.2 mmol) in dimethyl sulfoxide (70 mL) under argon was stirred at 100° C. for 18 h. The cooled reaction mixture was poured into water (100 mL), resulting in the precipitation of a brick-colored solid. After stirring for 10 min, the brown slurry was filtered to give a relatively pure crop of 4-(3-chloropyrazin-2-yloxy)aniline (3.67 g, 79% yield) as a brick-colored solid. [M+1]=222.1.

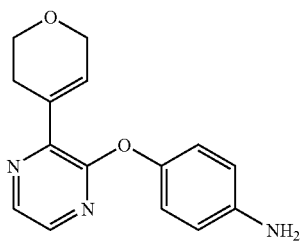 [SMILES: Nc1ccc(Oc2nccnc2C2=CCOCC2)cc1]

STEP 2. 4-(3-(3,6-DIHYDRO-2H-PYRAN-4-YL)PYRAZIN-2-YLOXY)ANILINE

Into a sealed tube were placed 4-(3-chloropyrazin-2-yloxy)aniline (1 g, 4.51 mmol), 2-(3,6-dihydro-2H-pyran-4-yl)-4,4,5,5-tetramethyl-1,3,2-dioxaborolane (1.42 g, 6.77 mmol), dichlorobis(triphenylphosphine) palladium (II) (0.25 g, 0.36 mmol), sodium carbonate (2.39 g, 22.5 mmol) and 18 mL of 4:1 DME-water. After the mixture was degassed for 5 min, the reaction was stirred at 80° C. for 18 h. The cooled reaction was diluted with CH$_2$Cl$_2$ and washed with aqueous saturated NaHCO$_3$ solution; the aqueous layer was back-extracted with CH$_2$Cl$_2$ (1×). The organic extracts were combined, dried (MgSO$_4$), filtered, and concentrated in vacuo. Flash column chromatography (10% to 50% EtOAc (10% MeOH)/Hexanes) afforded 4-(3-(3,6-dihydro-2H-pyran-4-yl)pyrazin-2-yloxy)aniline (1.09 g, 90% yield) as a light yellow solid. [M+1]=270.1.

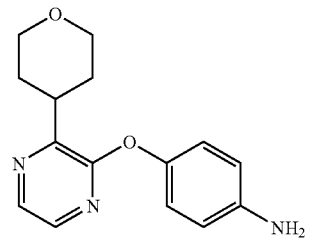 [SMILES: Nc1ccc(Oc2nccnc2C2CCOCC2)cc1]

STEP 3. 4-(3-(TETRAHYDRO-2H-PYRAN-4-YOPYRAZIN-2-YLOXY)ANILINE

A solution of 4-(3-(3,6-dihydro-2H-pyran-4-yl)pyrazin-2-yloxy)aniline (1.09 g, 4.0 mmol) in ethanol (40 mL) was added palladium hydroxide, 20 wt. % Pd (dry basis) on carbon, wet, Degussa type E101 NEW (0.284 g, 0.405 mmol) and hydrogenated (double-walled balloon pressure) at room temperature for 4 h. The reaction mixture was filtered via a pad of Celite, and the filtrate was concentrated in vacuo and chromatographed via flash column chromatography (20% to 80% EtOAc/Hexanes) to give 4-(3-(tetrahydro-2H-pyran-4-yl)pyrazin-2-yloxy)aniline (0.648 g, 59% yield) as a white solid. [M+1]=272.0.

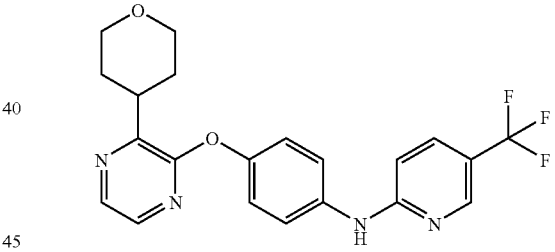

STEP 4. N-(4-(3-(TETRAHYDRO-2H-PYRAN-4-YL)PYRAZIN-2-YLOXY)PHENYL)-5-(TRIFLUOROMETHYL)PYRIDIN-2-AMINE 4-(3-(Tetrahydro-2H-pyran-4-yl)pyrazin-2-yloxy)aniline (0.1 g, 0.37 mmol) and 2-fluoro-5-(trifluoromethyl)puridine (0.073 mL, 0.44 mmol) were combined in a sealed tube and irradiated neat in a microwave synthesizer at 180° C. for 30 min, followed by 200° C. for 30 min. The cooled reaction mixture was directly chromatographed via flash column chromatography (15% to 50% EtOAc/Hexanes) to afford N-(4-(3-(tetrahydro-2H-pyran-4-yl)pyrazin-2-yloxy)phenyl)-5-(trifluoromethyl)pyridin-2-amine (0.105 g, 68.4% yield) as a white amorphous solid. MS (ESI, pos. ion) m/z: 417.0. IC50 (uM) 0.064.

TABLE XIIA

EXAMPLES 251 TO 252 ARE TABULATED BELOW:

| Ex. No. | Compound Structure | Compound Name | MS | PDE10 IC50 (uM) |
|---|---|---|---|---|
| 251 | 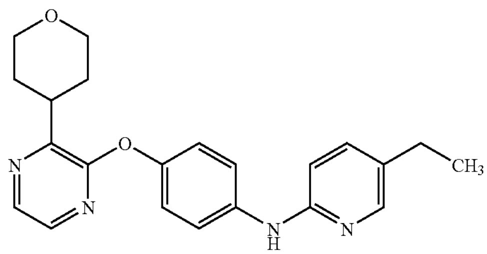 [SMILES: CCc1ccc(Nc2ccc(Oc3nccnc3C3CCOCC3)cc2)nc1] | 5-Ethyl-N-(4-(3-(tetrahydro-2H-pyran-4-yl)pyrazin-2-yloxy)phenyl)pyridin-2-amine | 377.1 | 0.003 |
| 252 | 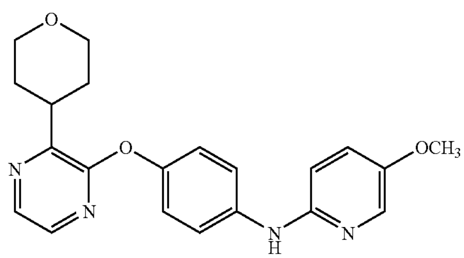 [SMILES: COc1ccc(Nc2ccc(Oc3nccnc3C3CCOCC3)cc2)nc1] | 5-Methoxy-N-(4-(3-(tetrahydro-2H-pyran-4-yl)pyrazin-2-yloxy)phenyl)pyridin-2-amine | 379.1 | 0.002 |

TABLE XIIB

PREPARATION OF EXAMPLES 251 TO 252 ARE TABULATED BELOW:

| Ex. No. | Scheme | Starting material 1 | Starting material 2 | Conditions or reagents that differ from scheme |
|---|---|---|---|---|
| 251 | 33 | | | |
| 252 | 33 | | | |

SCHEME 34

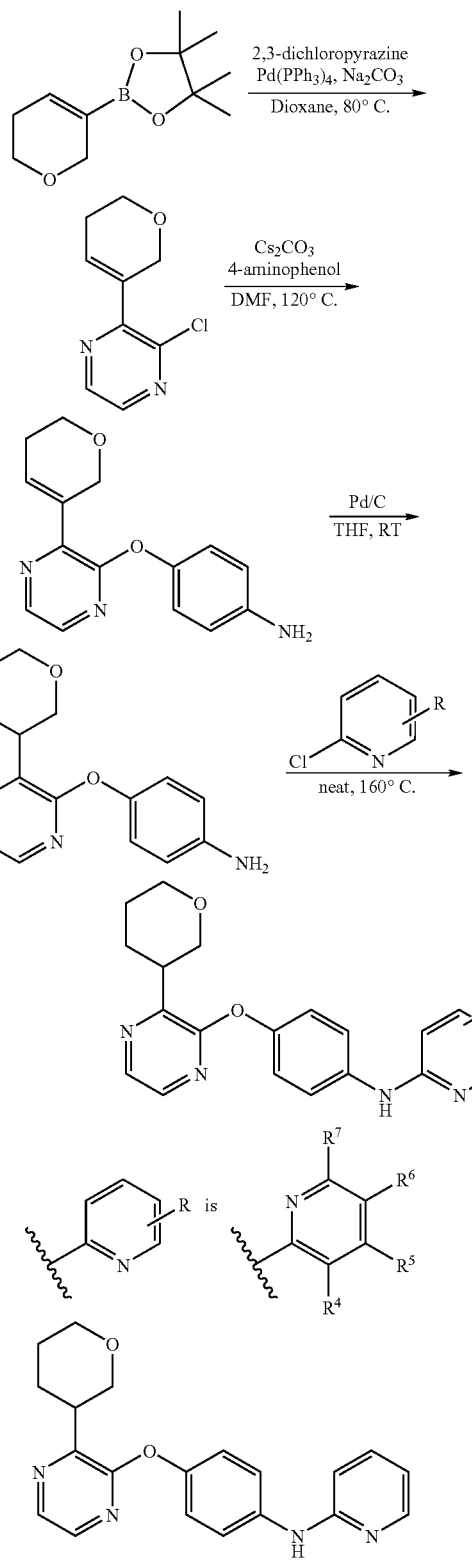

Example 253

N-(4-(3-(TETRAHYDRO-2H-PYRAN-3-YL)PYRAZIN-2-YLOXY)PHENYL)PYRIDIN-2-AMINE

STEP 1. 2-(5,6-DIHYDRO-2H-PYRAN-3-YL)-4,4,5,5-TETRAMETHYL-1,3,2-DIOXABOROLANE

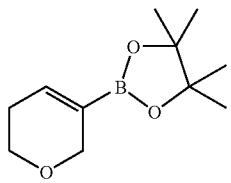

5,6-Dihydro-2H-pyran-3-yl trifluoromethanesulfonate (1.83 g, 7.88 mmol), 4,4,4',4',5,5,5',5'-octamethyl-2,2'-bi(1,3,2-dioxaborolane) (2.20 g, 8.67 mmol), [1-bis(diphenylphosphino)ferrocene]dichloride palladium(ii)complex with dichloromethane (0.193 g, 0.236 mmol), and potassium acetate (1.48 mL, 23.65 mmol) were mixed in dioxane (30 mL) under an argon atmosphere. The reaction mixture was stirred at 80° C. for 17 h. The reaction mixture was cooled to room temperature, diluted with water, and extracted with EtOAc. The organic layer was separated, washed with sat. aqueous sodium chloride, dried over magnesium sulfate, filtered, and concentrated in vacuo. The resulting crude product was purified by silica gel chromatography to give 2-(5,6-dihydro-2H-pyran-3-yl)-4,4,5,5-tetramethyl-1,3,2-dioxaborolane.

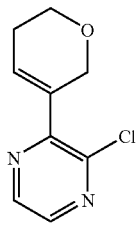 [SMILES: Clc1nccnc1C1=CCCOC1]

STEP 2. 2-CHLORO-3-(5,6-DIHYDRO-2H-PYRAN-3-YL)PYRAZINE

Sodium carbonate (6.48 mL, 12.95 mmol, 2.0 M in water) was added to a stirred mixture of 2,3-dichloropyrazine (1.28 mL, 8.63 mmol), 2-(5,6-dihydro-2H-pyran-3-yl)-4,4,5,5-tetramethyl-1,3,2-dioxaborolane (0.91 g, 4.32 mmol), and tetrakis(triphenylphosphine)palladium (0.50 g, 0.43 mmol) in dioxane (16 mL) under an argon atmosphere. The reaction mixture was stirred at 80° C. for 16 h before being cooled to room temperature and diluted with EtOAc. The mixture was washed with water, washed with sat. sodium chloride, dried over magnesium sulfate, filtered, and concentrated in vacuo. The resulting crude product was purified by silica gel chromatography to give 2-chloro-3-(5,6-dihydro-2H-pyran-3-yl)pyrazine. MS (ESI, pos. ion) m/z: 197.0 (M+1).

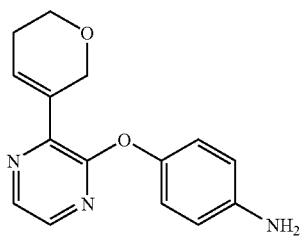 [SMILES: Nc1ccc(Oc2nccnc2C2=CCCOC2)cc1]

STEP 3. 4-(3-(5,6-DIHYDRO-2H-PYRAN-3-YL)PYRAZIN-2-YLOXY)ANILINE

2-Chloro-3-(5,6-dihydro-2H-pyran-3-yl)pyrazine (0.13 g, 0.68 mmol), 4-aminophenol (0.15 g, 1.35 mmol), and cesium carbonate (0.44 g, 1.35 mmol) were mixed in DMF (2 mL) in a microwave tube. The tube was sealed and placed under a nitrogen atmosphere. The reaction mixture was stirred at 120° C. for 2.5 h. The reaction mixture was cooled to room temperature and diluted with water. The resulting precipitate was filtered and washed with water to give 4-(3-(5,6-dihydro-2H-pyran-3-yl)pyrazin-2-yloxy)aniline. MS (ESI, pos. ion) m/z: 270.1 (M+1).

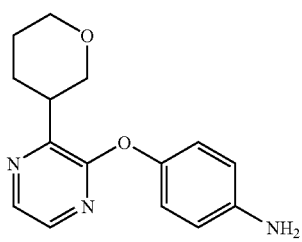 [SMILES: Nc1ccc(Oc2nccnc2C2CCCOC2)cc1]

STEP 4. 4-(3-(TETRAHYDRO-2H-PYRAN-3-YL)PYRAZIN-2-YLOXY)ANILINE

Palladium (10 mg, 0.0094 mmol, 10% wt. on activated carbon) was added to a stirred solution of 4-(3-(5,6-dihydro-2H-pyran-3-yl)pyrazin-2-yloxy)aniline (0.16 g, 0.59 mmol) in THF (3 mL). The reaction mixture was placed under a hydrogen atmosphere (balloon) and stirred at room temperature for 23 h. The reaction mixture was filtered through Celite, and the filtrate was concentrated in vacuo to give 4-(3-(tetrahydro-2H-pyran-3-yl)pyrazin-2-yloxy)aniline. MS (ESI, pos. ion) m/z: 272.1 (M+1).

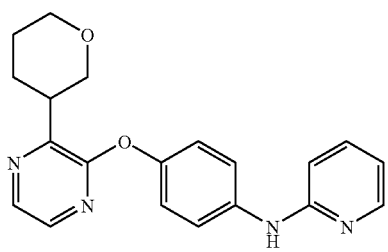 [SMILES: c1ccc(Nc2ccc(Oc3nccnc3C3CCCOC3)cc2)nc1]

STEP 5. N-(4-(3-(TETRAHYDRO-2H-PYRAN-3-YL)PYRAZIN-2-YLOXY)PHENYL)PYRIDIN-2-AMINE 4-(3-(Tetrahydro-2H-pyran-3-yl)pyrazin-2-yloxy)aniline (0.10 g, 0.38 mmol) and 2-chloropyridine (0.072 mL, 0.76 mmol) were mixed together neat in a microwave tube. The tube was sealed and stirred at 120° C. for 45 min before being warmed to 160° C. and stirred for 2 h. The reaction mixture was cooled to room temperature, diluted with sat. sodium bicarbonate, and extracted with EtOAc (2×). The combined organic layers were washed with sat. sodium chloride, dried over magnesium sulfate, filtered, and concentrated in vacuo. The resulting crude product was purified by silica gel chromatography to give N-(4-(3-(tetrahydro-2H-pyran-3-yl)pyrazin-2-yloxy)phenyl)pyridin-2-amine. MS (ESI, pos. ion) m/z: 349.1 (M+1). IC50 (uM) 0.021.

SCHEME 35A

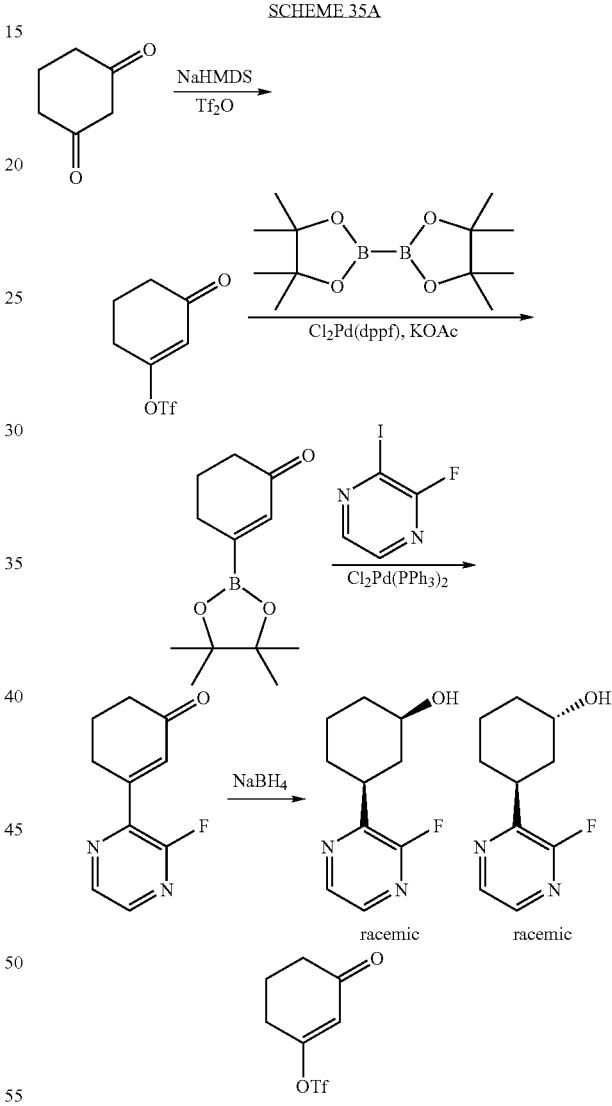

STEP 1: 3-OXOCYCLOHEX-1-ENYL TRIFLUOROMETHANESULFONATE

A 1.0M solution of sodium bis(trimethylsilyl)amide in THF (102 mL, 102 mmol) was added drop wise to a solution of cyclohexane-1,3-dione (11.4 g, 102 mmol) in THF (200 ml) at −50° C. The mixture was stirred at −50° C. for 15 min and trifluoromethanesulfonic anhydride (30.1 g, 107 mmol) was added through an addition funnel. After completion of the addition the reaction mixture was allowed to slowly warm to RT. The reaction mixture was then cooled to −30° C., and 200 mL of saturated aqueous sodium bicarbonate was added slowly. The solvent was removed under reduced pressure and the remaining aqueous layer was extracted with EtOAc (2×400 ml). The combined organic layers were washed with brine and dried over sodium sulfate. Filtration and concentration under reduced pressure, followed by flash chromatography on silica gel (0% to 10% EtOAc in hexanes) afforded 3-oxocyclohex-1-enyl trifluoromethanesulfonate as a yellow oil. MS (ESI, pos. ion) m/z: 245.0(M+1).

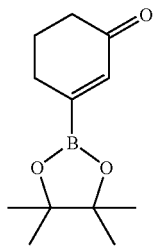 [SMILES: CC1(C)OB(C2=CC(=O)CCC2)OC1(C)C]

STEP 2. 3-(4,4,5,5-TETRAMETHYL-1,3,2-DIOXABOROLAN-2-YL)CYCLOHEX-2-ENONE

3-Oxocyclohex-1-enyl trifluoromethanesulfonate (9 g, 36.9 mmol), 4,4,4',4',5,5,5',5'-octamethyl-2,2'-bi(1,3,2-dioxaborolane) (10.30 g, 40.5 mmol), and potassium acetate (7.23 g, 73.7 mmol) were suspended in 100 ml dioxane. Argon was bubbled through the reaction mixture for 5 minutes, and dichloro 1,1'-bis(diphenylphosphino)ferrocene palladium (ii) (2.107 g, 2.58 mmol) was added. The mixture was stirred at 80° C. for 3 h, cooled to RT, and concentrated under reduced pressure. Water (300 ml) was added and the mixture was extracted with EtOAc (3×200 ml). The combined organic layer were washed by brine and dried over sodium sulfate. Filtration and concentration under reduced pressure, followed by flash chromatography on silica gel (0% to 20% EtOAc in hexanes) afforded 3-(4,4,5,5-tetramethyl-1,3,2-dioxaborolan-2-yl)cyclohex-2-enone as colorless crystals.

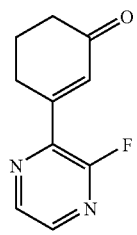 [SMILES: O=C1C=C(c2nccnc2F)CCC1]

STEP 3. 3-(3-FLUOROPYRAZIN-2-YL)CYCLOHEX-2-ENONE

2-Fluoro-3-iodopyrazine (2.5 g, 11.16 mmol), 3-(4,4,5,5-tetramethyl-1,3,2-dioxaborolan-2-yl)cyclohex-2-enone (3.10 g, 13.95 mmol), and sodium carbonate (3.55 g, 33.5 mmol) were suspended in DME (20 ml) and distilled water (5 ml). Argon was bubbled through the resulting mixture for 3 minutes, and dichlorobis(triphenylphosphino)palladium (ii) (0.431 g, 0.614 mmol) was added. The resulting mixture was stirred at 80° C. for 16 hours, the reaction was cooled to RT, and water (200 ml) was added. The resulting mixture was concentrated under reduced pressure and was extracted with EtOAc (3×200 ml). The combined organic layers were washed with brine and dried over sodium sulfate. Filtration and concentration under reduced pressure, followed by flash chromatography on silica gel (0% to 20% EtOAc in hexanes) afforded 3-(3-fluoropyrazin-2-yl)cyclohex-2-enone as a light yellow solid. MS (ESI, pos. ion) m/z: 193.1 (M+1).

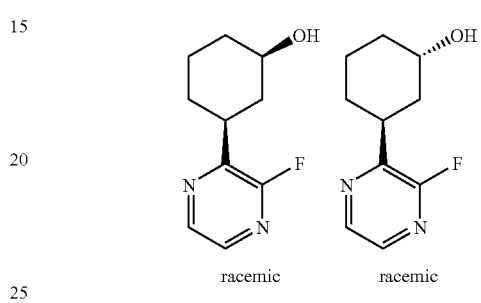

STEP 4. (RAC)-CIS-3-(3-FLUOROPYRAZIN-2-YL)CYCLOHEXANOL AND (RAC)-TRANS-3-(3-FLUOROPYRAZIN-2-YL)CYCLOHEXANOL

Sodium borohydride (295 mg, 7.80 mmol) was added was added portion wise to a solution of 3-(3-fluoropyrazin-2-yl)cyclohex-2-enone (500 mg, 2.60 mmol) in MeOH (15 ml) at RT. After completion of the addition the reaction mixture was stirred at RT for 30 minutes. It was then cooled in an ice-water bath, saturated aqueous ammonium chloride (25 ml) was added drop wise, and the resulting mixture was extracted with EtOAc (2×100 ml). The combined organic layers were washed with brine and dried over sodium sulfate. Filtration and concentration under reduced pressure, followed by flash chromatography on silica gel (0% to 20% EtOAc in hexanes) afforded (rac)-cis-3-(3-fluoropyrazin-2-yl)cyclohexanol and (rac)-trans-3-(3-fluoropyrazin-2-yl)cyclohexanol as colorless oils. MS (ESI, pos. ion) m/z: 197.0 (M+1) and MS (ESI, pos. ion) m/z: 197.0 (M+1), respectively.

SCHEME 35B

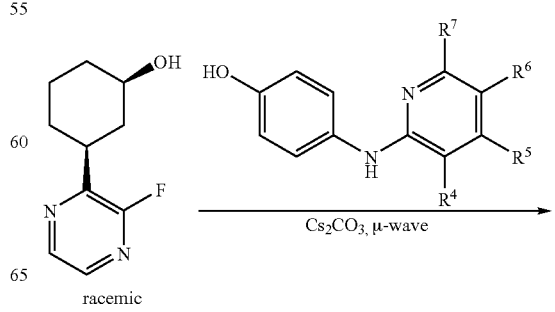

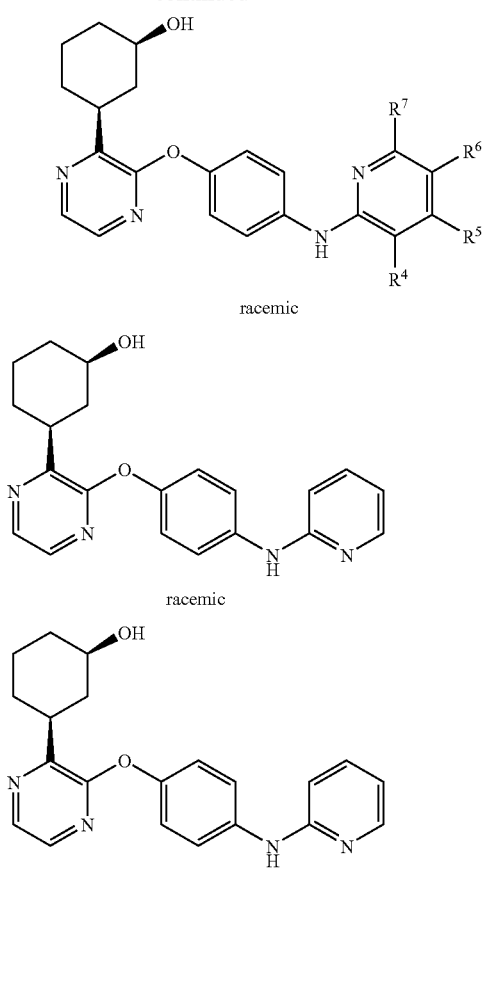

Example 254

(RAC)-CIS-3-(3-(4-(PYRIDIN-2-YLAMINO)PHE-NOXY)PYRAZIN-2-YL)CYCLOHEXANOL

A mixture of (rac)-cis-3-(3-fluoropyrazin-2-yl)cyclohexanol, prepared according to Scheme 35a, (48 mg, 0.245 mmol), 4-(pyridin-2-ylamino)phenol (91 mg, 0.489 mmol), and cesium carbonate (159 mg, 0.489 mmol) in NMP (2 mL) was heated in a Biotage™ microwave reactor at 150° C. for 0.5 h. The mixture was partitioned between $H_2O$ (10 ml) and $CH_2Cl_2$ (20 ml), the layers were separated, and the aqueous layer was extracted with $CH_2Cl_2$ (3×20 ml). The combined organic layers were dried ($MgSO_4$), concentrated under reduced pressure, and the resulting brown oil was purified by reversed phase HPLC (Gilson Gemini-NX 10u C18 110A, 100×50.0 mm, 10% to 95% $H_2O$/MeCN, 0.1% TFA). The product containing fractions were combined, neutralized by the addition of solid $Na_2CO_3$, and extracted with $CH_2Cl_2$ (3×20 mL). The combined organic layers were dried ($MgSO_4$) and concentrated under reduced pressure to deliver (rac)-cis-3-(3-(4-(pyridin-2-ylamino)phenoxy)pyrazin-2-yl)cyclohexanol as a light yellow solid. MS (ESI, pos. ion) m/z: 363.0 (M+1). IC50 (uM) 0.02837.

SCHEME 36

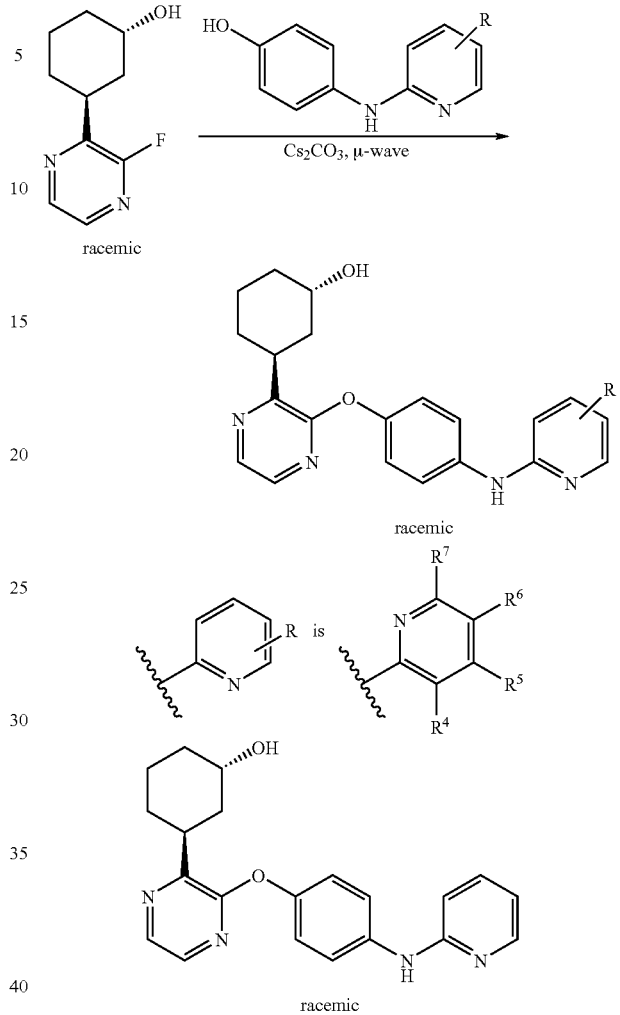

Example 255

(RAC)-TRANS-3-(3-(4-(PYRIDIN-2-YLAMINO)PHENOXY)PYRAZIN-2-YL)CYCLOHEXANOL

A mixture of (rac)-trans-3-(3-fluoropyrazin-2-yl)cyclohexanol (35 mg, 0.178 mmol), as prepared according to Scheme 35a, 4-(pyridin-2-ylamino)phenol (66.4 mg, 0.357 mmol), and cesium carbonate (116 mg, 0.357 mmol) in NMP (1 ml) was heated in a Biotage™ microwave reactor at 150° C. for 30 min. The mixture was partitioned between $H_2O$ (10 ml) and $CH_2Cl_2$ (20 ml), the layers were separated, and the aqueous layer was extracted with $CH_2Cl_2$ (3×20 ml). The combined organic layers were dried ($MgSO_4$), concentrated under reduced pressure, and the resulting brown oil was purified by reversed phase HPLC (Gilson Gemini-NX 10u C18 110A, 100×50.0 mm, 10% to 95% $H_2O$/MeCN, 0.1% TFA). The product containing fractions were combined, neutralized by the addition of solid $Na_2CO_3$, and extracted with $CH_2Cl_2$ (3×20 mL). The combined organic layers were dried ($MgSO_4$) and concentrated under reduced pressure to deliver (rac)-trans-3-(3-(4-(pyridin-2-ylamino)phenoxy)pyrazin-2-yl)cyclohexanol as a tan solid. MS (ESI, pos. ion) m/z: 363.0 (M+1). IC50 (uM) 0.01049.

SCHEME 37

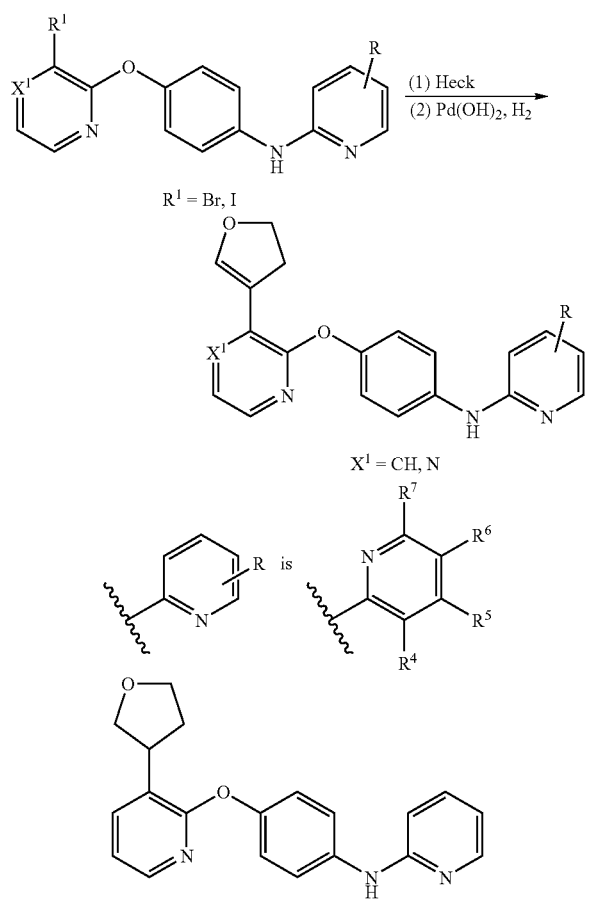

$R^1 =$ Br, I $X^1 =$ CH, N

R is

Example 256

N-(4-(3-(TETRAHYDROFURAN-3-YL)PYRIDIN-2-YLOXY)PHENYL)PYRIDIN-2-AMINE

A 20 mL microwave vessel containing N-(4-(3-bromopyridin-2-yloxy)phenyl)pyridin-2-amine (0.603 g, 1.762 mmol) and bis(tri-tert-butylphosphine)palladium (0) (0.094 g, 0.184 mmol) was capped under an atmosphere of argon. To the vessel was added DMF (3 mL), 2,5-dihydrofuran (0.700 mL, 9.26 mmol) and N-methyldicyclohexylamine (1.000 mL, 4.71 mmol). The vessel was heated at 80° C. for 8 h. The reaction mixture was diluted with THF (10 mL) and filtered. The the mixture was added palladium hydroxide, 20 wt % pd (dry basis) on carbon, wet, degussa type e101 ne/w (0.221 g, 0.315 mmol) under an atmosphere of argon. The mixture was evacuated/purged with hydrogen (balloon, 3×) and stirred at rt for 7 h. The reaction was filtered through a syringe filter and the filtrate was evaporated onto silica gel and purified by flash chromatography (Isco, (80 gram)) eluting with 2M $NH_3$ in $MeOH:CH_2Cl_2$ (0:1→3:97) to give 256 mg of a light-orange tar. The material was dissolved in MeOH and further purified by reverse-phase HPLC (Gilson; Gemini-NX 10 C18 110A AXIA, 100×50 mm column) eluting with 0.1% TFA-$H_2O$: 0.1% TFA $CH_3CN$ (9:1→1:9). The fractions containing the desired product were combined and concentrated in vacuo. The residue was dissolved in MeOH and loaded onto an SCX 2 cartridge eluting with MeOH then 2M $NH_3$ in MeOH to give a white crystalline solid. MS (ESI, pos. ion) m/z: 334.0 (M+1). IC50 (uM) 0.01027.

TABLE XIIIA

EXAMPLES 257 TO 263 ARE TABULATED BELOW:

| Ex. No. | Compound Structure | Compound Name | MS | PDE10 IC50 (uM) |
|---|---|---|---|---|
| 257 | 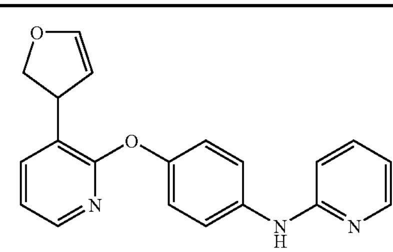 | N-(4-(3-(2,3-dihydrofuran-3-yl)pyridin-2-yloxy)phenyl)pyridin-2-amine | 332 | 0.06603 |
| 258 | 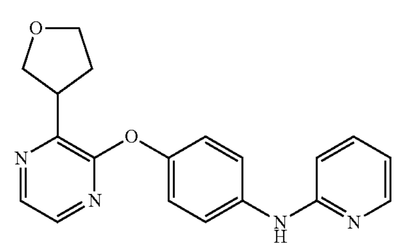 [SMILES: c1ccc(Nc2ccc(Oc3nccnc3C3CCOC3)cc2)nc1] | N-(4-(3-(tetrahydrofuran-3-yl)pyrazin-2-yloxy)phenyl)pyridin-2-amine | 335 | 0.01785 |

TABLE XIIIA-continued

EXAMPLES 257 TO 263 ARE TABULATED BELOW:

| Ex. No. | Compound Structure | Compound Name | MS | PDE10 IC50 (uM) |
|---|---|---|---|---|
| 259 | 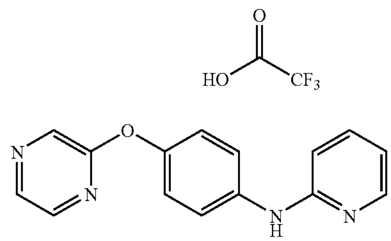 | N-(4-(pyrazin-2-yloxy)phenyl)pyridin-2-amine 2,2,2-trifluoroacetate | 265 | 1.274 |
| 260 | 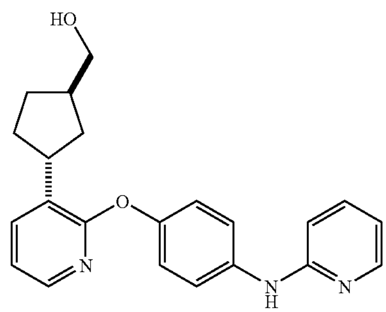 | ((1R,3R)-3-(2-(4-(pyridin-2-ylamino)phenoxy)pyridin-3-yl)cyclopentyl)methanol | 362 | 0.01122 |
| 261 | 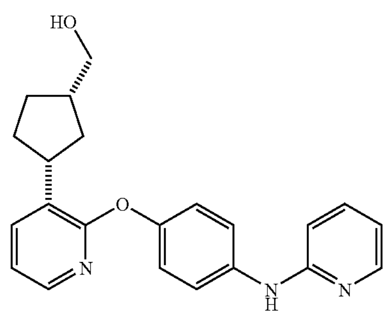 | ((1S,3R)-3-(2-(4-(pyridin-2-ylamino)phenoxy)pyridin-3-yl)cyclopentyl)methanol | 362 | 0.01269 |
| 262 | 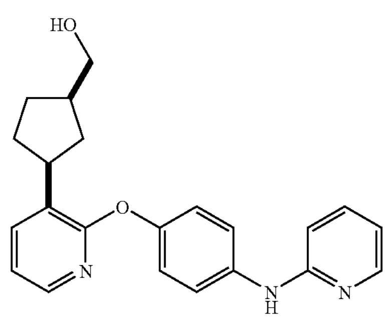 | ((1R,3S)-3-(2-(4-(pyridin-2-ylamino)phenoxy)pyridin-3-yl)cyclopentyl)methanol | 362 | 0.01486 |
| 263 | 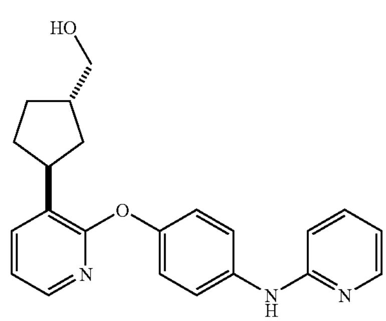 | ((1S,3S)-3-(2-(4-(pyridin-2-ylamino)phenoxy)pyridin-3-yl)cyclopentyl)methanol | 362 | 0.01263 |

TABLE XIIIB

PREPARATION OF EXAMPLES 257 TO 263 ARE TABULATED BELOW:

| Ex. No. | Scheme | Starting material 1 | Starting material 2 | Conditions or reagents that differ from scheme |
|---|---|---|---|---|
| 257 | 37 | (2,5-dihydrofuran) | 3-iodo-2-[4-(pyridin-2-ylamino)phenoxy]pyridine | Pd(OAc)$_2$, Bu$_4$NCl, NaOAc, DMF, RT 2.5 d |
| 258 | 37 | (2,5-dihydrofuran) | 3-chloro-2-[4-(pyridin-2-ylamino)phenoxy]pyrazine | Purified by reversed phase HPLC; free-based |
| 259 | 37 | | By-product of above reaction | Purified by reversed phase HPLC |
| 260 | 37 | (cyclopent-3-enyl)methanol | 3-bromo-2-[4-(pyridin-2-ylamino)phenoxy]pyridine · HCl | Purified by chiral separation; absolute stereochemistry arbitrarily assigned |
| 261 | 37 | (cyclopent-3-enyl)methanol | 3-bromo-2-[4-(pyridin-2-ylamino)phenoxy]pyridine · HCl | Purified by chiral separation; absolute stereochemistry arbitrarily assigned |
| 262 | 37 | (cyclopent-3-enyl)methanol | 3-bromo-2-[4-(pyridin-2-ylamino)phenoxy]pyridine · HCl | Purified by chiral separation; absolute stereochemistry arbitrarily assigned |
| 263 | 37 | (cyclopent-3-enyl)methanol | 3-bromo-2-[4-(pyridin-2-ylamino)phenoxy]pyridine · HCl | Purified by chiral separation; absolute stereochemistry arbitrarily assigned |

SCHEME 38

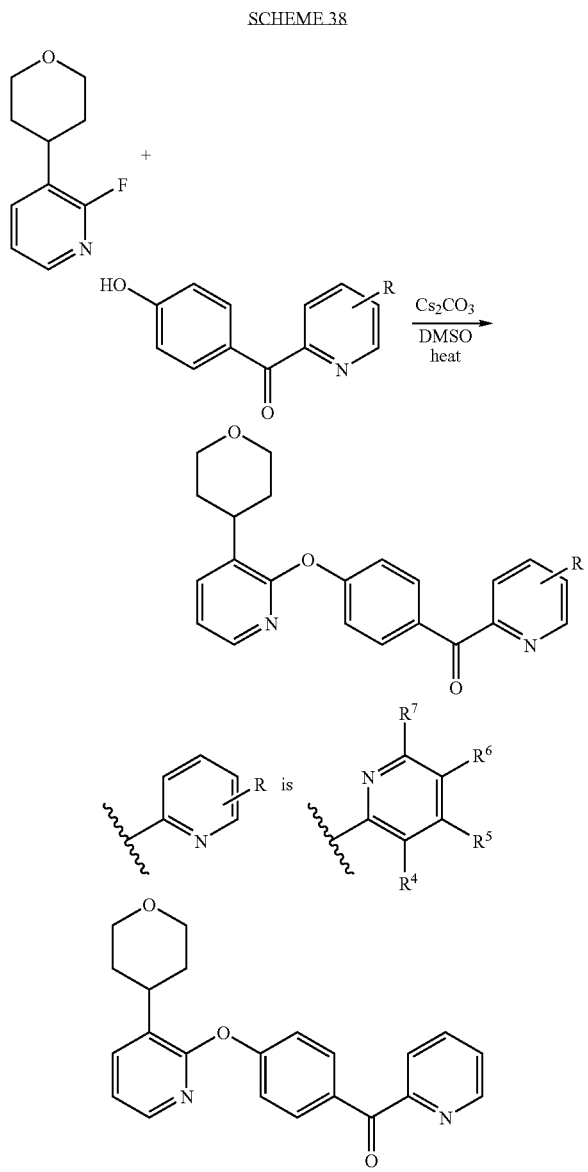

Example 264

PYRIDIN-2-YL(4-(3-(TETRAHYDRO-2H-PYRAN-4-YL)PYRIDIN-2-YLOXY)PHENYL)METHANONE

A glass microwave reaction vessel was charged with 2-fluoro-3-(tetrahydro-2H-pyran-4-yl)pyridine (0.4000 g, 2.207 mmol), (4-hydroxyphenyl)(pyridin-2-yl)methanone (0.660 g, 3.31 mmol), and cesium carbonate (2.158 g, 6.62 mmol) in N-Methyl-2-pyrrolidinone (7.36 mL). The reaction mixture was stirred and heated in a Biotage Initiator microwave reactor at 180° C. for 30 min. The reaction mixture was diluted with water and extracted with dichloromethane. The organic extract was washed with water, sat NaCl, dried with magnesium sulfate, filtered, and concentrated. The crude product was purified by chromatography to give the title compound. MS (ESI, pos. ion) m/z: 361.0 (M+1). IC50 (uM) 0.5561.

SCHEME 39

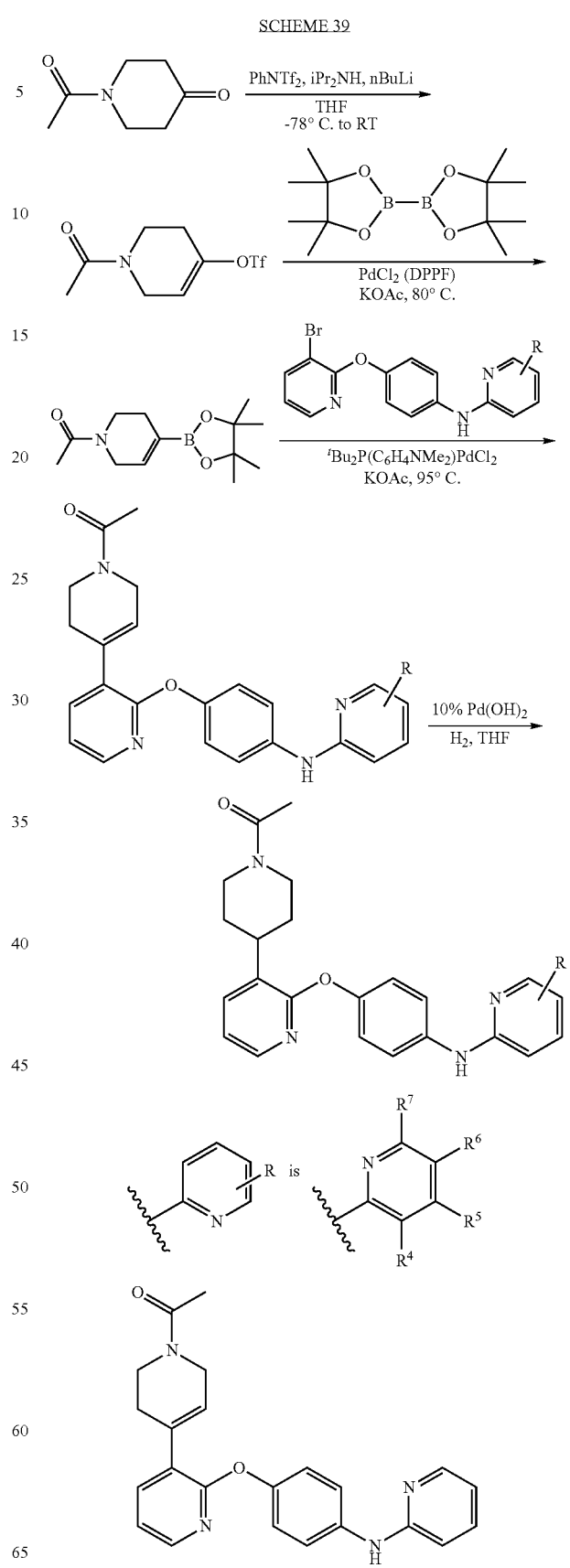

Example 265

1-(4-(2-(4-(PYRIDIN-2-YLAMINO)PHENOXY)PYRIDIN-3-YL)-5,6-DIHYDROPYRIDIN-1(2H)-YL)ETHANONE

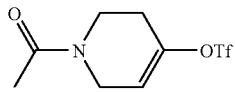 [SMILES: CC(=O)N1CC=C(OS(=O)(=O)C(F)(F)F)CC1]

STEP 1. 1-ACETYL-1,2,3,6-TETRAHYDROPYRIDIN-4-YL TRIFLUOROMETHANESULFONATE

Diisopropylamine (18.0 mL, 128 mmol) was taken up in 50 mL of THF and chilled to −78° C. Butyllithium, 2.5 M in hexanes (51.0 mL, 128 mmol) was added dropwise. After 10 min, 1-acetylpiperidin-4-one (15.0 g, 106 mmol) was added in 60 mL of THF with rigorous stirring. After 30 min, n-phenyltriflimide (41.8 g, 117 mmol) was added dropwise in 120 mL of THF. The reaction mixture was stirred at −78° C. for 1 h, then allowed to slowly warm to RT for 16 h. The reaction mixture was quenched by saturated NaHCO₃, followed by extraction with EtOAc and 5% citric acid. The organic layer was washed with 1 N NaOH (2×), water (2×), and brine, then dried over MgSO₄. Filtration and concentration under reduced pressure, followed by flash chromatography on silica gel (0% to 60% EtOAc/hexanes) afforded 1-acetyl-1,2,3,6-tetrahydropyridin-4-yl trifluoromethanesulfonate as a yellow oil.

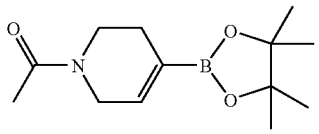 [SMILES: CC(=O)N1CC=C(B2OC(C)(C)C(C)(C)O2)CC1]

STEP 2. 1-(4-(4,4,5,5-TETRAMETHYL-1,3,2-DIOXABOROLAN-2-YL)-5,6-DIHYDROPYRIDIN-1(2H)-YL)ETHANONE 1-acetyl-1,2,3,6-tetrahydropyridin-4-yl trifluoromethanesulfonate (6.77 g, 24.8 mmol), bis(pinacolato)diboron (6.92 g, 27.3 mmol), potassium acetate (2.93 g, 49.6 mmol), and 1,1′-bis(diphenylphosphino)ferrocene]dichloride palladium (ii)complex with dichloramethane (1.01 g, 1.24 mmol) were taken up in dioxane (83 mL). The mixture was purged with nitrogen and then was heated to 80° C. After 16 h, the reaction mixture was cooled to RT, diluted with 150 mL of EtOAc and washed with 50 mL of water and 50 mL of brine, then dried over MgSO₄. Filtration and concentration under reduced pressure, followed by flash chromatography on silica gel (0% to 90% EtOAc/hexanes) afforded 1-(4-(4,4,5,5-tetramethyl-1,3,2-dioxaborolan-2-yl)-5,6-dihydropyridin-1(2H)-yl)ethanone as an orange oil. MS (ESI, pos. ion) m/z: 252.1 (M+1).

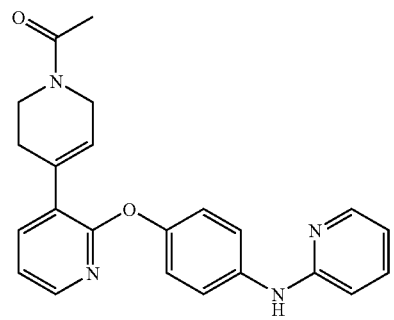 [SMILES: CC(=O)N1CC=C(c2cccnc2Oc2ccc(Nc3ccccn3)cc2)CC1]

STEP 3. 1-(4-(2-(4-(PYRIDIN-2-YLAMINO)PHENOXY)PYRIDIN-3-YL)-5,6-DIHYDROPYRIDIN-1(2H)-YL)ETHANONE

N-(4-(3-bromopyridin-2-yloxy)phenyl)pyridin-2-amine hydrochloride (0.388 g, 1.14 mmol), 1-(4-(4,4,5,5-tetramethyl-1,3,2-dioxaborolan-2-yl)-5,6-dihydropyridin-1(2H)-yl)ethanone (0.30 g, 1.2 mmol), potassium acetate (0.60 g, 10.2 mmol), and Amphos (0.063 g, 0.090 mmol) were taken up in 12 mL of 3:1 mixture of acetonitrile and water. The mixture was purged with nitrogen and heated to 90° C. for 15 h. The reaction mixture was diluted with water and extracted with EtOAc (3×). The combined organics was washed with 30 mL of brine and dried over MgSO₄. Filtration and concentration under reduced pressure, followed by flash chromatography on silica gel (10 to 100% EtOAc/hexane, then 5% MeOH in EtOAc) afforded 1-(4-(2-(4-(pyridin-2-ylamino)phenoxy)pyridin-3-yl)-5,6-dihydropyridin-1(2H)-yl)ethanone as tan solid. MS (ESI, pos. ion) m/z: 387.0 (M+1). IC50 (uM) 0.002698.

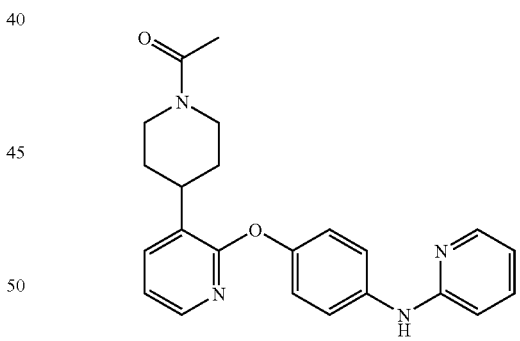

Example 266

1-(4-(2-(4-(PYRIDIN-2-YLAMINO)PHENOXY)PYRIDIN-3-YL)PIPERIDIN-1-YL)ETHANONE 1-(4-(2-(4-(pyridin-2-ylamino)phenoxy)pyridin-3-yl)-5,6-dihydropyridin-1(2)-yl)ethanone (0.15 g, 0.39 mmol), acetic acid, glacial (0.090 mL, 1.5 mmol) and palladium hydroxide, 20 wt % pd (dry basis) on carbon, wet (0.055 g, 0.078 mmol)were suspended in THF (7.8 mL) in a pressure reactor. The mixture was hydrogenated at 50 psi. for 16 h. The reaction mixture was filtered through celite and to the filtrate was added palladium hydroxide, 20 wt % pd (dry basis) on carbon, wet (0.055 g, 0.078 mmol). The mixture was hydrogenated at 50 psi. for another 24 h. The mixture was filtered throguh celite and washed with THF. The solvent was removed under reduced pressure and the residue was dissolved in DCM and treated with solid $Na_2CO_3$. The crude material was chromatographed through a Redi-Sep pre-packed silica gel column (40 g), eluting with a gradient of 10% to 100% EtOAc in hexane, then 5% MeOH in EtOAc to provide 1-(4-(2-(4-(pyridin-2-ylamino)phenoxy)pyridin-3-yl)piperidin-1-yl)ethanone as white solid. MS (ESI, pos. ion) m/z: 389.1 (M+1). IC50 (uM) 0.002844.

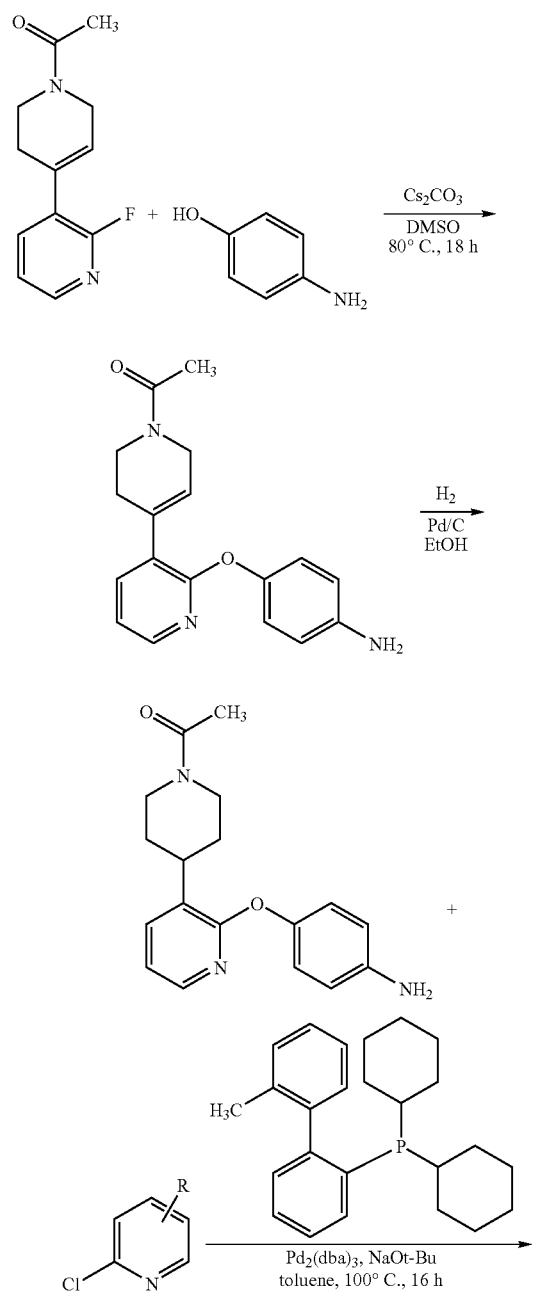

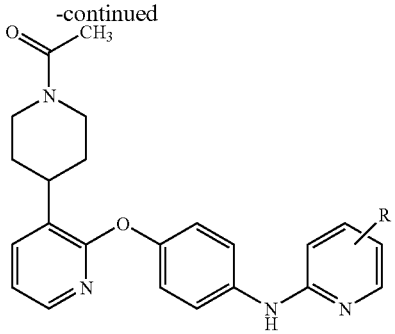

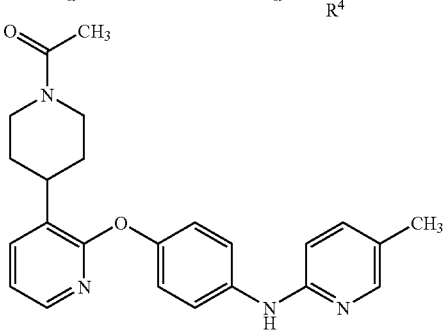

Example 267

1-(4-(2-(4-(5-METHYLPYRIDIN-2-YLAMINO) PHENOXY)PYRIDIN-3-YL)PIPERIDIN-1-YL) ETHANONE

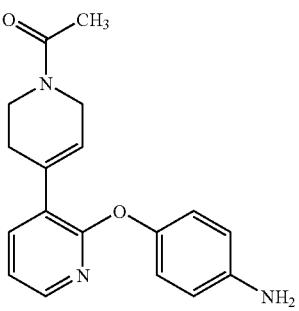 [SMILES: CC(=O)N1CC=C(c2cccnc2Oc2ccc(N)cc2)CC1]

STEP 1. 1-(4-(2-(4-AMINOPHENOXY)PYRIDIN-3-YL)-5,6-DIHYDROPYRIDIN-1(2H)-YL)ETHANONE

A solution of 1-(4-(2-fluoropyridin-3-yl)-5,6-dihydropyridin-1(2H)-yl)ethanone (1.68 g, 7.63 mmol) in dimethylsulfoxide (25 mL) under argon was added cesium carbonate (2.73 g, 8.39 mmol), followed by 4-aminophenol (0.874 g, 8.01 mmol). The reaction was stirred at 80° C. for 18 h. The cooled reaction mixture was diluted with EtOAc and washed with water; the aqueous layer was back-extracted with EtOAc (1×). The organic layers were combined, dried (MgSO$_4$), filtered, and concentrated in vacuo. Flash column chromatography (20% to 50% EtOAc/Hexanes) afforded 1-(4-(2-(4-aminophenoxy)-pyridin-3-yl)-5,6-dihydropyridin-1(2H)-yl)ethanone as a tan solid. MS (ESI, pos. ion) m/z: 310.0 (M+1).

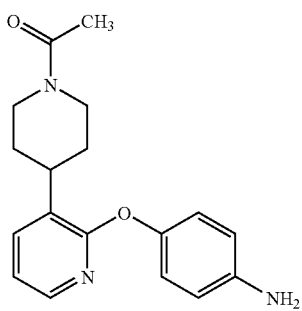 [SMILES: CC(=O)N1CCC(c2cccnc2Oc2ccc(N)cc2)CC1]

STEP 2. 1-(4-(2-(4-AMINOPHENOXY)PYRIDIN-3-YL)PIPERIDIN-1-YL)ETHANONE

A solution of 1-(4-(2-(4-aminophenoxy)pyridin-3-yl)-5,6-dihydropyridin-1(2H)-yl)ethanone (0.98 g, 3.17 mmol) in ethanol (16 mL) was added palladium, 10 wt. % on carbon (0.1 g, 0.094 mmol) and hydrogenated (double-walled balloon pressure) at room temperature for 18 h. The reaction mixture was filtered via a pad of Celite, and the filtrate was concentrated in vacuo and chromatographed via flash column chromatography (20% to 80% EtOAc/Hexanes) to give 1-(4-(2-(4-aminophenoxy)pyridin-3-yl)piperidin-1-yl)ethanone as a light tan solid. MS (ESI, pos. ion) m/z: 312.0 (M+1).

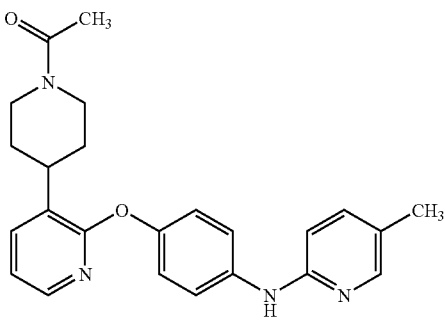 [SMILES: CC(=O)N1CCC(c2cccnc2Oc2ccc(Nc3ccc(C)cn3)cc2)CC1]

STEP 3. 1-(4-(2-(4-(5-METHYLPYRIDIN-2-YLAMINO)PHENOXY)PYRIDIN-3-YL)PIPERIDIN-1-YL)ETHANONE

Into a sealed tube were added 1-(4-(2-(4-aminophenoxy)pyridin-3-yl)piperidin-1-yl)ethanone (0.11 g, 0.37 mmol), 2-chloro-5-methylpyridine (0.043 g, 0.33 mmol), tris(dibenzylideneacetone)dipalladium(0) (0.019 g, 0.02 mmol), 2-(dicyclohexylphosphino)-2'-methylbiphenyl (0.012 g, 0.034 mmol), sodium tert-butoxide (0.097 g, 1.01 mmol), and toluene (1.6 mL). After the mixture was degassed for 5 min, the reaction was stirred at 100° C. for 16 h. The cooled reaction was diluted with CH$_2$Cl$_2$ and washed with water. The organic layer was dried (MgSO$_4$), filtered, and concentrated in vacuo. Flash column chromatography (20% to 80% EtOAc(10% MeOH)/Hexanes) gave a crude crop of the desired product. Further purification via reverse phase HPLC afforded 1-(4-(2-(4-(5-methylpyridin-2-ylamino)phenoxy)pyridin-3-yl)piperidin-1-yl)ethanone as a white amorphous solid. MS (ESI, pos. ion) m/z: 403.0 (M+1). IC50 (uM) 0.002844.

TABLE XIVA

EXAMPLES 268 TO 273 ARE TABULATED BELOW:

| Ex. No. | Compound Structure | Compound Name | MS | PDE10 IC50 (uM) |
|---|---|---|---|---|
| 268 | 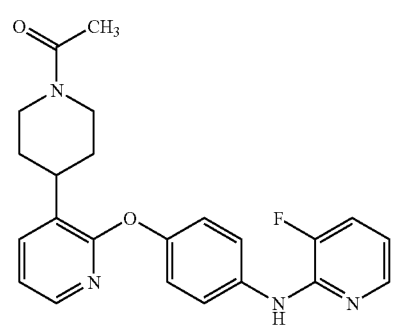 [SMILES: CC(=O)N1CCC(c2cccnc2Oc2ccc(Nc3ncccc3F)cc2)CC1] | 1-(4-(2-(4-(3-Fluoropyridin-2-ylamino)phenoxy)pyridin-3-yl)piperidin-1-yl)ethanone | 407.1 | 0.012 |

TABLE XIVA-continued

EXAMPLES 268 TO 273 ARE TABULATED BELOW:

| Ex. No. | Compound Structure | Compound Name | MS | PDE10 IC50 (uM) |
|---|---|---|---|---|
| 269 | 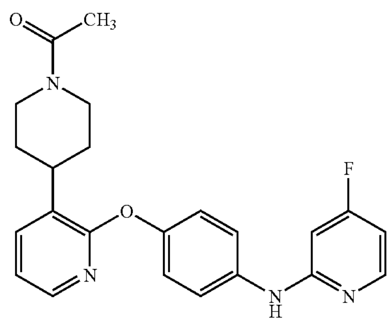 [SMILES: CC(=O)N1CCC(c2cccnc2Oc2ccc(Nc3cc(F)ccn3)cc2)CC1] | 1-(4-(2-(4-(4-Fluoropyridin-2-ylamino)phenoxy)pyridin-3-yl)piperidin-1-yl)ethanone | 407.1 | 0.021 |
| 270 | 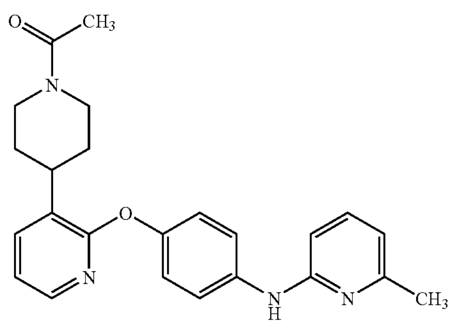 [SMILES: CC(=O)N1CCC(c2cccnc2Oc2ccc(Nc3cccc(C)n3)cc2)CC1] | 1-(4-(2-(4-(6-Methylpyridin-2-ylamino)phenoxy)pyridin-3-yl)piperidin-1-yl)ethanone | 403.0 | 0.11 |
| 271 | 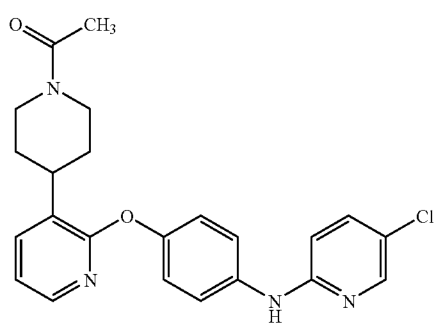 [SMILES: CC(=O)N1CCC(c2cccnc2Oc2ccc(Nc3ccc(Cl)cn3)cc2)CC1] | 1-(4-(2-(4-(5-Chloropyridin-2-ylamino)phenoxy)pyridin-3-yl)piperidin-1-yl)ethanone | 423.8 | 0.001 |
| 272 | 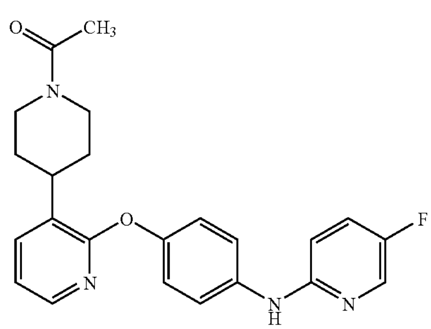 [SMILES: CC(=O)N1CCC(c2cccnc2Oc2ccc(Nc3ccc(F)cn3)cc2)CC1] | 1-(4-(2-(4-(5-Fluoropyridin-2-ylamino)phenoxy)pyridin-3-yl)piperidin-1-yl)ethanone | 407.1 | 0.005 |

TABLE XIVA-continued

EXAMPLES 268 TO 273 ARE TABULATED BELOW:

| Ex. No. | Compound Structure | Compound Name | MS | PDE10 IC50 (uM) |
|---|---|---|---|---|
| 273 | 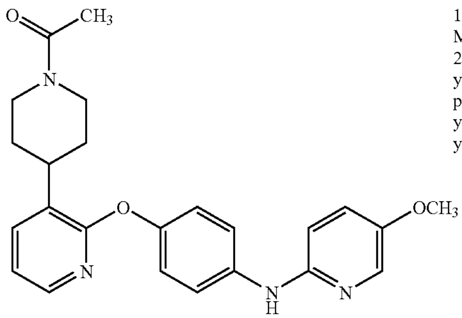 | 1-(4-(2-(4-(5-Methoxypyridin-2-ylamino)phenoxy)pyridin-3-yl)piperidin-1-yl)ethanone | 419.0 | 0.002 |

TABLE XIVB

PREPARATION OF EXAMPLES 268 TO 273 ARE TABULATED BELOW:

| Ex. No. | Scheme | Starting material 1 | Starting material 2 | Conditions or reagents that differ from scheme |
|---|---|---|---|---|
| 268 | 40 | | | |
| 269 | 40 | | | |
| 270 | 40 | | | |

TABLE XIVB-continued
PREPARATION OF EXAMPLES 268 TO 273 ARE TABULATED BELOW:
| Ex. No. | Scheme | Starting material 1 | Starting material 2 | Conditions or reagents that differ from scheme |
|---|---|---|---|---|
| 271 | 40 | | | |
| 272 | 40 | | | |
| 273 | 40 | | | |
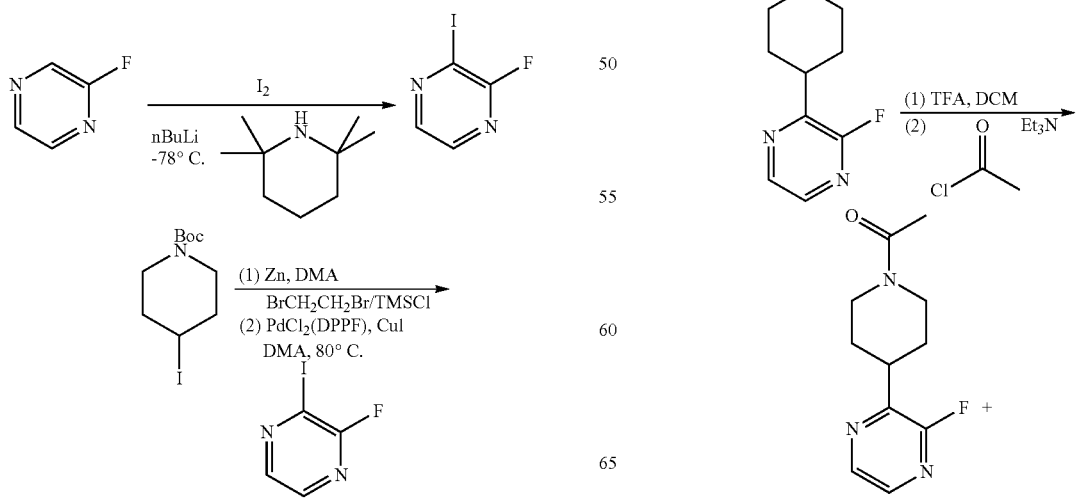

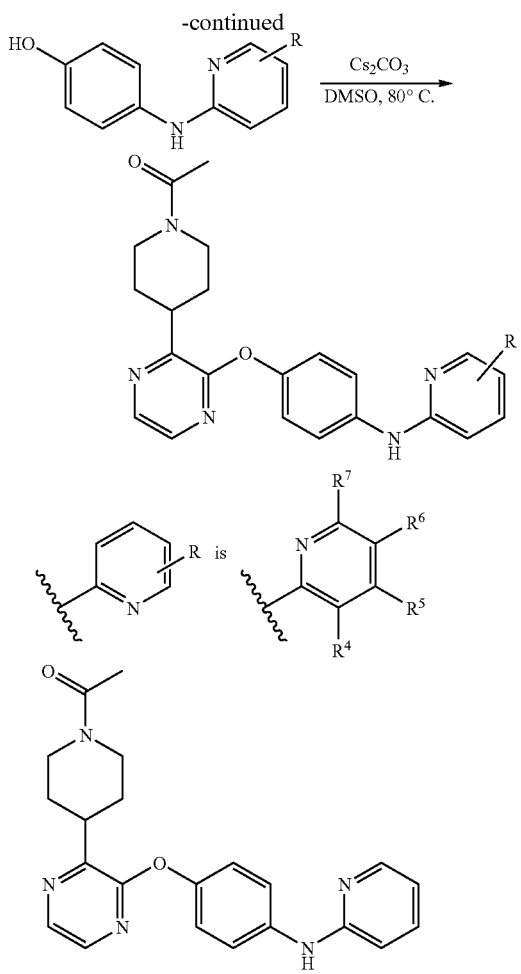

Example 274

1-(4-(3-(4-(PYRIDIN-2-YLAMINO)PHENOXY) PYRAZIN-2-YL)PIPERIDIN-1-YL)ETHANONE

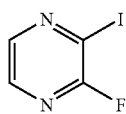

STEP 1. 2-FLUORO-3-IODOPYRAZINE

Butyl lithium solution (2.5 M in hexane, 881 mL, 2.01 mol) and 1.5 L of dry THF were charged into a flame-dried 5.0 L round-bottomed flask. The flask was cooled to −50° C. and 2,2,6,6-tetramethylpiperidine (312.0 mL, 2.20 mol) was added dropwise. The reaction mixture was warmed to 0° C. without taking the cold bath away and kept at that temperature for 20 min. The reaction was then cooled to −78° C., and 2-fluoropyrazine (180 g, 1.84 mol) in 150 mL of THF was added dropwise. The mixture was kept at −78° C. for 5 min. Iodine (464 g, 1.84 mol) in 500 mL of THF was added dropwise and the reaction mixture was kept at −78° C. for 1 h. The reaction was quenched with the addition of 250 mL of concentrated HCl, 250 mL MeOH and 250 mL THF at −78° C. The cold bath was then removed, and aqueous sodium bisulfite was added to get rid of traces of unreacted iodine. The solvent was then evaporated and the residue was diluted with water and adjusted to pH 8. The mixture was extracted with ethyl acetate (3×1.5 L). Combined ethyl acetate layer was dried over sodium sulfate and concentrated. The crude product was purified by column chromatography (Silica:100-200 mess, solvent: 10% EtOAc/hexanes) to give the title compound as a white solid.

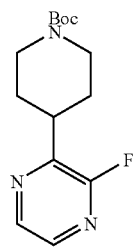 [SMILES: CC(C)(C)OC(=O)N1CCC(c2nccnc2F)CC1]

STEP 2: TERT-BUTYL 4-(3-FLUOROPYRAZIN-2-YL)PIPERIDINE-1-CARBOXYLATE

In an oven-dried 25 mL round-bottomed flask was charged dry DMA (1 mL), zinc dust (0.430 g, 6.58 mmol). The mixture was stirred at RT while the mixture of chlorotrimethylsilane (0.07 mL, 0.553 mmol) and 1,2-dibromoethane (0.05 mL, 0.580 mmol) was added slowly. The resulting slurry was aged for 15 min. A solution of n-boc-4-iodo-piperidine (1.65 g, 5.30 mmol) in DMA (2.6 mL) was added slowly to the above mixture. Zinc slurry reacted exothermically with the gradual addition of the iodide. After stirring for 30 min, the resulting milky solution was cooled to RT and used directly in the next step.

In an oven-dried flask were charged 2-fluoro-3-iodopyrazine (0.829 g, 3.70 mmol), 1,1'-bis(diphenylphosphino)ferrocene]dichloride palladium(ii)complex with dichloramethane (0.091 g, 0.111 mmol), copper(i) iodide (0.042 g, 0.222 mmol), and DMA (3 mL). The resulting mixture was degassed with alternating vacuum/nitrogen purges. The (1-(tert-butoxycarbonyl)piperidin-4-yl)zinc(II) iodide (1.951 g, 5.18 mmol) solution from previous step was filtered into the mixture. It was degassed one more time and then heated to 80° C. with stirring for 16 h. After cooling to RT, the reaction mixture was treated with methyl tert-butylether (13 ml) and 1 N NH$_4$Cl (13 ml). The organic layer was partitioned between EtOAc and 1 N NH$_4$Cl and the aqueous layer was back extracted with EtOAc (2 x). The combined organic layer was washed with water, brine, dried (Na$_2$SO$_4$) and concentrated. The crude material was chromatographed through a Redi-Sep pre-packed silica gel column (40 g), eluting with a gradient of 0% to 20% EtOAc in hexane, to provide tert-butyl 4-(3-fluoropyrazin-2-yl)piperidine-1-carboxylate as orange oil. MS (ESI, pos. ion) m/z: 226.0 (M−56).

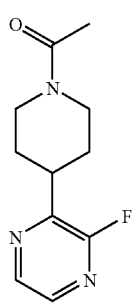 [SMILES: CC(=O)N1CCC(c2nccnc2F)CC1]

STEP 3. 1-(4-(3-FLUOROPYRAZIN-2-YL)PIPERIDIN-1-YL)ETHANONE

To tert-butyl 4(3-fluoropyrazin-2-yl)piperidine-1-carboxylate (0.658 g, 2.34 mmol) dissolved in DCM (5 mL) was added trifluoroacetic acid, 99% (1.39 mL, 18.7 mmol) dropwise. The reaction mixture was stirred at RT for 1 h. The solvent was evaporated and to the residue was added DCM and then evaporated. The process was repeated twice. The residue was redissolved in DCM and treated with solid NaHCO₃. The mixture was stirred for 1 h, filtered and concentrated. The orange oil was used directly in the following step.

To 2-fluoro-3-(piperidin-4-yl)pyrazine (0.311 g, 1.716 mmol) dissolved in DCM (5 mL) was added triethylamine (0.286 mL, 2.06 mmol), then acetyl chloride (0.134 mL, 1.89 mmol). The reaction mixture was stirred at RT for 1 h then partitioned between DCM and water. The aqueous layer was extracted with DCM (3×) and the combined organic layers were washed with brine, dried (Na₂SO₄) and concentrated to give 1-(4-(3-fluoropyrazin-2-yl)piperidin-1-yl)ethanone as a yellow oil. MS (ESI, pos. ion) m/z: 224.0 (M−56).

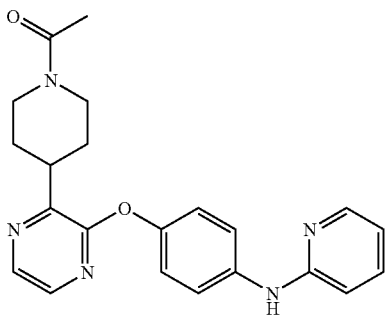

STEP 4. 1-(4-(3-(4-(PYRIDIN-2-YLAMINO)PHENOXY)PYRAZIN-2-YL)PIPERIDIN-1-YL)ETHANONE

The mixture of 4-(pyridin-2-ylamino)phenol (47 mg, 0.25 mmol), 1-(4-(3-fluoropyrazin-2-yl)piperidin-1-yl)ethanone (56 mg, 0.25 mmol), and cesium carbonate (123 mg, 0.376 mmol) in DMSO (0.85 mL) was heated at 80° C. for 20 h. The reaction mixture was partitioned between EtOAc and brine. The aqueous layer was back extracted with EtOAc (2×) and the combined organic layer was dried (Na₂SO₄) and concentrated. The crude material was purified by chromatography through a Redi-Sep pre-packed silica gel column (40 g), eluting with a gradient of 0% to 100% EtOAc in hexane, then 3% MeOH in EtOAc, to provide 1-(4-(3-(4-(pyridin-2-ylamino)phenoxy)pyrazin-2-yl)piperidin-1-yl)ethanone as off-white solid. MS (ESI, pos. ion) m/z: 389.9 (M+1). IC50 (uM) 0.003589.

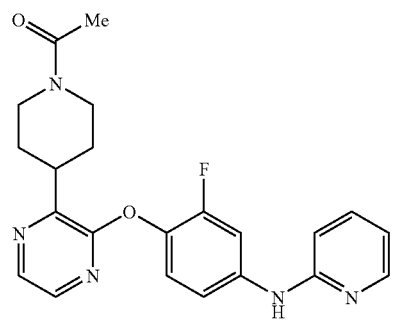 [SMILES: CC(=O)N1CCC(c2nccnc2Oc2ccc(Nc3ccccn3)cc2F)CC1]

Example 275

1-(4-(3-(2-FLUORO-4-(PYRIDIN-2-YLAMINO)PHENOXY)PYRAZIN-2-YL)PIPERIDIN-1-YL)ETHANONE

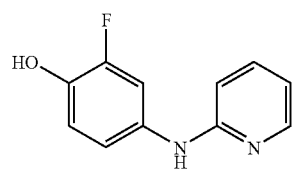 [SMILES: Oc1ccc(Nc2ccccn2)cc1F]

STEP 1.
2-FLUORO-4-(PYRIDIN-2-YLAMINO)PHENOL

To 4-amino-2-fluorophenol (0.983 g, 7.73 mmol) was added NMP (3 mL) and 2-fluoropyridine (0.670 mL, 7.78 mmol). The reaction mixture was heated to 120° C. for 12.5 h and the temperature was increased to 150° C. After 9 h, the reaction mixture was diluted with EtOAc and the organic phase was washed with saturated NaHCO₃ (1×), brine (1×), dried over MgSO₄, filtered, and concentrated. Purification by flash column chromatography on silica gel (10% to 70% EtOAc in hexanes) gave 2-fluoro-4-(pyridin-2-ylamino)phenol as a pale yellow oil. MS (ESI, pos. ion) m/z: 205.2 (M+1).

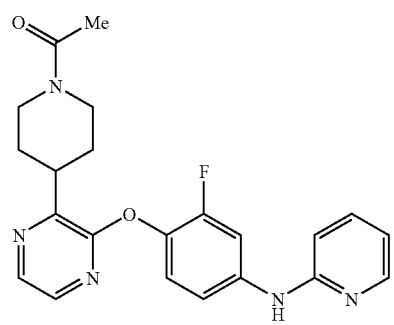 [SMILES: CC(=O)N1CCC(c2nccnc2Oc2ccc(Nc3ccccn3)cc2F)CC1]

STEP 2. 1-(4-(3-(2-FLUORO-4-(PYRIDIN-2-YLAMINO)PHENOXY)PYRAZIN-2-YL)PIPERIDIN-1-YL)ETHANONE

To a mixture of cesium carbonate (1.11 g, 3.41 mmol), 1-(4-(3-chloropyrazin-2-yl)piperidin-1-yl)ethanone (0.336 g, 1.40 mmol), and 2-fluoro-4-(pyridin-2-ylamino)phenol (0.547 g, 2.68 mmol) was added NMP (3 mL). The reaction mixture was degassed and heated to 120° C. for 1.5 h. The reaction mixture was diluted with EtOAc and the organic phase was washed with water (2×), brine (1×), dried over MgSO$_4$, filtered, and concentrated. Purification by flash column chromatography on silica gel (40% to 100% EtOAc in hexanes) gave 1-(4-(3-(2-fluoro-4-(pyridin-2-ylamino)phenoxy)pyrazin-2-yl)piperidin-1-yl)ethanone as a white solid. MS (ESI, pos. ion) m/z: 408.2 (M+1). IC50 (uM) 0.008056.

SCHEME 42

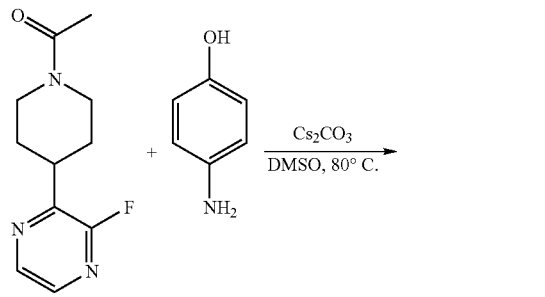

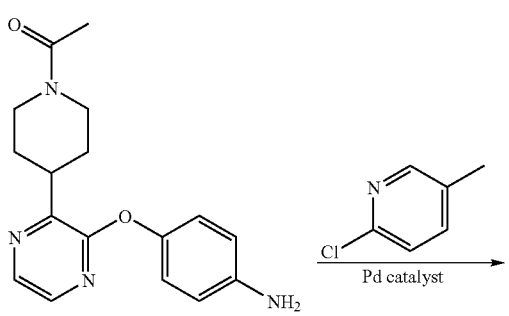

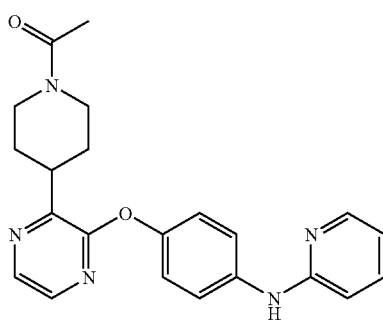

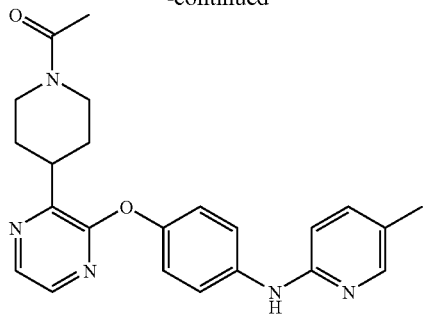

Example 276

1-(4-(3-(4-(5-METHYLPYRIDIN-2-YLAMINO)PHENOXY)PYRAZIN-2-YL)PIPERIDIN-1-YL)ETHANONE

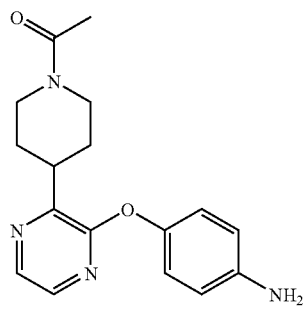 [SMILES: CC(=O)N1CCC(c2nccnc2Oc2ccc(N)cc2)CC1]

STEP 1. 1-(4-(3-(4-AMINOPHENOXY)PYRAZIN-2-YL)PIPERIDIN-1-YL)ETHANONE 1-(4-(3-fluoropyrazin-2-yl)piperidin-1-yl)ethanone (0.153 g, 0.685 mmol), 4-aminophenol (0.079 g, 0.720 mmol), cesium carbonate (0.246 g, 0.754 mmol), and 1-methyl-2-pyrrolidinone (0.685 mL, 0.685 mmol) were combined in a sealed tube and heated at 80° C. for 20 h. The cooled reaction mixture was diluted with EtOAc and washed with water; the aqueous layer was back-extracted with EtOAc (1×). The organic layers were combined, dried (MgSO$_4$), filtered, and concentrated in vacuo. ISCO purification (20% to 80% EtOAc/Hexanes) afforded 1-(4-(3-(4-aminophenoxy)pyrazin-2-yl)piperidin-1-yl)ethanone as a light brown oil. MS (ESI, pos. ion) m/z: 313.0 (M+1).

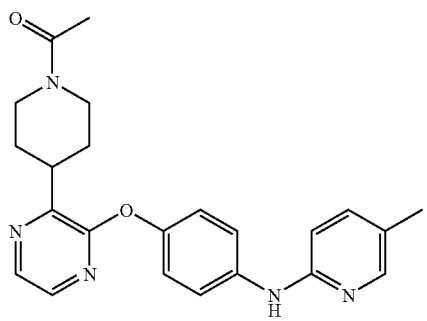 [SMILES: CC(=O)N1CCC(c2nccnc2Oc2ccc(Nc3ccc(C)cn3)cc2)CC1]

STEP 2. 1-(4-(3-(4-(5-METHYLPYRIDIN-2-YLAMINO)PHENOXY)PYRAZIN-2-YL)PIPERIDIN-1-YL)ETHANONE

Into a sealed tube were added 2-chloro-5-methylpyridine (0.055 g, 0.431 mmol), 1-(4-(3-(4-aminophenoxy)pyrazin-2-yl)piperidin-1-yl)ethanone (0.148 g, 0.474 mmol), tris(dibenzylideneacetone)dipalladium(0) (0.024 g, 0.026 mmol), 2-(dicyclohexylphosphino)-2'-methylbiphenyl (0.016 g, 0.043 mmol), sodium tert-butoxide (0.124 g, 1.293 mmol), and toluene (2.16 mL, 0.431 mmol). After the mixture was degassed for 5 min, the reaction was stirred at 100° C. for 18 h. The cooled reaction was diluted with $CH_2Cl_2$ and washed with water. The organic layer was dried ($MgSO_4$), filtered, and concentrated in vacuo. ISCO purification (20% to 80% EtOAc (10% MeOH)/Hexanes), followed by reverse phase HPLC (Shimadzu) afforded 1-(4-(3-(4-(5-methylpyridin-2-ylamino)phenoxy)pyrazin-2-yl)piperidin-1-yl)ethanone as a white amorphous solid. MS (ESI, pos. ion) m/z: 404.0 (M+1). IC50 (uM) 0.00004.

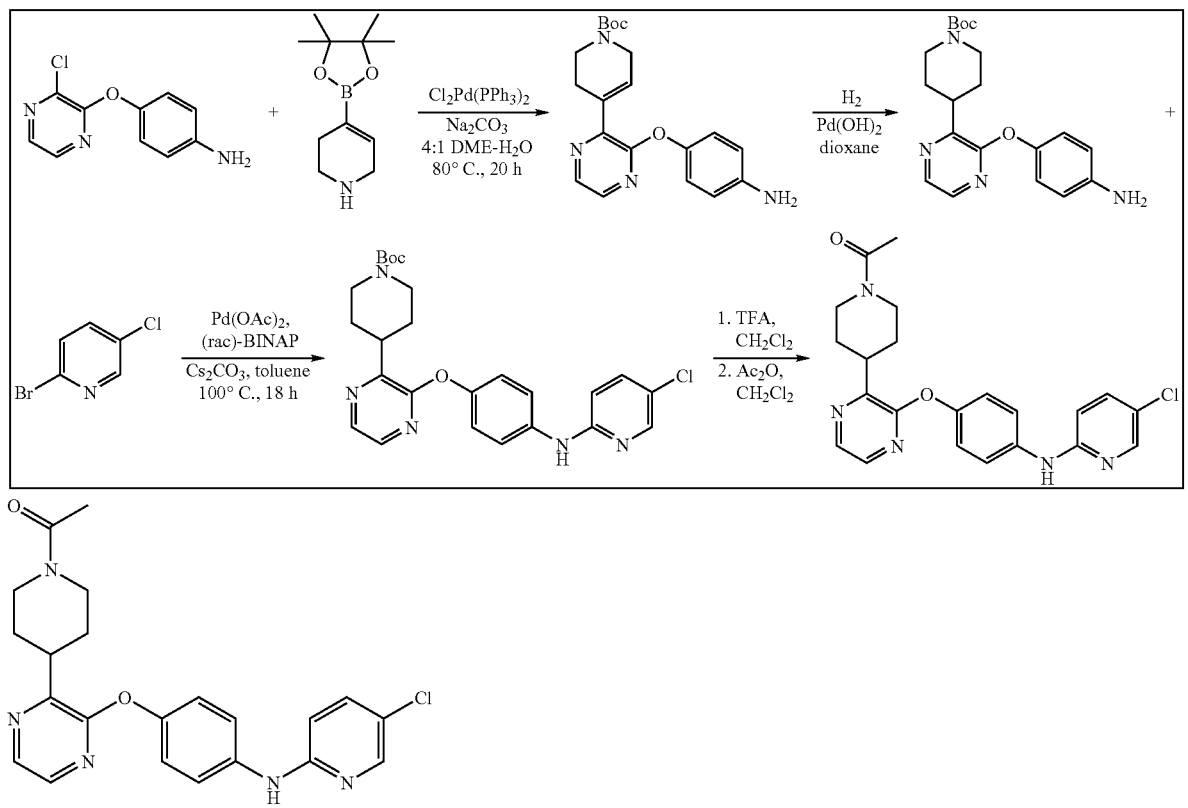

SCHEME 43

Example 277

1-(4-(3-(4-(5-CHLOROPYRIDIN-2-YLAMINO)PHENOXY)PYRAZIN-2-YL)PIPERIDIN-1-YL)ETHANONE

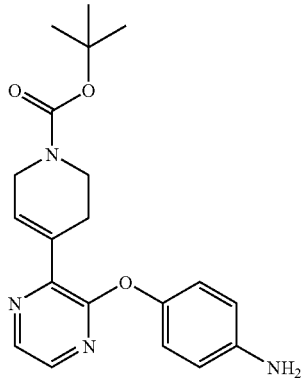 [SMILES: CC(C)(C)OC(=O)N1CC=C(c2nccnc2Oc2ccc(N)cc2)CC1]

STEP 1. TERT-BUTYL 4-(3-(4-AMINOPHENOXY)PYRAZIN-2-YL)-5,6-DIHYDROPYRIDINE-1(2H)-CARBOXYLATE

Into a sealed 150-mL flask were placed 4-(3-chloropyrazin-2-yloxy)aniline (2 g, 9 mmol) (see Step 1, Example 215), tert-butyl 4-(4,4,5,5-tetramethyl-1,3,2-dioxaborolan-2-yl)-5,6-dihydropyridine-1(2H)-carboxylate (4.19 g, 13.5 mmol), trans-dichlorobis-(triphenylphosphine)palladium (II) (0.5 g, 0.72 mmol), sodium carbonate (4.78 g, 45.1 mmol) and 30 mL of 4:1 DME-water. After the mixture was degassed for 5 min, the reaction was stirred at 80° C. for 18 h. The cooled reaction was diluted with $CH_2Cl_2$ and washed with aqueous saturated $NaHCO_3$ solution; the aqueous layer was back-extracted with $CH_2Cl_2$ (2×). The organic extracts were combined, dried ($MgSO_4$), filtered, and concentrated in vacuo. Flash column chromatography (20% to 60% EtOAc/Hexanes) afforded tert-butyl 4-(3-(4-aminophenoxy)pyrazin-2-yl)-5,6-dihydropyridine-1(2H)-carboxylate) as a cream solid. MS (ESI, pos. ion) m/z: 369.0 (M+1).

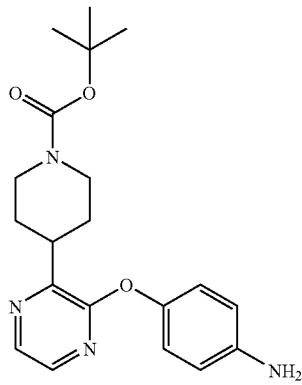 [SMILES: CC(C)(C)OC(=O)N1CCC(c2nccnc2Oc2ccc(N)cc2)CC1]

STEP 2. TERT-BUTYL 4-(3-(4-AMINOPHENOXY)PYRAZIN-2-YL)PIPERIDINE-1-CARBOXYLATE

A solution of tert-butyl 4-(3-(4-aminophenoxy)pyrazin-2-yl)-5,6-dihydropyridine-1(2H)-carboxylate (2.87 g, 7.79 mmol) in 1,4-dioxane (39 mL) was added palladium hydroxide, 20 wt. % Pd (dry basis) on carbon, wet, Degussa type E101 NEW (0.27 g, 0.39 mmol) and hydrogenated (double-walled balloon pressure) at room temperature for 1 day. The reaction was filtered via a pad of Celite, and the filtrate was concentrated in vacuo and chromatographed via flash column chromatography (20% to 60% EtOAc/Hexanes) to provide tert-butyl 4-(3-(4-aminophenoxy)pyrazin-2-yl)piperidine-1-carboxylate as a cream solid. MS (ESI, pos. ion) m/z: 393.0 [M+1+Na].

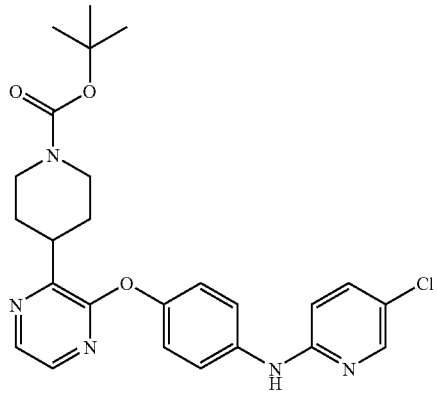 [SMILES: CC(C)(C)OC(=O)N1CCC(c2nccnc2Oc2ccc(Nc3ccc(Cl)cn3)cc2)CC1]

STEP 3. TERT-BUTYL 4-(3-(4-(5-CHLOROPYRIDIN-2-YLAMINO)PHENOXY)PYRAZIN-2-YL)PIPERIDINE-1-CARBOXYLATE

Into a sealed tube were added tert-butyl 4-(3-(4-aminophenoxy)pyrazin-2-yl)piperidine-1-carboxylate (0.31 g, 0.84 mmol), 2-bromo-5-chloropyridine (0.17 g, 0.92 mmol), palladium (II) acetate (0.019 g, 0.084 mmol), (rac)-BINAP (0.073 g, 0.12 mmol), cesium carbonate (0.49 g, 1.51 mmol), and toluene (4 mL). After the mixture was degassed for 5 min, the reaction was stirred at 100° C. for 18 h. The cooled reaction was diluted with $CH_2Cl_2$ and washed with water; the aqueous layer was back-extracted with $CH_2Cl_2$ (1×). The organic extracts were combined, dried ($MgSO_4$), filtered, and concentrated in vacuo. Flash column chromatography (10% to 40% EtOAc (10% MeOH)/Hexanes) provided tert-butyl 4-(3-(4-(5-chloropyridin-2-ylamino)phenoxy)-pyrazin-2-yl)piperidine-1-carboxylate as a yellow foam. MS (ESI, pos. ion) m/z: 482.1 (M+1).

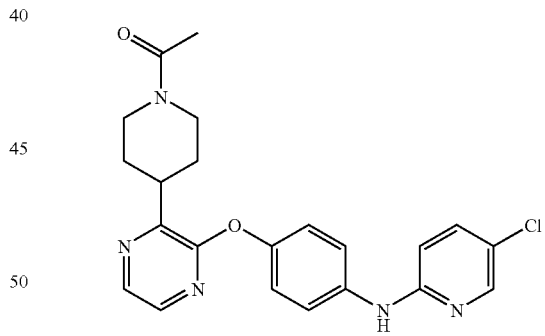

STEP 4. 1-(4-(3-(4-(5-CHLOROPYRIDIN-2-YLAMINO)PHENOXY)PYRAZIN-2-YL)PIPERIDIN-1-YL)ETHANONE

A solution of tert-butyl 4-(3-(4-(5-chloropyridin-2-ylamino)phenoxy)pyrazin-2-yl)piperidine-1-carboxylate (0.14 g, 0.29 mmol) in dichloromethane (1 mL) was added trifluoroacetic acid (0.22 mL, 2.9 mmol) and stirred at room temperature for 2 h. The reaction was concentrated in vacuo, and the residue was partitioned between $CH_2Cl_2$ and aqueous saturated $NaHCO_3$ solution. The organic layer was dried ($MgSO_4$), filtered, and concentrated in vacuo to give a golden yellow oil. A solution of the crude golden yellow oil in CH$_2$Cl$_2$ (1 mL) was cooled to 0° C. and added acetic anhydride (0.041 mL, 0.43 mmol). The reaction was gradually allowed to warm to room temperature and stirred for 1 h. The reaction was diluted with CH$_2$Cl$_2$ and washed with aqueous saturated NaHCO$_3$ solution. The organic layer was dried (MgSO$_4$), filtered, and concentrated in vacuo. Flash column chromatography (20% to 70% EtOAc/Hexanes) provided a crude crop of the desired product. Further purification via reverse phase HPLC afforded 1-(4-(3-(4-(5-chloropyridin-2-ylamino)phenoxy)pyrazin-2-yl)piperidin-1-yl)ethanone as an off-white amorphous solid. MS (ESI, pos. ion) m/z: 424.9 (M+1). IC50 (uM) 0.001.

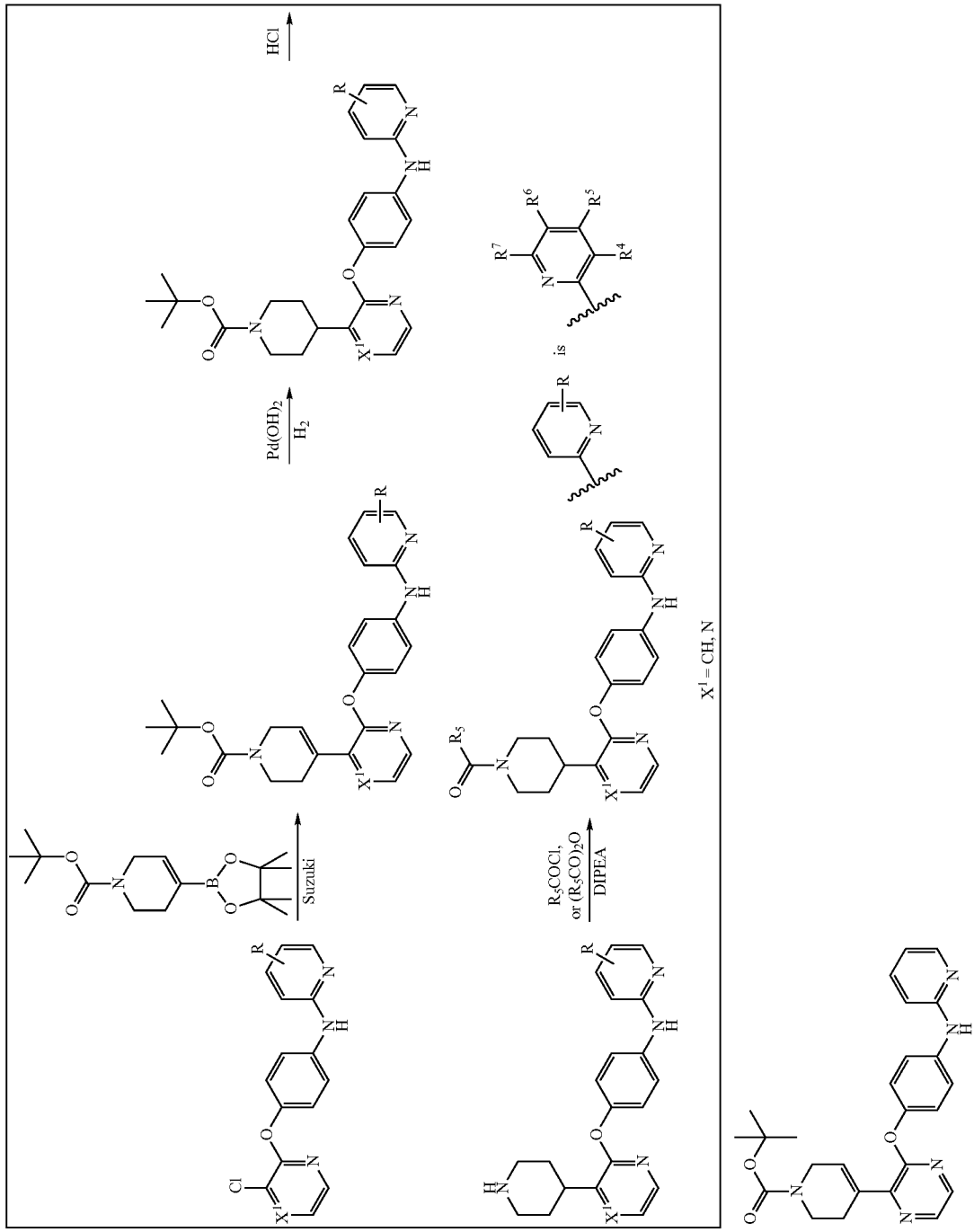

Example 278

TERT-BUTYL 4-(3-(4-(PYRIDIN-2-YLAMINO)PHENOXY)PYRAZIN-2-YL)-5,6-DIHYDROPYRIDINE-1(2H)-CARBOXYLATE

To a $N_2$ purged solution of N-(4-(3-chloropyrazin-2-yloxy)phenyl)pyridin-2-amine (4.891 g, 16.37 mmol), potassium acetate (6.54 g, 66.6 mmol), dioxane:water (160 mL, 10:1), and tert-butyl 4-(4,4,5,5-tetramethyl-1,3,2-dioxaborolan-2-yl)-5,6-dihydropyridine-1 (2H)-carboxylate (6.03 g, 19.50 mmol) was added A-Phos (1.5 g, 2.118 mmol). The vial was capped and placed in a preheated oil bath (120° C.) and stirred for 1.5 hours. The solution was allowed to cool to room temperature and poured into water. The aqueous solution was extracted with EtOAc (3×70 mL). The combined organic layers were concentrated in vacuo and adsorbed onto a plug of silica gel and chromatographed through a Redi-Sep® pre-packed silica gel column (120 g), eluting with 0% to 50% EtOAc in hexane, to provide tert-butyl 4-(3-(4-(pyridin-2-ylamino)phenoxy)pyrazin-2-yl)-5,6-dihydropyridine-1 (2H)-carboxylate as a yellow foam. MS (ESI, pos. ion) m/z: 446.1 (M+1). IC50 (uM) 0.01298.

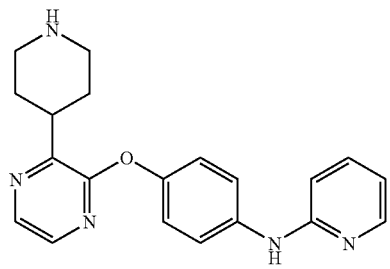 [SMILES: c1ccc(Nc2ccc(Oc3nccnc3C3CCNCC3)cc2)nc1]

Example 279

N-(4-(3-(PIPERIDIN-4-YL)PYRAZIN-2-YLOXY)PHENYL)PYRIDIN-2-AMINE

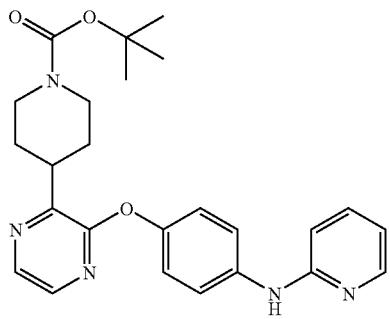 [SMILES: CC(C)(C)OC(=O)N1CCC(c2nccnc2Oc2ccc(Nc3ccccn3)cc2)CC1]

STEP 1. TERT-BUTYL 4-(3-(4-(PYRIDIN-2-YLAMINO)PHENOXY)PYRAZIN-2-YL)PIPERIDINE-1-CARBOXYLATE

To a $N_2$ purged flask containing tert-butyl 4-(3-(4-(pyridin-2-ylamino)phenoxy)pyrazin-2-yl)-5,6-dihydropyridine-1 (2H)-carboxylate (10.0 g, 22.45 mmol) and pearlman's catalyst (4.1 g, 5.84 mmol) was added THF (350 mL). $H_2$ was bubbled through the solution for 4 minutes, then the solution was capped with a balloon of $H_2$. After 48 hours, LC-MS shows complete conversion. The solution was filtered over a pad of celite, and the celite washed with EtOAc (150 mL). The filtrate was concentrated in vacuo. The residue was taken up in DCM (50 mL) and loaded onto a plug of silica gel (800 mL frit) and eluted with 0% to 50% EtOAc in hexanes to give tert-butyl 4-(3-(4-(pyridin-2-ylamino)phenoxy)pyrazin-2-yl)piperidine-1-carboxylate as a light yellow foam. MS (ESI, pos. ion) m/z: 448.1 (M+1).

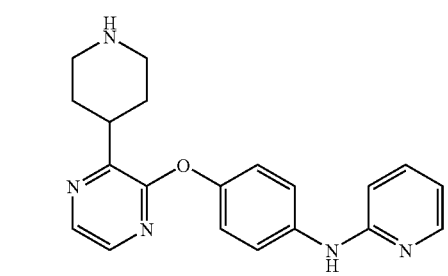 [SMILES: c1ccc(Nc2ccc(Oc3nccnc3C3CCNCC3)cc2)nc1]

STEP 2. N-(4-(3-(PIPERIDIN-4-YL)PYRAZIN-2-YLOXY)PHENYL)PYRIDIN-2-AMINE

To a solution of tert-butyl 4-(3-(4-(pyridin-2-ylamino)phenoxy)pyrazin-2-yl)-5,6-dihydropyridine-1(2H)-carboxylate (5.2 g, 11.67 mmol) and DCM (100 mL) was added 4M HCl in dioxane (12 mL, 48.0 mmol). After 4 hours, another 5 mL of 4M HCl in dioxane was added. After a further 16 hours, the precipitates had clung to the walls of the flask and the clear stirring solution was decanted away. The precipitates were washed with another 50 mL of DCM and the solution again decanted away. The flask was placed under vacuum for 30 minutes to give N-(4-(3-(piperidin-4-yl)pyrazin-2-yloxy)phenyl)pyridin-2-amine dihydrochloride as a hydroscopic yellow solid.

To a suspension of N-(4-(3-(piperidin-4-yl)pyrazin-2-yloxy)phenyl)pyridin-2-amine dihydrochloride (218 mg, 0.519 mmol) and DCM (20 mL) was added sat'd $NaHCO_3$ (7 mL). The organic layer was eluted through a Redi-Sep® pre-packed silica gel column (4 g), with 15% MeOH in DCM, to provide N-(4-(3-(piperidin-4-yl)pyrazin-2-yloxy)phenyl)pyridin-2-amine as an off-white foam. MS (ESI, pos. ion) m/z: 348.2 (M+1). IC50 (uM) 0.2215.

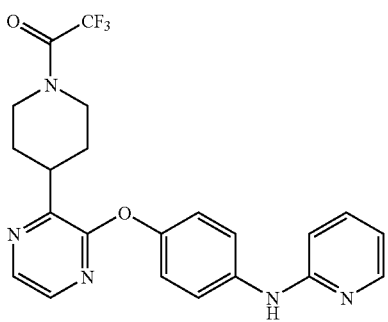 [SMILES: O=C(N1CCC(c2nccnc2Oc2ccc(Nc3ccccn3)cc2)CC1)C(F)(F)F]

Example 280

2,2,2-TRIFLUORO-1-(4-(3-(4-(PYRIDIN-2-YLAMINO)PHENOXY)PYRAZIN-2-YL)PIPERIDIN-1-YL)ETHANONE

To a solution of N-(4-(3-(piperidin-4-yl)pyrazin-2-yloxy)phenyl)pyridin-2-amine dihydrochloride (169 mg, 0.402 mmol) and DCM (10 mL) was added DIPEA (280 μL, 1.608 mmol) followed by trifluoroacetic anhydride (50.0 μl, 0.360 mmol). After 16 hours, LC-MS shows ~10% starting material remains, more trifluoroacetic anhydride (5 μl) was added. After 30 minutes the solution was concentrated to a volume of 3 mL and loaded onto a Redi-Sep® pre-packed silica gel column (4 g). The column was stacked on top of another Redi-Sep® pre-packed silica gel column (4 g), and eluted with 0% to 100% EtOAc in hexane, to provide 2,2,2-trifluoro-1-(4-(3-(4-(pyridin-2-ylamino)phenoxy)pyrazin-2-yl)piperidin-1-yl)ethanone as an off-white foam. MS (ESI, pos. ion) m/z: 444.0 (M+1). IC50 (uM) 0.001537.

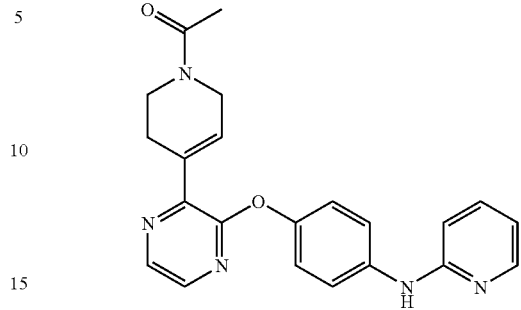

Example 281

1-(4-(3-(4-(PYRIDIN-2-YLAMINO)PHENOXY)PYRAZIN-2-YL)-5,6-DIHYDROPYRIDIN-1(2H)-YL)ETHANONE

During a resynthesis of Example 279 (Step 1) an incomplete hydrogenation resulted in a small fraction of tert-butyl 4-(3-(4-(pyridin-2-ylamino)phenoxy)pyrazin-2-yl)-5,6-dihydropyridine-1(2H)-carboxylate (Example 278) to be carried forward through Example 279 (Step 2), which was subsequently treated in similar fashion using acetyl chloride. The impurity was separated from the major product by SFC using MeOH (1% diethyl amine) to give 1-(4-(3-(4-(pyridin-2-ylamino)phenoxy)pyrazin-2-yl)-5,6-dihydropyridin-1(2H)-yl)ethanone as a white solid. MS (ESI, pos. ion) m/z: 388.1 (M+1). IC50 (uM) 0.00234.

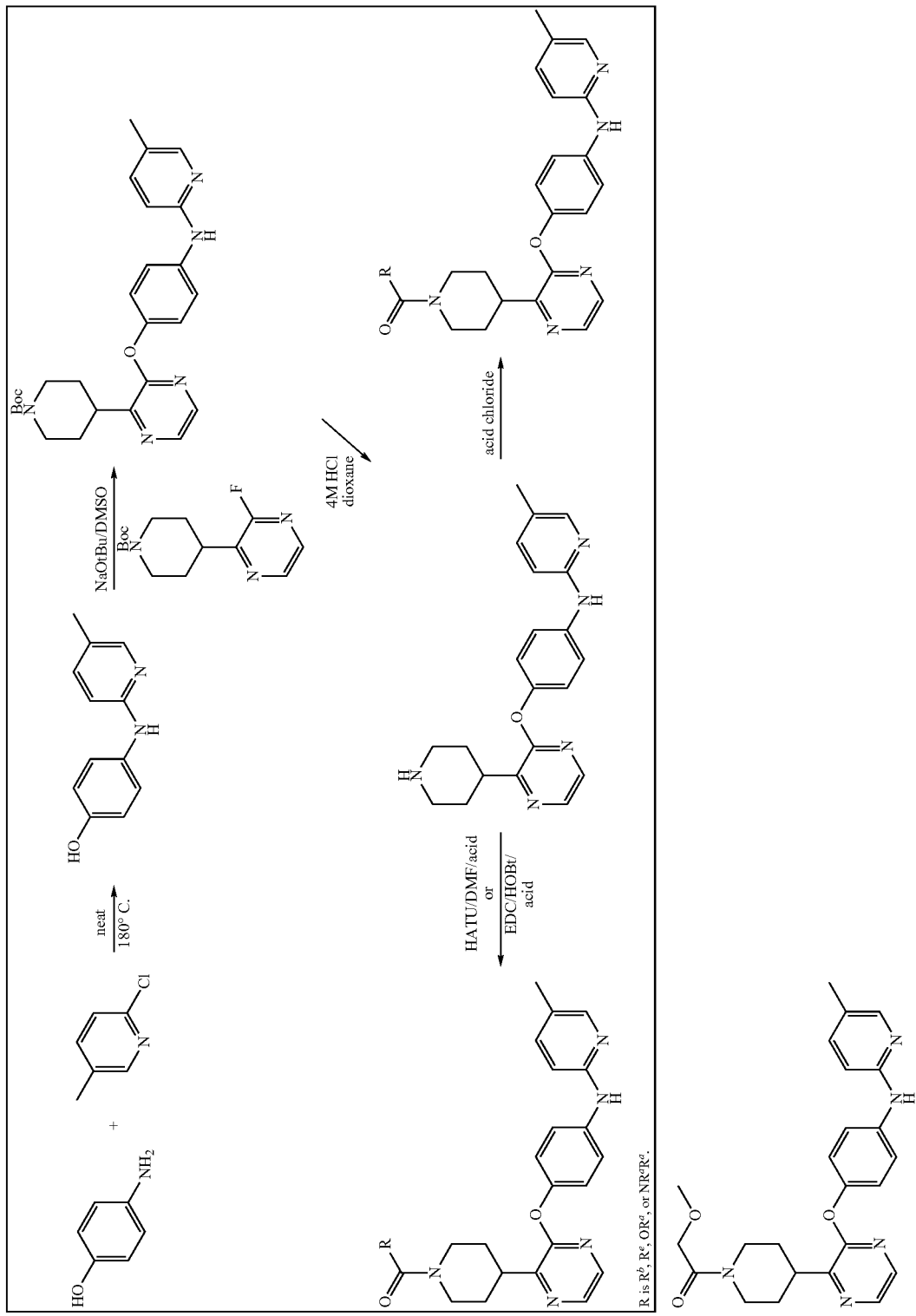

Example 282

2-METHOXY-1-(4-(3-(4-(5-METHYLPYRIDIN-2-YLAMINO)PHENOXY)PYRAZIN-2-YL)PIPERIDIN-1-YL)ETHANONE

STEP 1. 4-(5-METHYLPYRIDIN-2-YLAMINO)PHENOL

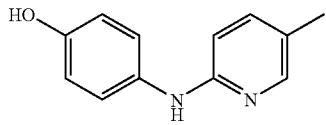

A mixture of 4-aminophenol (2 g, 18.33 mmol) and 2-chloro-5-methylpyridine (2.57 g, 20.16 mmol) was heated neat at 180° C. in 2 h. The reaction mixture was cooled, taken up in H₂O, neutralized with saturated NaHCO₃, extracted with DCM (3×). The extracts were dried over MgSO₄, concentrated to give the dark purple solid. MS (ESI, pos. ion) m/z: 201.1 (M+1).

STEP 2. TERT-BUTYL-4-(3-(4-(5-METHYLPYRIDIN-2-YLAMINO)PHENOXY)PYRAZIN-2-YL)PIPERIDINE-1-CARBOXYLATE

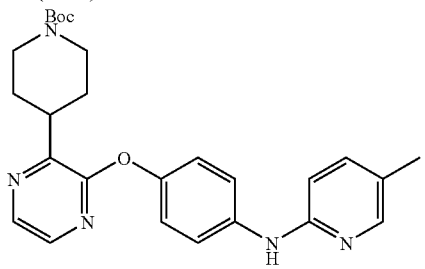

A mixture of tert-butyl 4-(3-fluoropyrazin-2-yl)piperidine-1-carboxylate (9.55 mL, 3.73 mmol), 4-(5-methylpyridin-2-ylamino)phenol (0.747 g, 3.73 mmol), and sodium tert-butoxide (1.07 g, 11.20 mmol) in DMSO (15 mL) was stirred at RT in 24 h. Water was added, and the reaction mixture was extracted with ether (3×), dried over MgSO₄, concentrated and purified by ISCO (0-60% EtOAc/Hexanes) to give the light brown oil. MS (ESI, pos. ion) m/z: 462.2 (M+1).

STEP 3. 2-METHOXY-1-(4-(3-(4-(5-METHYLPYRIDIN-2-YLAMINO)PHENOXY)PYRAZIN-2-YL)PIPERIDIN-1-YL)ETHANONE

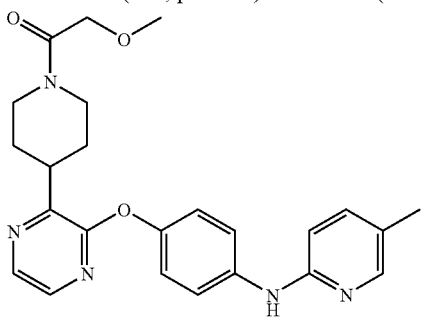

A solution of tert-butyl 4-(3-(4-(5-methylpyridin-2-ylamino)phenoxy)pyrazin-2-yl)piperidine-1-carboxylate (0.220 g, 0.434 mmol) in DCM (5 mL) was added 4M HCl in dioxane (2 mL). After stirring for 2 h at RT, diisopropylethylamine (0.525 mL, 3.01 mmol), 2-methoxyacetic acid (0.077 mL, 1.004 mmol), and HATU (0.305 g, 0.803 mmol) was added and the reaction mixture was stirred at RT in 2 h. Water was added and the mixture was extracted with DCM (3×), dried over Na₂SO₄, concentrated. The crude material was purified by reverse phase HPLC, then neutralized with saturated NaHCO₃, extracted with DCM (3×), dried over Na₂SO₄, concentrated to give the title compound. MS (ESI, pos. ion) m/z: 434.2 (M+1). IC50 (uM) 0.000058.

Example 283

METHYL 4-(3-(4-(5-METHYLPYRIDIN-2-YLAMINO)PHENOXY)PYRAZIN-2-YL)PIPERIDINE-1-CARBOXYLATE

To a stirred mixture of 5-methyl-N-(4-(3-(piperidin-4-yl)pyrazin-2-yloxy)phenyl)pyridin-2-amine (0.278 g, 0.548 mmol) (See step 3, Example 282), and diisopropylethylamine (0.502 mL, 2.88 mmol) in DCM (5 mL) was added methyl chloroformate (0.051 mL, 0.658 mmol). The reaction mixture was stirred at RT for 2 h. The reaction mixture was purified by ISCO column (40% EtOAc/Hexanes) to give the title compound. MS (ESI, pos. ion) m/z: 420.2 (M+1). IC50 (uM) 0.000107.

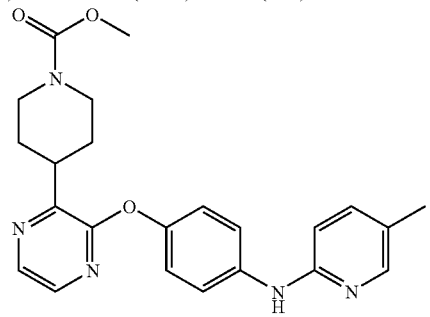

Example 284

(R)-2-METHOXY-1-(4-(3-(4-(5-METHYLPYRIDIN-2-YLAMINO)PHENOXY)PYRAZIN-2-YL)PIPERIDIN-1-YL)PROPAN-1-ONE

A mixture of 5-methyl-N-(4-(3-(piperidin-4-yl)pyrazin-2-yloxy)phenyl)pyridin-2-amine (3.58 mL, 0.394 mmol) (See step 3, Example 282), HOBT (0.015 g, 0.099 mmol), (R)-2-methoxypropanoic acid (0.049 g, 0.473 mmol), diisopropylethylamine (0.364 mL, 2.090 mmol), and EDC (0.091 g, 0.473 mmol) in DCM (5 mL) was stirred at RT overnight. The

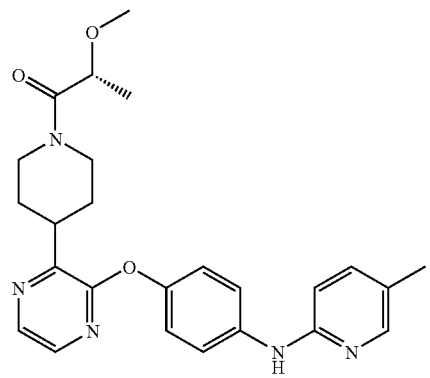 [SMILES: CO[C@H](C)C(=O)N1CCC(c2nccnc2Oc2ccc(Nc3ccc(C)cn3)cc2)CC1]

reaction mixture was concentrated in vacuo, then taken up in H₂O. The solid was collected by filtration, air-dried and purified by ISCO column (75% EtOAc/Hexanes) to give the title compound. MS (ESI, pos. ion) m/z: 448.2 (M+1). IC50 (uM) 0.000452.

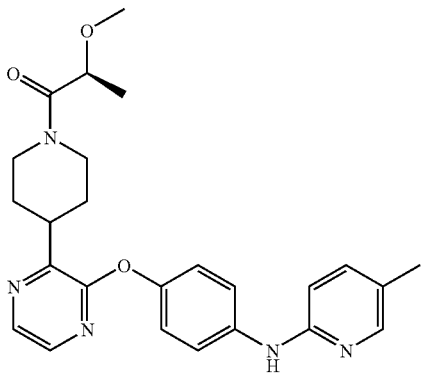 [SMILES: CO[C@@H](C)C(=O)N1CCC(c2nccnc2Oc2ccc(Nc3ccc(C)cn3)cc2)CC1]

Example 285

(S)-2-METHOXY-1-(4-(3-(4-(5-METHYLPYRI-DIN-2-YLAMINO)PHENOXY)PYRAZIN-2-YL)PIPERIDIN-1-YL)PROPAN-1-ONE

A mixture of 5-methyl-N-(4-(3-(piperidin-4-yl)pyrazin-2-yloxy)phenyl)pyridin-2-amine (3.58 mL, 0.394 mmol) (See step 3, Example 282), HOBT (0.015 g, 0.099 mmol), (S)-2-methoxypropanoic acid (0.049 g, 0.473 mmol), diisopropylethylamine (0.364 mL, 2.090 mmol), and EDC (0.091 g, 0.473 mmol) in DCM (5 mL) was stirred at RT overnight. The reaction mixture was concentrated, then taken up in H₂O. The solid was collected by filtration, air-dried and purified by ISCO column (75% EtOAc/Hexanes) to give the title compound. MS (ESI, pos. ion) m/z: 448.2 (M+1). IC50 (uM) 0.000335.

TABLE XVA

EXAMPLES 286 TO 299 ARE TABULATED BELOW:

| Ex. No. | Compound Structure | Compound Name | MS | PDE10 IC50 (uM) |
|---|---|---|---|---|
| 286 | 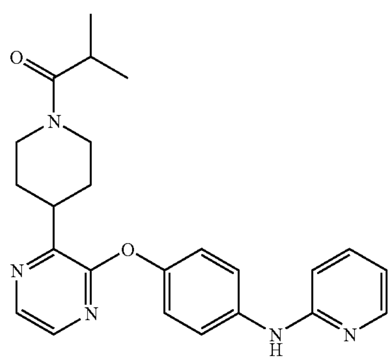 [SMILES: CC(C)C(=O)N1CCC(c2nccnc2Oc2ccc(Nc3ccccn3)cc2)CC1] | 2-methyl-1-(4-(3-(4-(pyridin-2-ylamino)phenoxy)pyrazin-2-yl)piperidin-1-yl)propan-1-one | 418 | 0.002319 |
| 287 | 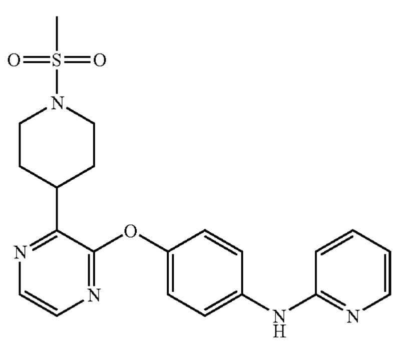 [SMILES: CS(=O)(=O)N1CCC(c2nccnc2Oc2ccc(Nc3ccccn3)cc2)CC1] | N-(4-(3-(1-(methylsulfonyl)piperidin-4-yl)pyrazin-2-yloxy)phenyl)pyridin-2-amine | 426 | 0.002298 |

TABLE XVA-continued

EXAMPLES 286 TO 299 ARE TABULATED BELOW:

| Ex. No. | Compound Structure | Compound Name | MS | PDE10 IC50 (uM) |
|---|---|---|---|---|
| 288 | 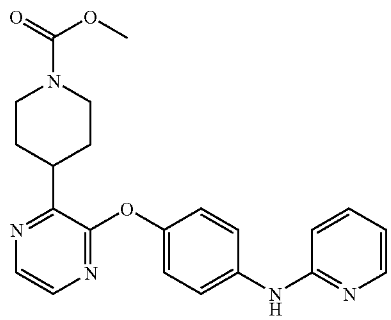 [SMILES: COC(=O)N1CCC(c2nccnc2Oc2ccc(Nc3ccccn3)cc2)CC1] | methyl 4-(3-(4-(pyridin-2-ylamino)phenoxy)pyrazin-2-yl)piperidine-1-carboxylate | 406 | 0.001134 |
| 289 | 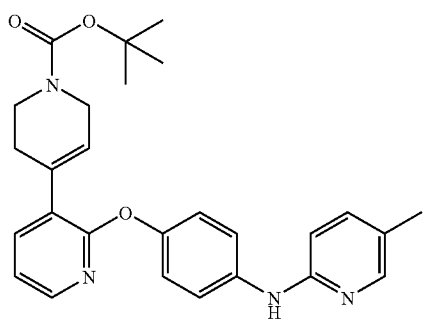 [SMILES: Cc1ccc(Nc2ccc(Oc3ncccc3C3=CCN(C(=O)OC(C)(C)C)CC3)cc2)nc1] | tert-butyl 4-(2-(4-(5-methylpyridin-2-ylamino)phenoxy)pyridin-3-yl)-5,6-dihydropyridine-1(2H)-carboxylate | 459 | 0.002064 |
| 290 | 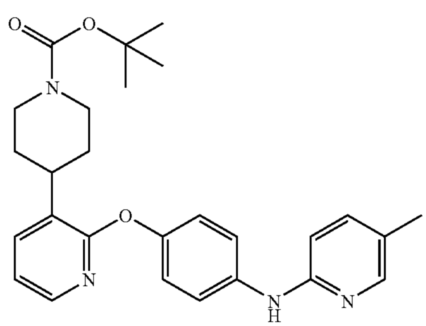 [SMILES: Cc1ccc(Nc2ccc(Oc3ncccc3C3CCN(C(=O)OC(C)(C)C)CC3)cc2)nc1] | tert-butyl 4-(2-(4-(5-methylpyridin-2-ylamino)phenoxy)pyridin-3-yl)piperidine-1-carboxylate | 461 | 0.001148 |
| 291 | 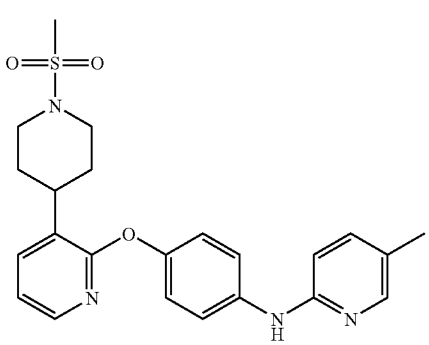 [SMILES: Cc1ccc(Nc2ccc(Oc3ncccc3C3CCN(S(C)(=O)=O)CC3)cc2)nc1] | 5-methyl-N-(4-(3-(1-(methylsulfonyl)piperidin-4-yl)pyridin-2-yloxy)phenyl)pyridin-2-amine | 439 | 0.000189 |

TABLE XVA-continued

EXAMPLES 286 TO 299 ARE TABULATED BELOW:

| Ex. No. | Compound Structure | Compound Name | MS | PDE10 IC50 (uM) |
|---|---|---|---|---|
| 292 | 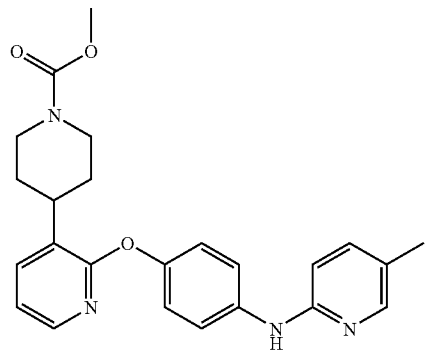 [SMILES: COC(=O)N1CCC(c2cccnc2Oc2ccc(Nc3ccc(C)cn3)cc2)CC1] | methyl 4-(2-(4-(5-methylpyridin-2-ylamino)phenoxy)pyridin-3-yl)piperidine-1-carboxylate | 419 | 0.000502 |
| 293 | 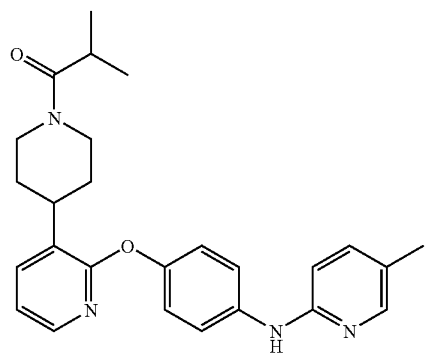 [SMILES: Cc1ccc(Nc2ccc(Oc3ncccc3C3CCN(C(=O)C(C)C)CC3)cc2)nc1] | 2-methyl-1-(4-(2-(4-(5-methylpyridin-2-ylamino)phenoxy)pyridin-3-yl)piperidin-1-yl)propan-1-one | 431 | 0.000098 |
| 294 | 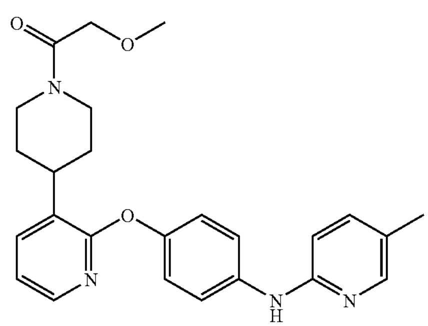 | 2-methoxy-1-(4-(2-(4-(5-methylpyridin-2-ylamino)phenoxy)pyridin-3-yl)piperidin-1-yl)ethanone | 433 | 0.000132 |
| 295 | 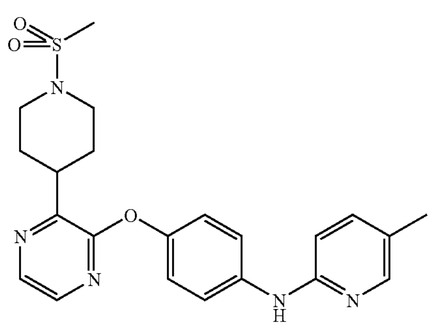 [SMILES: Cc1ccc(Nc2ccc(Oc3nccnc3C3CCN(S(C)(=O)=O)CC3)cc2)nc1] | 5-methyl-N-(4-(3-(1-(methylsulfonyl)piperidin-4-yl)pyrazin-2-yloxo)phenyl)pyridine-2-amine | 439 | 0.000369 |

TABLE XVA-continued

EXAMPLES 286 TO 299 ARE TABULATED BELOW:

| Ex. No. | Compound Structure | Compound Name | MS | PDE10 IC50 (uM) |
|---|---|---|---|---|
| 296 | 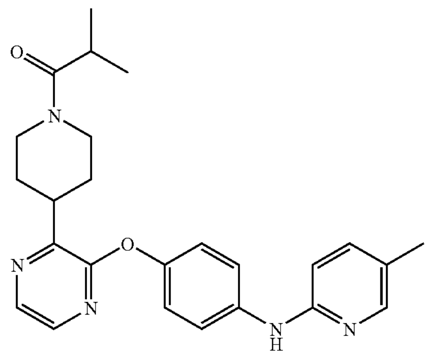 [SMILES: Cc1ccc(Nc2ccc(Oc3nccnc3C3CCN(C(=O)C(C)C)CC3)cc2)nc1] | 2-methyl-1-(4-(3-(4-(5-methylpyridin-2-ylamino)phenoxy)pyrazin-2-yl)piperidin-1-yl)propan-1-one | 431 | 0.000055 |
| 297 | 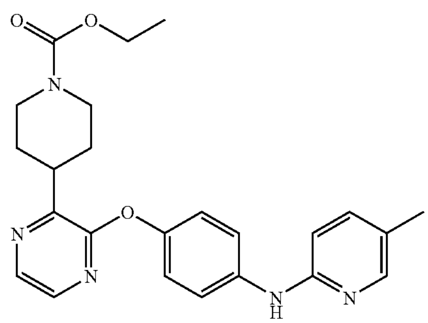 [SMILES: CCOC(=O)N1CCC(c2nccnc2Oc2ccc(Nc3ccc(C)cn3)cc2)CC1] | ethyl 4-(3-(4-(5-methylpyridin-2-ylamino)phenoxy)pyrazin-2-yl)piperidine-1-carboxylate | 433 | 0.000056 |
| 298 | 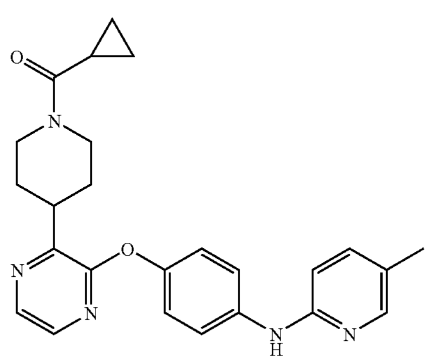 [SMILES: Cc1ccc(Nc2ccc(Oc3nccnc3C3CCN(C(=O)C4CC4)CC3)cc2)nc1] | cyclopropyl(4-(3-(4-(5-methylpyridin-2-ylamino)phenoxy)pyrazin-2-yl)piperidin-1-yl)methanone | 429 | 0.000171 |
| 299 | 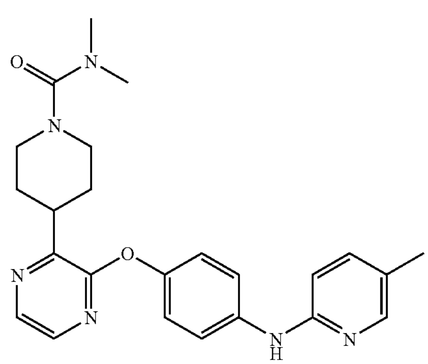 [SMILES: Cc1ccc(Nc2ccc(Oc3nccnc3C3CCN(C(=O)N(C)C)CC3)cc2)nc1] | N,N-dimethyl-4-(3-(4-(5-methylpyridin-2-ylamino)phenoxy)pyrazin-2-yl)piperidine-1-carboxamide | 432 | 0.000045 |

TABLE XVB

PREPARATION OF EXAMPLES 286 TO 299 ARE TABULATED BELOW:

| Ex. No. | Scheme | Starting material 1 | Starting material 2 | Conditions or reagents that differ from scheme |
|---|---|---|---|---|
| 286 | 44 | | | Isobutyl chloride |
| 287 | 44 | | | Methanesulfonyl chloride |
| 288 | 44 | | | Methyl chloroformate |
| 289 | 44 | | | |
| 290 | 44 | | | |

TABLE XVB-continued

PREPARATION OF EXAMPLES 286 TO 299 ARE TABULATED BELOW:

| Ex. No. | Scheme | Starting material 1 | Starting material 2 | Conditions or reagents that differ from scheme |
|---|---|---|---|---|
| 291 | 44 | methanesulfonyl chloride | 4-(2-(4-((5-methylpyridin-2-yl)amino)phenoxy)pyridin-3-yl)piperidine | |
| 292 | 44 | methyl chloroformate | 4-(2-(4-((5-methylpyridin-2-yl)amino)phenoxy)pyridin-3-yl)piperidine | Methyl chloroformate |
| 293 | 44 | isobutyryl chloride | 4-(2-(4-((5-methylpyridin-2-yl)amino)phenoxy)pyridin-3-yl)piperidine | Isobutyl chloride |
| 294 | 44 | 2-methoxyacetyl chloride | 4-(2-(4-((5-methylpyridin-2-yl)amino)phenoxy)pyridin-3-yl)piperidine | 2-methoxyacetyl chloride |
| 295 | 45 | methanesulfonyl chloride | 4-(3-(4-((5-methylpyridin-2-yl)amino)phenoxy)pyrazin-2-yl)piperidine | |

TABLE XVB-continued

PREPARATION OF EXAMPLES 286 TO 299 ARE TABULATED BELOW:

| Ex. No. | Scheme | Starting material 1 | Starting material 2 | Conditions or reagents that differ from scheme |
|---|---|---|---|---|
| 296 | 45 | | | |
| 297 | 45 | | | |
| 298 | 45 | | | |
| 299 | 45 | | | |

SCHEME 46

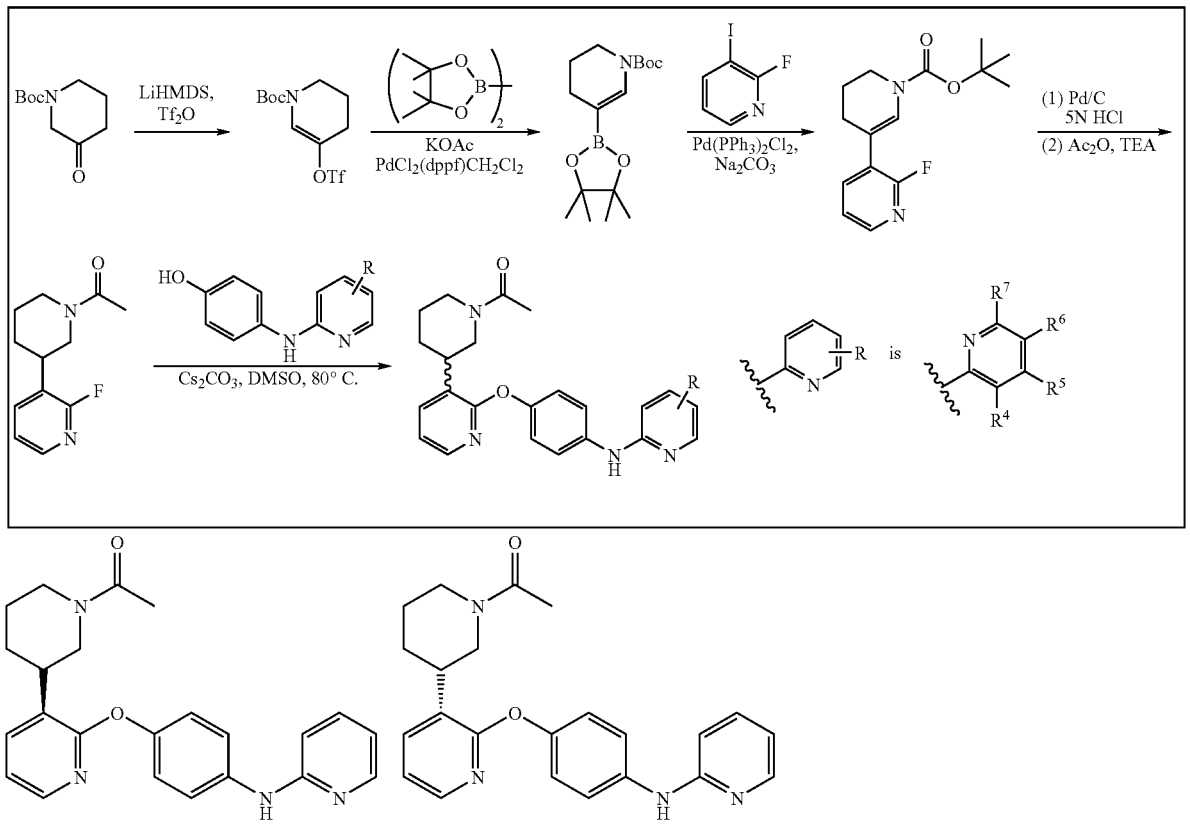

Example 300

N-(4-43-((3R)-1-ACETYL-3-PIPERIDINYL)-2-PYRIDINYL)OXY)PHENYL)-2-PYRIDINAMINE AND N-(4-((3-((3S)-1-ACETYL-3-PIPERIDINYL)-2-PYRIDINYL)OXY)PHENYL)-2-PYRIDINAMINE

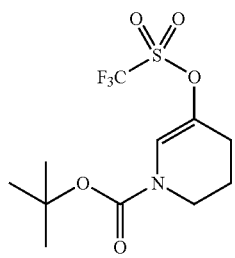 [SMILES: CC(C)(C)OC(=O)N1C=C(OS(=O)(=O)C(F)(F)F)CCC1]

STEP 1. TERT-BUTYL 5-(TRIFLUOROMETHYL-SULFONYLOXY)-3,4-DIHYDROPYRIDINE-1 (2H)-CARBOXYLATE

To a −78° C. solution of diisopropylamine (5.2 mL, 36.8 mmol) in dry THF (60 mL) was added butyllithium (13.25 mL, 33.1 mmol) dropwise. After the addition was complete the reaction was allowed to stir at −78° C. for 30 minutes, then a solution of tert-butyl 3-oxopiperidine-1-carboxylate (6.0 g, 30.1 mmol) in dry THF (10 mL) was added dropwise. After a further 20 minutes, a solution of N-(4-chloropyridin-2-yl)-1,1,1-trifluoro-N-(trifluoromethylsulfonyl)methanesulfonamide (13.2 g, 33.6 mmol) in dry THF (30 mL) was added dropwise to the reaction. The solution was allowed to slowly warm to room temperature. After 16 hours, the reaction was quenched with sat'd NH$_4$Cl and the diluted with water (20 mL). The aqueous solution was basified and extracted with EtOAc (4×30 mL). The combined organics were washed with brine and concentrated in vacuo. The crude product was adsorbed onto a plug of silica gel and chromatographed through a Redi-Sep® pre-packed silica gel column (40 g), eluting with 0% to 70% EtOAc in hexane, to provide tert-butyl 5-(trifluoromethylsulfonyloxy)-3,4-dihydropyridine-1(2H)-carboxylate as a colorless oil. MS (ESI, pos. ion) m/z: 354.0 (M+Na).

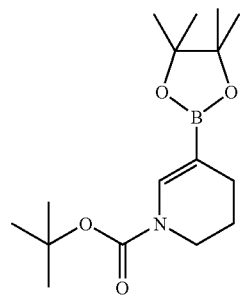 [SMILES: CC(C)(C)OC(=O)N1C=C(B2OC(C)(C)C(C)(C)O2)CCC1]

STEP 2. TERT-BUTYL 5-(4,4,5,5-TETRAM-ETHYL-1,3,2-DIOXABOROLAN-2-YL)-3,4-DI-HYDROPYRIDINE-1(2H)-CARBOXYLATE

To a N₂ purged solution of tert-butyl 5-(trifluoromethylsulfonyloxy)-3,4-dihydropyridine-1(2H)-carboxylate (5.725 g, 17.28 mmol), bis(pinacolato)diboron (5.714 g, 22.50 mmol), potassium acetate (4.7 g, 47.9 mmol), and dioxane (100 mL) was added 1,1'-bis(diphenylphosphino)ferrocenedichloro palladium(ii) dichloromethane complex (863 mg, 1.179 mmol). The mixture was then heated to 80° C. After 16 h, the mixture was cooled to room temperature. The mixture was filtered through a cartridge of celite and the celite washed with dioxane (40 mL) and THF (40 mL). The filtrate was concentrated in vacuo and eluted through a 4×17 cm column of silica gel using $CH_2Cl_2$ to give crude product contaminated with bis(pinacolato)diboron. The filtrate was concentrated in vacuo and adsorbed onto a plug of silica gel and chromatographed through a Redi-Sep® pre-packed silica gel column (120 g), eluting with 0% to 20% EtOAc in hexane, to provide tert-butyl 5-(4,4,5,5-tetramethyl-1,3,2-dioxaborolan-2-yl)-3,4-dihydropyridine-1(2H)-carboxylate as a colorless syrup. MS (ESI, pos. ion) m/z: 332.1 (M+Na).

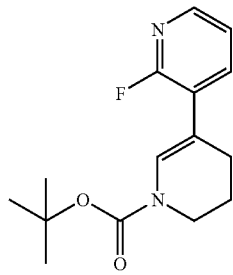 [SMILES: CC(C)(C)OC(=O)N1C=C(c2cccnc2F)CCC1]

STEP 3. TERT-BUTYL 5-(2-FLUOROPYRIDIN-3-YL)-3,4-DIHYDROPYRIDINE-1(2H)-CARBOXYLATE

A microwave vial was charged with 2-fluoro-3-iodopyridine (1.325 g, 5.94 mmol), tert-butyl 5-(4,4,5,5-tetramethyl-1,3,2-dioxaborolan-2-yl)-3,4-dihydropyridine-1(2H)-carboxylate (1.8 g, 5.82 mmol), sodium carbonate hydrate (2166 mg, 17.46 mmol), catalyst (211 mg, 0.301 mmol), DME (3 mL), Ethanol (0.857 mL) and Water (1.286 mL). The vial was capped and heated in a Biotage Initiator to 140° C. for 15 minutes. The reaction was diluted with water (20 ml) and ethyl acetate (30 ml). The organic layer was washed with water (2×10 mL), brine (10 mL), and concentrated in vacuo. The crude product was adsorbed onto a plug of silica gel and chromatographed through a Redi-Sep® pre-packed silica gel column (40 g), eluting with 0% to 50% EtOAc in hexane, to provide tert-butyl 5-(2-fluoropyridin-3-yl)-3,4-dihydropyridine-1(2H)-carboxylate as a colorless syrup. MS (ESI, pos. ion) m/z: 332.1 (M+Na).

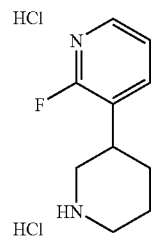 [SMILES: Cl ; Cl ; Fc1ncccc1C1CCCNC1]

STEP 4. 2-FLUORO-3-(PIPERIDIN-3-YL)PYRIDINE DIHYDROCHLORIDE

To a N₂ purged RBF containing tert-butyl 5-(2-fluoropyridin-3-yl)-3,4-dihydropyridine-1(2H)-carboxylate (673 mg, 2.418 mmol) was added 10% Pd/C (50 mg, 0.470 mmol) and EtOH (15 mL). After stirring for 5 minutes, 5N HCl in iPrOH (4.0 mL, 20.00 mmol) was added and the flask capped with a balloon of H₂. After 16 hours, LC-MS shows ~30% conversion. The balloon was refilled. After a further 5 days, LC-MS shows complete consumption of starting material. The reaction was filtered through a celite cartridge and the cartridge rinsed with DCM:10% EtOH (50 mL). The filtrate was concentrated in vacuo to give 2-fluoro-3-(piperidin-3-yl)pyridine dihydrochloride as a yellow foam. The material was carried forward without further purification.

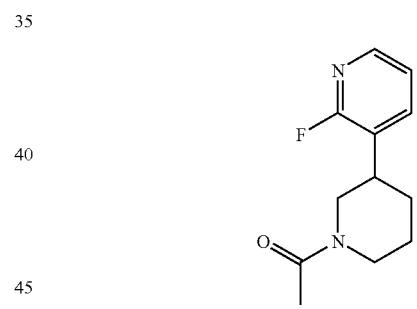

STEP 5. 1-(3-(2-FLUOROPYRIDIN-3-YL)PIPERIDIN-1-YL)ETHANONE

To an ice cooled solution of 2-fluoro-3-(piperidin-3-yl)pyridine dihydrochloride (612 mg, 2.418 mmol), DCM (20 mL) and triethylamine (2022 μL, 14.51 mmol) was added acetic anhydride (229 μL, 2.418 mmol) dropwise. After 1 hour, the reaction was poured into water and the aqueous mixture back extracted once with DCM (10 mL). The combined organics were washed with 0.5M NaOH and concentrated in vacuo. The crude product was adsorbed onto a plug of silica gel and chromatographed through a Redi-Sep® pre-packed silica gel column (12 g), eluting with 0% to 100% EtOAc in hexane, to provide 1-(3-(2-fluoropyridin-3-yl)piperidin-1-yl)ethanone (100 mg, 0.450 mmol) as a light yellow syrup. MS (ESI, pos. ion) m/z: 223.1 (M+1).

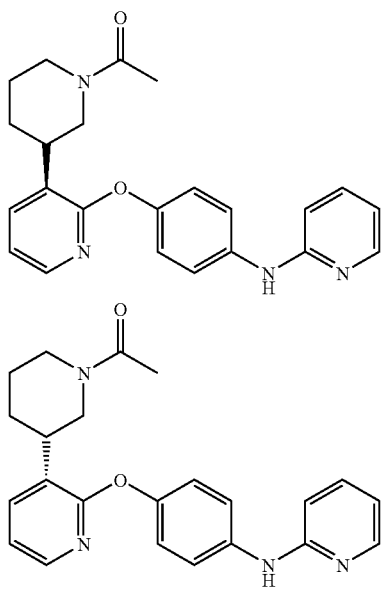

STEP 6. N-(4-((3-((3R)-1-ACETYL-3-PIPERIDI-NYL)-2-PYRIDINYL)OXY)PHENYL)-2-PYRIDINAMINE AND N-(4-((3-((3S)-1-ACETYL-3-PIPERIDINYL)-2-PYRIDINYL)OXY)PHENYL)-2-PYRIDINAMINE

To a solution of 1-(3-(2-fluoropyridin-3-yl)piperidin-1-yl)ethanone (95 mg, 0.427 mmol), NMP (2.0 mL) was added cesium carbonate (139 mg, 0.427 mmol) and 4-(pyridin-2-ylamino)phenol (108 mg, 0.580 mmol). The reaction mixture was stirred and heated in a Biotage Initiator at 160° C. for 30 minutes. The heating was repeated in the microwave at 180° C. for 2 h. The reaction was poured into water (40 mL) and extracted with EtOAc (3×10 mL). The combined organics were washed with brine, dried over $MgSO_4$, and concentrated in vacuo. The crude product was adsorbed onto a plug of silica gel and chromatographed through a Redi-Sep® pre-packed silica gel column (12 g), eluting with 0% to 5% MeOH in EtOAc, to provide a 1:1 mixture of N-(4-((3-((3R)-1-acetyl-3-piperidinyl)-2-pyridinyl)oxy)phenyl)-2-pyridinamine and N-(4-((3-((3S)-1-acetyl-3-piperidinyl)-2-pyridinyl)oxy)phenyl)-2-pyridinamine (44 mg, 0.057 mmol) as an off-white foam. MS (ESI, pos. ion) m/z: 389.1 (M+1). IC50 (uM) 0.002248.

TABLE XVIA

EXAMPLE 301 IS TABULATED BELOW:

| Ex. No. | Compound Structure | Compound Name | MS | PDE10 IC50 (uM) |
|---|---|---|---|---|
| 301 | 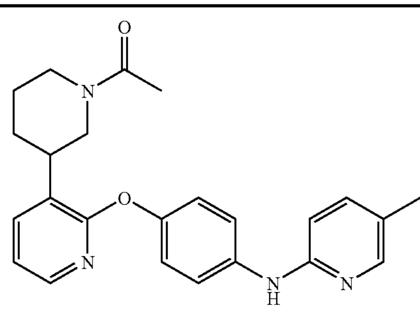 | 1-(3-(2-(4-(5-methylpyridin-2-ylamino)phenoxy)pyridin-3-yl)piperidin-1-yl)ethanone | 403 | 0.002 |

TABLE XVIB

PREPARATION OF EXAMPLE 301 IS TABULATED BELOW:

| Ex. No. | Scheme | Starting material 1 | Starting material 2 | Conditions or reagents that differ from scheme |
|---|---|---|---|---|
| 301 | 46 | | | |

SCHEME 47

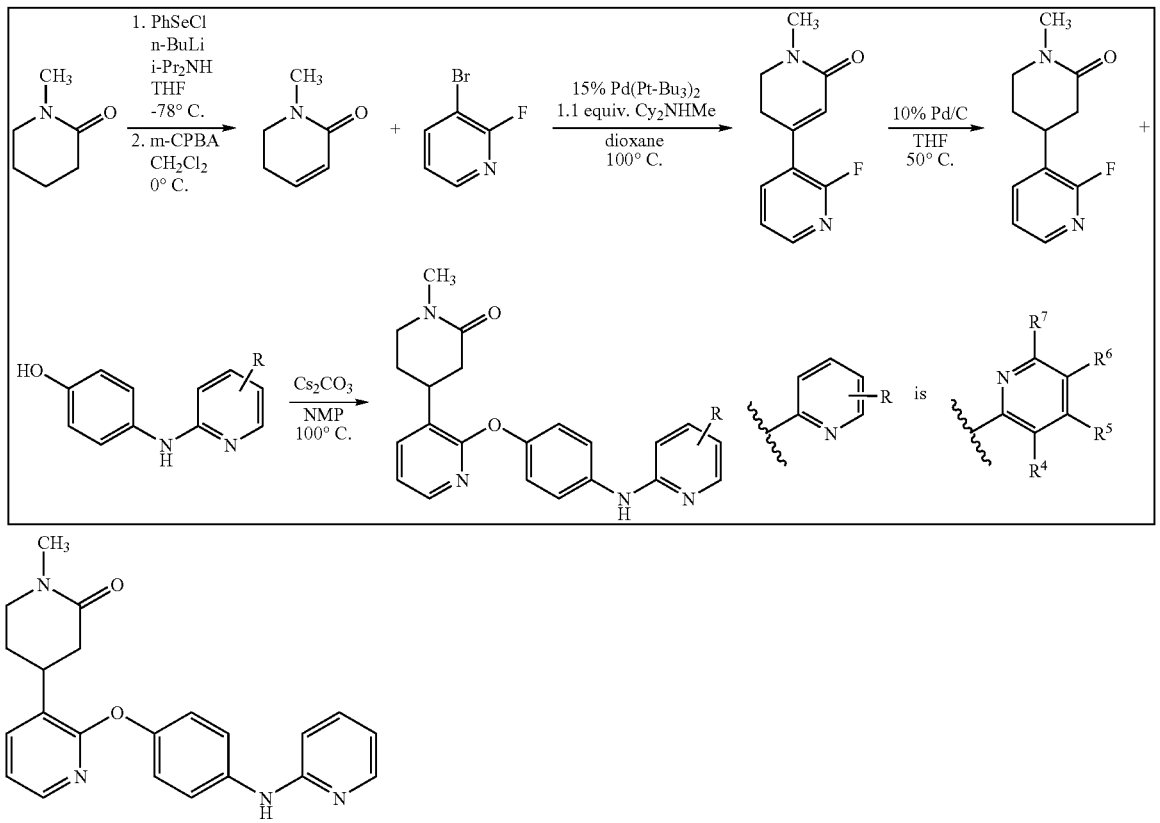

Example 302

1-METHYL-4-(2-(4-(PYRIDIN-2-YLAMINO)PHE-NOXY)PYRIDIN-3-YL)PIPERIDIN-2-ONE

STEP 1.
1-METHYL-5,6-DIHYDROPYRIDIN-2(1H)-ONE

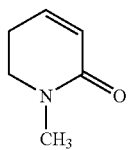

A solution of diisopropylamine (3 mL, 21.2 mmol) in tetrahydrofuran (44 mL) under argon was cooled to −78° C. and added butyllithium solution, 2.5 M in hexanes (8 mL, 21.2 mmol). After 5 min, a solution of 1-methylpiperidin-2-one (2 g, 17.6 mmol) in tetrahydrofuran (2 mL) was added dropwise. After stirring for 10 min, a solution of phenylselenenyl chloride (4.0 g, 21.2 mmol) in 16 mL of tetrahydrofuran was added, and the reaction was stirred at −78° C. for 2 h. The reaction was quenched with aqueous saturated NH$_4$Cl solution and diluted with CH$_2$Cl$_2$; the aqueous layer was back-extracted with CH$_2$Cl$_2$ (1×). The combined organic extracts were dried (MgSO$_4$), filtered, and concentrated in vacuo to afford a crude crop of 1-methyl-3-(phenylselanyl)piperidin-2-one in dichloromethane. To the crude 1-methyl-3-(phenylselanyl)piperidin-2-one in dichloromethane (50 mL) at 0° C. under argon was added 3-chlorobenzoperoxoic acid (7.92 g, 35.3 mmol). The resulting mixture was allowed to gradually warm to room temperature overnight. The orange suspension was filtered, and the filtrate was concentrated in vacuo and partitioned between CH$_2$Cl$_2$ and aqueous saturated NaHCO$_3$ solution; the aqueous layer was back-extracted with CH$_2$Cl$_2$ (5×). The combined organic extracts were dried (MgSO$_4$), filtered, and concentrated in vacuo. Flash column chromatography (20% EtOAc/Hexanes to 100% EtOAc) afforded 1-methyl-5,6-dihydropyridin-2(1H)-one as a brown oil. MS (ESI, pos. ion) m/z: 112.2 (M+1).

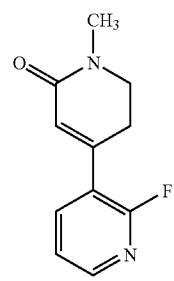

STEP 2. 4-(2-FLUOROPYRIDIN-3-YL)-1-METHYL-5,6-DIHYDROPYRIDIN-2(1H)-ONE

Into a sealed tube were placed 3-bromo-2-fluoropyridine (0.10 g, 0.60 mmol), 1-methyl-5,6-dihydropyridin-2(1H)-one (0.134 g, 1.20 mmol), bis(tri-tert-butylphosphine)palladium (0) (0.046 g, 0.09 mmol), N,N-dicyclohexylmethylamine (0.13 mL, 0.66 mmol), and 1,4-dioxane (0.5 mL). After the mixture was degassed for 5 min, the reaction was heated at 100° C. for 3 h. The cooled reaction was concentrated in vacuo, and the brown residue was directly purified via flash column chromatography (20% EtOAc/Hexanes to 100% EtOAc) to give 4-(2-fluoropyridin-3-yl)-1-methyl-5,6-dihydropyridin-2(1H)-one as a tan solid. MS (ESI, pos. ion) m/z: 207.1 (M+1).

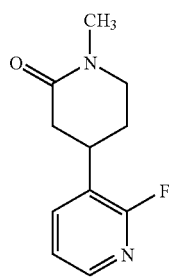

STEP 3. 4-(2-FLUOROPYRIDIN-3-YL)-1-METHYLPIPERIDIN-2-ONE

A solution of 4-(2-fluoropyridin-3-yl)-1-methyl-5,6-dihydropyridin-2(1H)-one (0.067 g, 0.32 mmol) in tetrahydrofuran (1.6 mL) was added palladium, 10 wt. % on activated carbon (0.035 g, 0.032 mmol) and hydrogenated (double-walled balloon pressure) at 40° C. for 3 h. The mixture was filtered via a pad of Celite, and the filtrate was concentrated in vacuo to give a relatively pure crop of 4-(2-fluoropyridin-3-yl)-1-methylpiperidin-2-one as a milky oil. MS (ESI, pos. ion) m/z: 209.0 (M+1).

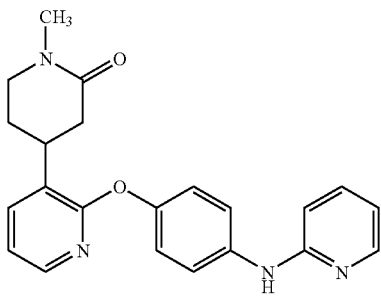 [SMILES: CN1CCC(c2cccnc2Oc2ccc(Nc3ccccn3)cc2)CC1=O]

STEP 4. 1-METHYL-4-(2-(4-(PYRIDIN-2-YLAMINO)PHENOXY)PYRIDIN-3-YL)PIPERIDIN-2-ONE 4-(2-Fluoropyridin-3-yl)-1-methylpiperidin-2-one (0.07 g, 0.33 mmol), 4-(pyridin-2-ylamino)phenol (0.144 g, 0.77 mmol), cesium carbonate (0.274 g, 0.84 mmol), and 1-methyl-2-pyrrolidinone (1 mL) were combined in a sealed tube and heated at 100° C. for 18 h. The cooled mixture was diluted with EtOAc and washed with water; the aqueous layer was back-washed with EtOAc (1×). The combined organic extracts were dried (MgSO$_4$), filtered, and concentrated in vacuo. ISCO purification with 20% to 80% EtOAc (10% MeOH)/Hexanes afforded 1-methyl-4-(2-(4-(pyridin-2-ylamino)phenoxy)pyridin-3-yl)piperidin-2-one (0.053 g, 42.1% yield) as a tan amorphous solid. MS (ESI, pos. ion) m/z: 375.0 (M+1). IC50 (uM) 0.005.

SCHEME 48

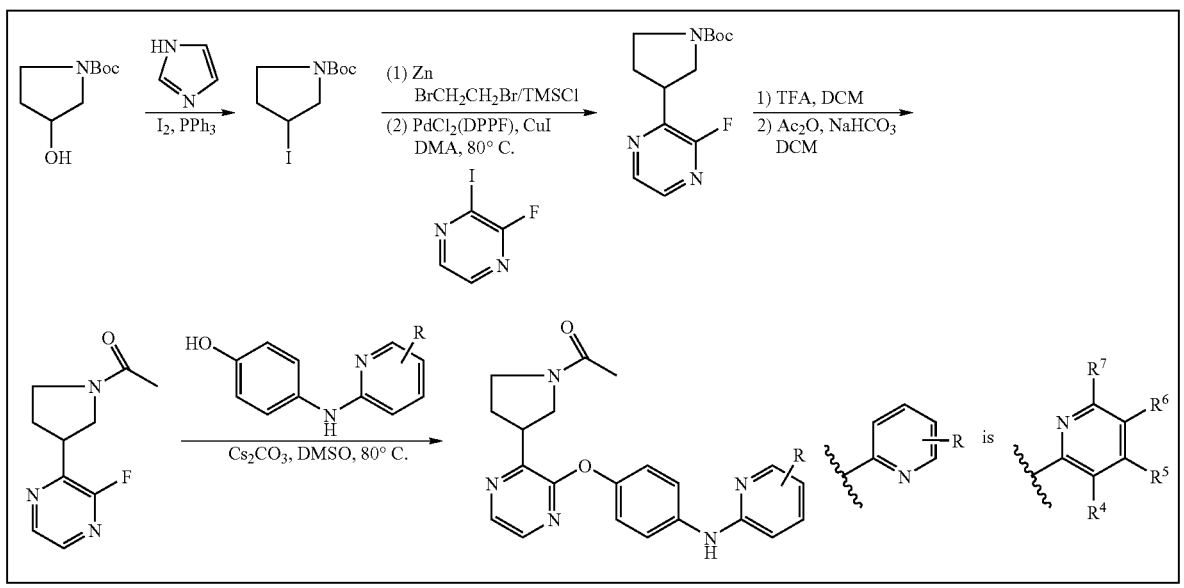

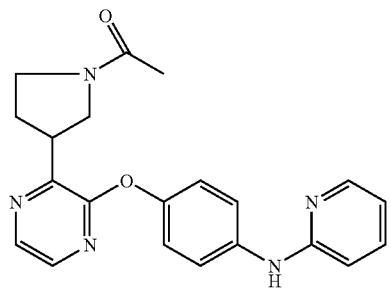

Example 303

1-(3-(3-(4-(PYRIDIN-2-YLAMINO)PHENOXY)PYRAZIN-2-YL)PYRROLIDIN-1-YL)ETHANONE

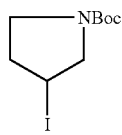

STEP 1. TERT-BUTYL 3-IODOPYRROLIDINE-1-CARBOXYLATE

Imidazole (2.62 g, 38.5 mmol), triphenylphosphine (10.1 g, 38.5 mmol), and tert-butyl 3-hydroxypyrrolidine-1-carboxylate (6.0 g, 32 mmol) were combined in 20 mL of THF and cooled in an ice bath. A freshly prepared solution of iodine (9.76 g, 38.5 mmol) in 20 mL of THF was then added at the rate of maintaining the internal temperature below 12° C. After the addition was complete, the reaction was allowed to warm to RT and stirred for 16 h. The reaction mixture was partitioned between MeO$^t$Bu and 10% NaHSO$_3$. The aqueous layer was back extracted with MeO$^t$Bu (2×) and the combined orgnia layers were washed with brine, dried (Na$_2$SO$_4$) and concentrated. The crude material was chromatographed through a Redi-Sep pre-packed silica gel column (120 g), eluting with a gradient of 0% to 20% EtOAc in hexane, to provide tert-butyl 3-iodopyrrolidine-1-carboxylate as a colorless oil. MS (ESI, pos. ion) m/z: 241.6 (M−56).

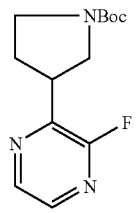

STEP 2. TERT-BUTYL 3-(3-FLUORO-PYRAZIN-2-YL)PYRROLIDINE-1-CARBOXYLATE

Into an oven-dried 25 mL RBF was charged dry DMA (4 mL), zinc dust (1.56 g, 23.9 mmol). The mixture was stirred at RT while the mixture of chlorotrimethylsilane (0.24 mL, 1.9 mmol) and 1,2-dibromoethane (0.17 mL, 1.9 mmol) was added slowly. The resulting slurry was aged for 15 min. A solution of tert-butyl 3-iodopyrrolidine-1-carboxylate (5.72 g, 19.3 mmol) in DMA (10 mL) was added slowly to the above mixture. Zinc slurry reacted exothermically with the gradual addition of the iodide. After stirring for 60 min, the resulting milky solution was cooled to RT and used directly in the next step.

Into an oven-dried flask were charged 2-fluoro-3-iodopyrazine (3.08 g, 13.8 mmol), 1,1'-bis(diphenylphosphino)ferrocene]dichloride palladium(ii)complex with dichloramethane (0.34 g, 0.41 mmol), copper(i) iodide (0.16 g, 0.83 mmol), and DMA (20 mL). The resulting mixture was degassed with alternating vacuum/nitrogen purges. The (1-(tert-butoxycarbonyl)pyrrolidin-3-yl)zinc(II) iodide (6.98 g, 19.3 mmol) solution from previous step was filtered through a regular filter into the mixture. It was degassed one more time and then heated to 80° C. with stirring for 16 h. After cooling to RT, the reaction mixture was partitioned between EtOAc and 1 N NH$_4$Cl. The aqueous layer was back extracted with EtOAc (2×) and the combined EtOAc layers were washed once again with 1 N NH$_4$Cl, then with brine, dried (Na$_2$SO$_4$) and concentrated. The crude material as chromatographed through a Redi-Sep pre-packed silica gel column (120 g), eluting with a gradient of 0% to 30% EtOAc in hexane, to provide tert-butyl 3-(3-fluoropyrazin-2-yl)pyrrolidine-1-carboxylate as orange oil. MS (ESI, pos. ion) m/z: 212.0 (M−56).

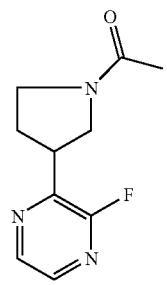

STEP 3. 1-(3-(3-FLUOROPYRAZIN-2-YL)PYRROLIDIN-1-YL)ETHANONE

To tert-butyl 3-(3-fluoropyrazin-2-yl)pyrrolidine-1-carboxylate (0.32 g, 1.2 mmol) dissolved in DCM (4 mL) was added trifluoroacetic acid, (1.3 mL, 18 mmol). The reaction mixture was stirred at RT for 1 h. The solvent was evaporated in vacuo and washed with DCM several times and used directly in the following step.

To 2-fluoro-3-(pyrrolidin-3-yl)pyrazine (0.2 g, 1.2 mmol) dissolved in DCM (2.4 mL) was added acetic anhydride (0.56 mL, 6.0 mmol) and sodium bicarbonate (0.502 g, 5.98 mmol). The reaction mixture was stirred at RT under $N_2$ for 3 h. The reaction mixture was partitioned between 1N NaOH and DCM. The aqueous layer was back extracted with DCM (3×) and the combined DCM layer was washed with brine, dried ($Na_2SO_4$) and concentrated to provide 1-(3-(3-fluoropyrazin-2-yl)pyrrolidin-1-yl)ethanone as a yellow oil. MS (ESI, pos. ion) m/z: 210.0 (M+1).

STEP 4. 1-(3-(3-(4-(PYRIDIN-2-YLAMINO)PHE-NOXY)PYRAZIN-2-YL)PYRROLIDIN-1-YL) ETHANONE

A glass microwave reaction vessel was charged with 1-(3-(3-fluoropyrazin-2-yl)pyrrolidin-1-yl)ethanone (78 mg, 0.37 mmol), 4-(pyridin-2-ylamino)phenol (139 mg, 0.746 mmol), cesium carbonate (243 mg, 0.746 mmol), and DMSO (1.2 mL). The reaction mixture was degassed and flushed with $N_2$ and heated in an oil bath at 80° C. for 20 h. After cooling to RT, the reaction mixture was partitioned between EtOAc and 1 N $NH_4Cl$. The aqueous layer was back extracted with EtOAc (2×) and the combined organic layer was washed with water, brine, dried ($Na_2SO_4$) and concentrated. The crude material was chromatographed through a Redi-Sep pre-packed silica gel column (40 g), eluting with a gradient of 0% to 100% EtOAc in hexane, then 5% MeOH in EtOAc, to provide 1-(3-(3-(4-(pyridin-2-ylamino)phenoxy)pyrazin-2-yl)pyrrolidin-1-yl)ethanone as an off-white solid. MS (ESI, pos. ion) m/z: 376.1 (M+1). IC50 (uM) 0.0164.

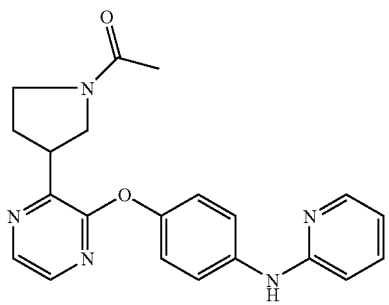 [SMILES: CC(=O)N1CCC(c2nccnc2Oc2ccc(Nc3ccccn3)cc2)C1]

SCHEME 49

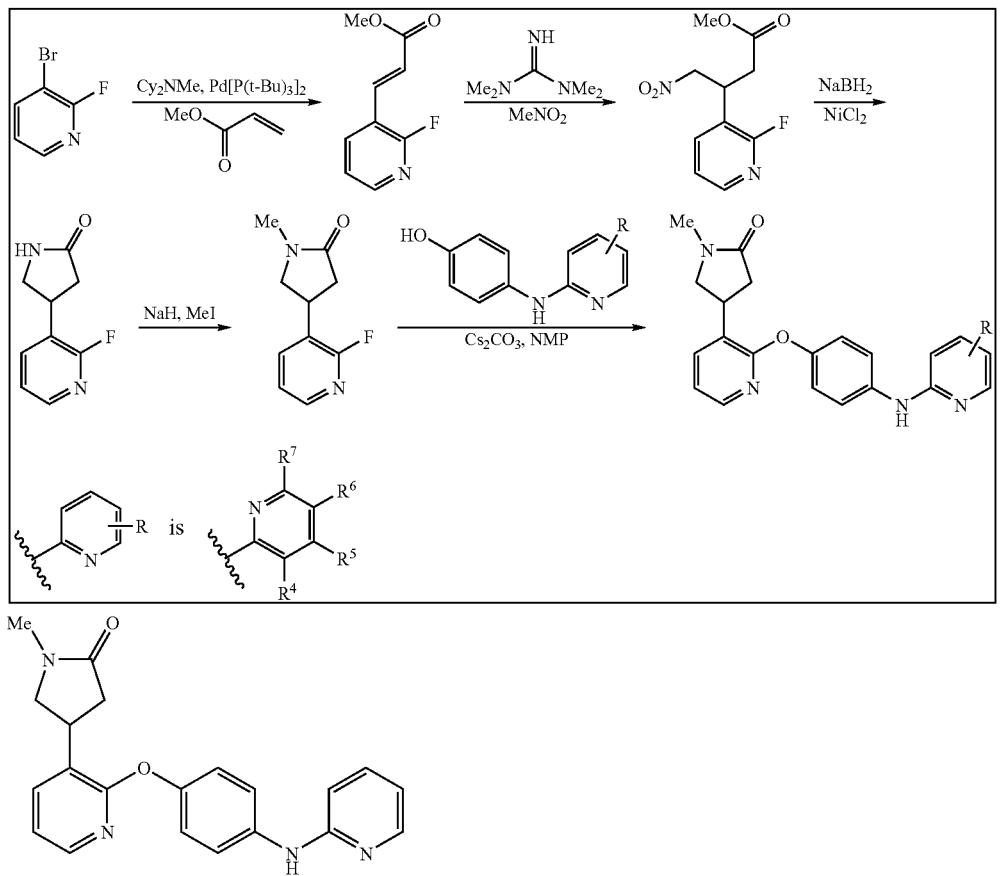

Example 304

1-METHYL-4-(2-(4-(PYRIDIN-2-YLAMINO)PHENOXY)PYRIDIN-3-YL)PYRROLIDIN-2-ONE

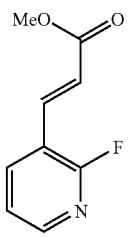

STEP 1. (E)-METHYL 3-(2-FLUOROPYRIDIN-3-YL)ACRYLATE

To Pd[P(t-Bu)$_3$]$_2$ (0.210 g, 0.411 mmol) was added dioxane (6 mL), methyl acrylate (2.00 mL, 22.2 mmol), N,N-dicyclohexylmethylamine (3.60 mL, 17.0 mmol), and 3-bromo-2-fluoropyridine (1.02 g, 5.80 mmol). The reaction mixture was degassed and heated to 110° C. for 5 min. The reaction was cooled to room temperature and diluted with EtOAc. The organic phase was washed with water (1×), brine (1×), dried over MgSO$_4$, filtered, and concentrated. Purification by flash column chromatography on silica gel (10% to 50% EtOAc in hexanes) gave the product which contained Cy$_2$NMe. The Cy$_2$NMe was removed by dissolving the mixture in DCM (5 mL) and diluting with hexanes (10 mL). The solution was concentrated to a volume of 5 mL and the solid precipitate was collected by filtration and dried under high vacuum to give (E)-methyl 3-(2-fluoropyridin-3-yl)acrylate as a white solid. MS (ESI, pos. ion) m/z: 182.1 (M+1).

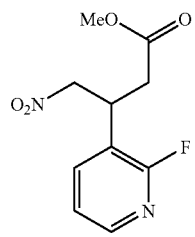 [SMILES: COC(=O)CC(C[N+](=O)[O-])c1cccnc1F]

STEP 2. METHYL 3-(2-FLUOROPYRIDIN-3-YL)-4-NITROBUTANOATE

To (E)-methyl 3-(2-fluoropyridin-3-yl)acrylate (0.945 g, 5.22 mmol) was added nitromethane (10.0 mL, 186 mmol) and 1,1,3,3-tetramethylguanidine (0.120 mL, 0.956 mmol). The reaction mixture was stirred at room temperature for 30 min, heated to 50° C. for 1 h, and diluted with EtOAc and water. The aqueous phase was extracted with EtOAc (2×) and the combined organic extracts were washed with brine (1×), dried over MgSO$_4$, filtered, and concentrated. Purification by flash column chromatography on silica gel (20% to 60% EtOAc in hexanes) gave methyl 3-(2-fluoropyridin-3-yl)-4-nitrobutanoate as a colorless oil. MS (ESI, pos. ion) m/z: 243.1 (M+1).

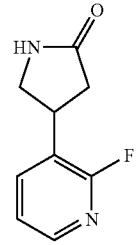

STEP 3. 4-(2-FLUOROPYRIDIN-3-YL)PYRROLIDIN-2-ONE

To a solution of methyl 3-(2-fluoropyridin-3-yl)-4-nitrobutanoate (0.991 g, 4.09 mmol) in EtOH (20 mL) at 0° C. was added nickel chloride (0.532 g, 4.10 mmol) and sodium borohydride (1.60 g, 42.3 mmol). The reaction mixture was stirred at 0° C. for 30 min, warmed to room temperature over 30 min, and stirred at room temperature for 30 min. The reaction mixture was quenched with saturated aqueous KH$_2$PO$_4$ and diluted with water and EtOAc. The mixture was filtered through a pad of Celite. The filtrate was extracted with EtOAc (6×) and the combined organic extracts were washed with brine (1×), dried over MgSO$_4$, filtered, and concentrated. Purification by flash column chromatography on silica gel (5% to 10% MeOH in DCM) gave 4-(2-fluoropyridin-3-yl)pyrrolidin-2-one as a colorless oil. MS (ESI, pos. ion) m/z: 181.1 (M+1).

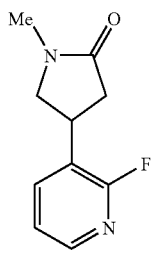 [SMILES: CN1CC(c2cccnc2F)CC1=O]

STEP 4. 4-(2-FLUOROPYRIDIN-3-YL)-1-METHYLPYRROLIDIN-2-ONE

To a solution of 4-(2-fluoropyridin-3-yl)pyrrolidin-2-one (0.254 g, 1.41 mmol) in DMF (5 mL) at 0° C. was added iodomethane (0.090 mL, 1.4 mmol) and sodium hydride (60% weight dispersion in mineral oil, 0.056 g, 1.4 mmol). The reaction mixture was stirred at 0° C. for 30 min, warmed to room temperature, and stirred for 30 min. The reaction mixture was diluted with EtOAc, quenched with water, and diluted with brine and water. The aqueous phase was extracted with EtOAc (6×) and the combined organic extracts were washed with brine (1×), dried over MgSO₄, filtered, and concentrated. Purification by flash column chromatography on silica gel (50% to 100% EtOAc (10% MeOH) in hexanes) gave 4-(2-fluoropyridin-3-yl)-1-methylpyrrolidin-2-one as a pale yellow oil. MS (ESI, pos. ion) m/z: 195.1 (M+1).

STEP 5. 1-METHYL-4-(2-(4-(PYRIDIN-2-YLAMINO)PHENOXY)PYRIDIN-3-YL)PYRROLIDIN-2-ONE

To a mixture of cesium carbonate (0.559 g, 1.72 mmol), 4-(pyridin-2-ylamino)phenol (0.320 g, 1.72 mmol), and 4-(2-fluoropyridin-3-yl)-1-methylpyrrolidin-2-one (0.110 g, 0.566 mmol) was added NMP (2 mL). The reaction mixture was degassed and heated to 100° C. for 2 h. The reaction mixture was diluted with EtOAc and water. The aqueous phase was extracted with EtOAc (4×) and the combined organic extracts were washed with 1 M NaOH (1×), brine (1×), dried over MgSO₄, filtered, and concentrated. Purification by flash column chromatography on silica gel (30% to 100% EtOAc (10% MeOH) in hexanes) gave 1-methyl-4-(2-(4-(pyridin-2-ylamino)phenoxy)pyridin-3-yl)pyrrolidin-2-one as a white solid and a 1:1 mixture of enantiomers. MS (ESI, pos. ion) m/z: 361.1 (M+1). IC50 (uM) 0.01406.

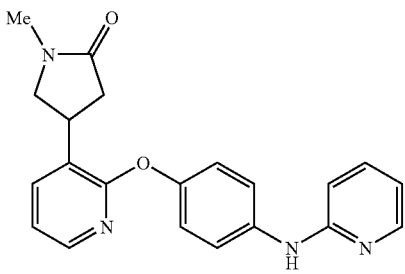 [SMILES: CN1CC(c2cccnc2Oc2ccc(Nc3ccccn3)cc2)CC1=O]

SCHEME 50

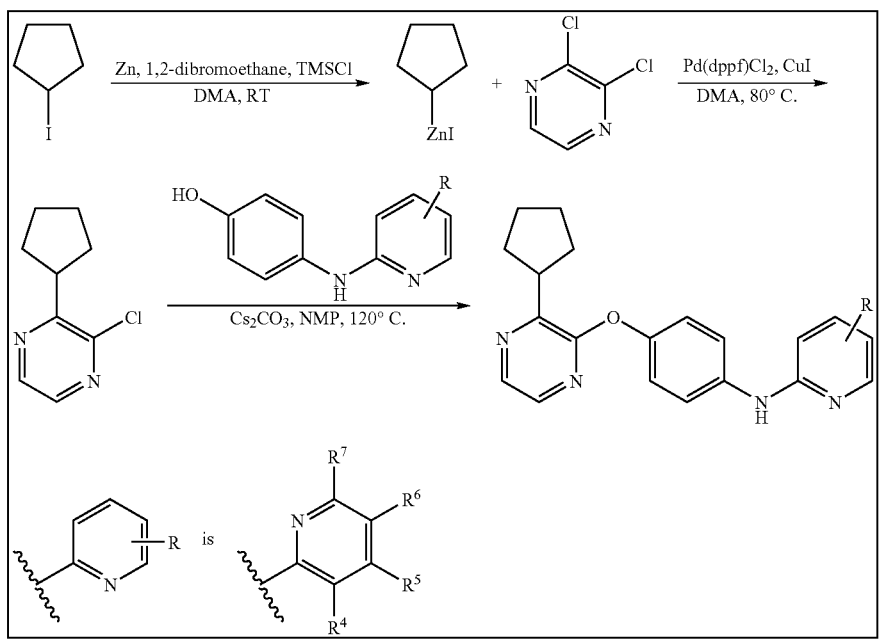

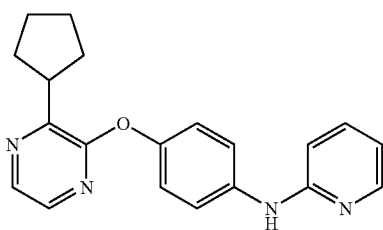 [SMILES: c1ccc(Nc2ccc(Oc3nccnc3C3CCCC3)cc2)nc1]

Example 305

N-(4-(3-CYCLOPENTYLPYRAZIN-2-YLOXY)PHENYL)PYRIDIN-2-AMINE

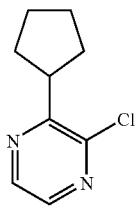

STEP 1. 2-CHLORO-3-CYCLOPENTYLPYRAZINE

To a suspension of zinc dust (2.00 g, 30.6 mmol) in N,N-dimethylacetamide (20 mL) was added a mixture of trimethylsilyl chloride and 1,2-dibromoethane (7:5, v/v, 0.95mL total volume) dropwise over 5 minutes. The mixture was stirred for 15 min before cyclopentyl iodide (5.00 g, 25.5 mmol) was added dropwise over 15 min. This mixture was stirred for an additional 15 min and then was added via syringe over 5 min to a mixture of copper(I) iodide (0.30 g, 1.60 mmol), dichloro(1,1-bis(diphenylphosphinoferrocene)) palladium(II) (0.65 g, 0.80 mmol), and 2,3-dichloropyrazine (1.66 mL, 16.0 mmol) in N,N-dimethylacetamide (30 mL) under argon atmosphere. The mixture was heated to 80° C. for 7 h, cooled to room temperature and partitioned between ethyl acetate and saturated aqueous ammonium chloride. The resulting layers were separated and the aqueous layer was extracted with ethyl acetate (1×). The combined extracts were washed with water (2×), saturated aqueous sodium chloride, dried over anhydrous magnesium sulfate, filtered, and concentrated in vacuo. The residue was purified by silica gel chromatography to give 2-chloro-3-cyclopentylpyrazine.

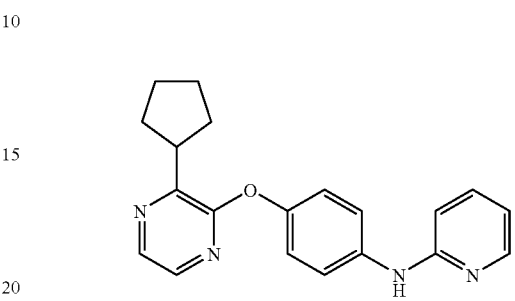

STEP 2. N-(4-(3-CYCLOPENTYLPYRAZIN-2-YLOXY)PHENYL)PYRIDIN-2-AMINE

A mixture of 4-(pyridin-2-ylamino)phenol (0.30 g, 1.60 mmol), cesium carbonate (1.56 g, 4.80 mmol), and 2-chloro-3-cyclopentylpyrazine (0.29 g, 1.60 mmol) under argon was heated to 120° C. for 20 h. The mixture was cooled to RT and partitioned between ethyl acetate and water. The layers were separated and the organic layer was washed with aqueous 1N sodium hydroxide (2×), saturated aqueous sodium chloride (1×), dried over anhydrous magnesium sulfate, filtered, and concentrated in vacuo. The resulting oil was purified by silica gel chromatography to give N-(4-(3-cyclopentylpyrazin-2-yloxy)phenyl)pyridin-2-amine. MS (ESI, pos. ion) m/z: 333.3 (M+1). IC50 (uM) 0.012.

SCHEME 51

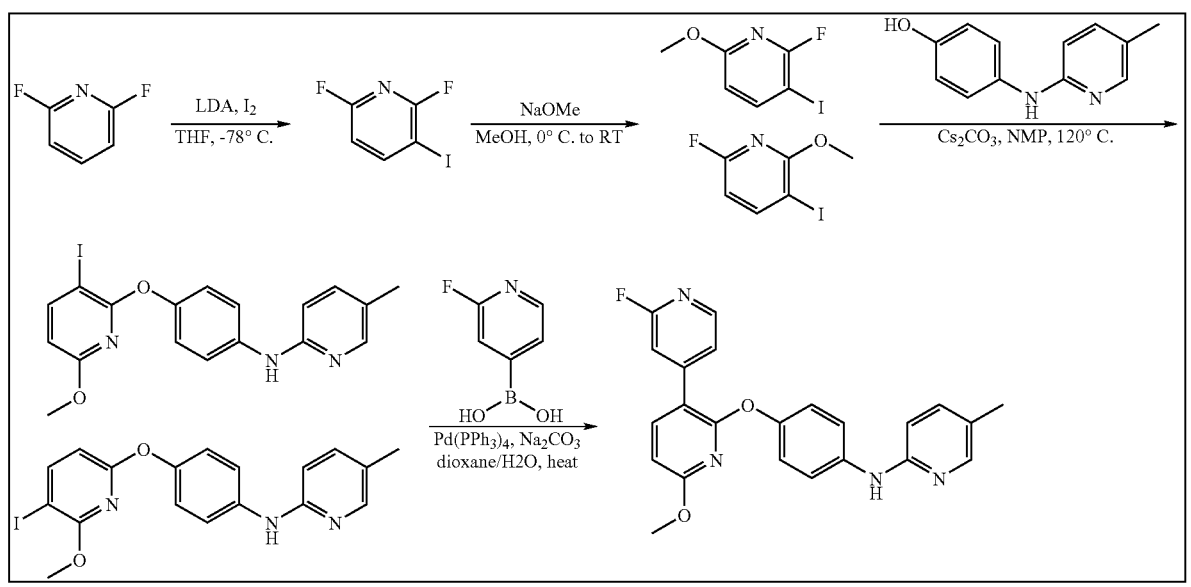

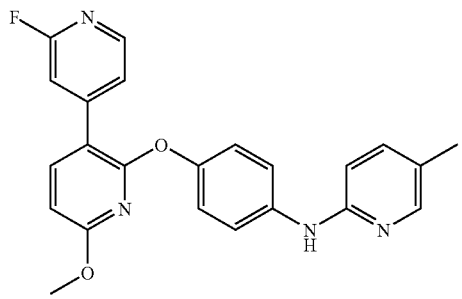

Example 306

N-(4-(2'-FLUORO-6-METHOXY-3,4'-BIPYRIDIN-2-YLOXY)PHENYL)-5-METHYLPYRIDIN-2-AMINE

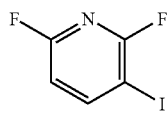

STEP 1. 2,6-DIFLUORO-3-IODOPYRIDINE

To a stirred solution of lithium diisopropylamide (4.34 mL, 8.69 mmol, 2.0 M solution in heptane/THF/ethylbenzene) in THF (20 mL) at −78° C. under a nitrogen atmosphere was added 2,6-difluoropyridine (0.79 mL, 8.69 mmol). The mixture was stirred at −78° C. for 45 min before iodine (2.21 g, 8.69 mmol) in THF (10 mL) was added via syringe. The reaction was stirred for an additional 30 min at −78° C. The reaction mixture was diluted with EtOAc and washed with 10% aqueous sodium sulfite. The organic layer was separated, dried over magnesium sulfate, filtered, and concentrated. The resulting crude product was purified by silica gel chromatography to give 2,6-difluoro-3-iodopyridine.

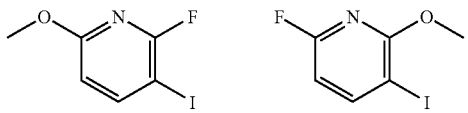

STEP 2. 2-FLUORO-3-IODO-6-METHOXYPYRIDINE AND 6-FLUORO-3-IODO-2-METHOXYPYRIDINE

Sodium metal (0.14 g, 5.89 mmol) was dissolved in MeOH (3 mL) under a nitrogen atmosphere. The solution was cooled to 0° C. before 2,6-difluoro-3-iodopyridine (1.42 g, 5.89 mmol) in MeOH (3 mL) was added via syringe. The reaction mixture was stirred at 0° C. for 3 h before being allowed to warm to room temperature gradually overnight. The reaction mixture was concentrated and then partitioned between EtOAc and water. The organic layer was separated, washed with sat. sodium chloride, dried over magnesium sulfate, filtered, and concentrated to give a mixture of 2-fluoro-3-iodo-6-methoxypyridine and 6-fluoro-3-iodo-2-methoxypyridine. 2-fluoro-3-iodo-6-methoxypyridine.

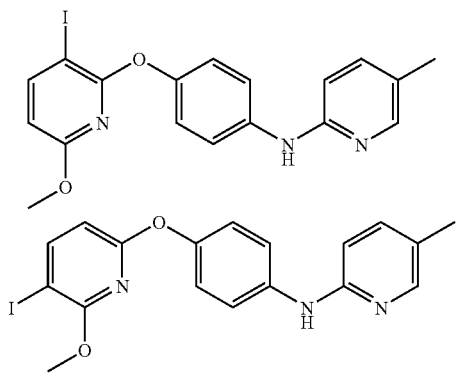

STEP 3. N-(4-(3-IODO-6-METHOXYPYRIDIN-2-YLOXY)PHENYL)-5-METHYLPYRIDIN-2-AMINE AND N-(4-(5-IODO-6-METHOXYPYRIDIN-2-YLOXY)PHENYL)-5-METHYLPYRIDIN-2-AMINE

A mixture of 2-fluoro-3-iodo-6-methoxypyridine and 6-fluoro-3-iodo-2-methoxypyridine (0.25 g, 0.99 mmol), 4-(5-methylpyridin-2-ylamino)phenol (0.40 g, 1.98 mmol), and cesium carbonate (0.64 g, 1.98 mmol) were mixed in NMP (3 mL). The reaction mixture was placed under a nitrogen atmosphere and stirred at 120° C. for 3 h. The reaction mixture was cooled to room temperature, diluted with water, and extracted with EtOAc (2×). The combined organic layers were washed with sat. sodium chloride, dried over magnesium sulfate, filtered, and concentrated. The resulting crude product was purified by silica gel chromatography to give a mixture of N-(4-(3-iodo-6-methoxypyridin-2-yloxy)phenyl)-5-methylpyridin-2-amine and N-(4-(5-iodo-6-methoxypyridin-2-yloxy)phenyl)-5-methylpyridin-2-amine. MS (ESI, pos. ion) m/z: 472.0 (M+1). for both isomers.

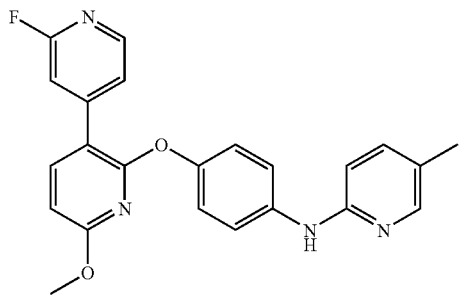 [SMILES: COc1ccc(-c2ccnc(F)c2)c(Oc2ccc(Nc3ccc(C)cn3)cc2)n1]

STEP 4. N-(4-(2'-FLUORO-6-METHOXY-3,4'-BIPYRIDIN-2-YLOXY)PHENYL)-5-METHYLPYRIDIN-2-AMINE

A mixture of N-(4-(3-iodo-6-methoxypyridin-2-yloxy)phenyl)-5-methylpyridin-2-amine and N-(4-(5-iodo-6-methoxypyridin-2-yloxy)phenyl)-5-methylpyridin-2-amine (0.13 g, 0.29 mmol), 2-fluoropyridine-4-boronic acid (0.049 g, 0.35 mmol), and tetrakis(triphenylphosphine)palladium (0.033 g, 0.029 mmol) were mixed in dioxane (1.2 mL) under an argon atmosphere. Sodium carbonate (0.43 mL, 0.87 mmol, 2.0 M in water) was added via syringe, and the reaction mixture was stirred at 80° C. for 16 h. The reaction mixture was then stirred at 120° C. for an additional 4 h before being cooled to room temperature. The reaction mixture was diluted with water and extracted with EtOAc (2×). The combined organic layers were washed with sat. sodium chloride, dried over magnesium sulfate, filtered, and concentrated. The resulting crude product was purified by silica gel chromatography to give a mixture of N-(4-(2'-fluoro-6-methoxy-3,4'-bipyridin-2-yloxy)phenyl)-5-methylpyridin-2-amine and N-(4-(2'-fluoro-2-methoxy-3,4'-bipyridin-6-yloxy)phenyl)-5-methylpyridin-2-amine. The regioisomers were then separated by reverse phase HPLC. The desired regioisomer was then partitioned between DCM and sat. aqueous sodium bicarbonate. The organic layers were separated, dried over magnesium sulfate, filtered, and concentrated to give N-(4-(2'-fluoro-6-methoxy-3,4'-bipyridin-2-yloxy)phenyl)-5-methylpyridin-2-amine. MS (ESI, pos. ion) m/z: 403.1 (M+1). IC50 (uM) 0.002.

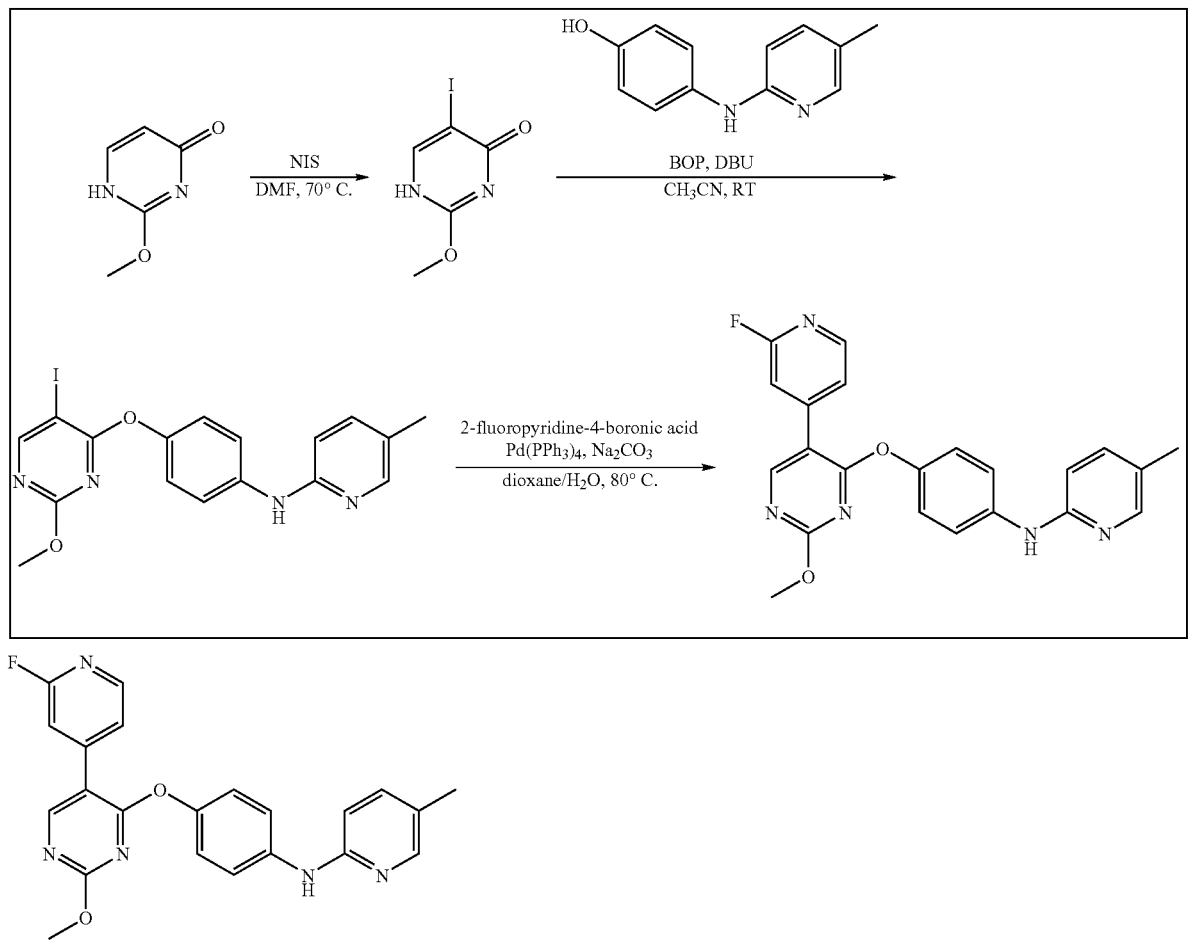

SCHEME 52

Example 307

N-(4-(5-(2-FLUOROPYRIDIN-4-YL)-2-METHOXYPYRIMIDIN-4-YLOXY)PHENYL)-5-METHYLPYRIDIN-2-AMINE

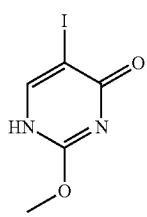

STEP 1. 5-IODO-2-METHOXYPYRIMIDIN-4(1H)-ONE

2-Methoxypyrimidin-4(1H)-one (1.00 g, 7.93 mmol) and n-iodosuccinimide (3.57 g, 15.86 mmol) were mixed in DMF (8 mL) under a nitrogen atmosphere. The reaction mixture was stirred at 70° C. for 2.5 h. The reaction mixture was cooled to room temperature, diluted with water, and extracted with EtOAc (3×). The combined organic layers were washed with sat. sodium chloride, dried over magnesium sulfate, filtered, and concentrated. The resulting solid was suspended in DCM, filtered, and washed with DCM to give 5-iodo-2-methoxypyrimidin-4(1H)-one. MS (ESI, pos. ion) m/z: 252.9 (M+1).

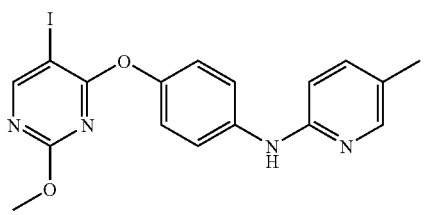 [SMILES: COc1ncc(I)c(Oc2ccc(Nc3ccc(C)cn3)cc2)n1]

STEP 2. N-(4-(5-IODO-2-METHOXYPYRIMIDIN-4-YLOXY)PHENYL)-5-METHYLPYRIDIN-2-AMINE

To a stirred mixture of 5-iodo-2-methoxypyrimidin-4(1H)-one (0.12 g, 0.46 mmol) and (1H-benzo[d][1,2,3]triazol-1-yloxy)tris(dimethylamino)phosphonium hexafluorophosphate(V) (0.24 g, 0.55 mmol) in acetonitrile (4 mL) was added 1,8-diazabicyclo[5.4.0]undec-7-ene (0.14 mL, 0.91 mmol). The reaction mixture was stirred at room temperature for 30 min before 4-(5-methylpyridin-2-ylamino)phenol (0.27 g, 1.37 mmol) was added. The reaction mixture was stirred at room temperature for an additional 1 h. The reaction mixture was diluted with EtOAc and washed with water. The organic layer was separated, washed with sat. sodium chloride, dried over magnesium sulfate, filtered, and concentrated. The resulting crude product was purified by silica gel chromatography to give N-(4-(5-iodo-2-methoxypyrimidin-4-yloxy)phenyl)-5-methylpyridin-2-amine. MS (ESI, pos. ion) m/z: 435.1 (M+1).

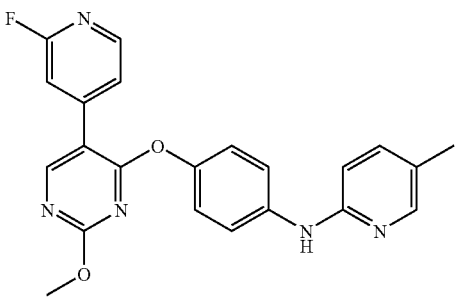 [SMILES: COc1ncc(-c2ccnc(F)c2)c(Oc2ccc(Nc3ccc(C)cn3)cc2)n1]

STEP 3. N-(4-(5-(2-FLUOROPYRIDIN-4-YL)-2-METHOXYPYRIMIDIN-4-YLOXY)PHENYL)-5-METHYLPYRIDIN-2-AMINE

N-(4-(5-Iodo-2-methoxypyrimidin-4-yloxy)phenyl)-5-methylpyridin-2-amine (0.061 g, 0.14 mmol), 2-fluoropyridine-4-boronic acid (0.030 g, 0.21 mmol), and tetrakis(triphenylphosphine)palladium (0.016 g, 0.014 mmol) were mixed in dioxane (0.5 mL) under an argon atmosphere. Sodium carbonate (0.21 mL, 0.42 mmol, 2.0 M in water) was added via syringe, and the reaction mixture was stirred at 80° C. for 20 h. The reaction mixture was cooled to room temperature, diluted with water, and extracted with EtOAc. The organic layer was separated, washed with sat. sodium chloride, dried over magnesium sulfate, filtered, and concentrated. The resulting crude product was purified by silica gel chromatography to give N-(4-(5-(2-fluoropyridin-4-yl)-2-methoxypyrimidin-4-yloxy)phenyl)-5-methylpyridin-2-amine. MS (ESI, pos. ion) m/z: 404.2 (M+1). IC50 (uM) 0.016.

SCHEME 53

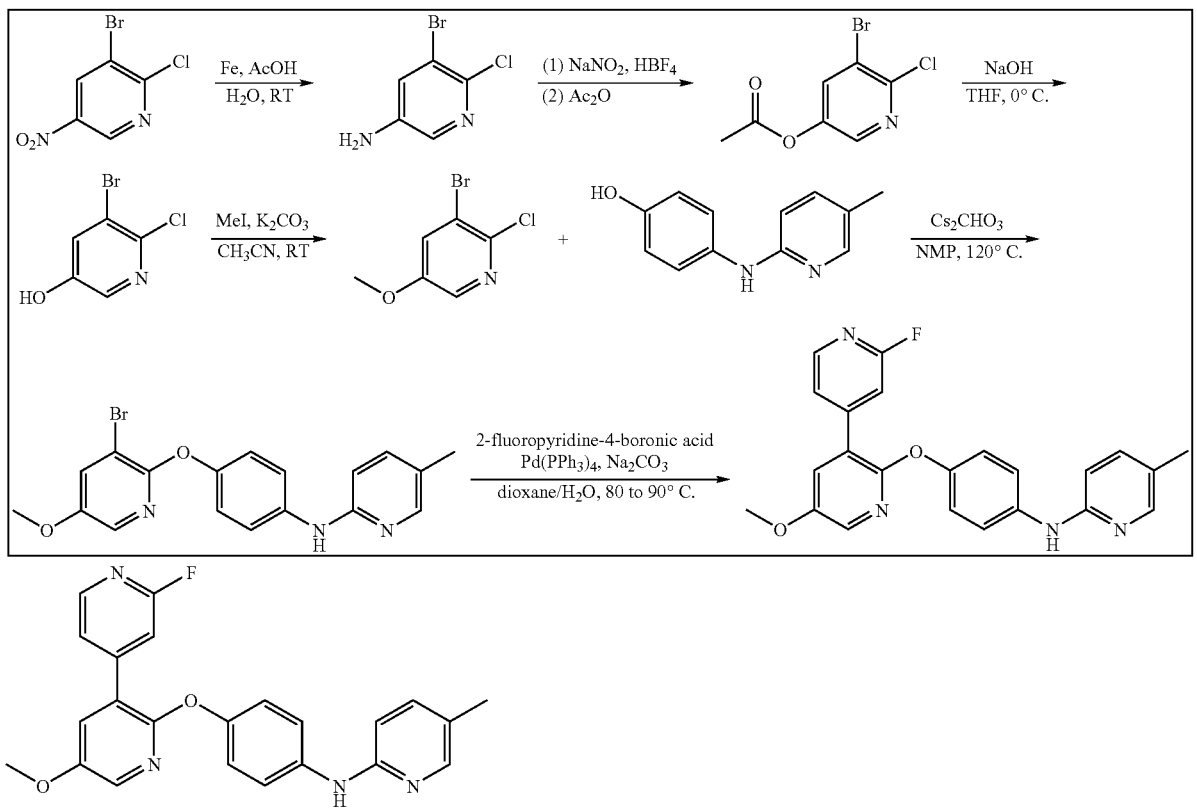

Example 308

N-(4-(2'-FLUORO-5-METHOXY-3,4'-BIPYRIDIN-2-YLOXY)PHENYL)-5-METHYLPYRIDIN-2-AMINE

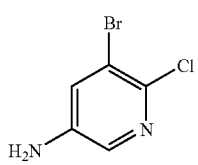

STEP 1. 5-BROMO-6-CHLOROPYRIDIN-3-AMINE

To a stirred mixture of 3-bromo-2-chloro-5-nitropyridine (10.00 g, 42.1 mmol) and acetic acid (12.16 mL, 211 mmol) in water (100 mL) at 0° C. was added iron (11.76 g, 211 mmol, powder −325 mesh). The mixture was warmed to room temperature and stirred for 4 h. The reaction mixture was filtered and washed with water. The filtrate was then extracted with EtOAc. The filter cake was then washed with EtOAc, and the resulting filtrate was combined with the previous organic layer from the aqueous extraction. The two organic mixtures were then washed with water (2×), washed with sat. sodium chloride, dried over magnesium sulfate, filtered, and concentrated to give 5-bromo-6-chloropyridin-3-amine. MS (ESI, pos. ion) m/z: 207.9 and 209.9 (M+1).

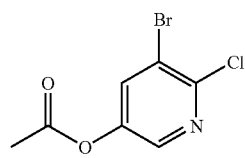

STEP 2. 5-BROMO-6-CHLOROPYRIDIN-3-YL ACETATE

To a stirred mixture of 5-bromo-6-chloropyridin-3-amine (7.57 g, 36.5 mmol) in tetrafluoroboric acid (70 mL, 536 mmol, 48 wt. % solution in water) at 0° C. was added sodium nitrite (2.64 g, 38.3 mmol) in water (70 mL) slowly over 10 min. The reaction mixture was stirred at 0° C. for 1 h. The reaction mixture was filtered and washed with water. The resulting solid was dissolved in acetic anhydride (70 mL, 742 mmol) and stirred at 70° C. for 1 h. The reaction mixture was cooled to room temperature, diluted with EtOAc, washed with water, washed with sat. sodium chloride, dried over magnesium sulfate, filtered, and concentrated. The resulting crude product was purified by silica gel chromatography to give 5-bromo-6-chloropyridin-3-yl acetate. MS (ESI, pos. ion) m/z: 249.9 and 251.9 (M+1).

STEP 3. 5-BROMO-6-CHLOROPYRIDIN-3-OL

To a stirred mixture of 5-bromo-6-chloropyridin-3-yl acetate (3.98 g, 15.89 mmol) in THF (20 mL) at 0° C. was added sodium hydroxide (20 mL, 50.0 mmol, 2.5 M in water). The reaction mixture was stirred at 0° C. for 45 min. The reaction mixture was partially concentrated and then taken to a pH of around 7 by adding acetic acid. The resulting precipitate was filtered and washed with water to give 5-bromo-6-chloropyridin-3-ol. MS (ESI, pos. ion) m/z: 207.9 and 209.9 (M+1).

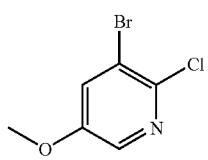

STEP 4.

3-BROMO-2-CHLORO-5-METHOXYPYRIDINE

To a stirred mixture of 5-bromo-6-chloropyridin-3-ol (2.95 g, 14.15 mmol) and potassium carbonate (1.28 mL, 21.23 mmol) in acetonitrile (45 mL) under a nitrogen atmosphere was added iodomethane (0.93 mL, 14.86 mmol). The reaction mixture was stirred at room temperature for 24 h. The reaction mixture was diluted with water and extracted with EtOAc (2×). The combined organic layers were washed with sat. sodium chloride, dried over magnesium sulfate, filtered, and concentrated. The resulting crude product was purified by silica gel chromatography to give 3-bromo-2-chloro-5-methoxypyridine. MS (ESI, pos. ion) m/z: 221.9 and 223.9 (M+1).

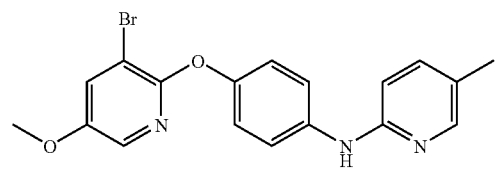

STEP 5. N-(4-(3-BROMO-5-METHOXYPYRIDIN-2-YLOXY)PHENYL)-5-METHYLPYRIDIN-2-AMINE

3-Bromo-2-chloro-5-methoxypyridine (0.30 g, 1.35 mmol), 4-(5-methylpyridin-2-ylamino)phenol (0.68 g, 3.37 mmol), and cesium carbonate (1.32 g, 4.05 mmol) were mixed in NMP (4 mL) under a nitrogen atmosphere. The reaction mixture was stirred at 120° C. for 16 h. The reaction mixture was cooled to room temperature, diluted with water, and extracted with EtOAc (2×). The combined organic layers were washed with sat. sodium chloride (1×), dried over magnesium sulfate, filtered, and concentrated in vacuo. The resulting crude product was purified by silica gel chromatography. The isolated product contained a significant impurity. The impurity was removed by reverse phase HPLC. The desired product was partitioned between DCM and sat. aqueous sodium bicarbonate. The organic layers were separated, dried over magnesium sulfate, filtered, and concentrated in vacuo to give N-(4-(3-bromo-5-methoxypyridin-2-yloxy)phenyl)-5-methylpyridin-2-amine. MS (ESI, pos. ion) m/z: 386.1 and 388.1 (M+1).

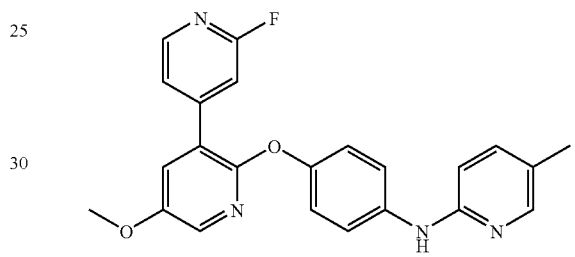

STEP 6. N-(4-(2'-FLUORO-5-METHOXY-3,4'-BIPYRIDIN-2-YLOXY)PHENYL)-5-METHYLPYRIDIN-2-AMINE

N-(4-(3-bromo-5-methoxypyridin-2-yloxy)phenyl)-5-methylpyridin-2-amine (0.076 g, 0.20 mmol), 2-fluoropyridine-4-boronic acid (0.056 g, 0.39 mmol), and tetrakis(triphenylphosphine)palladium (0.023 g, 0.020 mmol) were mixed in dioxane (0.8 mL) under an argon atmosphere. Sodium carbonate (0.30 mL, 0.59 mmol, 2.0 M in water) was added via syringe, and the reaction mixture was stirred at 80° C. for 20 h before being warmed to 90° C. and stirred for 24 h. The reaction mixture was cooled to room temperature, diluted with water, and extracted with EtOAc. The organic layer was separated, washed with sat. sodium chloride, dried over magnesium sulfate, filtered, and concentrated. The resulting crude product was purified by silica gel chromatography to give N-(4-(2'-fluoro-5-methoxy-3,4'-bipyridin-2-yloxy)phenyl)-5-methylpyridin-2-amine. MS (ESI, pos. ion) m/z: 403.2 (M+1). IC50 (uM) 0.004.

SCHEME 54

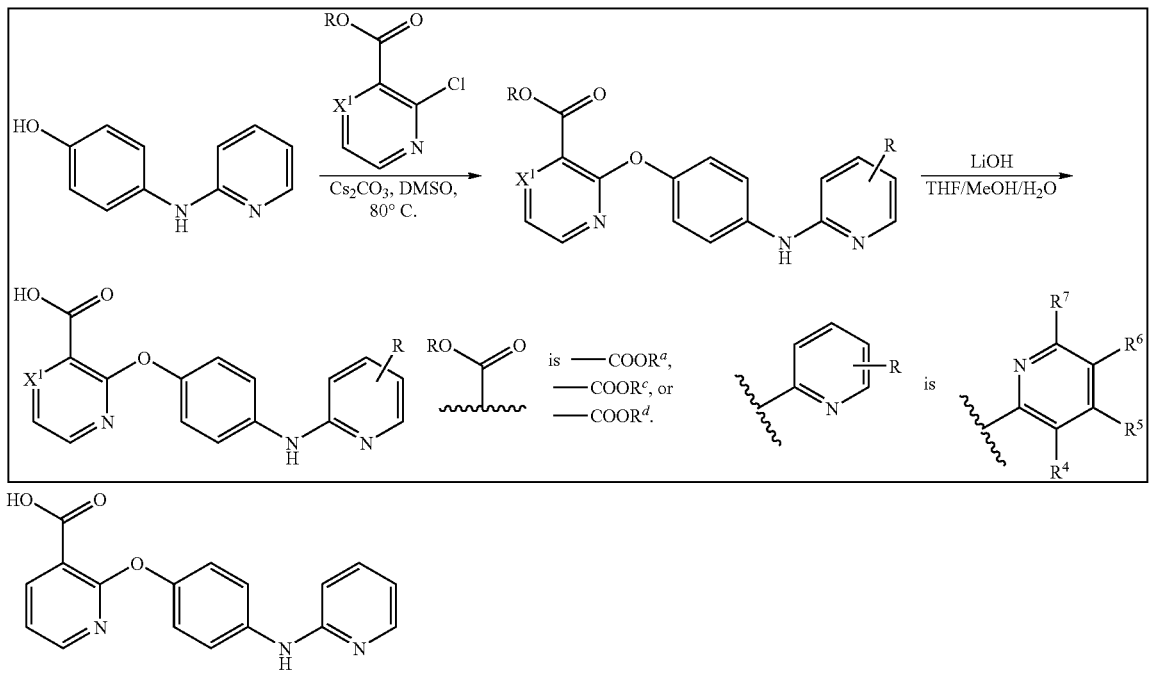

Example 309

2-(4-(PYRIDIN-2-YLAMINO)PHENOXY) NICOTINIC ACID

STEP 1: ETHYL 2-(4-(PYRIDIN-2-YLAMINO)PHENOXY)NICOTINATE

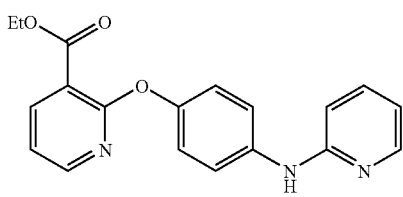 [SMILES: O=C(O)c1cccnc1Oc1ccc(Nc2ccccn2)cc1]

To a 150 mL pressure vessel was added ethyl 2-chloronicotinate (3.1 g, 17 mmol), 4-(pyridin-2-ylamino)phenol (3.14 g, 17 mmol), and cesium carbonate (5.8 g, 18 mmol) followed by DMSO. The solution was sealed and heated to 100° C. for 20 h. It was cooled and diluted with water and extracted five times with ethyl acetate. The combined organic were washed with brine, dried over sodium sulfate, filtered, and concentrated to a dark brown residue. The residue was taken up in dichlormethane and adsorbed onto silica gel before being purified with flash chromatography (0 to 50% ethyl acetate: hexanes), affording the product as a pale orange solid. MS (ESI, pos. ion) m/z: 336.0 (M+1).

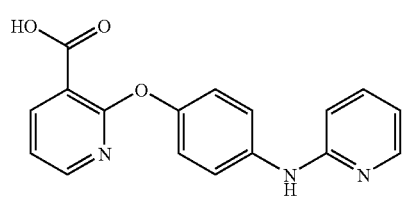

STEP 2: 2-(4-(PYRIDIN-2-YLAMINO) PHENOXY)NICOTINIC ACID

To a solution of ethyl 2-(4-(pyridin-2-ylamino)phenoxy) nicotinate (6.23 g, 18.6 mmol) in THF (0.28 M) was added lithium hydroxide (1.33 g, 55.7 mmol). The reaction was stirred for 16 h before adding an addition equivalent of lithium hydroxide and a volume of methanol and water relative to THF to make a 3:2:1 solution of THF:methanol:water. The resulting suspension was heated to 40° C. for 1.5 h. The solid was filtered away from the filtrate to afford the product as a pale orange solid. MS (ESI, pos. ion) m/z: 308.0 (M+1). IC50 (uM) 8.955.

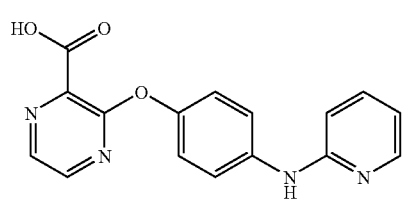 [SMILES: O=C(O)c1nccnc1Oc1ccc(Nc2ccccn2)cc1]

Example 310

3-(4-(PYRIDIN-2-YLAMINO)PHENOXY)PYRAZINE-2-CARBOXYLIC ACID

STEP 1: METHYL 3-CHLOROPYRAZINE-2-CARBOXYLATE

To a suspension of 3-chloropyrazine-2-carboxylic acid (10 g, 63 mmol) and cesium carbonate (31 g, 95 mmol) in DMF was added iodomethane (5.9 ml, 95 mmol). The solution was stirred for 48 hours. After that time, the reaction was removed from stirring, acidified to pH 5 with 1.0 N HCl and extracted five times with ethyl acetate. The combined organics were dried over sodium sulfate, filtered, and concentrated, affording to target material as an orange oil. MS (ESI, pos. ion) m/z: 173.0 (M+1).

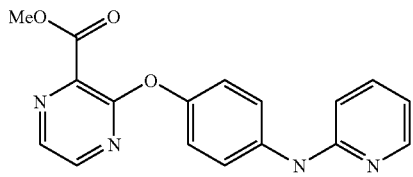 [SMILES: COC(=O)c1nccnc1Oc1ccc(Nc2ccccn2)cc1]

STEP 2: METHYL 3-(4-(PYRIDIN-2-YLAMINO)PHENOXY)PYRAZINE-2-CARBOXYLATE

To a 350 mL sealable tubed was added 4-(pyridin-2-ylamino)phenol (5.16 g, 27.7 mmol), methyl 3-chloropyrazine-2-carboxylate (4.78 g, 27.7 mmol), and cesium carbonate (9.93 g, 30.5 mmol) with DMSO. The tube was sealed and heated to 100° C. for three days. After cooling to temperature, the reaction was diluted with water and extracted with ethyl acetate. The combined, dark brown organics were dried over sodium sulfate, filtered, and concentrated in vacuo. The brown residue was adsorbed onto silica under high vacuum and flash purified on (0.5 to 10% MeOH/DCM), affording the product as a pale tan solid (7.44 g, 23.1 mmol, 83%). MS (ESI, pos. ion) m/z: 323.0 (M+1).

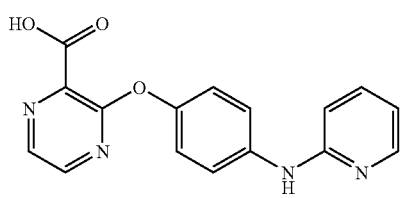 [SMILES: O=C(O)c1nccnc1Oc1ccc(Nc2ccccn2)cc1]

STEP 3: 3-(4-(PYRIDIN-2-YLAMINO)PHENOXY)PYRAZINE-2-CARBOXYLIC ACID

To a 250 mL round-bottomed flask containing methyl 3-(4-(pyridin-2-ylamino)phenoxy)pyrazine-2-carboxylate (7.44 g, 23.1 mmol) was added the mixed solvent of THF/MeOH/water. The tan solution was stirred at room temperature with addition of lithium hydroxide (1.66 g, 69.2 mmol). A white precipitate quickly formed. The suspension was acidified to pH 3 with 1 N HCl:diethyl ether, basified to pH 9 with 10 N NaOH, and reneutralized to pH 7 with concentrated HCl. The precipitate was collected by filtration and identified as the product. MS (ESI, pos. ion) m/z: 309.0 (M+1). IC50 (uM) 18.835.

SCHEME 55

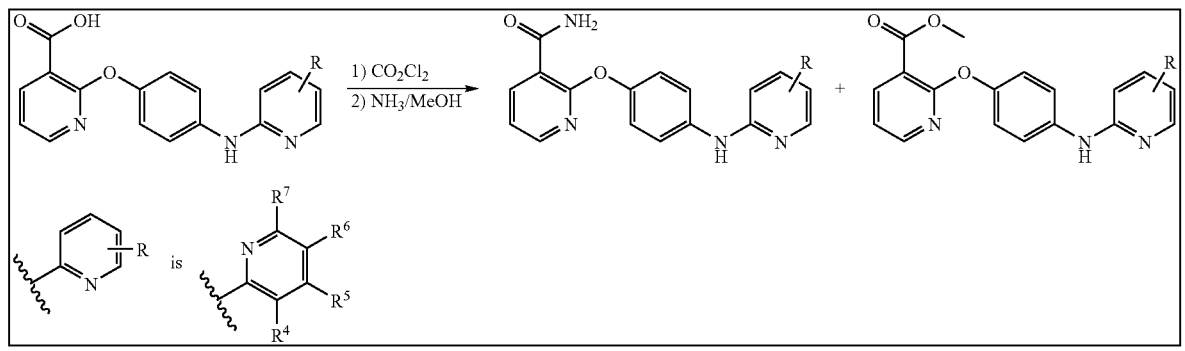

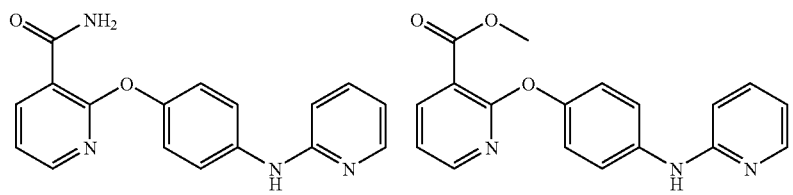

Examples 311 and 312

2-(4-(PYRIDIN-2-YLAMINO)PHENOXY)NICO-TINAMIDE AND METHYL 2-(4-(PYRIDIN-2-YLAMINO)PHENOXY)NICOTINATE

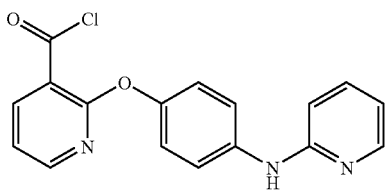

STEP 1. 2-(4-(PYRIDIN-2-YLAMINO) PHENOXY)NICOTINOYL CHLORIDE

A 2M solution of oxaloyl chloride (3.86 mL, 7.71 mmol) was added slowly to a suspension of 2-(4-(pyridin-2-ylamino)phenoxy)nicotinic acid (1580 mg, 5.14 mmol) in CH$_2$Cl$_2$ (20 mL). DMF (0.040 mL, 0.514 mmol) was added drop wise and the mixture was stirred at RT for 2 h. The mixture was concentrated under reduced pressure to deliver a yellow solid. The solid was suspended in CH$_2$Cl$_2$ (5 ml) and filtered to deliver 2-(4-(pyridin-2-ylamino)phenoxy)nicotinoyl chloride as a yellow solid that was taken on without further purification.

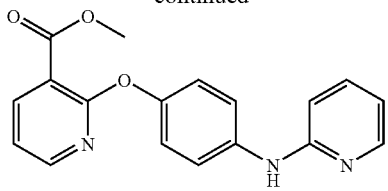

STEP 2: 2-(4-(PYRIDIN-2-YLAMINO)PHENOXY) NICOTINAMIDE AND METHYL 2-(4-(PYRIDIN-2-YLAMINO)PHENOXY)NICOTINATE

The crude product from the previous step was dissolved in a 2M solution of ammonia in methanol (20 ml, 40.0 mmol) and the mixture was stirred at RT for 20 h. The mixture was concentrated under reduced pressure to deliver a yellow oil that was purified by chromatography on silica gel to deliver 2-(4-(pyridin-2-ylamino)phenoxy)nicotinamide and methyl 2-(4-(pyridin-2-ylamino)phenoxy)nicotinate as white solids. MS (ESI, pos. ion) m/z: 307.0 (M+1). IC50 (uM) 0.9198 and MS (ESI, pos. ion) m/z: 322.0 (M+1). IC50 (uM) 0.1949 (M+1), respectively.

SCHEME 56

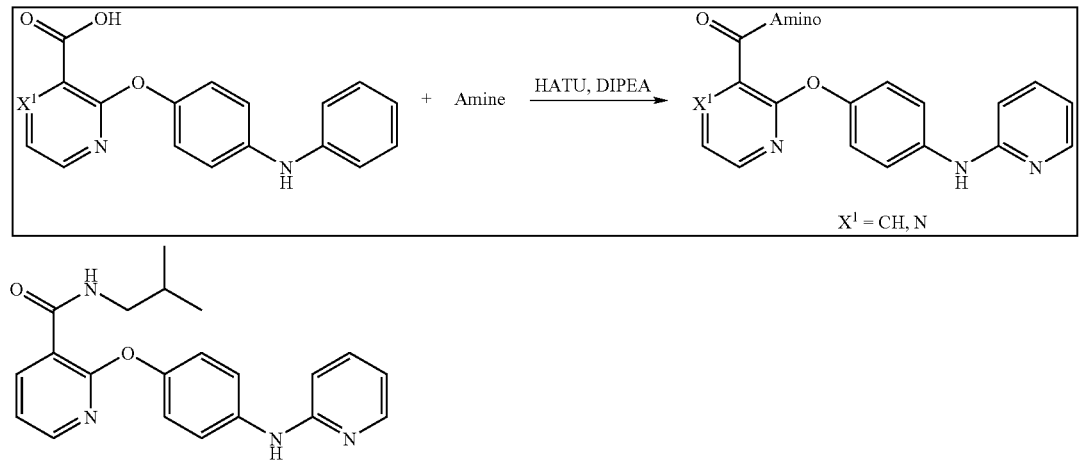

X$^1$ = CH, N

Example 313

N-ISOBUTYL-2-(4-(PYRIDIN-2-YLAMINO)PHE-NOXY)NICOTINAMIDE

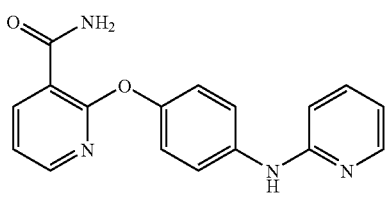

HATU (178 mg, 0.469 mmol) was added to a mixture of 2-(4-(pyridin-2-ylamino)phenoxy)nicotinic acid (131 mg, 0.426 mmol) and diisopropylethylamine (148 µL, 0.853 mmol) in DMF (1 mL) and the mixture was stirred at rt for 10 min. Isobutylamine (63.5 µL, 0.639 mmol) was added and the mixture was stirred at rt for 1 h. The mixture was purified by chromatography on silica gel to deliver N-isobutyl-2-(4-(pyridin-2-ylamino)phenoxy)nicotinamide as a white solid. MS (ESI, pos. ion) m/z: 363.1 (M+1). IC50 (uM) 0.09344.

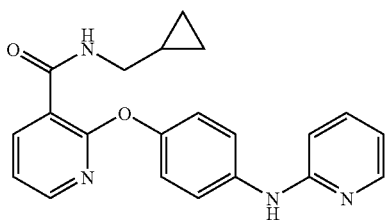 [SMILES: O=C(NCC1CC1)c1cccnc1Oc1ccc(Nc2ccccn2)cc1]

Example 314

N-(CYCLOPROPYLMETHYL)-2-(4-(PYRIDIN-2-YLAMINO)PHENOXY)NICOTINAMIDE

To a 100 mL round-bottomed flask was added 2-(4-(pyridin-2-ylamino)phenoxy)nicotinic acid (0.333 g, 1.08 mmol), cyclopropylmethanamine hydrochloride (0.116 g, 1.08 mmol), and TEA (0.4500 mL, 3.25 mmol) in DMF to stir for 5 min. EDC (0.2314 g, 1.19 mmol) and HOBT (0.1870 g, 1.19 mmol) was then added and allowed to stir overnight. The reaction mixture was diluted with water (10 mL) and extracted with DCM (3×10 mL). The organic extract was washed with water (1×10 mL), saturated sodium chloride (1×10 mL), saturated sodium bicarbonate (1×10 mL), dried with magnesium sulfate, filtered, and concentrated. The crude product was adsorbed onto a plug of silica gel and chromatographed through a Biotage™ pre-packed silica gel column (25M), eluting with a gradient of 1% to 5% methanol in DCM, to provide N-(cyclopropylmethyl)-2-(4-(pyridin-2-ylamino)phenoxy)nicotinamide. MS (ESI, pos. ion) m/z: 361.1 (M+1). IC50 (uM) 0.831.

TABLE XVIIA

EXAMPLES 315 TO 441 ARE TABULATED BELOW:

| Ex. No. | Compound Structure | Compound Name | MS | PDE10 IC50 (uM) |
|---|---|---|---|---|
| 315 | 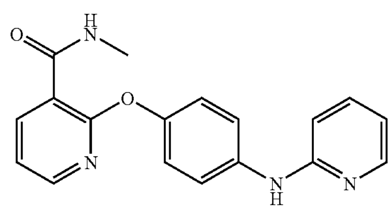 [SMILES: CNC(=O)c1cccnc1Oc1ccc(Nc2ccccn2)cc1] | N-methyl-2-(4-(pyridin-2-ylamino)phenoxy)nicotinamide | 321.1 | 0.637 |
| 316 | 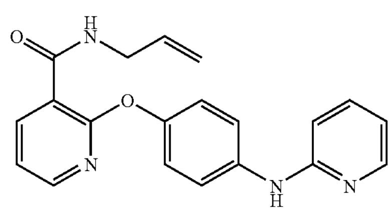 [SMILES: C=CCNC(=O)c1cccnc1Oc1ccc(Nc2ccccn2)cc1] | N-allyl-2-(4-(pyridin-2-ylamino)phenoxy)nicotinamide | 347.1 | 0.113 |
| 317 | 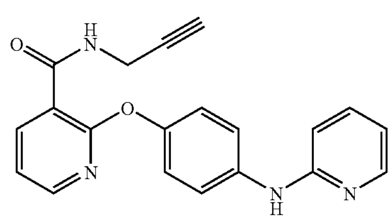 [SMILES: C#CCNC(=O)c1cccnc1Oc1ccc(Nc2ccccn2)cc1] | N-(prop-2-ynyl)-2-(4-(pyridin-2-ylamino)phenoxy)nicotinamide | 345.0 | 0.2306 |
| 318 | 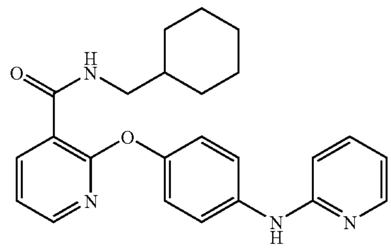 [SMILES: O=C(NCC1CCCCC1)c1cccnc1Oc1ccc(Nc2ccccn2)cc1] | N-(cyclohexylmethyl)-2-(4-(pyridin-2-ylamino)phenoxy)nicotinamide | 403.1 | 0.3215 |

TABLE XVIIA-continued

EXAMPLES 315 TO 441 ARE TABULATED BELOW:

| Ex. No. | Compound Structure | Compound Name | MS | PDE10 IC50 (uM) |
|---|---|---|---|---|
| 319 | 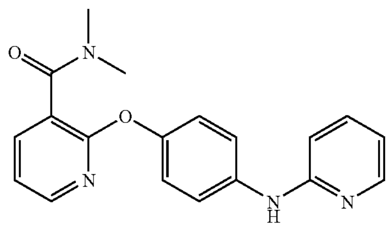 [SMILES: CN(C)C(=O)c1cccnc1Oc1ccc(Nc2ccccn2)cc1] | N,N-dimethyl-2-(4-(pyridin-2-ylamino)phenoxy)nicotinamide | 335.1 | 2.32 |
| 320 | 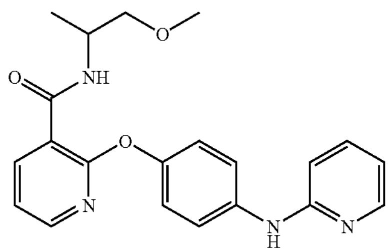 [SMILES: COCC(C)NC(=O)c1cccnc1Oc1ccc(Nc2ccccn2)cc1] | (rac)-N-(1-methoxypropan-2-yl)-2-(4-(pyridin-2-ylamino)phenoxy)nicotinamide | 379.0 | 0.08832 |
| 321 | 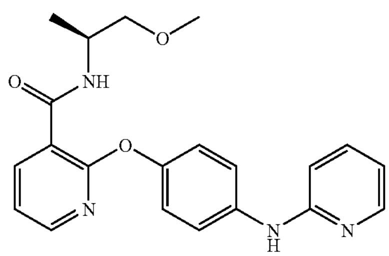 [SMILES: COC[C@H](C)NC(=O)c1cccnc1Oc1ccc(Nc2ccccn2)cc1] | (S)-N-(1-methoxypropan-2-yl)-2-(4-(pyridin-2-ylamino)phenoxy)nicotinamide | 379.1 | 0.37275 |
| 322 | 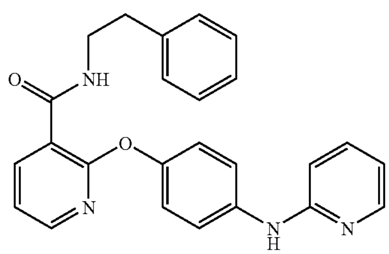 [SMILES: O=C(NCCc1ccccc1)c1cccnc1Oc1ccc(Nc2ccccn2)cc1] | N-phenethyl-2-(4-(pyridin-2-ylamino)phenoxy)nicotinamide | 411.1 | 0.04334 |
| 323 | 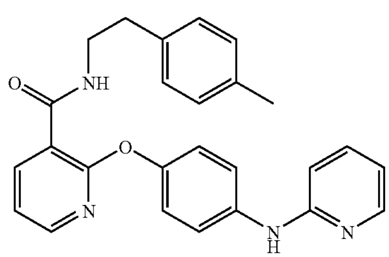 [SMILES: Cc1ccc(CCNC(=O)c2cccnc2Oc2ccc(Nc3ccccn3)cc2)cc1] | N-(4-methylphenethyl)-2-(4-(pyridin-2-ylamino)phenoxy)nicotinamide | 425.0 | 0.061885 |
| 324 | 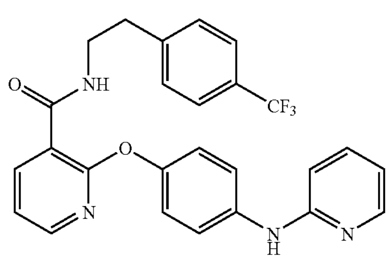 [SMILES: O=C(NCCc1ccc(C(F)(F)F)cc1)c1cccnc1Oc1ccc(Nc2ccccn2)cc1] | 2-(4-(pyridin-2-ylamino)phenoxy)-N-(4-(trifluoromethyl)phenethyl)nicotinamide | 479.1 | 0.068235 |

TABLE XVIIA-continued

EXAMPLES 315 TO 441 ARE TABULATED BELOW:

| Ex. No. | Compound Structure | Compound Name | MS | PDE10 IC50 (uM) |
|---|---|---|---|---|
| 325 | 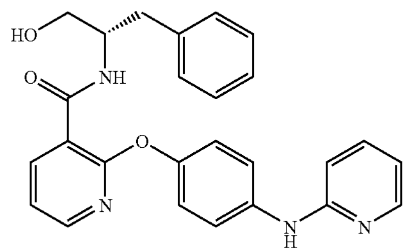 [SMILES: O=C(N[C@H](CO)Cc1ccccc1)c1cccnc1Oc1ccc(Nc2ccccn2)cc1] | (S)-N-(1-hydroxy-3-phenylpropan-2-yl)-2-(4-(pyridin-2-ylamino)phenoxy)nicotinamide | 441.0 | 0.02388 |
| 326 | 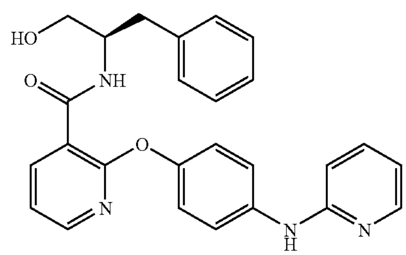 [SMILES: O=C(N[C@@H](CO)Cc1ccccc1)c1cccnc1Oc1ccc(Nc2ccccn2)cc1] | (R)-N-(1-hydroxy-3-phenylpropan-2-yl)-2-(4-(pyridin-2-ylamino)phenoxy)nicotinamide | 441.0 | 0.2357 |
| 327 | 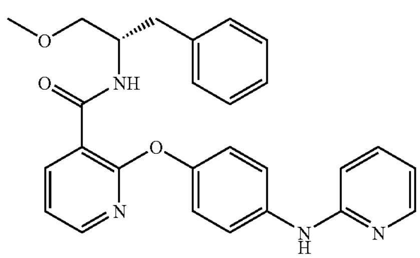 [SMILES: COC[C@H](Cc1ccccc1)NC(=O)c1cccnc1Oc1ccc(Nc2ccccn2)cc1] | (S)-N-(1-methoxy-3-phenylpropan-2-yl)-2-(4-(pyridin-2-ylamino)phenoxy)nicotinamide | 455.1 | 0.03996 |
| 328 | 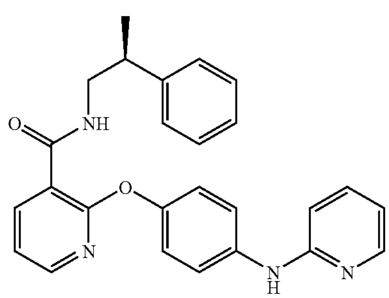 [SMILES: C[C@H](CNC(=O)c1cccnc1Oc1ccc(Nc2ccccn2)cc1)c1ccccc1] | (S)-N-(2-phenylpropyl)-2-(4-(pyridin-2-ylamino)phenoxy)nicotinamide | 425.0 | 0.1438 |
| 329 | 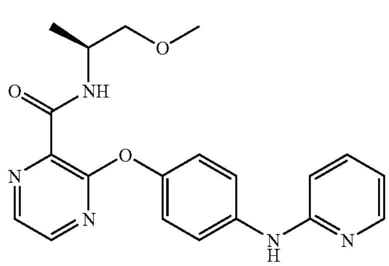 [SMILES: COC[C@H](C)NC(=O)c1nccnc1Oc1ccc(Nc2ccccn2)cc1] | (S)-N-(1-methoxypropan-2-yl)-3-(4-(pyridin-2-ylamino)phenoxy)pyrazine-2-carboxamide | 380.0 | 0.76885 |

TABLE XVIIA-continued

EXAMPLES 315 TO 441 ARE TABULATED BELOW:

| Ex. No. | Compound Structure | Compound Name | MS | PDE10 IC50 (uM) |
|---|---|---|---|---|
| 330 | 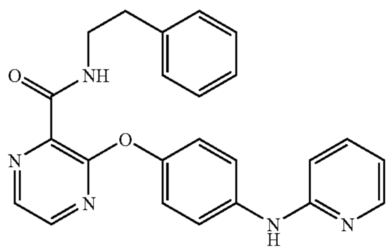 | N-phenethyl-3-(4-(pyridin-2-ylamino)phenoxy)pyrazine-2-carboxamide | 412.1 | 0.05744 |
| 331 | 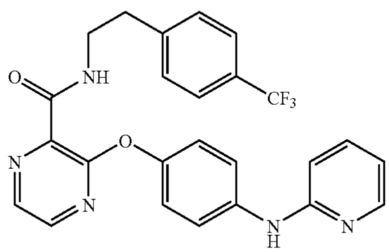 [SMILES: O=C(NCCc1ccc(C(F)(F)F)cc1)c1nccnc1Oc1ccc(Nc2ccccn2)cc1] | 3-(4-(pyridin-2-ylamino)phenoxy)-N-(4-(trifluoromethyl)phenethyl)pyrazine-2-carboxamide | 480.1 | 0.0765 |
| 332 | 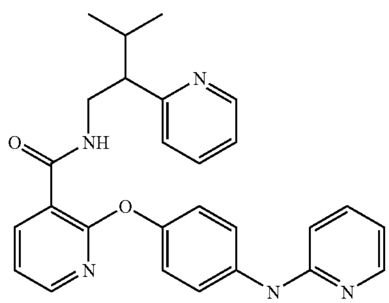 [SMILES: CC(C)C(CNC(=O)c1cccnc1Oc1ccc(Nc2ccccn2)cc1)c1ccccn1] | (rac)-N-(3-methyl-2-(pyridin-2-yl)butyl)-2-(4-(pyridin-2-ylamino)phenoxy)nicotinamide | 454.1 | 0.087 |
| 333 | 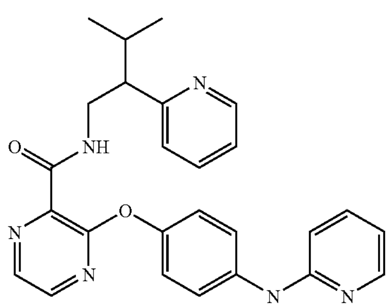 [SMILES: CC(C)C(CNC(=O)c1nccnc1Oc1ccc(Nc2ccccn2)cc1)c1ccccn1] | (rac)-N-(3-methyl-2-(pyridin-2-yl)butyl)-3-(4-(pyridin-2-ylamino)phenoxy)pyrazine-2-carboxamide | 455.1 | 0.121 |
| 334 | 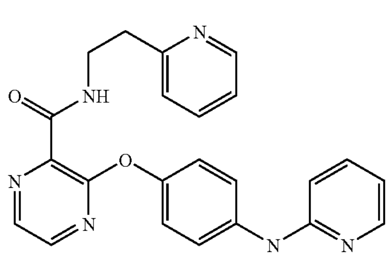 [SMILES: O=C(NCCc1ccccn1)c1nccnc1Oc1ccc(Nc2ccccn2)cc1] | N-(2-(pyridin-2-yl)ethyl)-3-(4-(pyridin-2-ylamino)phenoxy)pyrazine-2-carboxamide | 413.1 | 0.143 |

TABLE XVIIA-continued

EXAMPLES 315 TO 441 ARE TABULATED BELOW:

| Ex. No. | Compound Structure | Compound Name | MS | PDE10 IC50 (uM) |
|---|---|---|---|---|
| 335 | 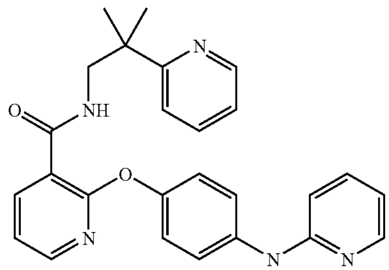 [SMILES: CC(C)(CNC(=O)c1cccnc1Oc1ccc(Nc2ccccn2)cc1)c1ccccn1] | N-(2-methyl-2-(pyridin-2-yl)propyl)-2-(4-(pyridin-2-ylamino)phenoxy)nicotinamide | 440.0 | 0.034 |
| 336 | 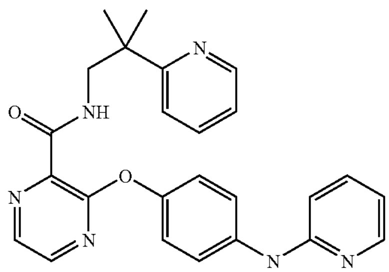 [SMILES: CC(C)(CNC(=O)c1nccnc1Oc1ccc(Nc2ccccn2)cc1)c1ccccn1] | N-(2-methyl-2-(pyridin-2-yl)propyl)-3-(4-(pyridin-2-ylamino)phenoxy)pyrazine-2-carboxamide | 441.0 | 0.0232 |
| 337 | 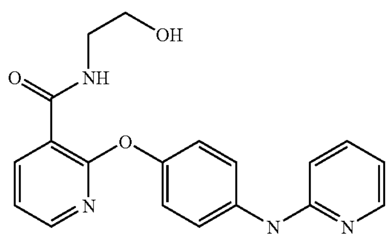 [SMILES: O=C(NCCO)c1cccnc1Oc1ccc(Nc2ccccn2)cc1] | N-(2-hydroxyethyl)-2-(4-(pyridin-2-ylamino)phenoxy)nicotinamide | 351.1 | 0.367 |
| 338 | 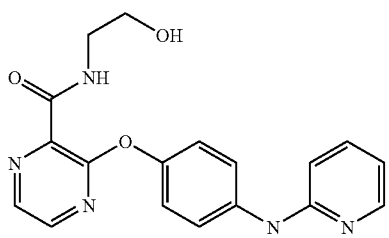 [SMILES: O=C(NCCO)c1nccnc1Oc1ccc(Nc2ccccn2)cc1] | N-(2-hydroxyethyl)-3-(4-(pyridin-2-ylamino)phenoxy)pyrazine-2-carboxamide | 352.1 | 1.162 |
| 339 | 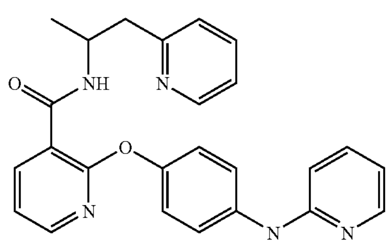 [SMILES: CC(Cc1ccccn1)NC(=O)c1cccnc1Oc1ccc(Nc2ccccn2)cc1] | (rac)-N-(1-(pyridin-2-yl)propan-2-yl)-2-(4-(pyridin-2-ylamino)phenoxy)nicotinamide | 426.1 | 0.038 |
| 340 | 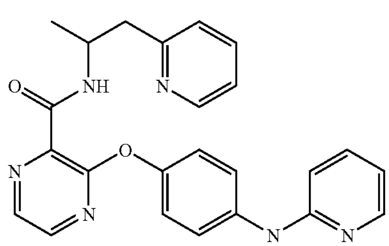 | (rac)-N-methyl-2-(4-(pyridin-2-ylamino)phenoxy)nicotinamide | 427.1 | 0.0487 |

TABLE XVIIA-continued

EXAMPLES 315 TO 441 ARE TABULATED BELOW:

| Ex. No. | Compound Structure | Compound Name | MS | PDE10 IC50 (uM) |
|---|---|---|---|---|
| 341 | 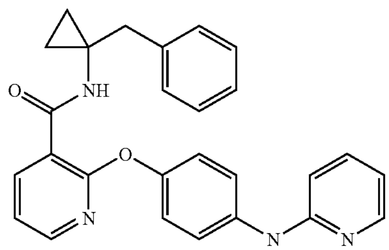 [SMILES: O=C(NC1(Cc2ccccc2)CC1)c1cccnc1Oc1ccc(Nc2ccccn2)cc1] | N-(1-benzylcyclopropyl)-2-(4-(pyridin-2-ylamino)phenoxy)nicotinamide | 437.0 | 0.0102 |
| 342 | 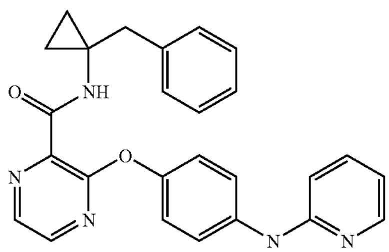 [SMILES: O=C(NC1(Cc2ccccc2)CC1)c1nccnc1Oc1ccc(Nc2ccccn2)cc1] | N-(1-benzylcyclopropyl)-3-(4-(pyridin-2-ylamino)phenoxy)pyrazine-2-carboxamide | 438.1 | 0.0352 |
| 343 | 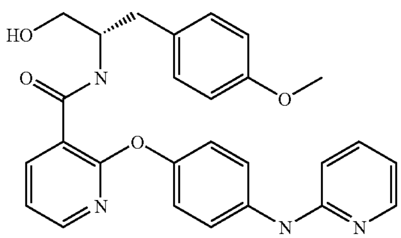 [SMILES: COc1ccc(C[C@@H](CO)NC(=O)c2cccnc2Oc2ccc(Nc3ccccn3)cc2)cc1] | (S)-N-(1-hydroxy-3-(4-methoxyphenyl)propan-2-yl)-2-(4-(pyridin-2-ylamino)phenoxy)nicotinamide | 471.1 | 0.0171 |
| 344 | 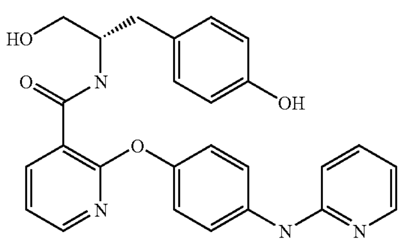 [SMILES: O=C(N[C@H](CO)Cc1ccc(O)cc1)c1cccnc1Oc1ccc(Nc2ccccn2)cc1] | (S)-N-(1-hydroxy-3-(4-hydroxyphenyl)propan-2-yl)-2-(4-(pyridin-2-ylamino)phenoxy)nicotinamide | 457.1 | 0.0895 |
| 345 | 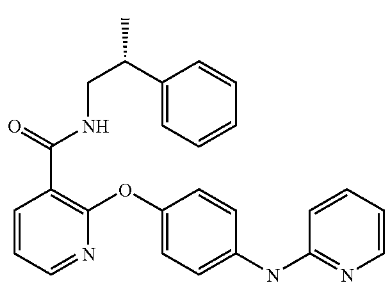 [SMILES: C[C@@H](CNC(=O)c1cccnc1Oc1ccc(Nc2ccccn2)cc1)c1ccccc1] | (R)-N-(2-phenylpropyl)-2-(4-(pyridin-2-ylamino)phenoxy)nicotinamide | 425.1 | 0.138 |
| 346 | 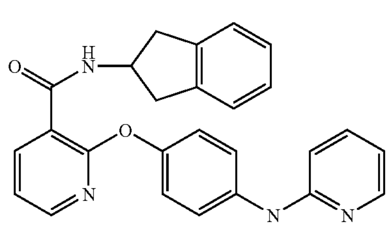 [SMILES: O=C(NC1Cc2ccccc2C1)c1cccnc1Oc1ccc(Nc2ccccn2)cc1] | N-(2,3-dihydro-1H-inden-2-yl)-2-(4-(pyridin-2-ylamino)phenoxy)nicotinamide | 423.1 | 0.546 |

TABLE XVIIA-continued

EXAMPLES 315 TO 441 ARE TABULATED BELOW:

| Ex. No. | Compound Structure | Compound Name | MS | PDE10 IC50 (uM) |
|---|---|---|---|---|
| 347 | 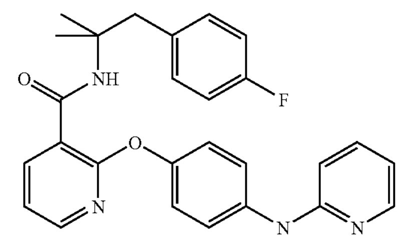 [SMILES: CC(C)(Cc1ccc(F)cc1)NC(=O)c1cccnc1Oc1ccc(Nc2ccccn2)cc1] | N-(1-(4-fluorophenyl)-2-methylpropan-2-yl)-2-(4-(pyridin-2-ylamino)phenoxy)nicotinamide | 457.1 | 0.0800 |
| 348 | 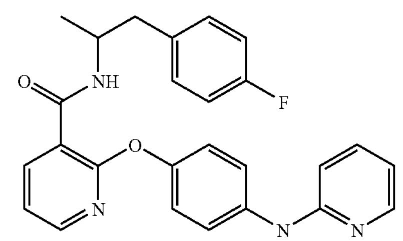 [SMILES: CC(Cc1ccc(F)cc1)NC(=O)c1cccnc1Oc1ccc(Nc2ccccn2)cc1] | (rac)-N-(1-(4-fluorophenyl)propan-2-yl)-2-(4-(pyridin-2-ylamino)phenoxy)nicotinamide | 443.0 | 0.0448 |
| 349 | 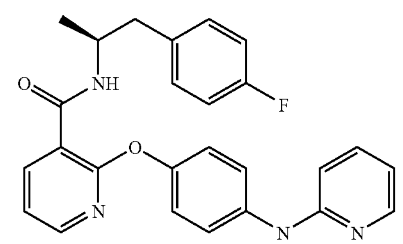 [SMILES: C[C@@H](Cc1ccc(F)cc1)NC(=O)c1cccnc1Oc1ccc(Nc2ccccn2)cc1] | (S)-N-(1-(4-fluorophenyl)propan-2-yl)-2-(4-(pyridin-2-ylamino)phenoxy)nicotinamide | 443.0 | 0.0642 |
| 350 | 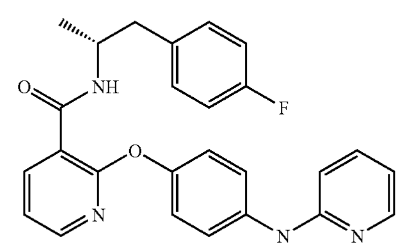 [SMILES: C[C@H](Cc1ccc(F)cc1)NC(=O)c1cccnc1Oc1ccc(Nc2ccccn2)cc1] | (R)-N-(1-(4-fluorophenyl)propan-2-yl)-2-(4-(pyridin-2-ylamino)phenoxy)nicotinamide | 443.0 | 0.0099 |
| 351 | 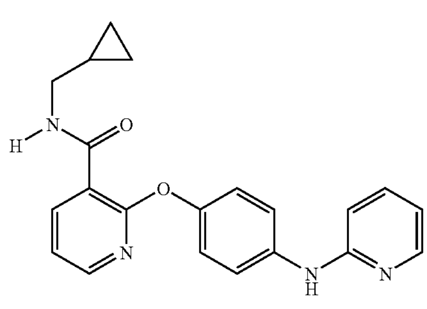 [SMILES: O=C(NCC1CC1)c1cccnc1Oc1ccc(Nc2ccccn2)cc1] | N-(cyclopropylmethyl)-2-(4-(pyridin-2-ylamino)phenoxy)nicotinamide | 361.2 | 0.656467 |

TABLE XVIIA-continued

EXAMPLES 315 TO 441 ARE TABULATED BELOW:

| Ex. No. | Compound Structure | Compound Name | MS | PDE10 IC50 (uM) |
|---|---|---|---|---|
| 352 | 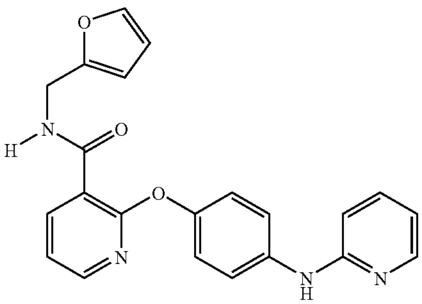 [SMILES: O=C(NCc1ccco1)c1cccnc1Oc1ccc(Nc2ccccn2)cc1] | N-(furan-2-ylmethyl)-2-(4-(pyridin-2-ylamino)phenoxy)nicotinamide | 387.2 | 0.448667 |
| 353 | 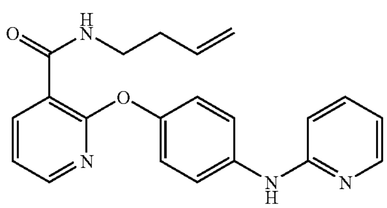 [SMILES: C=CCCNC(=O)c1cccnc1Oc1ccc(Nc2ccccn2)cc1] | N-(but-3-enyl)-2-(4-(pyridin-2-ylamino)phenoxy)nicotinamide | 360.8 | 0.08562 |
| 354 | 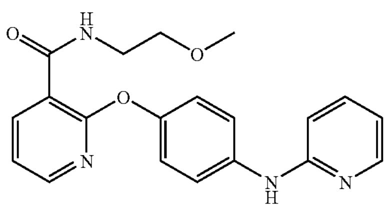 [SMILES: COCCNC(=O)c1cccnc1Oc1ccc(Nc2ccccn2)cc1] | N-(2-methoxyethyl)-2-(4-(pyridin-2-ylamino)phenoxy)nicotinamide | 365.2 | 0.3634 |
| 355 | 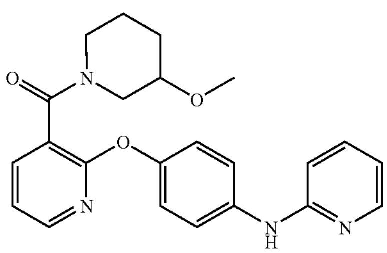 [SMILES: COC1CCCN(C(=O)c2cccnc2Oc2ccc(Nc3ccccn3)cc2)C1] | (rac)-(3-methoxypiperidin-1-yl)(2-(4-(pyridin-2-ylamino)phenoxy)pyridin-3-yl)methanone | 405.2 | 2.633 |
| 356 | 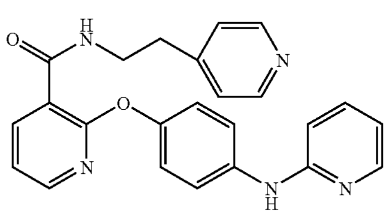 [SMILES: O=C(NCCc1ccncc1)c1cccnc1Oc1ccc(Nc2ccccn2)cc1] | 2-(4-(pyridin-2-ylamino)phenoxy)-N-(2-(pyridin-2-yl)ethyl)nicotinamide | 412.4 | 0.102 |
| 357 | 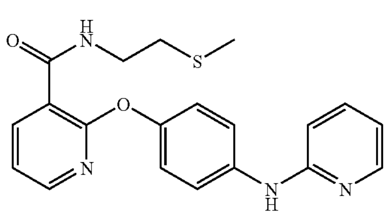 [SMILES: CSCCNC(=O)c1cccnc1Oc1ccc(Nc2ccccn2)cc1] | N-(2-(methylthio)ethyl)-2-(4-(pyridin-2-ylamino)phenoxy)nicotinamide | 381.2 | 0.1315 |

TABLE XVIIA-continued

EXAMPLES 315 TO 441 ARE TABULATED BELOW:

| Ex. No. | Compound Structure | Compound Name | MS | PDE10 IC50 (uM) |
|---|---|---|---|---|
| 358 | 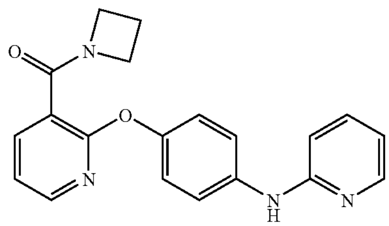 [SMILES: O=C(c1cccnc1Oc1ccc(Nc2ccccn2)cc1)N1CCC1] | azetidin-1-yl(2-(4-(pyridin-2-ylamino)phenoxy)pyridin-3-yl)methanone | 347.2 | 2.204 |
| 359 | 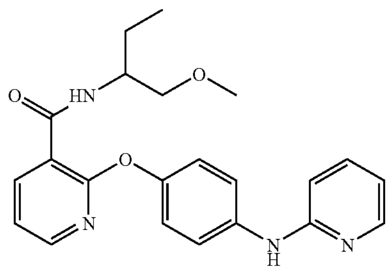 [SMILES: CCC(COC)NC(=O)c1cccnc1Oc1ccc(Nc2ccccn2)cc1] | (rac)-N-(1-methoxybutan-2-yl)-2-(4-(pyridin-2-ylamino)phenoxy)nicotinamide | 393.2 | 0.06166 |
| 360 | 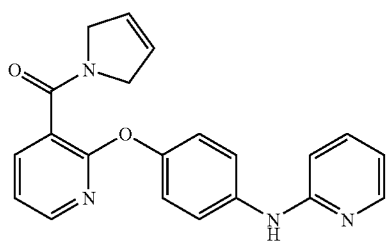 [SMILES: O=C(c1cccnc1Oc1ccc(Nc2ccccn2)cc1)N1CC=CC1] | (2-(4-(pyridin-2-ylamino)phenoxy)pyridin-3-yl)(2H-pyrrol-1(5H)-yl)methanone | 359.2 | 0.5791 |
| 361 | 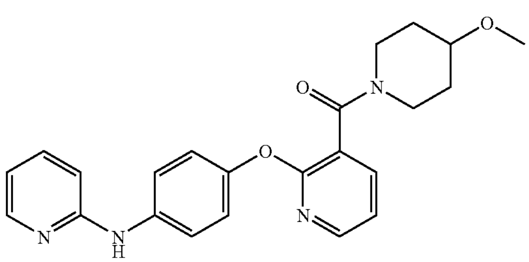 [SMILES: COC1CCN(C(=O)c2cccnc2Oc2ccc(Nc3ccccn3)cc2)CC1] | (4-methoxypiperidin-1-yl)(2-(4-(pyridin-2-ylamino)phenoxy)pyridin-3-yl)methanone | 404.8 | 3.768 |
| 362 | 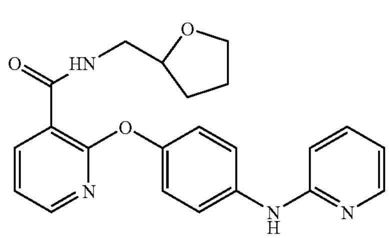 [SMILES: O=C(NCC1CCCO1)c1cccnc1Oc1ccc(Nc2ccccn2)cc1] | (rac)-2-(4-(pyridin-2-ylamino)phenoxy)-N-((tetrahydrofuran-2-yl)methyl)nicotinamide | 391.2 | 0.2475 |

TABLE XVIIA-continued

EXAMPLES 315 TO 441 ARE TABULATED BELOW:

| Ex. No. | Compound Structure | Compound Name | MS | PDE10 IC50 (uM) |
|---|---|---|---|---|
| 363 | 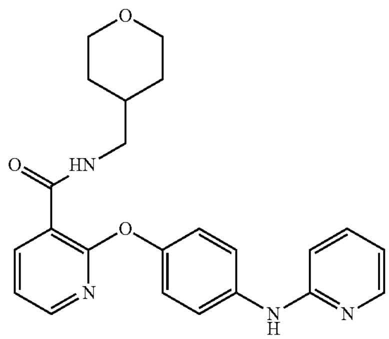 [SMILES: O=C(NCC1CCOCC1)c1cccnc1Oc1ccc(Nc2ccccn2)cc1] | 2-(4-(pyridin-2-ylamino)phenoxy)-N-((tetrahydro-2H-pyran-4-yl)methyl)nicotinamide | 405.2 | 0.8227 |
| 364 | 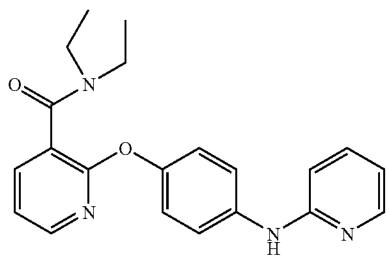 [SMILES: CCN(CC)C(=O)c1cccnc1Oc1ccc(Nc2ccccn2)cc1] | N,N-diethyl-2-(4-(pyridin-2-ylamino)phenoxy)nicotinamide | 363.2 | 1.983 |
| 365 | 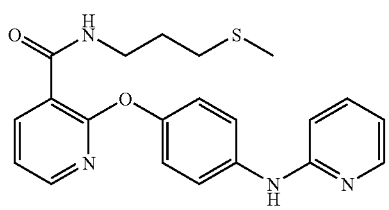 [SMILES: CSCCCNC(=O)c1cccnc1Oc1ccc(Nc2ccccn2)cc1] | N-(3-(methylthio)propyl)-2-(4-(pyridin-2-ylamino)phenoxy)nicotinamide | 404.8 | 0.1529 |
| 366 | 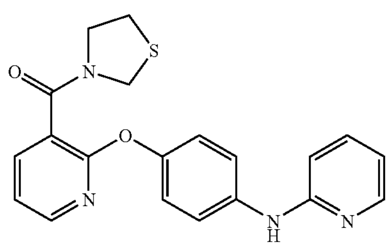 [SMILES: O=C(c1cccnc1Oc1ccc(Nc2ccccn2)cc1)N1CCSC1] | (2-(4-(pyridin-2-ylamino)phenoxy)pyridin-3-yl)(thiazolidin-3-yl)methanone | 378.8 | 1.207 |
| 367 | 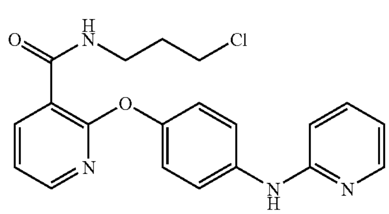 [SMILES: O=C(NCCCCl)c1cccnc1Oc1ccc(Nc2ccccn2)cc1] | N-(3-chloropropyl)-2-(4-(pyridin-2-ylamino)phenoxy)nicotinamide | 383.2 | 0.1677 |
| 368 | 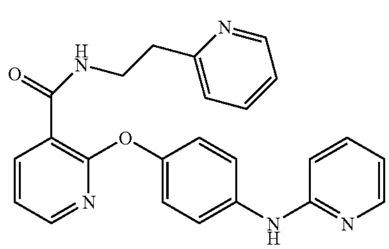 [SMILES: O=C(NCCc1ccccn1)c1cccnc1Oc1ccc(Nc2ccccn2)cc1] | N-(2-(pyridin-2-yl)ethyl)-2-(4-(pyridin-2-ylamino)phenoxy)nicotinamide | 412.4 | 0.04377 |

TABLE XVIIA-continued

EXAMPLES 315 TO 441 ARE TABULATED BELOW:

| Ex. No. | Compound Structure | Compound Name | MS | PDE10 IC50 (uM) |
|---|---|---|---|---|
| 369 | 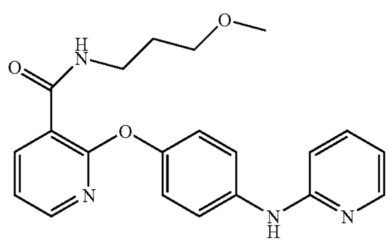 [SMILES: COCCCNC(=O)c1cccnc1Oc1ccc(Nc2ccccn2)cc1] | N-(3-methoxypropyl)-2-(4-(pyridin-2-ylamino)phenoxy)nicotinamide | 378.8 | 0.121 |
| 370 | 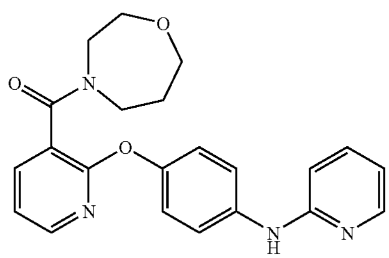 [SMILES: O=C(c1cccnc1Oc1ccc(Nc2ccccn2)cc1)N1CCCOCC1] | (1,4-oxazepan-4-yl)(2-(4-(pyridin-2-ylamino)phenoxy)pyridin-3-yl)methanone | 391.2 | 3.102 |
| 371 | 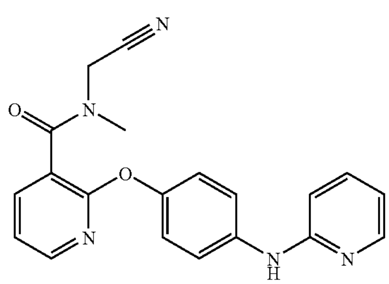 [SMILES: CN(CC#N)C(=O)c1cccnc1Oc1ccc(Nc2ccccn2)cc1] | N-methyl-N-(prop-2-ynyl)-2-(4-(pyridin-2-ylamino)phenoxy)nicotinamide | 359.2 | 0.6166 |
| 372 | 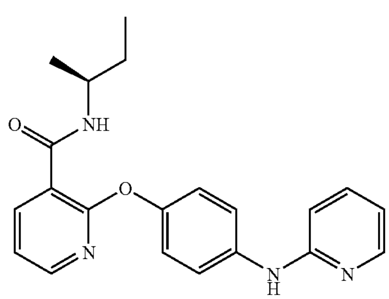 [SMILES: CC[C@H](C)NC(=O)c1cccnc1Oc1ccc(Nc2ccccn2)cc1] | (R)-N-sec-butyl-2-(4-(pyridin-2-ylamino)phenoxy)nicotinamide | 363.0 | 0.07463 |
| 373 | 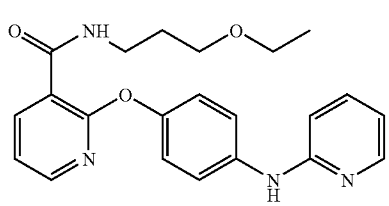 [SMILES: CCOCCCNC(=O)c1cccnc1Oc1ccc(Nc2ccccn2)cc1] | N-(3-ethoxypropyl)-2-(4-(pyridin-2-ylamino)phenoxy)nicotinamide | 392.8 | 0.1257 |

TABLE XVIIA-continued

EXAMPLES 315 TO 441 ARE TABULATED BELOW:

| Ex. No. | Compound Structure | Compound Name | MS | PDE10 IC50 (uM) |
|---|---|---|---|---|
| 374 | 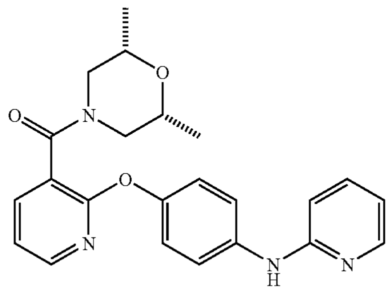 [SMILES: C[C@@H]1CN(C(=O)c2cccnc2Oc2ccc(Nc3ccccn3)cc2)C[C@H](C)O1] | ((2S,6R)-2,6-dimethylmorpholino)(2-(4-(pyridin-2-ylamino)phenoxy)pyridin-3-yl)methanone | 405.0 | 0.4317 |
| 375 | 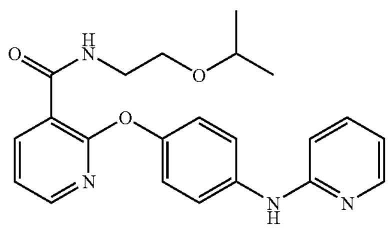 [SMILES: CC(C)OCCNC(=O)c1cccnc1Oc1ccc(Nc2ccccn2)cc1] | N-(2-isopropoxyethyl)-2-(4-(pyridin-2-ylamino)phenoxy)nicotinamide | 393.0 | 0.1189 |
| 376 | 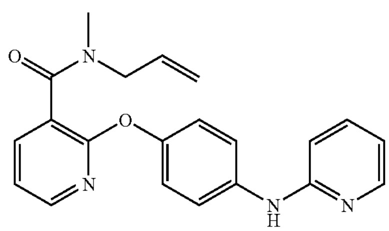 [SMILES: C=CCN(C)C(=O)c1cccnc1Oc1ccc(Nc2ccccn2)cc1] | N-allyl-N-methyl-2-(4-(pyridin-2-ylamino)phenoxy)nicotinamide | 361.0 | 2.22 |
| 377 | 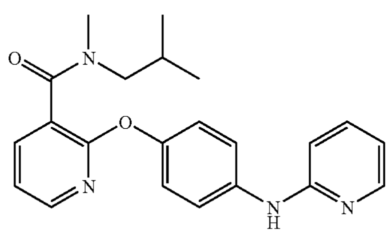 [SMILES: CC(C)CN(C)C(=O)c1cccnc1Oc1ccc(Nc2ccccn2)cc1] | N-isobutyl-N-methyl-2-(4-(pyridin-2-ylamino)phenoxy)nicotinamide | 377.0 | 4.428 |
| 378 | 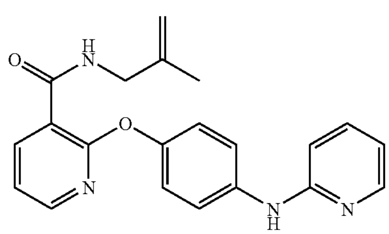 [SMILES: C=C(C)CNC(=O)c1cccnc1Oc1ccc(Nc2ccccn2)cc1] | N-(2-methylallyl)-2-(4-(pyridin-2-ylamino)phenoxy)nicotinamide | 361.0 | 0.05864 |
| 379 | 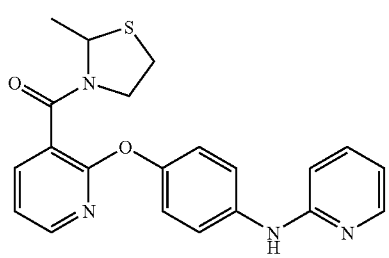 [SMILES: CC1SCCN1C(=O)c1cccnc1Oc1ccc(Nc2ccccn2)cc1] | (2-methylthiazolidin-3-yl)(2-(4-(pyridin-2-ylamino)phenoxy)pyridin-3-yl)methanone | 392.9 | 2.569 |

TABLE XVIIA-continued

EXAMPLES 315 TO 441 ARE TABULATED BELOW:

| Ex. No. | Compound Structure | Compound Name | MS | PDE10 IC50 (uM) |
|---|---|---|---|---|
| 380 | 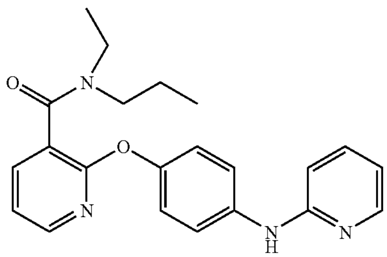 [SMILES: CCCN(CC)C(=O)c1cccnc1Oc1ccc(Nc2ccccn2)cc1] | N-ethyl-N-propyl-2-(4-(pyridin-2-ylamino)phenoxy)nicotinamide | 377.0 | 4.531 |
| 381 | 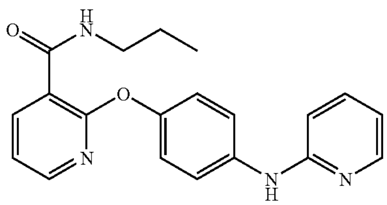 [SMILES: CCCNC(=O)c1cccnc1Oc1ccc(Nc2ccccn2)cc1] | N-propyl-2-(4-(pyridin-2-ylamino)phenoxy)nicotinamide | 349.0 | 0.5749 |
| 382 | 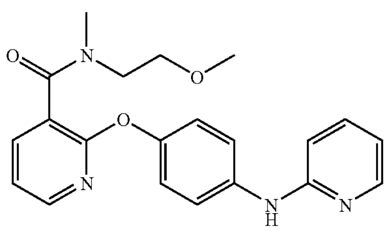 [SMILES: COCCN(C)C(=O)c1cccnc1Oc1ccc(Nc2ccccn2)cc1] | N-(2-methoxyethyl)-N-methyl-2-(4-(pyridin-2-ylamino)phenoxy)nicotinamide | 379.0 | 4.137 |
| 383 | 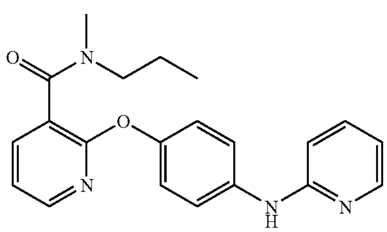 [SMILES: CCCN(C)C(=O)c1cccnc1Oc1ccc(Nc2ccccn2)cc1] | N-methyl-N-propyl-2-(4-(pyridin-2-ylamino)phenoxy)nicotinamide | 349.0 | 3.574 |
| 384 | 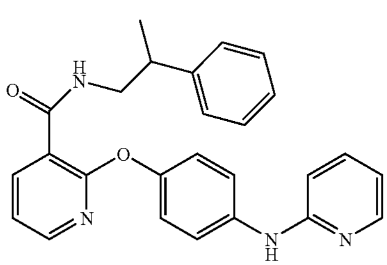 [SMILES: CC(CNC(=O)c1cccnc1Oc1ccc(Nc2ccccn2)cc1)c1ccccc1] | (rac)-N-(2-phenylpropyl)-2-(4-(pyridin-2-ylamino)phenoxy)nicotinamide | 424.8 | 0.093183 |

TABLE XVIIA-continued

EXAMPLES 315 TO 441 ARE TABULATED BELOW:

| Ex. No. | Compound Structure | Compound Name | MS | PDE10 IC50 (uM) |
|---|---|---|---|---|
| 385 | 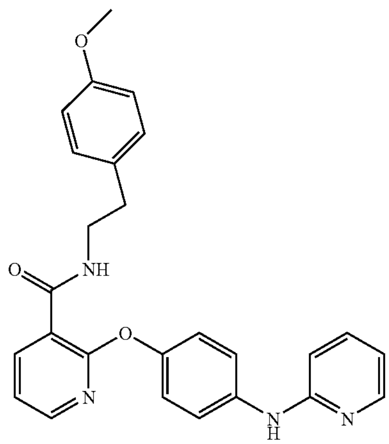 [SMILES: COc1ccc(CCNC(=O)c2cccnc2Oc2ccc(Nc3ccccn3)cc2)cc1] | N-(4-methoxyphenethyl)-2-(4-(pyridin-2-ylamino)phenoxy)nicotinamide | 441.0 | 0.023365 |
| 386 | 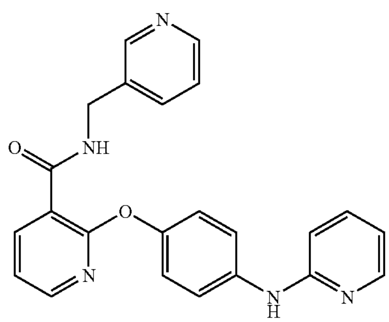 [SMILES: O=C(NCc1cccnc1)c1cccnc1Oc1ccc(Nc2ccccn2)cc1] | 2-(4-(pyridin-2-ylamino)phenoxy)-N-(pyridin-3-ylmethyl)nicotinamide | 397.9 | 0.13255 |
| 387 | 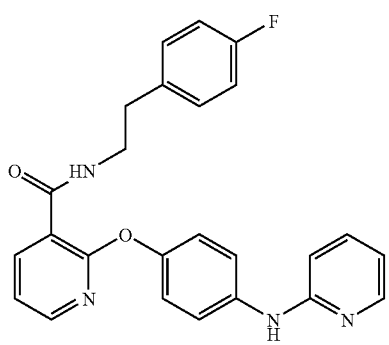 [SMILES: O=C(NCCc1ccc(F)cc1)c1cccnc1Oc1ccc(Nc2ccccn2)cc1] | N-(4-fluorophenethyl)-2-(4-(pyridin-2-ylamino)phenoxy)nicotinamide | 428.9 | 0.04987 |
| 388 | 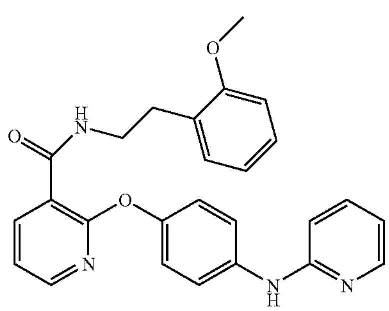 [SMILES: COc1ccccc1CCNC(=O)c1cccnc1Oc1ccc(Nc2ccccn2)cc1] | N-(2-methoxyphenethyl)-2-(4-(pyridin-2-ylamino)phenoxy)nicotinamide | 441.0 | 0.038927 |

TABLE XVIIA-continued

EXAMPLES 315 TO 441 ARE TABULATED BELOW:

| Ex. No. | Compound Structure | Compound Name | MS | PDE10 IC50 (uM) |
|---|---|---|---|---|
| 389 | 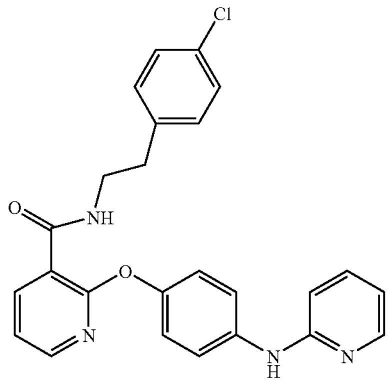 [SMILES: O=C(NCCc1ccc(Cl)cc1)c1cccnc1Oc1ccc(Nc2ccccn2)cc1] | N-(4-chlorophenethyl)-2-(4-(pyridin-2-ylamino)phenoxy)nicotinamide | 444.9 | 0.05469 |
| 390 | 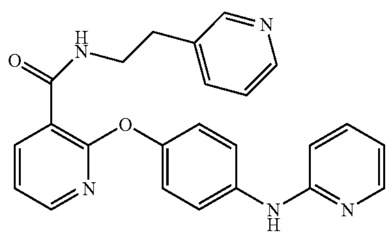 [SMILES: O=C(NCCc1cccnc1)c1cccnc1Oc1ccc(Nc2ccccn2)cc1] | 2-(4-(pyridin-2-ylamino)phenoxy)-N-(2-(pyridin-3-yl)ethyl)nicotinamide | 411.9 | 0.08163 |
| 391 | 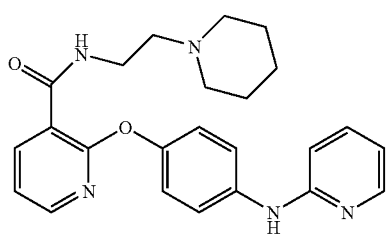 [SMILES: O=C(NCCN1CCCCC1)c1cccnc1Oc1ccc(Nc2ccccn2)cc1] | N-(2-(piperidin-1-yl)ethyl)-2-(4-(pyridin-2-ylamino)phenoxy)nicotinamide | 418.0 | 0.786565 |
| 392 | 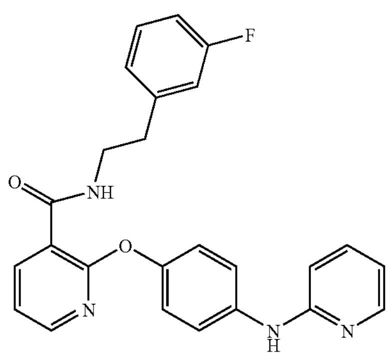 [SMILES: O=C(NCCc1cccc(F)c1)c1cccnc1Oc1ccc(Nc2ccccn2)cc1] | N-(3-fluorophenethyl)-2-(4-(pyridin-2-ylamino)phenoxy)nicotinamide | 428.9 | 0.05998 |
| 393 | 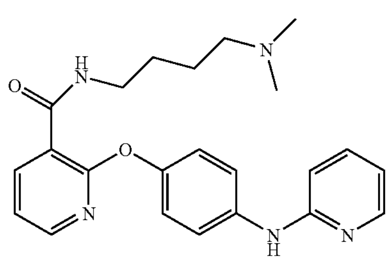 [SMILES: CN(C)CCCCNC(=O)c1cccnc1Oc1ccc(Nc2ccccn2)cc1] | N-(4-(dimethylamino)butyl)-2-(4-(pyridin-2-ylamino)phenoxy)nicotinamide | 406.0 | 6.2835 |

TABLE XVIIA-continued

EXAMPLES 315 TO 441 ARE TABULATED BELOW:

| Ex. No. | Compound Structure | Compound Name | MS | PDE10 IC50 (uM) |
|---|---|---|---|---|
| 394 | 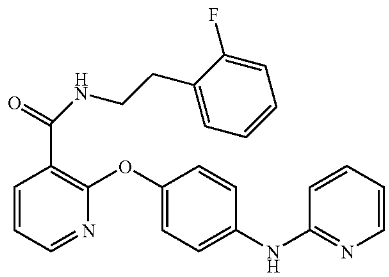 [SMILES: O=C(NCCc1ccccc1F)c1cccnc1Oc1ccc(Nc2ccccn2)cc1] | N-(2-fluorophenethyl)-2-(4-(pyridin-2-ylamino)phenoxy)nicotinamide | 428.9 | 0.057277 |
| 395 | 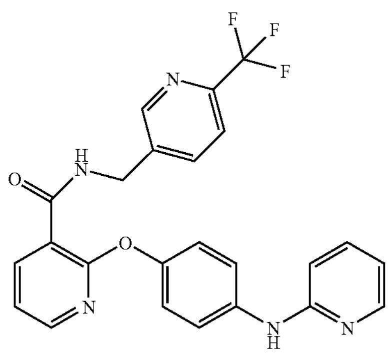 [SMILES: O=C(NCc1ccc(C(F)(F)F)nc1)c1cccnc1Oc1ccc(Nc2ccccn2)cc1] | 2-(4-(pyridin-2-ylamino)phenoxy)-N-((6-(trifluoromethyl)pyridin-3-yl)methyl)nicotinamide | 466.4 | 0.4001 |
| 396 | 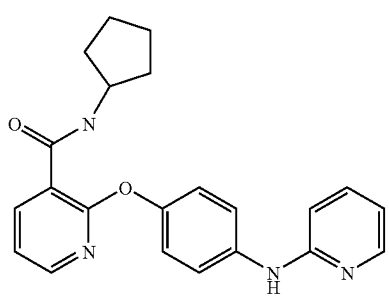 [SMILES: O=C(NC1CCCC1)c1cccnc1Oc1ccc(Nc2ccccn2)cc1] | N-cyclopentyl-2-(4-(pyridin-2-ylamino)phenoxy)nicotinamide | 375.0 | 0.07841 |
| 397 | 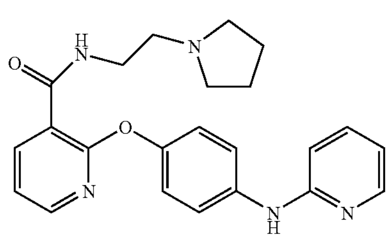 [SMILES: O=C(NCCN1CCCC1)c1cccnc1Oc1ccc(Nc2ccccn2)cc1] | 2-(4-(pyridin-2-ylamino)phenoxy)-N-(2-(pyrrolidin-1-yl)ethyl)nicotinamide | 404.0 | 2.6525 |
| 398 | 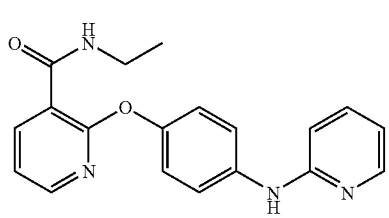 [SMILES: CCNC(=O)c1cccnc1Oc1ccc(Nc2ccccn2)cc1] | N-ethyl-2-(4-(pyridin-2-ylamino)phenoxy)nicotinamide | 335.0 | 0.17265 |

TABLE XVIIA-continued

EXAMPLES 315 TO 441 ARE TABULATED BELOW:

| Ex. No. | Compound Structure | Compound Name | MS | PDE10 IC50 (uM) |
|---|---|---|---|---|
| 399 | 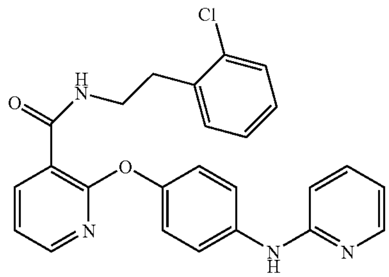 | N-(2-chlorophenethyl)-2-(4-(pyridin-2-ylamino)phenoxy)nicotinamide | 444.9 | 0.0737 |
| 400 | 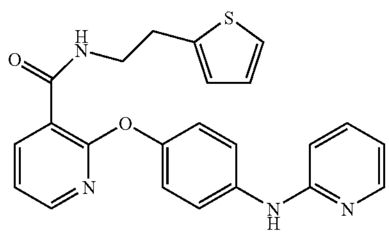 [SMILES: O=C(NCCc1cccs1)c1cccnc1Oc1ccc(Nc2ccccn2)cc1] | 2-(4-(pyridin-2-ylamino)phenoxy)-N-(2-(thiophen-2-yl)ethyl)nicotinamide | 416.9 | 0.036195 |
| 401 | 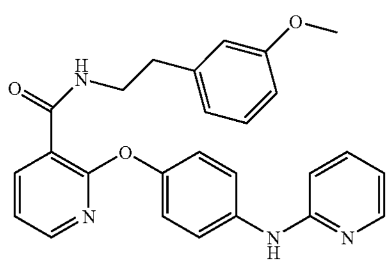 [SMILES: COc1cccc(CCNC(=O)c2cccnc2Oc2ccc(Nc3ccccn3)cc2)c1] | N-(3-methoxyphenethyl)-2-(4-(pyridin-2-ylamino)phenoxy)nicotinamide | 441.0 | 0.03144 |
| 402 | 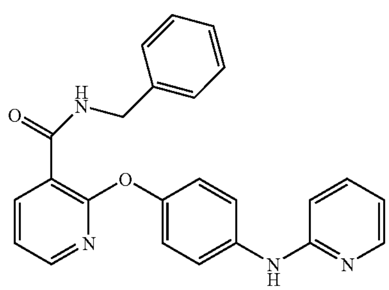 [SMILES: O=C(NCc1ccccc1)c1cccnc1Oc1ccc(Nc2ccccn2)cc1] | N-benzyl-2-(4-(pyridin-2-ylamino)phenoxy)nicotinamide | 397.2 | 0.7556 |
| 403 | 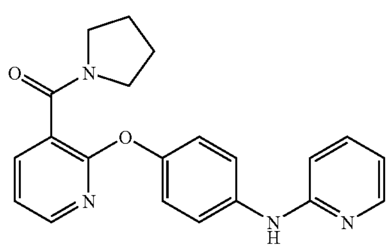 | (2-(4-(pyridin-2-ylamino)phenoxy)pyridin-3-yl)(pyrrolidin-1-yl)methanone | 361.2 | 3.115 |

TABLE XVIIA-continued

EXAMPLES 315 TO 441 ARE TABULATED BELOW:

| Ex. No. | Compound Structure | Compound Name | MS | PDE10 IC50 (uM) |
|---|---|---|---|---|
| 404 | 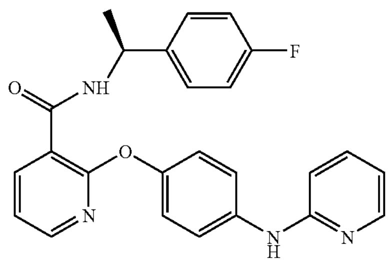 [SMILES: C[C@H](NC(=O)c1cccnc1Oc1ccc(Nc2ccccn2)cc1)c1ccc(F)cc1] | (S)-N-(1-(4-fluorophenyl)ethyl)-2-(4-(pyridin-2-ylamino)phenoxy)nicotinamide | 429.2 | 0.5669 |
| 405 | 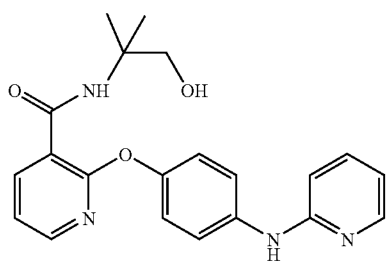 [SMILES: CC(C)(CO)NC(=O)c1cccnc1Oc1ccc(Nc2ccccn2)cc1] | N-(1-hydroxy-2-methylpropan-2-yl)-2-(4-(pyridin-2-ylamino)phenoxy)nicotinamide | 379.2 | 0.2565 |
| 406 | 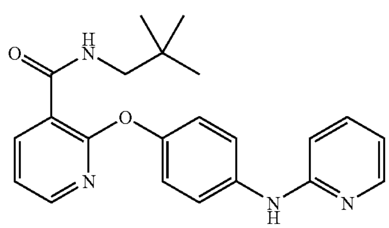 [SMILES: CC(C)(C)CNC(=O)c1cccnc1Oc1ccc(Nc2ccccn2)cc1] | N-neopentyl-2-(4-(pyridin-2-ylamino)phenoxy)nicotinamide | 377.2 | 0.2559 |
| 407 | 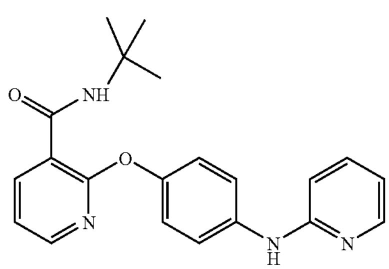 [SMILES: CC(C)(C)NC(=O)c1cccnc1Oc1ccc(Nc2ccccn2)cc1] | N-tert-butyl-2-(4-(pyridin-2-ylamino)phenoxy)nicotinamide | 363.2 | 0.09222 |
| 408 | 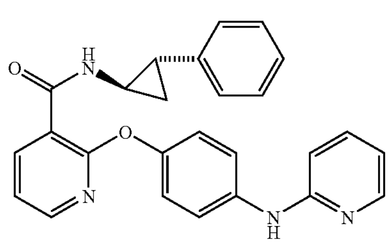 [SMILES: O=C(N[C@@H]1C[C@H]1c1ccccc1)c1cccnc1Oc1ccc(Nc2ccccn2)cc1] | N-((1S,2R)-2-phenylcyclopropyl)-2-(4-(pyridin-2-ylamino)phenoxy)nicotinamide hydrochloride | 423.2 | 0.1878 |

TABLE XVIIA-continued

EXAMPLES 315 TO 441 ARE TABULATED BELOW:

| Ex. No. | Compound Structure | Compound Name | MS | PDE10 IC50 (uM) |
|---|---|---|---|---|
| 409 | 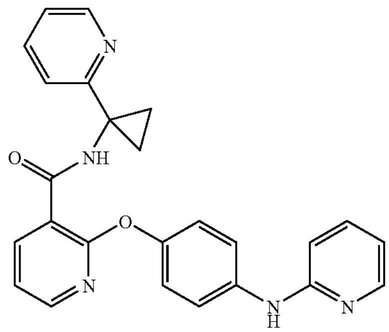 [SMILES: O=C(NC1(c2ccccn2)CC1)c1cccnc1Oc1ccc(Nc2ccccn2)cc1] | N-(1-(pyridin-2-yl)cyclopropyl)-2-(4-(pyridin-2-ylamino)phenoxy)nicotinamide | 424.4 | 0.1832 |
| 410 | 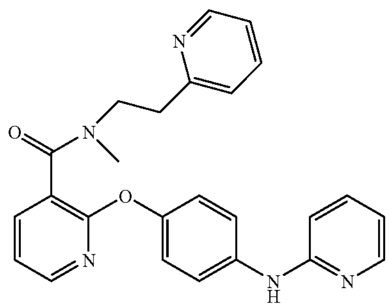 [SMILES: CN(CCc1ccccn1)C(=O)c1cccnc1Oc1ccc(Nc2ccccn2)cc1] | N-methyl-N-(2-(pyridin-2-yl)ethyl)-2-(4-(pyridin-2-ylamino)phenoxy)nicotinamide | 428.8 | 2.292 |
| 411 | 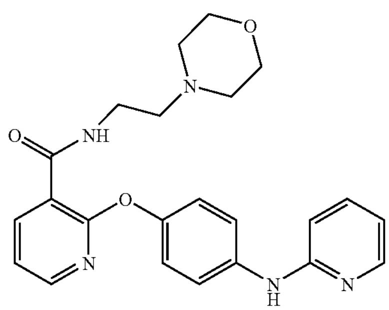 [SMILES: O=C(NCCN1CCOCC1)c1cccnc1Oc1ccc(Nc2ccccn2)cc1] | N-(2-morpholinoethyl)-2-(4-(pyridin-2-ylamino)phenoxy)nicotinamide | 420.4 | 0.5682 |
| 412 | 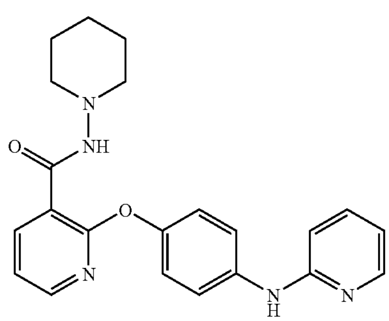 [SMILES: O=C(NN1CCCCC1)c1cccnc1Oc1ccc(Nc2ccccn2)cc1] | N-(piperidin-1-yl)-2-(4-(pyridin-2-ylamino)phenoxy)nicotinamide | 390.4 | 0.4969 |
| 413 | 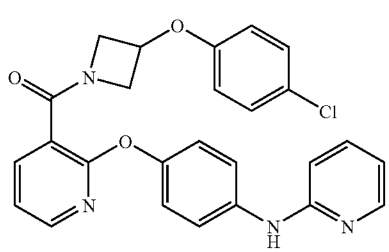 [SMILES: O=C(c1cccnc1Oc1ccc(Nc2ccccn2)cc1)N1CC(Oc2ccc(Cl)cc2)C1] | (3-(4-chlorophenoxy)azetidin-1-yl)(2-(4-(pyridin-2-ylamino)phenoxy)pyridin-3-yl)methanone | 473.2 | 0.6924 |

TABLE XVIIA-continued

EXAMPLES 315 TO 441 ARE TABULATED BELOW:

| Ex. No. | Compound Structure | Compound Name | MS | PDE10 IC50 (uM) |
|---|---|---|---|---|
| 414 | 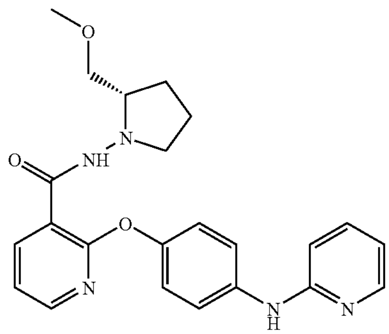 [SMILES: COC[C@@H]1CCCN1NC(=O)c1cccnc1Oc1ccc(Nc2ccccn2)cc1] | (R)-N-(2-(methoxymethyl)pyrrolidin-1-yl)-2-(4-(pyridin-2-ylamino)phenoxy)nicotinamide | 420.4 | 0.1472 |
| 415 | 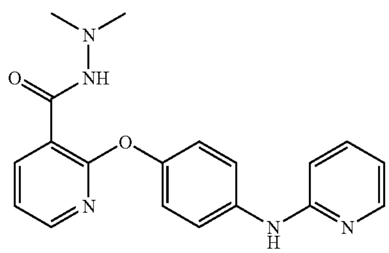 [SMILES: CN(C)NC(=O)c1cccnc1Oc1ccc(Nc2ccccn2)cc1] | N',N'-dimethyl-2-(4-(pyridin-2-ylamino)phenoxy)nicotinohydrazide | 350.4 | 1.833 |
| 416 | 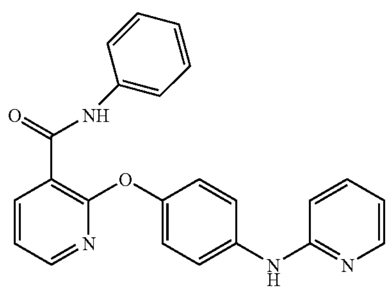 [SMILES: O=C(Nc1ccccc1)c1cccnc1Oc1ccc(Nc2ccccn2)cc1] | N-phenyl-2-(4-(pyridin-2-ylamino)phenoxy)nicotinamide | 383.2 | 0.1971 |
| 417 | 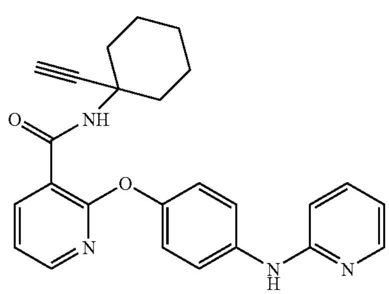 [SMILES: C#CC1(NC(=O)c2cccnc2Oc2ccc(Nc3ccccn3)cc2)CCCCC1] | N-(1-ethynylcyclohexyl)-2-(4-(pyridin-2-ylamino)phenoxy)nicotinamide | 413.2 | 0.0492 |

TABLE XVIIA-continued

EXAMPLES 315 TO 441 ARE TABULATED BELOW:

| Ex. No. | Compound Structure | Compound Name | MS | PDE10 IC50 (uM) |
|---|---|---|---|---|
| | *structure* | | | |
| 418 | *structure* | N-(2,6-dimethylpiperidin-1-yl)-2-(4-(pyridin-2-ylamino)phenoxy)nicotinamide | 418.4 | 0.4114 |
| 419 | *structure* | (rac)-N-(2-phenylpropyl)-2-(4-(pyridin-2-ylamino)phenoxy)nicotinamide | 425.0 | 0.0569 |
| 420 | *structure* | 2-(4-(pyridin-2-ylamino)phenoxy)-N-(pyrimidin-2-yl)nicotinamide | 335.0 | 0.265 |
| 421 | *structure* | (rac)-N-sec-butyl-2-(4-(pyridin-2-ylamino)phenoxy)nicotinamide | 363.0 | 0.02529 |

TABLE XVIIA-continued

EXAMPLES 315 TO 441 ARE TABULATED BELOW:

| Ex. No. | Compound Structure | Compound Name | MS | PDE10 IC50 (uM) |
|---|---|---|---|---|
| 422 | 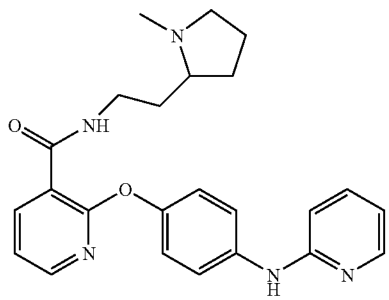 [SMILES: CN1CCCC1CCNC(=O)c1cccnc1Oc1ccc(Nc2ccccn2)cc1] | (rac)-N-(2-(1-methylpyrrolidin-2-yl)ethyl)-2-(4-(pyridin-2-ylamino)phenoxy)nicotinamide | 417.2 | 3.943 |
| 423 | 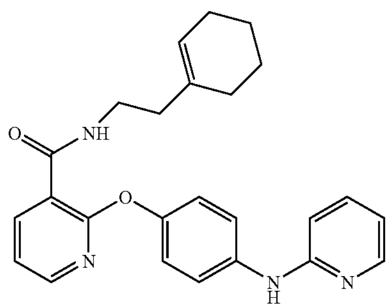 [SMILES: O=C(NCCC1=CCCCC1)c1cccnc1Oc1ccc(Nc2ccccn2)cc1] | N-(2-cyclohexenylethyl)-2-(4-(pyridin-2-ylamino)phenoxy)nicotinamide | 414.2 | 0.08328 |
| 424 | 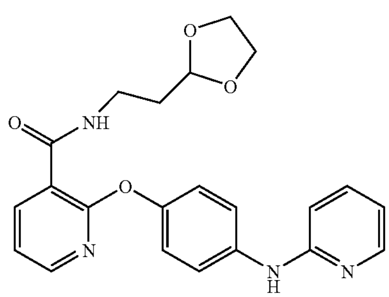 [SMILES: O=C(NCCC1OCCO1)c1cccnc1Oc1ccc(Nc2ccccn2)cc1] | N-(2-(1,3-dioxolan-2-ylamino)phenoxy)nicotinamide | 406.2 | 0.03568 |
| 425 | 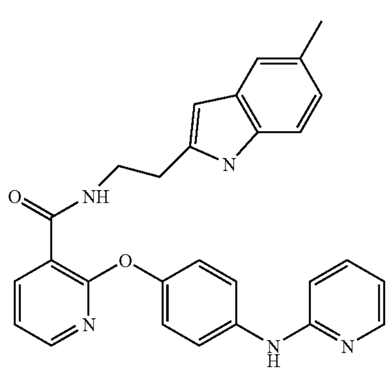 [SMILES: Cc1ccc2[nH]c(CCNC(=O)c3cccnc3Oc3ccc(Nc4ccccn4)cc3)cc2c1] | N-(2-(5-methyl-1H-indol-3-yl)ethyl)-2-(4-(pyridin-2-ylamino)phenoxy)nicotinamide | 463.2 | 0.0747 |

TABLE XVIIA-continued

EXAMPLES 315 TO 441 ARE TABULATED BELOW:

| Ex. No. | Compound Structure | Compound Name | MS | PDE10 IC50 (uM) |
|---|---|---|---|---|
| 426 | 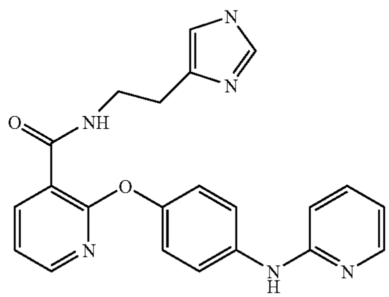 [SMILES: O=C(NCCc1c[nH]cn1)c1cccnc1Oc1ccc(Nc2ccccn2)cc1] | N-(2-(1H-imidazol-4-ylamino)phenoxy)nicotinamide | 400.2 | 0.35255 |
| 427 | 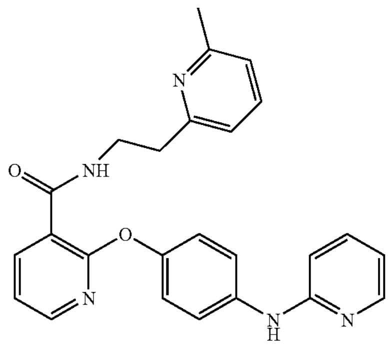 [SMILES: Cc1cccc(CCNC(=O)c2cccnc2Oc2ccc(Nc3ccccn3)cc2)n1] | N-(2-(6-methylpyridin-2-ylamino)phenoxy)nicotinamide | 425.2 | 0.02949 |
| 428 | 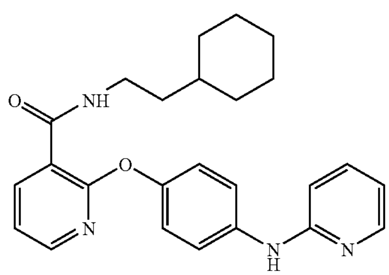 [SMILES: O=C(NCCC1CCCCC1)c1cccnc1Oc1ccc(Nc2ccccn2)cc1] | N-(2-cyclohexylethyl)-2-(4-(pyridin-2-ylamino)phenoxy)nicotinamide | 416.2 | 0.4554 |
| 429 | 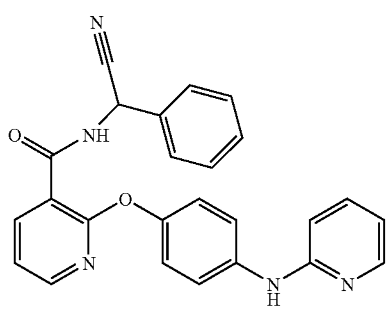 [SMILES: N#CC(NC(=O)c1cccnc1Oc1ccc(Nc2ccccn2)cc1)c1ccccc1] | (rac)-N-(cyano(phenyl)methyl)-2-(4-(pyridin-2-ylamino)phenoxy)nicotinamide | 421.1 | 0.01346 |
| 430 | 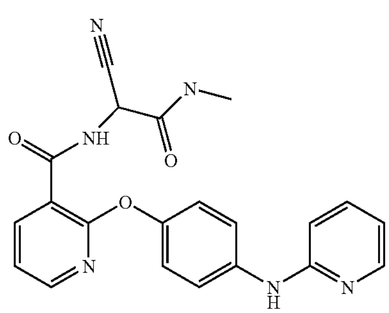 [SMILES: CNC(=O)C(C#N)NC(=O)c1cccnc1Oc1ccc(Nc2ccccn2)cc1] | (rac)-N-(1-cyano-2-(methylamino)-2-oxoethyl)-2-(4-(pyridin-2-ylamino)phenoxy)nicotinamide | 402.1 | 0.04297 |

TABLE XVIIA-continued

EXAMPLES 315 TO 441 ARE TABULATED BELOW:

| Ex. No. | Compound Structure | Compound Name | MS | PDE10 IC50 (uM) |
|---|---|---|---|---|
| 431 | 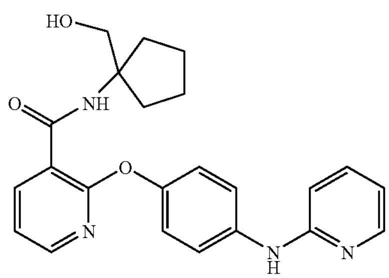 [SMILES: O=C(NC1(CO)CCCC1)c1cccnc1Oc1ccc(Nc2ccccn2)cc1] | N-(1-(hydroxymethyl)cyclopentyl)-2-(4-(pyridin-2-ylamino)phenoxy)nicotinamide | 404.2 | 0.4423 |
| 432 | 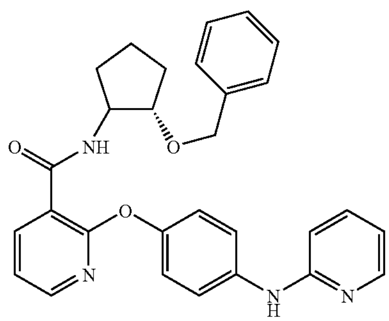 [SMILES: O=C(NC1CCC[C@@H]1OCc1ccccc1)c1cccnc1Oc1ccc(Nc2ccccn2)cc1] | (rac)-N-((1S,2S)-2-(benzyloxy)cyclopentyl)-2-(4-(pyridin-2-ylamino)phenoxy)nicotinamide | 480.2 | 0.6822 |
| 433 | 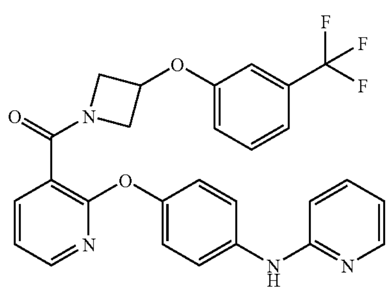 [SMILES: O=C(c1cccnc1Oc1ccc(Nc2ccccn2)cc1)N1CC(Oc2cccc(C(F)(F)F)c2)C1] | (2-(4-(pyridin-2-ylamino)phenoxy)pyridin-3-yl)(3-(3-trifluoromethyl)phenoxy)azetidin-1-yl)methanone | 506.2 | 0.291 |
| 434 | 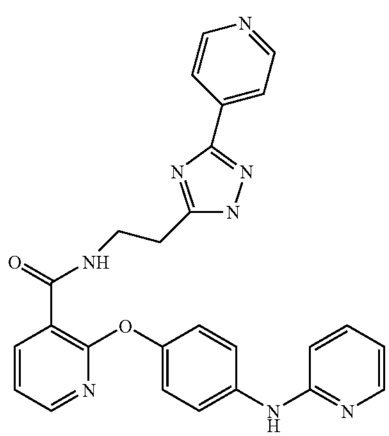 [SMILES: O=C(NCCc1nc(-c2ccncc2)n[nH]1)c1cccnc1Oc1ccc(Nc2ccccn2)cc1] | 2-(4-(pyridin-2-ylamino)phenoxy)-N-(2-(3-(pyridin-4-yl)-1H-1,2,4-triazol-5-yl)ethyl)nicotinamide | 478.2 | 1.923 |

TABLE XVIIA-continued

EXAMPLES 315 TO 441 ARE TABULATED BELOW:

| Ex. No. | Compound Structure | Compound Name | MS | PDE10 IC50 (uM) |
|---|---|---|---|---|
| 435 | 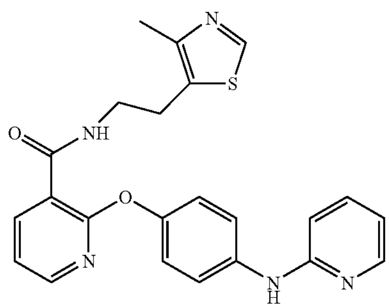 [SMILES: Cc1ncsc1CCNC(=O)c1cccnc1Oc1ccc(Nc2ccccn2)cc1] | N-(2-(4-methylthiazol-5-yl)ethyl-2-(4-(pyridin-2-ylamino)phenoxy)nicotinamide | 431.1 | 0.08018 |
| 436 | 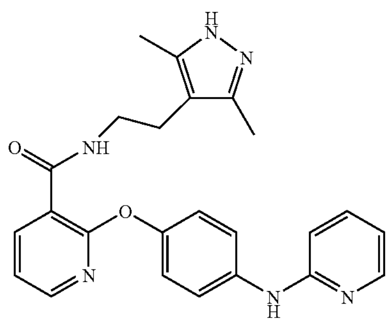 [SMILES: Cc1n[nH]c(C)c1CCNC(=O)c1cccnc1Oc1ccc(Nc2ccccn2)cc1] | N-(2-(3,5-dimethyl-1H-pyrazol-4-yl)ethyl)-2-(4-(pyridin-2-ylamino)phenoxy)nicotinamide | 428.2 | 0.1637 |
| 437 | 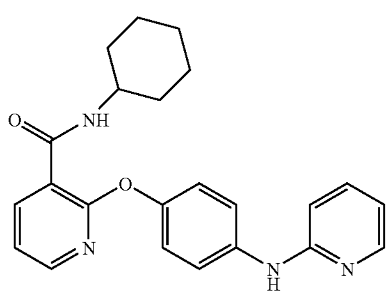 [SMILES: O=C(NC1CCCCC1)c1cccnc1Oc1ccc(Nc2ccccn2)cc1] | N-cyclohexyl-2-(4-(pyridin-2-ylamino)phenoxy)nicotinamide | 388.2 | 0.1435 |
| 438 | 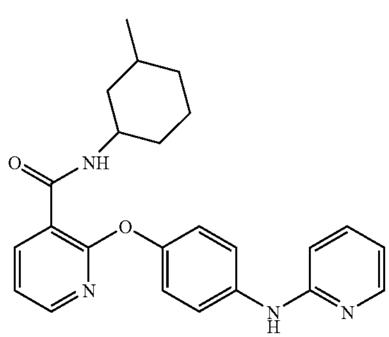 [SMILES: CC1CCCC(NC(=O)c2cccnc2Oc2ccc(Nc3ccccn3)cc2)C1] | (rac)-N-(3-methylcyclohexyl)-2-(4-(pyridin-2-ylamino)phenoxy)nicotinamide | 402.2 | 0.3048 |

TABLE XVIIA-continued

EXAMPLES 315 TO 441 ARE TABULATED BELOW:

| Ex. No. | Compound Structure | Compound Name | MS | PDE10 IC50 (uM) |
|---|---|---|---|---|
| 439 | 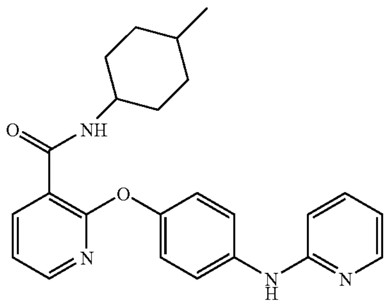 [SMILES: CC1CCC(NC(=O)c2cccnc2Oc2ccc(Nc3ccccn3)cc2)CC1] | N-(4-methylcyclohexyl)-2-(4-(pyridin-2-ylamino)phenoxy)nicotinamide | 402.2 | 0.2724 |
| 440 | 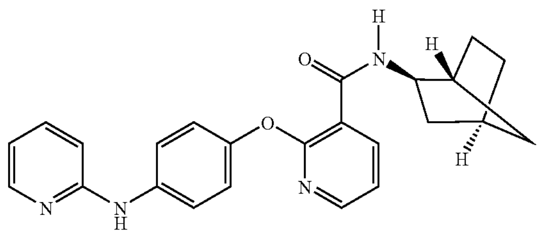 [SMILES: O=C(N[C@@H]1C[C@H]2CC[C@@H]1C2)c1cccnc1Oc1ccc(Nc2ccccn2)cc1] | N-((1R,2R,4S)-bicyclo[2.2.1]heptan-2-yl)-2-(4-(pyridin-2-ylamino)phenoxy)nicotinamide | 400.2 | 0.3019 |
| 441 | 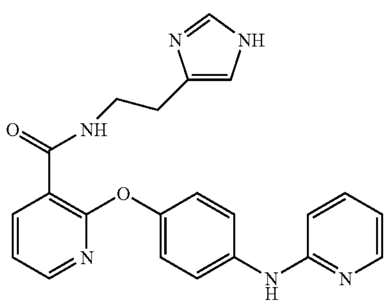 [SMILES: O=C(NCCc1c[nH]cn1)c1cccnc1Oc1ccc(Nc2ccccn2)cc1] | N-(2-(1H-imidazol-4-yl)ethyl)-2-(4-(pyridin-2-ylamino)phenoxy)nicotinamide | 400.2 | 0.35255 |

TABLE XVIIB

PREPARATION OF EXAMPLES 318 TO 444 ARE TABULATED BELOW:

| Ex. No. | Scheme | Starting material 1 | Starting material 2 | Conditions or reagents that differ from scheme |
|---|---|---|---|---|
| 315 | 2 | | H$_2$N— | — |
| 316 | 2 | | H$_2$N— | — |

TABLE XVIIB-continued

PREPARATION OF EXAMPLES 318 TO 444 ARE TABULATED BELOW:

| Ex. No. | Scheme | Starting material 1 | Starting material 2 | Conditions or reagents that differ from scheme |
|---|---|---|---|---|
| 317 | 2 | 2-[4-(pyridin-2-ylamino)phenoxy]nicotinic acid | propargylamine | — |
| 318 | 2 | 2-[4-(pyridin-2-ylamino)phenoxy]nicotinic acid | cyclohexylmethanamine | — |
| 319 | 2 | 2-[4-(pyridin-2-ylamino)phenoxy]nicotinic acid | dimethylamine | — |
| 320 | 2 | 2-[4-(pyridin-2-ylamino)phenoxy]nicotinic acid | 1-methoxypropan-2-amine | — |
| 321 | 2 | 2-[4-(pyridin-2-ylamino)phenoxy]nicotinic acid | (S)-1-methoxypropan-2-amine | — |
| 322 | 2 | 2-[4-(pyridin-2-ylamino)phenoxy]nicotinic acid | 2-phenylethanamine | — |
| 323 | 2 | 2-[4-(pyridin-2-ylamino)phenoxy]nicotinic acid | 2-(p-tolyl)ethanamine | — |

TABLE XVIIB-continued

PREPARATION OF EXAMPLES 318 TO 444 ARE TABULATED BELOW:

| Ex. No. | Scheme | Starting material 1 | Starting material 2 | Conditions or reagents that differ from scheme |
|---|---|---|---|---|
| 324 | 2 | (structure) | (structure) | — |
| 325 | 2 | (structure) | (structure) | — |
| 326 | 2 | (structure) | (structure) | — |
| 327 | 2 | (structure) | (structure) | — |
| 328 | 2 | (structure) | (structure) | — |
| 329 | 2 | (structure) | (structure) | — |
| 330 | 2 | (structure) | (structure) | — |

TABLE XVIIB-continued
PREPARATION OF EXAMPLES 318 TO 444 ARE TABULATED BELOW:
| Ex. No. | Scheme | Starting material 1 | Starting material 2 | Conditions or reagents that differ from scheme |
|---|---|---|---|---|
| 331 | 2 | 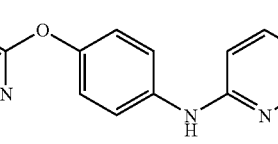 | 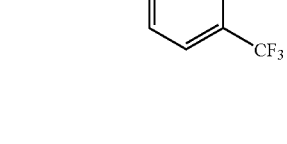 | — |
| 332 | 2 | 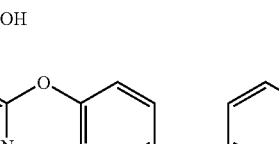 | 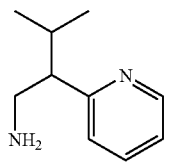 | — |
| 333 | 2 | 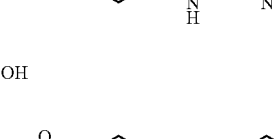 | 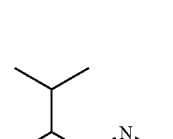 | — |
| 334 | 2 | 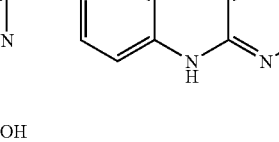 | 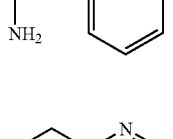 | — |
| 335 | 2 | 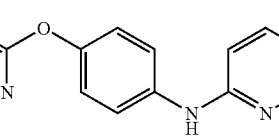 | 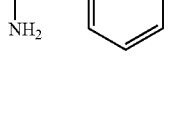 | — |
| 336 | 2 | 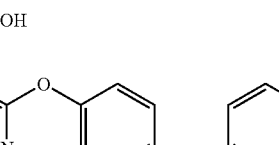 | 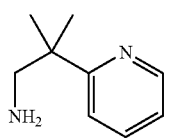 | — |
| 337 | 2 | 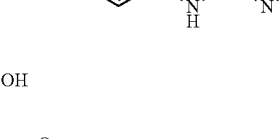 | 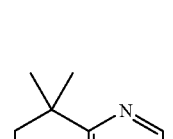 | — |

TABLE XVIIB-continued
PREPARATION OF EXAMPLES 318 TO 444 ARE TABULATED BELOW:
| Ex. No. | Scheme | Starting material 1 | Starting material 2 | Conditions or reagents that differ from scheme |
|---|---|---|---|---|
| 338 | 2 | 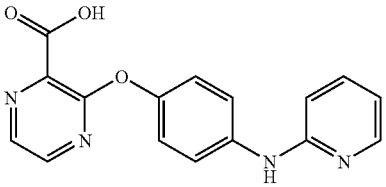 [SMILES: O=C(O)c1cccnc1Oc1ccc(Nc2ccccn2)cc1] | 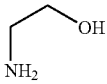 | — |
| 339 | 2 | 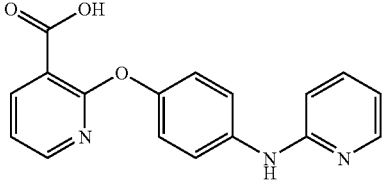 [SMILES: O=C(O)c1cccnc1Oc1ccc(Nc2ccccn2)cc1] | 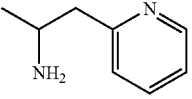 | — |
| 340 | 2 | 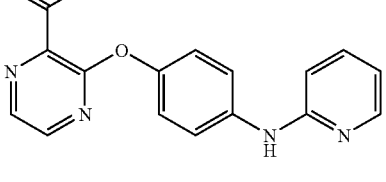 | 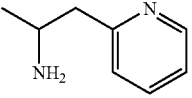 | — |
| 341 | 2 | 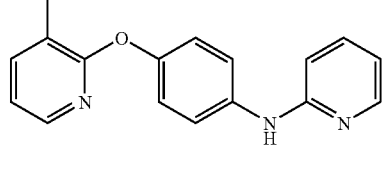 | 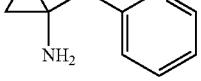 | — |
| 342 | 2 | 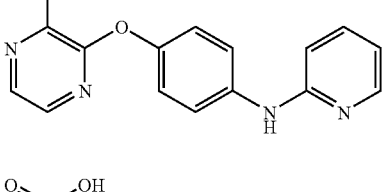 | 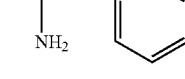 | — |
| 343 | 2 | 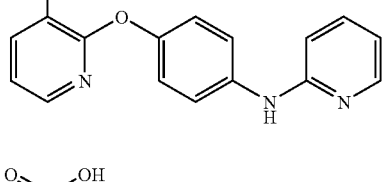 | 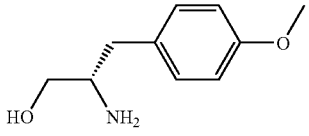 | — |
| 344 | 2 | 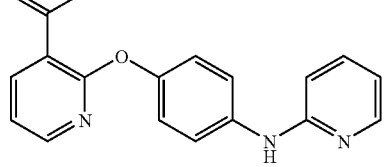 | 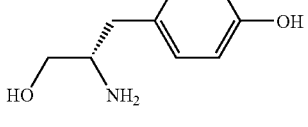 | — |

TABLE XVIIB-continued

PREPARATION OF EXAMPLES 318 TO 444 ARE TABULATED BELOW:

| Ex. No. | Scheme | Starting material 1 | Starting material 2 | Conditions or reagents that differ from scheme |
|---|---|---|---|---|
| 345 | 2 | 3-carboxy-2-[4-(pyridin-2-ylamino)phenoxy]pyridine | (S)-2-phenyl-1-aminoethyl (wedge to NH2) | — |
| 346 | 2 | 3-carboxy-2-[4-(pyridin-2-ylamino)phenoxy]pyridine | 2-aminoindane | — |
| 347 | 2 | 3-carboxy-2-[4-(pyridin-2-ylamino)phenoxy]pyridine | 1-(4-fluorophenyl)-2-methyl-2-aminopropane | — |
| 348 | 2 | 3-carboxy-2-[4-(pyridin-2-ylamino)phenoxy]pyridine | 1-(4-fluorophenyl)-2-aminopropane | — |
| 349 | 2 | 3-carboxy-2-[4-(pyridin-2-ylamino)phenoxy]pyridine | (R)-1-(4-fluorophenyl)-2-aminopropane | — |
| 350 | 2 | 3-carboxy-2-[4-(pyridin-2-ylamino)phenoxy]pyridine | (S)-1-(4-fluorophenyl)-2-aminopropane | — |
| 351 | 1 | 3-carboxy-2-[4-(pyridin-2-ylamino)phenoxy]pyridine | cyclopropylmethylamine HCl | — |

TABLE XVIIB-continued
PREPARATION OF EXAMPLES 318 TO 444 ARE TABULATED BELOW:
| Ex. No. | Scheme | Starting material 1 | Starting material 2 | Conditions or reagents that differ from scheme |
|---|---|---|---|---|
| 352 | 1 | 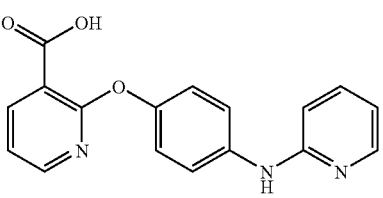 [SMILES: O=C(O)c1cccnc1Oc1ccc(Nc2ccccn2)cc1] | 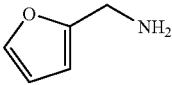 | — |
| 353 | 1 | 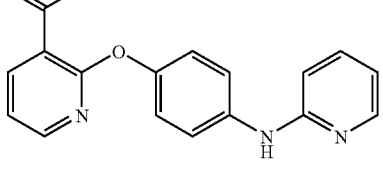 | 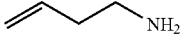 | — |
| 354 | 1 | 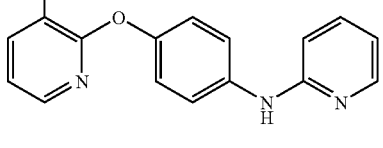 | 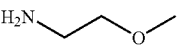 | — |
| 355 | 1 | 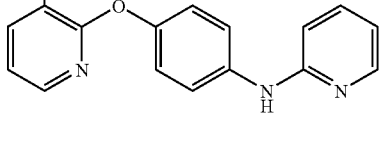 | 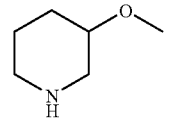 | — |
| 356 | 1 | 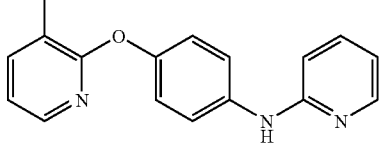 | 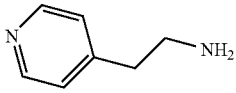 | — |
| 357 | 1 | 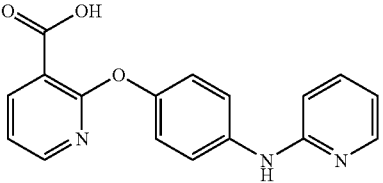 | 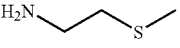 | — |
| 358 | 1 | 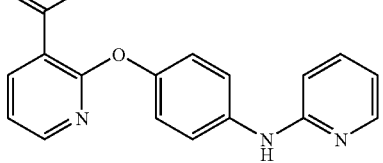 |  | — |

TABLE XVIIB-continued

PREPARATION OF EXAMPLES 318 TO 444 ARE TABULATED BELOW:

| Ex. No. | Scheme | Starting material 1 | Starting material 2 | Conditions or reagents that differ from scheme |
|---|---|---|---|---|
| 359 | 1 | (carboxylic acid-pyridinyloxy-phenyl-NH-pyridine) | 1-methoxy-2-butanamine | — |
| 360 | 1 | (carboxylic acid-pyridinyloxy-phenyl-NH-pyridine) | 2,5-dihydro-1H-pyrrole | — |
| 361 | 1 | (carboxylic acid-pyridinyloxy-phenyl-NH-pyridine) | 4-methoxypiperidine | — |
| 362 | 1 | (carboxylic acid-pyridinyloxy-phenyl-NH-pyridine) | (tetrahydrofuran-2-yl)methanamine | — |
| 363 | 1 | (carboxylic acid-pyridinyloxy-phenyl-NH-pyridine) | (tetrahydro-2H-pyran-4-yl)methanamine | — |
| 364 | 1 | (carboxylic acid-pyridinyloxy-phenyl-NH-pyridine) | diethylamine | — |
| 365 | 1 | (carboxylic acid-pyridinyloxy-phenyl-NH-pyridine) | 3-(methylthio)propan-1-amine | — |

TABLE XVIIB-continued

PREPARATION OF EXAMPLES 318 TO 444 ARE TABULATED BELOW:

| Ex. No. | Scheme | Starting material 1 | Starting material 2 | Conditions or reagents that differ from scheme |
|---|---|---|---|---|
| 366 | 1 | 2-(4-(pyridin-2-ylamino)phenoxy)nicotinic acid | thiazolidine | — |
| 367 | 1 | 2-(4-(pyridin-2-ylamino)phenoxy)nicotinic acid | 3-chloropropylamine·HCl | — |
| 368 | 1 | 2-(4-(pyridin-2-ylamino)phenoxy)nicotinic acid | 2-(pyridin-2-yl)ethanamine | — |
| 369 | 1 | 2-(4-(pyridin-2-ylamino)phenoxy)nicotinic acid | 3-methoxypropan-1-amine | — |
| 370 | 1 | 2-(4-(pyridin-2-ylamino)phenoxy)nicotinic acid | 1,4-oxazepane·HCl | — |
| 371 | 1 | 2-(4-(pyridin-2-ylamino)phenoxy)nicotinic acid | N-methylprop-2-yn-1-amine | — |
| 372 | 1 | 2-(4-(pyridin-2-ylamino)phenoxy)nicotinic acid | (S)-butan-2-amine | — |

TABLE XVIIB-continued
PREPARATION OF EXAMPLES 318 TO 444 ARE TABULATED BELOW:
| Ex. No. | Scheme | Starting material 1 | Starting material 2 | Conditions or reagents that differ from scheme |
|---|---|---|---|---|
| 373 | 1 | 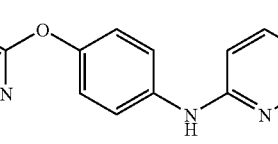 |  | — |
| 374 | 1 | 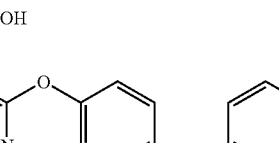 | 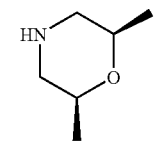 | — |
| 375 | 1 | 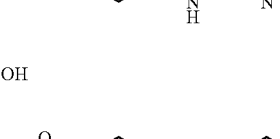 | 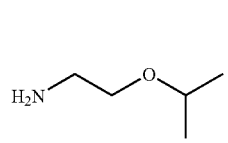 | — |
| 376 | 1 | 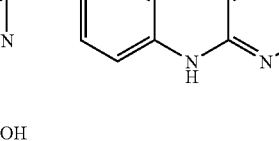 |  | — |
| 377 | 1 | 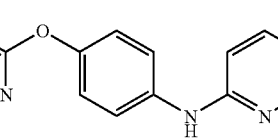 | 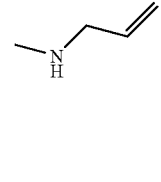 | — |
| 378 | 1 | 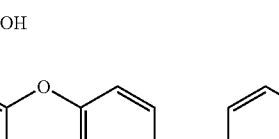 | 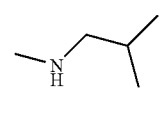 | — |
| 379 | 1 | 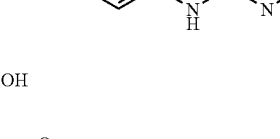 | 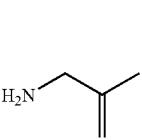 | — |

TABLE XVIIB-continued

PREPARATION OF EXAMPLES 318 TO 444 ARE TABULATED BELOW:

| Ex. No. | Scheme | Starting material 1 | Starting material 2 | Conditions or reagents that differ from scheme |
|---|---|---|---|---|
| 380 | 1 | | | — |
| 381 | 1 | | | — |
| 382 | 1 | | | — |
| 383 | 1 | | | — |
| 384 | 1 | | | — |
| 385 | 1 | | | — |
| 386 | 1 | | | — |

TABLE XVIIB-continued
PREPARATION OF EXAMPLES 318 TO 444 ARE TABULATED BELOW:
| Ex. No. | Scheme | Starting material 1 | Starting material 2 | Conditions or reagents that differ from scheme |
|---|---|---|---|---|
| 387 | 1 | 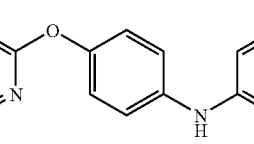 | 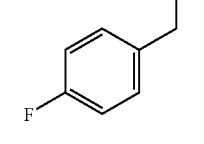 | — |
| 388 | 1 | 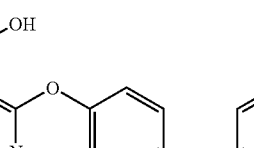 | 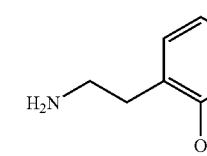 | — |
| 389 | 1 | 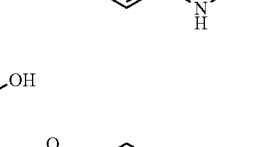 | 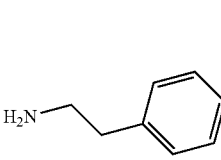 | — |
| 390 | 1 | 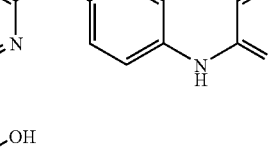 | 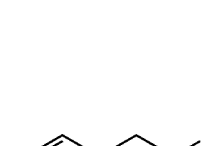 | — |
| 391 | 1 | 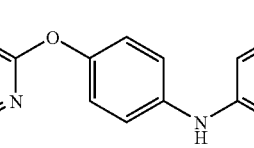 | 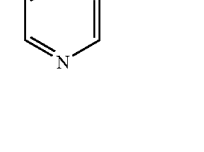 | — |
| 392 | 1 | 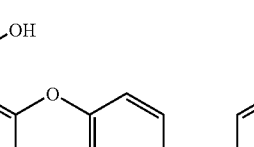 | 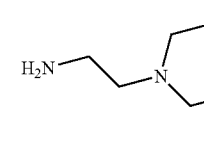 | — |
| 393 | 1 | 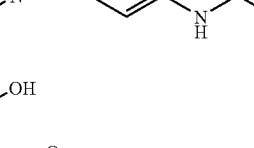 | 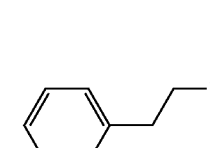 | — |

TABLE XVIIB-continued
PREPARATION OF EXAMPLES 318 TO 444 ARE TABULATED BELOW:
| Ex. No. | Scheme | Starting material 1 | Starting material 2 | Conditions or reagents that differ from scheme |
|---|---|---|---|---|
| 394 | 1 | 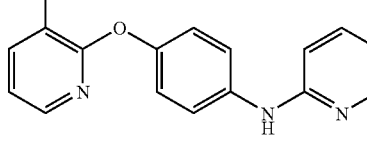 | 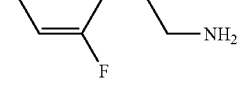 | — |
| 395 | 1 | 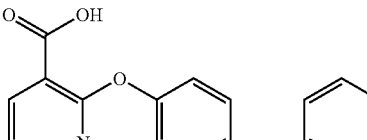 | 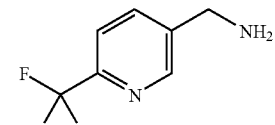 | — |
| 396 | 1 |  | 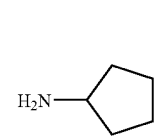 | — |
| 397 | 1 | 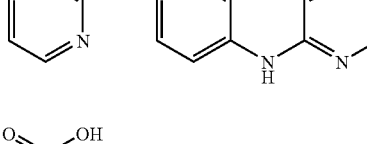 |  | — |
| 398 | 1 | 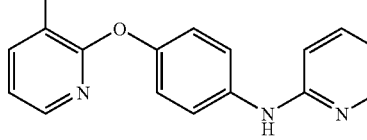 |  | — |
| 399 | 1 | 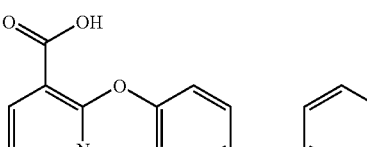 | 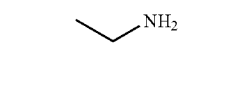 | — |
| 400 | 1 |  |  | — |

TABLE XVIIB-continued
PREPARATION OF EXAMPLES 318 TO 444 ARE TABULATED BELOW:
| Ex. No. | Scheme | Starting material 1 | Starting material 2 | Conditions or reagents that differ from scheme |
|---|---|---|---|---|
| 401 | 1 | 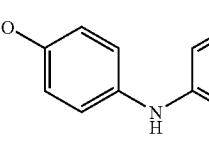 | 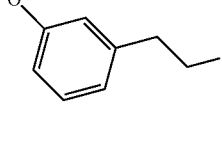 | — |
| 402 | 1 | 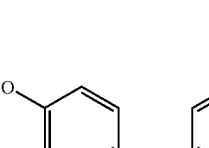 | 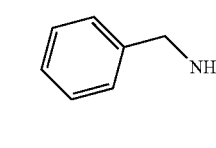 | — |
| 403 | 1 | 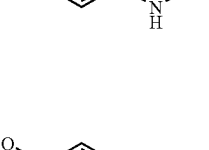 | 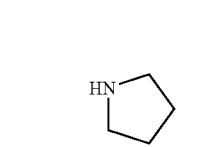 | — |
| 404 | 1 | 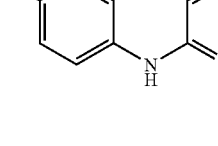 |  | — |
| 405 | 1 | 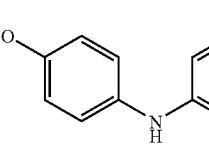 |  | — |
| 406 | 1 | 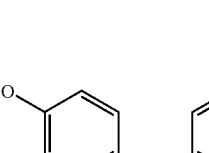 | 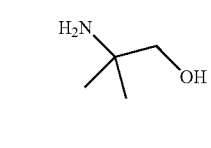 | — |
| 407 | 1 | 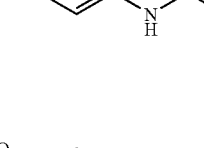 | 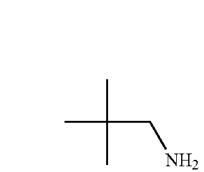 | — |

TABLE XVIIB-continued
PREPARATION OF EXAMPLES 318 TO 444 ARE TABULATED BELOW:
| Ex. No. | Scheme | Starting material 1 | Starting material 2 | Conditions or reagents that differ from scheme |
|---|---|---|---|---|
| 408 | 1 | 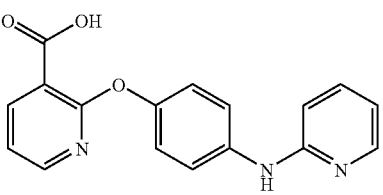 [SMILES: O=C(O)c1cccnc1Oc1ccc(Nc2ccccn2)cc1] | 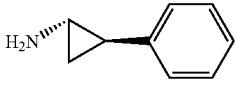 | — |
| 409 | 1 | 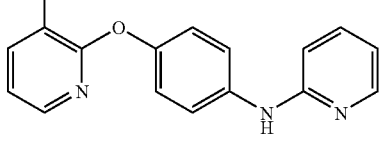 | 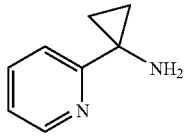 | — |
| 410 | 1 | 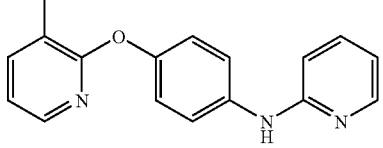 | 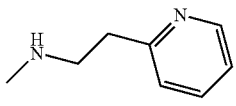 | — |
| 411 | 1 | 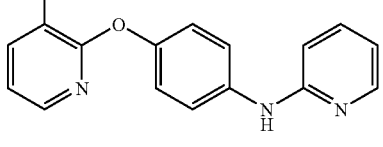 | 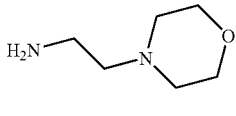 | — |
| 412 | 1 | 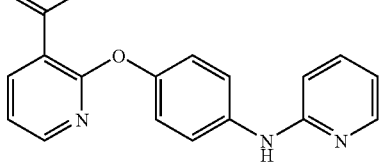 | 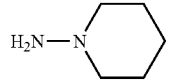 | — |
| 413 | 1 | 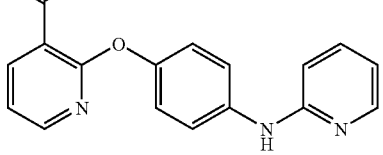 | 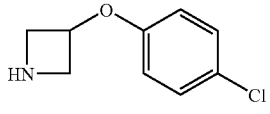 [SMILES: Clc1ccc(OC2CNC2)cc1] | — |
| 414 | 1 | 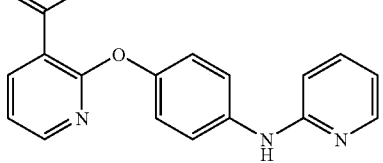 | 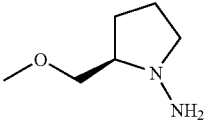 | — |

TABLE XVIIB-continued
PREPARATION OF EXAMPLES 318 TO 444 ARE TABULATED BELOW:
| Ex. No. | Scheme | Starting material 1 | Starting material 2 | Conditions or reagents that differ from scheme |
|---|---|---|---|---|
| 415 | 1 | 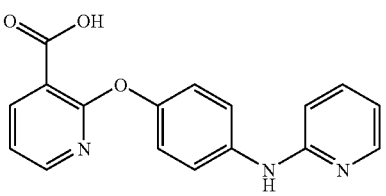 [SMILES: O=C(O)c1cccnc1Oc1ccc(Nc2ccccn2)cc1] |  | — |
| 416 | 1 | 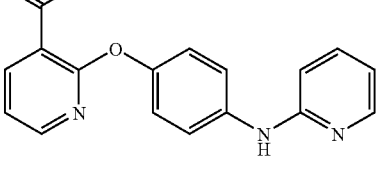 | 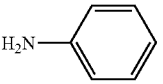 | — |
| 417 | 1 | 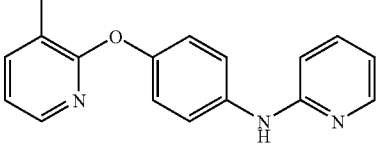 | 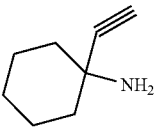 | — |
| 418 | 1 | 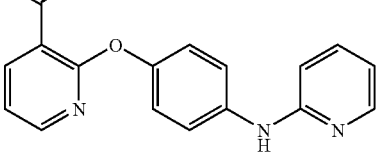 | 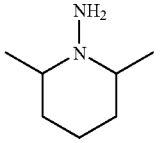 | — |
| 419 | 1 | 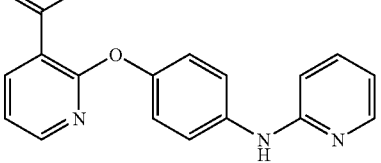 | 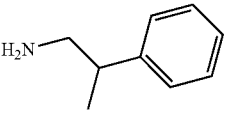 | — |
| 420 | 1 | 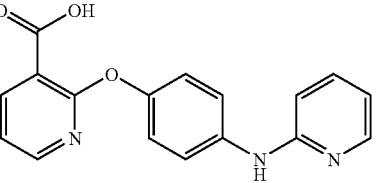 | 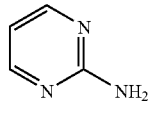 | — |
| 421 | 1 | 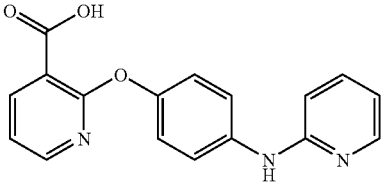 [SMILES: O=C(O)c1cccnc1Oc1ccc(Nc2ccccn2)cc1] | 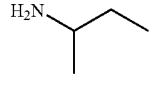 | — |

TABLE XVIIB-continued

PREPARATION OF EXAMPLES 318 TO 444 ARE TABULATED BELOW:

| Ex. No. | Scheme | Starting material 1 | Starting material 2 | Conditions or reagents that differ from scheme |
|---|---|---|---|---|
| 422 | 1 | 2-(4-(pyridin-2-ylamino)phenoxy)nicotinic acid | 2-(1-methylpyrrolidin-2-yl)ethanamine | — |
| 423 | 1 | 2-(4-(pyridin-2-ylamino)phenoxy)nicotinic acid | 2-(cyclohex-1-enyl)ethanamine | — |
| 424 | 1 | 2-(4-(pyridin-2-ylamino)phenoxy)nicotinic acid | 2-(1,3-dioxolan-2-yl)ethanamine | — |
| 425 | 1 | 2-(4-(pyridin-2-ylamino)phenoxy)nicotinic acid | 2-(5-methyl-1H-indol-3-yl)ethanamine·HCl | — |
| 426 | 1 | 2-(4-(pyridin-2-ylamino)phenoxy)nicotinic acid | 2-(1H-imidazol-4-yl)ethanamine | — |
| 427 | 1 | 2-(4-(pyridin-2-ylamino)phenoxy)nicotinic acid | 2-(6-methylpyridin-2-yl)ethanamine | — |
| 428 | 1 | 2-(4-(pyridin-2-ylamino)phenoxy)nicotinic acid | 2-cyclohexylethanamine | — |

TABLE XVIIB-continued

PREPARATION OF EXAMPLES 318 TO 444 ARE TABULATED BELOW:

| Ex. No. | Scheme | Starting material 1 | Starting material 2 | Conditions or reagents that differ from scheme |
|---|---|---|---|---|
| 429 | 1 | (structure) | (structure) | — |
| 430 | 1 | (structure) | (structure) | — |
| 431 | 1 | (structure) | (structure) | — |
| 432 | 1 | (structure) | (structure) | — |
| 433 | 1 | (structure) | (structure) | — |
| 434 | 1 | (structure) | (structure) | — |
| 435 | 1 | (structure) | (structure) | — |

TABLE XVIIB-continued

PREPARATION OF EXAMPLES 318 TO 444 ARE TABULATED BELOW:

| Ex. No. | Scheme | Starting material 1 | Starting material 2 | Conditions or reagents that differ from scheme |
|---|---|---|---|---|
| 436 | 1 | 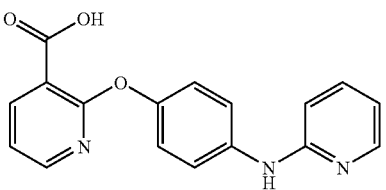 [SMILES: O=C(O)c1cccnc1Oc1ccc(Nc2ccccn2)cc1] | 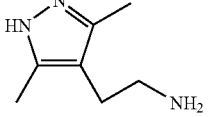 | — |
| 437 | 1 | 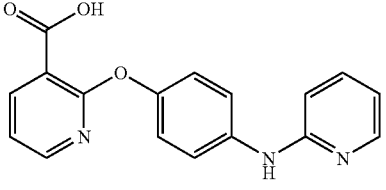 [SMILES: O=C(O)c1cccnc1Oc1ccc(Nc2ccccn2)cc1] | 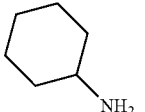 | — |
| 438 | 1 | 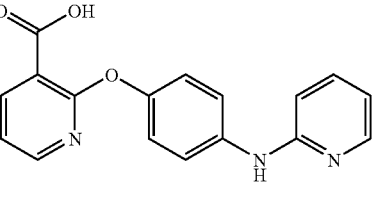 | 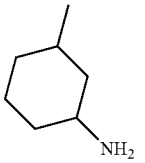 | — |
| 439 | 1 | 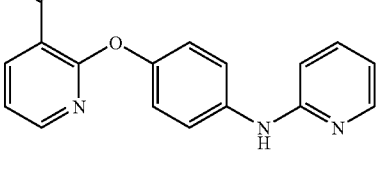 | 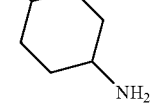 | — |
| 440 | 1 | 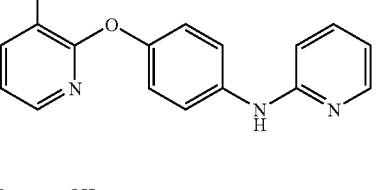 | 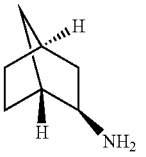 | — |
| 441 | 1 | 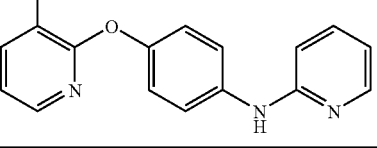 | 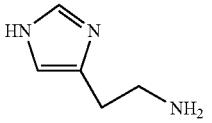 | — |

The following compounds were obtained by chiral HPLC separation from the racemate by known methods, such as, the series of samples were purified via supercritical fluid chromatography using Amylose or cellulose based chiral stationary phases (CSPs). Alcohols were used as additives to the supercritical fluid carbon dioxide as mobile phase. The absolute stereochemistry of each chiral compound is arbitrarily assigned.

TABLE XVIII

EXAMPLES 442 TO 455 ARE TABULATED BELOW:

| Ex. Nos.* | Compound Structure | Compound Name | MS | PDE10 IC50 (uM) |
|---|---|---|---|---|
| 442 and 443/ separated from racemic mixture from example 236/ Scheme 23 | 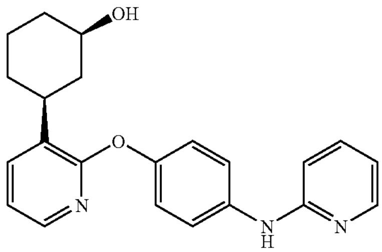 [SMILES: O[C@H]1CCC[C@@H](c2cccnc2Oc2ccc(Nc3ccccn3)cc2)C1] | (1R,3S)-3-(2-(4-(pyridin-2-ylamino)phenoxy)pyridin-3-yl)cyclohexanol and (1S,3R)-3-(2-(4-(pyridin-2-ylamino)phenoxy)pyridin-3-yl)cyclohexanol | 362.0 | 0.03563 and 0.012225 |
| 444 and 445/ separated from racemic mixture from example 237/Schemes 24a + 24b | 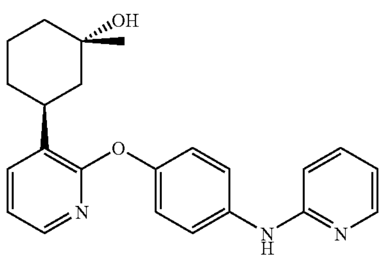 | (1S,3S)-1-methyl-3-(2-(4-(pyridin-2-ylamino)phenoxy)pyridin-3-yl)cyclohexanol and (1R,3R)-1-methyl-3-(2-(4-(pyridin-2-ylamino)phenoxy)pyridin-3-yl)cyclohexanol | 376.1 | 0.02419 and 0.06359 |
| 446, 447, 448, and 449/separated from racemic mixture from example 243/Scheme 28 | 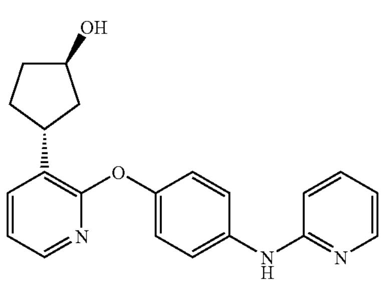 | (1R,3R)-3-(2-(4-(pyridin-2-ylamino)phenoxy)pyridin-3-yl)cyclopentanol and (1R,3S)-3-(2-(4-(pyridin-2-ylamino)phenoxy)pyridin-3-yl)cyclopentanol and (1S,3R)-3-(2-(4-(pyridin-2-ylamino)phenoxy)pyridin-3-yl)cyclopentanol and (1S,3S)-3-(2-(4-(pyridine-2-ylamino)phenoxy)pyridin-3-yl)cyclopentanol | 347 | 0.040 and 0.094 and 0.032 and 0.027 |

TABLE XVIII-continued
EXAMPLES 442 TO 455 ARE TABULATED BELOW:
| Ex. Nos.* | Compound Structure | Compound Name | MS | PDE10 IC50 (uM) |
|---|---|---|---|---|
| | 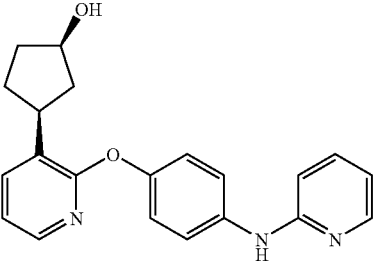 and | | | |
| | 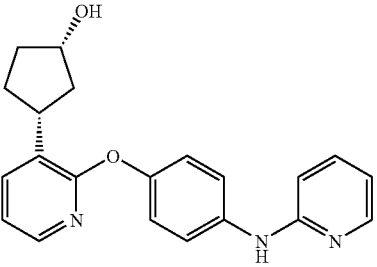 and | | | |
| | 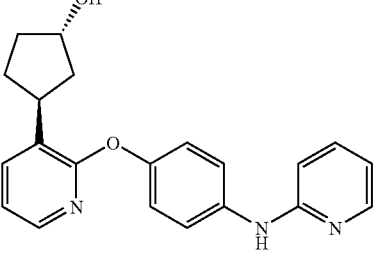 | | | |
| 450 and 451/255/ Schemes 35a + 36 | 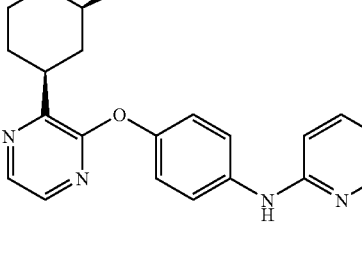 and 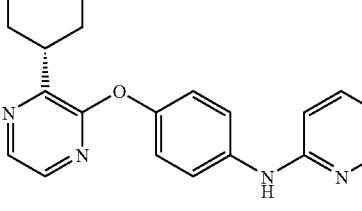 | (1R,3S)-3-(3-(4-(pyridine-2-ylamino)phenoxy)pyrazin-2-yl)cyclohexanol and (1S,3R)-3-(3-(4-(pyridin-2-ylamino)phenoxy)pyrazin-2-yl)cyclohexanol | 363.0 | 0.01531 and 0.02225 |

TABLE XVIII-continued

EXAMPLES 442 TO 455 ARE TABULATED BELOW:

| Ex. Nos.* | Compound Structure | Compound Name | MS | PDE10 IC50 (uM) |
|---|---|---|---|---|
| 452 and 453/ separated from racemic mixture from example 255/Schemes 35a + 36 | (structure) | (1R,3R)-3-(3-(4-(pyridin-2-ylamino)phenoxy)pyrazin-2-yl)cyclohexanol and (1S,3S)-3-(3-(4-(pyridin-2-ylamino)phenoxy)pyrazin-2-yl)cyclohexanol | 363.0 | 0.01337 and 0.02963 |
| 454 and 455/ separated from racemic mixture from example 300/Scheme 46 | (structure) | (S)-1-(3-(2-(4-(5-methylpyridin-2-ylamino)phenoxy)pyridin-3-yl)piperidin-1-yl)ethanone and (R)-1-(3-(2-(4-(5-methylpyridin-2-ylamino)phenoxy)pyridin-3-yl)piperidin-1-yl)ethanone | 403 | 0.00004 and 0.003 |

*refers to the Example # for the separated chiral compounds/Example # for the racemic mixture the chiral compound was separated from/as prepared according to the Schemes described above.

The PDE10 inhibitory activities of the compounds of the present invention can be tested, for example, using the in vitro and in vivo assays described in the Biological Examples below.

BIOLOGICAL EXAMPLES

Example 1

MPDE10A7 Enzyme Activity and Inhibition
Enzyme Activity.
An IMAP TR-FRET assay was used to analyze the enzyme activity (Molecular Devices Corp., Sunnyvale Calif.). 5 μL of serial diluted PDE10A (BPS Bioscience, San Diego, Calif.) or tissue homogenate was incubated with equal volumes of diluted fluorescein labeled cAMP or cGMP for 60 min in 384-well polystyrene assay plates (Corning, Corning, N.Y.) at room temperature. After incubation, the reaction was stopped by adding 60 μL of diluted binding reagents and was incubated for 3 hours to overnight at room temperature. The plates were read on an Envision (Perkin Elmer, Waltham, Mass.) for time resolved fluorescence resonance energy transfer. The data were analyzed with GraphPad Prism (La Jolla, Calif.).
Enzyme Inhibition.
To check the inhibition profile, 5 μL of serial diluted compounds were incubated with 5 μL of diluted PDE10 enzyme (BPS Bioscience, San Diego, Calif.) or tissue homogenate in a 384-well polystyrene assay plate (Corning, Corning, N.Y.) for 30 min at room temperature. After incubation, 10 μL of diluted fluorescein labeled cAMP or cGMP substrate were added and incubated for 60 min at room temperature. The reaction was stopped by adding 60 μL of diluted binding reagents and plates were read on an Envision (Perkin Elmer, Waltham, Mass.) for time resolved fluorescence resonance energy transfer. The data were analyzed with GraphPad Prism (La Jolla, Calif.).

Example 2

Apomorphine Induced Deficits in Prepulse Inhibition of the Startle Response in Rats, and In Vivo Test for Antipsychotic Activity The thought disorders that are characteristic of schizophrenia may result from an inability to filter, or gate, sensorimotor information. The ability to gate sensorimotor information can be tested in many animals as well as in humans. A test that is commonly used is the reversal of apomorphine-induced deficits in the prepulse inhibition of the startle response. The startle response is a reflex to a sudden intense stimulus such as a burst of noise. In this example, rats are exposed to a sudden burst of noise, at a level of 120 db for 40 msec, e.g., the reflex activity of the rats is measured. The reflex of the rats to the burst of noise may be attenuated by preceding the startle stimulus with a stimulus of lower intensity, at 3 db to 12 db above background (65 db), which attenuates the startle reflex by 20% to 80%.

The prepulse inhibition of the startle reflex, described above, may be attenuated by drugs that affect receptor signaling pathways in the CNS. One commonly used drug is the dopamine receptor agonist apomorphine. Administration of apomorphine reduces the inhibition of the startle reflex produced by the prepulse. Antipsychotic drugs such as haloperidol prevents apomorphine from reducing the prepulse inhibition of the startle reflex. This assay can be used to test the antipsychotic efficacy of PDE10 inhibitors, as they reduce the apomorphine-induced deficit in the prepulse inhibition of startle.

Example 3

Conditioned Avoidance Responding (CAR) in Rats, an In Vivo Test for Antipsychotic Activity Conditioned avoidance responding (CAR) occurs, for instance, when an animal learns that a tone and light predict the onset of a mild foot shock. The subject learns that when the tone and light are on, it must leave the chamber and enter a safe area. All known antipsychotic drugs reduce this avoidance response at doses which do not cause sedation. Examining the ability of test compounds to suppress the conditioned avoidance has been widely used for close to fifty years to screen for drugs with useful antipsychotic properties.

In this example, an animal is placed in a two-chambered shuttle box and presented with a neutral conditioned stimulus (CS) consisting of a light and tone, followed by an aversive unconditioned stimulus (US) consisting of a mild foot shock through a floor grid in the shuttle box chamber. The animal is free to escape the US by running from one chamber to the other, where the grid is not electrified. After several presentations of the CS-US pair, the animal typically learns to leave the chamber during the presentation of the CS and avoid the US altogether. Animals treated with clinically-relevant doses of antipsychotic drugs have a suppression of their rate of avoidances in the presence of the CS even though their escape response to the shock itself is unaffected.

Specifically, conditioned avoidance training is conducted using a shuttle box (Med Associates, St. Albans, Vt.). The shuttle box is divided into 2 equal compartments that each contain a light source, a speaker that emits an 85 dB tone when activated and an electrified grid that can deliver a scrambled foot shock. Sessions consist of 20 trials per day (intertrial interval of 25-40 sec) during which a 10 sec illumination and a concurrent 10 sec tone signals the subsequent delivery of a 0.5 mA shock applied for a maximum of 10 sec. Active avoidance, defined as the crossing into the opposite compartment during the 10 sec conditioning stimuli (light and tone) prevents the delivery of the shock. Crossing over to the other compartment after the delivery of the shock terminates shock delivery and is recorded as an escape response. If an animal does not leave the conditioning chamber during the delivery of the shock it is recorded as an escape failure. Training is continued daily until the avoidance of 16 or more shocks out of 20 trials (80% avoidance) on 2 consecutive days is achieved. After this criterion is reached the rats are given one day of pharmacological testing. On test day, rats are randomly assigned to experimental groups, weighed and injected intraperitoneally (i.p.) (1 cc tuberculin syringe, 26⅜ gauge needle) or per os (p.o.) (18 gauge feeding needle) with either control or compound solutions. Compounds are injected at 1.0 ml/kg for i.p. and 10 mL/kg for p.o. administration. Compounds can be administered either acutely or chronically. For testing, each rat is placed in the shuttle box, and given 20 trials with the same parameters as described above for training trials. The number of avoidances, escapes, and escape failures are recorded.

Example 4

PCP-Induced Hyperactivity (PCP-LMA)

Equipment Used: 4×8 home cage photobeam activity system (PAS) frame from San Diego Instruments. Open PAS program and prepare an experimental session using the following variables:
  Multiphase experiment
  300 sec/interval (5 min)
  12 intervals (1 h)
  Individual on screen switches.
  Start recording after first beam break.
  End session after end of interval.
Cage Preparation:
  Techniplast™ rat cage with filter top, but no wire lid. Place ~400 mL bedding and one food pellet in cage and place 250 mL techniplast water bottle in holder on filter top. Place the prepped cage in the PAS frame. Make sure bedding or pellet doesn't block the photobeams.
Animal Preparation:
  Mark rats and record their weights. Bring rats to testing room.
Phase I: Habituation
  Start the experiment session. Place the rat in the enclosure. The computer should start recording when it detects the rat breaking the beam. The computer will record for 1 h. During the habituation phase, prepare risperidone (positive control): Measure out risperidone, calculate final volume at 1 mg/mL concentration and add 1% glacial acetic acid of the final volume to dissolve risperidone. When risperidone is dissolved, add saline to final volume to make a concentration of 1 mg/mL. Fill syringes (3 mL syringes with 23 g ½ needle or oral gavage needle) with Amgen compound solution (5 mL/kg) or risperidone (1 mL syringe with 23 g ½ needle) control (1 mL/kg) s.c.

Phase II: Compound Pre-Treatment

Make sure Phase I has ended. Remove rat from enclosure, start the next phase using on-screen individual switch, administer compound p.o or i.p. and control s.c. and place rat back in the enclosure. The computer should start recording when it detects the rat breaking the beam. The computer will record for 1 h.

During phase II, prepare pcp: Dissolve pcp in saline to a concentration of 5 mg/mL.

Fill syringes (1 mL syringes with 26 g ⅜ needle) with pcp solution (1 mL/kg).

Phase III: PCP Administration.

Make sure phase II is ended. Remove rat from enclosure, start the next phase using on-screen individual switch, administer pcp s.c. and place rat back in the enclosure. The computer will record for 1 h.

Clean-Up:

End-session to terminate experiment and so that computer will compile data. Export raw data to excel file for data analysis. Euthanize rats and take necessary tissue/sample for PK.

Data Generation:

Export raw data to excel file for data analysis. Total time of movement is recorded as the number of photobeam breaks by the computer. Total time of movement (seconds) is combined into 5 minute bins and averaged for each treatment group for an N of 7-10 animals. Data are analyzed for statistical significance using a two-way ANOVA followed by a Bonferroni's post-hoc test for multiple comparisons.

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

All patents, patent applications and publications cited in this application are hereby incorporated by reference in their entirety for all purposes to the same extent as if each individual patent, patent application or publication were so individually denoted.

The compounds of the present invention may be administered orally, parentally, by inhalation spray, rectally, or topically in dosage unit formulations containing conventional pharmaceutically acceptable carriers, adjuvants, and vehicles, for the treatment of PDE10-related diseases, such as acute, inflammatory and neuropathic pain, dental pain, general headache, migraine, cluster headache, mixed-vascular and non-vascular syndromes, tension headache, general inflammation, arthritis, rheumatic diseases, osteoarthritis, inflammatory bowel disorders, inflammatory eye disorders, inflammatory or unstable bladder disorders, psoriasis, skin complaints with inflammatory components, chronic inflammatory conditions, inflammatory pain and associated hyperalgesia and allodynia, neuropathic pain and associated hyperalgesia and allodynia, diabetic neuropathy pain, causalgia, sympathetically maintained pain, deafferentation syndromes, asthma, epithelial tissue damage or dysfunction, herpes simplex, disturbances of visceral motility at respiratory, genitourinary, gastrointestinal or vascular regions, wounds, burns, allergic skin reactions, pruritus, vitiligo, general gastrointestinal disorders, gastric ulceration, duodenal ulcers, diarrhea, gastric lesions induced by necrotising agents, hair growth, vasomotor or allergic rhinitis, bronchial disorders or bladder disorders. The term parenteral as used herein includes, subcutaneous, intravenous, intramuscular, intrasternal, infusion techniques or intraperitoneally.

Treatment of diseases and disorders herein is intended to also include the prophylactic administration of a compound of the invention, a pharmaceutical salt thereof, or a pharmaceutical composition of either to a subject (i.e., an animal, preferably a mammal, most preferably a human) believed to be in need of preventative treatment, such as, for example, pain, inflammation and the like.

The dosage regimen for treating PDE10-receptor-mediated diseases, cancer, and/or hyperglycemia with the compounds of this invention and/or compositions of this invention is based on a variety of factors, including the type of disease, the age, weight, sex, medical condition of the patient, the severity of the condition, the route of administration, and the particular compound employed. Thus, the dosage regimen may vary widely, but can be determined routinely using standard methods. Dosage levels of the order from about 0.01 mg to 30 mg per kilogram of body weight per day, preferably from about 0.1 mg to 10 mg/kg, more preferably from about 0.25 mg to 1 mg/kg are useful for all methods of use disclosed herein.

The pharmaceutically active compounds of this invention can be processed in accordance with conventional methods of pharmacy to produce medicinal agents for administration to patients, including humans and other mammals.

For oral administration, the pharmaceutical composition may be in the form of, for example, a capsule, a tablet, a suspension, or liquid. The pharmaceutical composition is preferably made in the form of a dosage unit containing a given amount of the active ingredient. For example, these may contain an amount of active ingredient from about 1 to 2000 mg, preferably from about 1 to 500 mg, more preferably from about 5 to 150 mg. A suitable daily dose for a human or other mammal may vary widely depending on the condition of the patient and other factors, but, once again, can be determined using routine methods.

The active ingredient may also be administered by injection as a composition with suitable carriers including saline, dextrose, or water. The daily parenteral dosage regimen will be from about 0.1 to about 30 mg/kg of total body weight, preferably from about 0.1 to about 10 mg/kg, and more preferably from about 0.25 mg to 1 mg/kg.

Injectable preparations, such as sterile injectable aqueous or oleaginous suspensions, may be formulated according to the known are using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

Suppositories for rectal administration of the drug can be prepared by mixing the drug with a suitable non-irritating excipient such as cocoa butter and polyethylene glycols that are solid at ordinary temperatures but liquid at the rectal temperature and will therefore melt in the rectum and release the drug.

A suitable topical dose of active ingredient of a compound of the invention is 0.1 mg to 150 mg administered one to four, preferably one or two times daily. For topical administration, the active ingredient may comprise from 0.001% to 10% w/w, e.g., from 1% to 2% by weight of the formulation, although it may comprise as much as 10% w/w, but preferably not more than 5% w/w, and more preferably from 0.1% to 1% of the formulation.

Formulations suitable for topical administration include liquid or semi-liquid preparations suitable for penetration through the skin (e.g., liniments, lotions, ointments, creams, or pastes) and drops suitable for administration to the eye, ear, or nose.

For administration, the compounds of this invention are ordinarily combined with one or more adjuvants appropriate for the indicated route of administration. The compounds may be admixed with lactose, sucrose, starch powder, cellulose esters of alkanoic acids, stearic acid, talc, magnesium stearate, magnesium oxide, sodium and calcium salts of phosphoric and sulfuric acids, acacia, gelatin, sodium alginate, polyvinyl-pyrrolidine, and/or polyvinyl alcohol, and tableted or encapsulated for conventional administration. Alternatively, the compounds of this invention may be dissolved in saline, water, polyethylene glycol, propylene glycol, ethanol, corn oil, peanut oil, cottonseed oil, sesame oil, tragacanth gum, and/or various buffers. Other adjuvants and modes of administration are well known in the pharmaceutical art. The carrier or diluent may include time delay material, such as glyceryl monostearate or glyceryl distearate alone or with a wax, or other materials well known in the art.

The pharmaceutical compositions may be made up in a solid form (including granules, powders or suppositories) or in a liquid form (e.g., solutions, suspensions, or emulsions). The pharmaceutical compositions may be subjected to conventional pharmaceutical operations such as sterilization and/or may contain conventional adjuvants, such as preservatives, stabilizers, wetting agents, emulsifiers, buffers etc.

Solid dosage forms for oral administration may include capsules, tablets, pills, powders, and granules. In such solid dosage forms, the active compound may be admixed with at least one inert diluent such as sucrose, lactose, or starch. Such dosage forms may also comprise, as in normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting, sweetening, flavoring, and perfuming agents.

Compounds of the present invention can possess one or more asymmetric carbon atoms and are thus capable of existing in the form of optical isomers as well as in the form of racemic or non-racemic mixtures thereof. The optical isomers can be obtained by resolution of the racemic mixtures according to conventional processes, e.g., by formation of diastereoisomeric salts, by treatment with an optically active acid or base. Examples of appropriate acids are tartaric, diacetyltartaric, dibenzoyltartaric, ditoluoyltartaric, and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers. Still another available method involves synthesis of covalent diastereoisomeric molecules by reacting compounds of the invention with an optically pure acid in an activated form or an optically pure isocyanate. The synthesized diastereoisomers can be separated by conventional means such as chromatography, distillation, crystallization or sublimation, and then hydrolyzed to deliver the enantiomerically pure compound. The optically active compounds of the invention can likewise be obtained by using active starting materials. These isomers may be in the form of a free acid, a free base, an ester or a salt.

Likewise, the compounds of this invention may exist as isomers, that is compounds of the same molecular formula but in which the atoms, relative to one another, are arranged differently. In particular, the alkylene substituents of the compounds of this invention, are normally and preferably arranged and inserted into the molecules as indicated in the definitions for each of these groups, being read from left to right. However, in certain cases, one skilled in the art will appreciate that it is possible to prepare compounds of this invention in which these substituents are reversed in orientation relative to the other atoms in the molecule. That is, the substituent to be inserted may be the same as that noted above except that it is inserted into the molecule in the reverse orientation. One skilled in the art will appreciate that these isomeric forms of the compounds of this invention are to be construed as encompassed within the scope of the present invention.

The compounds of the present invention can be used in the form of salts derived from inorganic or organic acids. The salts include, but are not limited to, the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxyethanesulfonate, lactate, maleate, methansulfonate, nicotinate, 2-naphthalenesulfonate, oxalate, palmoate, pectinate, persulfate, 2-phenylpropionate, picrate, pivalate, propionate, succinate, tartrate, thiocyanate, tosylate, mesylate, and undecanoate. Also, the basic nitrogen-containing groups can be quaternized with such agents as lower alkyl halides, such as methyl, ethyl, propyl, and butyl chloride, bromides and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids that may be employed to from pharmaceutically acceptable acid addition salts include such inorganic acids as hydrochloric acid, sulfuric acid and phosphoric acid and such organic acids as oxalic acid, maleic acid, succinic acid and citric acid. Other examples include salts with alkali metals or alkaline earth metals, such as sodium, potassium, calcium or magnesium or with organic bases.

Also encompassed in the scope of the present invention are pharmaceutically acceptable esters of a carboxylic acid or hydroxyl containing group, including a metabolically labile ester or a prodrug form of a compound of this invention. A metabolically labile ester is one which may produce, for example, an increase in blood levels and prolong the efficacy of the corresponding non-esterified form of the compound. A prodrug form is one which is not in an active form of the molecule as administered but which becomes therapeutically active after some in vivo activity or biotransformation, such as metabolism, for example, enzymatic or hydrolytic cleavage. For a general discussion of prodrugs involving esters see Svensson and Tunek Drug Metabolism Reviews 165 (1988) and Bundgaard Design of Prodrugs, Elsevier (1985). Examples of a masked carboxylate anion include a variety of esters, such as alkyl (for example, methyl, ethyl), cycloalkyl (for example, cyclohexyl), aralkyl (for example, benzyl, p-methoxybenzyl), and alkylcarbonyloxyalkyl (for example, pivaloyloxymethyl). Amines have been masked as arylcarbonyloxymethyl substituted derivatives which are cleaved by esterases in vivo releasing the free drug and formaldehyde (Bungaard J. Med. Chem. 2503 (1989)). Also, drugs containing an acidic NH group, such as imidazole, imide, indole and the like, have been masked with N-acyloxymethyl groups (Bundgaard Design of Prodrugs, Elsevier (1985)). Hydroxy groups have been masked as esters and ethers. EP 039,051 (Sloan and Little, Apr. 11, 1981) discloses Mannich-base hydroxamic acid prodrugs, their preparation and use. Esters of a compound of this invention, may include, for example, the methyl, ethyl, propyl, and butyl esters, as well as other suitable esters formed between an acidic moiety and a hydroxyl containing moiety. Metabolically labile esters, may include, for example, methoxymethyl, ethoxymethyl, iso-propoxymethyl, α-methoxyethyl, groups such as α((C$_1$-C$_4$)alkyloxy)ethyl, for example, methoxyethyl, ethoxyethyl, propoxyethyl, iso-propoxyethyl, etc.; 2-oxo-1,3-dioxolen-4-ylmethyl groups, such as 5-methyl-2-oxo-1,3,dioxolen-4-ylmethyl, etc.; C$_1$-C$_3$ alkylthiomethyl groups, for example, methylthiomethyl, ethylthiomethyl, isopropylthiomethyl, etc.; acyloxymethyl groups, for example, pivaloyloxymethyl, α-acetoxymethyl, etc.; ethoxycarbonyl-1-methyl; or α-acyloxy-α-substituted methyl groups, for example α-acetoxyethyl.

Further, the compounds of the invention may exist as crystalline solids which can be crystallized from common solvents such as ethanol, N,N-dimethyl-formamide, water, or the like. Thus, crystalline forms of the compounds of the invention may exist as polymorphs, solvates and/or hydrates of the parent compounds or their pharmaceutically acceptable salts. All of such forms likewise are to be construed as falling within the scope of the invention.

While the compounds of the invention can be administered as the sole active pharmaceutical agent, they can also be used in combination with one or more compounds of the invention or other agents. When administered as a combination, the therapeutic agents can be formulated as separate compositions that are given at the same time or different times, or the therapeutic agents can be given as a single composition.

The foregoing is merely illustrative of the invention and is not intended to limit the invention to the disclosed compounds. Variations and changes which are obvious to one skilled in the art are intended to be within the scope and nature of the invention which are defined in the appended claims.

From the foregoing description, one skilled in the art can easily ascertain the essential characteristics of this invention, and without departing from the spirit and scope thereof, can make various changes and modifications of the invention to adapt it to various usages and conditions.

What is claimed:
1. A compound of the structure:

(I)

or any pharmaceutically-acceptable salt thereof, wherein:
$X^1$ is N;
$X^2$ is CH;
Each of $X^4$, $X^5$, $X^7$, and $X^8$ is independently CH; each of $X^3$ and $X^6$ is C;
m is independently in each instance 0, 1, 2, 3 or 4;
n is independently in each instance 0, 1, 2 or 3;
Y is $NR^8$; or
alternatively Y and $R^3$ may form a 5- to 6-membered ring fused to the ring containing both said Y and $R^3$;
$R^1$ is: Ring A, wherein said ring A is $R^c$:
$R^2$ is, independently in each instance, F, Cl, Br, CN, OH, $OC_{1-4}$alk, $C_{1-4}$alk or $C_{1-4}$haloalk;
$R^3$ is, independently in each instance, F, Br, CN, OH, $OC_{1-4}$alk, $C_{1-4}$alk or $C_{1-4}$haloalk;
$R^4$ is selected from H, F, Br, CN, —O—$C_{1-4}$alk, $C_{1-2}$alk, and $C_{1-2}$haloalk;
$R^5$ is selected from H, F, Cl, Br, CN, —O—$C_{1-4}$alk, $C_{1-2}$alk, and $C_{1-2}$haloalk;
$R^6$ is selected from H, F, Cl, Br, CN, —O—$C_{1-4}$alk, $C_{1-2}$alk, and $C_{1-2}$haloalk;
$R^7$ is selected from H, F, Cl, Br, CN, —O—$C_{1-4}$alk, $C_{1-2}$alk, and $C_{1-2}$haloalk;
$R^8$ is selected from H, $C_{1-8}$alk, or $C_{1-4}$haloalk;
$R^a$ is independently, at each instance, H or $R^b$;
$R^b$ is independently, at each instance, phenyl, benzyl, or $C_{1-6}$alk, wherein said phenyl, benzyl, and $C_{1-6}$alk is independently substituted by 0, 1, 2 or 3 substituents selected from halo, OH, $C_{1-4}$alk, $C_{1-3}$haloalk, —$OC_{1-4}$alk, —$NH_2$, —$NHC_{1-4}$alk, —$N(C_{1-4}$alk)$C_{1-4}$alk, $C_{1-4}$alk-$NH_2$, COOH, CN, —C(=O)—O—$C_{1-6}$alk, —C(=O)—N($C_{1-4}$alk)$C_{1-4}$alk, and —S—$C_{1-4}$alk;
$R^c$ is cyclopropyl, cyclopentyl, cyclopentenyl, cyclohexyl, cyclohexenyl, cycloheptyl, dihydropyranyl, 3-pyridyl, 2-pyridyl, morpholinyl, piperidinyl, tetrahydropyranyl, tetrahydrofuranyl, phenyl, benzyl, 5-quinolinyl, isoquinolinyl, dihydrofuranyl, dihydropyridinyl, tetrahydropyridinyl, pyrrolidinyl, benzo[d][1,3]dioxolyl, azetidinyl, oxepanyl, oxazepanyl, naphthyl, benzothiophenyl, piperazinyl, tetrahydrothiopyranyl, oxaspiro[3.5]nonyl, 1,4-diazepan-1-yl, and azepanyl, which is substituted by 0, 1, 2 or 3 groups selected from F, Cl, Br, $R^e$, $C_{1-6}$alk, $C_{1-4}$haloalk, —$OR^a$, —$OC_{1-4}$haloalk, CN, —C(=O)$R^b$, —C(=O)$R^e$, —C(=O)$OR^a$, —C(=O)$NR^aR^a$, —C(=$NR^a$)$NR^aR^a$, —OC(=O)$R^b$, —OC(=O)$NR^aR^a$, —$OC_{2-6}$alk$NR^aR^a$, —$OC_{2-6}$alk$(OR^a)_{1-3}$, —$SR^a$, —S(=O)$R^b$, —S(=O)$_2R^b$, —S(=O)(OH)$R^b$, —S(=O)$_2NR^aR^a$, —$NR^aR^a$, —$NR^aR^e$, —$NR^an^d$, —N($R^a$)C(=O)$R^b$, —N($R^a$)C(=O)$OR^b$, —N($R^a$)C(=O)$NR^aR^a$, —N($R^a$)C(=$NR^a$)$NR^aR^a$, —N($R^a$)S(=O)$_2R^b$, —N($R^a$)S(=O)$_2NR^aR^a$, —$NR^aC_{2-6}$alk$NR^aR^a$, —$NR^aC_{2-6}$alk$OR^a$, —$C_{1-6}$alk$NR^aR^a$, —$C_{1-6}$alk$(OR^a)_{1-3}$, —$C_{1-6}$alk$N(R^a)C(=O)R^b$, —$C_{1-6}$alkOC(=O)$R^b$, —$C_{1-6}$alkC(=O)$NR^aR^a$, —$C_{1-6}$alkC(=O)$OR^a$ and oxo;

$R^d$ is a nitrogen-linked saturated, partially-saturated or unsaturated 4-, 5-, 6- or 7-membered ring heterocycle containing the linking nitrogen and 0, 1 or 2 additional nitrogen atoms and containing 0 or 1 sulfur or oxygen atoms, the heterocycle being substituted by 0, 1, 2 or 3 substituents selected from oxo, halo, OH, CN, $C_{1-4}$alk, $C_{1-3}$haloalk, —$OC_{1-4}$alk, $R^e$, —$OR^e$, —$NH_2$, —$NHC_{1-4}$alk, —$N(C_{1-4}$alk$)C_{1-4}$alk, C(=O)$OR^a$, —$C_{1-6}$alk$(OR^a)_{1-3}$, —NH—C(=O)$OC_{1-4}$alk, C(=O)$R^a$, C(=O)$R^e$, C(=O)$NR^aR^a$, and C(=O)$NR^aR^a$; and $R^e$ is:

(a) $C_{0-4}$-alk-linked saturated, partially-saturated or unsaturated 3-, 4-, 5-, 6-, or 7-membered monocyclic containing 0, 1, 2 or 3 N atoms and 0, 1, or 2 atoms selected from O and S; which is substituted by 0, 1, 2 or 3 groups selected from oxo, halo, OH, $C_{1-4}$alk, $C_{1-3}$haloalk, —$OC_{1-4}$alk, —$NH_2$, —$NHC_{1-4}$alk, —$N(C_{1-4}$alk) $C_{1-4}$alk, $C_{1-4}$alk-$NH_2$, COOH, CN, —C(=O)—O—$C_{1-6}$alk, —C(=O)—$N(C_{1-4}$alk$)C_{1-4}$alk, and —S—$C_{1-4}$alk; or (b) nitrogen-linked saturated, partially-saturated or unsaturated 4-, 5-, 6- or 7-membered ring heterocycle containing the linking nitrogen and 0, 1 or 2 additional nitrogen atoms and containing 0 or 1 sulfur or oxygen atoms; which is substituted by 0, 1, 2 or 3 groups selected from oxo, halo, OH, $C_{1-4}$alk, $C_{1-3}$haloalk, —$OC_{1-4}$alk, —$NH_2$, —$NHC_{1-4}$alk, —$N(C_{1-4}$alk) $C_{1-4}$alk, $C_{1-4}$alk-$NH_2$, COOH, CN, —C(=O)—O—$C_{1-6}$alk, —C(=O)—$N(C_{1-4}$alk$)C_{1-4}$alk, and —S—$C_{1-4}$alk.

2. The compound of claim 1 wherein Y is NH.

3. The compound of claim 1 wherein $R^1$ is Ring A, wherein said ring A is $R^c$ selected from the group consisting of cyclopropyl, cyclopentyl, cyclopentenyl, cyclohexyl, cyclohexenyl, cycloheptyl, dihydropyranyl, 3-pyridyl, 2-pyridyl, morpholinyl, piperidinyl, tetrahydropyranyl, tetrahydrofuranyl, phenyl, benzyl, 5-quinolinyl, isoquinolinyl, dihydrofuranyl, tetrahydropyridinyl, pyrrolidinyl, benzo[d][1,3]dioxolyl, azetidinyl, oxepanyl, oxazepanyl, naphthyl, benzothiophenyl, piperazinyl, tetrahydrothiopyranyl, oxaspiro[3.5]nonyl, and azepanyl, all of which are substituted by 0, 1, 2 or 3 groups selected from F, Cl, Br, $R^e$, —$CH_3$, $C_{1-4}$haloalk, —OH, —$OCH_3$, —$OCH_2CH_3$, CN, —C(=O)—$CH_3$, —C(=O)$OR^a$, —$SR^a$, —$NR^aR^a$, —$NR^aR^e$, —$NR^an^d$, —$C_{1-6}$alk$(OR^a)_{1-3}$, and oxo.

4. The compound of claim 1 wherein $R^4$ is H, F, Br, methyl, or ethyl.

5. The compound of claim 1 wherein $R^5$ is H.

6. The compound of claim 1 wherein $R^6$ is H, F, Cl, Br, methyl, ethyl, $C_{1-2}$haloalk, CN, or —O—$C_{1-4}$haloalk.

7. The compound of claim 1 wherein $R^7$ is H.

8. The compound of claim 1 wherein $R^8$ is H.

9. The compound of claim 1 wherein $R^d$ is a nitrogen-linked saturated or partially-saturated 4-, 5-, 6- or 7-membered ring heterocycle containing the linking nitrogen and 0 additional nitrogen atoms and containing 0 or 1 sulfur or oxygen atoms, the heterocycle being substituted by 0, 1 or 2 substituents selected from oxo, halo, OH, CN, $C_{1-4}$alk, $C_{1-3}$haloalk, —$OC_{1-4}$alk, $R^e$, —$OR^e$, C(=O)$OR^a$, —$C_{1-6}$alk $(OR^a)_{1-3}$, —NH—C(=O)$OC_{1-4}$alk, C(=O)$R^a$, C(=O)$R^e$, C(=O)$NR^aR^a$, and C(=O)$NR^aR^a$.

10. The compound of claim 1 wherein $R^e$ is selected from the group consisting of $C_{0-4}$-alk-linked oxadiazolyl, $C_{0-4}$-alk-linked pyridyl, $C_{0-4}$-alk-linked phenyl, $C_{0-4}$alk-linked piperidinyl, which is substituted by 0, 1 or 2 groups selected from oxo, halo, OH, $C_{1-4}$alk, $C_{1-3}$haloalk, —$OC_{1-4}$alk, —$NH_2$, —$NHC_{1-4}$alk, —$N(C_{1-4}$alk$)C_{1-4}$alk, $C_{1-4}$alk-$NH_2$, COOH, CN, —C(=O)—O—$C_{1-6}$alk, —C(=O)—$N(C_{1-4}$alk) $C_{1-4}$alk, and —S—$C_{1-4}$alk.

11. The compound of claim 1 wherein m is 0 and n is 0.

12. The compound of claim 1 wherein $R^2$ is $OC_{1-4}$alk.

13. The compound of claim 1 wherein $R^4$ is selected from H, F, Br, —O—$C_{1-4}$alk, methyl, ethyl, and $CF_3$.

14. The compound of claim 1 wherein $R^5$ is selected from H, F, Cl, Br, CN, methyl, ethyl, and $CF_3$.

15. The compound of claim 1 wherein $R^6$ is selected from H, F, Cl, Br, methyl, ethyl, and $CF_3$.

16. The compound of claim 1 wherein $R^7$ is selected from H, F, methyl, ethyl, and $CF_3$.

17. The compound according to claim 1, or a pharmaceutically acceptable salt thereof, selected from the group consisting of:

1-(3-(4-(Pyridin-2-ylamino)phenoxy)pyrazin-2-yl)piperidine-4-carbonitrile;

2-(1-(3-(4-(pyridin-2-ylamino)phenoxy)pyrazin-2-yl)pyrrolidin-3-yl)propan-2-ol;

2-(1-(3-(4-(pyridin-2-ylamino)phenoxy)pyrazin-2-yl)piperidin-4-yl)propan-2-ol;

1-(3-(4-(pyridin-2-ylamino)phenoxy)pyrazin-2-yl)piperidin-4-ol;

1-(3-(4-(pyridin-2-ylamino)phenoxy)pyrazin-2-yl)piperidin-3-ol;

N-(4-(3-(pyrrolidin-1-yl)pyrazin-2-yloxy)phenyl)pyridin-2-amine;

N-(4-(3-(2,6-dimethylmorpholino)pyrazin-2-yloxy)phenyl)pyridin-2-amine;

(S)—N-(4-(3-(2-(methoxymethyl)pyrrolidin-1-yl) pyrazin-2-yloxy)phenyl)pyridin-2-amine;

(S)-(1-(3-(4-(pyridin-2-ylamino)phenoxy)pyrazin-2-yl) pyrrolidin-2-yl)methanol;

1-(3-(4-(pyridin-2-ylamino)phenoxy)pyrazin-2-yl)azetidine-3-carboxylic acid;

(R)—N-(4-(3-(2-(4-methoxyphenyl)morpholino)pyrazin-2-yloxy)phenyl)pyridin-2-amine;

(S)—N-(4-(3-(2-(4-methoxyphenyl)morpholino)pyrazin-2-yloxy)phenyl)pyridin-2-amine;

(R)—N-(4-(3-(2-(methoxymethyl)pyrrolidin-1-yl) pyrazin-2-yloxy)phenyl)pyridin-2-amine;

(R)-(1-(3-(4-(pyridin-2-ylamino)phenoxy)pyrazin-2-yl) pyrrolidin-2-yl)methanol;

(1-(3-(4-(pyridin-2-ylamino)phenoxy)pyrazin-2-yl)piperidin-3-yl)methanol;

N-(4-(3-(3-(methoxymethyl)piperidin-1-yl)pyrazin-2-yloxy)phenyl)pyridin-2-amine;

(1-(3-(4-(pyridin-2-ylamino)phenoxy)pyrazin-2-yl)piperidin-2-yl)methanol;

methyl 1-(3-(4-(pyridin-2-ylamino)phenoxy)pyrazin-2-yl)pyrrolidine-3-carboxylate;

N-(4-(3-morpholinopyrazin-2-yloxy)phenyl)pyridin-2-amine;

N-(4-(3-(piperidin-1-yl)pyrazin-2-yloxy)phenyl)pyridin-2-amine;

(R)-1-(3-(4-(pyridin-2-ylamino)phenoxy)pyrazin-2-yl) pyrrolidin-3-ol;

N-(4-(3-(4-methylpiperazin-1-yl)pyrazin-2-yloxy)phenyl)pyridin-2-amine;

N-(4-(3-(piperazin-1-yl)pyrazin-2-yloxy)phenyl)pyridin-2-amine;

N-(4-(3-(4-methoxypiperidin-1-yl)pyrazin-2-yloxy)phenyl)pyridin-2-amine;

(S)-1-(3-(4-(pyridin-2-ylamino)phenoxy)pyrazin-2-yl) pyrrolidin-3-ol;

(R)-(1-(3-(4-(pyridin-2-ylamino)phenoxy)pyrazin-2-yl)pyrrolidin-3-yl)methanol;
(S)-(1-(3-(4-(pyridin-2-ylamino)phenoxy)pyrazin-2-yl)pyrrolidin-3-yl)methanol;
N-(4-(3-(1,4-oxazepan-4-yl)pyrazin-2-yloxy)phenyl)pyridin-2-amine;
1-(4-(3-(4-(pyridin-2-ylamino)phenoxy)pyrazin-2-yl)-1,4-diazepan-1-yl)ethanone;
(rac)-N-(4-(3-(3-benzylpiperidin-1-yl)pyrazin-2-yloxy)phenyl)pyridin-2-amine;
N-(2-fluoro-4-(3-(2-methoxypyridin-3-yl)pyrazin-2-yloxy)phenyl)pyridin-2-amine;
N-(4-(3-(3-aminophenyl)pyrazin-2-yloxy)phenyl)pyridin-2-amine;
4-(3-(4-(pyridin-2-ylamino)phenoxy)pyrazin-2-yl)benzonitrile;
3-(3-(4-(pyridin-2-ylamino)phenoxy)pyrazin-2-yl)benzonitrile;
N-(4-(3-(4-aminophenyl)pyrazin-2-yloxy)phenyl)pyridin-2-amine;
N-(4-(3-phenylpyrazin-2-yloxy)phenyl)pyridin-2-amine;
N-(4-(3-(pyridin-3-yl)pyrazin-2-yloxy)phenyl)pyridin-2-amine;
(3-(3-(4-(pyridin-2-ylamino)phenoxy)pyrazin-2-yl)phenyl)methanol;
N-(4-(3-(isoquinolin-5-yl)pyrazin-2-yloxy)phenyl)pyridin-2-amine;
N-(4-(3-(3-chlorophenyl)pyrazin-2-yloxy)phenyl)pyridin-2-amine;
N-(4-(3-(3-(aminomethyl)phenyl)pyrazin-2-yloxy)phenyl)pyridin-2-amine;
N-(4-(3-(4-methoxyphenyl)pyrazin-2-yloxy)phenyl)pyridin-2-amine;
N-(4-(3-(2-methoxyphenyl)pyrazin-2-yloxy)phenyl)pyridin-2-amine;
N-(4-(3-(3-methoxyphenyl)pyrazin-2-yloxy)phenyl)pyridin-2-amine;
2-fluoro-3-(3-(4-(pyridin-2-ylamino)phenoxy)pyrazin-2-yl)benzonitrile;
N-(4-(3-(quinolin-5-yl)pyrazin-2-yloxy)phenyl)pyridin-2-amine;
4-fluoro-3-(3-(4-(pyridin-2-ylamino)phenoxy)pyrazin-2-yl)benzonitrile;
3-(3-(4-(pyridin-2-ylamino)phenoxy)pyrazin-2-yl)phenol;
N-(4-(3-(quinolin-4-yl)pyrazin-2-yloxy)phenyl)pyridin-2-amine;
N-(4-(3-(benzo[b]thiophen-7-yl)pyrazin-2-yloxy)phenyl)pyridin-2-amine;
N-(4-(3-(pyridin-3-yl)pyrazin-2-yloxy)phenyl)pyridin-2-amine;
N-(4-(3-cyclohexenylpyrazin-2-yloxy)phenyl)pyridin-2-amine;
N-(4-(3-cyclopentenylpyrazin-2-yloxy)phenyl)pyridin-2-amine;
N-(2-Fluoro-4-(3-(tetrahydro-2H-pyran-4-yl)pyrazin-2-yloxy)phenyl)pyridin-2-amine;
5-Methyl-N-(4-(3-(tetrahydro-2H-pyran-4-yl)pyrazin-2-yloxy)phenyl)pyridin-2-amine;
N-(4-(3-(Tetrahydro-2H-pyran-4-yl)pyrazin-2-yloxy)phenyl)-5-(trifluoromethyl)pyridin-2-amine;
5-Ethyl-N-(4-(3-(tetrahydro-2H-pyran-4-yl)pyrazin-2-yloxy)phenyl)pyridin-2-amine;
5-Methoxy-N-(4-(3-(tetrahydro-2H-pyran-4-yl)pyrazin-2-yloxy)phenyl)pyridin-2-amine;
N-(4-(3-(tetrahydro-2H-pyran-3-yl)pyrazin-2-yloxy)phenyl)pyridin-2-amine;
(rac)-cis-3-(3-(4-(Pyridin-2-ylamino)phenoxy)pyrazin-2-yl)cyclohexanol;
(rac)-trans-3-(3-(4-(Pyridin-2-ylamino)phenoxy)pyrazin-2-yl)cyclohexanol;
N-(4-(3-(tetrahydrofuran-3-yl)pyrazin-2-yloxy)phenyl)pyridin-2-amine;
1-(4-(3-(4-(pyridin-2-ylamino)phenoxy)pyrazin-2-yl)piperidin-1-yl)ethanone;
1-(4-(3-(2-fluoro-4-(pyridin-2-ylamino)phenoxy)pyrazin-2-yl)piperidin-1-yl)ethanone;
1-(4-(3-(4-(5-Methylpyridin-2-ylamino)phenoxy)pyrazin-2-yl)piperidin-1-yl)ethanone;
1-(4-(3-(4-(5-Chloropyridin-2-ylamino)phenoxy)pyrazin-2-yl)piperidin-1-yl)ethanone;
tert-butyl 4-(3-(4-(pyridin-2-ylamino)phenoxy)pyrazin-2-yl)-5,6-dihydropyridine-1(2H)-carboxylate;
N-(4-(3-(piperidin-4-yl)pyrazin-2-yloxy)phenyl)pyridin-2-amine;
2,2,2-trifluoro-1-(4-(3-(4-(pyridin-2-ylamino)phenoxy)pyrazin-2-yl)piperidin-1-yl)ethanone;
1-(4-(3-(4-(pyridin-2-ylamino)phenoxy)pyrazin-2-yl)-5,6-dihydropyridin-1(2H)-yl)ethanone;
2-methoxy-1-(4-(3-(4-(5-methylpyridin-2-ylamino)phenoxy)pyrazin-2-yl)piperidin-1-yl)ethanone;
methyl 4-(3-(4-(5-methylpyridin-2-ylamino)phenoxy)pyrazin-2-yl)piperidine-1-carboxylate;
(R)-2-methoxy-1-(4-(3-(4-(5-methylpyridin-2-ylamino)phenoxy)pyrazin-2-yl)piperidin-1-yl)propan-1-one;
(S)-2-methoxy-1-(4-(3-(4-(5-methylpyridin-2-ylamino)phenoxy)pyrazin-2-yl)piperidin-1-yl)propan-1-one;
2-methyl-1-(4-(3-(4-(pyridin-2-ylamino)phenoxy)pyrazin-2-yl)piperidin-1-yl)propan-1-one;
N-(4-(3-(1-(methylsulfonyl)piperidin-4-yl)pyrazin-2-yloxy)phenyl)pyridin-2-amine;
methyl 4-(3-(4-(pyridin-2-ylamino)phenoxy)pyrazin-2-yl)piperidine-1-carboxylate;
5-methyl-N-(4-(3-(1-(methylsulfonyl)piperidin-4-yl)pyrazin-2-yloxy)phenyl)pyridine-2-amine;
2-methyl-1-(4-(3-(4-(5-methylpyridin-2-ylamino)phenoxy)pyrazin-2-yl)piperidin-1-yl)propan-1-one;
ethyl 4-(3-(4-(5-methylpyridin-2-ylamino)phenoxy)pyrazin-2-yl)piperidine-1-carboxylate;
cyclopropyl(4-(3-(4-(5-methylpyridin-2-ylamino)phenoxy)pyrazin-2-yl)piperidin-1-yl)methanone;
N,N-dimethyl-4-(3-(4-(5-methylpyridin-2-ylamino)phenoxy)pyrazin-2-yl)piperidine-1-carboxamide;
1-(3-(3-(4-(pyridin-2-ylamino)phenoxy)pyrazin-2-yl)pyrrolidin-1-yl)ethanone;
N-(4-(3-cyclopentylpyrazin-2-yloxy)phenyl)pyridin-2-amine;
(1R,3S)-3-(3-(4-(pyridin-2-ylamino)phenoxy)pyrazin-2-yl)cyclohexanol;
(1S,3R)-3-(3-(4-(pyridin-2-ylamino)phenoxy)pyrazin-2-yl)cyclohexanol;
(1R,3R)-3-(3-(4-(pyridin-2-ylamino)phenoxy)pyrazin-2-yl)cyclohexanol; and
(1S,3S)-3-(3-(4-(pyridin-2-ylamino)phenoxy)pyrazin-2-yl)cyclohexanol.

18. A pharmaceutical composition comprising a compound according to claim 1 and a pharmaceutically-acceptable diluent or carrier.

* * * * *

UNITED STATES PATENT AND TRADEMARK OFFICE
CERTIFICATE OF CORRECTION

| | | |
|---|---|---|
| PATENT NO. | : 8,637,500 B2 | Page 1 of 1 |
| APPLICATION NO. | : 12/639931 | |
| DATED | : January 28, 2014 | |
| INVENTOR(S) | : Allen et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 768 days.

Signed and Sealed this
Second Day of June, 2015

Michelle K. Lee
*Director of the United States Patent and Trademark Office*